US012570645B2

(12) United States Patent
Vu et al.

(10) Patent No.: US 12,570,645 B2
(45) Date of Patent: *Mar. 10, 2026

(54) USES OF p53 X-RAY CO-CRYSTAL STRUCTURES

(71) Applicant: PMV Pharmaceuticals, Inc., Cranbury, NJ (US)

(72) Inventors: Binh Vu, North Caldwell, NJ (US); Andrew Good, Wallingford, CT (US)

(73) Assignee: PMV Pharmaceuticals, Inc., Princeton, NJ (US)

( * ) Notice: Subject to any disclaimer, the term of this patent is extended or adjusted under 35 U.S.C. 154(b) by 204 days.

This patent is subject to a terminal disclaimer.

(21) Appl. No.: 17/351,970

(22) Filed: Jun. 18, 2021

(65) Prior Publication Data

US 2023/0024905 A1 Jan. 26, 2023

Related U.S. Application Data

(60) Provisional application No. 63/162,693, filed on Mar. 18, 2021, provisional application No. 63/042,334, filed on Jun. 22, 2020.

(51) Int. Cl.

| | |
|---|---|
| ***C07D 409/14*** | (2006.01) |
| ***C07D 209/14*** | (2006.01) |
| ***C07D 401/12*** | (2006.01) |
| ***C07D 401/14*** | (2006.01) |
| ***C07D 405/14*** | (2006.01) |
| ***C07D 491/08*** | (2006.01) |
| ***C07K 14/47*** | (2006.01) |

(52) U.S. Cl.

CPC ......... *C07D 409/14* (2013.01); *C07D 209/14* (2013.01); *C07D 401/12* (2013.01); *C07D 401/14* (2013.01); *C07D 405/14* (2013.01); *C07D 491/08* (2013.01); *C07K 14/4746* (2013.01)

(58) Field of Classification Search

None

See application file for complete search history.

(56) References Cited

U.S. PATENT DOCUMENTS

| | | | | |
|---|---|---|---|---|
| 7,601,714 | B2 | 10/2009 | Barbosa, Jr. et al. | |
| 8,822,689 | B2 | 9/2014 | Soll et al. | |
| 8,859,780 | B2 | 10/2014 | Ehring et al. | |
| 8,865,715 | B2 | 10/2014 | Dorsch et al. | |
| 8,933,113 | B2 | 1/2015 | Crespo et al. | |
| 9,090,661 | B2 | 7/2015 | Coburn et al. | |
| 9,447,103 | B2 | 9/2016 | Lu et al. | |
| 10,138,219 | B2 * | 11/2018 | Vu ..................... | C07D 491/107 |
| 10,640,485 | B2 * | 5/2020 | Vu ....................... | C07D 401/12 |
| 11,339,141 | B2 * | 5/2022 | Vu ....................... | C07D 209/14 |
| 11,807,644 | B2 | 11/2023 | Vu et al. | |
| 11,938,124 | B2 | 3/2024 | Levine et al. | |
| 2002/0048271 | A1 | 4/2002 | Rastinejad et al. | |
| 2010/0130731 | A1 | 5/2010 | Fersht et al. | |
| 2012/0258920 | A1 | 10/2012 | Sal et al. | |
| 2017/0240525 | A1 * | 8/2017 | Vu ....................... | C07D 401/14 |
| 2019/0002460 | A1 | 1/2019 | Whitehead et al. | |
| 2019/0119249 | A1 | 4/2019 | Vu et al. | |
| 2021/0002252 | A1 | 1/2021 | Vu et al. | |
| 2022/0213062 | A1 | 7/2022 | Vu et al. | |
| 2022/0315564 | A1 * | 10/2022 | Vu ....................... | C07D 405/14 |
| 2023/0002403 | A1 | 1/2023 | Vu et al. | |
| 2023/0033324 | A1 * | 2/2023 | Levine ................. | A61K 31/438 |
| 2023/0044826 | A1 * | 2/2023 | Dumble .................. | A61P 35/00 |
| 2023/0049952 | A1 * | 2/2023 | Levine .................... | A61P 35/00 |
| 2023/0312539 | A1 | 10/2023 | Vu et al. | |
| 2024/0043436 | A1 | 2/2024 | Vu et al. | |
| 2024/0269126 | A1 | 8/2024 | Levine et al. | |

FOREIGN PATENT DOCUMENTS

| | | | |
|---|---|---|---|
| CA | 3084777 | A1 | 7/2019 |
| CN | 104119332 | A | 10/2014 |
| CN | 104672241 | | 6/2015 |
| WO | WO-0032175 | A2 | 6/2000 |
| WO | WO-03032911 | A3 | 7/2003 |
| WO | WO-2006136823 | A1 | 12/2006 |
| WO | WO-2009136175 | A1 | 11/2009 |
| WO | WO-2012135149 | A2 | 10/2012 |
| WO | WO-2012175962 | A1 | 12/2012 |
| WO | WO-2013036208 | A1 | 3/2013 |

(Continued)

OTHER PUBLICATIONS

Patani et al. "Bioisosterism: A Rational Approach in Drug Design" Chemical Reviews, 1996, vol. 96, pp. 3147-3176.*

Ansel, Howard C, et al. Pharmaceutical Dosage Forms and Drug Delivery Systems. Philadelphia, PA: Lippincott-Williams & Wilkins, 1999. Print.

Bilbao, et al., Two-Dimensional Nanoporous Networks Formed by Liquid-to-Solid Transfer of Hydrogen-Bonded Macrocycles Built from DNA Bases, 2015.

Coburn et al., (Caplus abstract of WO2010111483 (Sep. 30, 2010)).

Dell'Acqua, et al., MediaChrom: Discovering a Class of Pyrimidoindolone-Based Polarity-Sensitive Dyes, 2015, Journal of Organic Chemistry, vol. 80 (21, pp. 10939-10954.

English Translation of JP Application No. 2018-544186 Office Action mailed Jan. 27, 2021.

(Continued)

*Primary Examiner* — Adam C Milligan
*Assistant Examiner* — Jed A Kucharczk
(74) *Attorney, Agent, or Firm* — WILSON SONSINI GOODRICH & ROSATI

(57) ABSTRACT

Mutations in oncogenes and tumor suppressors contribute to the development and progression of cancer. Disclosed herein are compounds and methods to recover wild-type function of p53 mutants using x-ray co-crystal structures of mutant p53 and compounds of the disclosure. The compounds of the present invention can bind to mutant p53 and restore the ability of the p53 mutant to bind DNA and activate downstream effectors involved in tumor suppression. The disclosed compounds can be used to reduce the progression of cancers that contain a p53 mutation.

8 Claims, 27 Drawing Sheets

Specification includes a Sequence Listing.

(56) References Cited

FOREIGN PATENT DOCUMENTS

| | | | |
|---|---|---|---|
| WO | WO-2015178955 | A1 | 11/2015 |
| WO | WO-2016004513 | A1 | 1/2016 |
| WO | WO-2017143291 | A1 | 8/2017 |
| WO | WO-2018075937 | A1 | 4/2018 |
| WO | WO-2018191587 | A1 | 10/2018 |
| WO | WO-2022213975 | A1 | 10/2022 |

OTHER PUBLICATIONS

English Translation of Second Office Action issued in Chinese Application No. 2017800134506 on Apr. 13, 2021.
European Application No. 17753995.4 Office Action dated Jan. 13, 2021.
European Serial No. 17753995.4 Extended Search Report dated Jun. 17, 2019.
Fiandanese, et al., A straightforward synthesis of indole and benzofuran derivatives, 2007, Tetrahedron, Elsevier Science Publishers, vol. 64 (1), pp. 53-60.
Gangjee, et al., Synthesis and Biological Activity of N4-phenylsubstituted-6-(2,4-dichloro phenylmethyl)-7H-pyrrolo[2,3-d]pyrimidine-2,4-diamines as Vascular Endothelial Growth Factor Receptor-2 Inhibitors and Antiangiogenic and Antitumor Agents, 2010, Bioorg Med Chem, vol. 18(10), pp. 1-33.
Gennaro, A.R., Remington: The science and practice of pharmacy. 19th edition. 1995. 12 Pages.
Gergely, et al., C2-Selective Direct Alkynylation of Indoles, 2012, Organic Letters, vol. 15(1), pp. 112-115.
Guo, et al., PIM inhibitors target CD25-positive AML cells through concomitant suppression of STAT5 activation and degradation of MYC oncogene, 2014, Blood, vol. 124 (11), pp. 1777-1789.
Hoover, J. et al., Remington's Pharmaceutical science. 1970.
International Search Report and written opinion dated Jun. 21, 2017 for International Application No. PCT/US2017/018511.
Joerger, et al., Structure-function-rescue: the diverse nature of common p53 cancer mutants. Oncogene (2007) 26, 2226-2242.
Kubinyi. 3D QSAR in Drug Design: Ligand-Protein Interactions and Molecular Similarity. (vol. 2-3, Springer, 1998, 800 pages). pp. 243-244 provided.
Leblanc, et al., Homogeneous time-resolved fluorescence assay for identifying p53 interactions with its protein partners, directly in a cellular extract. Analytical Biochemistry 308 (2002) 247-254.
Liberman, H.A., Pharmaceutical Dosage Forms: Parenteral Medications. 1992. vol. 1. 4 pages.
Liu, et al., Small molecule induced reactivation of mutant p53 in cancer cells. Nucleic Acids Research, 2013, vol. 41, No. 12. 6034-6044.
Notice of Allowance issued in Israeli Patent Application No. 261175 issued Jun. 30, 2021.
Notice of Allowance issued in Japanese Patent Application No. 2018-544186 on Sep. 3, 2021.
Notice of Allowance issued in Mexican Patent Application No. MX/a/2018/009947 on Apr. 15, 2021.
Office Action issued in Brazilian Application No. BR112018016890-4 on Aug. 11, 2021.
Patent Certificate 371916 issued in Indian Application No. 201817032237 on Jul. 14, 2021.
Ribeiro, et al., Chemical Variations on the p53 reactivation theme. Pharmaceuticals, May 2016; 9(25):1-33.
Selivanova, et al., Reactivation of mutant p53: molecular mechanisms and therapeutic potential, Oncogene, Apr. 2, 2007; vol. 26: p. 2243-2254.
Shinohara, et al., Design of environmentally sensitive fluorescent 2-deoxyguanosine containing aryl ethynyl moieties: Distinction of thymine base by base-discriminating fluorescent (BDF) probe, 2010, Bioorganic & Medicinal Chemistry Letters, vol. 20, pp. 2817-2820.
U.S. Appl. No. 15/436,333 Notice of Allowance dated Aug. 27, 2018.
U.S. Appl. No. 15/436,333 Notice of Allowance dated Jul. 23, 2018.
U.S. Appl. No. 16/163,829 Notice of Allowance dated Dec. 20, 2019.
U.S. Appl. No. 16/163,829 Non-Final Office Action issued May 2, 2019.
U.S. Appl. No. 16/819,934 Non-Final Office Action issued May 25, 2021.
U.S. Appl. No. 15/436,333 Office Action dated Dec. 7, 2017.
Wermuth. The Practice of Medicinal Chemistry, 2d ed. 768 pages, chapters 9-10 provided (2003).
Wilcken, et al., Halogen-Enriched Fragment Libraries as Leads for Drug Rescue of Mutant p53.Journal of the American chemical society. 2012; 134:6810-6818.
Co-pending U.S. Appl. No. 18/330,978, inventors Vu; Binh et al., filed Jun. 7, 2023.
International Search Report and written opinion dated Dec. 22, 2020 for International Application No. PCT/US2020/051998.
Boeckler, F.M. et al., Targeted rescue of a destabilized mutant of p53 by an in silico screened drug, PNAS, vol. 105, 30 (2008):10360-10365.
Patani et al., Bioisosterism: A Rational Approach in Drug Design, Chemical Reviews. American Chemical Society, vol. 96, (1996):3147-3176.
Co-pending U.S. Appl. No. 18/421,550, inventors Arnold; Levine et al., filed Jan. 24, 2024.
Bauer, et al., Harnessing Fluorine-Sulfur Contacts and Multipolar Interactions for the Design of p53 Mutant Y220C Rescue Drugs, ACS Chem. Biol., 11:2265-2274, (2016).
Boeckler, et al., Targeted Rescue of a Destabilized Mutant of p53 by an In Silico Screened Drug, PNAS, 105:10360-10365, (2008).
Bohm, et al., Fluorine in Medicinal Chemistry. Chembiochem., 5:637-643, (2004).
Gillis, et al., Applications of Fluorine in Medicinal Chemistry, J. Med. Chem., 58:8315-8359, (2015).
Joerger, et al., Crystal Structure of a Superstable Mutant of Human p53 Core Domain. Insights into the Mechanism of Rescuing Oncogenic Mutations, J. Biol. Chem., 279:1291-1296, (2004).
Joerger, et al., Structural Basis for Understanding Oncogenic p53 Mutations and Designing Rescue Drugs, PNAS, 103:15056-15061, (2006).
Nairoukh, et al., Understanding the Conformational Behavior of Fluorinated Piperidines: The Origin of the Axial-F Preference, Chem. Eur. J., 26:6141-6146, (2020).
Welsch, et al., Privileged Scaffolds for Library Design and Drug Discovery, Curr. Opin. Chem. Biol., 14:347-361, (2010).
Wilcken, et al., Halogen-Enriched Fragment Libraries as Leads for Drug Rescue of Mutant p53, J. Am. Chem. Soc., 134:6810-6818, (2012).
Co-pending U.S. Appl. No. 19/209,328, inventors Vu; Binh et al., filed May 15, 2025.

* cited by examiner

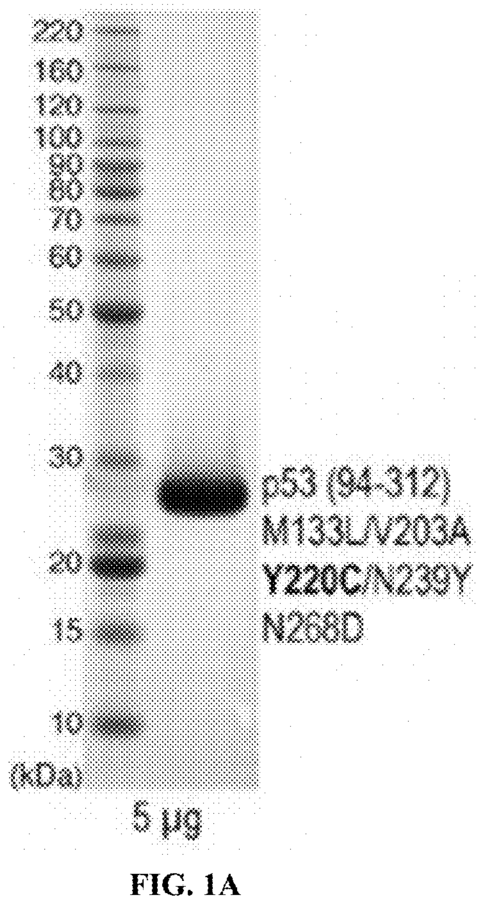
FIG. 1A
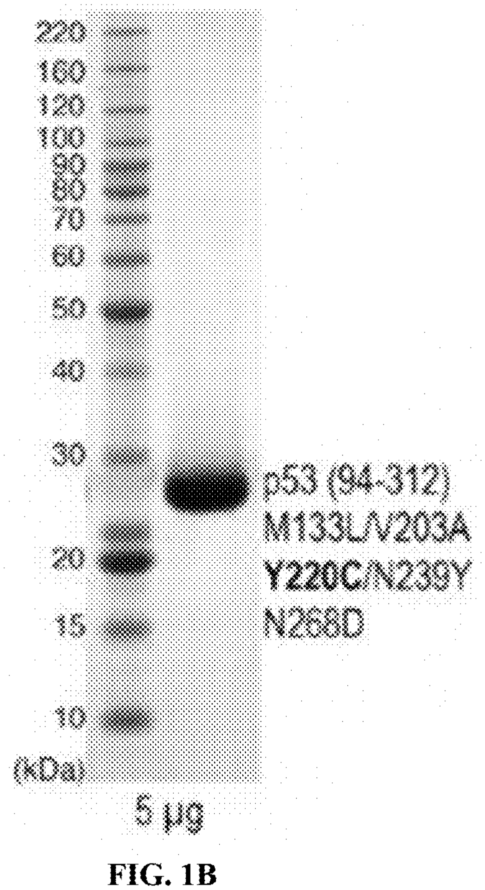
FIG. 1B
FIG. 1

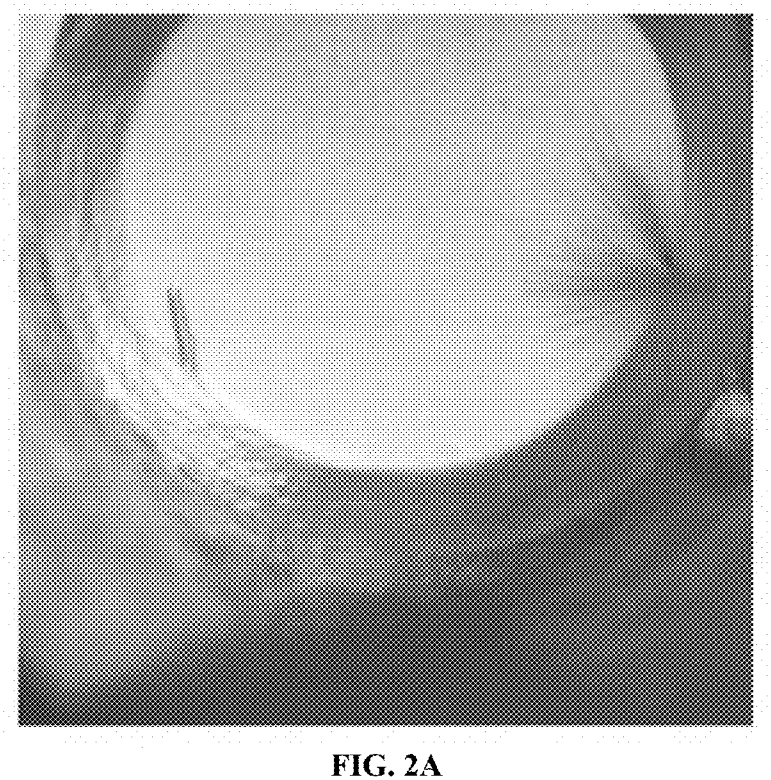
FIG. 2A
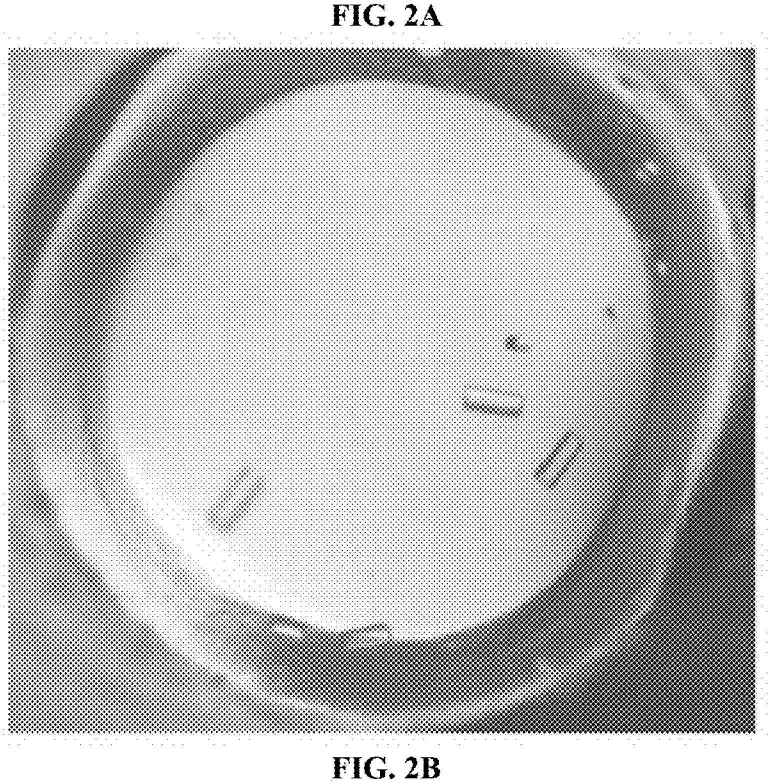
FIG. 2B
FIG. 2

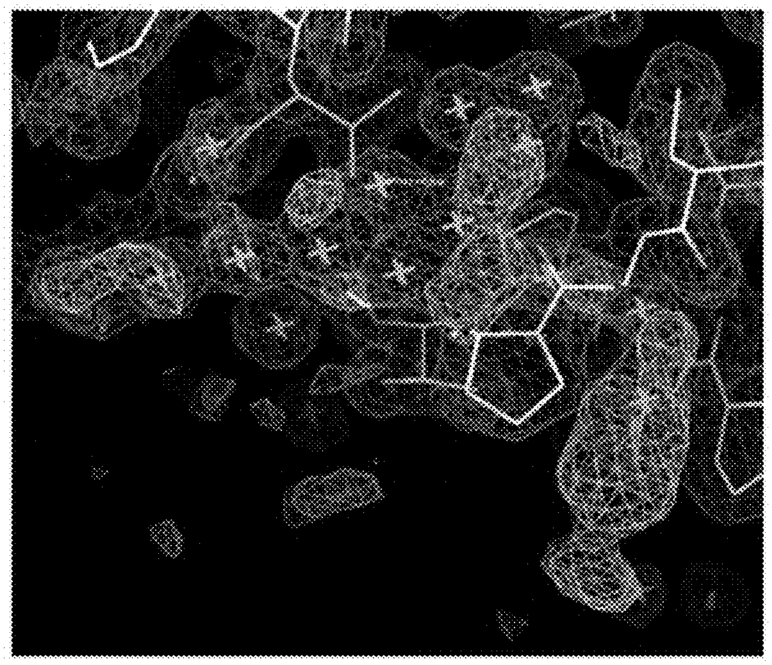
FIG. 3A
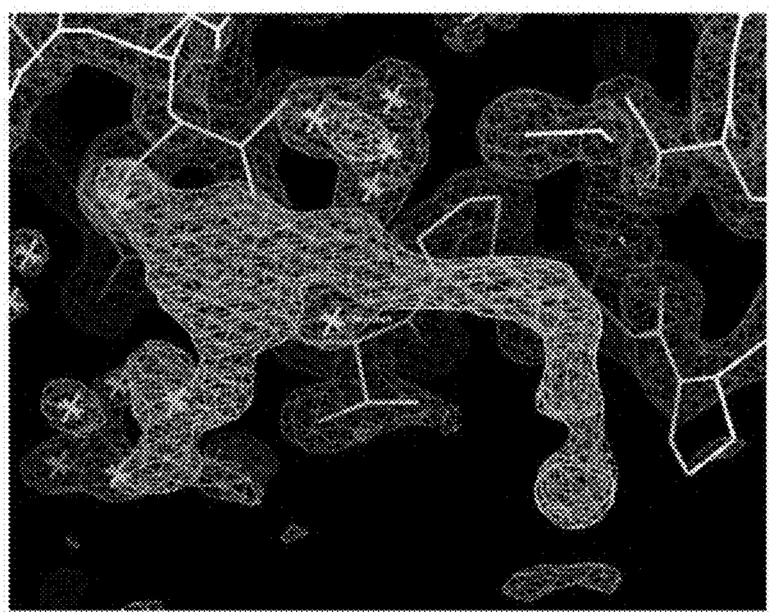
FIG. 3B
FIG. 3

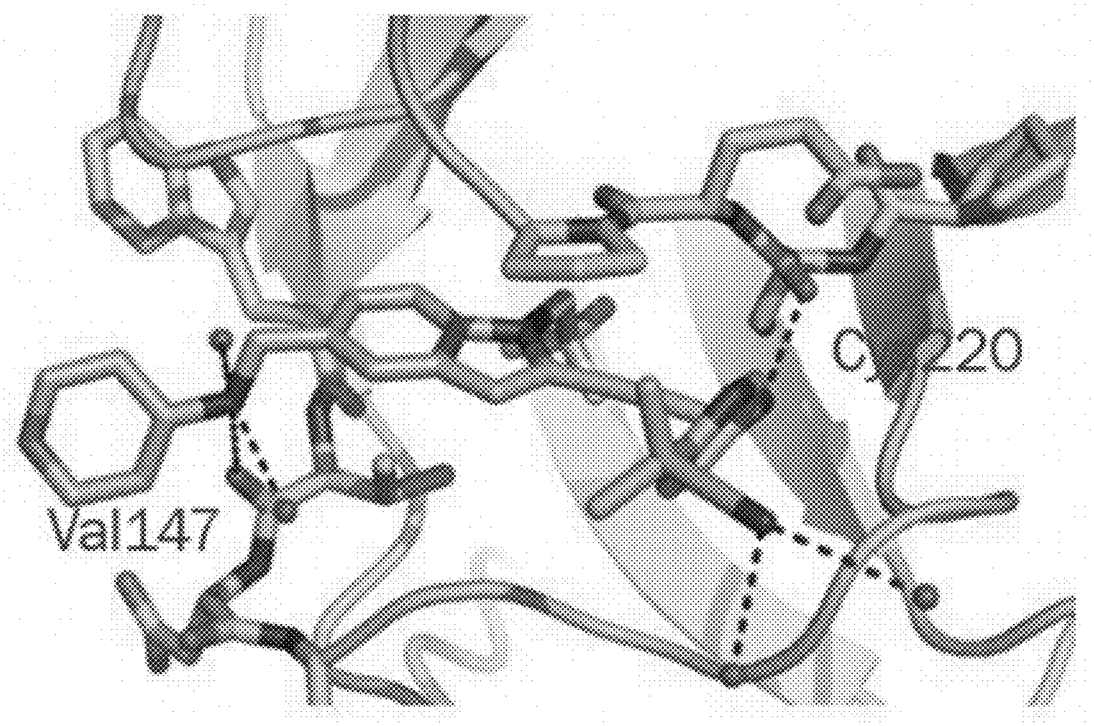
FIG. 6A
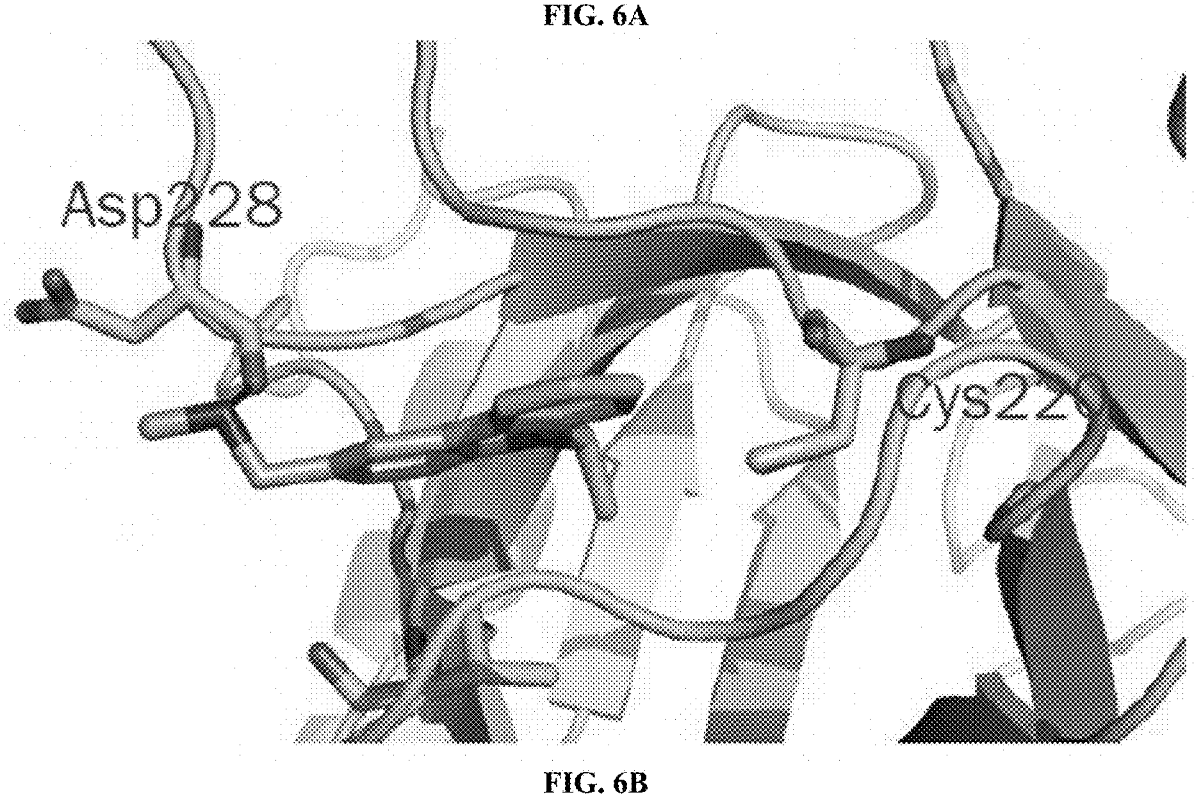
FIG. 6B
FIG. 6

FIG. 7A
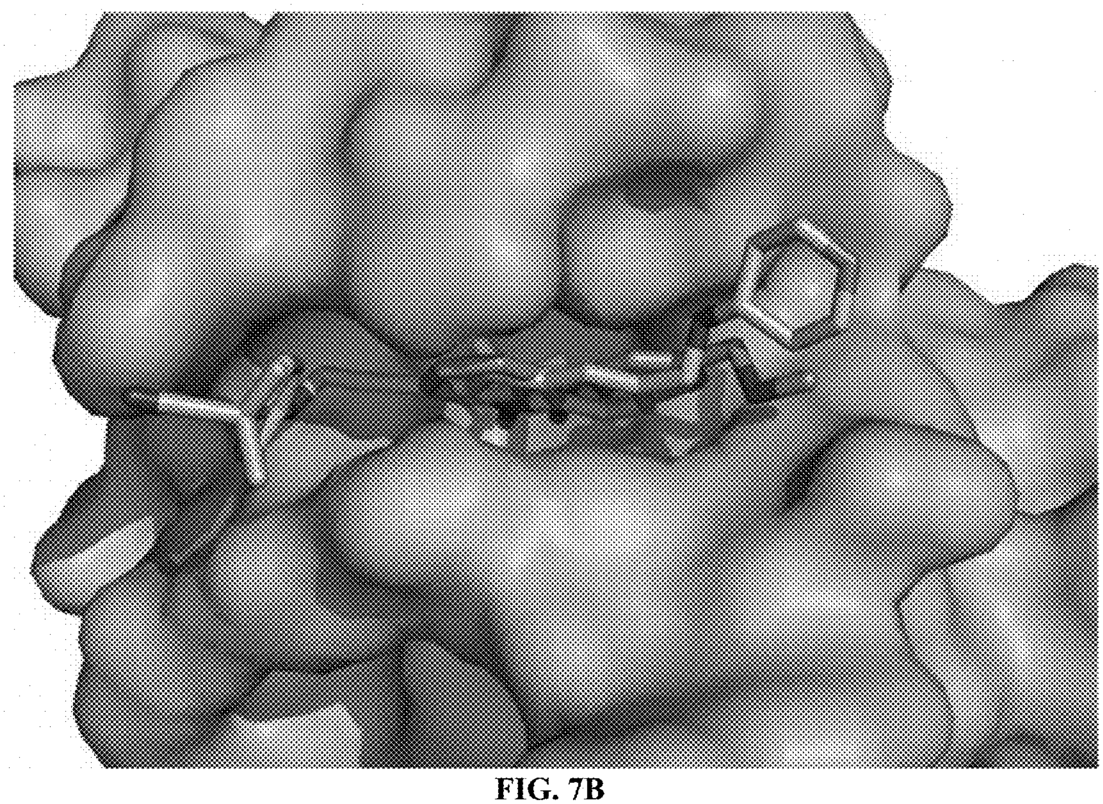
FIG. 7B
FIG. 7

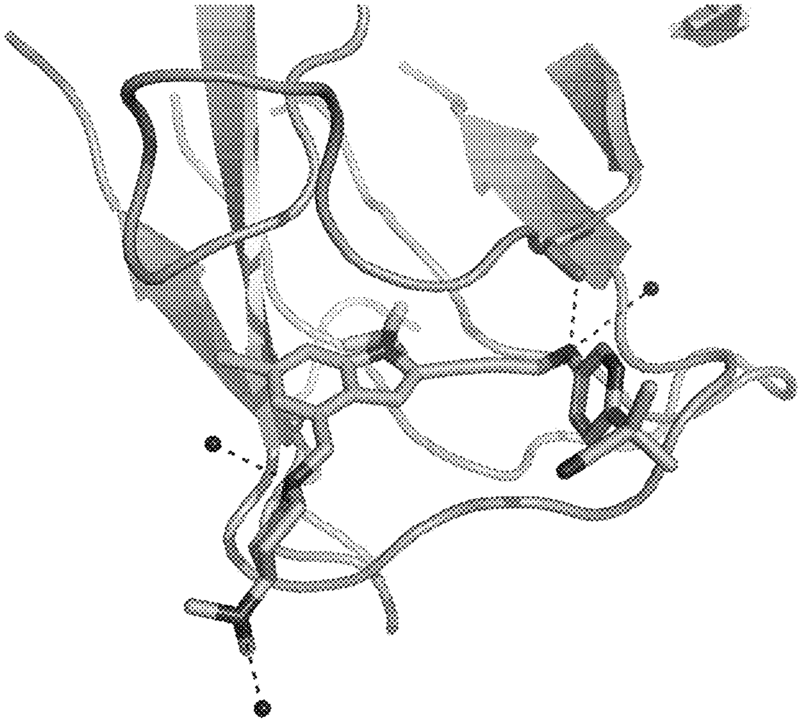
FIG. 9A
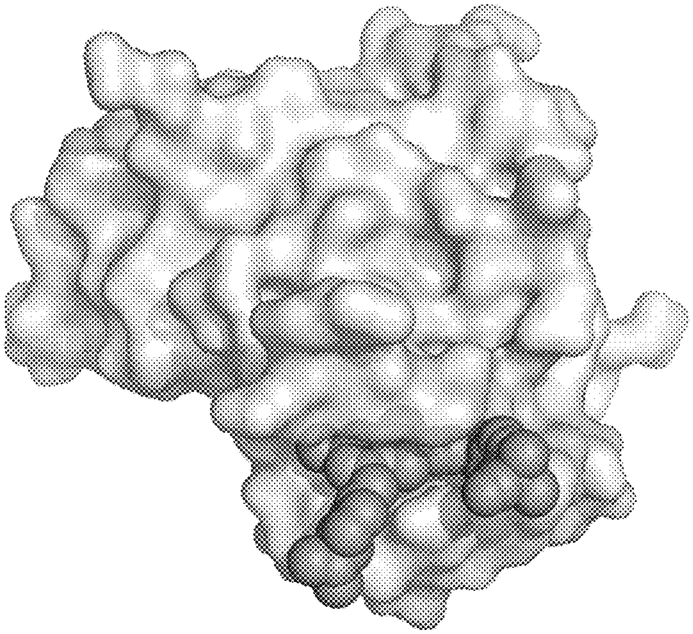
FIG. 9B
FIG. 9

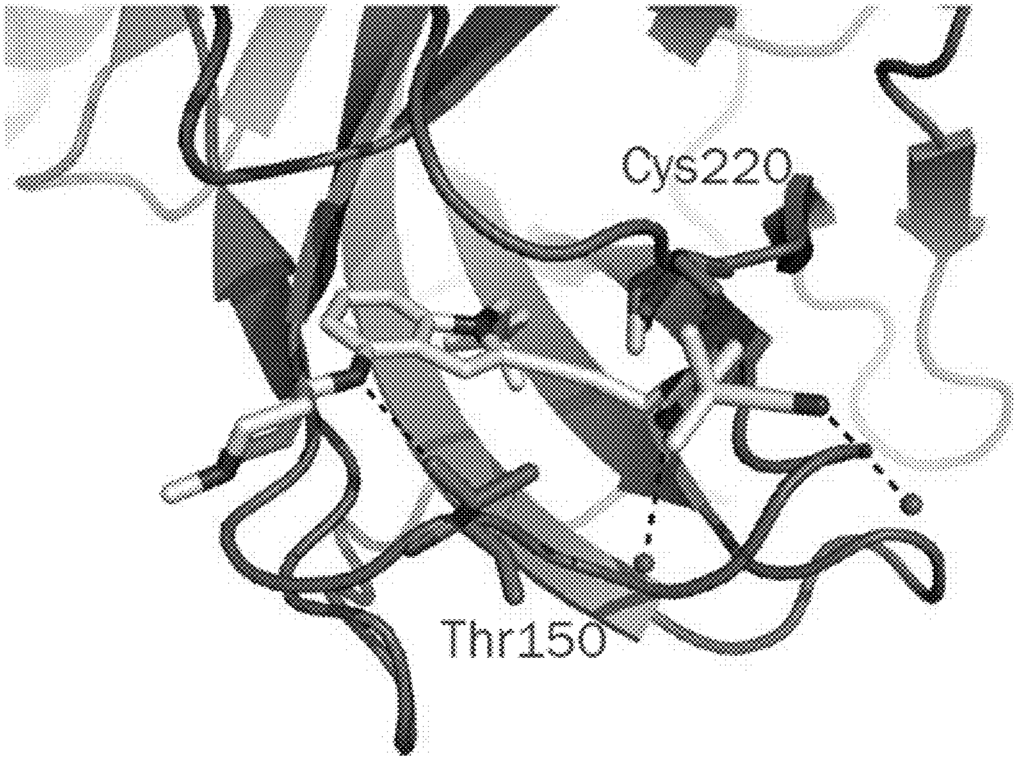
FIG. 14A
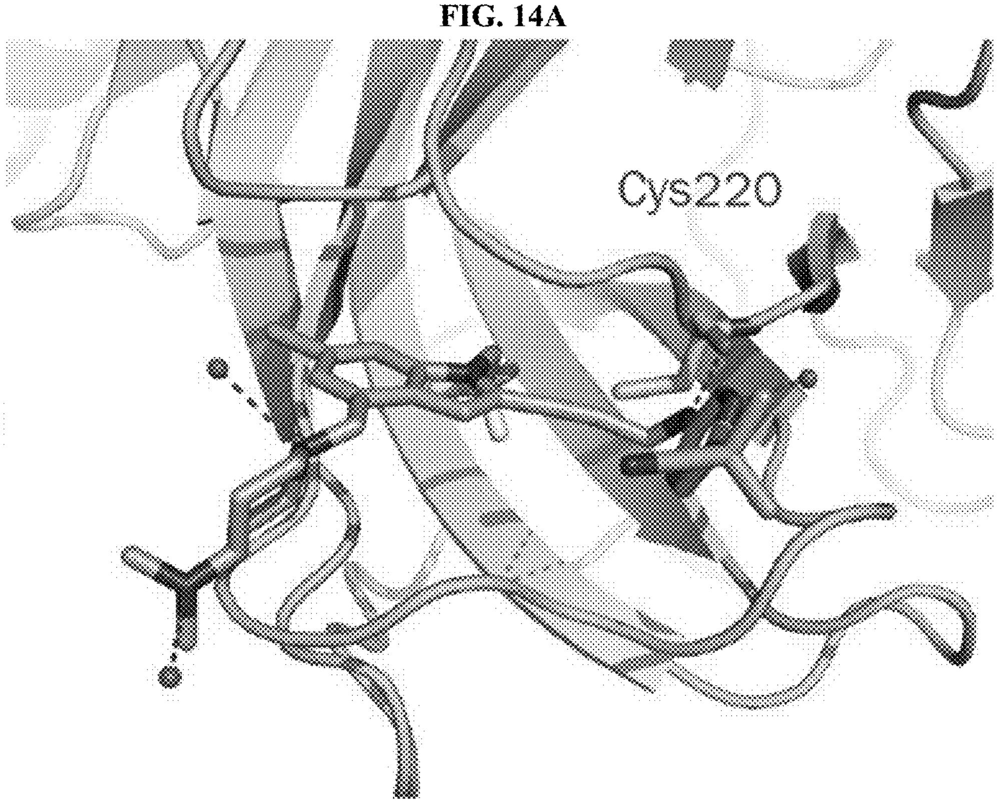
FIG. 14B
FIG. 14

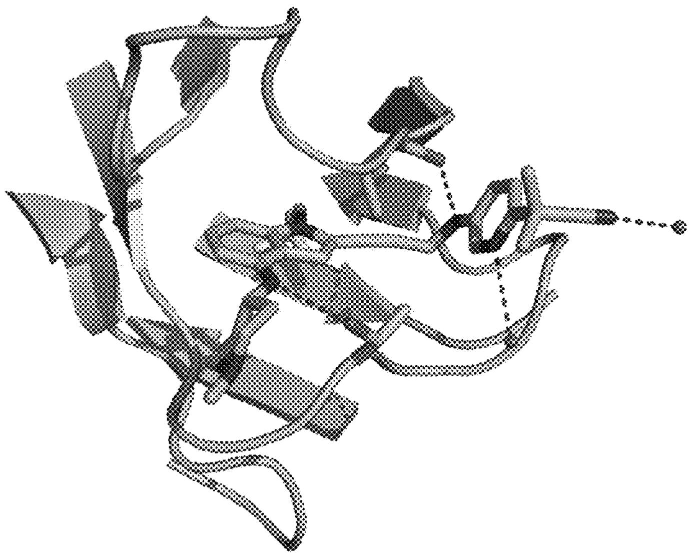
FIG. 15A
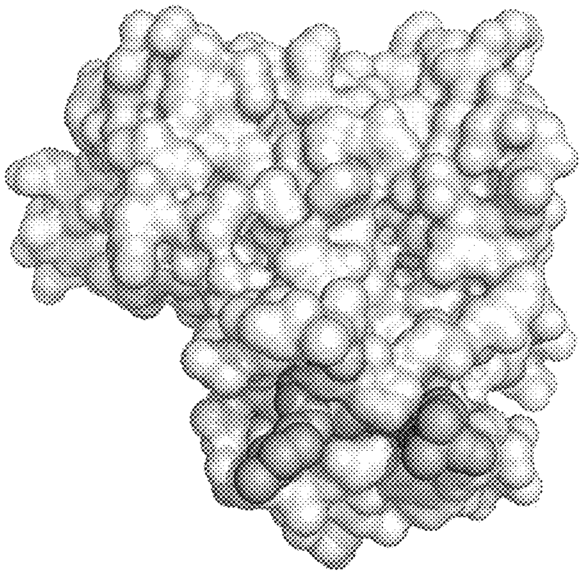
FIG. 15B
FIG. 15

FIG. 17A
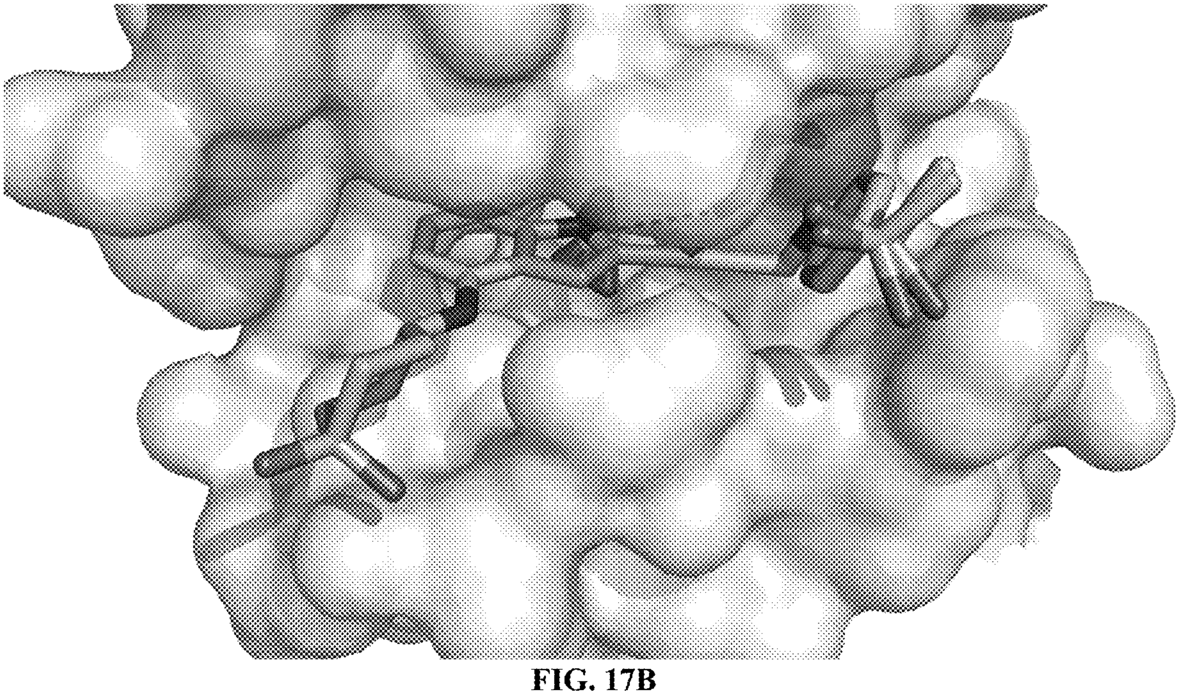
FIG. 17B
FIG. 17

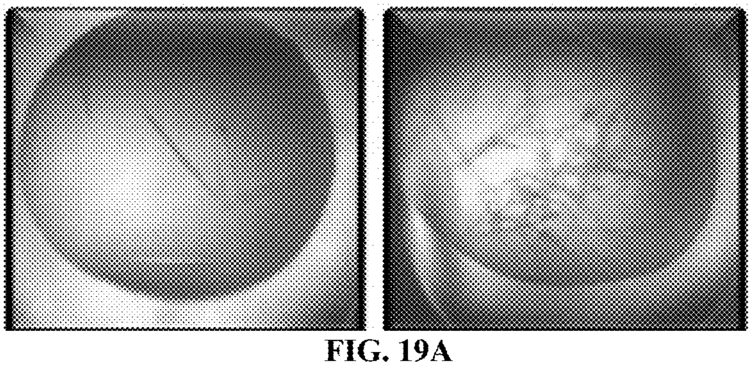
FIG. 19A
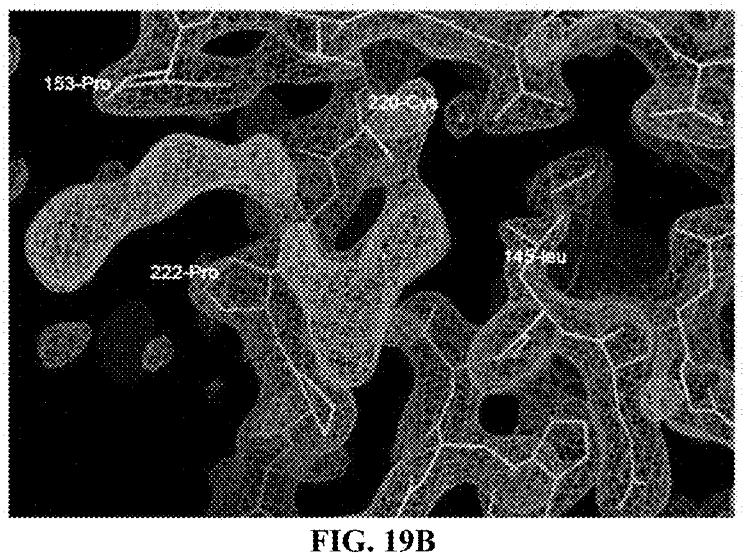
FIG. 19B
FIG. 19

Compound 6

Compound 7

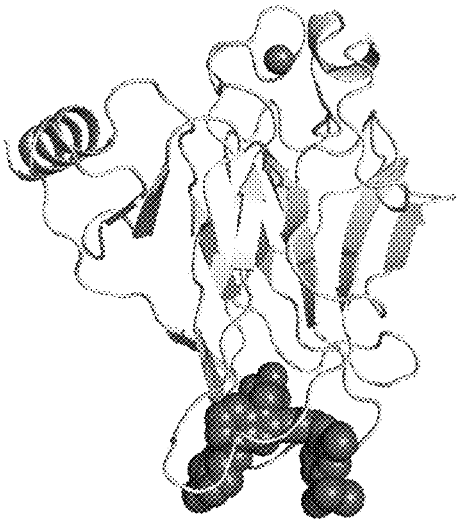
FIG. 26A
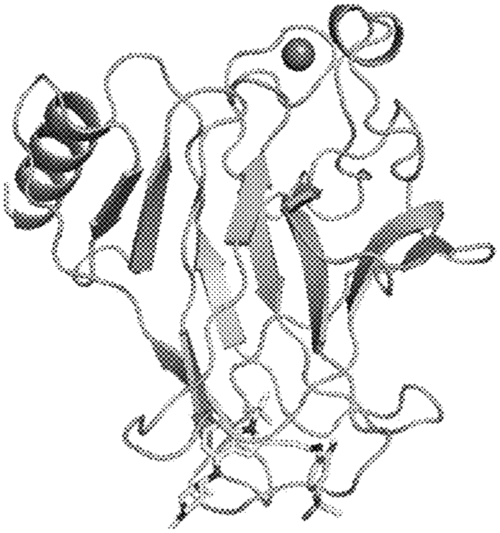
FIG. 26B
FIG. 26A-26B

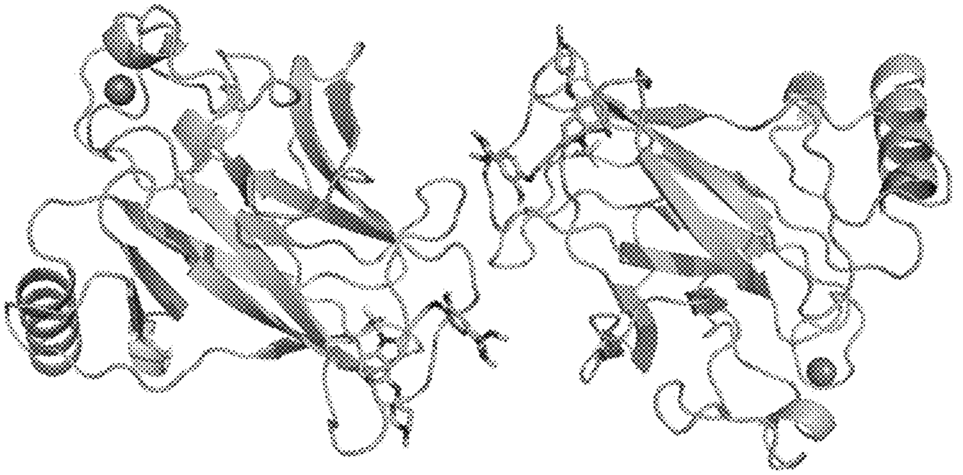
FIG. 27A
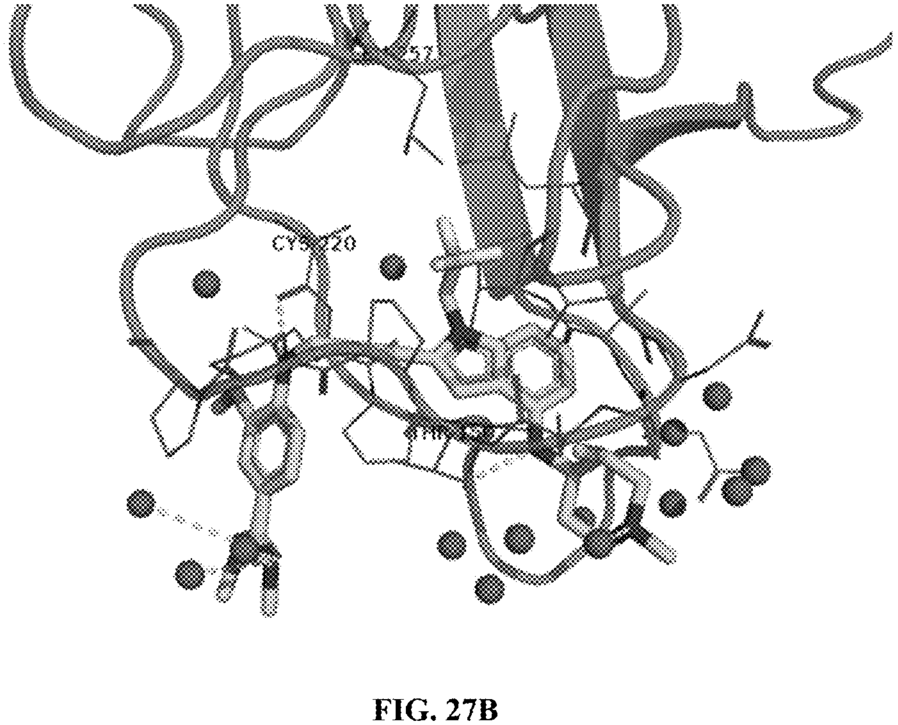
FIG. 27B
FIG. 27

USES OF p53 X-RAY CO-CRYSTAL STRUCTURES

CROSS-REFERENCE

This application claims the benefit of U.S. Provisional Application No. 63/042,334, filed Jun. 22, 2020; and U.S. Provisional Application No. 63/162,693, filed Mar. 18, 2021, which are incorporated herein by reference.

The instant application contains a Sequence Listing, which has been submitted electronically in ASCII format and is hereby incorporated by reference in its entirety. The ASCII copy, created on Jul. 28, 2021, is named 44727-709.201_SL.txt and is 4,096 bytes in size.

BACKGROUND

Cancer, an uncontrolled proliferation of cells, is a multifactorial disease characterized by tumor formation, growth, and in some instances, metastasis. Cells carrying an activated oncogene, damaged genome, or other cancer-promoting alterations can be prevented from replicating through an elaborate tumor suppression network. A central component of this tumor suppression network is p53, one of the most potent tumor suppressors in the cell. Both the wild type and mutant conformations of p53 are implicated in the progression of cancer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

Disclosed herein is a compound comprising a molecular structure that binds to a mutant p53 protein, wherein the mutant p53 protein has a mutant conformation, and the molecular structure modulates the mutant conformation of the mutant p53 protein into a conformation of p53 that possesses anti-cancer activity, wherein the molecular structure that binds to the mutant p53 protein comprises a hydrogen bond donor and an electron-withdrawing heteroatom, wherein the hydrogen bond donor is proximal to the electron-withdrawing heteroatom, wherein if a co-crystal is obtained of the compound and the mutant p53 protein with the compound bound to a binding site on the mutant p53 protein, and the co-crystal is obtained by sitting-drop vapor distillation, and if an x-ray co-crystal structure of the co-crystal is obtained by crystal soaking, and if the x-ray co-crystal structure has a resolution of about 2 Å, then in the x-ray co-crystal structure, the hydrogen bond donor forms a hydrogen bond with Thr-150 of the mutant p53 protein.

Disclosed herein is a compound comprising a molecular structure that binds to a mutant p53 protein, wherein the mutant p53 protein has a mutant conformation, and the molecular structure modulates the mutant conformation of the mutant p53 protein into a conformation that possesses a pro-apoptotic activity of a wild type p53 protein, wherein the mutant p53 protein is a Y220C mutant, wherein the molecular structure that binds to the mutant p53 protein comprises a tertiary ammonium cation and a fluorine atom, wherein the tertiary ammonium cation and the fluorine atom are substituents on a common ring, the tertiary ammonium cation and the fluorine atom are oriented syn to one another on the common ring, and the tertiary ammonium cation and the fluorine atom are disposed vicinally to one another on the common ring, wherein if a co-crystal is obtained of the compound and the mutant p53 protein with the compound bound to a binding site on the mutant p53 protein, and the co-crystal is obtained by sitting-drop vapor distillation, and if an x-ray co-crystal structure of the co-crystal is obtained by crystal soaking, and if the x-ray co-crystal structure has a resolution of about 2 Å, then in the x-ray co-crystal structure the tertiary ammonium cation forms a hydrogen bond with a side chain oxygen atom of Thr-150 of the mutant p53 protein, wherein the hydrogen bond has a mean length of from about 1.5 Å to about 3 Å, wherein the fluorine atom is bound to a stereocenter of the compound, wherein the stereocenter has a handedness, wherein the hydrogen bond is stronger than is an analogous hydrogen bond formed by a diastereomer of the compound, wherein the diastereomer of the compound differs from the compound only in the handedness of the stereocenter.

Disclosed herein is a method of treating a cancer associated with a mutant p53 protein, the method comprising administering to a subject in need thereof a therapeutically-effective amount of an organic molecule, wherein the organic molecule binds to a binding site on the mutant p53 protein and forms a hydrogen bond to a Thr-150 residue of the mutant p53 protein, wherein the organic molecule comprises a hydrogen bond donor and an electron-withdrawing heteroatom, wherein the hydrogen bond donor participates in the hydrogen bond, wherein the hydrogen bond donor is proximal to the electron-withdrawing heteroatom.

Disclosed herein is a method of treating a cancer associated with a mutant p53 protein, the method comprising administering to a subject in need thereof a therapeutically-effective amount of an organic molecule, wherein the organic molecule binds to a binding site on the mutant p53 protein, wherein the cancer is breast cancer, wherein the administering is oral, wherein the therapeutically-effective amount is from about 50 mg to about 500 mg, wherein the mutant p53 protein is a Y220C mutant, wherein the organic molecule comprises a tertiary ammonium cation and a fluorine atom, wherein the tertiary ammonium cation and the fluorine atom are substituents on a common ring, the tertiary ammonium cation and the fluorine atom are oriented syn to one another on the common ring, and the tertiary ammonium cation and the fluorine atom are disposed vicinally to one another on the common ring, wherein the mutant p53 protein has a conformation that is not pro-apoptotic, and the contacting to the mutant p53 protein the organic molecule that binds to the binding site on the mutant p53 protein modulates the conformation of the mutant p53 protein to a form that is pro-apoptotic, wherein if a co-crystal is obtained of the organic molecule and the mutant p53 protein with the organic molecule bound to the binding site on the mutant p53 protein, and the co-crystal is obtained by sitting-drop vapor distillation, and if an x-ray co-crystal structure of the co-crystal is obtained by crystal soaking, and if the x-ray co-crystal structure has a resolution of about 2 Å, then in the x-ray co-crystal structure the tertiary ammonium cation forms a hydrogen bond with a side chain oxygen atom of Thr-150 of the mutant p53 protein, wherein the hydrogen bond has a mean length of from about 1.5 Å to about 3 Å, wherein the fluorine atom is bound to a stereocenter of the organic molecule, wherein the stereocenter has a handedness, wherein the hydrogen bond is stronger than is an analogous hydrogen bond formed by a diastereomer of the organic molecule, wherein the diastereomer of the organic molecule differs from the organic molecule only in the handedness of the stereocenter.

Disclosed herein is a method comprising contacting to a mutant p53 protein an organic molecule that binds to a binding site on the mutant p53 protein and forms a hydrogen bond to a Thr-150 residue of the mutant p53 protein, wherein the mutant p53 protein has a conformation that is not pro-apoptotic, and the contacting to the mutant p53 protein the organic molecule that binds to the binding site on the mutant p53 protein and forms the hydrogen bond to the Thr-150 residue of the mutant p53 protein modulates the conformation of the mutant p53 protein to a form that is pro-apoptotic, wherein the organic molecule comprises a hydrogen bond donor and an electron-withdrawing heteroatom, wherein the hydrogen bond donor participates in the hydrogen bond, wherein the hydrogen bond donor is proximal to the electron-withdrawing heteroatom.

Disclosed herein is a method comprising contacting to a mutant p53 protein an organic molecule that binds to a binding site on the mutant p53 protein and forms a hydrogen bond to a side chain oxygen atom of a Thr-150 residue of the mutant p53 protein, wherein the mutant p53 protein is a Y220C mutant, wherein the organic molecule comprises a tertiary ammonium cation and a fluorine atom, wherein the tertiary ammonium cation and the fluorine atom are substituents on a common ring, the tertiary ammonium cation and the fluorine atom are oriented syn to one another on the common ring, and the tertiary ammonium cation and the fluorine atom are disposed vicinally to one another on the common ring, wherein the tertiary ammonium cation participates in the hydrogen bond, wherein the mutant p53 protein has a conformation that is not pro-apoptotic, and the contacting to the mutant p53 protein the organic molecule that binds to the binding site on the mutant p53 protein and modulates the conformation of the mutant p53 protein to a form that is pro-apoptotic, wherein if a co-crystal is obtained of the organic molecule and the mutant p53 protein with the organic molecule bound to a binding site on the mutant p53 protein, and the co-crystal is obtained by sitting-drop vapor distillation, and if an x-ray co-crystal structure of the co-crystal is obtained by crystal soaking, and if the x-ray co-crystal structure has a resolution of about 2 Å, then in the x-ray co-crystal structure the tertiary ammonium cation forms the hydrogen bond with the side chain oxygen atom of Thr-150 of the mutant p53 protein, wherein the hydrogen bond has a mean length of from about 1.5 Å to about 3 Å, wherein the fluorine atom is bound to a stereocenter of the organic molecule, wherein the stereocenter has a handedness, wherein the hydrogen bond is stronger than is an analogous hydrogen bond formed by a diastereomer of the organic molecule, wherein the diastereomer of the organic molecule differs from the organic molecule only in the handedness of the stereocenter.

Disclosed herein is a composition comprising a co-crystal, wherein the co-crystal comprises a mutant p53 protein and a small molecule ligand of the mutant p53 protein, wherein the small molecule ligand is bound to a binding site on the mutant p53 protein, wherein if the co-crystal is obtained by sitting-drop vapor distillation, and if an x-ray co-crystal structure of the co-crystal is obtained by crystal soaking, and if the x-ray co-crystal structure has a resolution of about 2 Å, then the mutant p53 protein has a conformation that is at least about 60% identical to a conformation of wild type p53 as determined by root-mean-square deviation (RMSD) of atomic positions.

BRIEF DESCRIPTION OF THE DRAWINGS

FIG. 1 PANEL A shows an SDS-PAGE gel of the first batch of mutant p53 protein. FIG. 1 PANEL B shows an SDS-PAGE gel of the first batch of mutant p53 protein.

FIG. 2 PANEL A shows an image of crystals of Compound 1 obtained in a buffer of 0.04 $K_2HPO_4$, 20% (v/v) glycerol, and 16% (w/v) PEG-8000 at a resolution of ~1.7 Å. FIG. 2 PANEL B shows an image of crystals of Compound 2 obtained in a buffer of 0.2 M $MgCl_2$, 0.1 M Tris-HCl, pH 8.5, and 25% (w/v) PEG-3350 at a resolution of ~1.7 Å.

FIG. 3 PANEL A shows a ligand density image of Compound 1. FIG. 3 PANEL B shows a ligand density image of Compound 1.

FIG. 6 PANEL A shows the structure of Compound 1 and mutant p53, with 4 water molecules and two backbone carbonyl interactions. FIG. 6 PANEL B shows the structure of 2VUK, which has one backbone carbonyl interaction.

FIG. 7 PANEL A shows the binding pocket of mutant p53 near the tri-fluorogroup of Compound 1, which shows that Compound 1 sits deep in the binding pocket of mutant p53. FIG. 7 PANEL B shows a surface rendering of 2VUK.

FIG. 9 PANEL A shows the active site of mutant p53 co-crystalized with Compound 2. FIG. 9 PANEL B shows the total surface interactions of mutant p53 with Compound 2.

FIG. 14 PANEL A shows the co-crystal structure of Compound 3. FIG. 14 PANEL B shows the co-crystal structure of Compound 2, which shows interaction of Compound 2 with three water molecules and one backbone carbonyl (Cys220).

FIG. 15 PANEL A shows the active site of mutant p53 co-crystalized with Compound 3. FIG. 15 PANEL B shows a co-crystal structure of mutant p53 with Compound 3.

FIG. 17 PANEL A shows the binding pocket of mutant p53 and Compound 5. FIG. 17 PANEL B shows the total surface interactions of mutant p53 co-crystallized with Compound 5 in the binding pocket.

FIG. 19 PANEL A shows images of co-crystal structures of Compound 7. The LEFT PANEL shows a well crystallized in 0.2 M sodium potassium tartrate, and 20% PEG-3350. The RIGHT PANEL shows a well crystallized in 0.2 M sodium chloride, 0.1 M Hepes buffer, pH 7.5, and 25% (w/v) PEG-3350. FIG. 19 PANEL B shows a ligand density image of the active site with Compound 7.

FIG. 21 RIGHT PANEL shows a bottom view of a mutant p53 and Compound 7 co-crystal structure.

FIG. 22 RIGHT PANEL shows a co-crystal structure of mutant p53 with Compound 7.

FIG. 26 PANEL A and PANEL B show co-crystal structures of Compound 13.

FIG. 27 PANEL A shows the co-crystal structure of mutant p53 and Compound 14. FIG. 27 PANEL B shows the active site of mutant p53 co-crystalized with Compound 14.

DETAILED DESCRIPTION OF THE INVENTION

Figure 4:
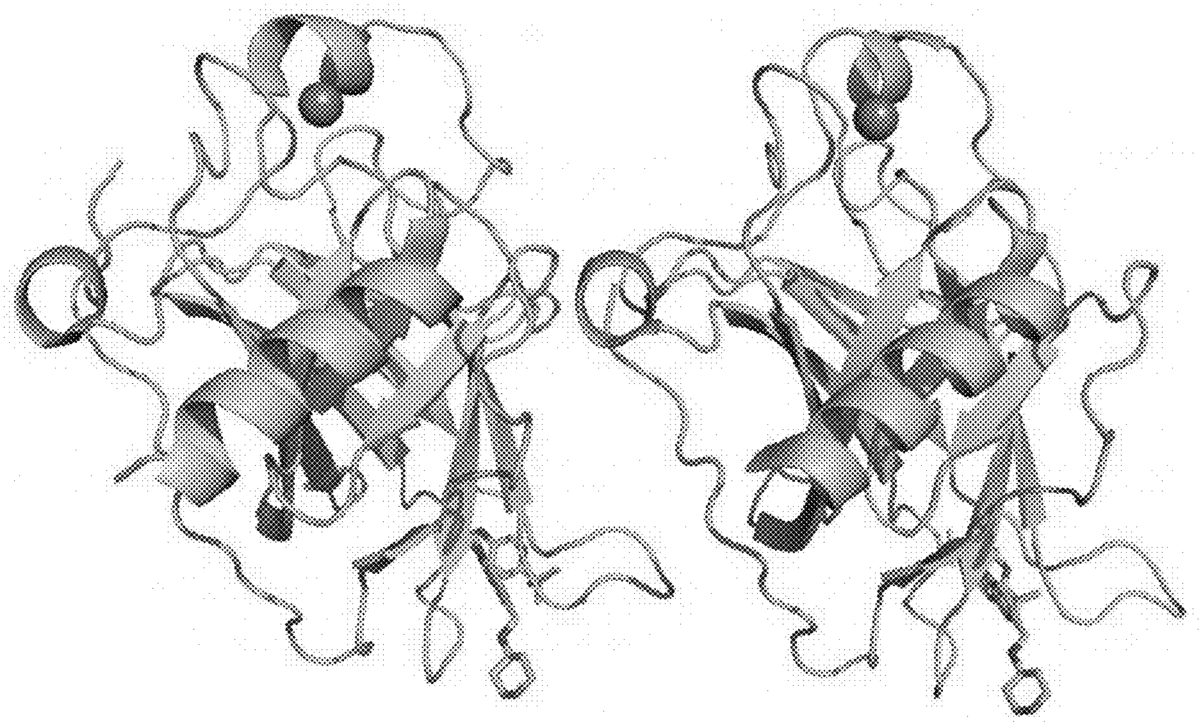
FIG. 4 shows a co-crystal structure with mutant p53 and Compound 1.

The present invention provides compounds and methods for restoring wild-type function to mutant p53. The compounds of the present invention can bind to mutant p53 and restore the ability of the p53 mutant to bind DNA. The restoration of activity of the p53 mutant can allow for the activation of downstream effectors of p53 leading to inhibition of cancer progression. The invention further provides methods of treatment of a cancerous lesion or a tumor harboring a p53 mutation.

Cancer is a collection of related diseases characterized by uncontrolled proliferation of cells with the potential to metastasize throughout the body. Cancer can be classified into five broad categories including, for example: carcinomas, which can arise from cells that cover internal and external parts of the body such as the lung, breast, and colon; sarcomas, which can arise from cells that are located in bone, cartilage, fat, connective tissue, muscle, and other supportive tissues; lymphomas, which can arise in the lymph nodes and immune system tissues; leukemia, which can arise in the bone marrow and accumulate in the bloodstream; and adenomas, which can arise in the thyroid, the pituitary gland, the adrenal gland, and other glandular tissues.

Although different cancers can develop in virtually any of the body's tissues, and contain unique features, the basic processes that cause cancer can be similar in all forms of the disease. Cancer begins when a cell breaks free from the normal restraints on cell division and begins to grow and divide out of control. Genetic mutations in the cell can preclude the ability of the cell to repair damaged DNA or initiate apoptosis, and can result in uncontrolled growth and division of cells.

The ability of tumor cell populations to multiply is determined not only by the rate of cell proliferation but also by the rate of cell attrition. Programmed cell death, or apoptosis, represents a major mechanism of cellular attrition. Cancer cells can evade apoptosis through a variety of strategies, for example, through the suppression of p53 function, thereby suppressing expression of pro-apoptotic proteins.

Oncogenes and tumor suppressor genes can regulate the proliferation of cells. Genetic mutations can affect oncogenes and tumor suppressors, potentially activating or suppressing activity abnormally, further facilitating uncontrolled cell division. Whereas oncogenes assist in cellular growth, tumor suppressor genes slow cell division by repairing damaged DNA and activating apoptosis. Cellular oncogenes that can be mutated in cancer include, for example, Cdk1, Cdk2, Cdk3, Cdk4, Cdk6, EGFR, PDGFR, VEGF, HER2, Raf kinase, K-Ras, and myc. Tumor suppressor genes that can be mutated in cancer include, for example, BRCA1, BRCA2, cyclin-dependent kinase inhibitor 1C, Retinoblastoma protein (pRb), PTEN, p16, p27, p53, and p73.

Tumor Suppressor p53.

The tumor suppressor protein p53 is a 393 amino acid transcription factor that can regulate cell growth in response to cellular stresses including, for example, UV radiation, hypoxia, oncogene activation, and DNA damage. p53 has various mechanisms for inhibiting the progression of cancer including, for example, initiation of apoptosis, maintenance of genomic stability, cell cycle arrest, induction of senescence, and inhibition of angiogenesis. Due to the critical role of p53 in tumor suppression, p53 is inactivated in almost all cancers either by direct mutation or through perturbation of associated signaling pathways involved in tumor suppression. Homozygous loss of the p53 gene occurs in almost all types of cancer, including carcinomas of the breast, colon, and lung. The presence of certain p53 mutations in several types of human cancer can correlate with less favorable patient prognosis.

In the absence of stress signals, p53 levels are maintained at low levels via the interaction of p53 with Mdm2, an E3 ubiquitin ligase. In an unstressed cell, Mdm2 can target p53 for degradation by the proteasome. Under stress conditions, the interaction between Mdm2 and p53 is disrupted, and p53 accumulates. The critical event leading to the activation of p53 is phosphorylation of the N-terminal domain of p53 by protein kinases, thereby transducing upstream stress signals. The phosphorylation of p53 leads to a conformational change, which can promote DNA binding by p53 and allow transcription of downstream effectors. The activation of p53 can induce, for example, the intrinsic apoptotic pathway, the extrinsic apoptotic pathway, cell cycle arrest, senescence, and DNA repair. p53 can activate proteins involved in the above pathways including, for example, Fas/Apol, KILLER/DR5, Bax, Puma, Noxa, Bid, caspase-3, caspase-6, caspase-7, caspase-8, caspase-9, and p21 (WAF1). Additionally, p53 can repress the transcription of a variety of genes including, for example, c-MYC, Cyclin B, VEGF, RAD51, and hTERT.

Each chain of the p53 tetramer is composed of several functional domains including the transactivation domain (amino acids 1-100), the DNA-binding domain (amino acids 101-306), and the tetramerization domain (amino acids 307-355), which are highly mobile and largely unstructured. Most p53 cancer mutations are located in the DNA-binding core domain of the protein, which contains a central β-sandwich of anti-parallel β-sheets that serves as a basic scaffold for the DNA-binding surface. The DNA-binding surface is composed of two β-turn loops, L2 and L3, which are stabilized by a zinc ion, for example, at Arg175 and Arg248, and a loop-sheet-helix motif. Altogether, these structural elements form an extended DNA-binding surface that is rich in positively-charged amino acids, and makes specific contact with various p53 response elements.

Due to the prevalence of p53 mutations in virtually every type of cancer, the reactivation of wild type p53 function in a cancerous cell can be an effective therapy. Mutations in p53 located in the DNA-binding domain of the protein or periphery of the DNA-binding surface result in aberrant protein folding required for DNA recognition and binding. Mutations in p53 can occur, for example, at amino acids Val143, His168, Arg175, Tyr220, Gly245, Arg248, Arg249, Phe270, Arg273, and Arg282. p53 mutations that can abrogate the activity of p53 include, for example, R175H, Y220C, G245S, R248Q, R248W, R273H, and R282H. These p53 mutations can either distort the structure of the DNA-binding site or thermodynamically destabilize the folded protein at body temperature. Wild-type function of p53 mutants can be recovered by binding of the p53 mutant to a compound that can shift the folding-unfolding equilibrium towards the folded state, thereby reducing the rate of unfolding and destabilization.

Non-limiting examples of amino acids include: alanine (A, Ala); arginine (R, Arg); asparagine (N, Asn); aspartic acid (D, Asp); cysteine (C, Cys); glutamic acid (E, Glu); glutamine (Q, Gin); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); and valine (V, Val).

Mechanism of Compounds of the Invention.

The compounds of the present invention can selectively bind to a p53 mutant and can recover wild-type activity of the p53 mutant including, for example, DNA binding function and activation of downstream targets involved in tumor suppression. In some embodiments, a compound of the invention selectively binds to the p53 Y220C mutant. The Y220C mutant is a temperature sensitive mutant, which binds to DNA at lower temperature and is denatured at body temperature. A compound of the invention can stabilize the Y220C mutant to reduce the likelihood of denaturation of the protein at body temperature.

Located in the periphery of the p53 β-sandwich connecting β-strands S7 and S8, the aromatic ring of Y220 is an integral part of the hydrophobic core of the β-sandwich. The Y220C mutation can be highly destabilizing, due to the formation of an internal surface cavity. A compound of the invention can bind to and occupy this surface crevice to stabilize the β-sandwich, thereby restoring wild-type p53 DNA-binding activity.

To determine the ability of a compound of the invention to bind and stabilize mutant p53, assays can be employed to detect, for example, a conformational change in the p53 mutant or activation of wild-type p53 targets. Conformational changes in p53 can be measured by, for example, differential scanning fluorimetry (DSF), isothermal titration calorimetry (ITC), nuclear magnetic resonance spectrometry (NMR), or X-ray crystallography. Additionally, antibodies specific for the wild type of mutant conformation of p53 can be used to detect a conformational change via, for example, immunoprecipitation (IP), immunofluorescence (IF), or immunoblotting.

Methods used to detect the ability of the p53 mutant to bind DNA can include, for example, DNA affinity immunoblotting, modified enzyme-linked immunosorbent assay (ELISA), electrophoretic mobility shift assay (EMSA), fluorescence resonance energy transfer (FRET), homogeneous time-resolved fluorescence (HTRF), and a chromatin immunoprecipitation (ChIP) assay.

To determine whether a compound described herein is able to reactivate the transcriptional activity of p53, the activation of downstream targets in the p53 signaling cascade can be measured. Activation of p53 effector proteins can be detected by, for example, immunohistochemistry (IHC—P), reverse transcription polymerase chain reaction (RT-PCR), and western blotting. The activation of p53 can also be measured by the induction of apoptosis via the caspase cascade and using methods including, for example, Annexin V staining, TUNEL assays, pro-caspase and caspase levels, and cytochrome c levels. Another consequence of p53 activation is senescence, which can be measured using methods such as β-galactosidase staining.

A p53 mutant that can be used to determine the effectiveness of a compound of the invention to increase the DNA binding ability of a p53 mutant is a p53 truncation mutant, which contains only amino acids 94-312, encompassing the DNA-binding domain of p53. For example, the sequence of the p53 Y220C mutant used for testing compound efficacy can be:

```
                                       (SEQ ID NO. 1)
SSSVPSQ KTYQGSYGFR LGFLHSGTAK SVTCTYSPAL

NKMFCQLAKT CPVQLWVDST PPPGTRVRAM AIYKQSQHMT

EVVRRCPHHE RCSDSDGLAP PQHLIRVEGN LRVEYLDDRN

TFRHSVVVPC EPPEVGSDCT TIHYNYMCNS SCMGGMNRRP

ILTIITLEDS SGNLLGRNSF EVHVCACPGR DRRTEEENLR

KKGEPHHELP PGSTKRALSN NT
```

A compound of the invention can increase the ability of a p53 mutant to bind DNA by at least or up to about 0.1%, at least or up to about 0.2%, at least or up to about 0.3%, at least or up to about 0.4%, at least or up to about 0.5%, at least or up to about 0.6%, at least or up to about 0.7%, at least or up to about 0.8%, at least or up to about 0.9%, at least or up to about 1%, at least or up to about 2%, at least or up to about 3%, at least or up to about 4%, at least or up to about 5%, at least or up to about 6%, at least or up to about 7%, at least or up to about 8%, at least or up to about 9%, at least or up to about 10%, at least or up to about 11%, at least or up to about 12%, at least or up to about 13%, at least or up to about 14%, at least or up to about 15%, at least or up to about 16%, at least or up to about 17%, at least or up to about 18%, at least or up to about 19%, at least or up to about 20%, at least or up to about 21%, at least or up to about 22%, at least or up to about 23%, at least or up to about 24%, at least or up to about 25%, at least or up to about 26%, at least or up to about 27%, at least or up to about 28%, at least or up to about 29%, at least or up to about 30%, at least or up to about 31%, at least or up to about 32%, at least or up to about 33%, at least or up to about 34%, at least or up to about 35%, at least or up to about 36%, at least or up to about 37%, at least or up to about 38%, at least or up to about 39%, at least or up to about 40%, at least or up to about 41%, at least or up to about 42%, at least or up to about 43%, at least or up to about 44%, at least or up to about 45%, at least or up to about 46%, at least or up to about 47%, at least or up to about 48%, at least or up to about 49%, at least or up to about 50%, at least or up to about 51%, at least or up to about 52%, at least or up to about 53%, at least or up to about 54%, at least or up to about 55%, at least or up to about 56%, at least or up to about 57%, at least or up to about 58%, at least or up to about 59%, at least or up to about 60%, at least or up to about 61%, at least or up to about 62%, at least or up to about 63%, at least or up to about 64%, at least or up to about 65%, at least or up to about 66%, at least or up to about 67%, at least or up to about 68%, at least or up to about 69%, at least or up to about 70%, at least or up to about 71%, at least or up to about 72%, at least or up to about 73%, at least or up to about 74%, at least or up to about 75%, at least or up to about 76%, at least or up to about 77%, at least or up to about 78%, at least or up to about 79%, at least or up to about 80%, at least or up to about 81%, at least or up to about 82%, at least or up to about 83%, at least or up to about 84%, at least or up to about 85%, at least or up to about 86%, at least or up to about 87%, at least or up to about 88%, at least or up to about 89%, at least or up to about 90%, at least or up to about 91%, at least or up to about 92%, at least or up to about 93%, at least or up to about 94%, at least or up to about 95%, at least or up to about 96%, at least or up to about 97%, at least or up to about 98%, at least or up to about 99%, at least or up to about 100%, at least or up to about 125%, at least or up to about 150%, at least or up to about 175%, at least or up to about 200%, at least or up to about 225%, or at least or up to about 250% as compared to the ability of the p53 mutant to bind DNA in the absence of a compound of the invention.

A compound described herein can increase the activity of the p53 mutant that is, for example, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 11-fold, at least or up to about 12-fold, at least or up to about 13-fold, at least or up to about 14-fold, at least or up to about 15-fold, at least or up to about 16-fold, at least or up to about 17-fold, at least or up to about 18-fold, at least or up to about 19-fold, at least or up to about 20-fold, at least or up to about 25-fold, at least or up to about 30-fold, at least or up to about 35-fold, at least or up to about 40-fold, at least or up to about 45-fold, at least or up to about 50-fold, at least or up to about 55-fold, at least or up to about 60-fold, at least or up to about 65-fold, at least or up to about 70-fold, at least or up to about 75-fold, at least or up to about 80-fold, at least or up to about 85-fold, at least or up to about 90-fold, at least or up to about 95-fold, at least or up to about 100-fold, at least or up to about 110-fold, at least or up to about 120-fold, at least or up to about 130-fold, at least or up to about 140-fold, at least or up to about 150-fold, at least or up to about 160-fold, at least or up to about 170-fold, at least or up to about 180-fold, at least or up to about 190-fold, at least or up to about 200-fold, at least or up to about 250-fold, at least or up to about 300-fold, at least or up to about 350-fold, at least or up to about 400-fold, at least or up to about 450-fold, at least or up to about 500-fold, at least or up to about 550-fold, at least or up to about 600-fold, at least or up to about 650-fold, at least or up to about 700-fold, at least or up to about 750-fold, at least or up to about 800-fold, at least or up to about 850-fold, at least or up to about 900-fold, at least or up to about 950-fold, at least or up to about 1,000-fold, at least or up to about 1,500-fold, at least or up to about 2.000-fold, at least or up to about 3,000-fold, at least or up to about 4,000-fold, at least or up to about 5.000-fold, at least or up to about 6,000-fold, at least or up to about 7,000-fold, at least or up to about 8.000-fold, at least or up to about 9,000-fold, or at least or up to about 10,000-fold greater than the activity of the p53 mutant in the absence of the compound.

A compound of the invention can be used, for example, to induce apoptosis, cell cycle arrest, or senescence in a cell. In some embodiments, the cell is a cancer cell. In some embodiments, the cell carries a mutation in p53.

Compounds of the Invention.

In some embodiments, a compound of the disclosure comprises a substituted heterocyclyl group, wherein the compound binds a mutant p53 protein and increases wild-type p53 activity of the mutant protein. In some embodiments, a compound of the disclosure comprises a heterocyclyl group comprising a halo substituent, wherein the compound binds a mutant p53 protein and increases wild-type p53 activity of the mutant protein. In some embodiments, the compound further comprises an indole group. In some embodiments, the indole group has a 1,1,1, -trifluoroethyl substituent at a 1-position of the indole group.

In some embodiments, the indole group has a propargyl substituent at a 2-position of the indole group. In some embodiments, the propargyl substituent is attached to the indole group via an sp carbon atom of the propargyl substituent. In some embodiments, the propargyl substituent is attached to a nitrogen atom of an aniline group via a methylene group of the propargyl substituent. In some embodiments, the indole group comprises an amino substituent at a 4-position of the indole group. In some embodiments, the amino substituent is attached to the heterocyclyl group. In some embodiments, the heterocyclyl group is a piperidine group. In some embodiments, the halo substituent is a fluoro group. In some embodiments, the halo substituent is a chloro group. In some embodiments, the compound has oral bioavailability that is at least about 50% greater than that of an analogous compound that lacks the halo substituent on the heterocyclyl group.

Non-limiting examples of compounds of the invention include compounds of any of the following formulae:

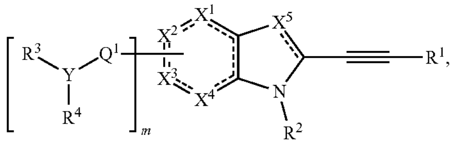

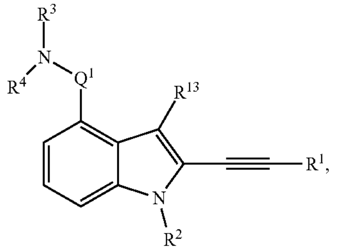

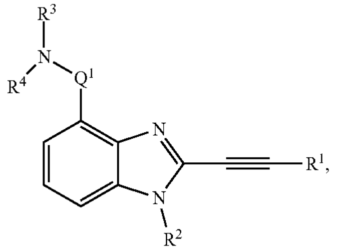

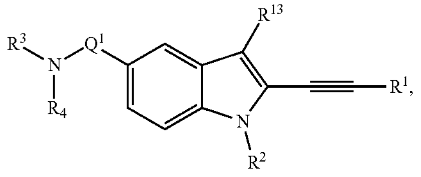

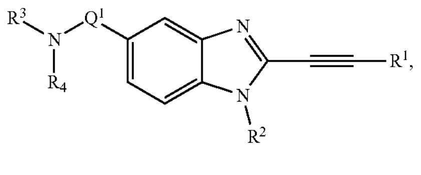

-continued
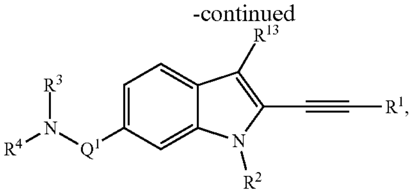
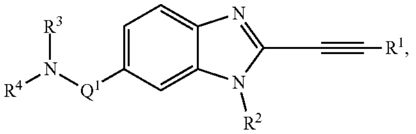
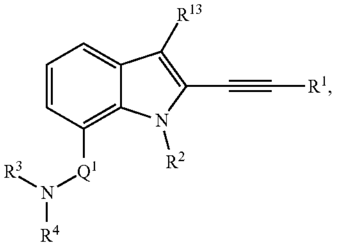
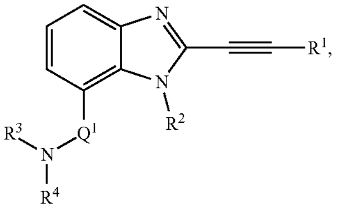
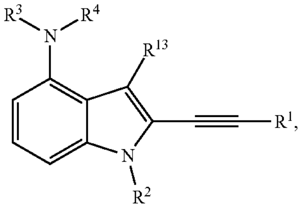
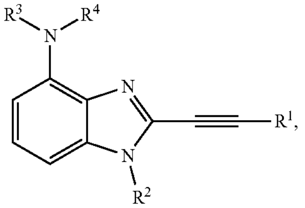
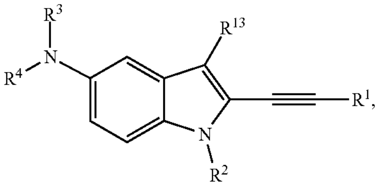
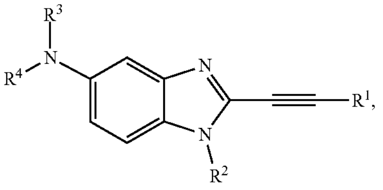
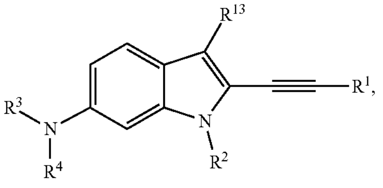
-continued
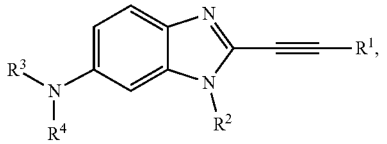
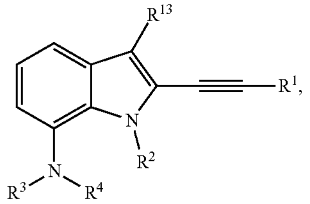
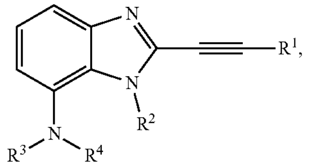
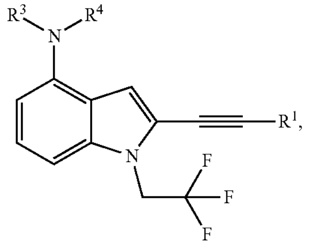
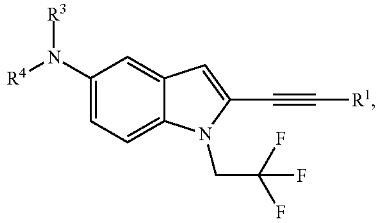
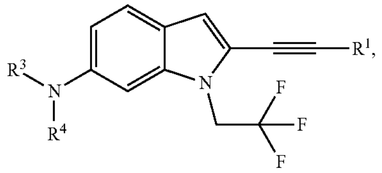
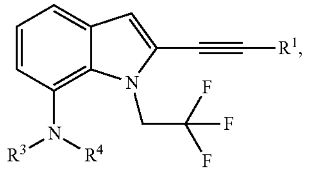
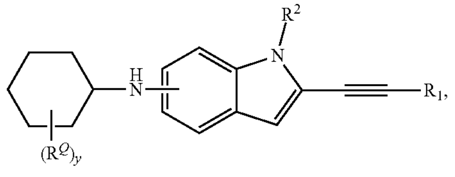

-continued
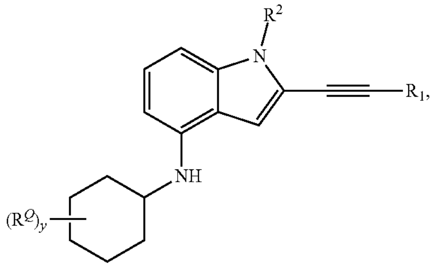
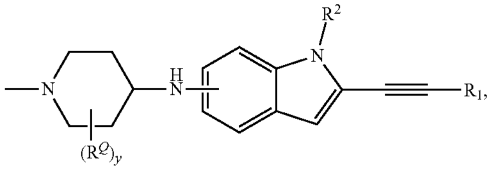
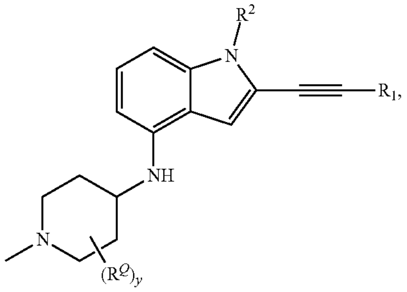
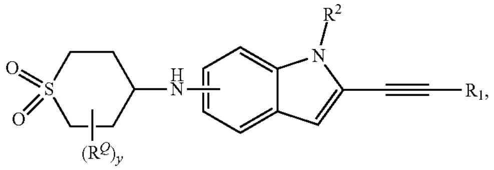
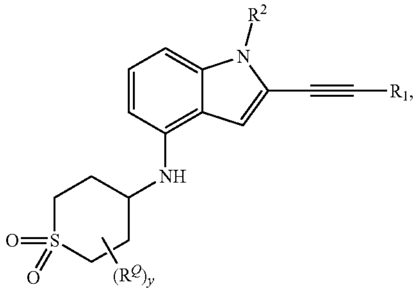
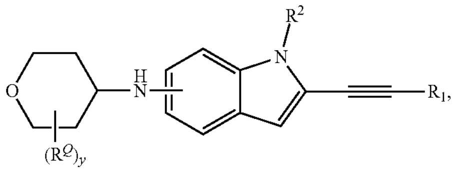
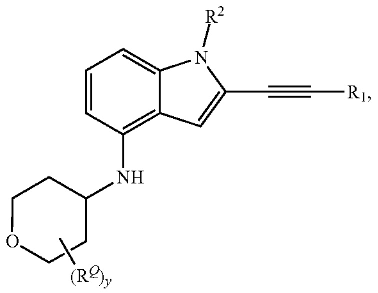
-continued
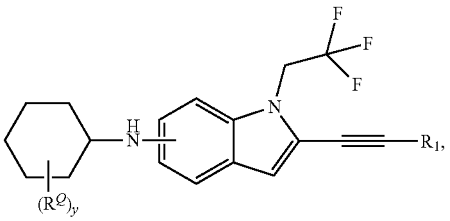
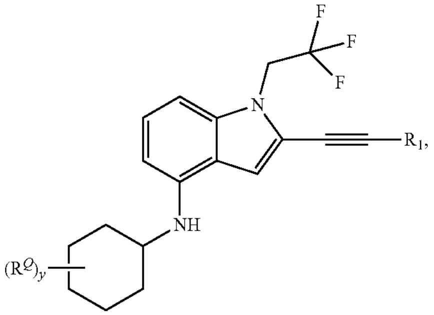
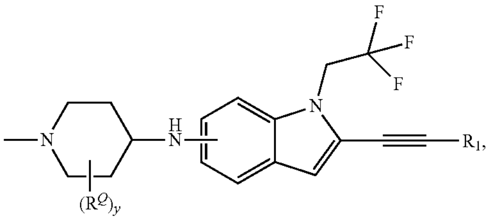
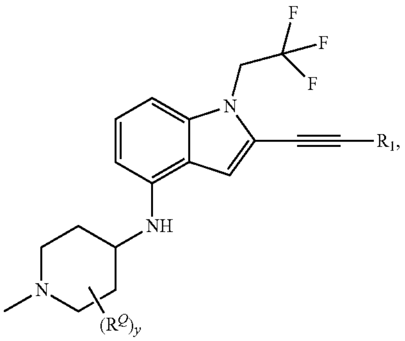
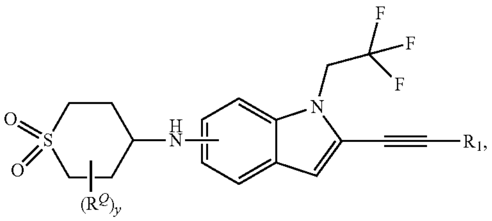
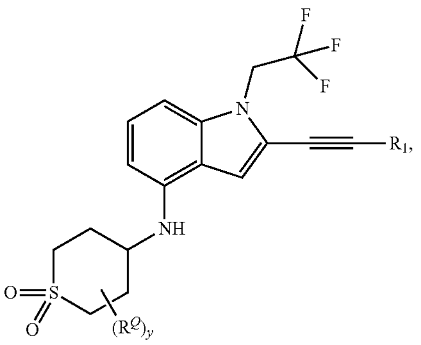

-continued
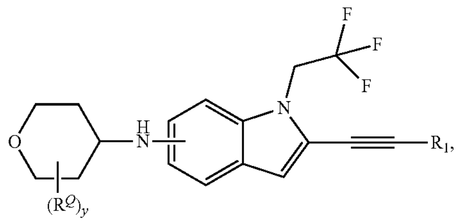
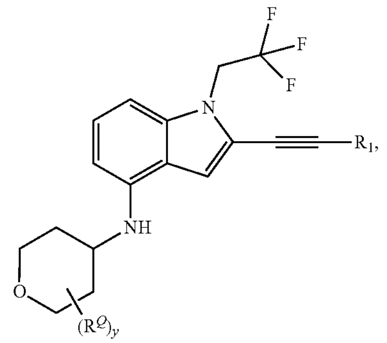
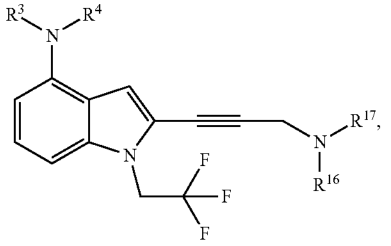
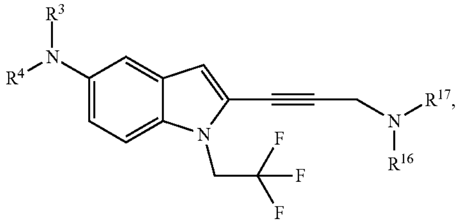
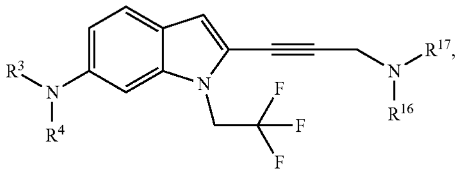
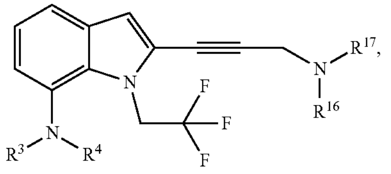
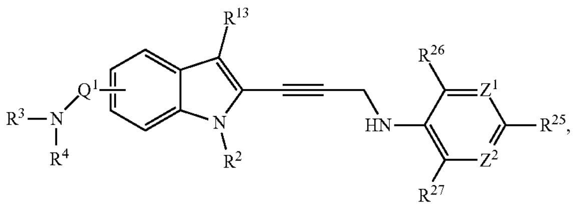
-continued
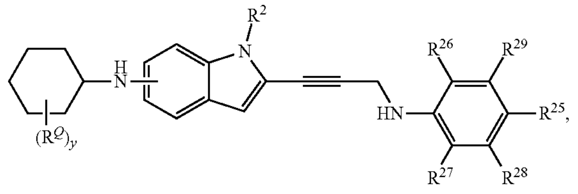
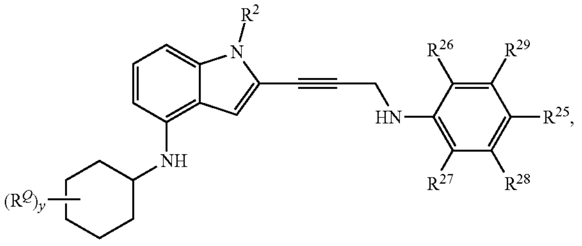
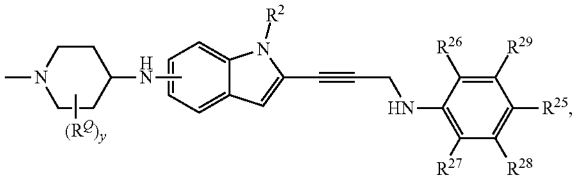
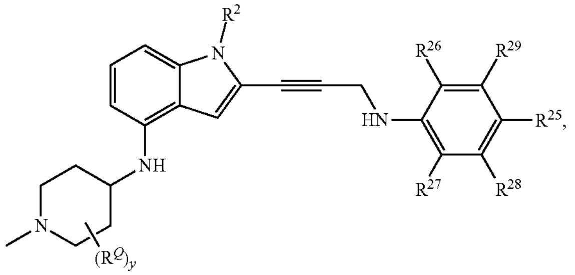
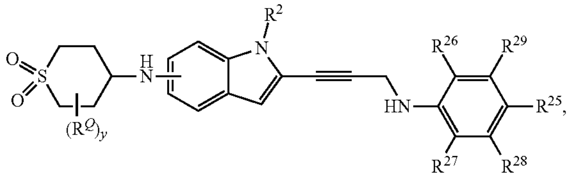
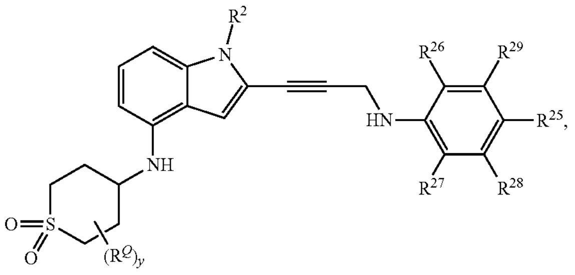
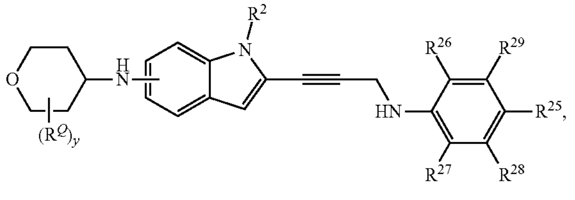

-continued
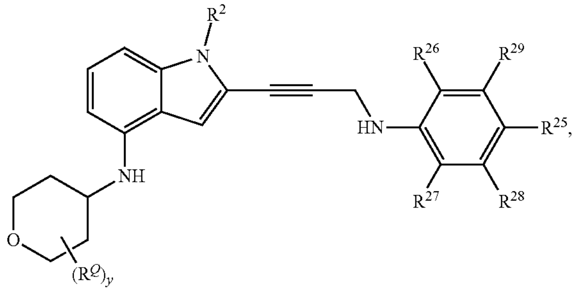
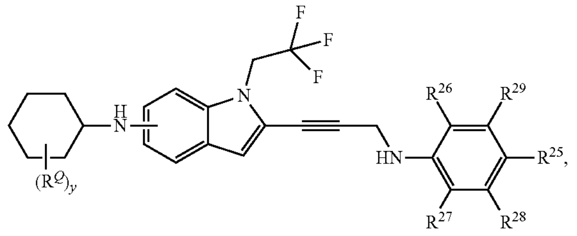
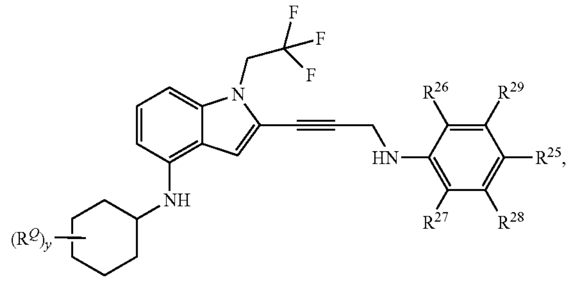
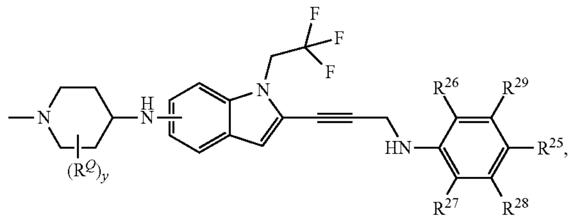
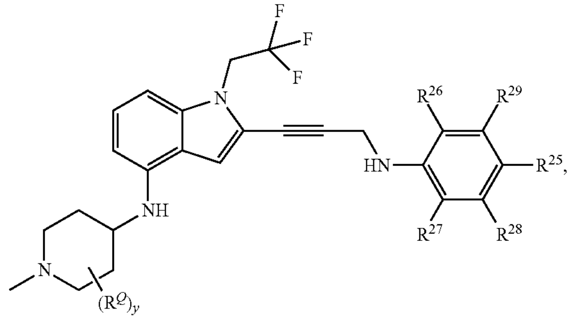
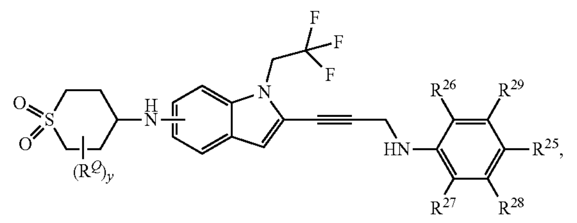
-continued
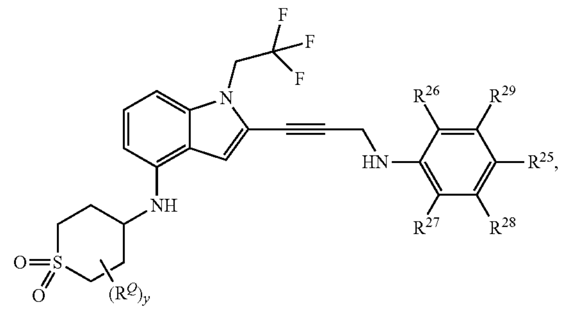
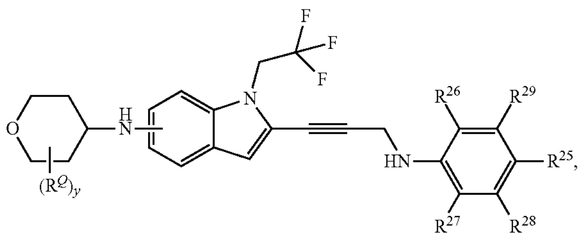
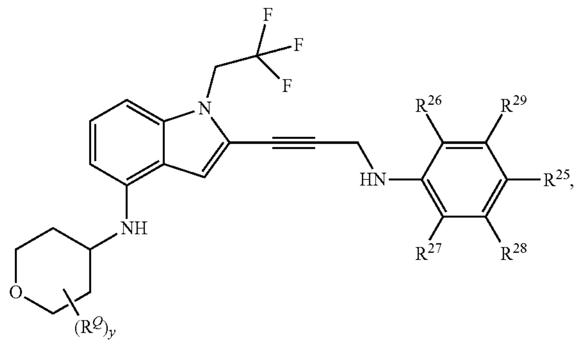
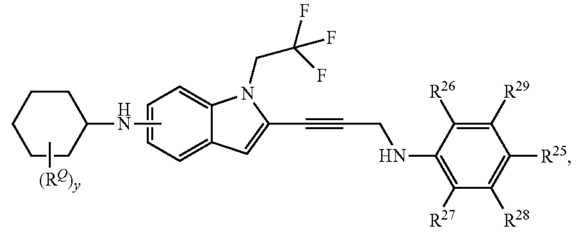
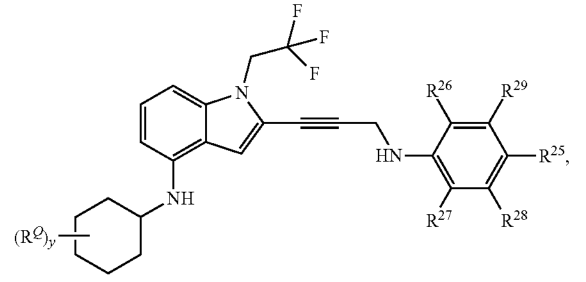
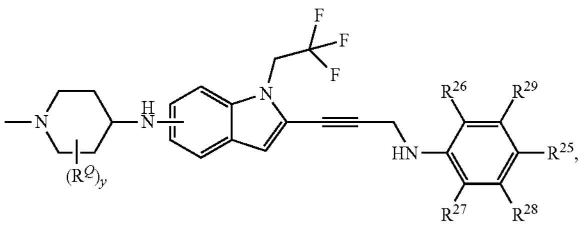

-continued
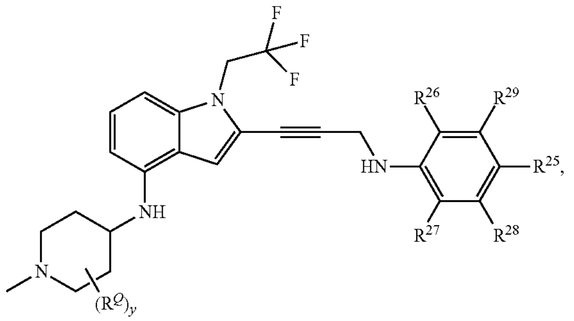
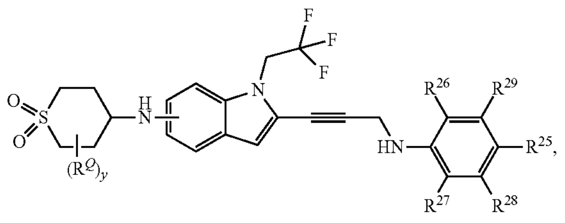
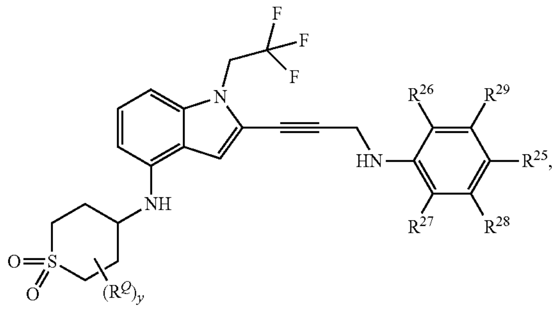
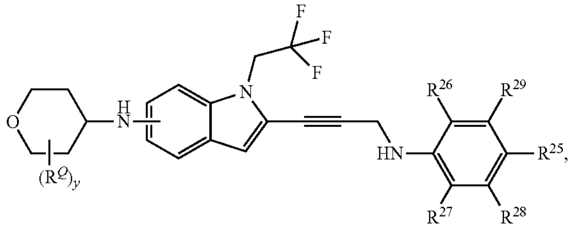
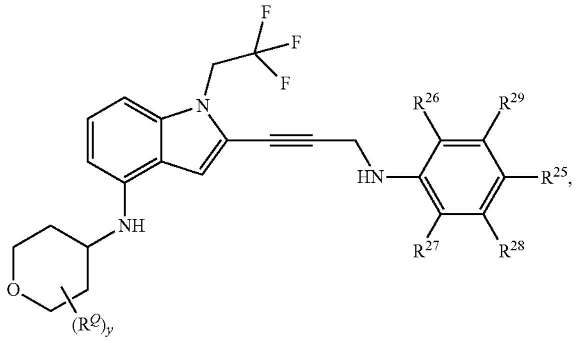
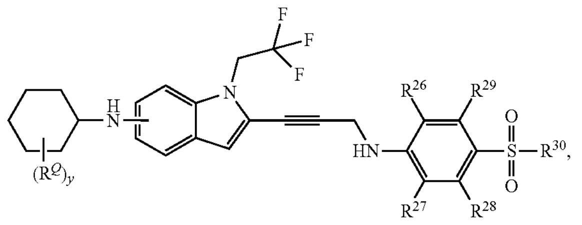
-continued
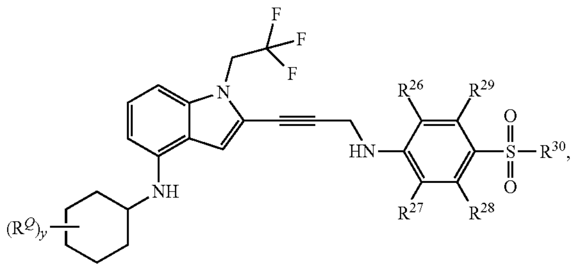
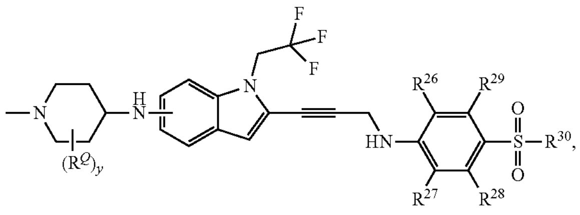
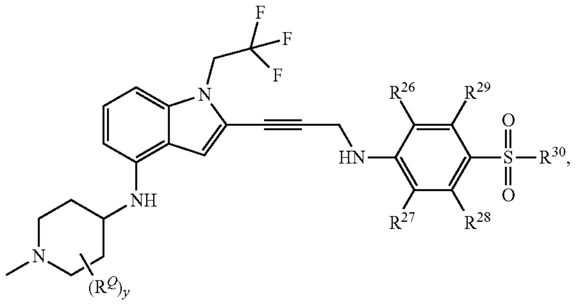
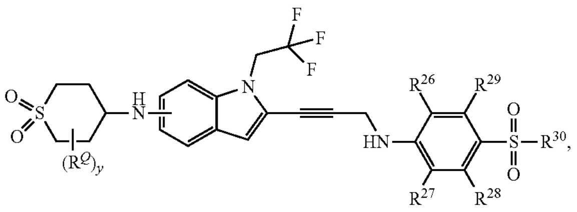
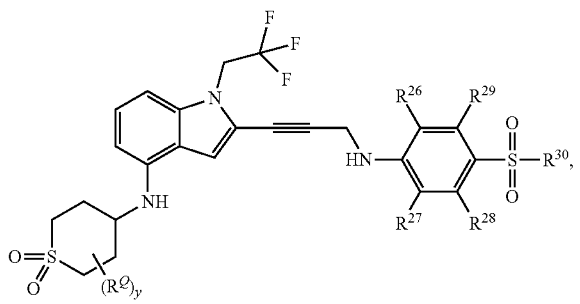
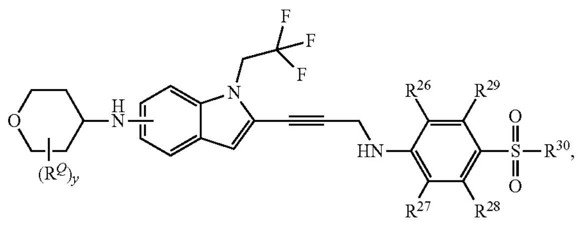

-continued

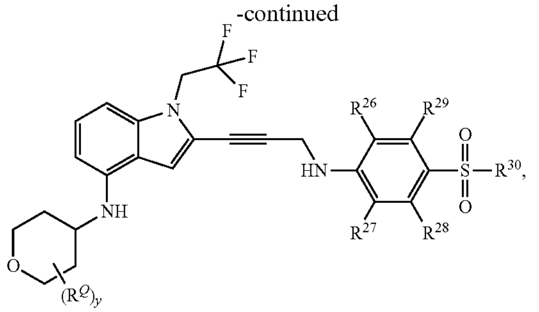

or

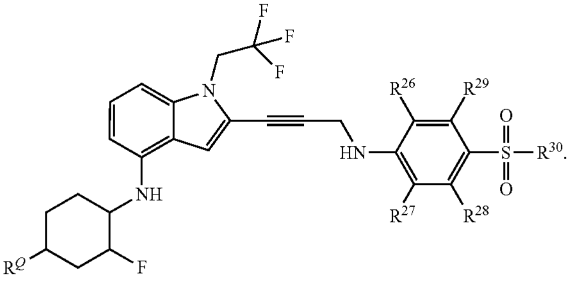

In some embodiments, the compound is of the formula:

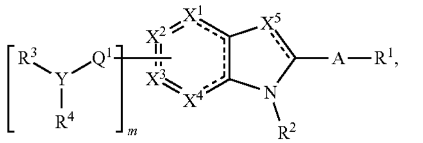

wherein:

each ⎓ is independently a single bond or a double bond;

$X^1$ is $CR^5$, $CR^5R^6$, N, $NR^5$, O, S, C═O, C═S, or a carbon atom connected to $Q^1$;

$X^2$ is $CR^7$, $CR^7R^8$, N, $NR^7$, O, S, C═O, C═S, or a carbon atom connected to $Q^1$;

$X^3$ is $CR^9$, $CR^9R^{10}$, N, $NR^9$, O, S, C═O, C═S, or a carbon atom connected to $Q^1$;

$X^4$ is $CR^{11}$, $CR^{11}R^{12}$, N, $NR^{11}$, O, S, C═O, C═S, or a carbon atom connected to $Q^1$;

$X^5$ is $CR^{13}$, N, or $NR^{13}$;

wherein at least one of $X^1$, $X^2$, $X^3$, and $X^4$ is a carbon atom connected to $Q^1$;

A is a linking group;

$Q^1$ is C═O, C═S, C═$CR^{14}R^{15}$, C═$NR^{14}$, alkylene, alkenylene, or alkynylene, each of which is independently substituted or unsubstituted, or a bond;

m is 1, 2, 3, or 4;

Y is N, O, or absent;

$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;

each $R^3$ and $R^4$ is independently —C(O)$R^{19}$, —C(O)O$R^{19}$, —C(O)N$R^{19}R^{20}$, —SO$R^{19}$, —$SO_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is independently —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, A is alkylene, alkenylene, or alkynylene, each of which is substituted or unsubstituted. In some embodiments, A is alkylene. In some embodiments, A is alkenylene. In some embodiments, A is alkynylene.

In some embodiments, A is aryl, heteroaryl, or heterocyclyl, each of which is substituted or unsubstituted. In some embodiments, A is substituted aryl. In some embodiments, A is substituted heteroaryl. In some embodiments, A is substituted heterocyclyl.

In some embodiments, $R^1$ is alkyl, alkenyl, —C(O)$R^{16}$, —C(O)O$R^{16}$, or —C(O)N$R^{16}R^{17}$, each of which is unsubstituted or substituted. In some embodiments, $R^1$ is substituted alkyl. In some embodiments, $R^1$ is alkyl substituted with N$R^{16}R^{17}$.

In some embodiments, the compound of the formula is:

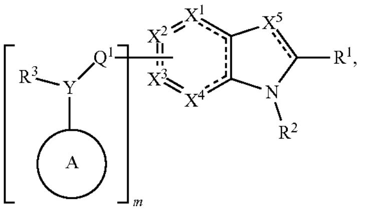

wherein:

each ⎓ is independently a single bond or a double bond;

$X^1$ is $CR^5$, $CR^5R^6$, N, $NR^5$, O, S, C═O, C═S, or a carbon atom connected to $Q^1$;

$X^2$ is $CR^7$, $CR^7R^8$, N, $NR^7$, O, S, C═O, C═S, or a carbon atom connected to $Q^1$;

$X^3$ is $CR^9$, $CR^9R^{10}$, N, $NR^9$, O, S, C═O, C═S, or a carbon atom connected to $Q^1$;

$X^4$ is $CR^{11}$, $CR^{11}R^{12}$, N, $NR^{11}$, O, S, C═O, C═S, or a carbon atom connected to $Q^1$;

$X^5$ is $CR^{13}$, N, or $NR^{13}$;

wherein at least one of $X^1$, $X^2$, $X^3$, and $X^4$ is a carbon atom connected to $Q^1$;

$Q^1$ is C═O, C═S, C═$CR^{14}R^{15}$, C═$NR^{14}$, alkylene, alkenylene, or alkynylene, each of which is independently substituted or unsubstituted, or a bond;

m is 1, 2, 3, or 4;

Y is N, O, or absent;

ring A is a cyclic group;

$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, C═O, C═S, —CN, —Si$R^{16}R^{17}R^{18}$, alkyl, alkenyl, alkynyl, aryl, heteroaryl, or heterocyclyl, each of which is independently substituted or unsubstituted, or hydrogen;

$R^3$ is —C(O)$R^{19}$, —C(O)O$R^{19}$, —C(O)N$R^{19}R^{20}$, —SO$R^{19}$, —$SO_2R^{19}$, alkyl, alkylene, alkenyl, alkenylene, alkynyl, aryl, heteroaryl, or heterocyclyl, each of which is independently substituted or unsubstituted, or hydrogen, or $R^3$ and A together with the nitrogen atom to which $R^3$ and A are bound form a ring, wherein the ring is substituted or unsubstituted, or $R^3$ is absent, each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, a compound of the invention is a compound of the formula

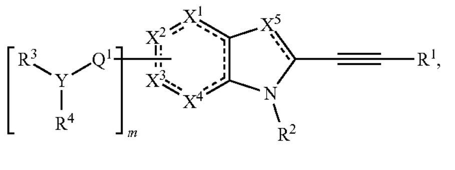

wherein:

each ⋯⋯ is independently a single bond or a double bond;

$X^1$ is $CR^5$, $CR^5R^6$, N, $NR^5$, O, S, C═O, C═S, or a carbon atom connected to $Q^1$;

$X^2$ is $CR^7$, $CR^7R^8$, N, $NR^7$, O, S, C═O, C═S, or a carbon atom connected to $Q^1$;

$X^3$ is $CR^9$, $CR^9R^{10}$, N, $NR^9$, O, S, C═O, C═S, or a carbon atom connected to $Q^1$;

$X^4$ is $CR^{11}$, $CR^{11}R^{12}$, N, $NR^{11}$, O, S, C═O, C═S, or a carbon atom connected to $Q^1$;

$X^5$ is $CR^{13}$, N, or $NR^{13}$;

wherein at least one of $X^1$, $X^2$, $X^3$, and $X^4$ is a carbon atom connected to $Q^1$;

$Q^1$ is C═O, C═S, C═$CR^{14}R^{15}$, C═$NR^{14}$, alkylene, alkenylene, or alkynylene, each of which is independently substituted or unsubstituted, or a bond;

m is 1, 2, 3, or 4;

Y is N, O, or absent;

$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, C═O, C═S, —CN, —Si$R^{16}R^{17}R^{18}$, alkyl, alkenyl, alkynyl, aryl, heteroaryl, or heterocyclyl, each of which is independently substituted or unsubstituted, or hydrogen;

each $R^3$ and $R^4$ is independently, —C(O)$R^{19}$, —C(O)O$R^{19}$, —C(O)N$R^{19}R^{20}$, —SO$R^{19}$, —$SO_2R^{19}$, alkyl, alkylene, alkenyl, alkenylene, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent, each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, the compound is of the formula:

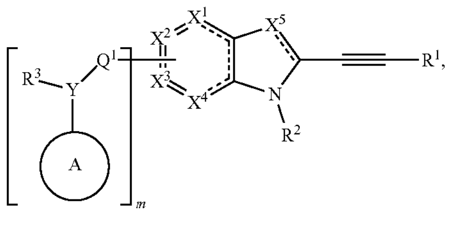

wherein:

each ⋯⋯ is independently a single bond or a double bond;

$X^1$ is $CR^5$, $CR^5R^6$, N, $NR^5$, O, S, C═O, C═S, or a carbon atom connected to $Q^1$;

$X^2$ is $CR^7$, $CR^7R^8$, N, $NR^7$, O, S, C═O, C═S, or a carbon atom connected to $Q^1$;

$X^3$ is $CR^9$, $CR^9R^{10}$, N, $NR^9$, O, S, C═O, C═S, or a carbon atom connected to $Q^1$;

$X^4$ is $CR^{11}$, $CR^{11}R^{12}$, N, $NR^{11}$, O, S, C═O, C═S, or a carbon atom connected to $Q^1$;

$X^5$ is $CR^{13}$, N, or $NR^{13}$;

wherein at least one of $X^1$, $X^2$, $X^3$, and $X^4$ is a carbon atom connected to $Q^1$;

$Q^1$ is C═O, C═S, C═$CR^{14}R^{15}$, C═$NR^{14}$, alkylene, alkenylene, or alkynylene, each of which is independently substituted or unsubstituted, or a bond;

m is 1, 2, 3, or 4;

Y is N, O, or absent;

ring A is a cyclic group;

$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, C═O, C═S, —CN, —Si$R^{16}R^{17}R^{18}$, alkyl, alkenyl, alkynyl, aryl, heteroaryl, or heterocyclyl, each of which is independently substituted or unsubstituted, or hydrogen;

$R^3$ is —C(O)$R^{19}$, —C(O)O$R^{19}$, —C(O)N$R^{19}R^{20}$, —SO$R^{19}$, —$SO_2R^{19}$, alkyl, alkylene, alkenyl, alkenylene, alkynyl, aryl, heteroaryl, or heterocyclyl, each of which is independently substituted or unsubstituted, or hydrogen, or $R^3$ and A together with the nitrogen atom to which $R^3$ and A are bound form a ring, wherein the ring is substituted or unsubstituted, or $R^3$ is absent, each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, the pattern of dashed bonds is chosen to provide an aromatic system, for example, an indole, an indolene, a pyrrolopyridine, a pyrrolopyrimidine, or a pyrrolopyrazine.

In some embodiments, $X^1$ is $CR^5$, $CR^5R^6$, or a carbon atom connected to $Q^1$. In some embodiments, $X^2$ is $CR^7$, $CR^7R^8$, or a carbon atom connected to $Q^1$. In some embodiments, $X^3$ is $CR^9$, $CR^9R^{10}$, or a carbon atom connected to $Q^1$. In some embodiments, $X^4$ is $CR^{11}$, $CR^{11}R^{12}$, or a carbon atom connected to $Q^1$. In some embodiments, $X^5$ is $CR^{13}$, N, or $NR^{13}$. In some embodiments, $X^1$ is a carbon atom connected to $Q^1$. In some embodiments, $X^2$ is a carbon atom connected to $Q^1$. In some embodiments, $X^3$ is a carbon atom connected to $Q^1$. In some embodiments, $X^4$ is a carbon atom connected to $Q^1$. In some embodiments, $X^5$ is N.

In some embodiments, $Q^1$ is a bond. In some embodiments, $Q^1$ is $C_1$-alkylene. In some embodiments, m is 1. In some embodiments, m is 2. In some embodiments, m is 3. In some embodiments, m is 4.

In some embodiments, $R^1$ is alkyl, alkenyl, —C(O)$R^{16}$, —C(O)O$R^{16}$, or —C(O)N$R^{16}R^{17}$, each of which is unsubstituted or substituted. In some embodiments, $R^1$ is substituted alkyl. In some embodiments, $R^1$ is alkyl substituted with $NR^{16}R^{17}$.

In some embodiments, ring A is aryl, heteroaryl, or heterocyclyl, each of which is substituted or unsubstituted. In some embodiments, ring A is substituted aryl. In some embodiments, ring A is aryl substituted with fluoro-. In some embodiments, ring A is aryl substituted with chloro-. In some embodiments, ring A is substituted heteroaryl, In some embodiments, ring A is heteroaryl substituted with fluoro-. In some embodiments, ring A is heteroaryl substituted with chloro-. In some embodiments, ring A is substituted heterocyclyl. In some embodiments, ring A is heterocyclyl substituted with fluoro-. In some embodiments, A is heterocyclyl substituted with chloro-.

In some embodiments, ring A is piperidinyl, piperazinyl, tetrahydropyranyl, morpholinyl, or pyrrodinyl, each of which is independently substituted or unsubstituted. In some embodiments, ring A is piperidinyl, piperazinyl, tetrahydropyranyl, morpholinyl, or pyrrodinyl, each of which is independently substituted with at least halo-. In some embodiments, ring A is piperidinyl substituted with halo-. In some embodiments, ring A is methylpiperidinyl substituted with halo-. In some embodiments, ring A is 3-fluoro-1-methylpiperidinyl. In some embodiments, ring A is 3-fluoro-1-(2-hydroxy-3-methoxypropyl)piperidinyl. In some embodiments, ring A is tetrahydropyranyl substituted with at least halo-.

In some embodiments, each $R^{16}$ and $R^{17}$ is independently alkyl, alkenyl, aryl, heteroaryl, heterocyclyl, each of which is independently substituted or unsubstituted, or hydrogen. In some embodiments, $R^{16}$ is hydrogen or alkyl. In some embodiments, $R^{17}$ is aryl, heteroaryl, or heterocyclyl, each of which is independently substituted or unsubstituted. In some embodiments, $R^{17}$ is substituted aryl. In some embodiments, $R^{17}$ is substituted phenyl. In some embodiments, $R^{17}$ is phenyl substituted with a sulfoxide group, carboxyl group, amide group, amino group, alkyl, alkoxy, hydroxy, halo, cyano, or heterocyclyl, each of which is independently substituted or unsubstituted. In some embodiments, $R^{17}$ is phenyl substituted with methoxy. In some embodiments, $R^{17}$ is phenyl substituted with a substituted sulfoxide group. In some embodiments, $R^{17}$ is phenyl substituted with a carboxyl group. In some embodiments, $R^{17}$ is phenyl substituted with a substituted amide group.

In some embodiments, the compound is of the formula:

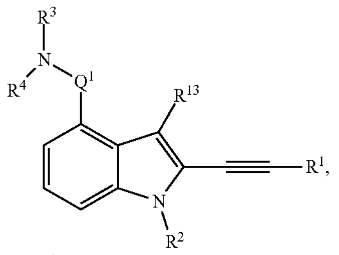

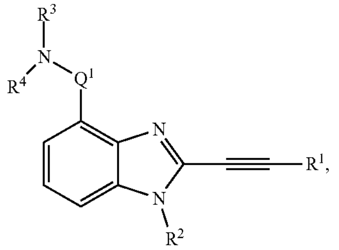

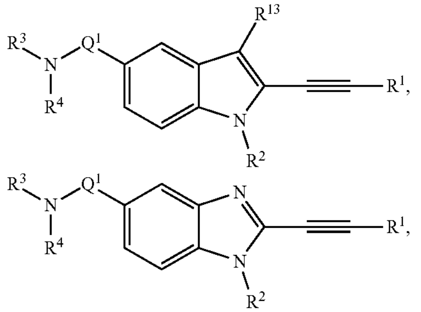

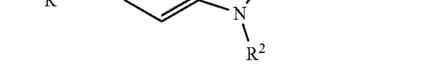

-continued

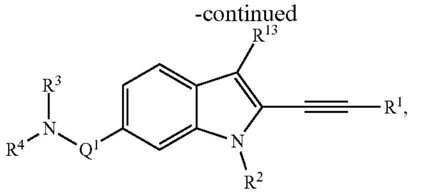

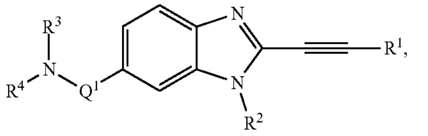

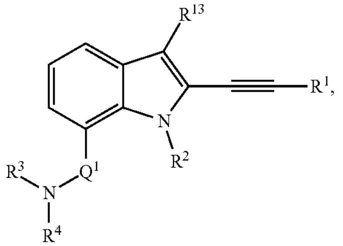

or

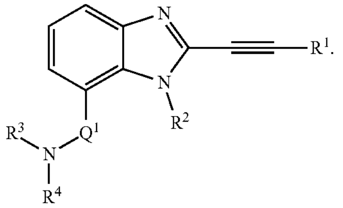

In some embodiments, $Q^1$ is C═O, C═S, C═$CR^{14}R^{15}$, C═$NR^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene or a bond. In some embodiments, $Q^1$ is $C_1$-alkylene. In some embodiments, $Q^1$ is a bond.

In some embodiments, Y is N. In some embodiments, Y is O. In some embodiments, Y is absent.

In some embodiments, $R^2$ is hydrogen or alkyl. In some embodiments, $R^2$ is alkyl. In some embodiments, $R^2$ is substituted $C_1$-$C_5$-alkyl. In some embodiments, $R^2$ is trifluoroethyl. In some embodiments, $R^2$ is cycloalkyl. In some embodiments, $R^2$ is cyclopropyl.

In some embodiments, $R^{13}$ is alkyl, alkenyl, hydrogen, or halogen. In some embodiments, $R^{13}$ is hydrogen.

In some embodiments, $R^2$ is $C_1$-$C_5$-alkyl, and $R^{13}$ is $C_1$-$C_5$-alkyl. In some embodiments, $R^2$ is $C_1$-$C_5$-alkyl, and $R^{13}$ is hydrogen. In some embodiments, $R^2$ is substituted $C_1$-$C_5$-alkylene. In some embodiments, $R^2$ is methyl, ethyl, propyl, iso-propyl, butyl, or tert-butyl, each of which is substituted or unsubstituted. In some embodiments, $R^{13}$ is methyl, ethyl, propyl, iso-propyl, butyl or tert-butyl. In some embodiments, $R^2$ is hydrogen, and $R^{13}$ is hydrogen. In some embodiments, $R^2$ is trifluoroethyl, and $R^{13}$ is hydrogen.

In some embodiments, the compound is of the formula:

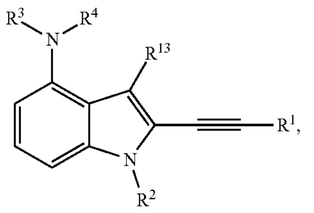

-continued

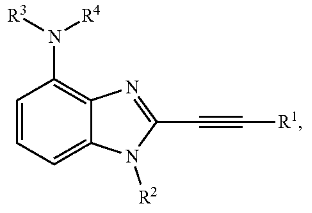

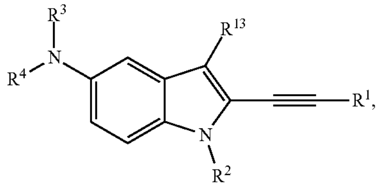

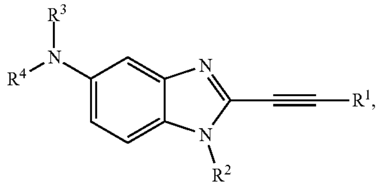

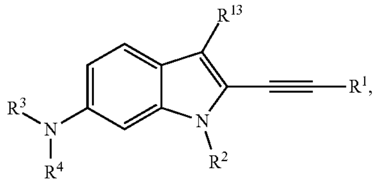

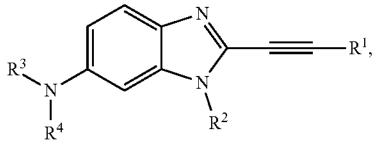

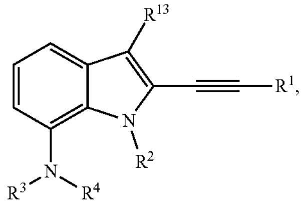

or

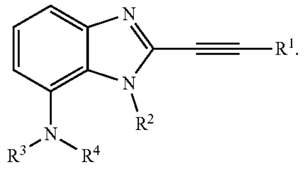

In some embodiments, the compound is of the formula:

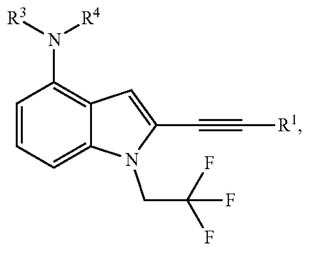

-continued

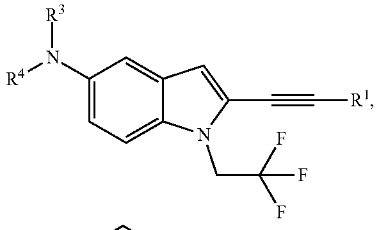

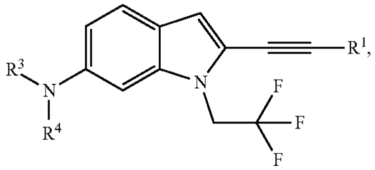

or

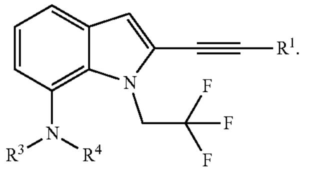

In some embodiments, $R^3$ is H, and $R^4$ is —C(O)$R^{19}$, —C(O)O$R^{19}$, —C(O)N$R^{19}R^{20}$, —SO$R^{19}$, —$SO_2R^{19}$, alkyl, alkylene, alkenyl, alkenylene, alkynyl, aryl, heteroaryl, or heterocyclyl, each of which is independently substituted or unsubstituted. In some embodiments, each $R^3$ and $R^4$ is independently substituted or unsubstituted $C_1$-$C_6$-alkylene. In some embodiments, $R^3$ is H, and $R^4$ is substituted or unsubstituted $C_1$-$C_4$ alkylene. In some embodiments, $R^3$ is H, and $R^4$ is substituted or unsubstituted heterocyclyl. In some embodiments, $R^3$ is H, and $R^4$ is substituted or unsubstituted piperidinyl. In some embodiments, $R^3$ is H, and $R^4$ is substituted or unsubstituted cycloalkyl. In some embodiments, $R^3$ is H, and $R^4$ is cycloalkyl substituted with an amino group. In some embodiments, $R^3$ is H, and $R^4$ is substituted or unsubstituted cyclobutyl. In some embodiments, $R^3$ is H, and $R^4$ is cyclobutyl substituted with an amino group. In some embodiments, $R^3$ is H, and $R^4$ is substituted or unsubstituted cyclohexyl. In some embodiments, $R^3$ is H, and $R^4$ is cyclohexyl substituted with an amino group.

In some embodiments, the compound is of the formula:

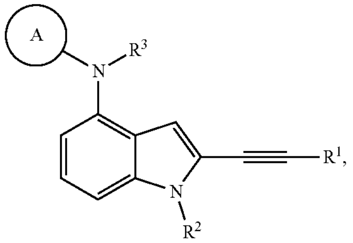

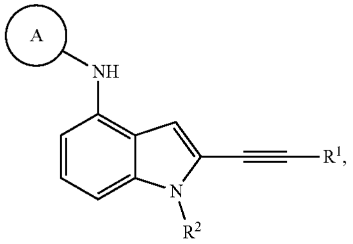

-continued

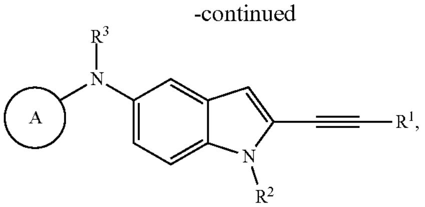

or

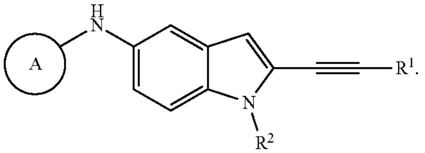

In some embodiments, the compound is of the formula:

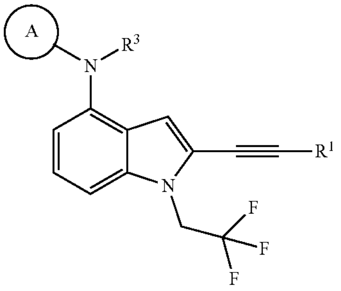

or

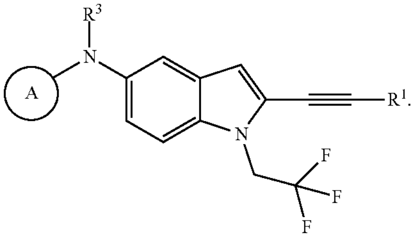

$R^1$ can be a group substituted with one or more substituents selected from a hydroxyl group, sulfhydryl group, halogens, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group. In some embodiments, $R^1$ is alkyl, alkenyl, —C(O)$R^{16}$, —C(O)O$R^{16}$, or —C(O)N$R^{16}R^{17}$.

In some embodiments, $R^1$ is substituted or unsubstituted $C_1$-$C_3$ alkyl. In some embodiments, $R^1$ is $C_1$-$C_3$-alkyl substituted with an amine group. In some embodiments, $R^1$ is $C_1$-alkyl substituted with N$R^{16}R^{17}$. In some embodiments, each $R^{16}$ and $R^{17}$ is independently aryl, heteroaryl, or heterocyclyl, each of which is independently substituted or unsubstituted, or hydrogen. In some embodiments, $R^{16}$ is H, and $R^{17}$ is substituted aryl. In some embodiments, $R^{16}$ is H, and $R^{17}$ is substituted phenyl. In some embodiments, $R^{16}$ is H, and $R^{17}$ is phenyl substituted with alkyl, alkoxy, halo, sulfonamide, a sulfone, or a carboxy group. In some embodiments, $R^{16}$ is H, and $R^{17}$ is substituted heteroaryl. In some embodiments, $R^{16}$ is H, and $R^{17}$ is substituted heterocyclyl.

In some embodiments, $Q^1$ is C═O, C═S, C═C$R^{14}R^{15}$, C═N$R^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene. In some embodiments, each $R^{16}$ and $R^{17}$ is independently alkyl, alkenyl, aryl, heteroaryl, heterocyclyl, or hydrogen. In some embodiments, $Q^1$ is $C_1$-alkylene, $R^{16}$ is aryl, and $R^{17}$ is alkyl. In some embodiments, $Q^1$ is $C_1$-alkylene, $R^{16}$ is aryl, and $R^{17}$ is hydrogen. In some embodiments, $Q^1$ is $C_1$-alkylene, $R^{16}$ is heteroaryl, and $R^{17}$ is alkyl. In some embodiments, $Q^1$ is $C_1$-alkylene, $R^{16}$ is heteroaryl, and $R^{17}$ is hydrogen. In some embodiments, $Q^1$ is $C_1$-alkylene, $R^{16}$ is substituted heteroaryl, and $R^{17}$ is hydrogen. In some embodiments, $Q^1$ is $C_1$-alkylene, $R^{16}$ is substituted alkyl, and $R^{17}$ is hydrogen. In some embodiments, $R^{17}$ is aryl, heteroaryl, or heterocyclyl, each of which is independently substituted or unsubstituted with halogen, alkyl, or hydroxyl. In some embodiments, $R^{16}$ is hydrogen, and $R^{17}$ is aryl or heteroaryl, substituted or unsubstituted with halogen or alkyl. In some embodiments, $R^{16}$ is alkyl, and $R^{17}$ is heteroaryl substituted with halogen or alkyl. In some embodiments, $R^{17}$ is aryl, heteroaryl, or heterocyclyl, each of which is independently substituted or unsubstituted with alkyl. In some embodiments, $R^{17}$ is aryl or heteroaryl, each of which is independently substituted with alkyl, wherein the alkyl is optionally substituted with fluorine, chlorine, bromine, iodine, or cyano.

In some embodiments, $R^2$ is alkyl, and $R^{13}$ is alkyl, each of which is substituted or substituted. In some embodiments, $R^2$ is hydrogen, and $R^{13}$ is unsubstituted or substituted alkyl. In some embodiments, $R^2$ is methyl, ethyl, propyl, iso-propyl, butyl, or tert-butyl, each of which is substituted or unsubstituted. In some embodiments, $R^{13}$ is methyl, ethyl, propyl, iso-propyl, butyl or tert-butyl. In some embodiments, $R^2$ is hydrogen, and $R^{13}$ is hydrogen. In some embodiments, $R^2$ is hydrogen, and $R^{13}$ is alkyl. In some embodiments, $R^2$ is trifluoroethyl, and $R^{13}$ is hydrogen.

In some embodiments, $R^3$ is —C(O)$R^{19}$, —C(O)O$R^{19}$, alkyl, alkenyl, alkynyl, aryl, heteroaryl, or heterocyclyl, each of which is independently substituted or unsubstituted, or hydrogen, and $R^4$ is —C(O)$R^{19}$, —C(O)O$R^{19}$, alkyl, alkenyl, alkynyl, aryl, heteroaryl, or heterocyclyl, each of which is independently substituted or unsubstituted, or hydrogen. In some embodiments, $R^3$ is alkyl, alkenyl, alkynyl, aryl, heteroaryl, or heterocyclyl, each of which is independently substituted or unsubstituted, or hydrogen. In some embodiments, $R^3$ is substituted alkyl. In some embodiments, $R^3$ is H.

In some embodiments, $R^3$ is H, and $R^4$ is unsubstituted or substituted alkyl. In some embodiments, $R^3$ is H, and $R^4$ is unsubstituted or substituted cycloalkyl. In some embodiments, $R^3$ is H, and $R^4$ is substituted cyclohexyl. In some embodiments, $R^3$ is H, and $R^4$ is substituted cyclobutyl.

In some embodiments, at least one of $R^3$ and $R^4$ is alkyl, alkylene, alkenyl, alkenylene, alkynyl, aryl, heteroaryl, or heterocyclyl, each of which is substituted at least with halo-. In some embodiments, $R^3$ is hydrogen and $R^4$ is a ring A. In some embodiments, $R^4$ or ring A is cycloalkyl, aryl, heteroaryl, or heterocyclyl, each of which is independently substituted or unsubstituted. In some embodiments, $R^4$ or ring A is substituted or unsubstituted aryl. In some embodiments, $R^4$ or ring A is substituted or unsubstituted phenyl. In some embodiments, $R^4$ or ring A is substituted or unsubstituted cycloalkyl. In some embodiments, $R^4$ or ring A is substituted or unsubstituted cyclopropyl. In some embodiments, $R^4$ or ring A is substituted cyclopropyl. In some embodiments, $R^4$ or ring A is substituted cyclohexyl. In some embodiments, $R^4$ or ring A is cyclohexyl substituted with an amino group.

In some embodiments, $R^3$ is H, and $R^4$ or ring A is unsubstituted or substituted heterocyclyl. In some embodiments, $R^4$ or ring A is heterocyclyl. In some embodiments, $R^4$ or ring A is piperidinyl, piperazinyl, tetrahydropyranyl, morpholinyl, or pyrrodinyl, each of which is independently substituted or unsubstituted. In some embodiments, $R^3$ is H, and $R^4$ or ring A is substituted piperidinyl. In some embodiments, $R^3$ is H, and $R^4$ or ring A is piperidine substituted with alkyl, carboxy, heterocyclyl, or an amide group. In some embodiments, $R^3$ is H, and $R^4$ or ring A is unsubstituted or substituted methyl piperidinyl. In some embodiments, $R^3$ is H, and $R^4$ or ring A is 3-fluoro-1-methylpiperidinyl. In some embodiments, $R^3$ is H, and $R^4$ or ring A is piperidinyl substituted with methoxypropanol. In some embodiments, $R^3$ is H, and $R^4$ or ring A is 3-fluoro-1-(2-hydroxy-3-methoxypropyl)piperidinyl. In some embodiments, $R^3$ is H, and $R^4$ or ring A is unsubstituted or substituted tetrahydropyranyl. In some embodiments, $R^3$ is H, and $R^4$ or ring A is unsubstituted tetrahydropyranyl. In some embodiments, $R^3$ is H, and $R^4$ or ring A is tetrahydropyranyl substituted with alkyl. In some embodiments, $R^3$ is H, and $R^4$ or ring A is tetrahydrothiopyran-1,1-diooxide.

In some embodiments, $R^4$ or ring A is cycloalkyl, aryl, heteroaryl, or heterocyclyl, each of which is substituted at least with halo-. In some embodiments, $R^4$ or ring A is $C_4$-$C_6$-cycloalkyl substituted with at least halo-. In some embodiments, $R^4$ or ring A is cyclohexyl substituted with at least halo-. In some embodiments, $R^4$ or ring A is aryl substituted with at least halo-. In some embodiments, $R^4$ or ring A is phenyl substituted with at least halo-. In some embodiments, $R^4$ or ring A is aryl substituted with fluoro-. In some embodiments, $R^4$ or ring A is phenyl substituted with fluoro-. In some embodiments, $R^4$ or ring A is aryl substituted with chloro-. In some embodiments, $R^4$ or ring A is phenyl substituted with chloro-. In some embodiments, $R^4$ or ring A is heteroaryl substituted with at least halo-. In some embodiments, $R^4$ or ring A is heteroaryl substituted with fluoro-. In some embodiments, $R^4$ or ring A is heteroaryl substituted with chloro-. In some embodiments, $R^4$ or ring A is $C_4$-$C_6$-heterocyclyl substituted with at least halo-. In some embodiments, $R^4$ or ring A is heterocyclyl substituted with fluoro-. In some embodiments, $R^4$ or ring A is heterocyclyl substituted with chloro-.

In some embodiments, $R^4$ or ring A is piperidinyl, piperazinyl, tetrahydropyranyl, morpholinyl, or pyrrodinyl, each of which is independently substituted with at least halo-. In some embodiments, $R^4$ or ring A is piperidinyl substituted with halo-. In some embodiments, $R^4$ or ring A is methylpiperidinyl substituted with halo-. In some embodiments, $R^4$ or ring A is 3-fluoro-1-methylpiperidinyl. In some embodiments, $R^4$ or ring A is 3-fluoro-1-(2-hydroxy-3-methoxypropyl)piperidinyl. In some embodiments, $R^4$ or ring A is tetrahydropyranyl substituted with at least halo-.

In some embodiments, $R^4$ or Ring A is a ring that is:

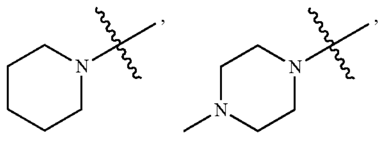

-continued

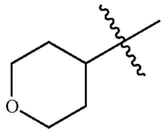,
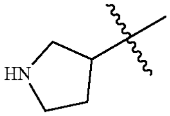,

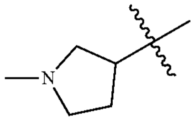, or 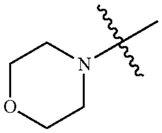, wherein the ring is substituted or unsubstituted. In some embodiments, the ring is substituted with halo-. In some embodiments, the ring is substituted with fluoro. In some embodiments, $R^3$ is H, and $R^4$ is a ring that is

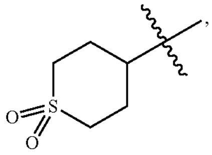 [SMILES: *C1CCS(=O)(=O)CC1], wherein the ring is substituted or unsubstituted. In some embodiments, the ring is substituted with halo-. In some embodiments, the ring is substituted with fluoro. In some embodiments, $R^3$ is H, and $R^4$ is a ring that is

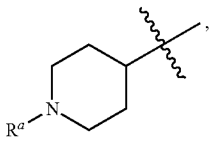, wherein the ring is substituted or unsubstituted. In some embodiments, $R^a$ is alkylene. In some embodiments, $R^a$ is methyl. In some embodiments, the ring is substituted with halo. In some embodiments, the ring is substituted with fluoro. In some embodiments, $R^3$ is H, and $R^4$ is a ring that is

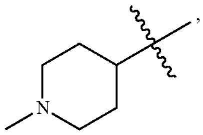 [SMILES: *C1CCN(C)CC1], wherein the ring is substituted or unsubstituted. In some embodiments, the ring is substituted with halo. In some embodiments, the ring is substituted with fluoro. In some embodiments, $R^3$ is H, and $R^4$ is a ring that is

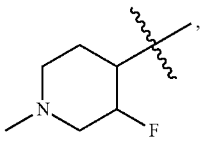 [SMILES: *C1CCN(C)CC1F], wherein the ring is substituted or unsubstituted.

In some embodiments, the $R^4$ or ring A is substituted with one or more substituents selected from a hydroxyl group, sulfhydryl group, halogens, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group.

In some embodiments, $R^3$ and $R^4$ together with the nitrogen atom to which $R^3$ and $R^4$ are bound form a ring, wherein the ring is substituted or unsubstituted. In some embodiments, $R^3$ and $R^4$ together with the nitrogen atom to which $R^3$ and $R^4$ are bound form a substituted heterocycle. In some embodiments, $R^3$ and $R^4$ together with the nitrogen atom to which $R^3$ and $R^4$ are bound form a heterocycle substituted with a hydroxyl group, halogen, amino group, or alkyl group. In some embodiments, $R^3$ and $R^4$ together with the nitrogen atom to which $R^3$ and $R^4$ are bound form a heterocycle, wherein the heterocycle is substituted by a substituted or unsubstituted heterocycle.

In some embodiments, $R^3$ and $R^4$ together with the nitrogen atom to which $R^3$ and $R^4$ are bound form a ring of a following formula:

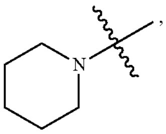, 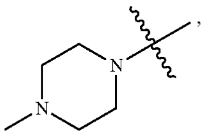, or

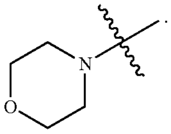.

In some embodiments, the compound is of the formula:

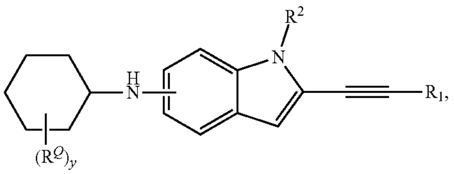

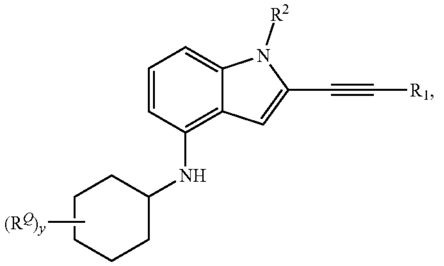

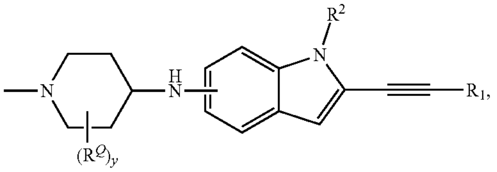

-continued

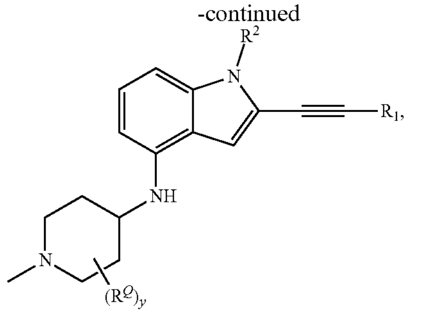

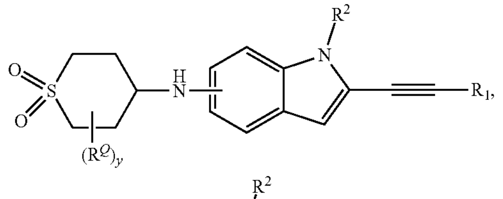

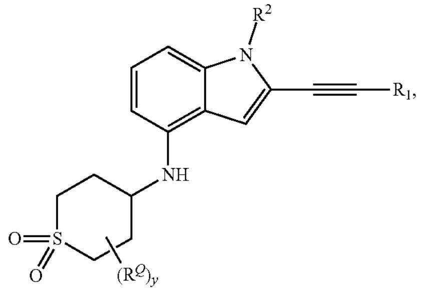

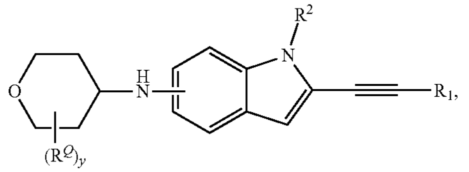

or

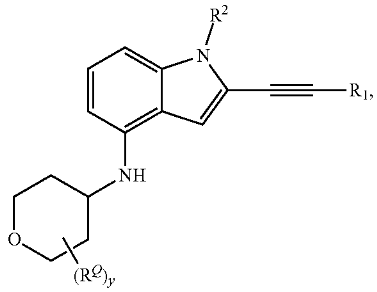

wherein:

$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, C═O, C═S, —CN, —Si$R^{16}R^{17}R^{18}$, alkyl, alkenyl, alkynyl, aryl, heteroaryl, or heterocyclyl, each of which is independently substituted or unsubstituted, or hydrogen;

each $R^Q$ IS independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

y is 0, 1, 2, 3, or 4;

each $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, $R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, or heterocyclyl, each of which is independently substituted or unsubstituted, or hydrogen. In some embodiments, $R^1$ is alkyl, alkylene, alkoxy, —N$R^{21}R^{22}$, or aryl, each of which is independently substituted or unsubstituted; halo or hydrogen.

In some embodiments, $R^1$ is substituted $C_1$-$C_3$-alkyl. In some embodiments, $R^1$ is $C_1$-$C_3$-alkyl substituted with N$R^{16}R^{17}$. In some embodiments, $R^1$ is methyl substituted with N$R^{16}R^{17}$, wherein each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^1$ is methyl substituted with N$R^{16}R^{17}$, wherein $R^{16}$ is hydrogen, and $R^{17}$ is a substituted carboxyl group. In some embodiments, $R^1$ is methyl substituted with N$R^{16}R^{17}$, wherein $R^{16}$ is hydrogen, and $R^{17}$ is substituted aryl. In some embodiments, $R^1$ is methyl substituted with N$R^{16}R^{17}$, wherein $R^{16}$ is hydrogen, and $R^{17}$ is substituted phenyl. In some embodiments, $R^1$ is methyl substituted with N$R^{16}R^{17}$, wherein $R^{16}$ is hydrogen, and $R^{17}$ is phenyl, substituted with a sulfoxide group, carboxyl group, amide group, amino group, alkyl, alkoxy, hydroxy, halo, cyano, or heterocyclyl, each of which is independently substituted or unsubstituted. In some embodiments, $R^{17}$ is phenyl substituted with methoxy. In some embodiments, $R^{17}$ is phenyl substituted with a substituted sulfoxide group. In some embodiments, $R^{17}$ is phenyl substituted with a carboxyl group. In some embodiments, $R^{17}$ is a substituted amide group. In some embodiments, $R^{17}$ is substituted with methoxy and sulfonamide.

In some embodiments, $R^2$ is hydrogen or alkyl. In some embodiments, $R^2$ is substituted $C_1$-$C_5$-alkylene. In some embodiments, $R^2$ is trifluoroethyl. In some embodiments, $R^{13}$ is alkyl, alkenyl, hydrogen, or halogen. In some embodiments, $R^2$ is alkyl, and $R^{13}$ is alkyl. In some embodiments, $R^2$ is hydrogen, and $R^{13}$ is alkyl. In some embodiments, $R^2$ is methyl, ethyl, propyl, iso-propyl, butyl, or tert-butyl. In some embodiments, $R^{13}$ is methyl, ethyl, propyl, iso-propyl, butyl or tert-butyl. In some embodiments, $R^2$ is hydrogen, and $R^{13}$ is hydrogen.

In some embodiments, the compound is of the formula:

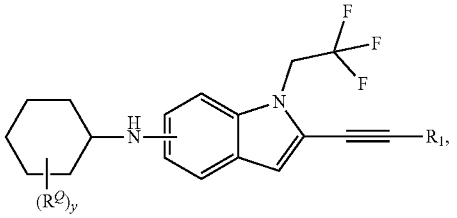

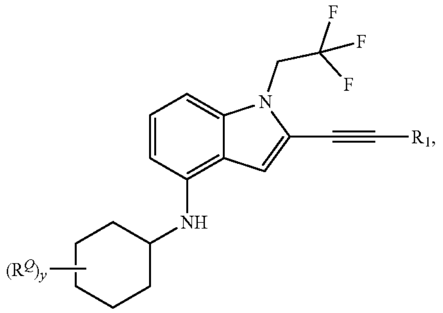

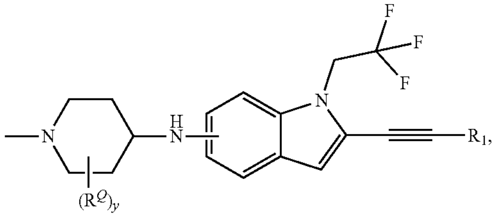

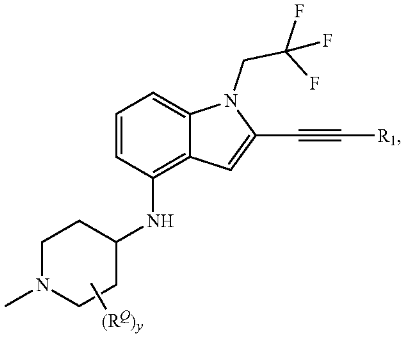

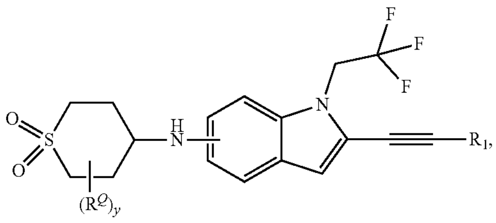

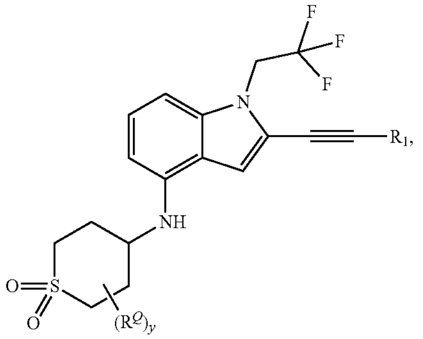

-continued

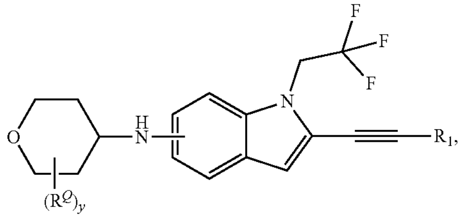

or

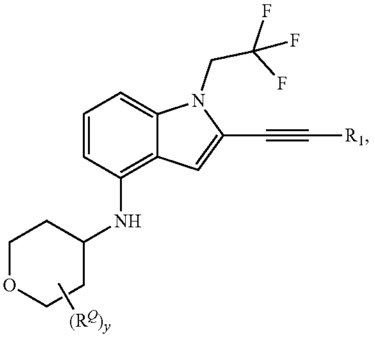

or a pharmaceutically-acceptable salt thereof, wherein the variables are as defined above.

In some embodiments, each $R^Q$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen. In some embodiments, each $R^Q$ is In some embodiments, y is 1. In some embodiments, y is 2. In some embodiments, y is 3. In some embodiments, y is 4.

In some embodiments, $R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, or heterocyclyl, each of which is independently substituted or unsubstituted, or hydrogen. In some embodiments, $R^1$ is alkyl, alkylene, alkoxy, —N$R^{21}R^{22}$, or aryl, each of which is independently substituted or unsubstituted; halo or hydrogen.

In some embodiments, $R^1$ is substituted alkyl. In some embodiments, $R^1$ is substituted $C_1$-$C_3$-alky 1. In some embodiments, $R^1$ is alkyl substituted with N$R^{16}R^{17}$. In some embodiments, $R^1$ is $C_1$-$C_3$-alky 1 substituted with N$R^{16}R^{17}$. In some embodiments, $R^1$ is methyl substituted with N$R^{16}R^{17}$, wherein each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^1$ is methyl substituted with N$R^{16}R^{17}$, wherein $R^{16}$ is hydrogen, and $R^{17}$ is a substituted carboxyl group.

In some embodiments, $R^{16}$ is alkyl, alkenyl, aryl, heteroaryl, heterocyclyl, or hydrogen, and $R^{17}$ is aryl, heteroaryl, or heterocyclyl. In some embodiments, $R^{16}$ is hydrogen, and $R^{17}$ is phenyl, indolyl, piperidinyl, imidazolyl, thiazolyl, morpholinyl, pyrrolyl, or pyridinyl, each of which is substituted or unsubstituted.

In some embodiments, the compound is of the formula:

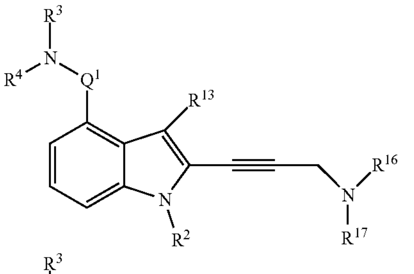

or

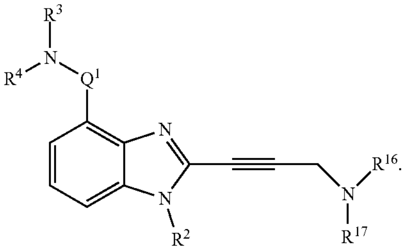

In some embodiments, the compound is of the formula:

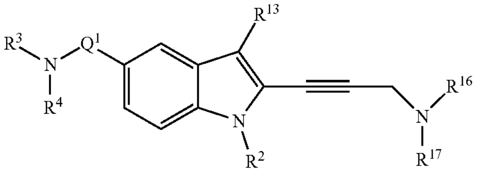

or

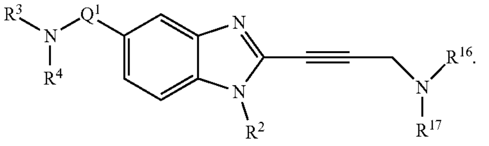

In some embodiments, the compound is of the formula:

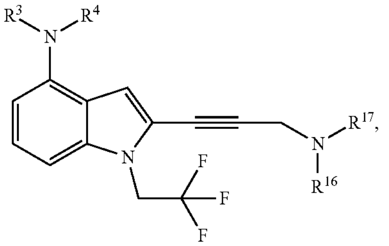

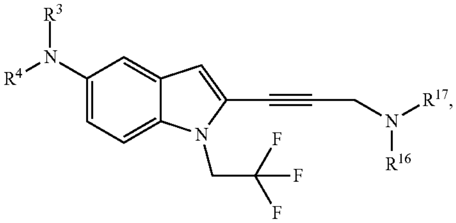

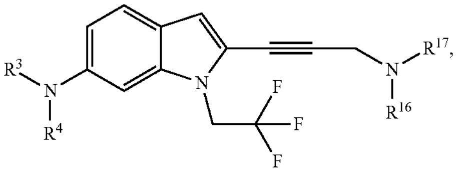

or

-continued

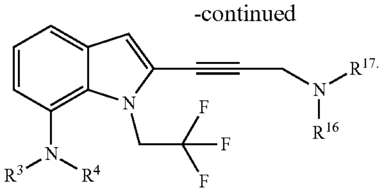

In some embodiments, each $R^{16}$ and $R^{17}$ is independently alkyl, alkenyl, aryl, heteroaryl, heterocyclyl, or hydrogen. In some embodiments, $R^{16}$ is aryl, and $R^{17}$ is alkyl. In some embodiments, $R^{16}$ is aryl, and $R^{17}$ is hydrogen. In some embodiments, $R^{16}$ is heteroaryl, and $R^{17}$ is alkyl. In some embodiments, $R^{16}$ is heteroaryl, and $R^{17}$ is hydrogen. In some embodiments, $R^{16}$ is substituted heteroaryl, and $R^{17}$ is hydrogen. In some embodiments, $R^{16}$ is substituted alkyl, and $R^{17}$ is hydrogen. In some embodiments, $R^{17}$ is aryl, heteroaryl, or heterocyclyl, each of which is independently substituted or unsubstituted with halogen, alkyl, or hydroxyl. In some embodiments, $R^{16}$ is hydrogen, and $R^{17}$ is aryl or heteroaryl, substituted or unsubstituted with halogen or alkyl. In some embodiments, $R^{16}$ is alkyl, and $R^{17}$ is heteroaryl substituted with halogen or alkyl. In some embodiments, $R^{16}$ is hydrogen. In some embodiments, $R^{17}$ is aryl, heteroaryl, or heterocyclyl, each of which is independently substituted or unsubstituted with alkyl. In some embodiments, $R^{17}$ is aryl or heteroaryl, each of which is independently substituted with alkyl, wherein the alkyl is optionally substituted with fluorine, chlorine, bromine, iodine, or cyano. In some embodiments, $R^{16}$ is alkyl, alkenyl, aryl, heteroaryl, heterocyclyl, or hydrogen, and $R^{17}$ is aryl, heteroaryl, or heterocyclyl. In some embodiments, $R^{16}$ is hydrogen, and $R^{17}$ is phenyl, indolyl, piperidinyl, imidazolyl, thiazolyl, morpholinyl, pyrrolyl, or pyridinyl, each of which is substituted or unsubstituted. In some embodiments, $R^{16}$ is hydrogen, and $R^{17}$ is substituted phenyl. In some embodiments, $R^{16}$ is hydrogen, and $R^{17}$ is phenyl substituted with a sulfoxide group, carboxyl group, amide group, amino group, alkyl, alkoxy, hydroxy, halo, cyano, or heterocyclyl, each of which is independently substituted or unsubstituted. In some embodiments, $R^{17}$ is phenyl substituted with methoxy. In some embodiments, $R^{17}$ is phenyl substituted with a substituted sulfoxide group. In some embodiments, $R^{17}$ is phenyl substituted with a carboxyl group. In some embodiments, $R^{17}$ is a substituted amide group. In some embodiments, $R^{17}$ is substituted with methoxy and sulfonamide.

In some embodiments, each $R^3$ and $R^4$ is independently unsubstituted or substituted alkyl. In some embodiments, $R^3$ is hydrogen and $R^4$ is —C(O)$R^{19}$, —C(O)O$R^{19}$, alkyl, alkenyl, alkynyl, aryl, heteroaryl, or heterocyclyl, each of which is independently substituted or unsubstituted. In some embodiments, $R^3$ is hydrogen, and $R^4$ is alkyl, aryl, heteroaryl, or heterocyclyl, each of which is independently substituted or unsubstituted. In some embodiments, $R^3$ is H, and $R^4$ is substituted heterocyclyl. In some embodiments, $R^3$ is H, and $R^4$ is substituted or unsubstituted $C_4$-$C_6$-heterocyclyl. In some embodiments, $R^3$ is H, and $R^4$ is substituted alkyl. In some embodiments, $R^3$ is H, and $R^4$ is substituted $C_1$-$C_6$-alkyl. In some embodiments, $R^3$ is H, and $R^4$ is substituted or unsubstituted cycloalkyl. In some embodiments, $R^3$ is H, and $R^4$ is substituted or unsubstituted $C_4$-$C_6$-cycloalkyl. In some embodiments, $R^3$ is H, and $R^4$ is $C_4$-$C_6$-cycloalkyl substituted with an amino group.

In some embodiments, the compound is of the formula:

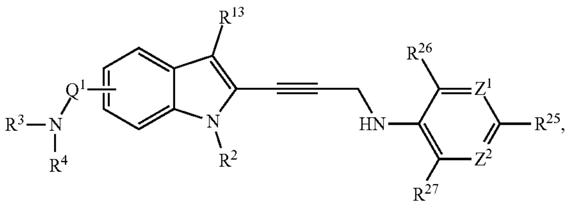

wherein:

$Q^1$ is C═O, C═S, $C═CR^{14}R^{15}$, $C═NR^{14}$, alkylene, alkenylene, or alkynylene, each of which is independently substituted or unsubstituted, or a bond;

$R^1$ is $—C(O)R^{16}$, $—C(O)OR^{16}$, $—C(O)NR^{16}R^{17}$, $—OR^{16}$, $—SR^{16}$, $—NR^{16}R^{17}$, $—NR^{16}C(O)R^{16}$, $—OC(O)R^{16}$, C═O, C═S, —CN, $—SiR^{16}R^{17}R^{18}$, alkyl, alkenyl, alkynyl, aryl, heteroaryl, or heterocyclyl, each of which is independently substituted or unsubstituted, or hydrogen;

each $R^3$ and $R^4$ is independently, $—C(O)R^{19}$, $—C(O)OR^{19}$, $—C(O)NR^{19}R^{20}$, $—SOR^{19}$, $—SO_2R^{19}$, alkyl, alkylene, alkenyl, alkenylene, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;

each $Z^1$ and $Z^2$ is independently $CR^{28}$, $CR^{29}$, or N;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently $—C(O)R^{21}$, $—C(O)OR^{21}$, $—C(O)NR^{21}R^{22}$, $—OR^{21}$, $—SR^{21}$, $—NR^{21}R^{22}$, $—NR^{21}C(O)R^{22}$, $—OC(O)R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is $C(O)R^{23}$, $—C(O)OR^{23}$, $—C(O)NR^{23}R^{24}$, $—OR^{23}$, $—SR^{23}$, $—NR^{23}R^{24}$, $—NR^{23}C(O)R^{24}$, $—OC(O)R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen;

each $R^{23}$ and $R^{24}$ is independently alkyl, alkenyl, alkynyl, aryl, heteroaryl, or heterocyclyl, each of which is independently substituted or unsubstituted, or hydrogen; and each $R^{25}$, $R^{26}$, $R^{27}$, $R^{28}$, and $R^{29}$ is independently hydrogen or a substituent selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and ester group, or a pharmaceutically-acceptable salt thereof.

In some embodiments, $Z^1$ is N. In some embodiments, $Z^1$ and $Z^2$ are N. In some embodiments, each $R^{25}$ and $R^{26}$ is independently a halogen. In some embodiments, $R^{25}$ is

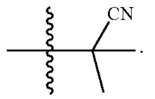 [SMILES: *C(C)(C)C#N]

In some embodiments, $R^{25}$ is a substituted sulfone group. In some embodiments, $R^{25}$ is a sulfone group substituted with alkyl. In some embodiments, $R^{25}$ is a methanesulfonyl group. In some embodiments, $R^{25}$ is a sulfone group substituted with an amino group. In some embodiments, $R^{25}$ is a sulfonamide. In some embodiments, $R^{25}$ is a carboxy group. In some embodiments, $R^{25}$ is a methoxycarbonyl group.

In some embodiments, the compound is of the formula:

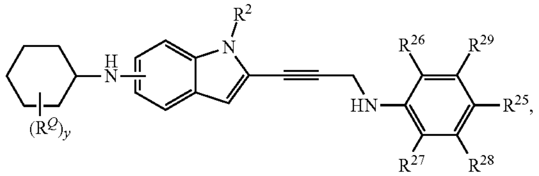

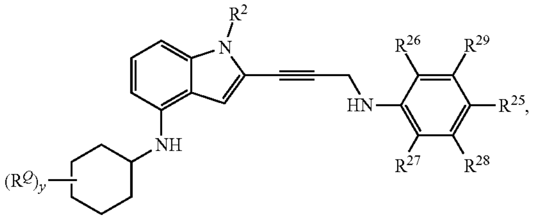

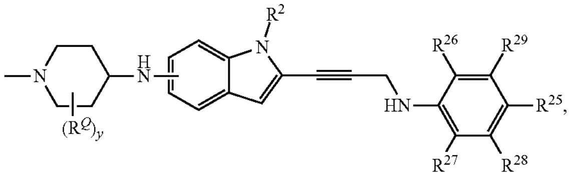

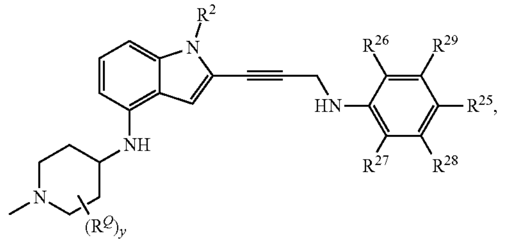

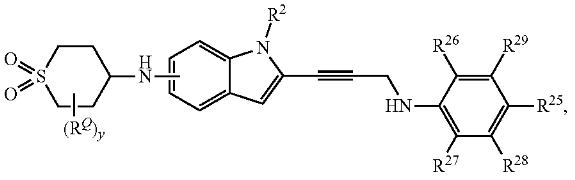

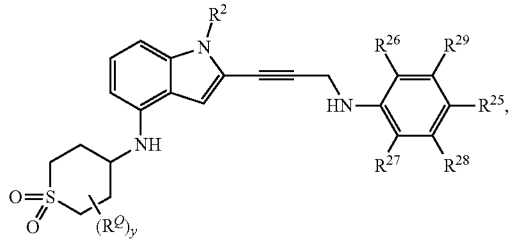

-continued

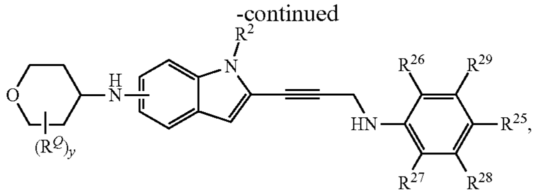

or

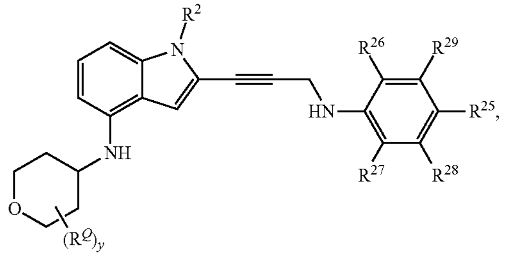

wherein:

$R^2$ is —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^Q$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted;

y is 0, 1, 2, 3, or 4;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{25}$, $R^{26}$, $R^{27}$, $R^{28}$, and $R^{29}$ is independently hydrogen or a substituent selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and ester group.

or a pharmaceutically-acceptable salt thereof.

In some embodiments, the compound is of the formula:

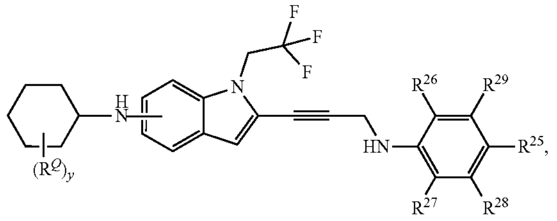

-continued

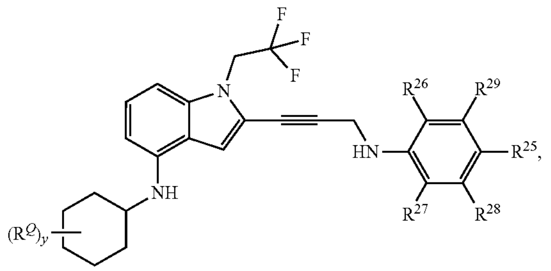

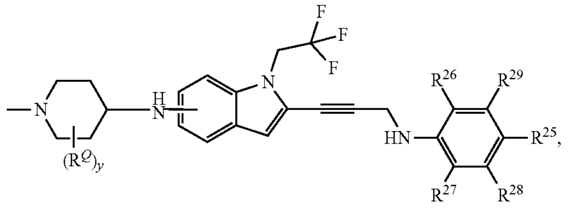

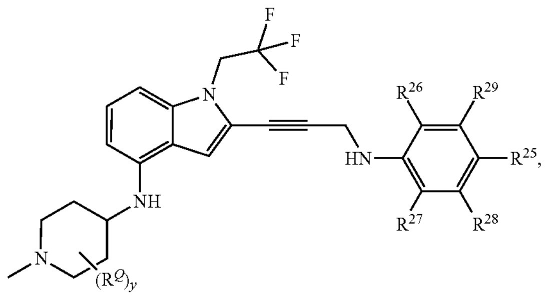

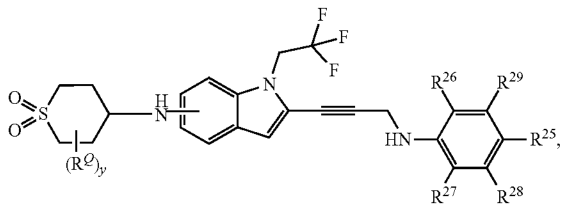

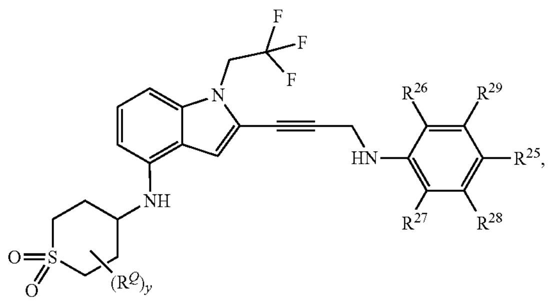

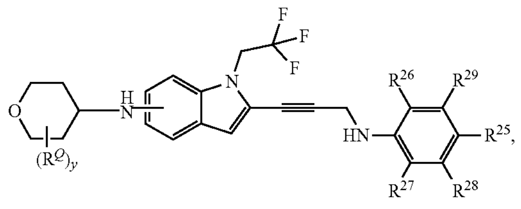

or

-continued

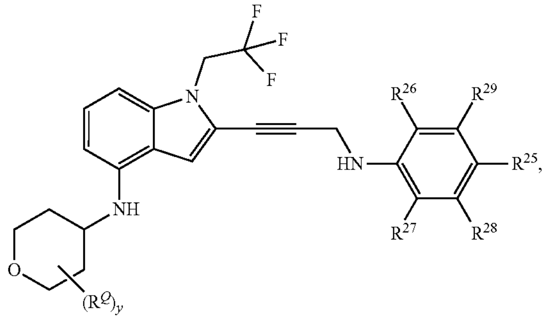

In some embodiments, $R^{25}$ is a substituted sulfone group. In some embodiments, $R^{25}$ is a sulfone group substituted with alkyl. In some embodiments, $R^{25}$ is a methanesulfonyl group. In some embodiments, $R^{25}$ is a sulfone group substituted with an amino group. In some embodiments, $R^{25}$ is a sulfonamide. In some embodiments, $R^{25}$ is a carboxy group. In some embodiments, $R^{25}$ is a methoxycarbonyl group.

In some embodiments, the compound is of the formula:

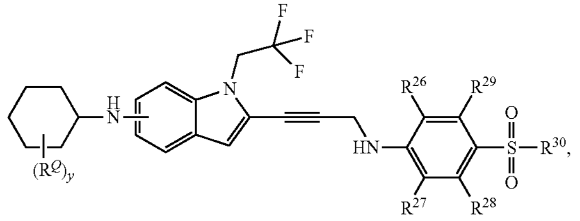

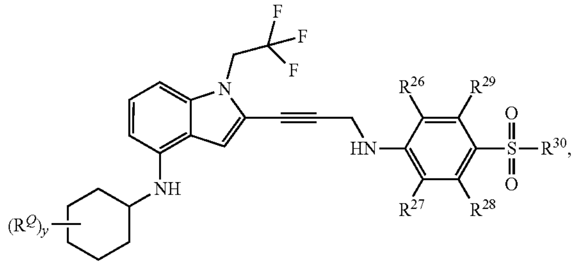

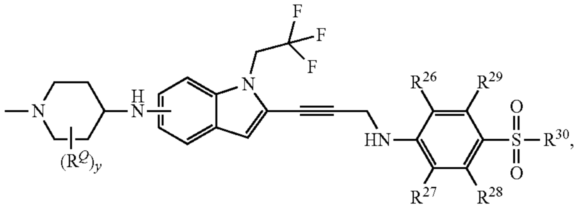

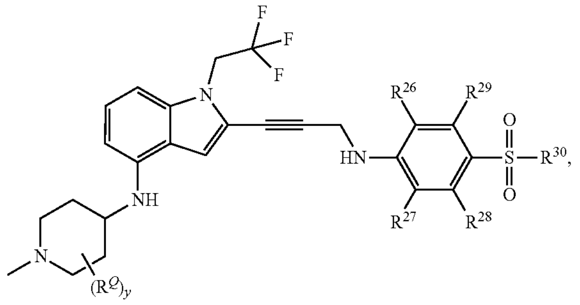

-continued

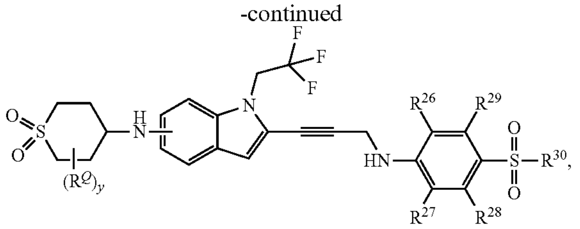

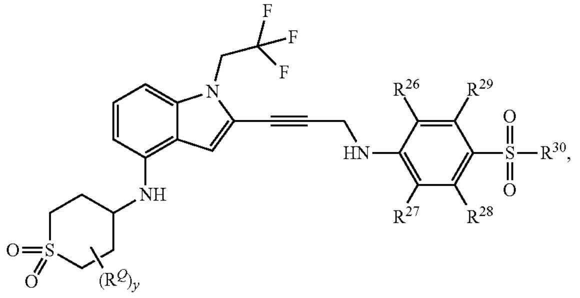

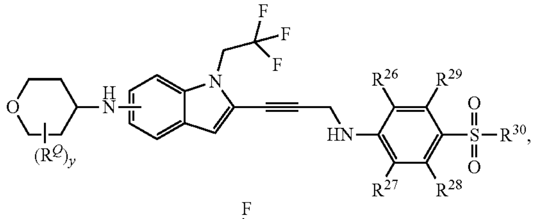

or

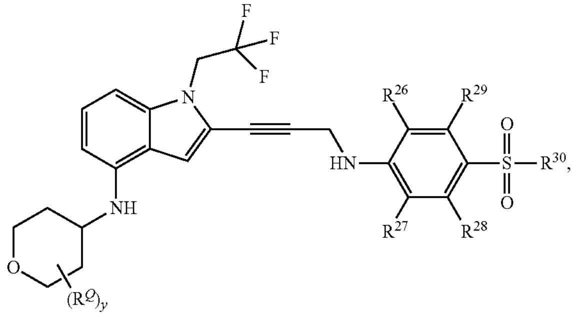

wherein:

each $R^Q$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted;

y is 0, 1, 2, 3, or 4;

each $R^{21}$ and $R^{22}$ is independently alkyl, alkenyl, alkynyl, aryl, heteroaryl, or heterocyclyl, each of which is independently substituted or unsubstituted, or hydrogen;

each $R^{26}$, $R^{27}$, $R^{28}$, and $R^{29}$ is independently hydrogen or a substituent selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, haloalkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and ester group; and $R^{30}$ is alkyl or an amino group, each of which is substituted or unsubstituted, or a pharmaceutically-acceptable salt thereof.

In some embodiments, $R^{30}$ is methyl. In some embodiments, $R^{30}$ is $NH_2$. In some embodiments, $R^{30}$ is NHMe. In some embodiments, $R^{30}$ is $NMe_2$.

In some embodiments, the compound is of the formula:

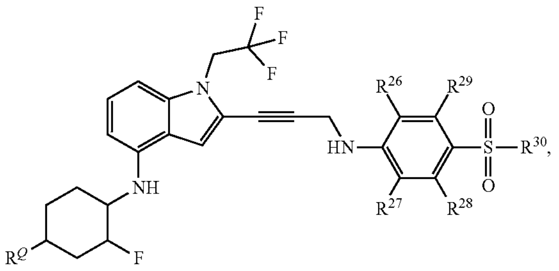

wherein $R^{30}$ is alkyl or an amino group, each of which is unsubstituted or substituted. In some embodiments, $R^{30}$ is methyl.

Non-limiting examples of compounds of the current disclosure include the following:

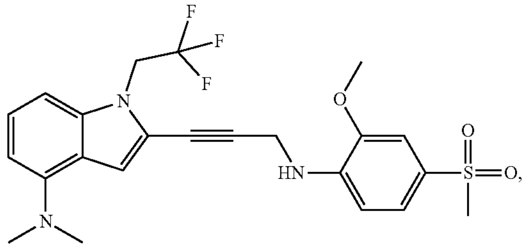

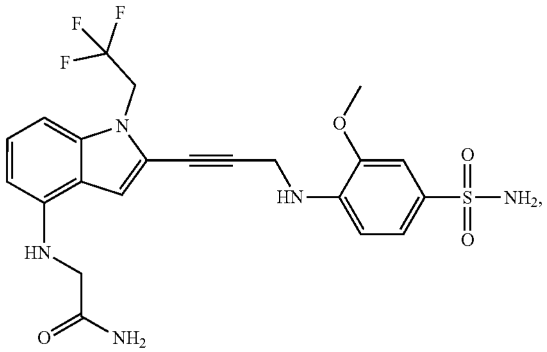

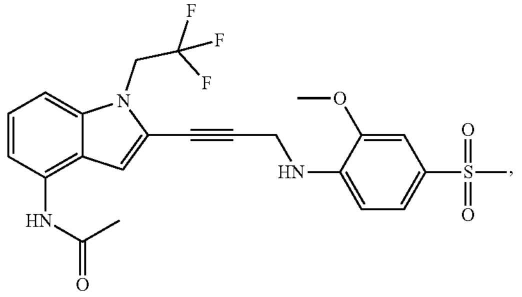

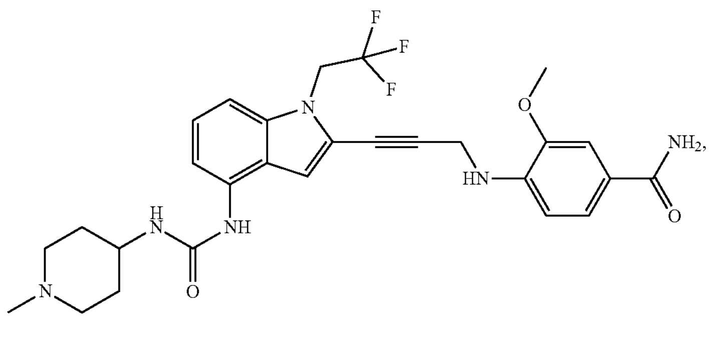

-continued
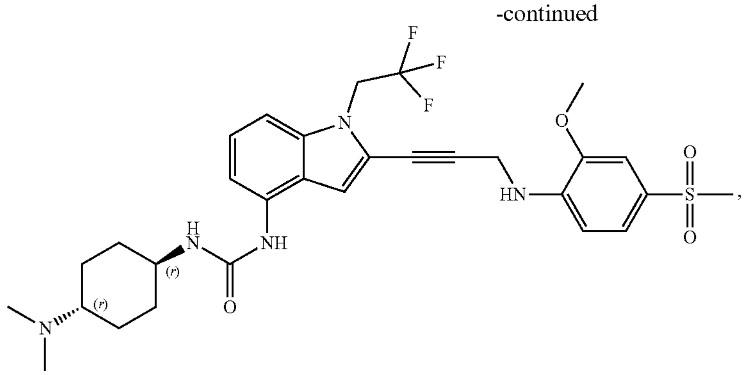
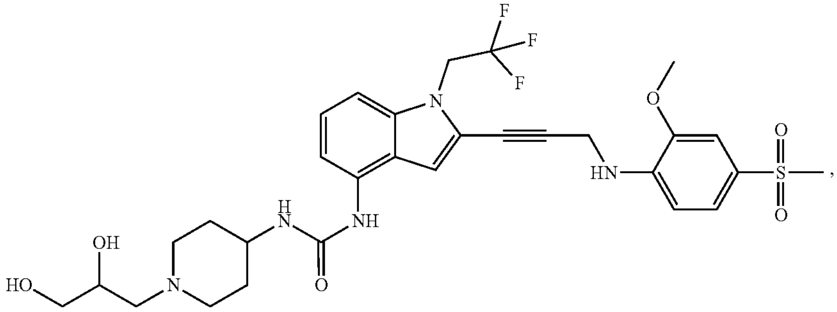
and
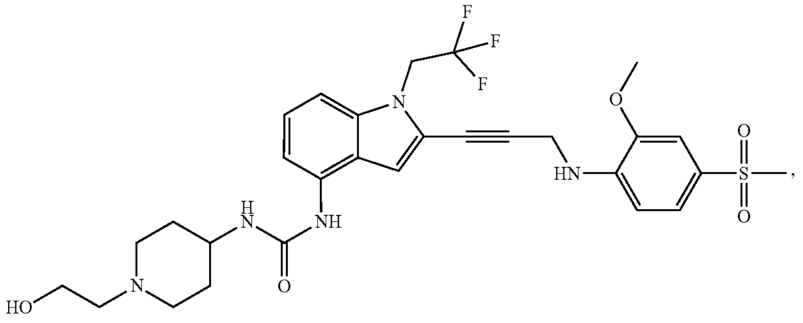
or a pharmaceutically-acceptable salt thereof.
Non-limiting examples of compounds of the current disclosure include the following:
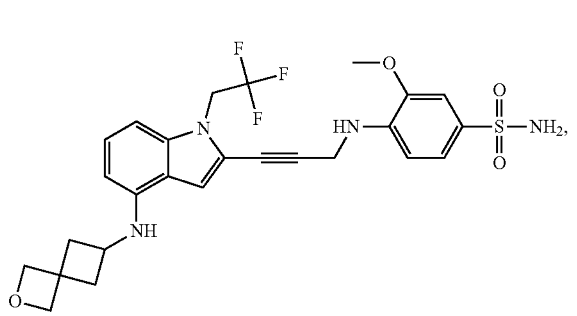
-continued
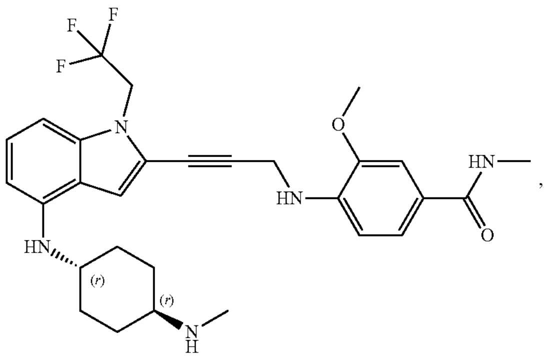

-continued
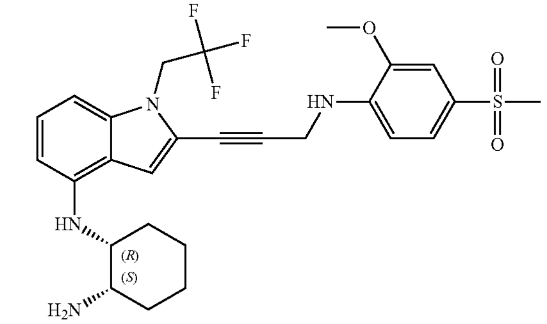
,
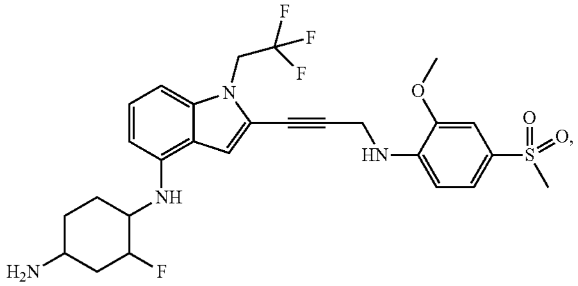
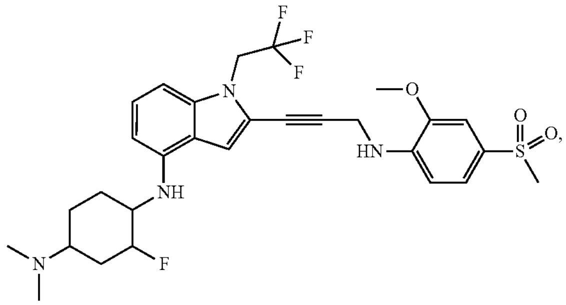
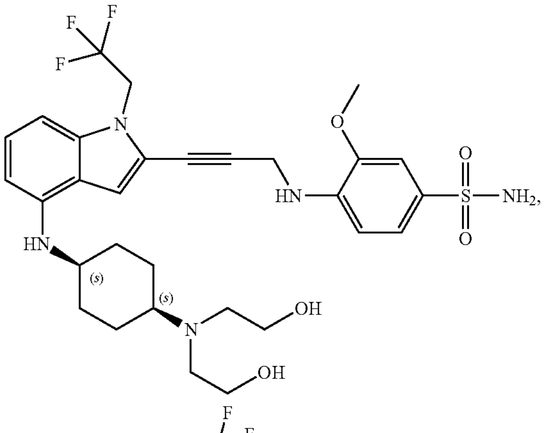
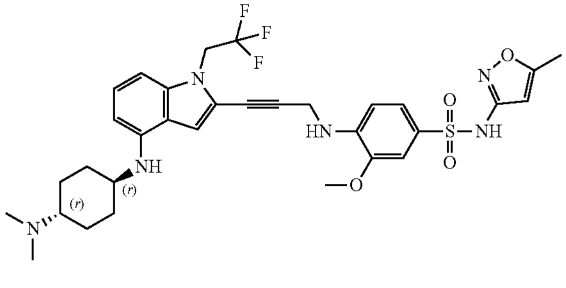
,
-continued
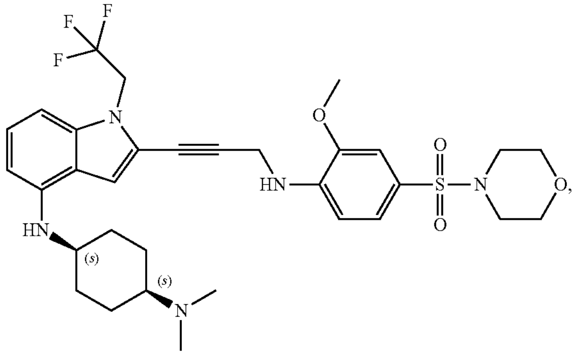
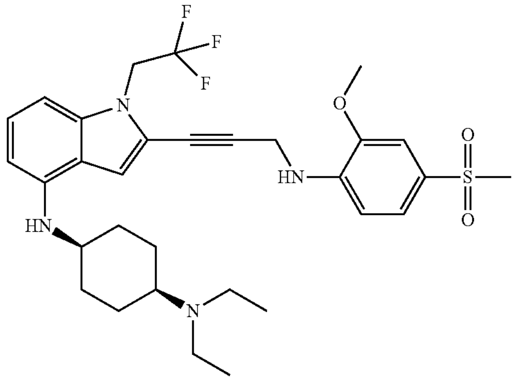
,
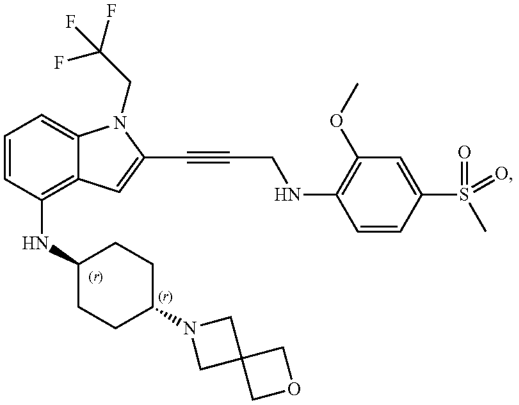
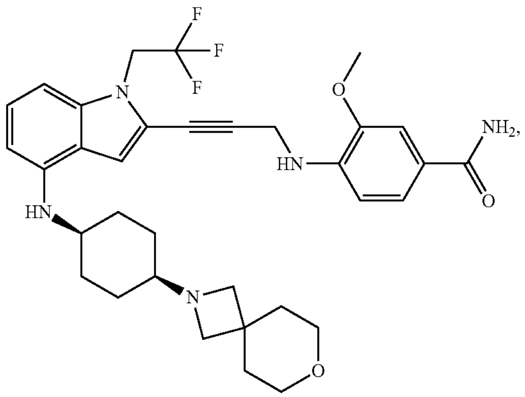
and -continued
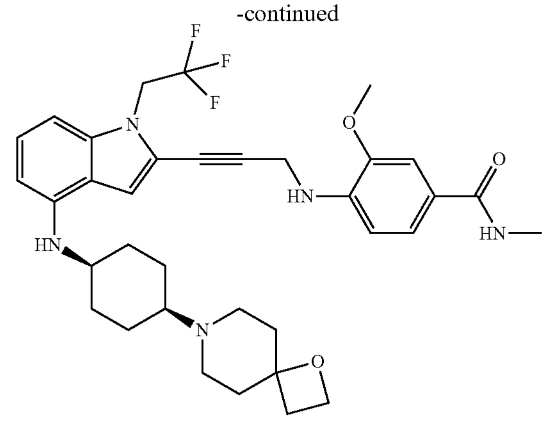
,
or a pharmaceutically-acceptable salt thereof.
Non-limiting examples of compounds of the current disclosure include the following:
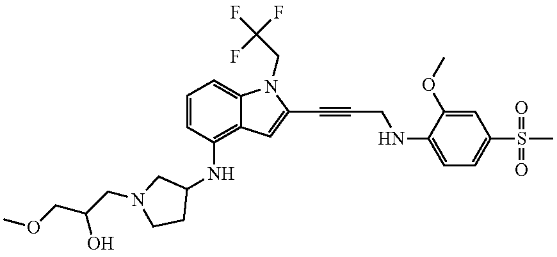
,
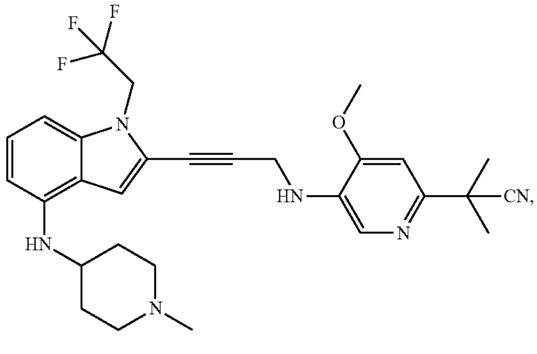
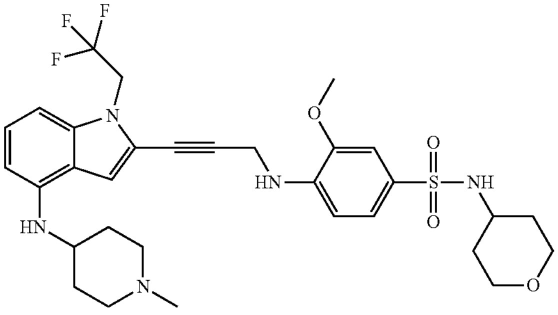
,
-continued
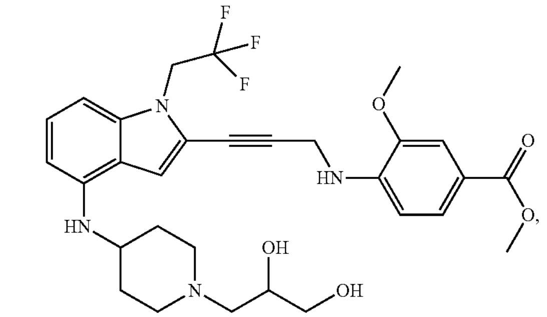
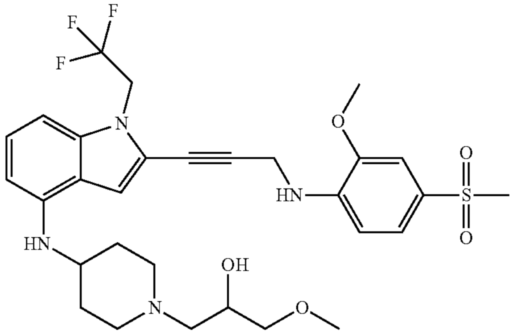
, and
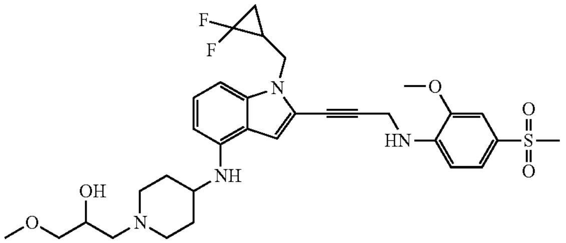
,
or a pharmaceutically-acceptable salt thereof.
Non-limiting examples of compounds of the current disclosure include the following:
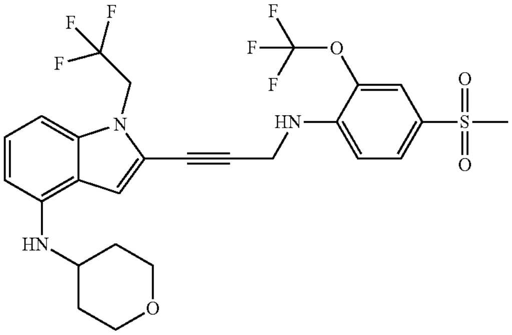
,
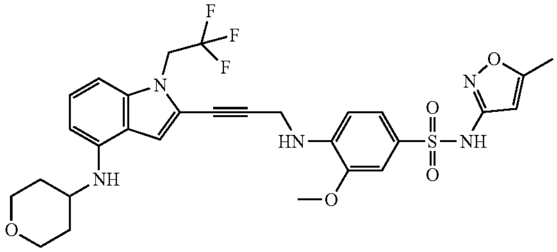
, -continued
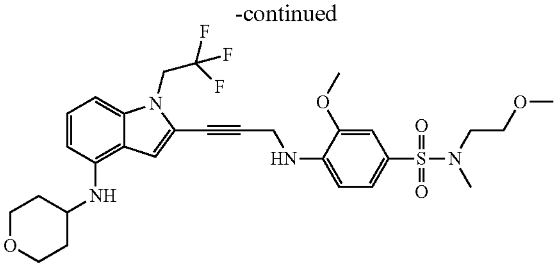
,
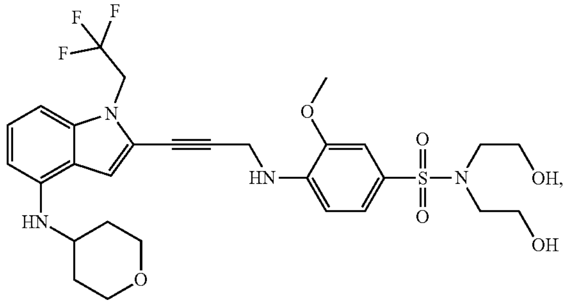
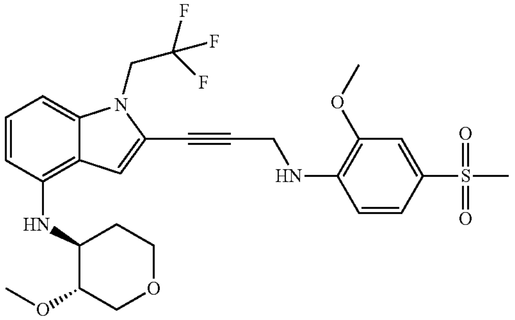
,
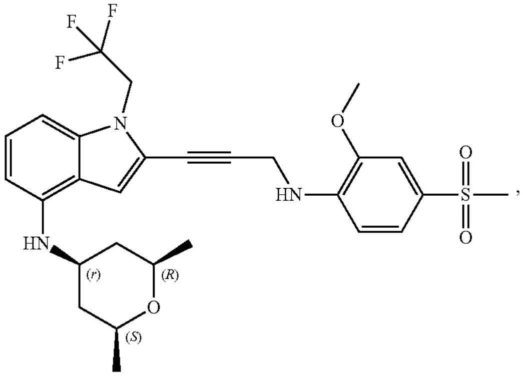
, and
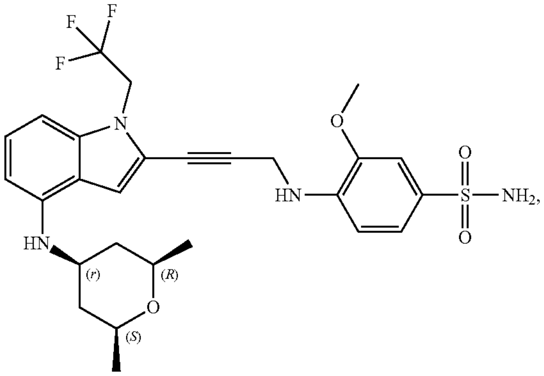
or a pharmaceutically-acceptable salt thereof.
Non-limiting examples of compounds of the current disclosure include the following:
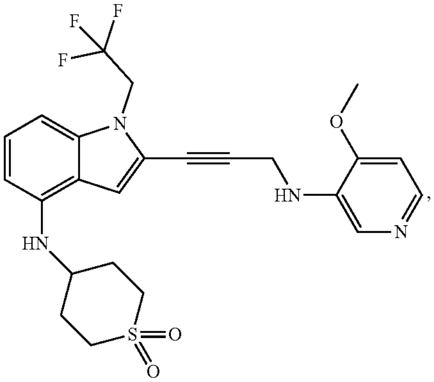
,
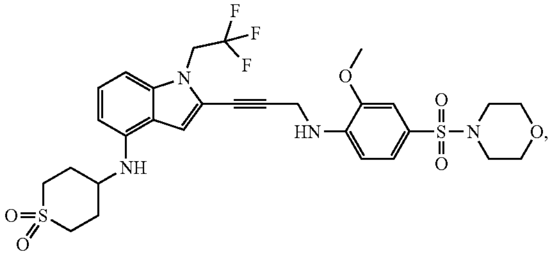
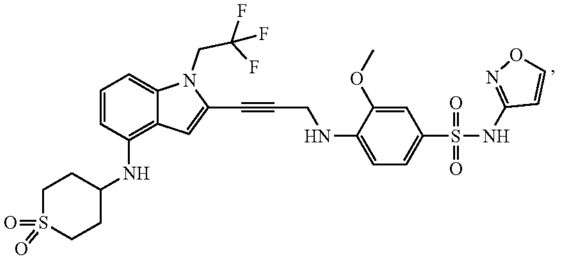
,
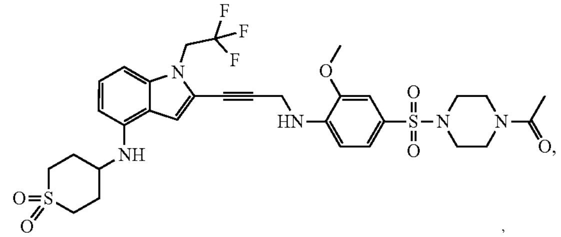
,
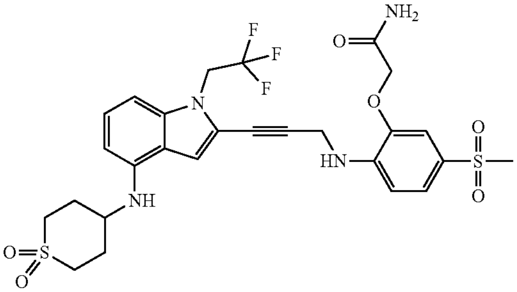
, and
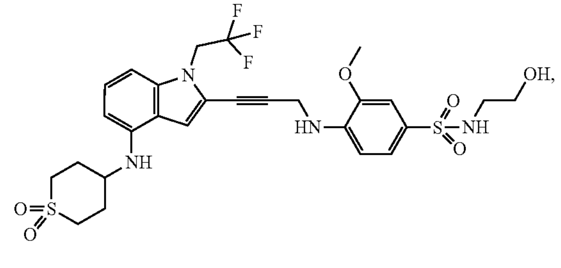
or a pharmaceutically-acceptable salt thereof.

Non-limiting examples of compounds of the current disclosure include the following:
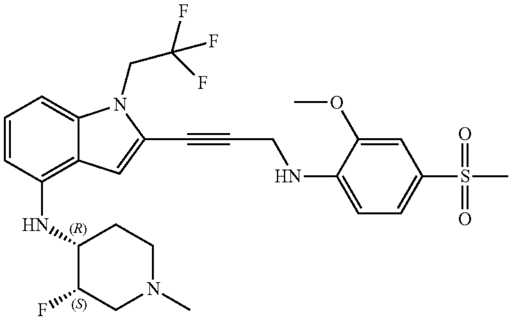
,
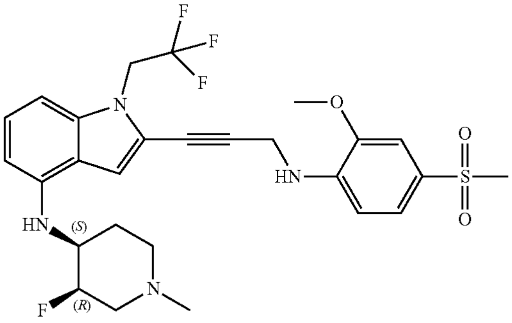
,
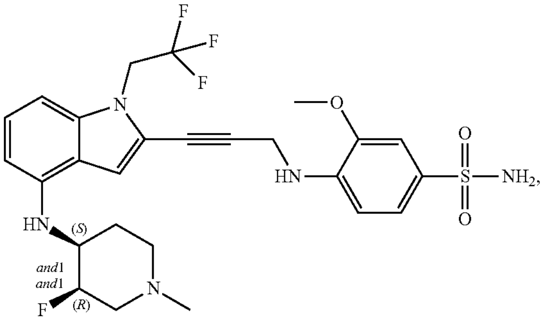
,
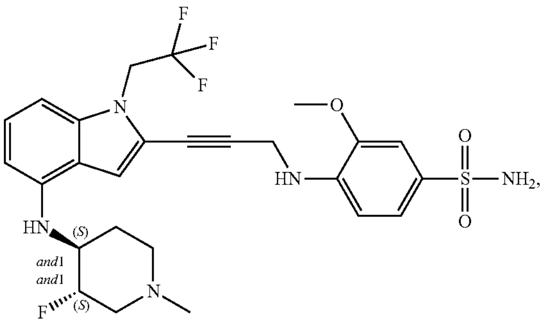
,
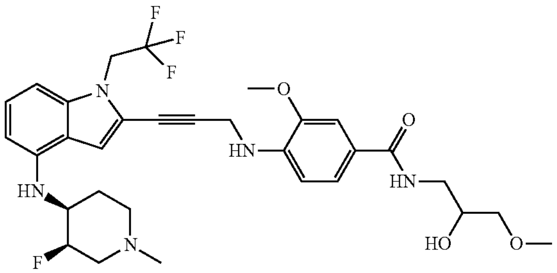
,
-continued
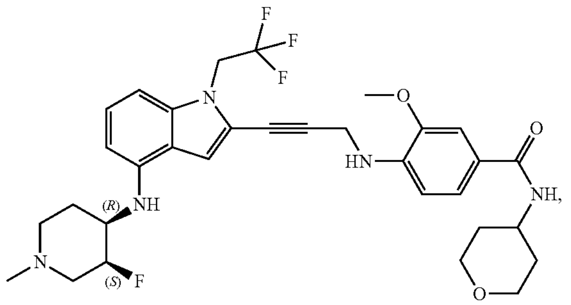
,
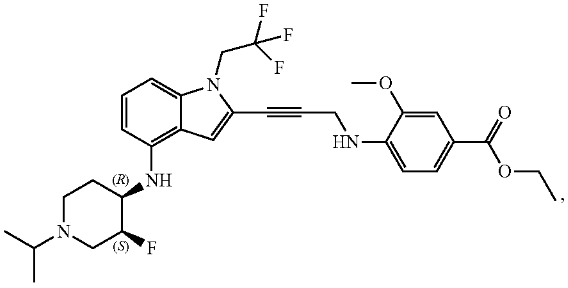
,
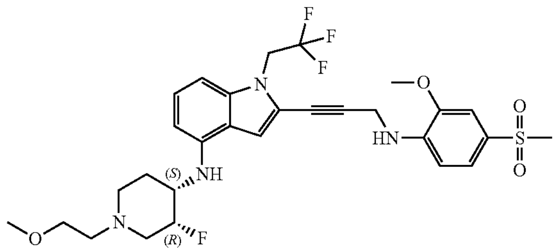
,
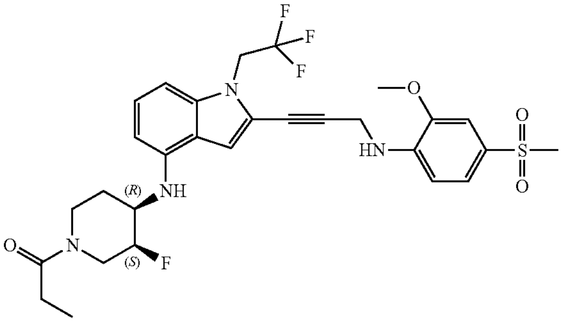
,
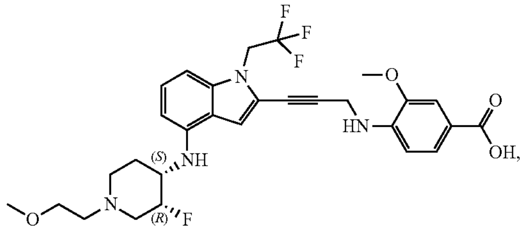
and -continued
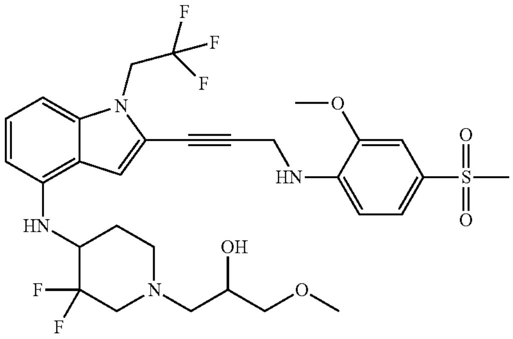
,
or a pharmaceutically-acceptable salt thereof.
Non-limiting examples of compounds of the current disclosure include the following:
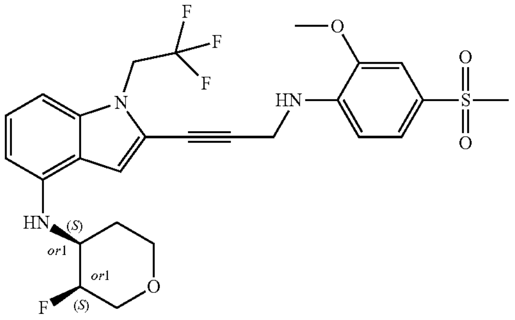
and
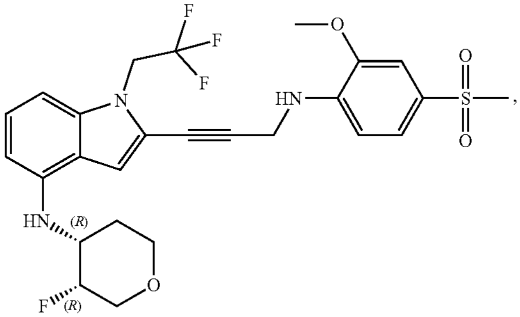
,
or a pharmaceutically-acceptable salt thereof.
Non-limiting examples of compounds of the current disclosure include the following:
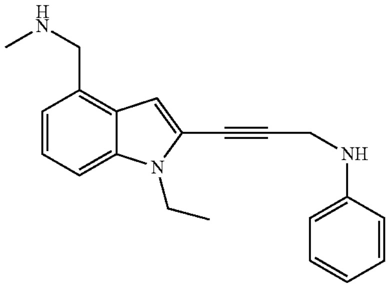
;
-continued
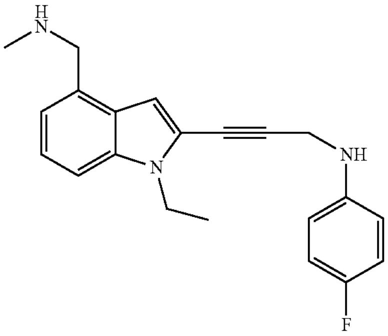
;
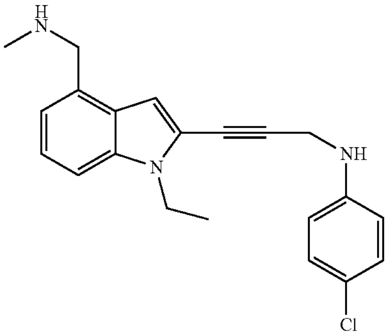
;
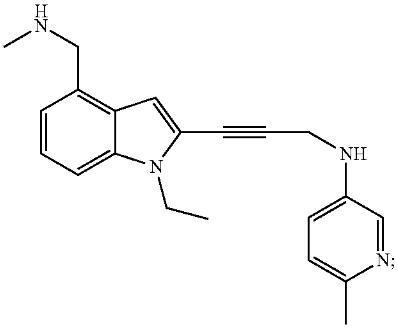
;
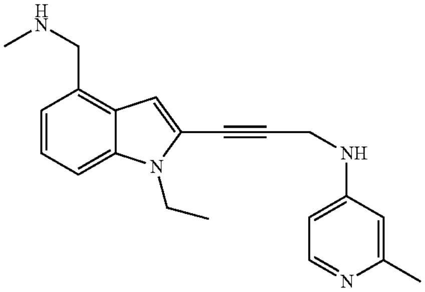
;
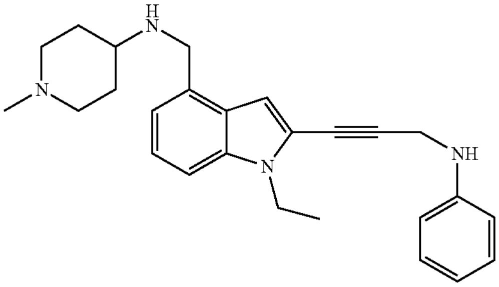
;

-continued
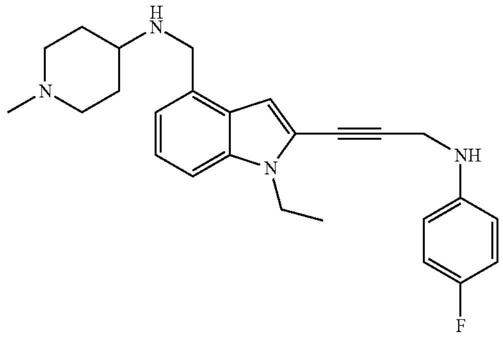
;
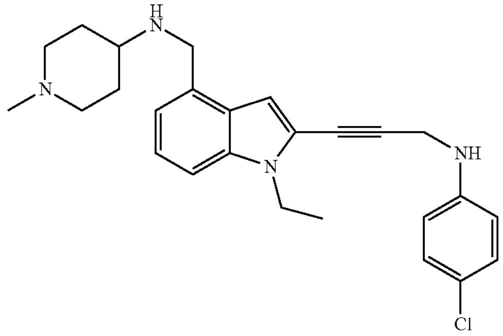
;
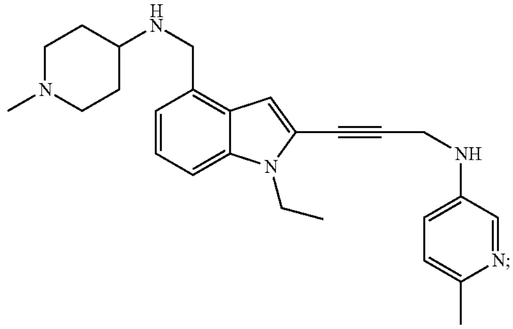
;
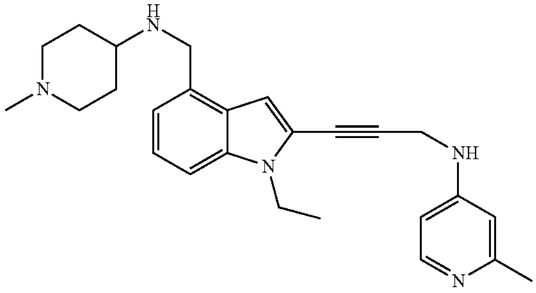
;
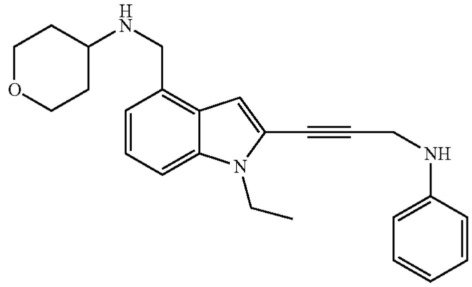
;
-continued
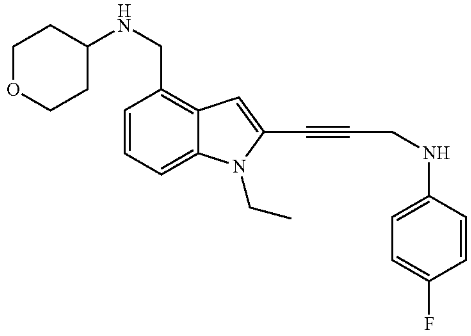
;
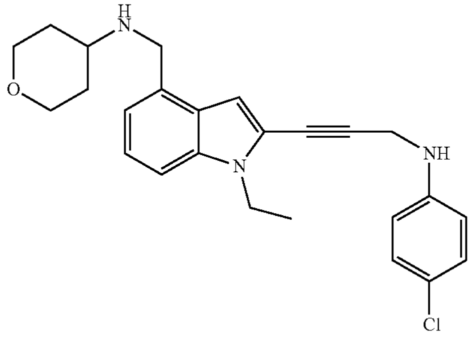
;
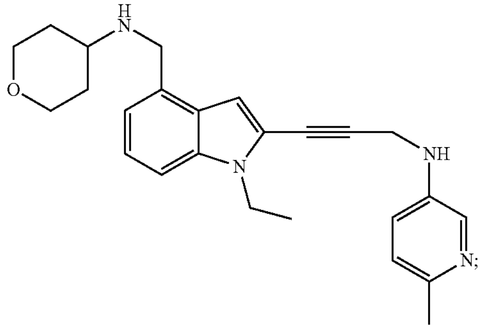
;
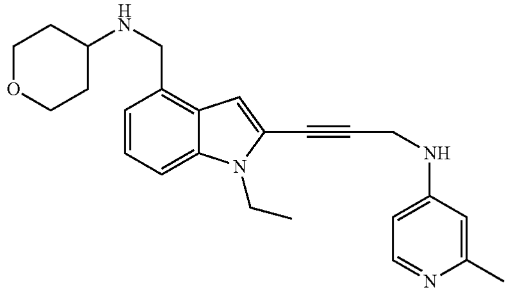
;
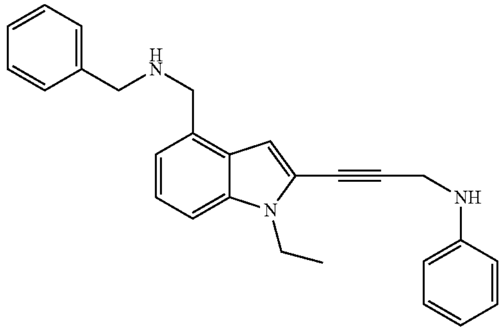
;

-continued
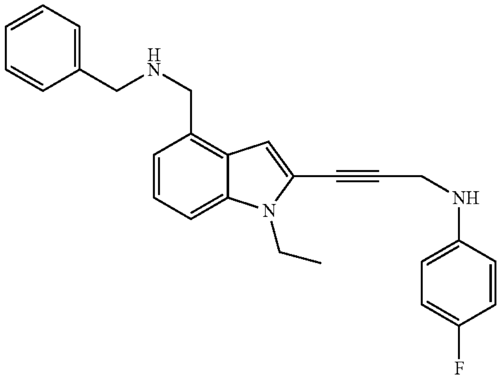
;
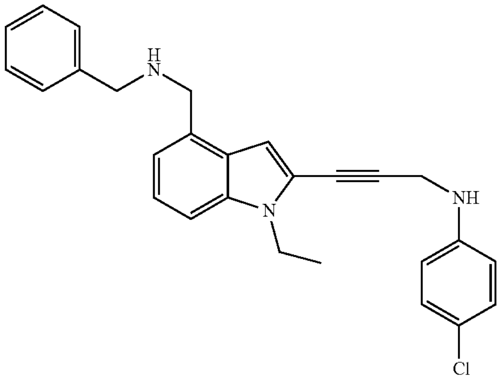
;
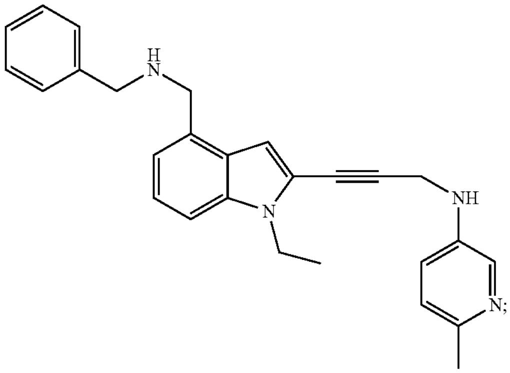
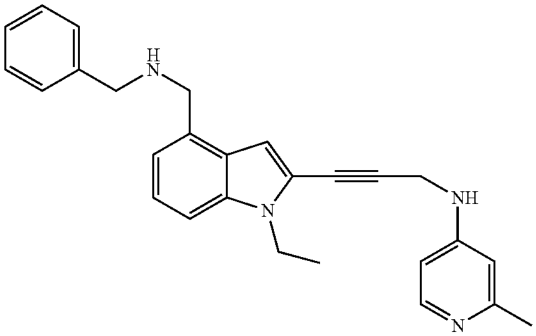
;
-continued
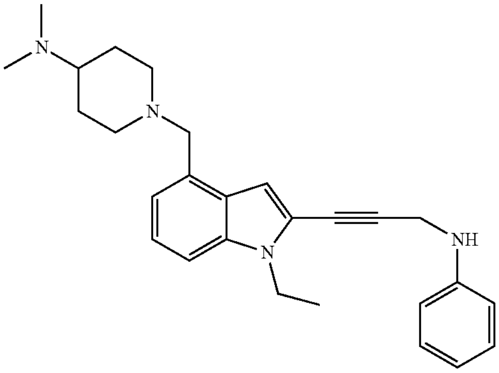
;
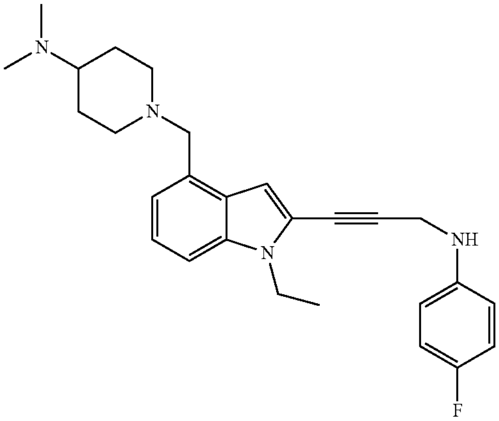
;
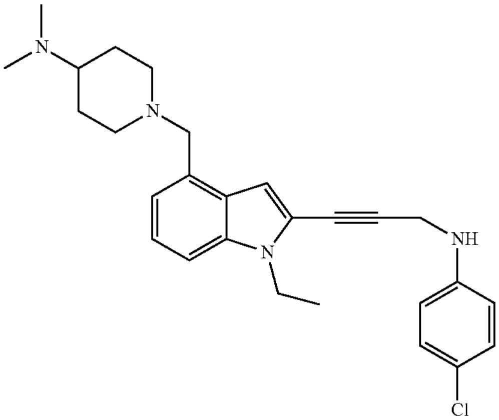
;
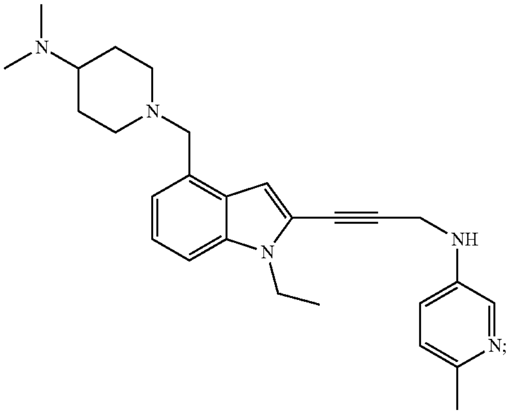

-continued
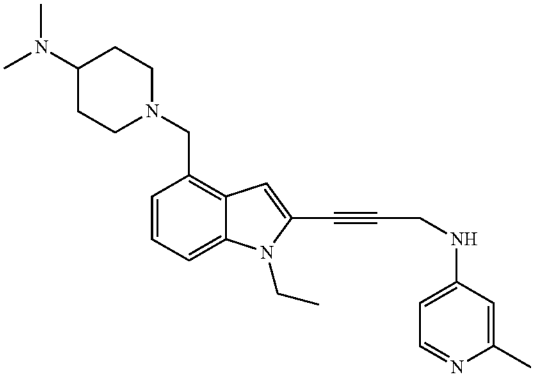
;
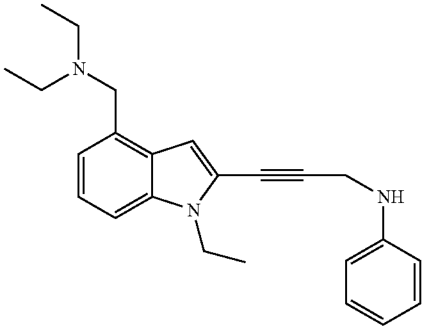
;
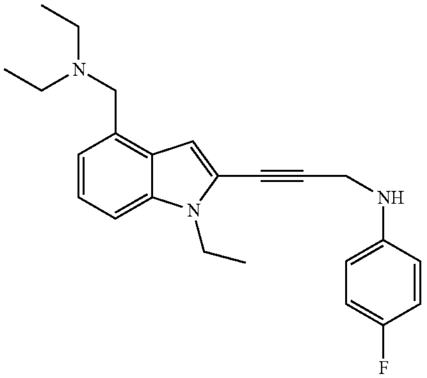
;
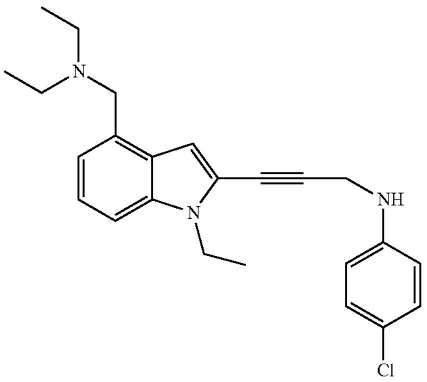
;
-continued
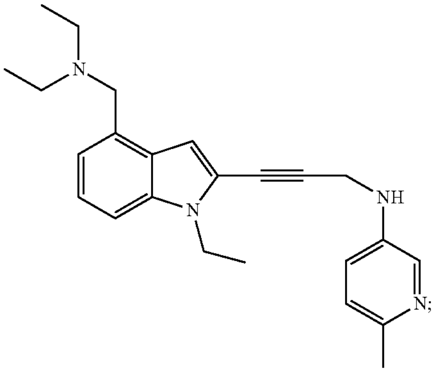
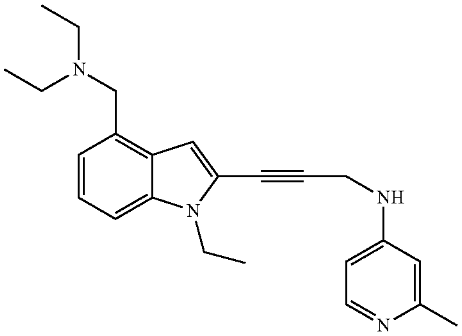
;
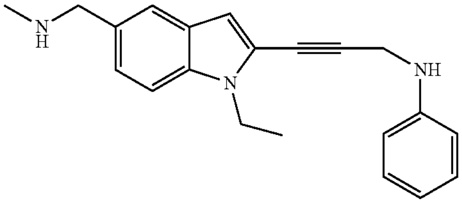
;
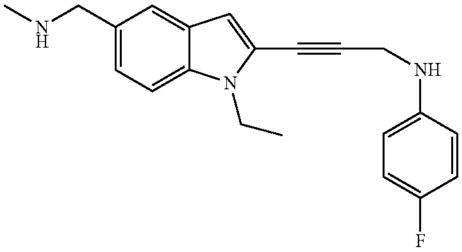
;
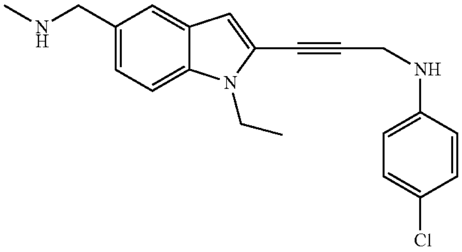
;
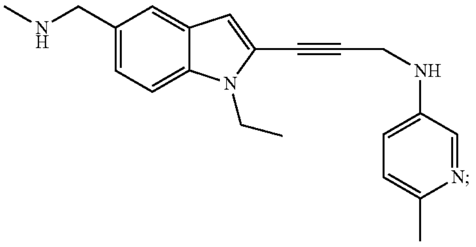

-continued
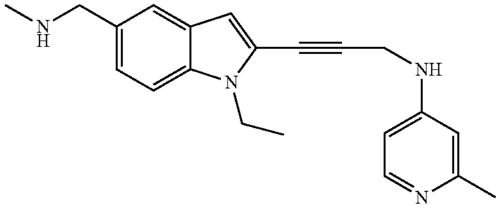
;
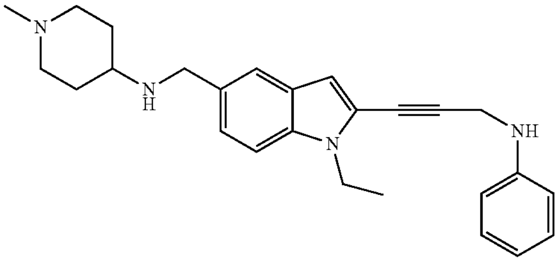
;
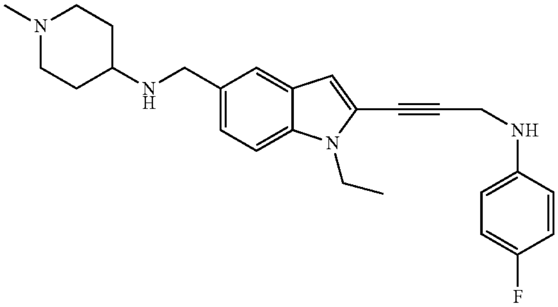
;
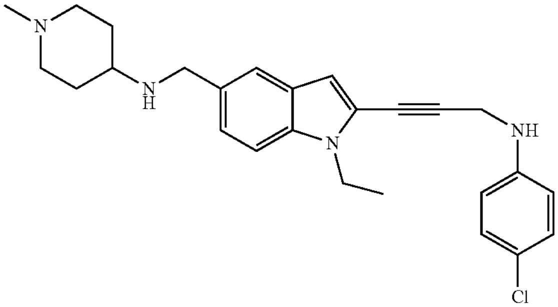
;
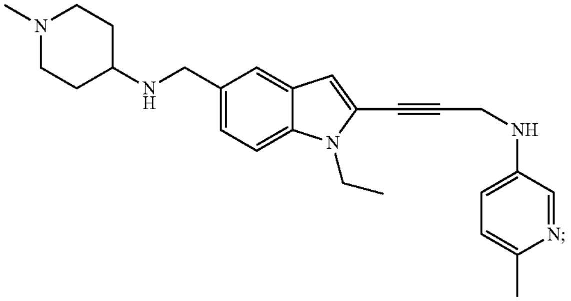
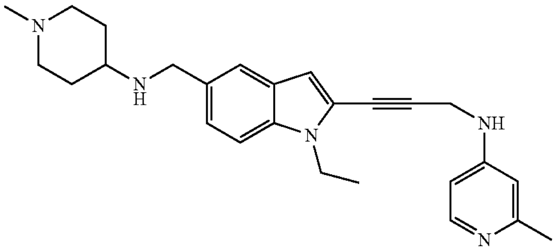
;
-continued
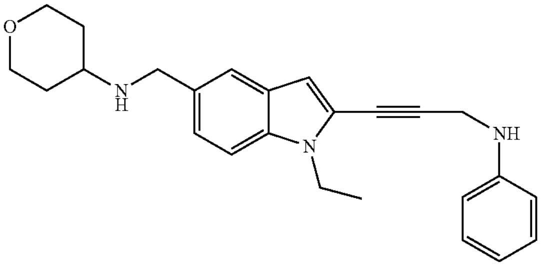
;
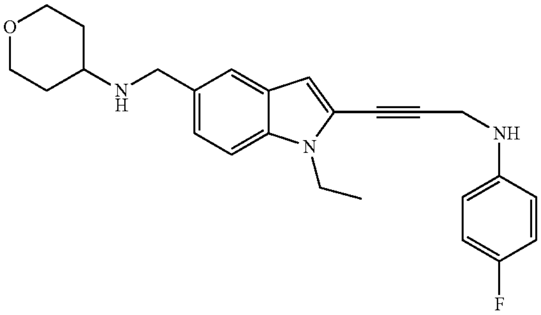
;
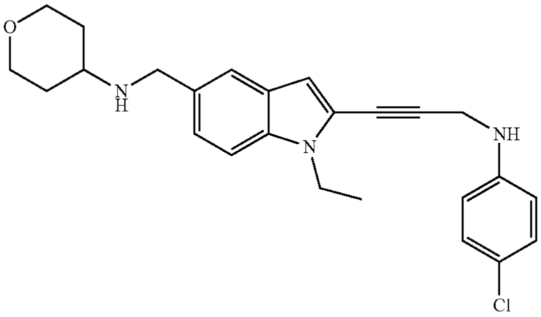
;
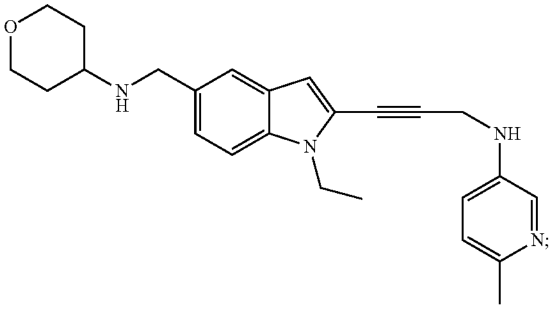
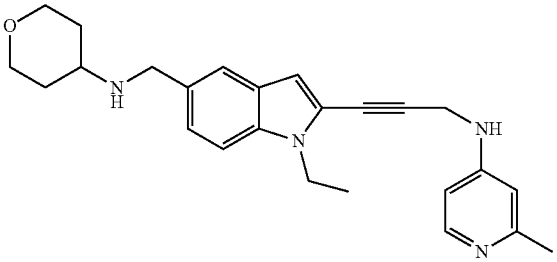
;
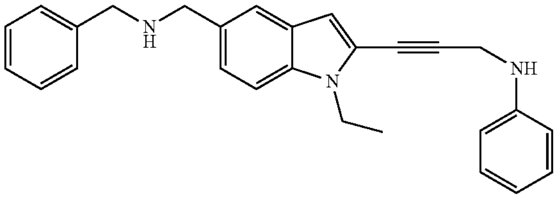
;

-continued
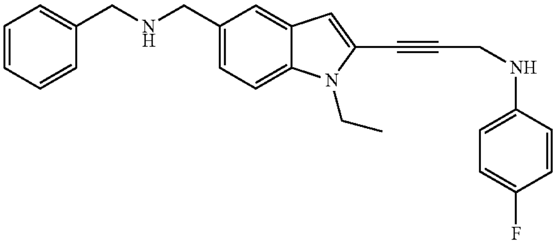
;
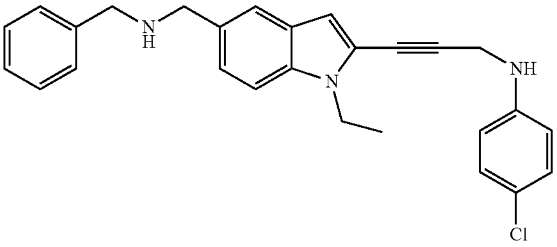
;
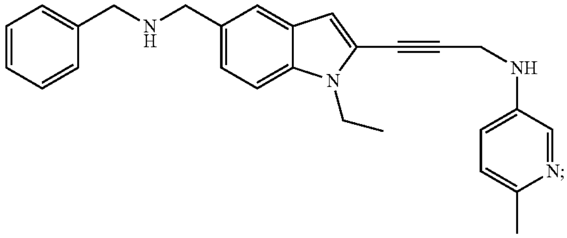
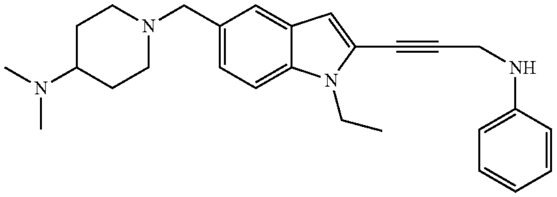
;
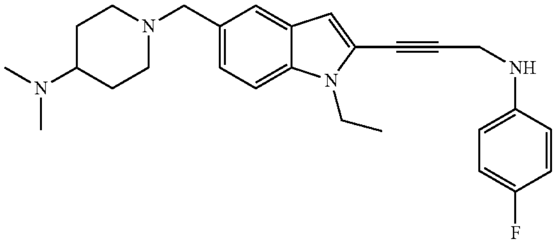
;
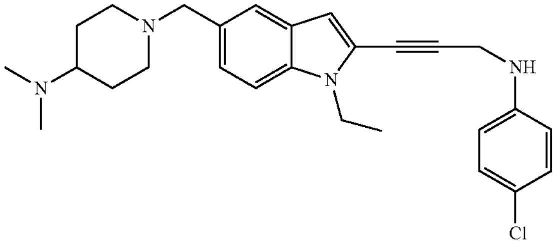
;
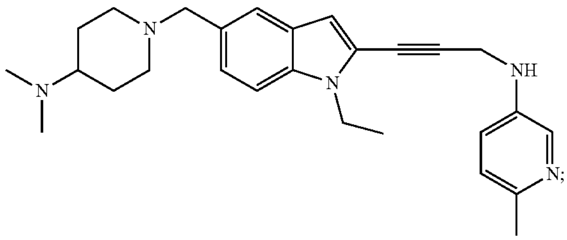
-continued
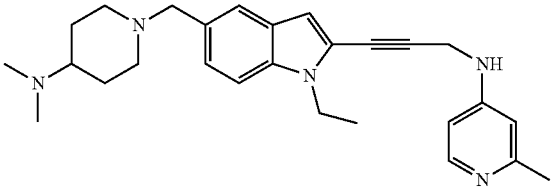
;
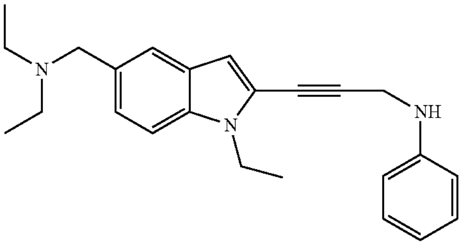
;
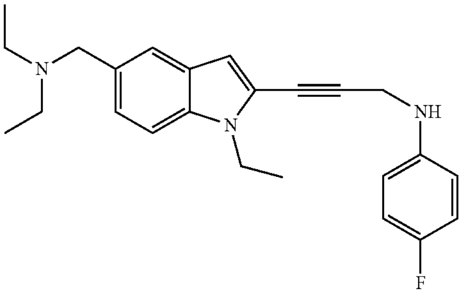
;
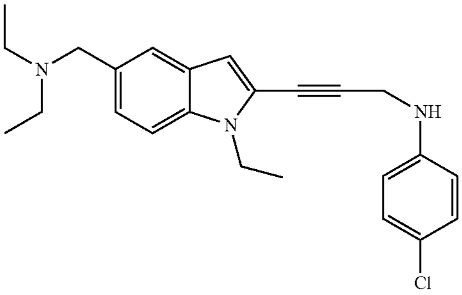
;
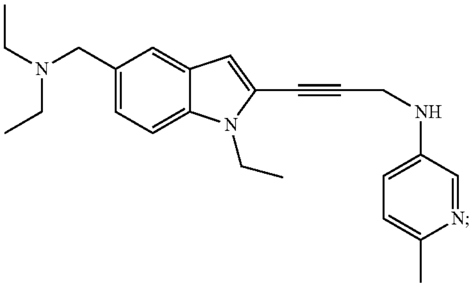

-continued
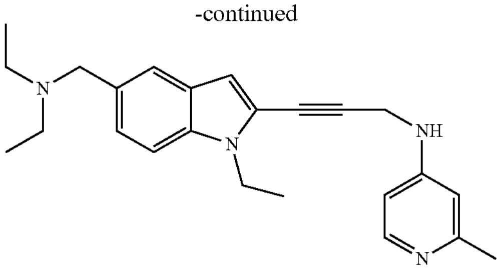
;
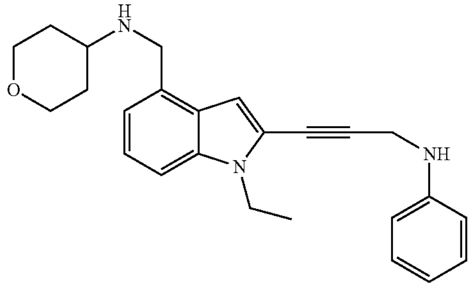
; and
-continued
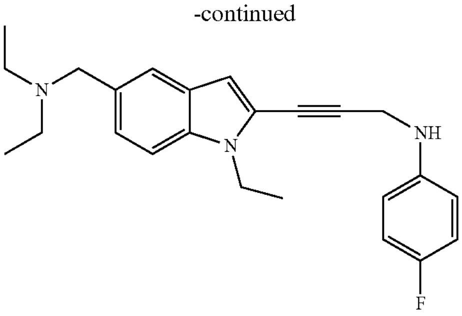
,
or a pharmaceutically-acceptable salt of any of the foregoing.
Non-limiting examples of compounds of the current disclosure include the following:
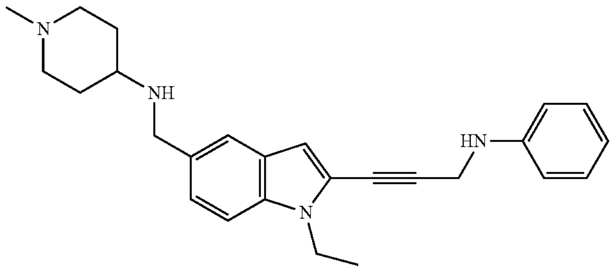
;
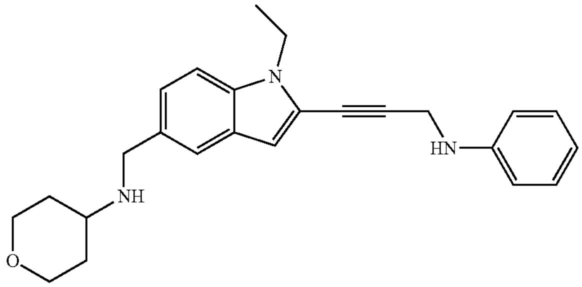
;
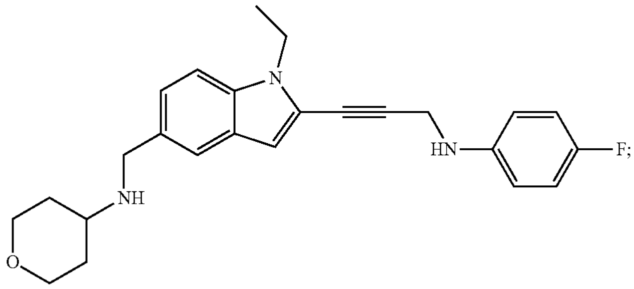
;
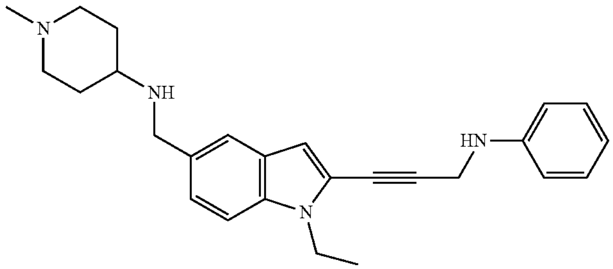
;
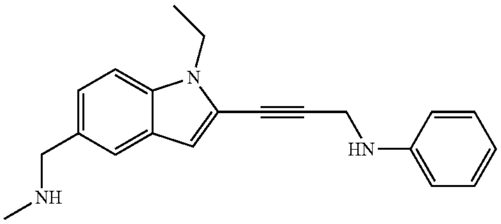
;

-continued
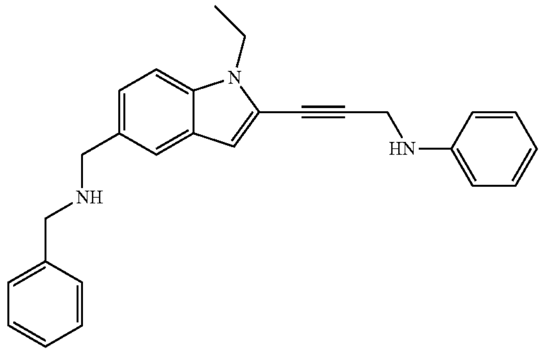
;
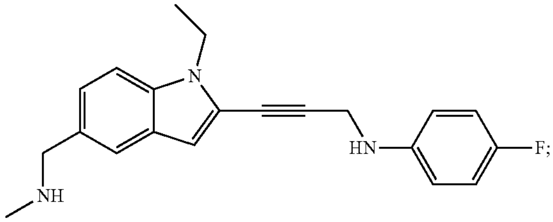
;
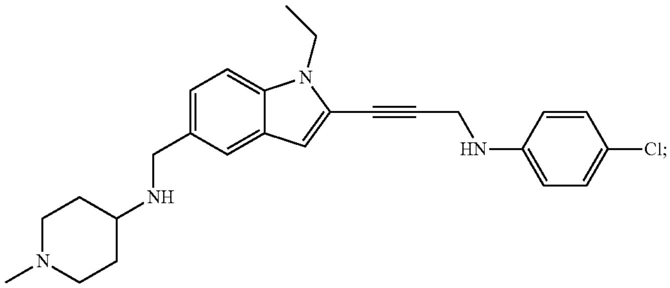
;
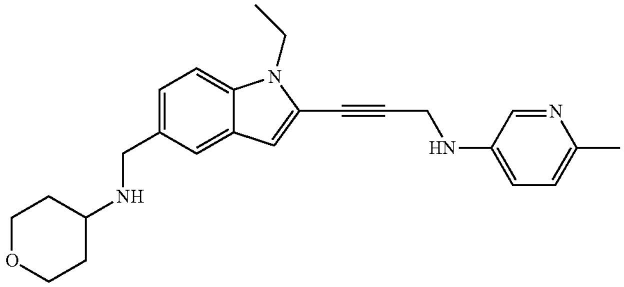
;
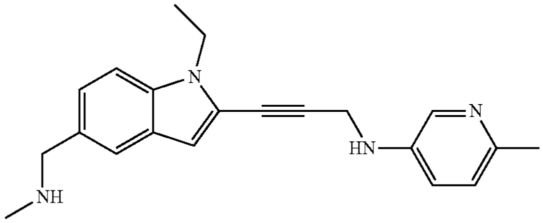
;
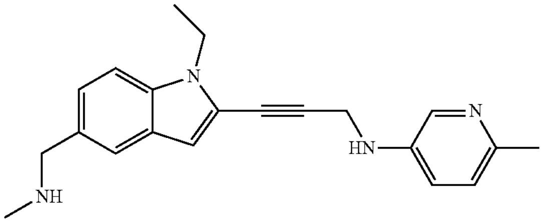
;
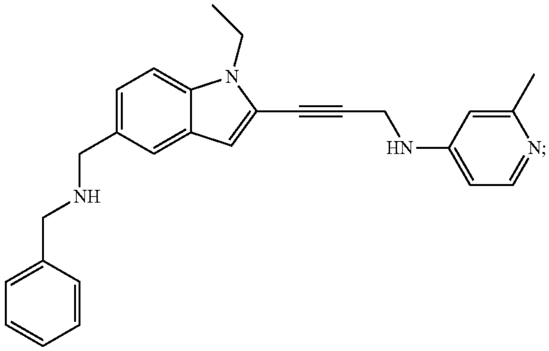
;
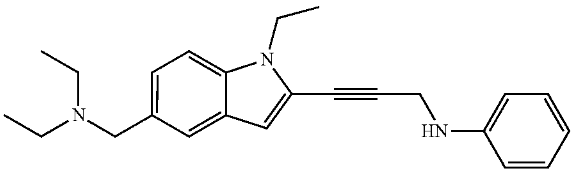
;

-continued
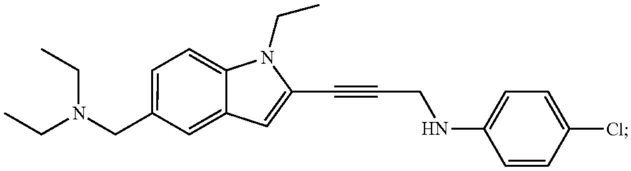
;
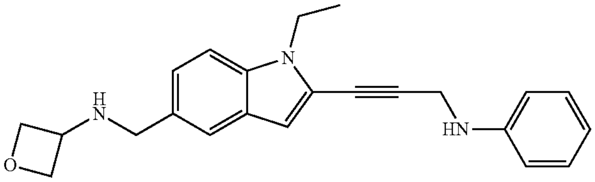
;
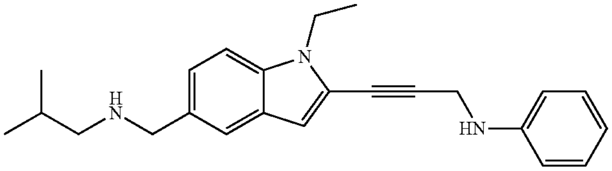
;
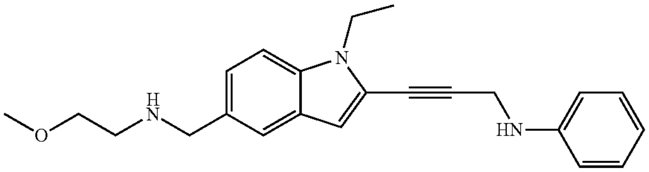
;
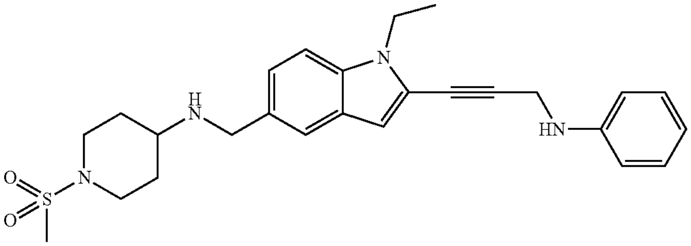
;
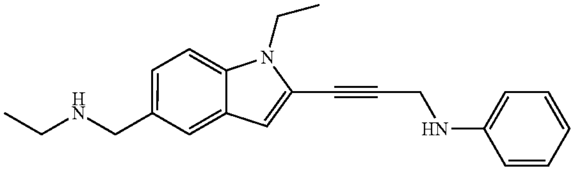
;
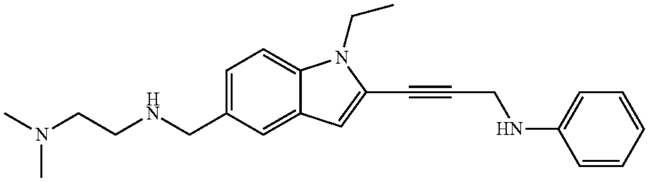
;
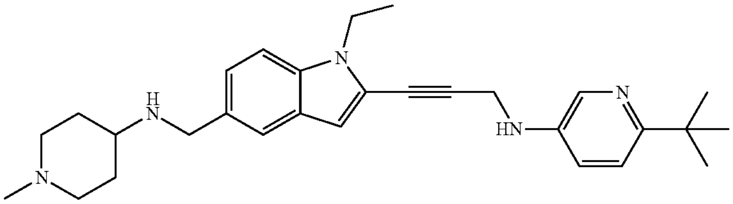
;
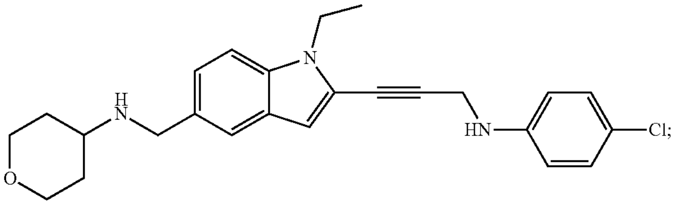
;

-continued
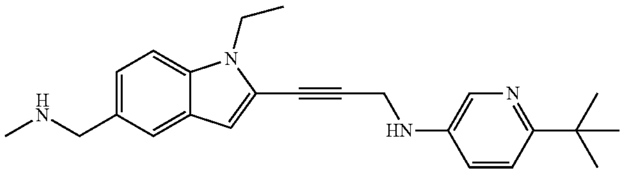
;
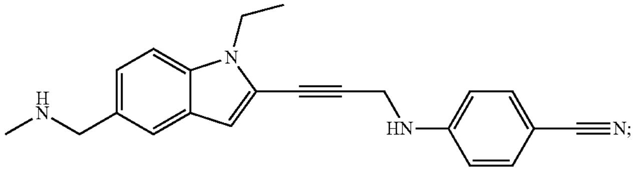
;
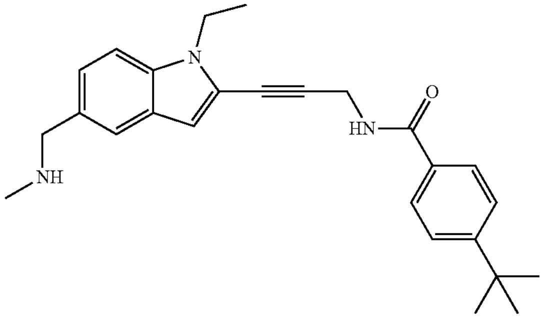
;
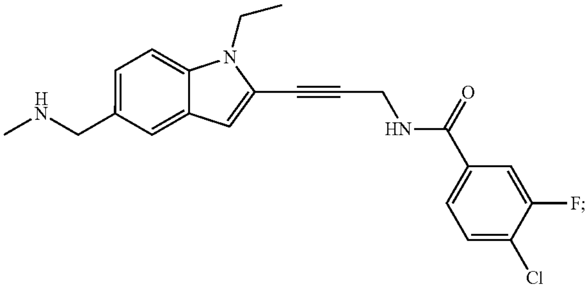
;
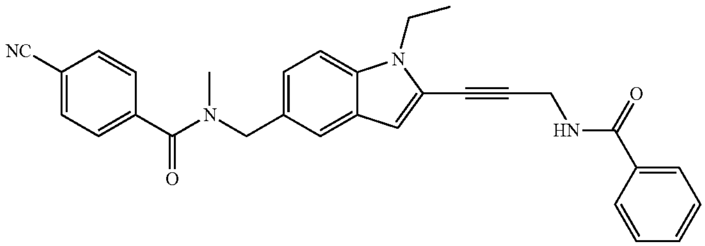
;
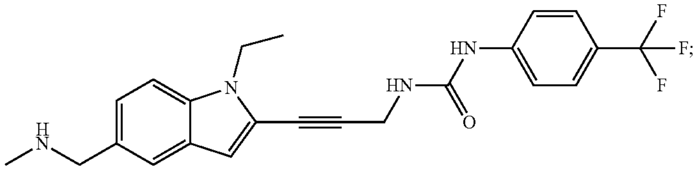
;
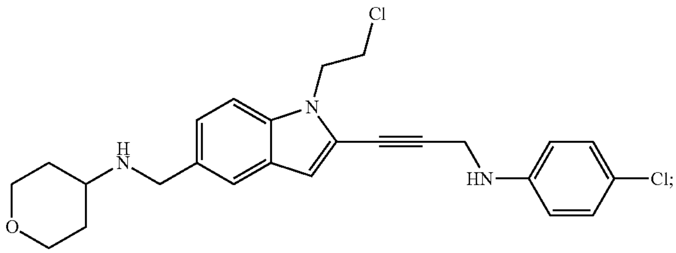
;
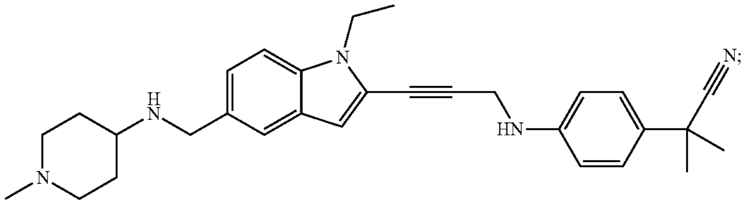
;

-continued
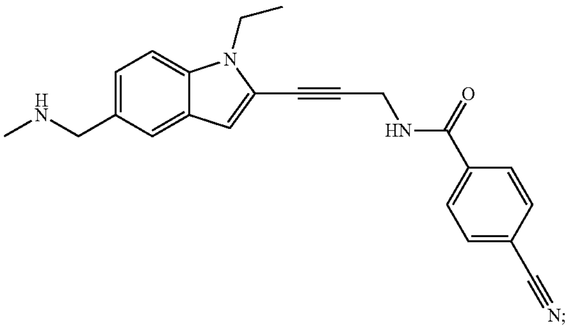
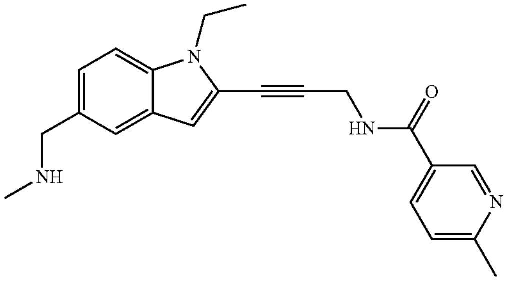
;
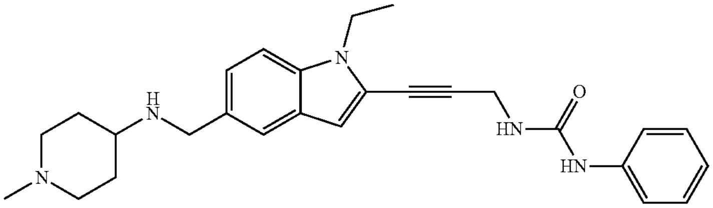
;
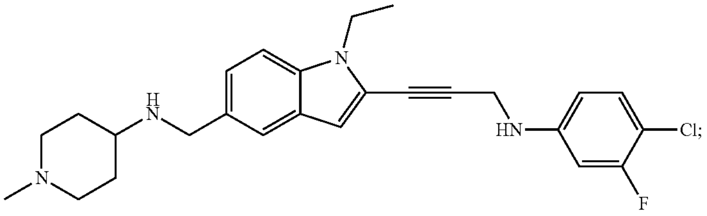
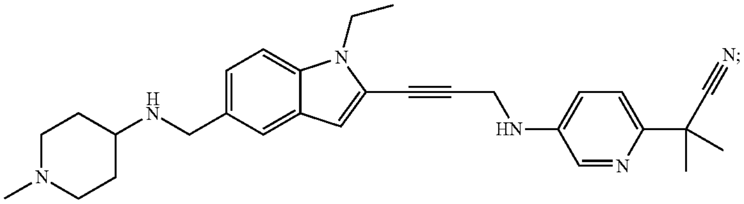
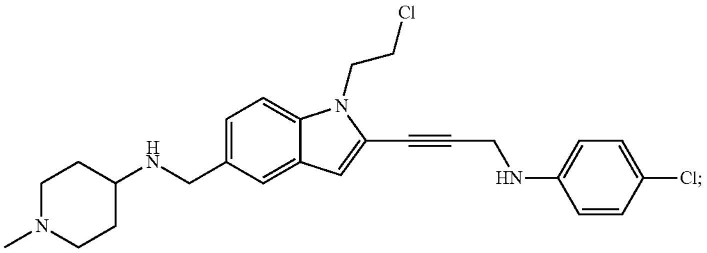
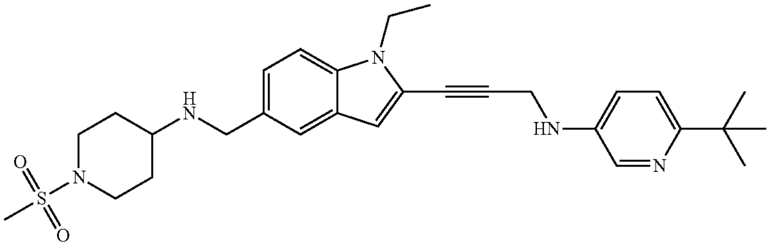
;
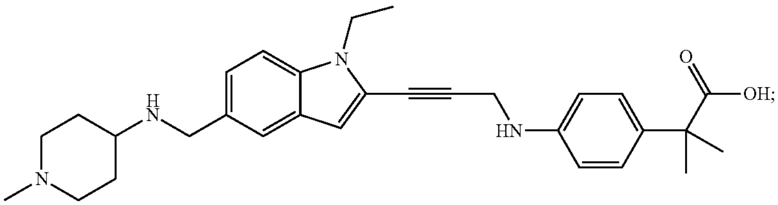

-continued
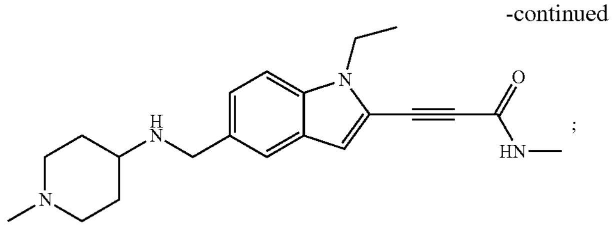
;
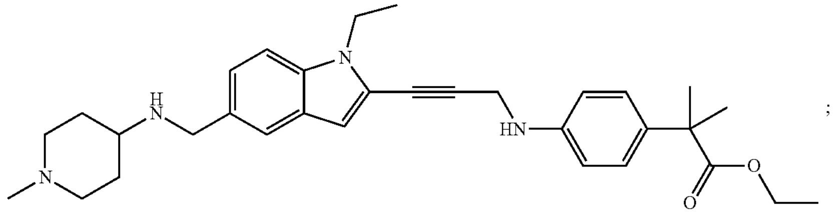
;
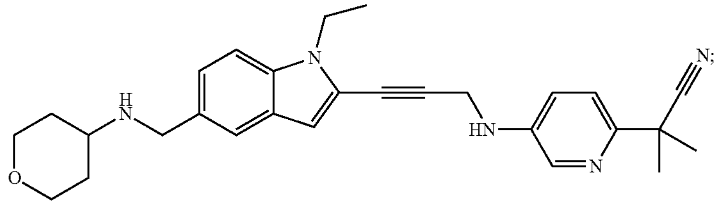
;
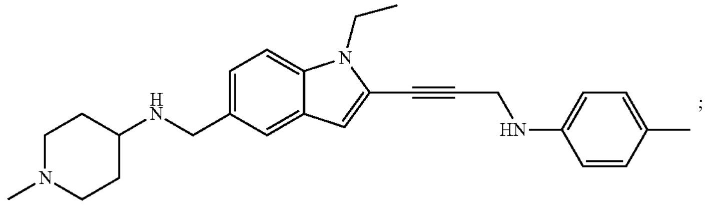
;
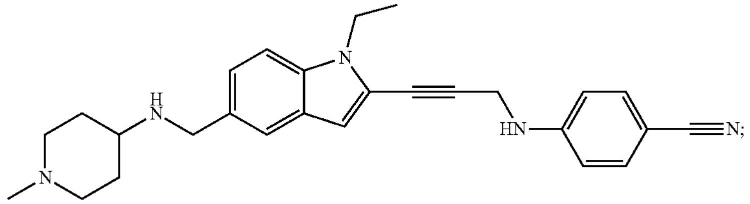
;
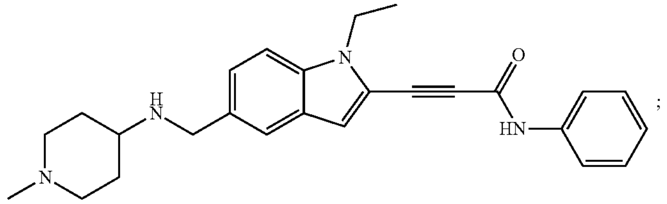
;
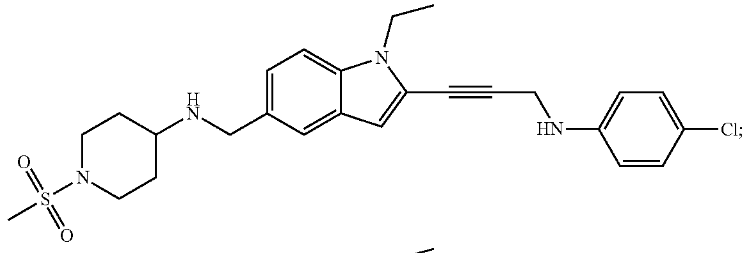
;
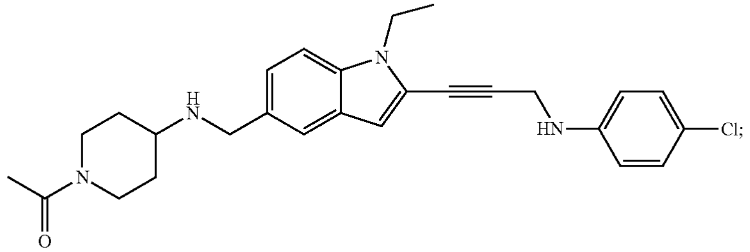
;

-continued
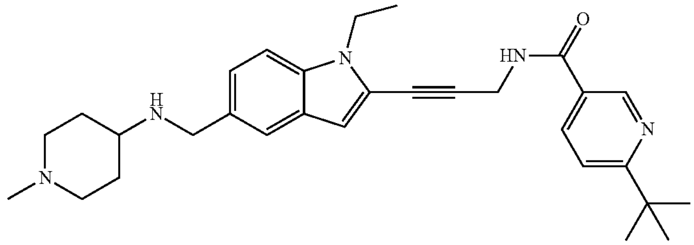
;
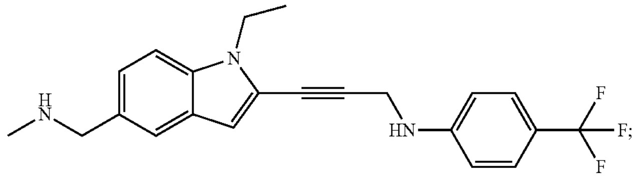
;
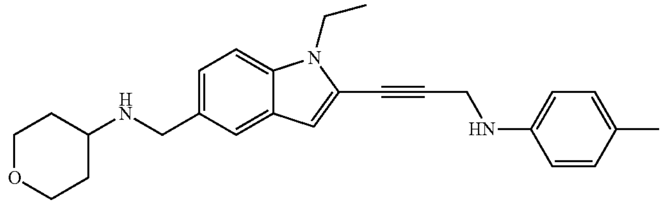
;
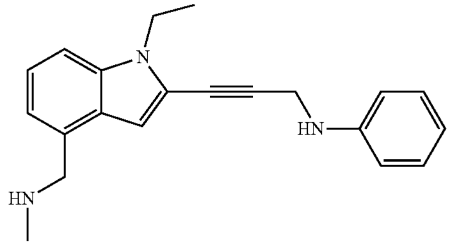
;
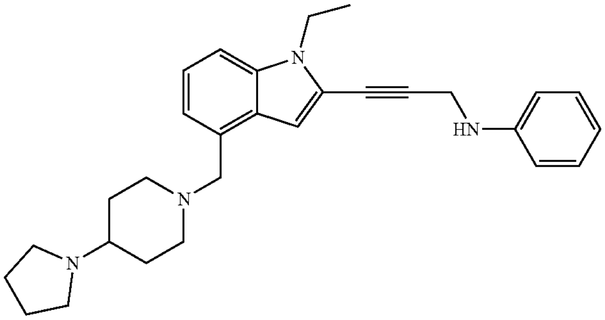
;
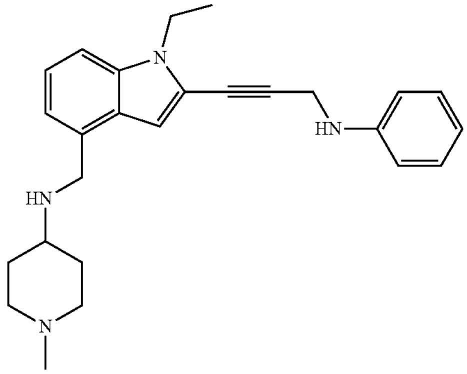
;
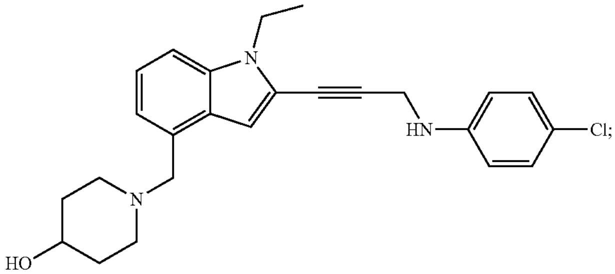
;
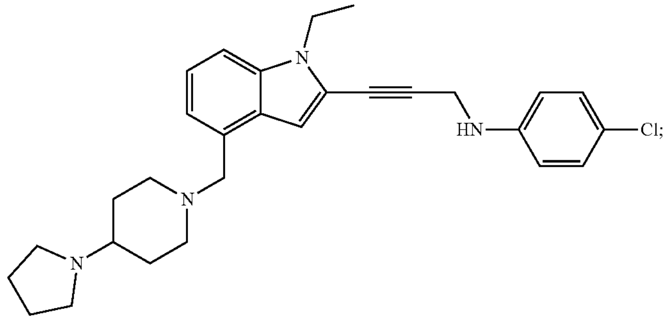
;

-continued
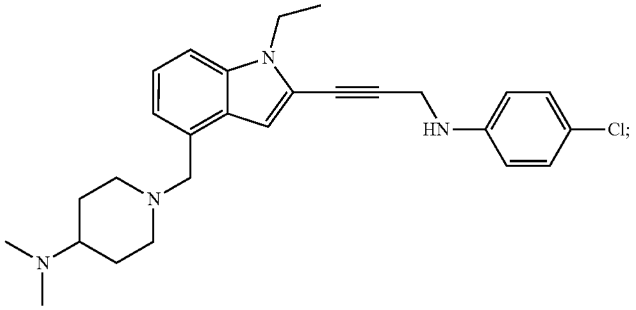
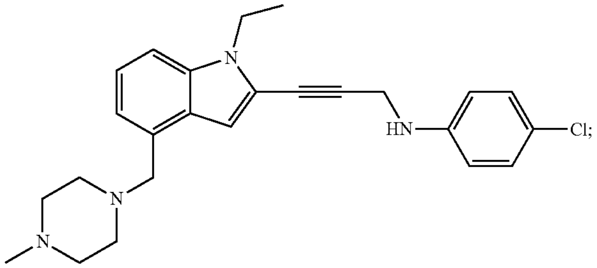
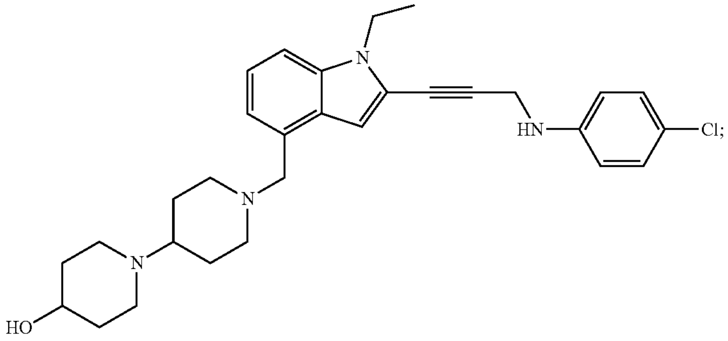
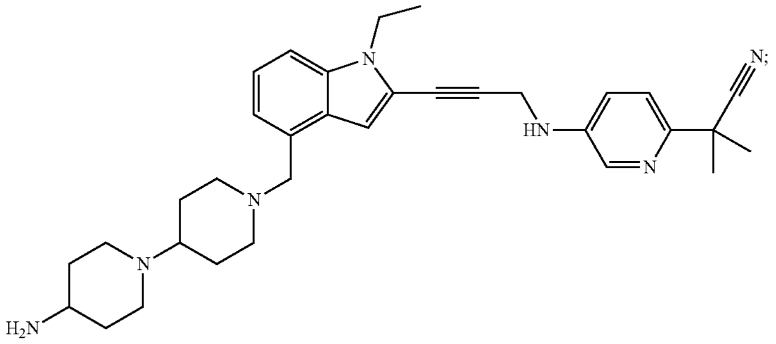
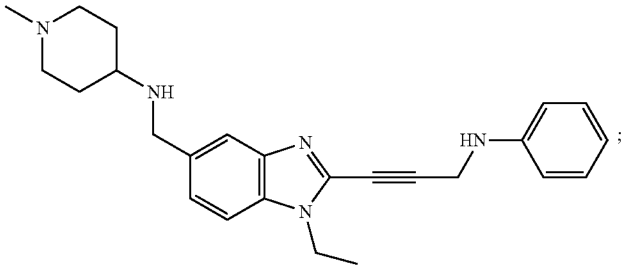

-continued
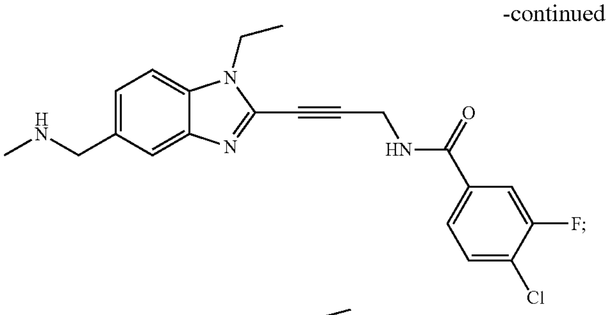
and
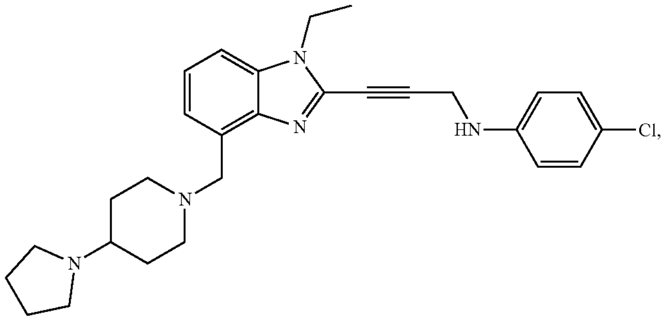
or a pharmaceutically-acceptable salt of any of the foregoing.
Non-limiting examples of compounds of the current disclosure include the following:
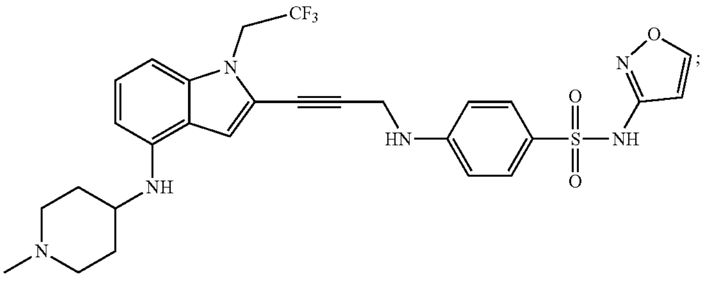
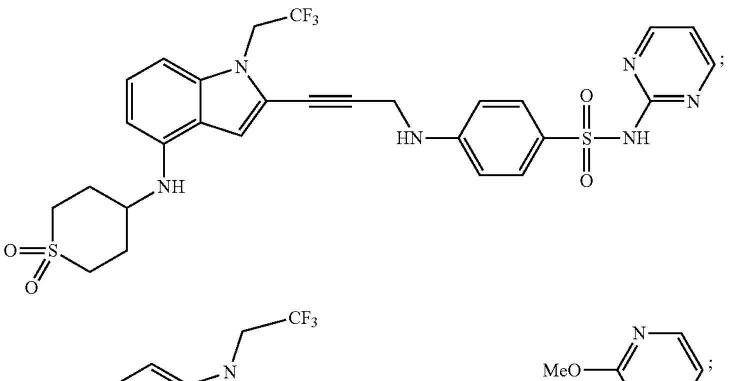
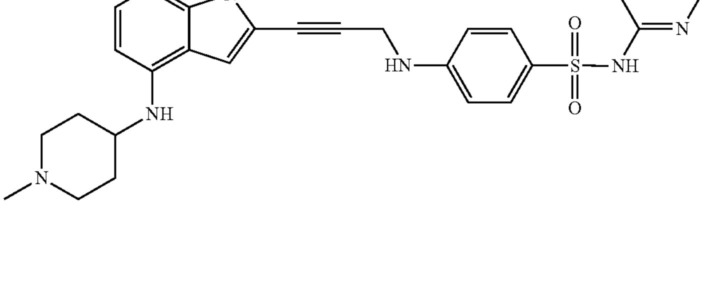

-continued
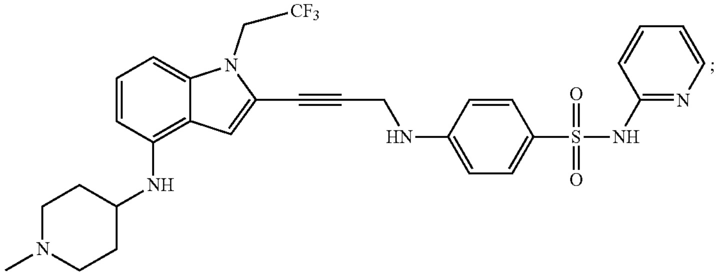
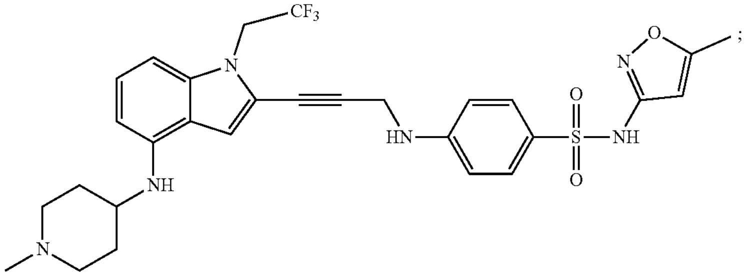
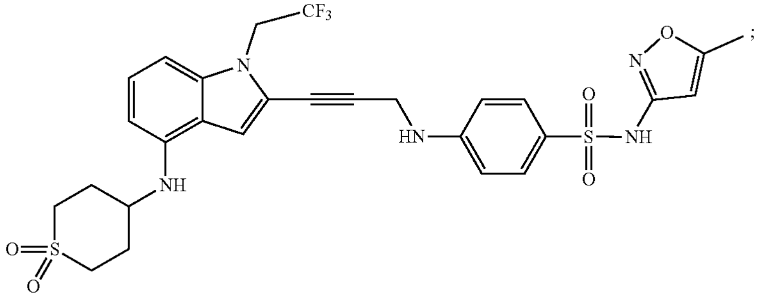
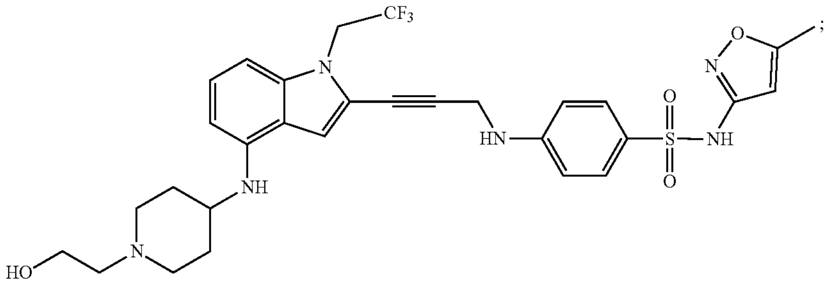
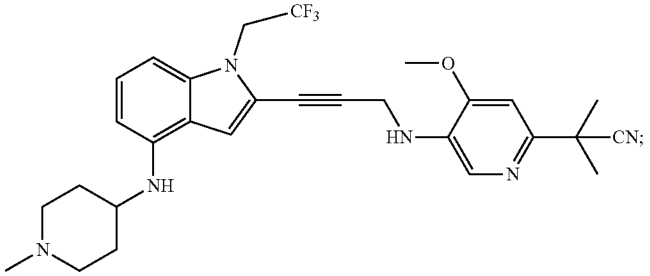
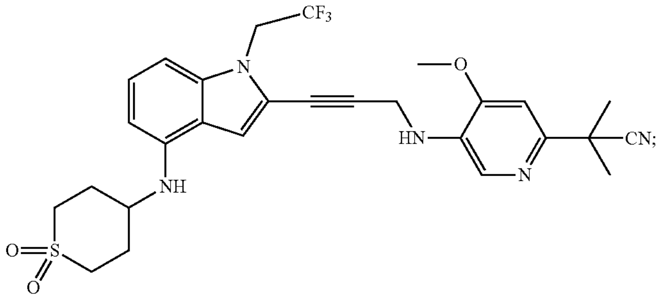

-continued
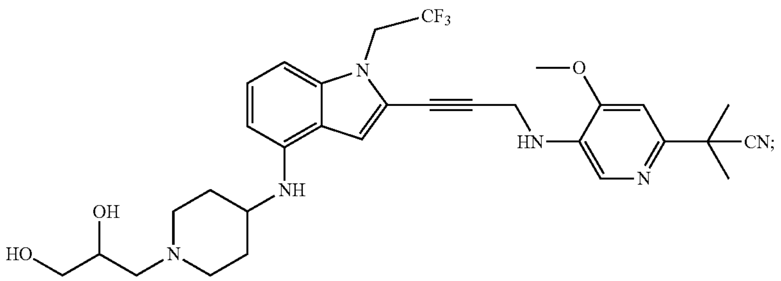
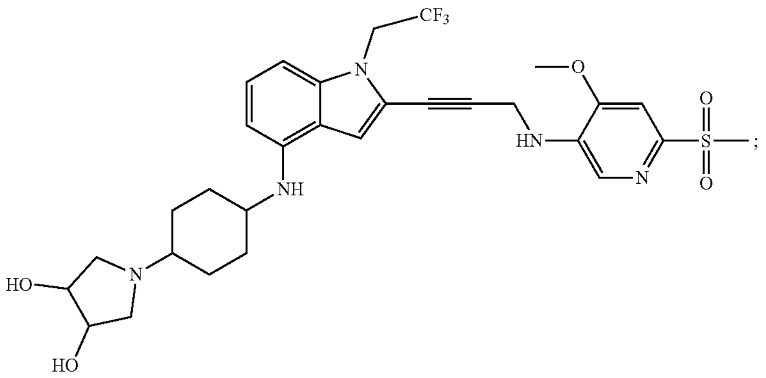
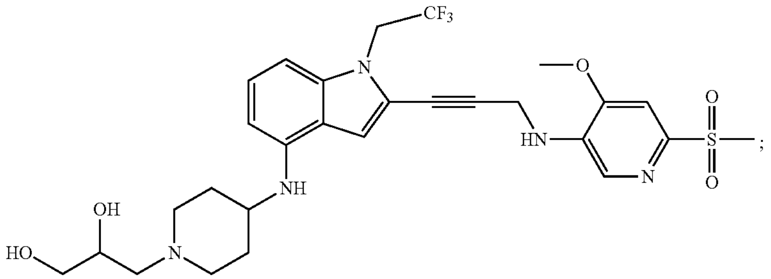
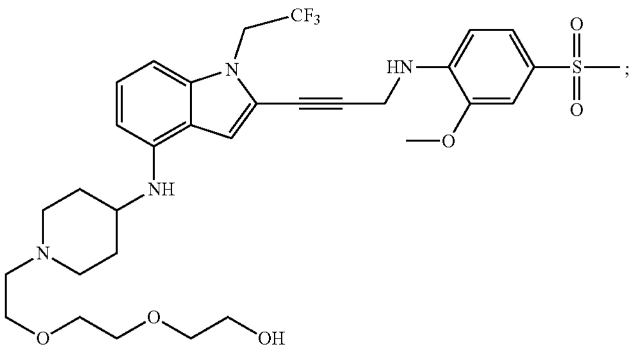
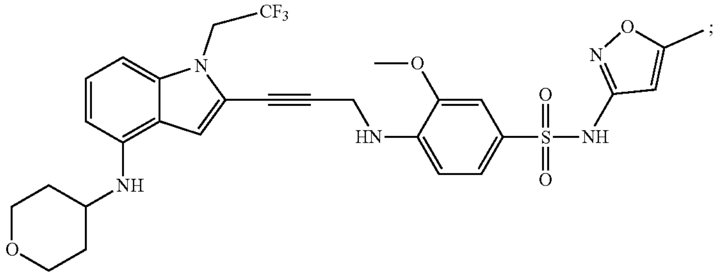

-continued
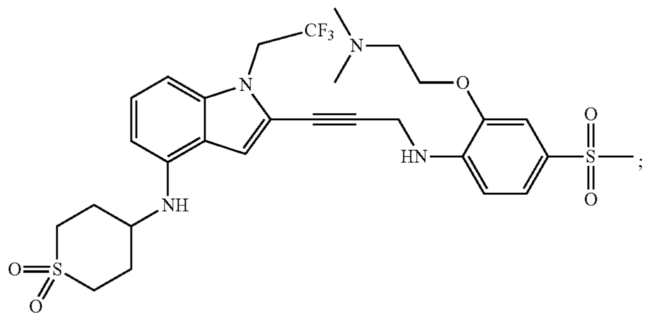
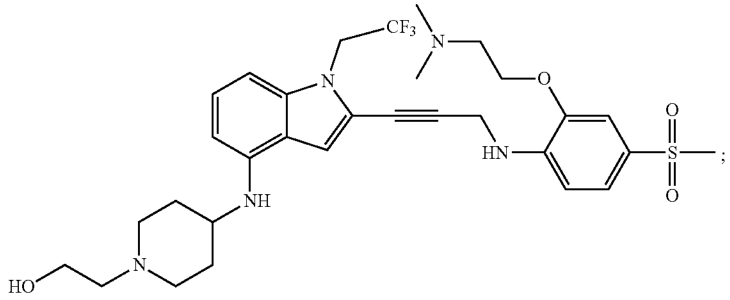
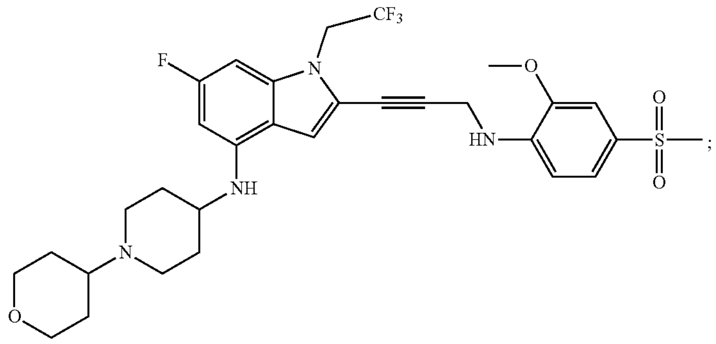
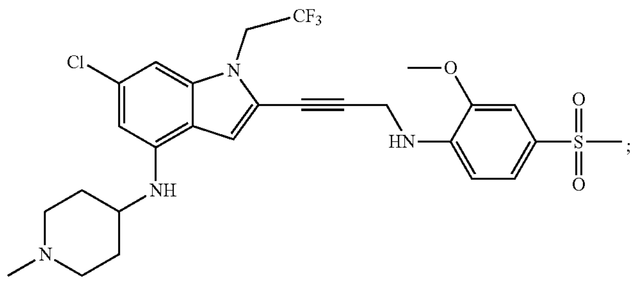
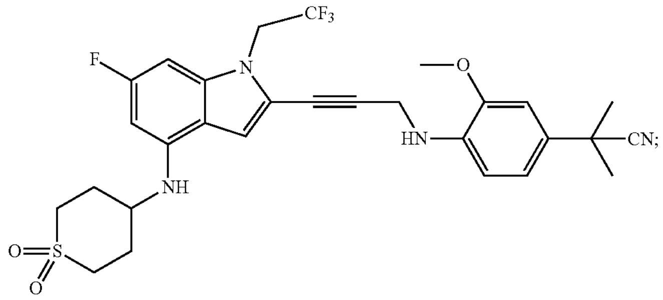

-continued
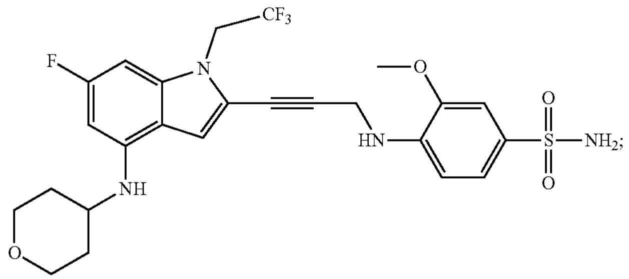
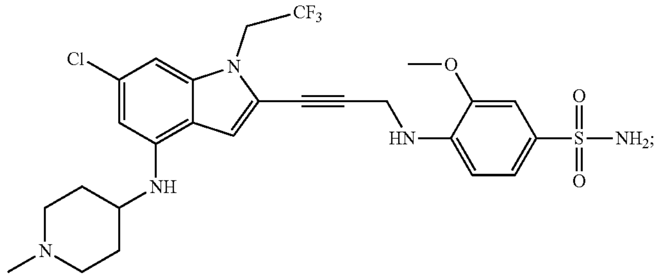
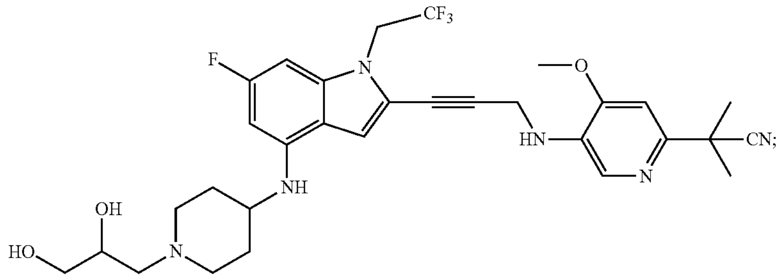
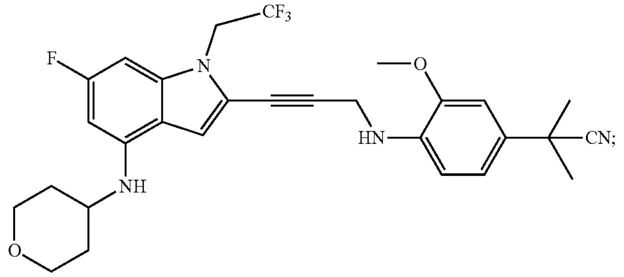
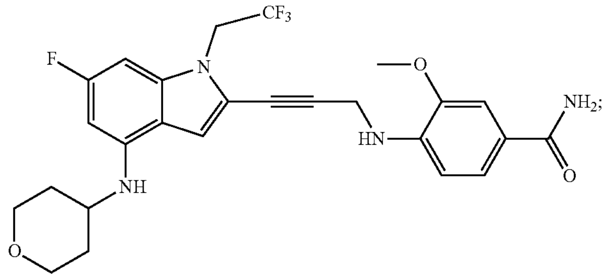
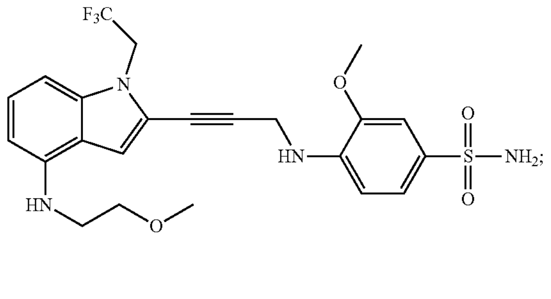
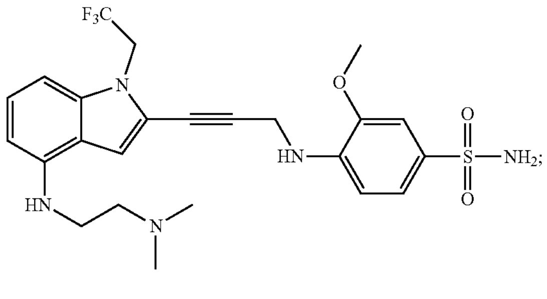

-continued
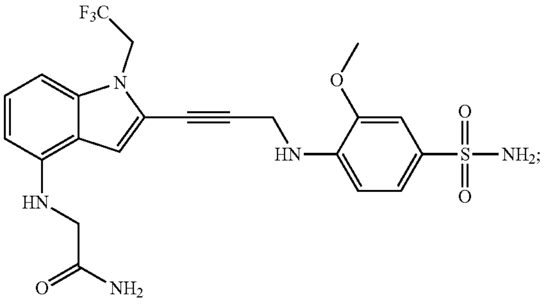
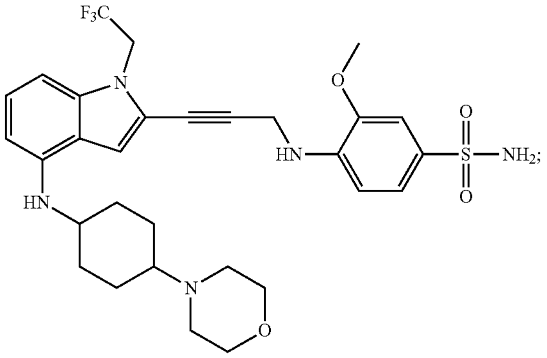
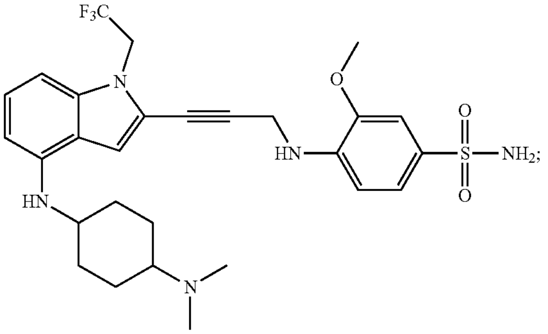
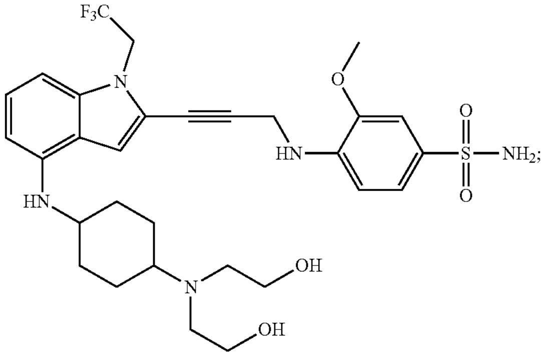
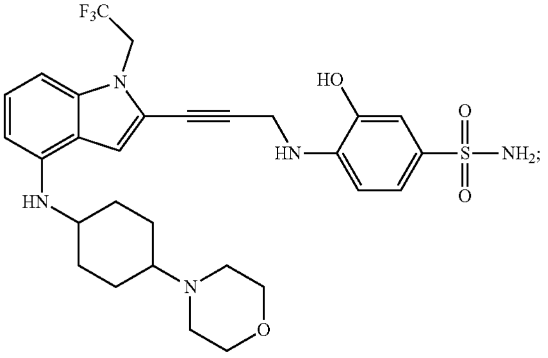
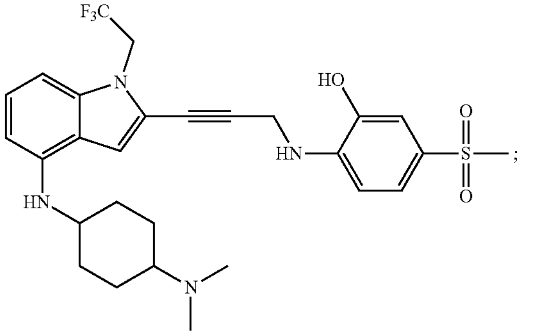
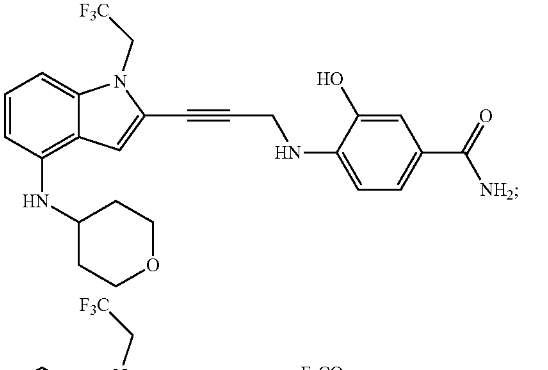
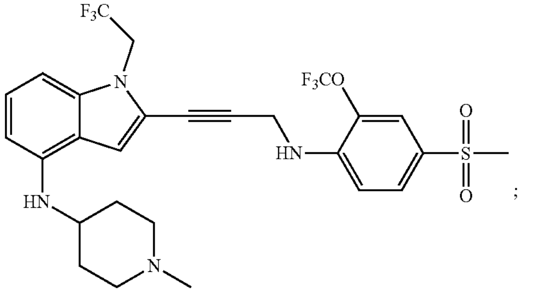
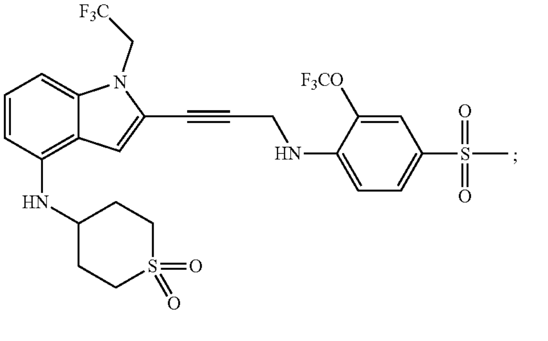
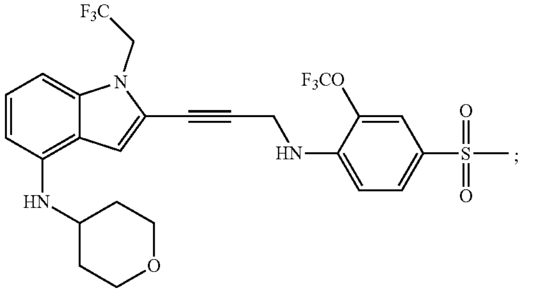

-continued
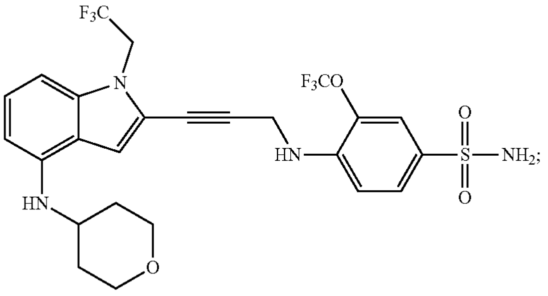
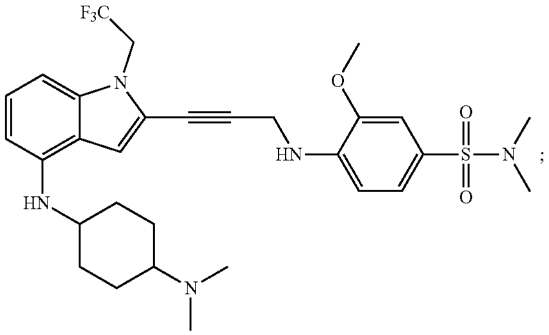
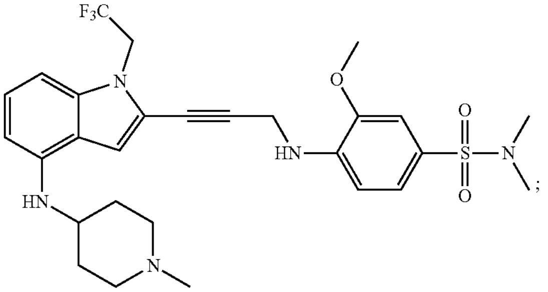
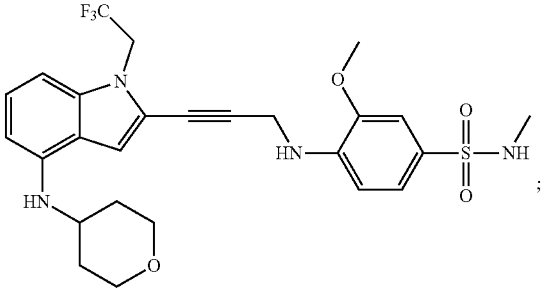
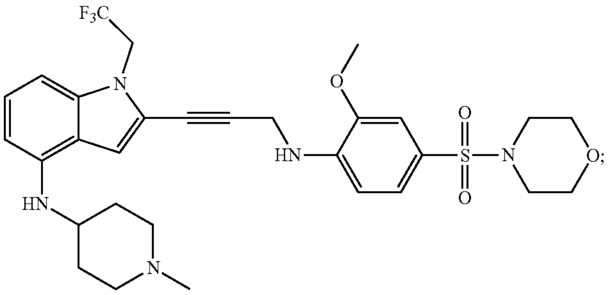
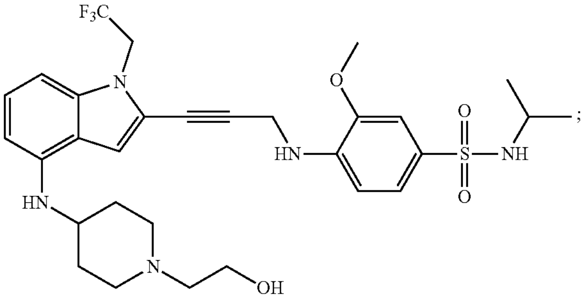
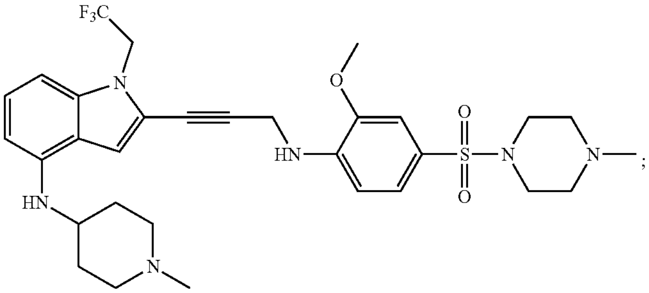

-continued
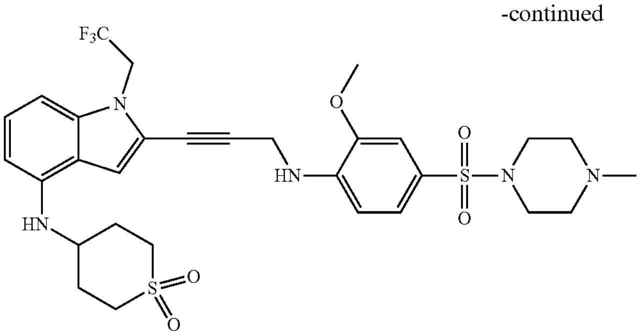
;
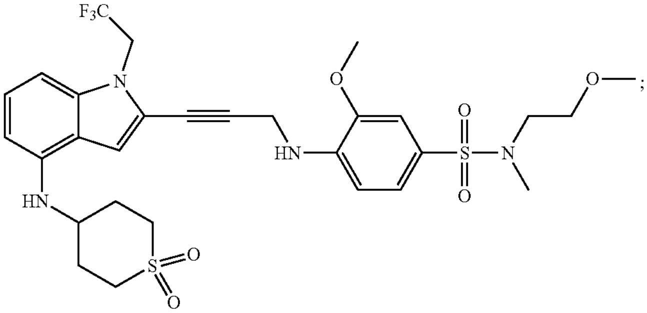
;
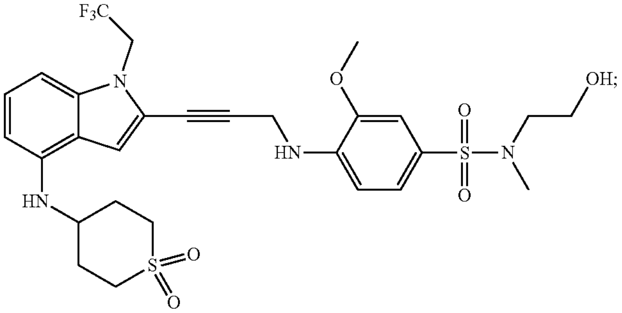
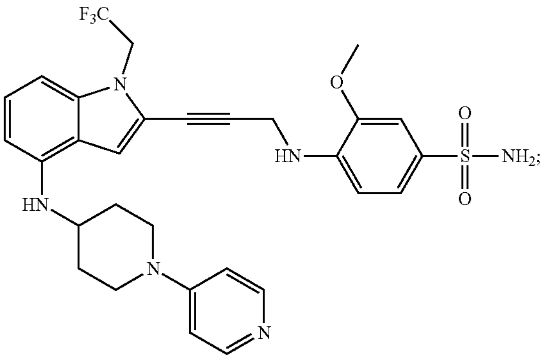
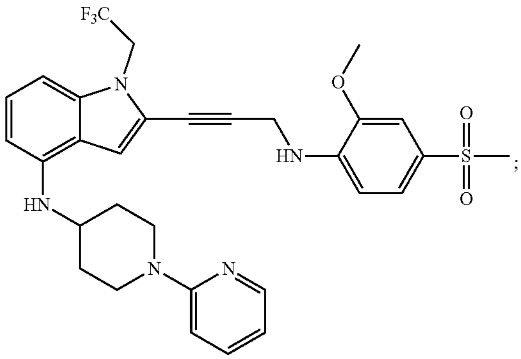
;
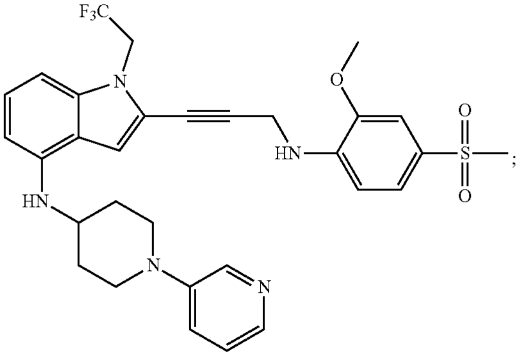
;
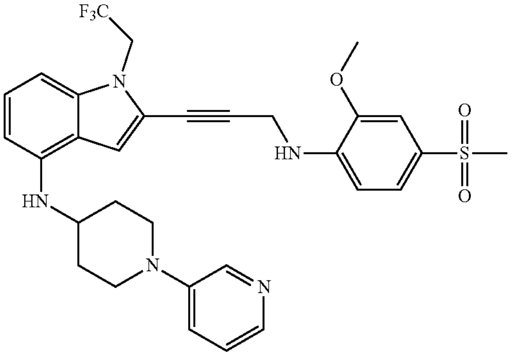
; and -continued
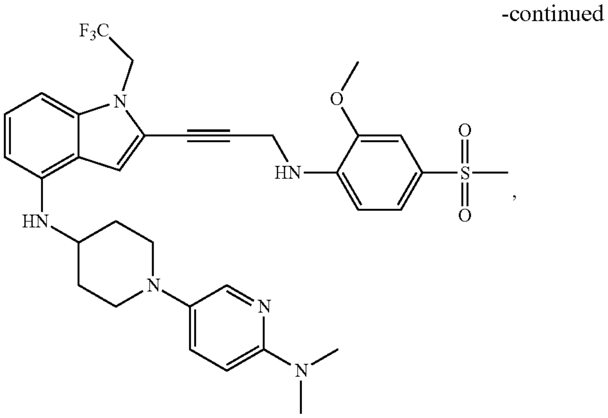
or a pharmaceutically-acceptable salt of any of the forgoing.
Non-limiting examples of compounds of the current disclosure include the following:
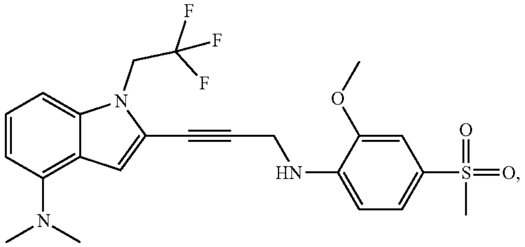
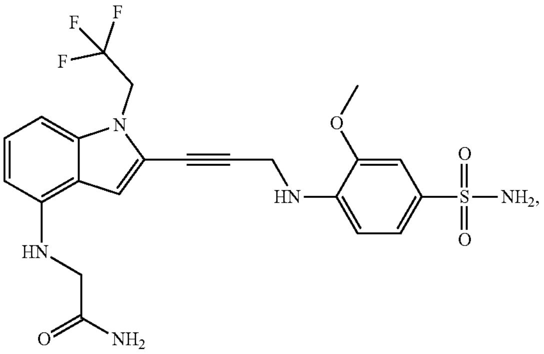
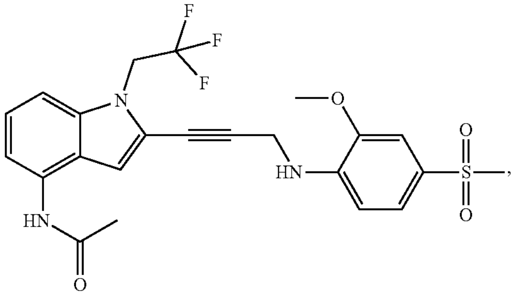
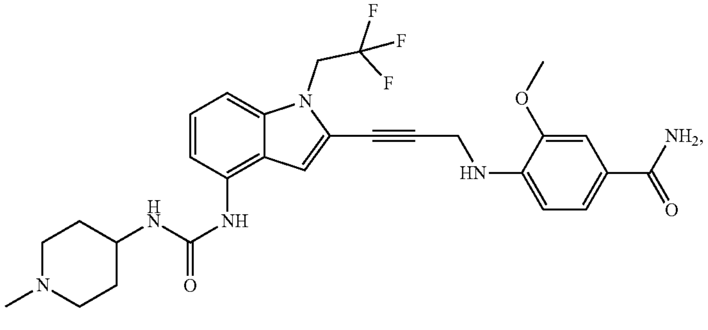

-continued
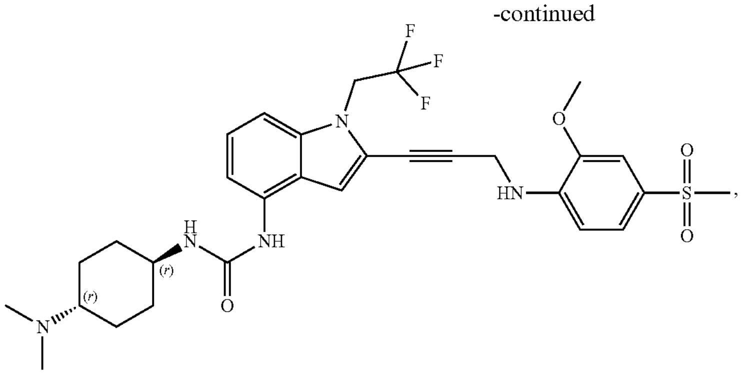
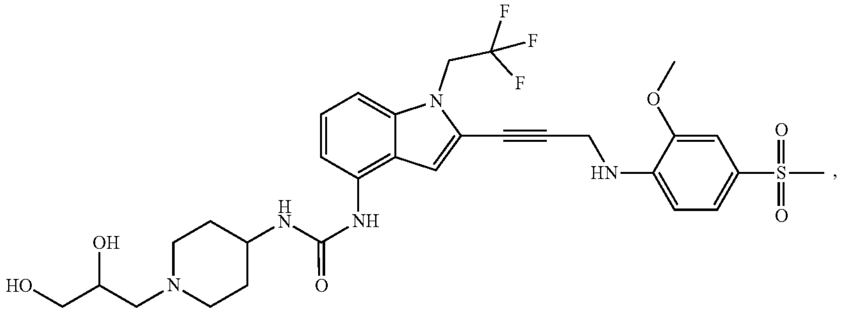
and
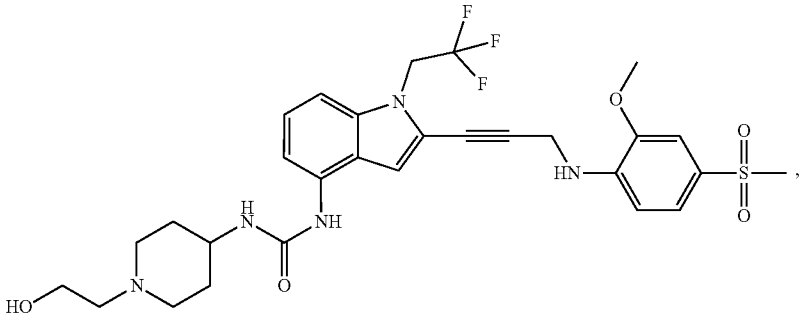
or a pharmaceutically-acceptable salt thereof.
Non-limiting examples of compounds of the current disclosure include the following:
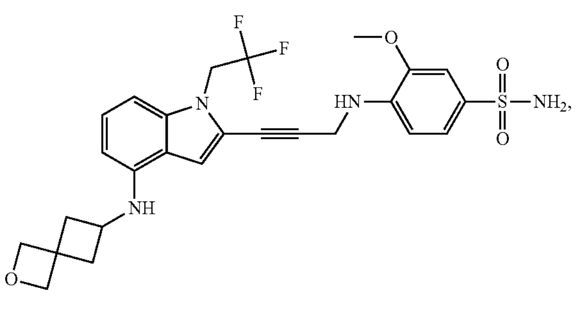
-continued
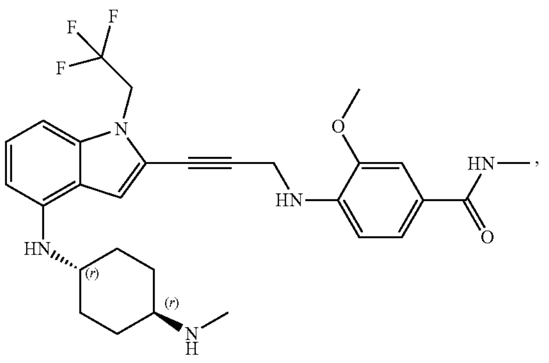

-continued
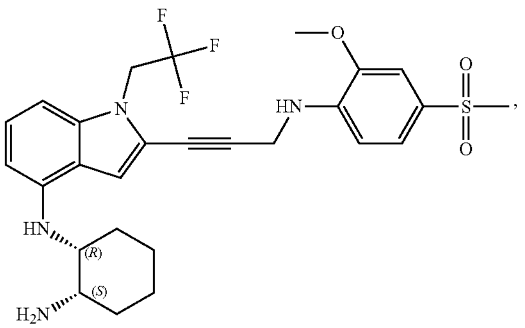
,
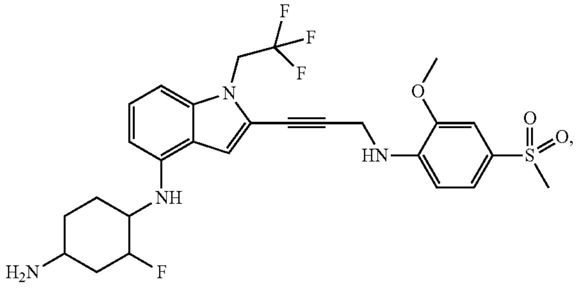
,
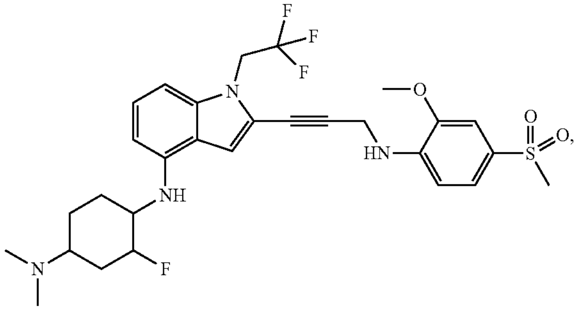
,
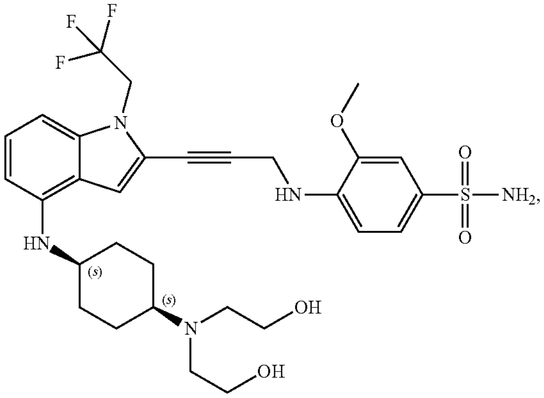
,
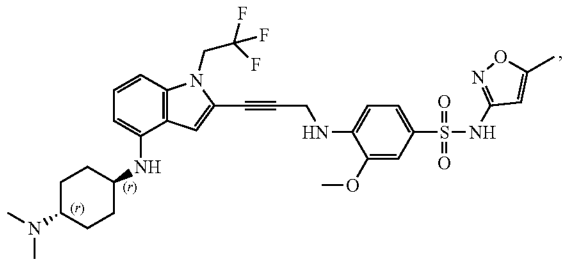
,
-continued
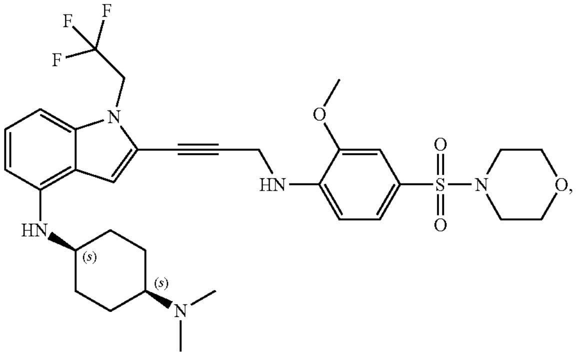
,
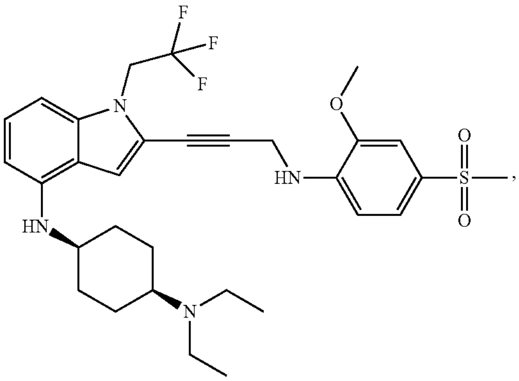
,
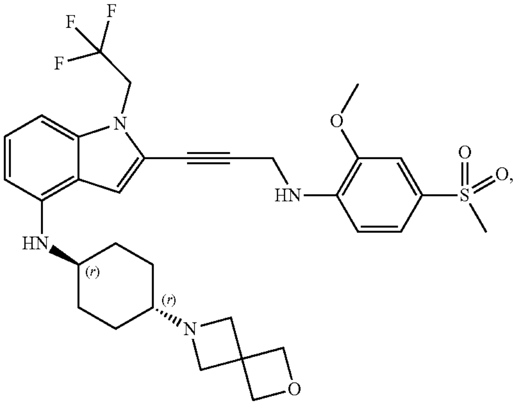
,
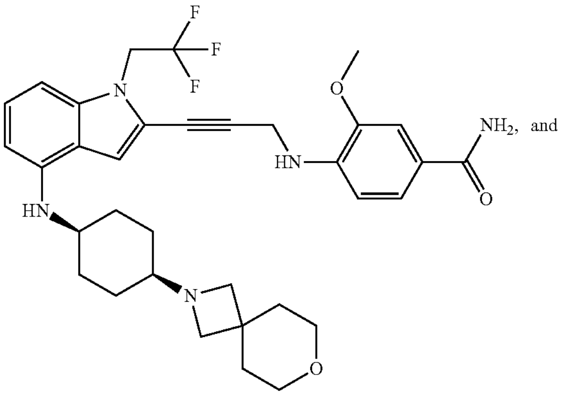
, and -continued
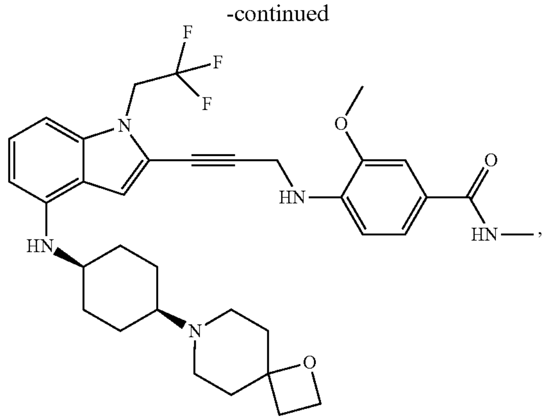
or a pharmaceutically-acceptable salt thereof.
Non-limiting examples of compounds of the current disclosure include the following:
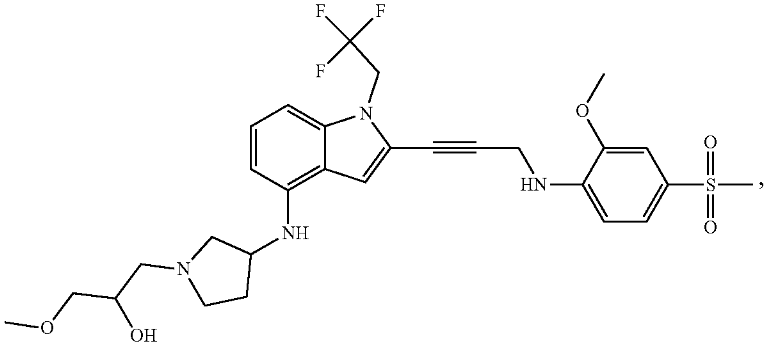
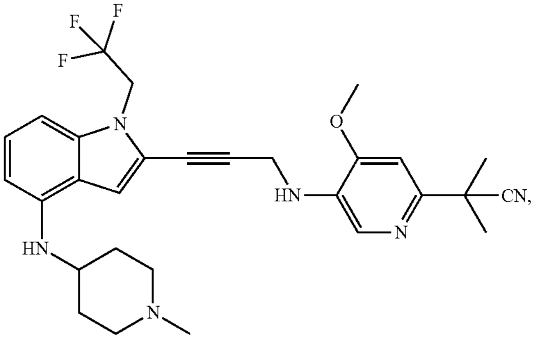
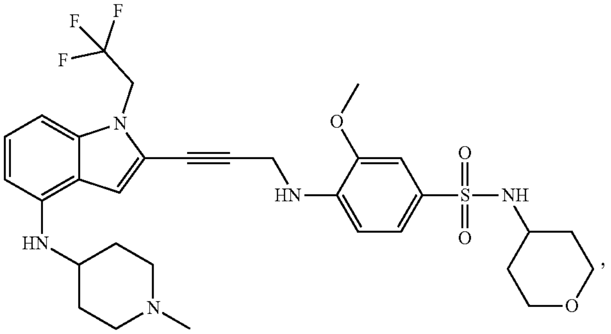
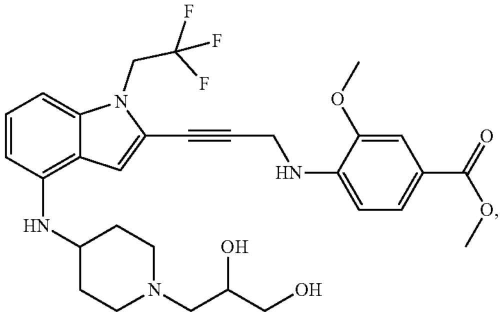

-continued
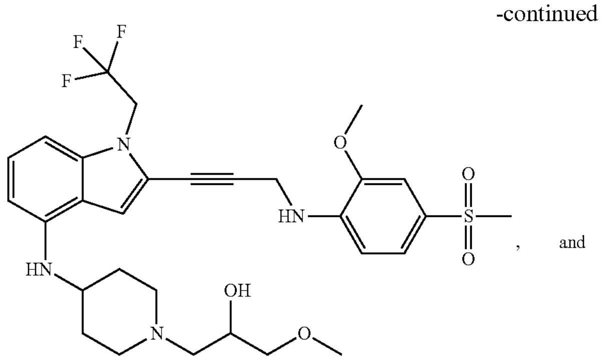
, and
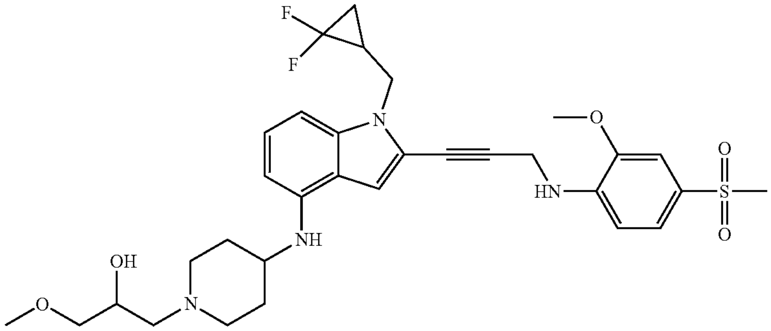
,
or a pharmaceutically-acceptable salt thereof.
Non-limiting examples of compounds of the current disclosure include the following:
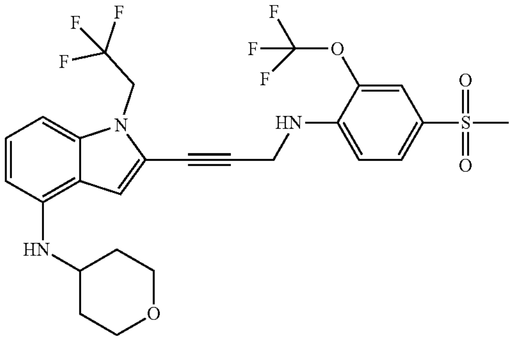
,
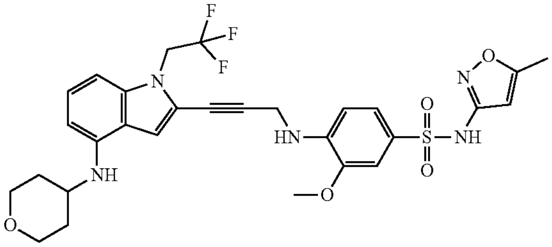
,
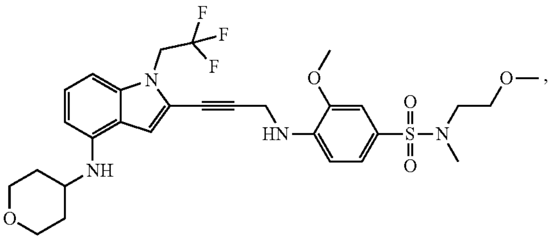
,
-continued
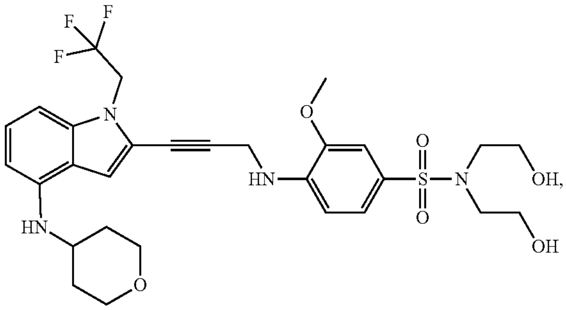
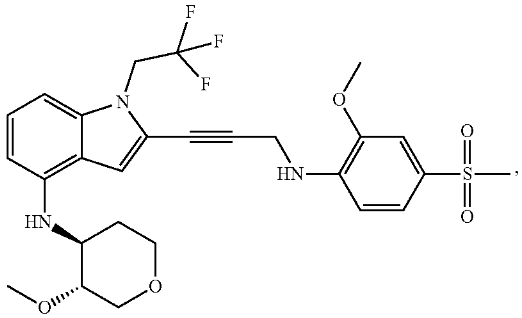
, -continued
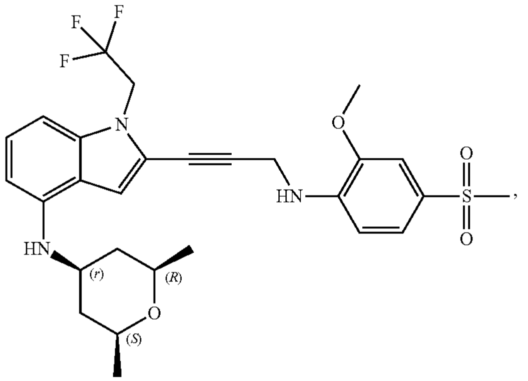
, and
-continued
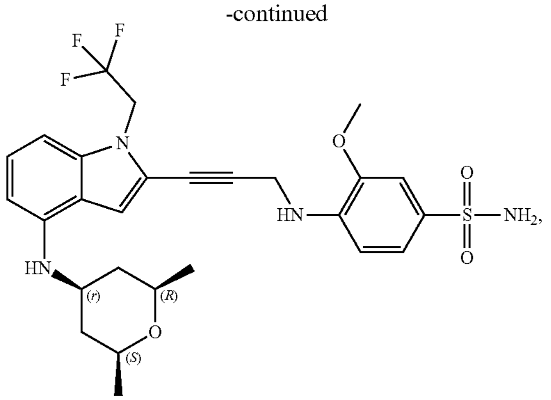
or a pharmaceutically-acceptable salt thereof.
Non-limiting examples of compounds of the current disclosure include the following:
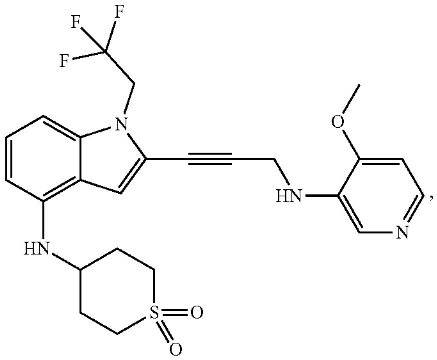
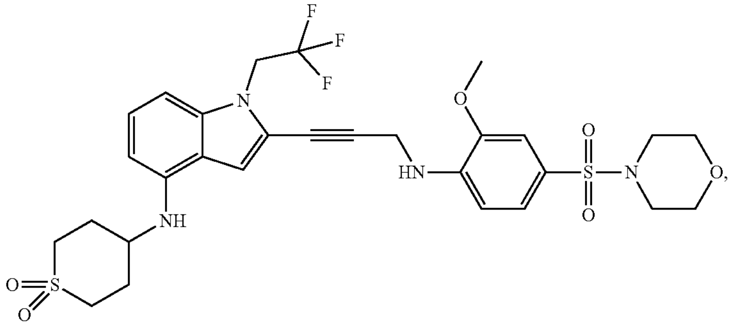
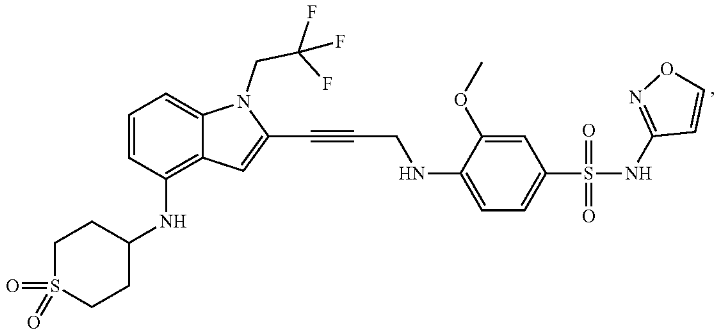

-continued
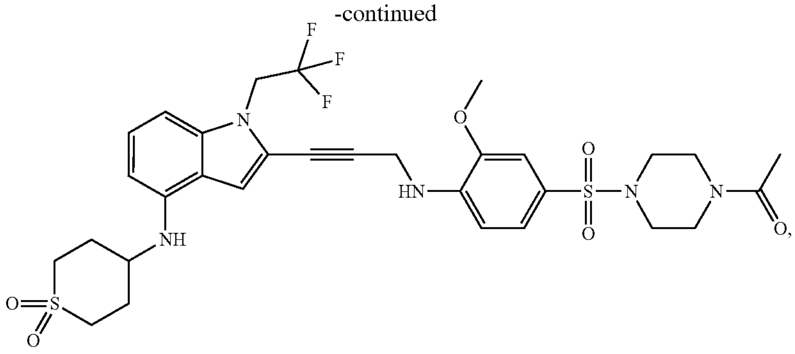
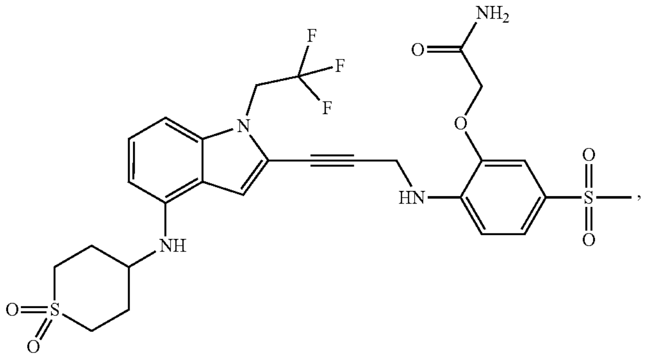
, and
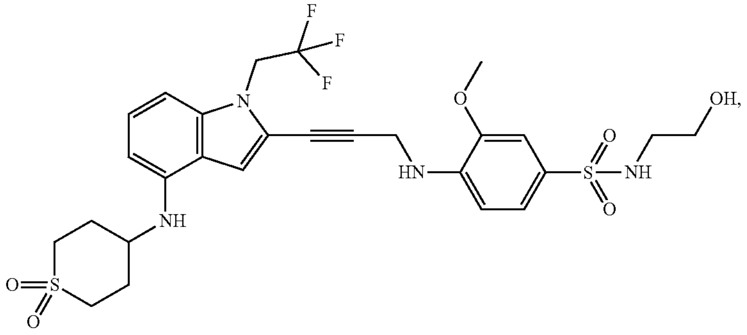
or a pharmaceutically-acceptable salt thereof.
Non-limiting examples of compounds of the current disclosure include the following:
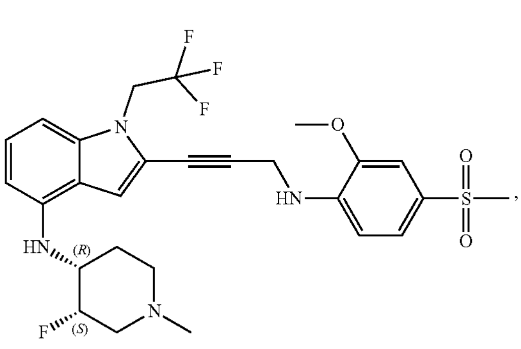
,
-continued
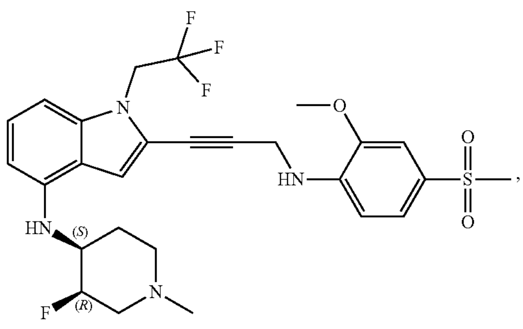
, -continued
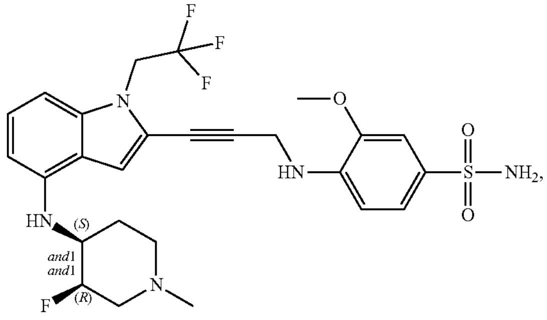
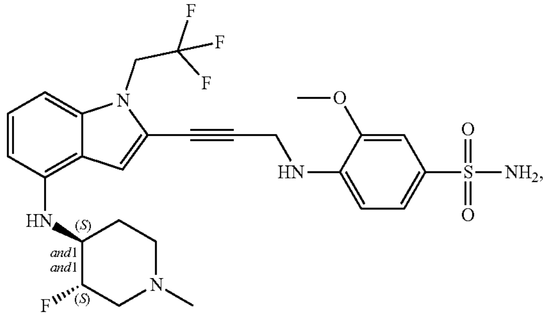
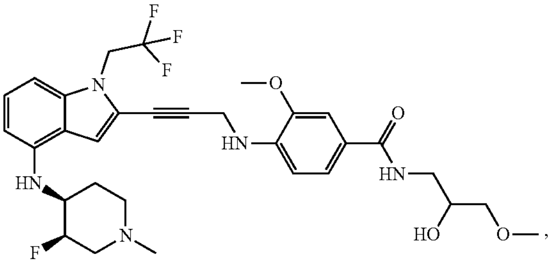
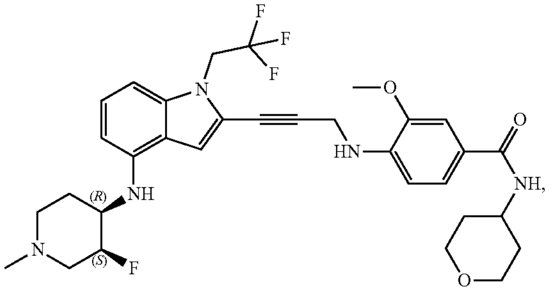
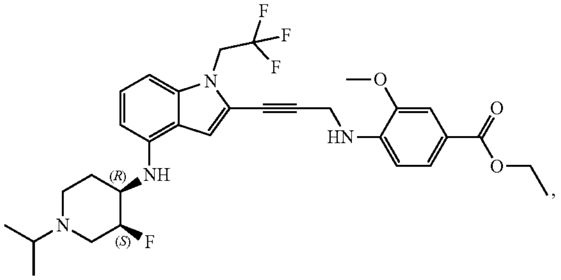
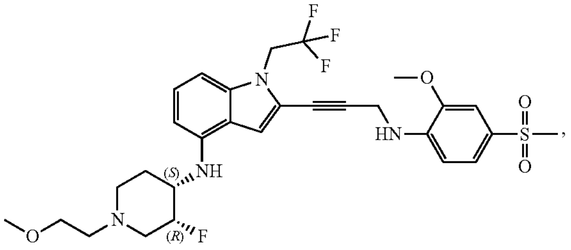
-continued
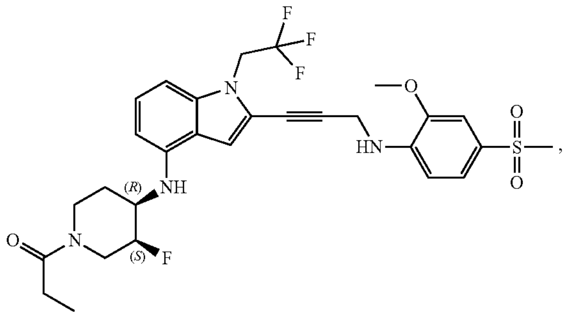
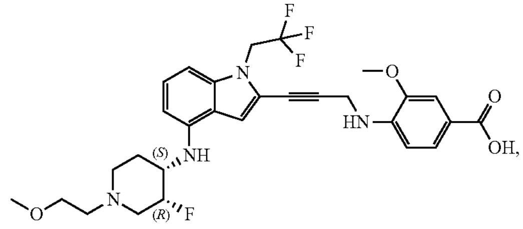
and
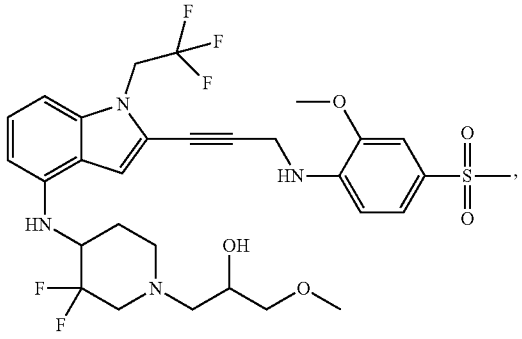 [SMILES: COCC(O)CN1CCC(Nc2cccc3c2cc(C#CCNc2ccc(S(C)(=O)=O)cc2OC)n3CC(F)(F)F)C(F)(F)C1]
or a pharmaceutically-acceptable salt thereof.
Non-limiting examples of compounds of the current disclosure include the following:
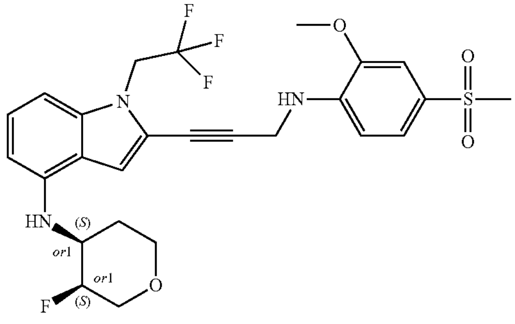
and -continued

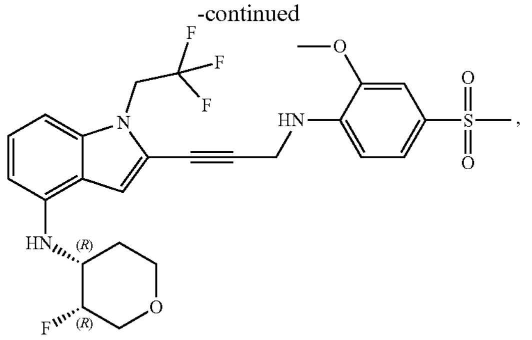

or a pharmaceutically-acceptable salt thereof.

Compounds herein can include all stereoisomers, enantiomers, diastereomers, mixtures, racemates, atropisomers, and tautomers thereof.

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, ureido groups, epoxy groups, and ester groups.

Non-limiting examples of alkyl and alkylene groups include straight, branched, and cyclic alkyl and alkylene groups. An alkyl or alkylene group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of substituted alkyl groups includes hydroxymethyl, chloromethyl, trifluoromethyl, aminomethyl, 1-chloroethyl, 2-hydroxy ethyl, 1,2-difluoroethyl, and 3-carboxypropyl.

Non-limiting examples of cyclic alkyl groups include cyclopropyl, cyclobutyl, cyclo pentyl, cyclohexyl, cycloheptlyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups. Non-limiting examples of cyclic alkyl groups include cyclopropyl, 2-methyl-cycloprop-1-yl, cycloprop-2-en-1-yl, cyclobutyl, 2,3-dihydroxycyclobut-1-yl, cyclobut-2-en-1-yl, cyclopentyl, cyclopent-2-en-1-yl, cyclopenta-2,4-dien-1-yl, cyclohexyl, cyclohex-2-en-1-yl, cycloheptyl, cyclooctanyl, 2,5-dimethylcyclopent-1-yl, 3,5-dichlorocyclohex-1-yl, 4-hydroxycyclohex-1-yl, 3,3,5-trimethylcyclohex-1-yl, octahydropentalenyl, octahydro-1H-indenyl, 3a,4,5,6,7,7a-hexahydro-3H-inden-4-yl, decahydroazulenyl, bicyclo-[2.1.1]hexanyl, bicyclo[2.2.1]heptanyl, bicyclo [3.1.1]heptanyl, 1,3-dimethyl[2.2.1]heptan-2-yl, bicyclo [2.2.2]octanyl, and bicyclo[3.3.3]undecanyl.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkenyl and alkenylene groups include ethenyl, prop-1-en-1-yl, isopropenyl, but-1-en-4-yl; 2-chloroethenyl, 4-hydroxybuten-1-yl, 7-hydroxy-7-methyloct-4-en-2-yl, and 7-hydroxy-7-methyloct-3,5-dien-2-yl.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkynyl or alkynylene groups include ethynyl, prop-2-yn-1-yl, prop-1-yn-1-yl, and 2-methyl-hex-4-yn-1-yl; 5-hydroxy-5-methylhex-3-yn-1-yl, 6-hydroxy-6-methylhept-3-yn-2-yl, and 5-hydroxy-5-ethylhept-3-yn-1-yl.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl. Non-limiting examples of substituted aryl groups include 3,4-dimethylphenyl, 4-tert-butylphenyl, 4-cyclopropylphenyl, 4-diethylaminophenyl, 4-(trifluoromethyl)phenyl, 4-(difluoromethoxy)-phenyl, 4-(trifluoromethoxy)phenyl, 3-chlorophenyl, 4-chlorophenyl, 3,4-dichlorophenyl, 2-fluorophenyl, 2-chlorophenyl, 2-iodophenyl, 3-iodophenyl, 4-iodophenyl, 2-methylphenyl, 3-fluorophenyl, 3-methylphenyl, 3-methoxyphenyl, 4-fluorophenyl, 4-methylphenyl, 4-methoxyphenyl, 2,3-difluorophenyl, 3,4-difluorophenyl, 3,5-difluorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, 3,5-dimethoxyphenyl, 2,4-difluorophenyl, 2,5-difluorophenyl, 2,6-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, 3,4,5-trichlorophenyl, 2,4,6-trichlorophenyl, 2,3-dimethylphenyl, 2,4-dimethylphenyl, 2,5-dimethylphenyl, 2,6-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, 2,4,6-triethylphenyl, 2-isopropylphenyl, 3-isopropylphenyl, and 4-isopropylphenyl.

Non-limiting examples of substituted aryl groups include 2-aminophenyl, 2-(N-methylamino)phenyl, 2-(N,N-dimethylamino)phenyl, 2-(N-ethylamino)phenyl, 2-(N,N-diethylamino)phenyl, 3-aminophenyl, 3-(N-methylamino)phenyl, 3-(N,N-dimethylamino)phenyl, 3-(N-ethylamino)phenyl, 3-(N,N-diethylamino)phenyl, 4-aminophenyl, 4-(N-methylamino)phenyl, 4-(N,N-dimethylamino)phenyl, 4-(N-ethylamino)phenyl, and 4-(N,N-diethylamino)phenyl.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

Non-limiting examples of heterocycles include: heterocyclic units having a single ring containing one or more heteroatoms, non-limiting examples of which include, diazirinyl, aziridinyl, azetidinyl, pyrazolidinyl, imidazolidinyl, oxazolidinyl, isoxazolinyl, thiazolidinyl, isothiazolinyl, oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl, 2,3,4,5-tetrahydro-1H-azepinyl, 2,3-dihydro-1H-indole, and 1,2,3,4-tetrahydroquinoline; and ii) heterocyclic units having 2 or more rings one of which is a heterocyclic ring, non-limiting examples of which include hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, and decahydro-1H-cycloocta[b]pyrrolyl.

Non-limiting examples of heteroaryl include: i) heteroaryl rings containing a single ring, non-limiting examples of which include, 1,2,3,4-tetrazolyl, [1,2,3]triazolyl, [1,2,4]triazolyl, triazinyl, thiazolyl, 1H-imidazolyl, oxazolyl, isoxazolyl, isothiazolyl, furanyl, thiophenyl, pyrimidinyl, 2-phenylpyrimidinyl, pyridinyl, 3-methylpyridinyl, and 4-dimethylaminopyridinyl; and ii) heteroaryl rings containing 2 or more fused rings one of which is a heteroaryl ring, non-limiting examples of which include: 7H-purinyl, 9H-purinyl, 6-amino-9H-purinyl, 5H-pyrrolo[3,2-d]pyrimidinyl, 7/7-pyrrolo[2,3-d]pyrimidinyl, pyrido[2,3-d]pyrimidinyl, 4,5,6,7-tetrahydro-1-H-indolyl, quinoxalinyl, quinazolinyl, quinolinyl, 8-hydroxy-quinolinyl, and isoquinolinyl.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

Pharmaceutically-Acceptable Salts.

The invention provides the use of pharmaceutically-acceptable salts of any therapeutic compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Pharmaceutical Compositions of the Invention.

A pharmaceutical composition of the invention can be used, for example, before, during, or after treatment of a subject with, for example, another pharmaceutical agent.

Subjects can be, for example, elderly adults, adults, adolescents, pre-adolescents, children, toddlers, infants, neonates, and non-human animals. In some embodiments, a subject is a patient.

A pharmaceutical composition of the invention can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration.

A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining the active compounds with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N,N'-bis(2-ethanesulfonic acid) buffer (PIPES), and saline sodium citrate buffer (SSC). Non-limiting examples of co-solvents used in an oral dissolvable formulation can include sucrose, urea, cremophor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compounds of the invention can be applied topically to the skin, or a body cavity, for example, oral, vaginal, bladder, cranial, spinal, thoracic, or pelvic cavity of a subject. The compounds of the invention can be applied to an accessible body cavity.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, can be melted.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulations can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include liquid, powder, gel, nanosuspension, nanoparticle, microgel, aqueous or oily suspensions, emulsion, and any combination thereof.

Non-limiting examples of pharmaceutically-acceptable excipients suitable for use in the invention include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Multiple therapeutic agents can be administered in any order or simultaneously. In some embodiments, a compound of the invention is administered in combination with, before, or after treatment with another therapeutic agent. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein.

A compound can be administered as soon as is practical after the onset of a disease or condition is detected or suspected, and for a length of time necessary for the treatment of the disease, such as, for example, from about 1 month to about 3 months. In some embodiments, the length of time a compound can be administered can be about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anticholinergics/antispasmotics, antidiabetic agents, antihypertensive agents, antineoplastics, cardiovascular agents, central nervous system agents, coagulation modifiers, hormones, immunologic agents, immunosuppressive agents, and ophthalmic preparations.

Compounds can be delivered via liposomal technology. The use of liposomes as drug carriers can increase the therapeutic index of the compounds. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Dosing.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a dose can be expressed in terms of an amount of the drug divided by the mass of the subject, for example, milligrams of drug per kilograms of subject body mass. In some embodiments, a compound is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg.

Methods of Treatment

In some embodiments, compounds of the invention can be used to treat cancer in a subject. A compound of the invention can, for example, slow the proliferation of cancer cell lines, or kill cancer cells. Non-limiting examples of cancer that can be treated by a compound of the invention include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

In some embodiments, the compounds of the invention show non-lethal toxicity.

Disclosed herein is a method of treating a cancer associated with a mutant p53 protein, the method comprising administering to a subject in need thereof a therapeutically-effective amount of an organic molecule, wherein the organic molecule binds to a binding site on the mutant p53 protein and forms a hydrogen bond to a Thr-150 residue of the mutant p53 protein, wherein the organic molecule comprises a hydrogen bond donor and an electron-withdrawing heteroatom, wherein the hydrogen bond donor participates in the hydrogen bond, wherein the hydrogen bond donor is proximal to the electron-withdrawing heteroatom.

Disclosed herein is a method of treating a cancer associated with a mutant p53 protein, the method comprising administering to a subject in need thereof a therapeutically-effective amount of an organic molecule, wherein the organic molecule binds to a binding site on the mutant p53 protein, wherein the cancer is breast cancer, wherein the administering is oral, wherein the therapeutically-effective amount is from about 50 mg to about 500 mg, wherein the mutant p53 protein is a Y220C mutant, wherein the organic molecule comprises a tertiary ammonium cation and a fluorine atom, wherein the tertiary ammonium cation and the fluorine atom are substituents on a common ring, the tertiary ammonium cation and the fluorine atom are oriented syn to one another on the common ring, and the tertiary ammonium cation and the fluorine atom are disposed vicinally to one another on the common ring, wherein the mutant p53 protein has a conformation that is not pro-apoptotic, and the contacting to the mutant p53 protein the organic molecule that binds to the binding site on the mutant p53 protein modulates the conformation of the mutant p53 protein to a form that is pro-apoptotic, wherein if a co-crystal is obtained of the organic molecule and the mutant p53 protein with the organic molecule bound to the binding site on the mutant p53 protein, and the co-crystal is obtained by sitting-drop vapor distillation, and if an x-ray co-crystal structure of the co-crystal is obtained by crystal soaking, and if the x-ray co-crystal structure has a resolution of about 2 Å, then in the x-ray co-crystal structure the tertiary ammonium cation forms a hydrogen bond with a side chain oxygen atom of Thr-150 of the mutant p53 protein, wherein the hydrogen bond has a mean length of from about 1.5 Å to about 3 Å, wherein the fluorine atom is bound to a stereocenter of the organic molecule, wherein the stereocenter has a handedness, wherein the hydrogen bond is stronger than is an analogous hydrogen bond formed by a diastereomer of the organic molecule, wherein the diastereomer of the organic molecule differs from the organic molecule only in the handedness of the stereocenter.

Disclosed herein is a method comprising contacting to a mutant p53 protein an organic molecule that binds to a binding site on the mutant p53 protein and forms a hydrogen bond to a Thr-150 residue of the mutant p53 protein, wherein the mutant p53 protein has a conformation that is not pro-apoptotic, and the contacting to the mutant p53 protein the organic molecule that binds to the binding site on the mutant p53 protein and forms the hydrogen bond to the Thr-150 residue of the mutant p53 protein modulates the conformation of the mutant p53 protein to a form that is pro-apoptotic, wherein the organic molecule comprises a hydrogen bond donor and an electron-withdrawing heteroatom, wherein the hydrogen bond donor participates in the hydrogen bond, wherein the hydrogen bond donor is proximal to the electron-withdrawing heteroatom.

Also disclosed herein is a method comprising contacting to a mutant p53 protein an organic molecule that binds to a binding site on the mutant p53 protein and forms a hydrogen bond to a side chain oxygen atom of a Thr-150 residue of the mutant p53 protein, wherein the mutant p53 protein is a Y220C mutant, wherein the organic molecule comprises a tertiary ammonium cation and a fluorine atom, wherein the tertiary ammonium cation and the fluorine atom are substituents on a common ring, the tertiary ammonium cation and the fluorine atom are oriented syn to one another on the common ring, and the tertiary ammonium cation and the fluorine atom are disposed vicinally to one another on the common ring, wherein the tertiary ammonium cation participates in the hydrogen bond, wherein the mutant p53 protein has a conformation that is not pro-apoptotic, and the contacting to the mutant p53 protein the organic molecule that binds to the binding site on the mutant p53 protein and modulates the conformation of the mutant p53 protein to a form that is pro-apoptotic, wherein if a co-crystal is obtained of the organic molecule and the mutant p53 protein with the organic molecule bound to a binding site on the mutant p53 protein, and the co-crystal is obtained by sitting-drop vapor distillation, and if an x-ray co-crystal structure of the co-crystal is obtained by crystal soaking, and if the x-ray co-crystal structure has a resolution of about 2 Å, then in the x-ray co-crystal structure the tertiary ammonium cation forms the hydrogen bond with the side chain oxygen atom of Thr-150 of the mutant p53 protein, wherein the hydrogen bond has a mean length of from about 1.5 Å to about 3 Å, wherein the fluorine atom is bound to a stereocenter of the organic molecule, wherein the stereocenter has a handedness, wherein the hydrogen bond is stronger than is an analogous hydrogen bond formed by a diastereomer of the organic molecule, wherein the diastereomer of the organic molecule differs from the organic molecule only in the handedness of the stereocenter.

In some embodiments, the hydrogen bond has a mean length of from about 1.5 Å to about 3 Å. In some embodiments, the hydrogen bond is to a side chain atom of Thr-150. In some embodiments, in the x-ray co-crystal structure, the compound or organic molecule further forms a second hydrogen bond with Cys-220 of the mutant p53 protein. In some embodiments, the second hydrogen bond is with a carbonyl group of Cys-220. In some embodiments, the electron-withdrawing heteroatom is a halogen atom. In some embodiments, the electron-withdrawing heteroatom is a fluorine atom. In some embodiments, the electron-withdrawing heteroatom is bound to a stereocenter of the compound or organic molecule. In some embodiments, the stereocenter has a handedness, wherein the hydrogen bond is stronger than is an analogous hydrogen bond formed by a stereoisomer of the compound or organic molecule, wherein the stereoisomer of the compound or organic molecule differs from the compound or organic molecule only in the handedness of the stereocenter. In some embodiments, the stereoisomer of the compound or organic molecule is a diastereomer of the compound or organic molecule. In some embodiments, the stereoisomer of the compound or organic molecule is an enantiomer of the compound or organic molecule. In some embodiments, the hydrogen bond donor is a hydrogen atom bound to a nitrogen atom having a formal positive charge. In some embodiments, the hydrogen bond donor is a hydrogen atom bound to a tetravalent nitrogen atom. In some embodiments, the hydrogen bond donor is a tertiary ammonium cation. In some embodiments, the hydrogen bond donor is a tertiary ammonium cation.

In some embodiments, the hydrogen bond donor and the electron-withdrawing heteroatom are substituents on a common ring. In some embodiments, the hydrogen bond donor and the electron-withdrawing heteroatom are substituents on a common ring, and the hydrogen bond donor and the electron-withdrawing group are oriented syn to one another on the common ring. In some embodiments, the hydrogen bond donor and the electron-withdrawing heteroatom are substituents on a common ring, and the hydrogen bond donor and the electron-withdrawing group are disposed vicinally to one another on the common ring. In some embodiments, the hydrogen bond donor and the electron-withdrawing heteroatom are substituents on a common ring, and the hydrogen bond donor and the electron-withdrawing group are oriented syn to one another on the common ring and are disposed vicinally to one another on the common ring. In some embodiments, the mutant p53 protein is a Y220C mutant.

Methods of Crystallization

X-ray crystallography is a tool used to determine the atomic and molecular structure of a crystal. The underlying principle is that crystalline atoms cause a beam of X-rays to diffract into many directions. By measuring the angles and intensities of the diffracted beams, a three-dimensional picture of the density of electrons within the crystal is created. From the electron density image, the mean positions of the atoms in the crystal can be determined, as can chemical bonds and disorder. In some embodiments, X-ray crystallography can be used to determine the interaction between a protein and a compound.

The co-crystal structures of the disclosure can be grown using vapor diffusion. Vapor diffusion uses droplets containing purified protein, buffer, and precipitant, which are equilibrated using a larger reservoir containing similar buffers and precipitants at higher concentrations. Initially, the droplet of protein solution contains comparatively low precipitant and protein concentrations. As the drop and reservoir equilibrate, the precipitant and protein concentrations increase in the drop. Vapor diffusion allows for gentle and gradual changes in concentration of protein and precipitant concentration, which aid in the growth of large and well-ordered crystals. In some embodiments, the co-crystal structures of the disclosure are grown using the microbatch technique, microdialysis, or free-interface diffusion.

Vapor diffusion can be performed using a hanging-drop or sitting-drop format. A hanging-drop apparatus involves a drop of protein solution placed on an inverted cover slip, which is then suspended above a reservoir. A sitting-drop crystallization apparatus places a drop of protein solution on a pedestal that is separated from the reservoir. Both methods require sealing of the environment to allow for equilibration between the drop and the reservoir. In some embodiments, the co-crystal structures of the disclosure can be grown using vapor diffusion in a hanging-drop or sitting drop format. In some embodiments, the co-crystal structures of the disclosure are grown using a sitting drop method.

The co-crystal structures of the disclosure can be grown at a temperature of about 15° C., about 15.5° C., about 16° C., about 16.5° C., about 17° C., about 17.5° C., about 18° C., about 18.5° C., about 19° C., about 19.5° C., about 20° C., about 20.5° C., about 21° C., about 21.5° C., about 22° C., about 22.5° C., about 23° C., about 23.5° C., about 24° C., about 24.5° C., or about 25° C. In some embodiments, the co-crystal structures of the disclosures are grown at a temperature of about 15° C. In some embodiments, the co-crystal structures of the disclosures are grown at a temperature of about 15.5° C. In some embodiments, the co-crystal structures of the disclosures are grown at a temperature of about 16° C. In some embodiments, the co-crystal structures of the disclosures are grown at a temperature of about 16.5° C.

The co-crystal structures of the disclosure can be grown using a protein concentration of about 0.15 mM, about 0.16 mM, about 0.17 mM, about 0.18 mM, about 0.19 mM, about 0.20 mM, about 0.21 mM, about 0.22 mM, about 0.23 mM, about 0.24 mM, about 0.25 mM, about 0.26 mM, about 0.27 mM, about 0.28 mM, about 0.29 mM, about 0.30 mM, about 0.31 mM, about 0.32 mM, about 0.33 mM, about 0.34 mM, about 0.35 mM, about 0.36 mM, about 0.37 mM, about 0.38 mM, about 0.39 mM, about 0.40 mM, about 0.41 mM, about 0.42 mM, about 0.43 mM, about 0.44 mM, about 0.45 mM, about 0.46 mM, about 0.47 mM, about 0.48 mM, about 0.49 mM, or about 0.50 mM. In some embodiments, the co-crystal structures of the disclosure are grown using a protein concentration of about 0.25 mM. In some embodiments, the co-crystal structures of the disclosure are grown using a protein concentration of about 0.28 mM. In some embodiments, the co-crystal structures of the disclosure are grown using a protein concentration of about 0.30 mM.

The co-crystal structures of the disclosure can be grown using a compound concentration of about 0.5 mM, about 0.6 mM, about 0.7 mM, about 0.8 mM, about 0.9 mM, about 1 mM, about 1.1 mM, about 1.2 mM, about 1.3 mM, about 1.4 mM, about 1.5 mM, about 1.6 mM, about 1.7 mM, about 1.8 mM, about 1.9 mM, or about 2 mM. In some embodiments, the co-crystal structures of the disclosure can be grown using a compound concentration of about 0.91 mM, about 0.92 mM, about 0.93 mM, about 0.94 mM, about 0.95 mM, about 0.96 mM, about 0.97 mM, about 0.98 mM, about 0.99 mM, about 1 mM, about 1.1 mM, about 1.12 mM, about 1.13 mM, about 1.14 mM, about 1.15 mM, about 1.16 mM, about 1.17 mM, about 1.18 mM, about 1.19 mM, or about 1.2 mM. In some embodiments, the co-crystal structures are grown using a compound concentration of about 0.8 mM. In some embodiments, the co-crystal structures are grown using a compound concentration of about 1 mM. In some embodiments, the co-crystal structures are grown using a compound concentration of about 1.2 mM.

The co-crystal structures of the disclosure can be grown in a reservoir solution comprising a buffer. In some embodiments, the reservoir solution comprises $MgCl_2$, Tris-HCl, polyethylene glycol (PEG), $K_2HPO_4$, glycerol, or diammonium tartrate. In some embodiments, the PEG is PEG-3350 or PEG-8000. In some embodiments, the crystallization solution comprises 0.2 M $MgCl_2$, 0.1 M Tris-HCl, pH 8.5, and 25% (w/v) PEG-3350. In some embodiments, the crystallization solution comprises 0.04 $K_2HPO_4$, 20% (v/v) glycerol, 16% (w/v) PEG-8000. In some embodiments, the crystallization solution comprises 0.2 M di-ammonium tartrate and 20% (w/v) PEG-3350.

In some embodiments, the crystallization solution has a pH of about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0. In some embodiments, the crystallization solution has a pH of about 7.0. In some embodiments, the crystallization solution has a pH of about 7.1. In some embodiments, the crystallization solution has a pH of about 7.2. In some embodiments, the crystallization solution has a pH of about 7.3. In some embodiments, the crystallization solution has a pH of about 7.4. In some embodiments, the crystallization solution has a pH of about 7.5.

The compounds of the disclosure can comprise a hydrogen bond donor. In some embodiments, the hydrogen bond donor is proximal to an electron-withdrawing group. In some embodiments, the electron-withdrawing group is an electron-withdrawing heteroatom. In some embodiments, the electron-withdrawing heteroatom is a halogen. In some embodiments, the electron-withdrawing heteroatom is fluoride.

In some embodiments, the compounds of the disclosure comprise a hydrogen bond donor that forms a hydrogen bond with Thr-150 of a mutant p53 protein. In some embodiments, the compounds of the disclosure comprise a hydrogen bond donor that forms a hydrogen bond with a side chain oxygen atom of Thr-150. In some embodiments, the compounds of the disclosure comprise a hydrogen bond donor that forms a hydrogen bond with Cys-220 of a mutant p53 protein. In some embodiments, the compounds of the disclosure comprise a hydrogen bond donor that forms a hydrogen bond with a carbonyl group of Cys-220 of a mutant p53 protein.

A hydrogen bond between a compound of the disclosure and an amino acid residue of a mutant p53 protein can have a mean length as determined by an X-ray co-crystal structure of about 2.0 Å, about 2.1 Å, about 2.2 Å, about 2.3 Å, about 2.4 Å, about 2.5 Å, about 2.6 Å, about 2.7 Å, about 2.8 Å, about 2.9 Å, about 3.0 Å, about 3.1 Å, about 3.2 Å, about 3.3 Å, about 3.4 Å, or about 3.5 Å. In some embodiments, a hydrogen bond between a compound of the disclosure and an amino acid residue of a mutant p53 protein can have a mean length of from about 1.5 Å to about 3 Å. In some embodiments, a hydrogen bond between a compound of the disclosure and an amino acid residue of a mutant p53 protein can have a mean length of from about 1.5 Å to about 2 Å. In some embodiments, a hydrogen bond between a compound of the disclosure and an amino acid residue of a mutant p53 protein can have a mean length of from about 2 Å to about 2.5 Å. In some embodiments, a hydrogen bond between a compound of the disclosure and an amino acid residue of a mutant p53 protein can have a mean length of from about 2.5 Å to about 3 Å. In some embodiments, a hydrogen bond between a compound of the disclosure and an amino acid residue of a mutant p53 protein can have a mean length of about 2.5 Å. In some embodiments, a hydrogen bond between a compound of the disclosure and an amino acid residue of a mutant p53 protein can have a mean length of about 2.8 Å.

EXAMPLES

Example 1: Compounds of the Disclosure

TABLE 1

| Comp No. | Structure | IUPAC |
|---|---|---|
| 1 | 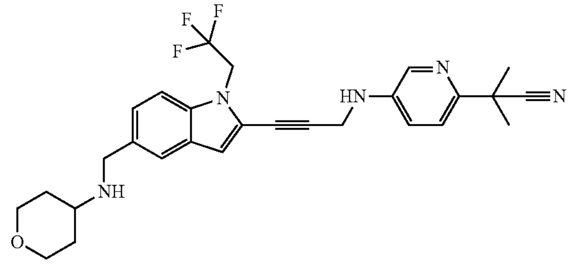 [SMILES: CC(C)(C#N)c1ccc(NCC#Cc2cc3cc(CNC4CCOCC4)ccc3n2CC(F)(F)F)cn1] | 2-methyl-2-(5-{[3-(5-{[(oxan-4-yl)amino]-methyl}-1-(2,2,2-trifluoroethyl)-1H-indol-2-yl)prop-2-yn-1-yl]amino}pyridin-2-yl)propanenitrile |
| 2 | 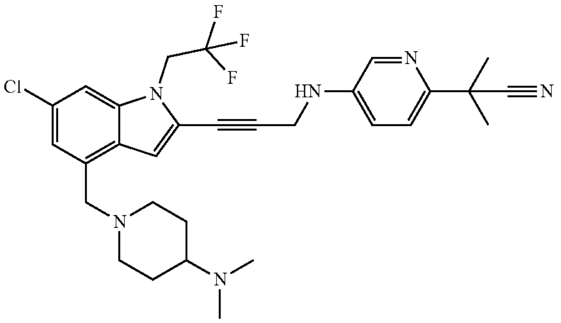 [SMILES: CN(C)C1CCN(Cc2cc(Cl)cc3c2cc(C#CCNc2ccc(C(C)(C)C#N)nc2)n3CC(F)(F)F)CC1] | 2-(5-{[3-(6-chloro-4-{[4-(dimethylamino)-piperidin-1-yl]meth-yl}-1-(2,2,2-trifluoro-ethyl)-1H-indol-2-yl)prop-2-yn-1-yl]-amino}pyridin-2-yl)-2-methylpropane-nitrile |
| 3 | 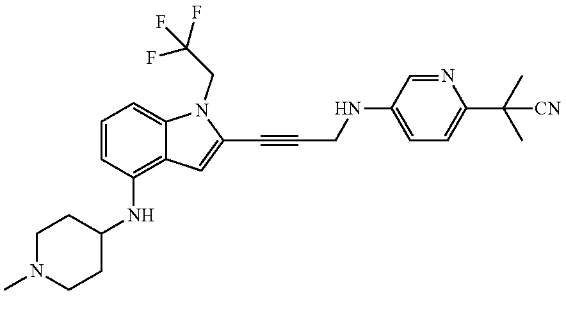 [SMILES: CN1CCC(Nc2cccc3c2cc(C#CCNc2ccc(C(C)(C)C#N)nc2)n3CC(F)(F)F)CC1] | 2-methyl-2-{5-[(3-{4-[(1-methylpiperi-din-4-yl)amino]-1-(2,2,2-trifluoroethyl)-1H-indol-2-yl}prop-2-yn-1-yl)amino]-pyridin-2-yl}propane-nitrile |
| 4 | 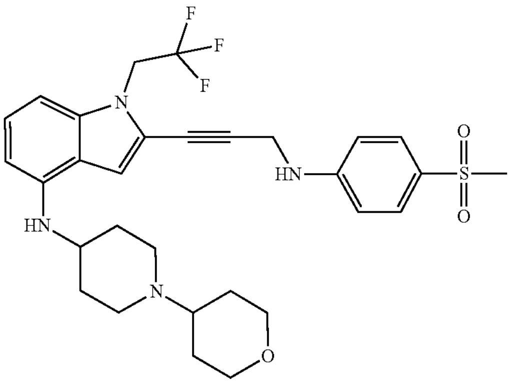 [SMILES: CS(=O)(=O)c1ccc(NCC#Cc2cc3c(NC4CCN(C5CCOCC5)CC4)cccc3n2CC(F)(F)F)cc1] | 2-{3-[(4-methanesul-fonylphenyl)amino]-prop-1-yn-1-yl}-N-[1-(oxan-4-yl)piperi-din-4-yl]-1-(2,2,2-tri-fluoroethyl)-1H-indol-4-amine |

TABLE 1-continued

| Comp No. | Structure | IUPAC |
|---|---|---|
| 5 | 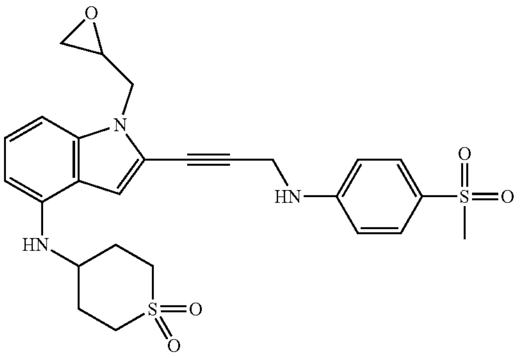 [SMILES: CS(=O)(=O)c1ccc(NCC#Cc2cc3c(NC4CCS(=O)(=O)CC4)cccc3n2CC2CO2)cc1] | 4-[(2-{3-[(4-methanesulfonylphenyl)amino]prop-1-yn-1-yl}-1-[(oxiran-2-yl)methyl]-1H-indol-4-yl)amino]-1λ$^6$-thiane-1,1-dione |
| 6 | 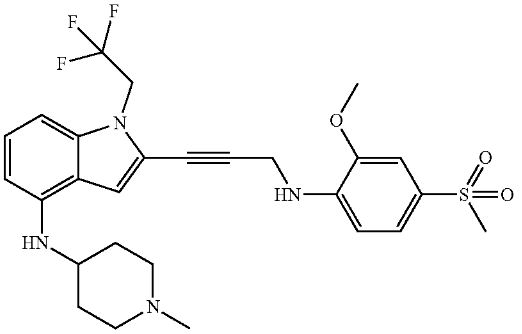 [SMILES: COc1cc(S(C)(=O)=O)ccc1NCC#Cc1cc2c(NC3CCN(C)CC3)cccc2n1CC(F)(F)F] | 2-{3-[(4-methanesulfonyl-2-methoxyphenyl)amino]prop-1-yn-1-yl}-N-(1-methylpiperidin-4-yl)-1-(2,2,2-trifluoroethyl)-1H-indol-4-amine |
| 7 | 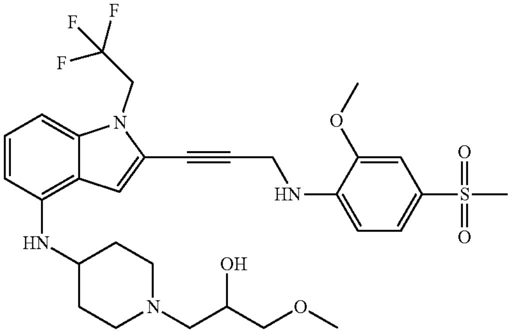 [SMILES: COCC(O)CN1CCC(Nc2cccc3c2cc(C#CCNc2ccc(S(C)(=O)=O)cc2OC)n3CC(F)(F)F)CC1] | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 10 | 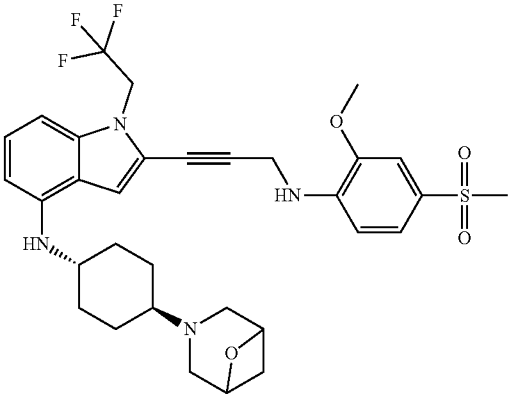 [SMILES: COc1cc(S(C)(=O)=O)ccc1NCC#Cc1cc2c(N[C@H]3CC[C@H](N4CC5CC(C4)O5)CC3)cccc2n1CC(F)(F)F] | 2-{3-[(4-methanesulfonyl-2-methoxyphenyl)amino]prop-1-yn-1-yl}-N-[(1r,4r)-4-{6-oxa-3-azabicyclo[3.1.1]heptan-3-yl}cyclohexyl]-1-(2,2,2-trifluoroethyl)-1H-indol-4-amine |

TABLE 1-continued

| Comp No. | Structure | IUPAC |
|---|---|---|
| 11 | 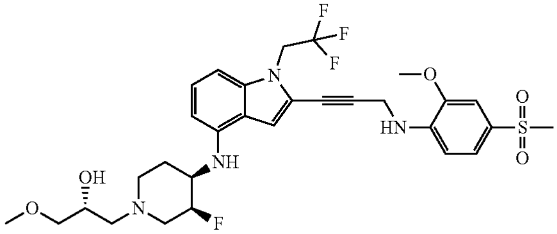 | (2R)-1-[(3S,4R)-3-fluoro-4-[(2-{3-[(4-methanesulfonyl-2-methoxyphenyl)-amino]prop-1-yn-1-yl}-1-(2,2,2-trifluoro-ethyl)-1H-indol-4-yl)amino]piperidin-1-yl]-3-methoxypropan-2-ol |
| 12 | 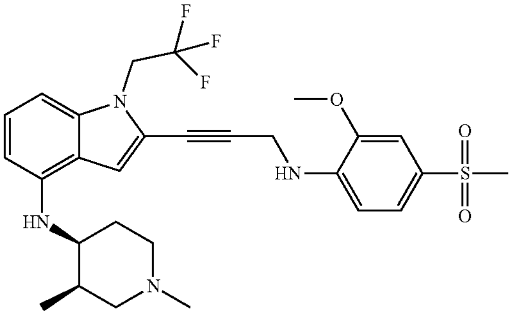 [SMILES: COc1cc(S(C)(=O)=O)ccc1NCC#Cc1cc2c(N[C@H]3CCN(C)C[C@H]3C)cccc2n1CC(F)(F)F] | rac-N-[(3R,4S)-1,3-dimethylpiperidin-4-yl]-2-{3-[(4-methane-sulfonyl-2-methoxy-phenyl)amino]prop-1-yn-1-yl}-1-(2,2,2-trifluoroethyl)-1H-indol-4-amine |
| 13 | 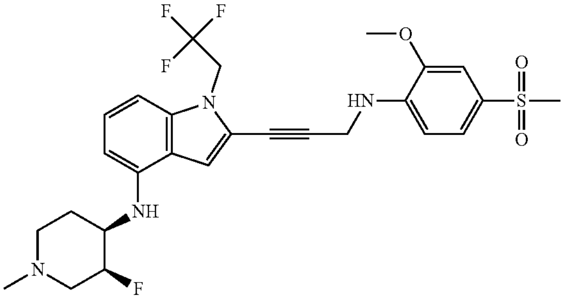 | N-[(3S,4R)-3-fluoro-1-methylpiperidin-4-yl]-2-{3-[(4-methane-sulfonyl-2-methoxy-phenyl)amino]prop-1-yn-1-yl}-1-(2,2,2-trifluoroethyl)-1H-indol-4-amine |
| 14 | 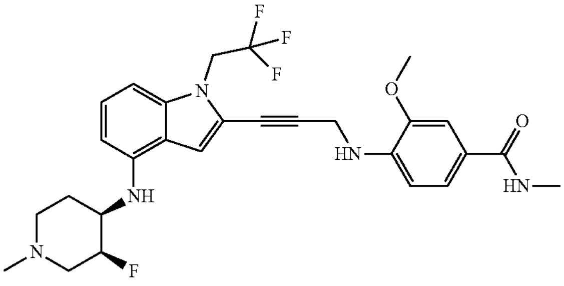 | 4-{[3-(4-{[(3S,4R)-3-fluoro-1-methyl-piperidin-4-yl]-amino}-1-(2,2,2-trifluoroethyl)-1H-indol-2-yl)prop-2-yn-1-yl]amino}-3-meth-oxy-N-methylbenz-amide |

Example 2: Co-Crystallization of Compound 1

Two batches of p53 protein were used for crystallization. The first batch contained 6.93 mg/mL mutant p53 in 25 mM Tris-HCl, pH 7.5, 100 mM KCl, and 5 mM DTT. FIG. 1 PANEL A shows an SDS-PAGE gel of the first batch of mutant p53 protein. The second batch contained 6.99 mg/mL mutant p53 in 25 mM $Na_2HPO_4$, pH 7.2, 150 mM KCl, and 5 mM DTT. FIG. 1 PANEL B shows an SDS-PAGE gel of the first batch of mutant p53 protein. 5 μg recombinant p53 (M133L/V203A/Y220C/N239Y/N268D) was loaded onto a 4-15% Novex® NuPAGE® SDS gel system and stained with Coumassie blue staining. The molecular sizes of marker polypeptides are shown on the left.

Co-crystallization trials were set up with the first batch of p53 protein across 8 screens. Samples included 6.93 mg/mL (0.28 mM) of mutant p53 and 1 mM Compound 1. Ligand occupancy was considered 100% if the Kd was better than 1 μM (TABLE 2). Crystals of mutant p53 were prepared in 25 mM Tris-HCl, pH 7.5, 100 mM KCl, 5 mM DTT were grown in a sparse matrix screen, Wizard III/TV, condition C8: 0.04 K2HPO4, 20% (v/v) glycerol, 16% (w/v) PEG-8000 and directly cryo-protected in the well solution supplemented with 1 mM Compound 1. Compound 1 was provided as a 100 mM stock solution in d6-DMSO. The dataset was collected at the synchrotron APS beamline 21-ID-F. Space group P 212121 with 2 molecules per ASU. The structure was solved by Molecular Replacement with 2VUK using Pfenix. TABLE 3 shows data collection and refinement statistics of the structure with Compound 1.

TABLE 2

| $K_d$ or $IC_{50}$ | $[E]_0$ | $[I]_0$ | x | % Occupancy |
|---|---|---|---|---|
| 1 nM | 0.00028 | 0.001 | 4E−10 | 100 |
| 1 μM | 0.00028 | 0.001 | 4E−07 | 99.9 |
| 1 mM | 0.00028 | 0.001 | 0.0001 | 46.5 |

$K_d = [E]_{eq}[I]/[EI]_{eq}$
$K_d = x([I]_i + x)/([EI]_i - x)$

TABLE 3

| Parameter | Overall |
|---|---|
| Protein | p53 (M133L/V203A/Y220C/N239Y/N268D) |
| Compound | Compound 1 |
| Beamline | APS 21 ID-G |
| Space group | P $2_1$ $2_1$ $2_1$ |
| Unit cell | a = 65.39 Å; b = 70.94 Å; c = 105.1 Å |
| | α = β = γ = 90° |
| Resolution | 50-1.80 Å (1.85-1.80) |
| I/σ | 17.25 (3.85) |
| Completeness | 99.8% (99.9%) |
| $R_{merge}$ | 0.070 (0.446) |
| Multiplicity | 6.1 (6.2) |
| Reflections | 45,972 (3,378) |
| Mosaicity | 0.1 |
| $R_{work}$ | 0.166 (0.201) |
| $R_{free}$ | 0.201 (0.271) |
| Ramachandran | Favored 100% |
| | Allowed 100% |
| | Outliers 0% |
| Molprobity score | 0.85 ($100^{th}$ percentile) |

Figure 5:
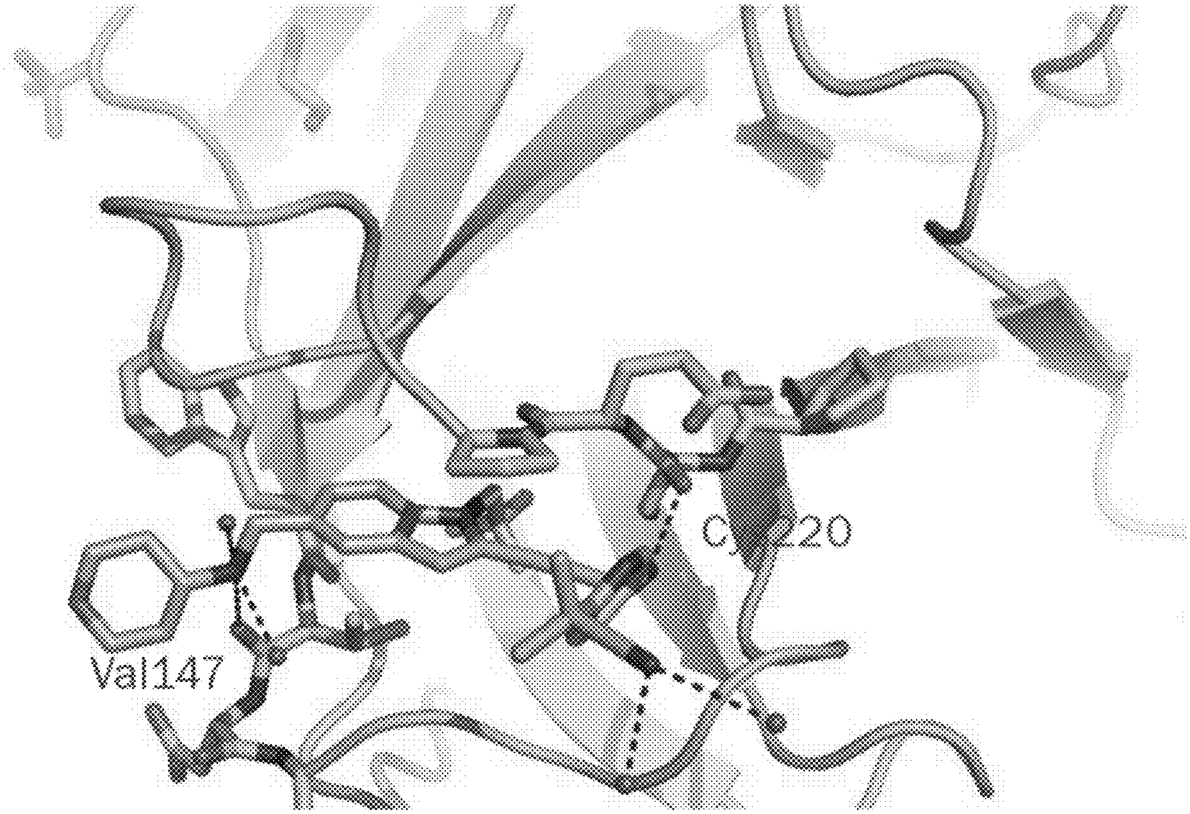
FIG. 5 shows the active site of mutant p53 with Compound 1.

FIG. 2 PANEL A shows an image of crystals of Compound 1 obtained in a buffer of 0.04 $K_2HPO_4$, 20% (v/v) glycerol, and 16% (w/v) PEG-8000 at a resolution of ~1.7 Å. FIG. 2 PANEL B shows an image of crystals of Compound 2 obtained in a buffer of 0.2 M $MgCl_2$, 0.1 M Tris-HCl, pH 8.5, and 25% (w/v) PEG-3350 at a resolution of ~1.7 Å. FIG. 3 PANEL A shows a ligand density image of Compound 1. FIG. 3 PANEL B shows a ligand density image of Compound 1. The images show the central core that is a 6-membered ring; a trifluoro group on top of the core; a long side group coming off the core to the right; and a group coming off the ring to the left that looks larger in Compound 2 than in Compound 1. FIG. 4 shows a co-crystal structure with mutant p53 and Compound 1. FIG. 5 shows the active site of mutant p53 with Compound 1. The figure shows that Compound 1 interacts with 4 water molecules and the carbonyl oxygen of Vail 47 and Cys220.

Figure 8:
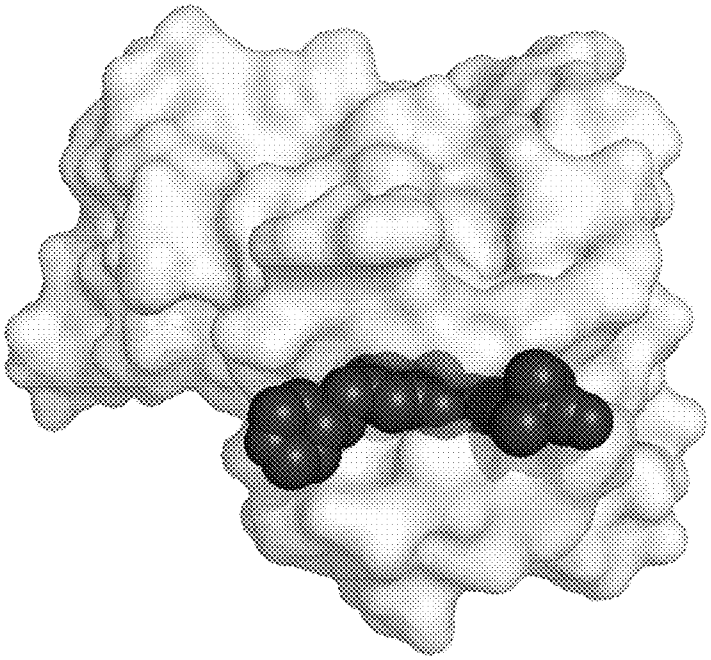
FIG. 8 shows an image of mutant p53 co-crystalized with Compound 1.

The structure of Compound 1 with mutant p53 was compared to the structure of 2VUK. FIG. 6 PANEL A shows the structure of Compound 1 and mutant p53, with 4 water molecules and two backbone carbonyl interactions. FIG. 6 PANEL B shows the structure of 2VUK with Phikan083, which has one backbone carbonyl interaction. FIG. 7 PANEL A shows the binding pocket of mutant p53 near the tri-fluoroethyl group of Compound 1. This figure shows that Compound 1 sits deep in the binding pocket of mutant p53. FIG. 7 PANEL B shows a surface rendering of 2VUK. FIG. 8 shows an image of mutant p53 co-crystalized with Compound 1.

Example 3: Co-Crystallization of Compound 2

Compound 2 was co-crystalized with mutant p53 using the methods described in EXAMPLE 2. FIG. 9 PANEL A shows the active site of mutant p53 co-crystalized with Compound 2. FIG. 9 PANEL B shows the total surface interactions of mutant p53 with Compound 2.

Example 4: Co-Crystallization of Mutant p53 with Compound 3

Figure 10:
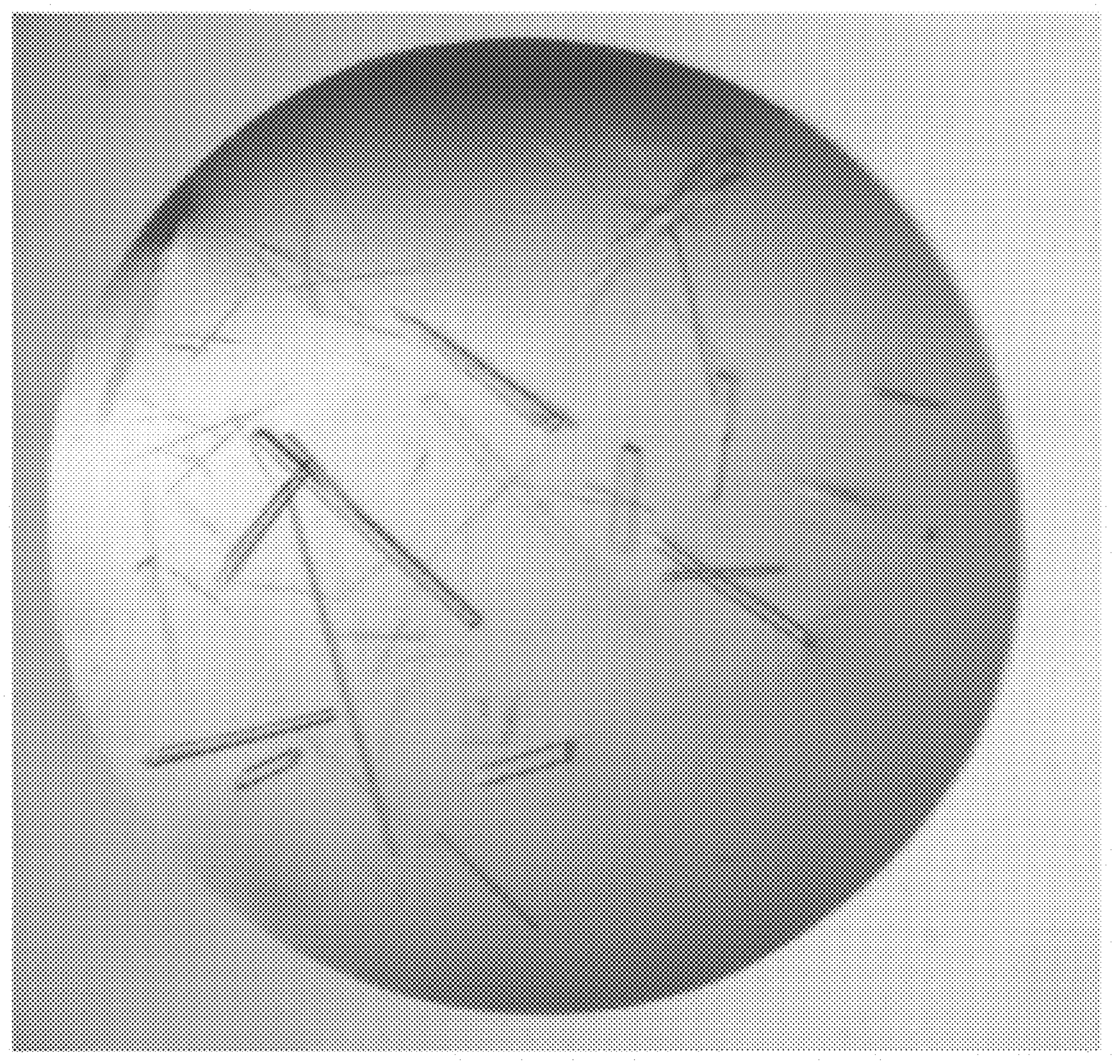
FIG. 10 shows an image of a full dataset collected of mutant p53 co-crystallized with Compound 3 at a resolution of ~1.7 Å in 0.02M $K_2HPO_4$, 20% (v/v) glycerol, and 14% (w/v) PEG-8000.
Figure 11:
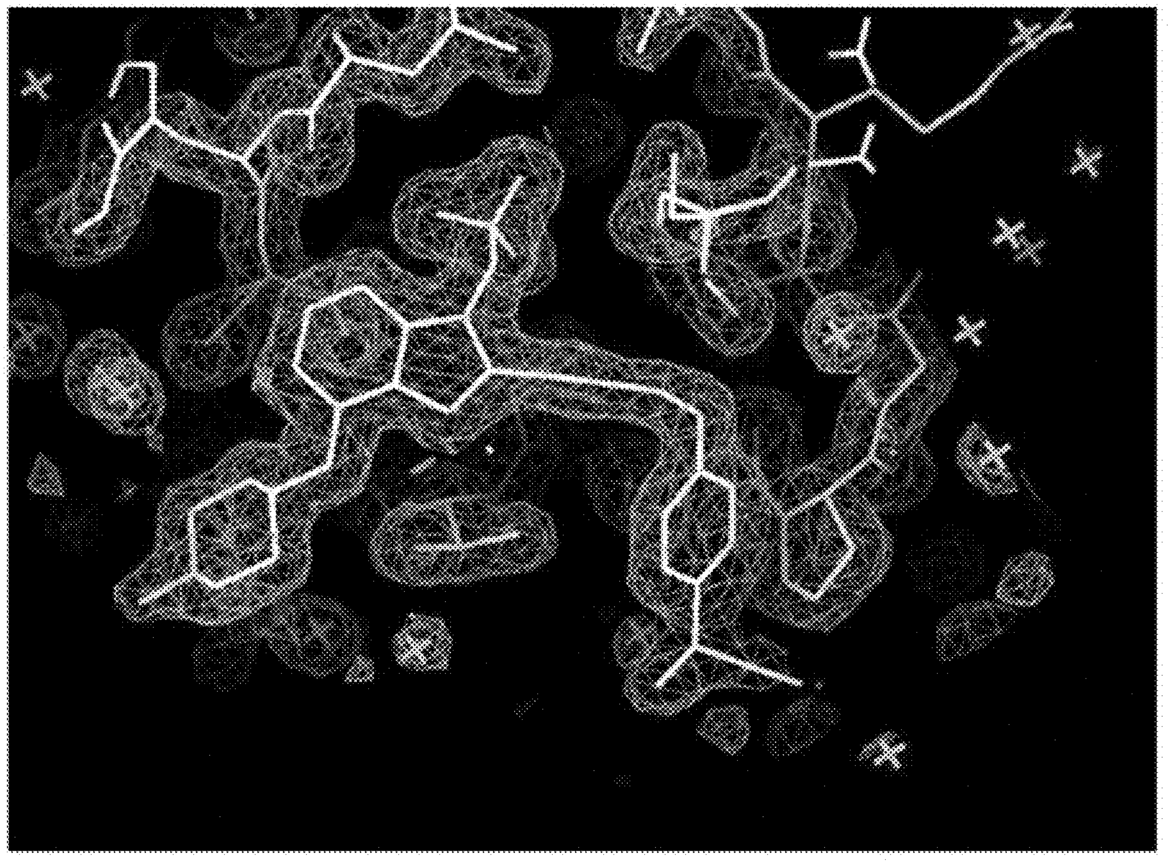
FIG. 11 shows an image of ligand density of Compound 3 co-crystallized with mutant p53.

The two batches of mutant p53 protein described in EXAMPLE 2 were used to co-crystalize Compound 3. FIG. 10 shows an image of a full dataset collected of mutant p53 co-crystallized with Compound 3 at a resolution of ~1.7 Å in 0.02M $K_2HPO_4$, 20% (v/v) glycerol, and 14% (w/v) PEG-8000. FIG. 11 shows an image of ligand density of Compound 3 co-crystallized with mutant p53. TABLE 4 shows data collection and refinement statistics of Compound 3 co-crystallized with mutant p53.

TABLE 4

| Parameter | |
|---|---|
| Protein | p53 (M133L/V203A/Y220C/N239Y/N268D) |
| Compound | Compound 3 |
| Beamline | CLSI 08ID |
| Space group | P $2_1$ $2_1$ $2_1$ |
| Unit cell | a = 64.72 Å; b = 70.98 Å; c = 104.90 Å |
| | α = β = γ = 90° |
| Resolution | 50-1.70 Å (1.74-1.70) |
| I/σ | 18.3 (3.43) |
| Completeness | 99.7% (97.3%) |
| $R_{merge}$ | 0.071 (0.481) |
| Multiplicity | 5.9 (4.3) |
| Reflections | 53,719 (4584) |
| Mosaicity | |
| $R_{work}$ | 0.1549 (0.2128) |
| $R_{free}$ | 0.175 (0.2802) |
| Ramachandran | Favored 100% |
| | Allowed 100% |
| | Outliers 0% |
| Molprobity score | 1.22 ($100^{th}$ percentile) |

Figure 12:
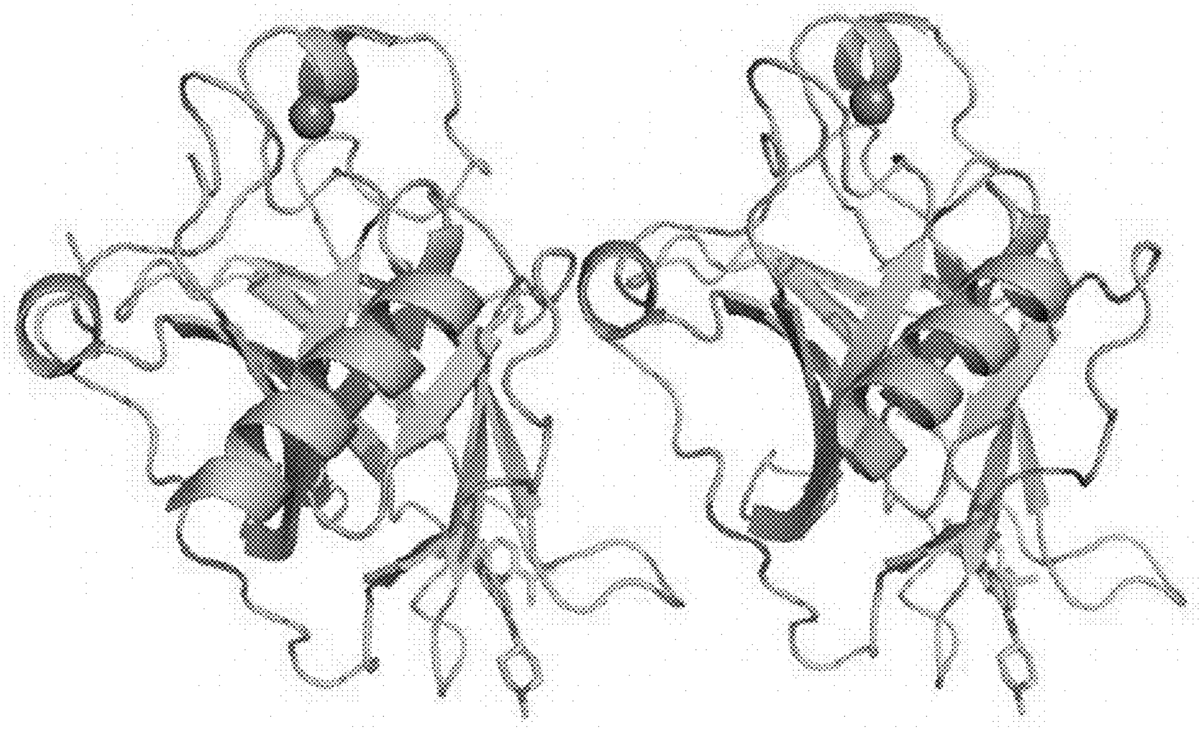
FIG. 12 shows mutant p53 co-crystalized with Compound 3.

Crystals of p53 in 25 mM $Na_2HPO_4$, pH 7.2, 150 mM KCl, 5 mM DTT were grown in a sparse matrix screen, condition E2: 0.02 $K_2HPO_4$, 20% (v/v) glycerol, 14% (w/v) PEG-8000 and directly cryo-protected in the well solution supplemented with 1 mM compound. The dataset was collected at the Canadian Light Source beamline 08-ID. Space group P 21 21 21 with 2 molecules per ASI. The structure was solved by Molecular Replacement with 2VUK using Pfenix. FIG. 12 shows mutant p53 co-crystalized with Compound 3.

Figure 13:
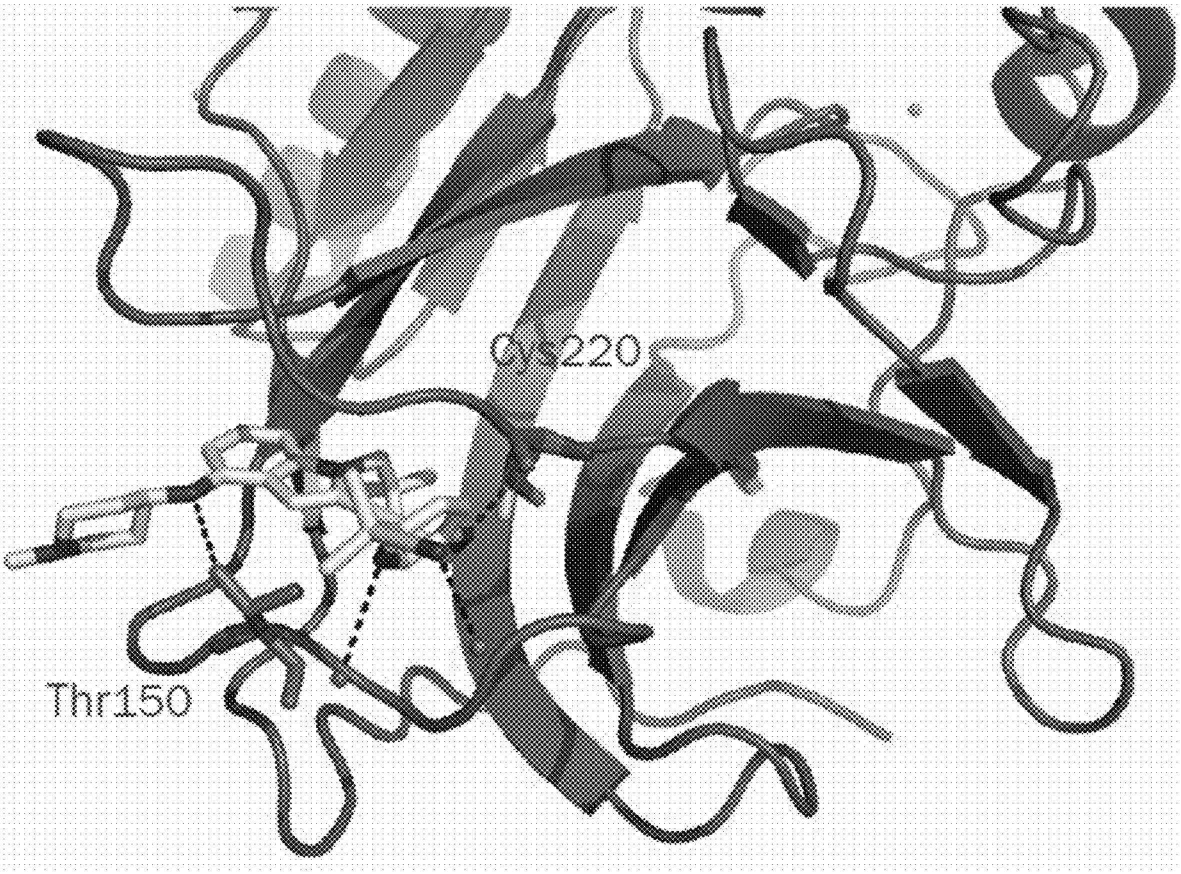
FIG. 13 shows the active site of mutant p53 with Compound 3.

FIG. 13 shows the active site of mutant p53 with Compound 3. The image shows that Compound 3 interacts with two water molecules and side chain oxygen atoms of Thr150 and Cys220. Cys220 was observed in two orientations. Compared to Compound 2, co-crystallization of mutant p53 with Compound 3 showed that the loop from Cys220 to Cys229 was rearranged, with a movement of Gly226 of 3.7 Å. Additionally, the loop from Leu114 to Lys120 was visible in the structure with Compound 3 but disordered in the structure with Compound 2 (data not shown). FIG. 14 PANEL A shows the co-crystal structure of Compound 3. The image shows interaction of Compound 3 with two water molecules and two backbone carbonyl moieties (Cys220 and Thr150). FIG. 14 PANEL B shows the co-crystal structure of Compound 2, which shows interaction of Compound 2 with three water molecules and one backbone carbonyl (Cys220). FIG. 15 PANEL A shows the active site of mutant p53 co-crystalized with Compound 3. FIG. 15 PANEL B shows a co-crystal structure of mutant p53 with Compound 3.

Example 5: Co-Crystallization of Mutant p53 with Compound 4, Compound 5, and Compound 6

Figure 16:
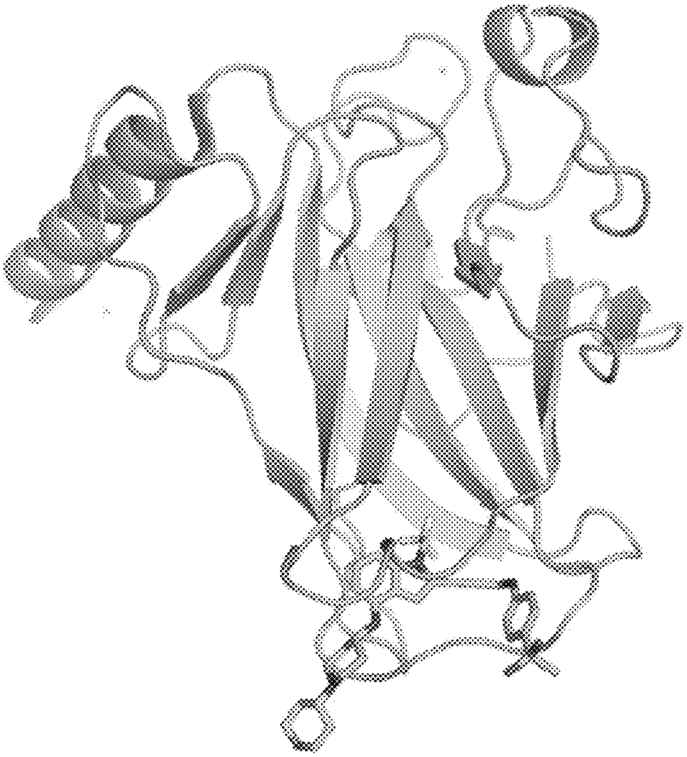
FIG. 16 shows a co-crystal structure of Compound 4 with mutant p53.

FIG. 16 shows a co-crystal structure of Compound 4 with mutant p53.

FIG. 17A shows the binding pocket of mutant p53 and Compound 5. FIG. 17B shows the total surface interactions of mutant p53 co-crystallized with Compound 5 in the binding pocket.

Figure 18:
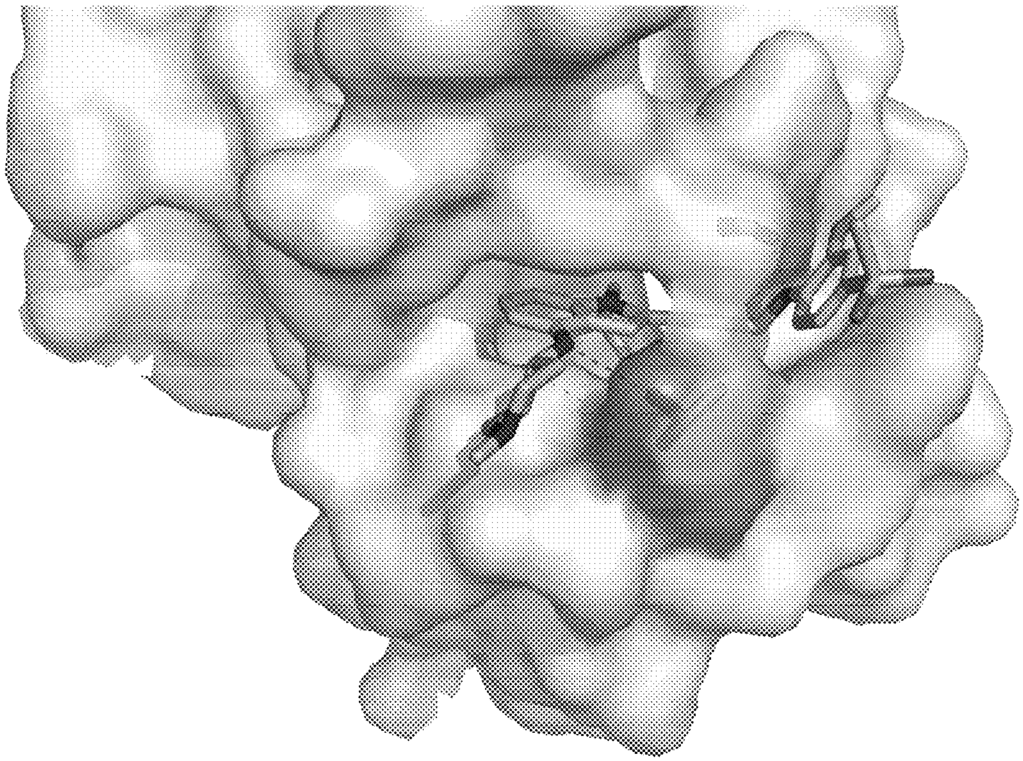
FIG. 18 shows the total surface interactions of mutant p53 co-crystallized with Compound 6 in the binding pocket.

FIG. 18 shows the total surface interactions of mutant p53 co-crystallized with Compound 6 in the binding pocket.

Example 6: Co-Crystallization of Mutant p53 with Compound 7

Figure 20:
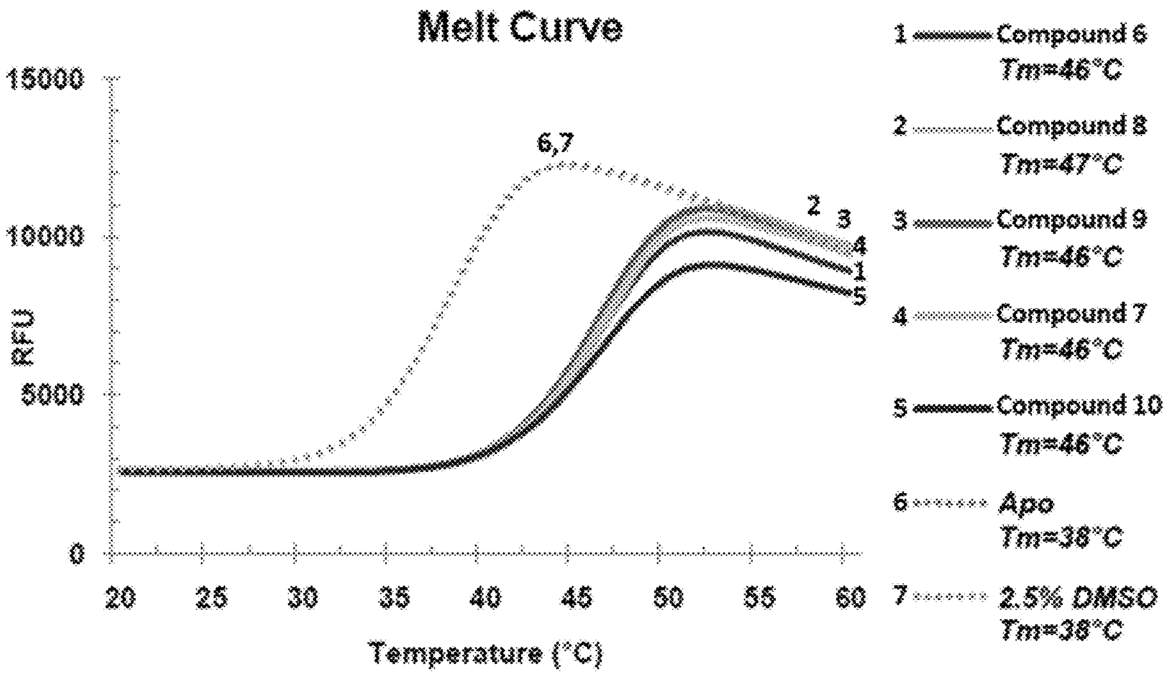
FIG. 20 shows a melt curve of Compounds 6, 8, 9, 7, and 10. Apo and 2.5% DMSO solutions were used as controls.

FIG. 19 PANEL A shows images of co-crystal structures of Compound 7. The LEFT PANEL shows a well crystallized in 0.2 M sodium potassium tartrate, and 20% PEG-3350. The RIGHT PANEL shows a well crystallized in 0.2 M sodium chloride, 0.1 M Hepes buffer, pH 7.5, and 25% (w/v) PEG-3350. FIG. 19 PANEL B shows a ligand density image of the active site with Compound 7. FIG. 20 shows a melt curve of Compounds 6, 8, 9, 7, and 10. Apo (protein without ligand) and 2.5% DMSO solutions were used as controls.

Figure 21:
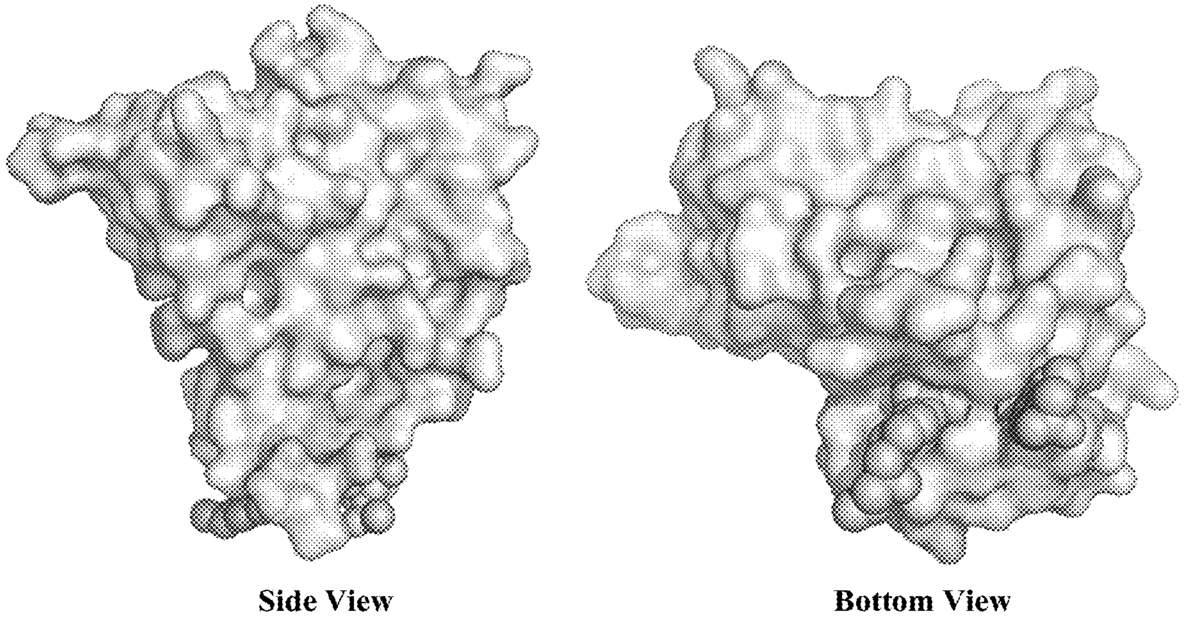
FIG. 21 LEFT PANEL shows a side view of a mutant p53 and Compound 7 co-crystal structure.
Figure 22:
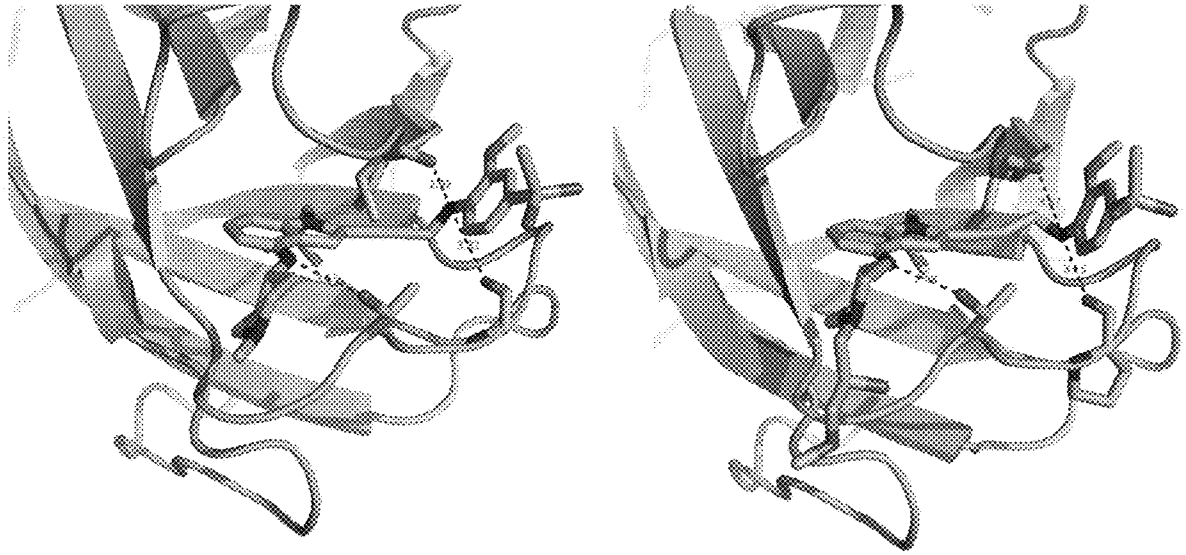
FIG. 22 LEFT PANEL shows a co-crystal structure of mutant p53 with Compound 6.

FIG. 21 LEFT PANEL shows a side view of a mutant p53 and Compound 7 co-crystal structure. FIG. 21 RIGHT PANEL shows a bottom view of a mutant p53 and Compound 7 co-crystal structure. FIG. 22 LEFT PANEL shows a co-crystal structure of mutant p53 with Compound 6. FIG. 22 RIGHT PANEL shows a co-crystal structure of mutant p53 with Compound 7.

Example 7: Co-Crystallization of Mutant p53 with Compound 10

Figure 23:
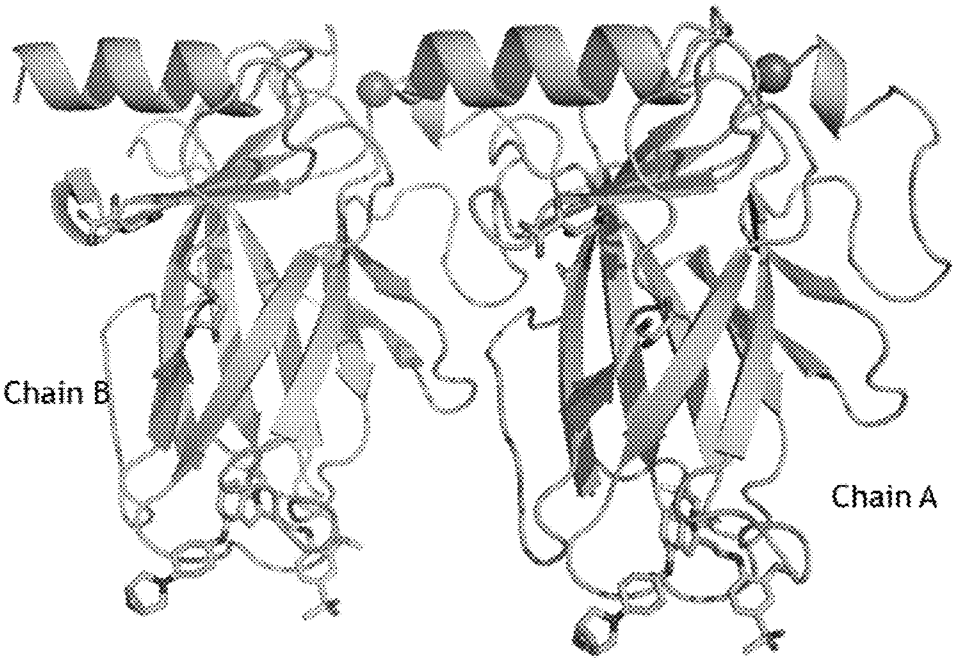
FIG. 23 shows the co-crystal structure of mutant p53 with Compound 10.

Mutant p53 (M133L/V203 Å/Y220C7N239Y/N268D) was used at a concentration of 6.09 mg/mL. The protein was incubated with Compound 10 at a molar ratio of 1:5 for 1 hour at 4° C. prior to crystallization. The crystals were grown using sitting drop vapor diffusion in a 96-well place. The reservoir solution was 0.1 M Hepes, pH 7.0, 0.2 M K/Na tartrate, and 20% PEG-3350. The crystals were grown at 22° C. for 2-3 days, and cryo-protected with 15% glycerol in the reservoir solution. TABLE 5 shows the data collection statistics and refinement statistics for the co-crystal structure. FIG. 23 shows the co-crystal structure of mutant p53 with Compound 10.

TABLE 5

| Parameter | Settings |
|---|---|
| Data collection statistics | |
| Number of frames | 105 |
| Oscillation width (°) | 1 |
| Exposure per frame (sec) | 720 |
| Space group | P $2_1$ $2_1$ $2_1$ |
| Resolution range (Å) | 50.00-1.97 (2.04-1.97) |
| Unit cell constants | (Å) a = 64.620; b = 70.946; c = 104.501<br>(°) α = β = γ = 90° |
| $R_{merge}$ (%) | 11.1 (51) |
| $R_{pim}$ (%) | 5.8 (30.6) |
| Completeness (%) | 92.8 (92.2) |
| <I>/σ(<I>) | 11.2 (2.12) |
| Average redunancy | 4.2 (3.3) |
| Refinement statistics | |
| Number of molecules in asymmetric unit | 2 |
| N-term amino acid | A chain - 94 (ser)<br>B chain - 95 (ser) |
| C-term amino acid | A chain - 290 (Arg)<br>B chain - 289 (Leu) |
| Final R-factor ($R_{free}$) | 0.209 (0.244) |

TABLE 5-continued

| Parameter | Settings |
|---|---|
| Ramachandran Statistics (%) | Core: 91.3; Allowed: 8.7 |
| No of water molecules | 264 |
| Ligand bound status | Yes (A & B chain) |
| Bound metal atoms and solvents | 2 $Zn^{2+}$ ions; 2 tartaric acid; 2 glycerol |

Example 8: Co-Crystallization of Mutant p53 with Compounds 11, 12, and 13

Figure 24:
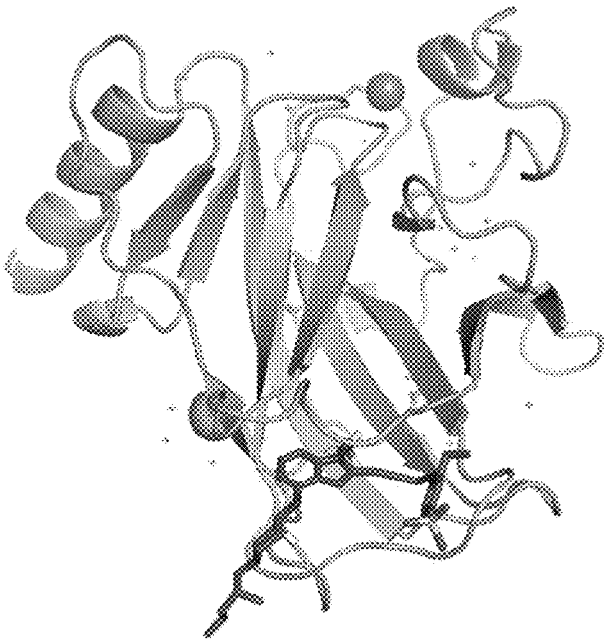
FIG. 24 shows the co-crystal structure of mutant p53 with Compound 11.
Figure 25:
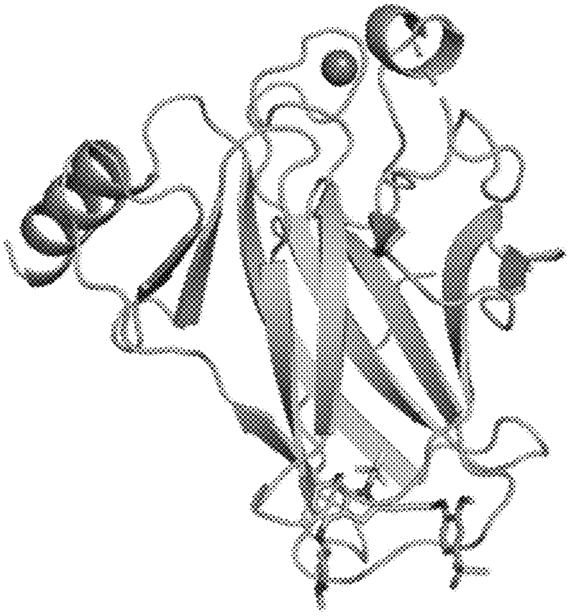
FIG. 25 shows the co-crystal structure of mutant p53 with Compound 12.

FIG. 24 shows the co-crystal structure of mutant p53 with Compound 11. FIG. 25 shows the co-crystal structure of mutant p53 with Compound 12. FIG. 26 PANEL A and PANEL B show co-crystal structures of Compound 13.

Example 9: Co-Crystallization of Mutant p53 with Compound 14

Co-crystals of mutant p53 with Compound 14 were grown using 6 mg of mutant p53. The protein and compound were incubated for 1 hr at 4° C. and crystallized using the sitting drop method at room temperature. A 1:1 ratio of the protein and reservoir ratio solution was used. The reservoir solution contained 0.2 M sodium potassium tartarate and 25% PEG-3350. The crystals were cryoprotected using a solution of 18% glycerol in the reservoir solution.

TABLE 6 shows refinement statistics used to co-crystalize mutant p53 with Compound 14. FIG. 27 PANEL A shows the co-crystal structure of mutant p53 and Compound 14. FIG. 27 PANEL B shows the active site of mutant p53 co-crystalized with Compound 14.

TABLE 6

| Parameter | Settings |
|---|---|
| Data collection statistics | |
| Number of frames | 3600 |
| Oscillation widthΦ (°) | 0.1 |
| Exposure per frame (sec) | 0.01 |
| Distance (mm) | 215 |
| Space Group | P $2_1$ $2_1$ $2_1$ |
| Resolution Range (Å) | 50.00-1.63 (1.69-1.63) |
| Unit cell constants | (Å) a = 65.116; b = 71.205; c = 105.233<br>(°) α = β = γ = 90° |
| $R_{merge}$ (%) | 9.8 (51.1) |
| $R_{pim}$ (%) | 2.8 (15.5) |
| $CC_{1/2}$ | 0.997 (0.960) |
| Completeness (%) | 100 (100) |
| <I>/σ(<I>) | 30.7 (3.85) |
| Average redundancy | 12.6 (11.6) |
| Refinement statistics | |
| No. of molecules in asymmetric unit | 2 |
| N-terminal amino acid | A chain - 95 (Ser)<br>B chain - 95 (Ser) |
| C-terminal amino acid | A chain - 292 (Lys)<br>B chain - 292 (Lys) |
| Final R-factor ($R_{free}$) | 0.180 (0.205) |
| Ramachandran Statistics (%) | Core: 89.9; Allowed: 10.1;<br>Generous: 0.0; Disallowed: 0.0 |
| No. of water molecules | 405 |
| Ligand bound status | Yes |
| Number of metal atoms | Zn |

101 Lys, 120 Lys, 290Arg, 291 Lys, and 292 Lys side chains of the A chain were disordered. 95 Ser, 120 Lys, 290 Arg, 291 Lys, and 292 Lys side chains of the B chain were disordered. The region containing amino acids 182-185 was disordered in both the A chain and the B chains. The areas around residues 115 His of chains A and B were left unmodeled because predictions were not possible. $H_2O$ 394 was modeled as a secondary sphere near the Compound.

Example 10: Additional Compounds of the Disclosure

Indole compounds with alkynyl, aryl, and heteroaryl linkers were prepared. Alkynyl-linked indole compounds are shown in TABLE 7. Aryl-linked indole compounds are shown in TABLE 8. Heteroaryl-linked indole compounds are shown in TABLE 9.

TABLE 7

Alkynyl indole compounds of the disclosure.

| Mol # | IUPAC name |
|---|---|
| 1. | 1-Anilino-3-{1-ethyl-5-[(1-methyl-4-piperidylamino)methyl]-1H-indol-2-yl}-2-propyne |
| 2. | 1-Anilino-3-{1-ethyl-5-[(methylamino)methyl]-1H-indol-2-yl}-2-propyne |
| 3. | 1-Anilino-3-{1-ethyl-5-[(tetrahydro-2H-pyran-4-ylamino)methyl]-1H-indol-2-yl}-2-propyne |
| 4. | 1-Anilino-3-[5-(benzylaminomethyl)-1-ethyl-1H-indol-2-yl]-2-propyne |
| 5. | 3-{1-Ethyl-5-[(methylamino)methyl]-1H-indol-2-yl}-1-(p-fluorophenylamino)-2-propyne |
| 6. | 3-{1-Ethyl-5-[(tetrahydro-2H-pyran-4-ylmino)methyl]-1H-indol-2-yl}-1-(p-fluorophenylamino)-2-propyne |
| 7. | 1-(p-Chlorophenylamino)-3-{1-ethyl-5-[(1-methyl-4-piperidylamino)methyl]-1H-indol-2-yl}-2-propyne |
| 8. | 3-{1-Ethyl-5-[(tetrahydro-2H-pyran-4-ylamino)methyl]-1H-indol-2-yl}-1-(6-methyl-3-pyridylamino)-2-propyne |
| 9. | 3-{1-Ethyl-5-[(methylamino)methyl]-1H-indol-2-yl}-1-(6-methyl-3-pyridylamino)-2-propyne |
| 10. | 3-{1-Ethyl-5-[(1-methyl-4-piperidylamino)methyl]-1H-indol-2-yl}-1-(2-methyl-4-pyridylamino)-2-propyne |
| 11. | 3-[5-(Benzylaminomethyl)-1-ethyl-1H-indol-2-yl]-1-(2-methyl-4-pyridylamino)-2-propyne |
| 12. | N-(3-{5-[(Diethylamino)methyl]-1-ethyl-1H-indol-2-yl}prop-2-yn-1-yl)aniline |
| 13. | 4-Chloro-N-(3-{5-[(diethylamino)methyl]-1-ethyl-1H-indol-2-yl}prop-2-yn-1-yl)aniline |
| 14. | N-({1-Ethyl-2-[3-(phenylamino)prop-1-yn-1-yl]-1H-indol-5-yl}methyl)oxetan-3-amine |
| 15. | N-[3-(1-Ethyl-5-{[(2-methylpropyl)amino]methyl}-1H-indol-2-yl)prop-2-yn-1-yl]aniline |
| 16. | N-[3-(1-Ethyl-5-{[(2-methoxyethyl)amino]methyl}-1H-indol-2-yl)prop-2-yn-1-yl]aniline |
| 17. | N-({1-ethyl-2-[3-(phenylamino)prop-1-yn-1-yl]-1H-indol-5-yl}methyl)-1-methanesulfonylpiperidin-4-amine |
| 18. | N-(3-{1-Ethyl-5-[(ethylamino)methyl]-1H-indol-2-yl}prop-2-yn-1-yl)aniline |
| 19. | N-{3-[5-({[2-(Dimethylamino)ethyl]amino}methyl)-1-ethyl-1H-indol-2-yl]prop-2-yn-1-yl}aniline |
| 20. | 6-tert-Butyl-N-[3-(1-ethyl-5-{[(1-methylpiperidin-4-yl)amino]methyl}-1H-indol-2-yl)prop-2-yn-1-yl]pyridin-3-amine |
| 21. | N-[(2-{3-[(4-Chlorophenyl)amino]prop-1-yn-1-yl}-1-ethyl-1H-indol-5-yl)methyl]oxan-4-amine |
| 22. | 6-tert-Butyl-N-(3-{1-ethyl-5-[(methylamino)methyl]-1H-indol-2-yl}prop-2-yn-1-yl)pyridin-3-amine |
| 23. | 4-[(3-{1-Ethyl-5-[(methylamino)methyl]-1H-indol-2-yl}prop-2-yn-1-yl)amino]benzonitrile |
| 24. | 4-tert-Butyl-N-(3-{1-ethyl-5-[(methylamino)methyl]-1H-indol-2-yl}prop-2-yn-1-yl)benzamide |
| 25. | 4-Chloro-N-(3-{1-ethyl-5-[(methylamino)methyl]-1H-indol-2-yl}prop-2-yn-1-yl)-3-fluorobenzamide |
| 26. | 4-Cyano-N-({1-ethyl-2-[3-(phenylformamido)prop-1-yn-1-yl]-1H-indol-5-yl}methyl)-N-methylbenzamide |
| 27. | 3-(3-{1-Ethyl-5-[(methylamino)methyl]-1H-indol-2-yl}prop-2-yn-1-yl)-1-[4-(trifluoromethyl)phenyl]urea |
| 28. | N-{[1-(2-Chloroethyl)-2-{3-[(4-chlorophenyl)amino]prop-1-yn-1-yl}-1H-indol-5-yl]methyl}oxan-4-amine |
| 29. | 2-(4-{[3-(1-Ethyl-5-{[(1-methylpiperidin-4-yl)amino]methyl}-1H-indol-2-yl)prop-2-yn-1-yl]amino}phenyl)-2-methylpropanenitrile |
| 30. | 4-Cyano-N-(3-{1-ethyl-5-[(methylamino)methyl]-1H-indol-2-yl}prop-2-yn-1-yl)benzamide |
| 31. | N-(3-{1-Ethyl-5-[(methylamino)methyl]-1H-indol-2-yl}prop-2-yn-1-yl)-6-methylpyridine-3-carboxamide |
| 32. | 3-[3-(1-Ethyl-5-{[(1-methylpiperidin-4-yl)amino]methyl}-1H-indol-2-yl)prop-2-yn-1-yl]-1-phenylurea |
| 33. | N-[(2-{3-[(4-Chloro-3-fluorophenyl)amino]prop-1-yn-1-yl}-1-ethyl-1H-indol-5-yl)methyl]-1-methylpiperidin-4-amine |
| 34. | 2-(5-{[3-(1-Ethyl-5-{[(1-methylpiperidin-4-yl)amino]methyl}-1H-indol-2-yl)prop-2-yn-1-yl]amino}pyridin-2-yl)-2-methylpropanenitrile |
| 35. | N-{[1-(2-Chloroethyl)-2-{3-[(4-chlorophenyl)amino]prop-1-yn-1-yl}-1H-indol-5-yl]methyl}-1-methylpiperidin-4-amine |
| 36. | 6-tert-Butyl-N-[3-(1-ethyl-5-{[(1-methanesulfonylpiperidin-4-yl)amino]methyl}-1H-indol-2-yl)prop-2-yn-1-yl]pyridin-3-amine |

TABLE 7-continued

Alkynyl indole compounds of the disclosure.

| Mol # | IUPAC name |
|---|---|
| 37. | 2-(4-{[3-(1-Ethyl-5-{[(1-methylpiperidin-4-yl)amino]methyl}-1H-indol-2-yl)prop-2-yn-1-yl]amino}phenyl)-2-methylpropanoic acid |
| 38. | 3-(1-Ethyl-5-{[(1-methylpiperidin-4-yl)amino]methyl}-1H-indol-2-yl)-N-methylprop-2-ynamide |
| 39. | Ethyl 2-(4-{[3-(1-ethyl-5-{[(1-methylpiperidin-4-yl)amino]methyl}-1H-indol-2-yl)prop-2-yn-1-yl]amino}phenyl)-2-methylpropanoate |
| 40. | 2-(5-{[3-(1-Ethyl-5-{[(oxan-4-yl)amino]methyl}-1H-indol-2-yl)prop-2-yn-1-yl]amino}pyridin-2-yl)-2-methylpropanenitrile |
| 41. | N-[(1-Ethyl-2-{3-[(4-methylphenyl)amino]prop-1-yn-1-yl}-1H-indol-5-yl)methyl]-1-methylpiperidin-4-amine |
| 42. | 4-{[3-(1-Ethyl-5-{[(1-methylpiperidin-4-yl)amino]methyl}-1H-indol-2-yl)prop-2-yn-1-yl]amino}benzonitrile |
| 43. | 3-(1-Ethyl-5-{[(1-methylpiperidin-4-yl)amino]methyl}-1H-indol-2-yl)-N-phenylprop-2-ynamide |
| 44. | N-[(2-{3-[(4-Chlorophenyl)amino]prop-1-yn-1-yl}-1-ethyl-1H-indol-5-yl)methyl]-1-methanesulfonylpiperidin-4-amine |
| 45. | 1-(4-{[(2-{3-[(4-Chlorophenyl)amino]prop-1-yn-1-yl}-1-ethyl-1H-indol-5-yl)methyl]amino}piperidin-1-yl)ethan-1-one |
| 46. | 6-tert-Butyl-N-[3-(1-ethyl-5-{[(1-methylpiperidin-4-yl)amino]methyl}-1H-indol-2-yl)prop-2-yn-1-yl]pyridine-3-carboxamide |
| 47. | N-(3-{1-Ethyl-5-[(methylamino)methyl]-1H-indol-2-yl}prop-2-yn-1-yl)-4-(trifluoromethyl)aniline |
| 48. | N-[(1-Ethyl-2-{3-[(4-methylphenyl)amino]prop-1-yn-1-yl}-1H-indol-5-yl)methyl]oxan-4-amine |
| 49. | N-(3-{1-ethyl-4-[(methylamino)methyl]-1H-indol-2-yl}prop-2-yn-1-yl)aniline |
| 50. | N-[3-(1-ethyl-4-{[4-(pyrrolidin-1-yl)piperidin-1-yl]methyl}-1H-indol-2-yl)prop-2-yn-1-yl]aniline |
| 51. | N-({1-ethyl-2-[3-(phenylamino)prop-1-yn-1-yl]-1H-indol-4-yl}methyl)-1-methylpiperidin-4-amine |
| 52. | 1-[(2-{3-[(4-chlorophenyl)arnino]prop-1-yn-1-yl}-1-ethyl-1H-indol-4-yl)methyl]piperidin-4-ol |
| 53. | 4-Chloro-N-[3-(1-ethyl-4-{[4-(pyrrolidin-1-yl)piperidin-1-yl]methyl}-1H-indol-2-yl)prop-2-yn-1-yl]aniline |
| 54. | 1-[(2-{3-[(4-chlorophenyl)amino]prop-1-yn-1-yl}-1-ethyl-1H-indol-4-yl)methyl]-N,N-dimethylpiperidin-4-amine |
| 55. | 4-Chloro-N-(3-{1-ethyl-4-[(4-methylpiperazin-1-yl)methyl]-1H-indol-2-yl}prop-2-yn-1-yl)aniline |
| 56. | 1-{1-[(2-{3-[(4-Chlorophenyl)amino]prop-1-yn-1-yl}-1-ethyl-1H-indol-4-yl)methyl]piperidin-4-yl}piperidin-4-ol |
| 57. | 2-(5-{[3-(4-{[4-(4-Aminopiperidin-1-yl)piperidin-1-yl]methyl}-1-ethyl-1H-indol-2-yl)prop-2-yn-1-yl]amino]pyridin-2-yl)-2-methylpropanenitrile |
| 58. | 1-[(1-ethyl-2-{3-[(4-fluorophenyl)amino]prop-1-yn-1-yl}-1H-indol-5-yl)methyl]-N,N-dimethylpiperidin-4-amine |
| 59. | 4-N-({1-ethyl-2-[3-(phenylamino)prop-1-yn-1-yl]-1H-indol-5-yl}methyl)-1-N,1-N-dimethylcyclohexane-1,4-diamine |
| 60. | 4-chloro-N-(3-{1-ethyl-5-[(methylamino)methyl]-1H-indol-2-yl}prop-2-yn-1-yl)-3-fluoroaniline |
| 61. | 6-tert-butyl-N-(3-{1-ethyl-5-[(methylamino)methyl]-1H-indol-2-yl}prop-2-yn-1-yl)pyridine-3-carboxamide |
| 62. | N-(3-{1-ethyl-5-[(methylamino)methyl]-1H-indol-2-yl}prop-2-yn-1-yl)benzamide |
| 63. | 3-(3-{1-ethyl-5-[(methylamino)methyl]-1H-indol-2-yl}prop-2-yn-1-yl)-1-(4-methylphenyl)urea |
| 64. | 4-chloro-N-(3-{1-ethyl-5-[(methylamino)methyl]-1H-indol-2-yl}prop-2-yn-1-yl)aniline |
| 65. | 4-{[3-(1-ethyl-5-{[(oxan-4-yl)amino]methyl}-1H-indol-2-yl)prop-2-yn-1-yl]amino}benzonitrile |
| 66. | N-[(2-{3-[(4-chloro-3-fluorophenyl)amino]prop-1-yn-1-yl}-1-ethyl-1H-indol-5-yl)methyl]oxan-4-amine |
| 67. | 3-[3-(1-ethyl-5-{[(oxan-4-yl)amino]methyl}-1H-indol-2-yl)prop-2-yn-1-yl]-1-phenylurea |
| 68. | 6-tert-butyl-N-[3-(1-ethyl-5-{[(oxan-4-yl)amino]methyl}-1H-indol-2-yl)prop-2-yn-1-yl]pyridin-3-amine |
| 69. | 4-{[(2-{3-[(4-chlorophenyl)amino]prop-1-yn-1-yl}-1-ethyl-1H-indol-5-yl)methyl]amino}-1$\lambda^6$-thiane-1,1-dione |
| 70. | N-[(2-{3-[(4-chlorophenyl)amino]prop-1-yn-1-yl}-1-ethyl-1H-indol-5-yl)methyl]-1-(2-methanesulfonylethyl)piperidin-4-amine |
| 71. | 1-(4-{[(2-{3-[(4-chlorophenyl)amino]prop-1-yn-1-yl}-1-ethyl-1H-indol-5-yl)methyl]amino}piperidin-1-yl)-2-(dimethylamino)ethan-1-one |
| 72. | 2-(4-{[(2-{3-[(4-chlorophenyl)amino]prop-1-yn-1-yl}-1-ethyl-1H-indol-5-yl)methyl]amino}piperidin-1-yl)-N,N-dimethylacetamide |
| 73. | 2-tert-butyl-N-[3-(1-ethyl-5-{[(1-methylpiperidin-4-yl)amino]methyl}-1H-indol-2-yl)prop-2-yn-1-yl]pyrimidin-5-amine |
| 74. | 2-methyl-2-(5-{[3-(5-{[(oxan-4-yl)amino]methyl}-1-(2,2,2-trifluoroethyl)-1H-indol-2-yl)prop-2-yn-1-yl]amino}pyridin-2-yl)propanenitrile |
| 75. | 2-[5-({3-[1-(2-fluoroethyl)-5-{[(oxan-4-yl)amino]methyl}-1H-indol-2-yl]prop-2-yn-1-yl}amino)pyridin-2-yl]-2-methylpropanenitrile |
| 76. | 3-(1-ethyl-5-{[(1-methylpiperidin-4-yl)amino]methyl}-1H-indol-2-yl)prop-2-yn-1-ol |

TABLE 7-continued

| Alkynyl indole compounds of the disclosure. | |
|---|---|
| Mol # | IUPAC name |
| 77. | 2-[5-({3-[1-(2-chloroethyl)-5-{[(oxan-4-yl)amino]methyl}-1H-indol-2-yl]prop-2-yn-1-yl}amino)pyridin-2-yl]-2-methylpropanenitrile |
| 78. | 2-[5-({3-[1-(2,2-difluoroethyl)-5-{[(oxan-4-yl)amino]methyl}-1H-indol-2-yl]prop-2-yn-1-yl}amino)pyridin-2-yl]-2-methylpropanenitrile |
| 79. | 6-chloro-N-[3-(1-ethyl-5-{[(1-methylpiperidin-4-yl)amino]methyl}-1H-indol-2-yl)prop-2-yn-1-yl]pyridin-3-amine |
| 80. | tert-butyl N-({3-ethyl-2-[3-(phenylamino)prop-1-yn-1-yl]-1H-indol-6-yl}methyl)-N-(oxan-4-yl)carbamate |
| 81. | 6-Chloro-N-[3-(1-ethyl-4-{[4-(pyrrolidin-1-yl)piperidin-1-yl]methyl}-1H-indol-2-yl)prop-2-yn-1-yl]pyridin-3-amine |
| 82. | 3-(1-ethyl-5-{[(1-methylpiperidin-4-yl)amino]methyl}-1H-indol-2-yl)prop-2-yn-1-yl benzoate |
| 83. | 2-[5-({3-[1-(2-chloroethyl)-5-{[(1-methylpiperidin-4-yl)amino]methyl}-1H-indol-2-yl]prop-2-yn-1-yl}amino)pyridin-2-yl]-2-methylpropanenitrile |
| 84. | N-(6-chloropyridin-3-yl)-3-(1-ethyl-5-{[(1-methylpiperidin-4-yl)amino]methyl}-1H-indol-2-yl)prop-2-ynamide |
| 85. | N-[6-(1-cyano-1-methylethyl)pyridin-3-yl]-3-(1-ethyl-5-{[(1-methylpiperidin-4-yl)amino]methyl}-1H-indol-2-yl)prop-2-ynamide |
| 86. | N-({3-ethyl-2-[3-(phenylamino)prop-1-yn-1-yl]-1H-indol-6-yl}methyl)oxan-4-amine |
| 87. | 2-[5-({3-[1-(2-chloroethyl)-4-{[4-(pyrrolidin-1-yl)piperidin-1-yl]methyl}-1H-indol-2-yl]prop-2-yn-1-yl}amino)pyridin-2-yl]-2-methylpropanenitrile |
| 88. | 2-(5-{[3-(5-{[(1-methanesulfonylpiperidin-4-yl)amino]methyl}-1-(2,2,2-trifluoroethyl)-1H-indol-2-yl)prop-2-yn-1-yl]amino}pyridin-2-yl)-2-methylpropanenitrile |
| 89. | 2-[5-({3-[5-({[1-(2-methanesulfonylethyl)piperidin-4-yl]amino}methyl)-1-(2,2,2-trifluoroethyl)-1H-indol-2-yl]prop-2-yn-1-yl}amino)pyridin-2-yl]-2-methylpropanenitrile |
| 90. | 2-(5-{[3-(5-{[(1-acetylpiperidin-4-yl)amino]methyl}-1-(2,2,2-trifluoroethyl)-1H-indol-2-yl)prop-2-yn-1-yl]amino}pyridin-2-yl)-2-methylpropanenitrile |
| 91. | 2-{5-[(3-{5-[({1-[2-(dimethylamino)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 92. | 2-methyl-2-(5-{[3-(5-{[(1-methylpiperidin-4-yl)amino]methyl}-1-(2,2,2-trifluoroethyl)-1H-indol-2-yl)prop-2-yn-1-yl]amino}pyridin-2-yl)propanenitrile |
| 93. | 2-methyl-2-{5-[(3-{5-[(methylamino)methyl]-1-(2,2,2-trifluoroethyl)-1H-indol-2-yl}prop-2-yn-1-yl)amino]pyridin-2-yl}propanenitrile |
| 94. | 6-Chloro-N-[3-(5-{[(1-methylpiperidin-4-yl)amino]methyl}-1-(2,2,2-trifluoroethyl)-1H-indol-2-yl)prop-2-yn-1-yl]pyridin-3-amine |
| 95. | 6-chloro-N-[3-(5-{[(oxan-4-yl)amino]methyl}-1-(2,2,2-trifluoroethyl)-1H-indol-2-yl)prop-2-yn-1-yl]pyridin-3-amine |
| 96. | 2-[5-({3-[1-(cyclopropylmethyl)-5-{[(oxan-4-yl)amino]methyl}-1H-indol-2-yl]prop-2-yn-1-yl}amino)pyridin-2-yl]-2-methylpropanenitrile |
| 97. | 2-(5-{[3-(4-{[4-(diethylamino)piperidin-1-yl]methyl}-1-(2,2,2-trifluoroethyl)-1H-indol-2-yl)prop-2-yn-1-yl]amino}pyridin-2-yl)-2-methylpropanenitrile |
| 98. | 2-methyl-2-{5-[(3-{4-[(4-methylpiperazin-1-yl)methyl]-1-(2,2,2-trifluoroethyl)-1H-indol-2-yl}prop-2-yn-1-yl)amino]pyridin-2-yl}propanenitrile |
| 99. | 2-(5-{[3-(1-ethyl-7-fluoro-4-{[4-(pyrrolidin-1-yl)piperidin-1-yl]methyl}-1H-indol-2-yl)prop-2-yn-1-yl]amino}pyridin-2-yl)-2-methylpropanenitrile |
| 100. | 2-methyl-2-(5-{[3-(4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)propanenitrile |
| 101. | 2-(5-{[3-(4-{[4-(4-hydroxypiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 102. | N-(6-cyanopyridin-3-yl)-3-(1-ethyl-5-{[(1-methylpiperidin-4-yl)amino]methyl}-1H-indol-2-yl)prop-2-ynamide |
| 103. | N-[6-(1-cyano-1-methylethyl)pyridin-3-yl]-3-(5-{[(oxan-4-yl)amino]methyl}-1-(2,2,2-trifluoroethyl)-1H-indol-2-yl)prop-2-ynamide |
| 104. | N-[6-(1-cyano-1-methylethyl)pyridin-3-yl]-3-(5-{[(1-methylpiperidin-4-yl)amino]methyl}-1-(2,2,2-trifluoroethyl)-1H-indol-2-yl)prop-2-ynamide |
| 105. | 2-methyl-2-(5-{[3-(5-{[(oxan-4-yl)amino]methyl}-1-(oxiran-2-ylmethyl)-1H-indol-2-yl)prop-2-yn-1-yl]amino}pyridin-2-yl)propanenitrile |
| 106. | 2-(5-{[3-(5-{[(2-methoxyethyl)amino]methyl}-1-(2,2,2-trifluoroethyl)-1H-indol-2-yl)prop-2-yn-1-yl]amino}pyridin-2-yl)-2-methylpropanenitrile |
| 107. | 2-methyl-2-[5-({3-[5-({[2-(morpholin-4-yl)ethyl]amino}methyl)-1-(2,2,2-trifluoroethyl)-1H-indol-2-yl]prop-2-yn-1-yl}amino)pyridin-2-yl]propanenitrile |
| 108. | 2-methyl-2-(5-{[3-(4-{[(1-methylpiperidin-4-yl)amino]methyl}-1-(2,2,2-trifluoroethyl)-1H-indol-2-yl)prop-2-yn-1-yl]amino}pyridin-2-yl)propanenitrile |
| 109. | 2-methyl-2-(5-{[3-(4-{[(oxan-4-yl)amino]methyl}-1-(2,2,2-trifluoroethyl)-1H-indol-2-yl)prop-2-yn-1-yl]amino}pyridin-2-yl)propanenitrile |
| 110. | 2-[5-({3-[5-({[2-(dimethylamino)ethyl]amino}methyl)-1-(2,2,2-trifluoroethyl)-1H-indol-2-yl]prop-2-yn-1-yl}amino)pyridin-2-yl]-2-methylpropanenitrile |
| 111. | 2-(5-{[3-(7-fluoro-4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 112. | 2-methyl-2-[5-({3-[1-(2,2,2-trifluoroethyl)-5-{[(2,2,2-trifluoroethyl)amino]methyl}-1H-indol-2-yl]prop-2-yn-1-yl}amino)pyridin-2-yl]propanenitrile |
| 113. | 2-[5-({3-[5-({[1-(2-hydroxyethyl)piperidin-4-yl]amino}methyl)-1-(2,2,2-trifluoroethyl)-1H-indol-2-yl]prop-2-yn-1-yl}amino)pyridin-2-yl]-2-methylpropanenitrile |
| 114. | 2-[5-({3-[5-({[1-(2-methoxyethyl)piperidin-4-yl]amino}methyl)-1-(2,2,2-trifluoroethyl)-1H-indol-2-yl]prop-2-yn-1-yl}amino)pyridin-2-yl]-2-methylpropanenitrile |

TABLE 7-continued

| Mol # | IUPAC name |
| --- | --- |
| | Alkynyl indole compounds of the disclosure. |
| 115. | 2-[5-({3-[5-({[4-(dimethylamino)cyclohexyl]amino}methyl)-1-(2,2,2-trifluoroethyl)-1H-indol-2-yl]prop-2-yn-1-yl}amino)pyridin-2-yl]-2-methylpropanenitrile |
| 116. | 2-methyl-2-{5-[(3-{5-[({1-[2-(morpholin-4-yl)acetyl]piperidin-4-yl}amino)methyl]-1-(2,2,2-trifluoroethyl)-1H-indol-2-yl}prop-2-yn-1-yl)amino]pyridin-2-yl}propanenitrile |
| 117. | 2-(5-{[3-(4-{[(2-methoxyethyl)amino]methyl}-1-(2,2,2-trifluoroethyl)-1H-indol-2-yl)prop-2-yn-1-yl]amino}pyridin-2-yl)-2-methylpropanenitrile |
| 118. | 2-methyl-2-{5-[(3-{4-[(methylamino)methyl]-1-(2,2,2-trifluoroethyl)-1H-indol-2-yl}prop-2-yn-1-yl)amino]pyridin-2-yl}propanenitrile |
| 119. | 2-{5-[(3-{4-[(4-acetylpiperazin-1-yl)methyl]-1-(2,2,2-trifluoroethyl)-1H-indol-2-yl}prop-2-yn-1-yl)amino]pyridin-2-yl}-2-methylpropanenitrile |
| 120. | 2-methyl-2-[5-({3-[4-(morpholin-4-ylmethyl)-1-(2,2,2-trifluoroethyl)-1H-indol-2-yl]prop-2-yn-1-yl}amino)pyridin-2-yl]propanenitrile |
| 121. | 2-(5-{[3-(4-{[4-(dimethylamino)piperidin-1-yl]methyl}-1-(2,2,2-trifluoroethyl)-1H-indol-2-yl)prop-2-yn-1-yl]amino}pyridin-2-yl)-2-methylpropanenitrile |
| 122. | 2-[5-({3-[4-(hydroxymethyl)-1-(2,2,2-trifluoroethyl)-1H-indol-2-yl]prop-2-yn-1-yl}amino)pyridin-2-yl]-2-methylpropanenitrile |
| 123. | 2-methyl-2-[5-({3-[4-({4-[2-(morpholin-4-yl)-2-oxoethyl]piperazin-1-yl}methyl)-1-(2,2,2-trifluoroethyl)-1H-indol-2-yl]prop-2-yn-1-yl}amino)pyridin-2-yl]propanenitrile |
| 124. | 2-(5-{[3-(3-ethyl-7-{[4-(pyrrolidin-1-yl)piperidin-1-yl]methyl}-1H-indol-2-yl)prop-2-yn-1-yl]amino}pyridin-2-yl)-2-methylpropanenitrile |
| 125. | methyl 5-{[3-(5-{[(oxan-4-yl)amino]methyl}-1-(2,2,2-trifluoroethyl)-1H-indol-2-yl)prop-2-yn-1-yl]amino}pyridine-2-carboxylate |
| 126. | N-methyl-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 127. | N-(2-hydroxyethyl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 128. | N-(2-methoxyethyl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 129. | 2-[(5-{[3-(5-{[(oxan-4-yl)amino]methyl}-1-(2,2,2-trifluoroethyl)-1H-indol-2-yl)prop-2-yn-1-yl]amino}pyridin-2-yl)formamido]acetic acid |
| 130. | 5-{[3-(5-{[(oxan-4-yl)amino]methyl}-1-(2,2,2-trifluoroethyl)-1H-indol-2-yl)prop-2-yn-1-yl]amino}pyridine-2-carboxylic acid |
| 131. | N-(2-methanesulfonylethyl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 132. | 2-[5-({3-[1-(cyanomethyl)-5-{[(oxan-4-yl)amino]methyl}-1H-indol-2-yl]prop-2-yn-1-yl}amino)pyridin-2-yl]-2-methylpropanenitrile |
| 133. | 2-methyl-2-[5-({3-[1-(2-methylpropyl)-5-{[(oxan-4-yl)amino]methyl}-1H-indol-2-yl]prop-2-yn-1-yl}amino)pyridin-2-yl]propanenitrile |
| 134. | 2-methyl-2-{5-[(3-{4-[(oxan-4-yl)amino]-1-(2,2,2-trifluoroethyl)-1H-indol-2-yl}prop-2-yn-1-yl)amino]pyridin-2-yl}propanenitrile |
| 135. | 5-{[3-(5-{[(oxan-4-yl)amino]methyl}-1-(2,2,2-trifluoroethyl)-1H-indol-2-yl)prop-2-yn-1-yl]amino}pyridine-2-carbonitrile |
| 136. | N,N-dimethyl-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 137. | N-(oxan-4-yl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 138. | 2-tert-butyl-N-[3-(5-{[(oxan-4-yl)amino]methyl}-1-(2,2,2-trifluoroethyl)-1H-indol-2-yl)prop-2-yn-1-yl]pyrimidin-5-amine |
| 139. | N-(1-methylpiperidin-4-yl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 140. | N-[6-(1-cyano-1-methylethyl)pyridin-3-yl]-3-[1-(2-fluoroethyl)-5-{[(oxan-4-yl)amino]methyl}-1H-indol-2-yl]prop-2-ynamide |
| 141. | 2-(5-{[3-(7-chloro-4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 142. | 2-(5-{[3-(6-fluoro-4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 143. | 2-(5-{[3-(1-ethyl-5-{[(oxan-4-yl)amino]methyl}-1H-pyrrolo[2,3-c]pyridin-2-yl)prop-2-yn-1-yl]amino}pyridin-2-yl)-2-methylpropanenitrile |
| 144. | 2-methyl-2-(5-{[3-(5-{[(oxan-4-yl)amino]methyl}-1-(2,2,2-trifluoroethyl)-1H-pyrrolo[2,3-c]pyridin-2-yl)prop-2-yn-1-yl]amino}pyridin-2-yl)propanenitrile |
| 145. | 2-(5-{[3-(5-{[4-(dimethylamino)piperidin-1-yl]methyl}-1-(2,2,2-trifluoroethyl)-1H-pyrrolo[2,3-c]pyridin-2-yl)prop-2-yn-1-yl]amino}pyridin-2-yl)-2-methylpropanenitrile |
| 146. | 2-(5-{[3-(7-chloro-4-{[4-(pyrrolidin-1-yl)piperidin-1-yl]methyl}-1-(2,2,2-trifluoroethyl)-1H-pyrrolo[2,3-c]pyridin-2-yl)prop-2-yn-1-yl]amino}pyridin-2-yl)-2-methylpropanenitrile |
| 147. | 2-(5-{[3-(4-{[4-(dimethylamino)-piperidin-1-yl]methyl}-6-fluoro-1-(2,2,2-trifluoroethyl)-1H-indol-2-yl)prop-2-yn-1-yl]amino}pyridin-2-yl)-2-methylpropanenitrile |
| 148. | 2-(5-{[3-(4-{[4-(diethylamino)piperidin-1-yl]methyl}-6-fluoro-1-(2,2,2-trifluoroethyl)-1H-indol-2-yl)prop-2-yn-1-yl]amino}pyridin-2-yl)-2-methylpropanenitrile |
| 149. | 2-(5-{[3-(6-fluoro-4-{[4-(4-hydroxypiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 150. | 2-(5-{[3-(6-fluoro-5-{[(oxan-4-yl)amino]methyl}-1-(2,2,2-trifluoroethyl)-1H-indol-2-yl)prop-2-yn-1-yl]amino}pyridin-2-yl)-2-methylpropanenitrile |
| 151. | 2-(5-{[3-(5-{[(1-acetylpiperidin-4-yl)amino]methyl}-6-fluoro-1-(2,2,2-trifluoroethyl)-1H-indol-2-yl)prop-2-yn-1-yl]amino}pyridin-2-yl)-2-methylpropanenitrile |

TABLE 7-continued

Alkynyl indole compounds of the disclosure.

| Mol # | IUPAC name |
|---|---|
| 152. | 2-(5-{[3-(6-chloro-4-{[4-(dimethylamino)piperidin-1-yl]methyl}-1-(2,2,2-trifluoroethyl)-1H-indol-2-yl)prop-2-yn-1-yl]amino}pyridin-2-yl)-2-methylpropanenitrile |
| 153. | 2-(5-{[3-(6-chloro-4-{[4-(diethylamino)piperidin-1-yl]methyl}-1-(2,2,2-trifluoroethyl)-1H-indol-2-yl)prop-2-yn-1-yl]amino}pyridin-2-yl)-2-methylpropanenitrile |
| 154. | 2-(5-{[3-(6-chloro-4-{[4-(4-hydroxypiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 155. | 2-(5-{[3-(4-{[4-(2-methanesulfonyl-ethyl)piperazin-1-yl]methyl}-1-(2,2,2-trifluoroethyl)-1H-indol-2-yl)prop-2-yn-1-yl]amino}pyridin-2-yl)-2-methylpropanenitrile |
| 156. | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]methyl}piperazin-1-yl)-N,N-dimethylacetamide |
| 157. | 2-methyl-2-{5-[(3-{4-[(3-oxopiperazin-1-yl]methyl]-1-(2,2,2-trifluoroethyl)-1H-indol-2-yl}prop-2-yn-1-yl)amino]pyridin-2-yl}propanenitrile |
| 158. | 2-methyl-2-[5-({3-[4-({4-[2-(morpholin-4-yl)-2-oxoethyl]piperidin-1-yl}methyl)-1-(2,2,2-trifluoroethyl)-1H-indol-2-yl]prop-2-yn-1-yl}amino)pyridin-2-yl]propanenitrile |
| 159. | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]methyl}piperazin-1-yl)acetamide |
| 160. | N-[6-(1-cyano-1-methylethyl)pyridin-3-yl]-3-(4-{[4-(pyrrolidin-1-yl)piperidin-1-yl]methyl}-1-(2,2,2-trifluoroethyl)-1H-indol-2-yl)prop-2-ynamide |
| 161. | 2-(1-{[2-(3-{[6-(1-cyano-1-methylethyl)pyridin-3-yl]amino}prop-1-yn-1-yl)-1-(2,2,2-trifluoroethyl)-1H-indol-4-yl]methyl}piperidin-4-yl)acetamide |
| 162. | 2-(5-{[3-(4-{[4-(2-aminoethyl)-piperazin-1-yl]methyl}-1-(2,2,2-trifluoroethyl)-1H-indol-2-yl)prop-2-yn-1-yl]amino}pyridin-2-yl)-2-methylpropanenitrile |
| 163. | 2-(1-{[2-(3-{[6-(1-cyano-1-methylethyl)pyridin-3-yl]amino}prop-1-yn-1-yl)-1-(2,2,2-trifluoroethyl)-1H-indol-4-yl]methyl}piperidin-4-yl)-N,N-dimethylacetamide |
| 164. | 2-methyl-2-(5-{[3-(4-{[4-(morpholin-4-yl)piperidin-1-yl]methyl}-1-(2,2,2-trifluoroethyl)-1H-indol-2-yl)prop-2-yn-1-yl]amino}pyridin-2-yl)propanenitrile |
| 165. | 2-(5-{[3-(4-{[4-(4-aminopiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile |
| 166. | 2-methyl-2-[5-({3-[1-(oxiran-2-ylmethyl)-4-{[4-(pyrrolidin-1-yl)piperidin-1-yl]methyl}-1H-indol-2-yl]prop-2-yn-1-yl}amino)pyridin-2-yl]propanenitrile |
| 167. | 2-(5-{[3-(3-ethyl-6-{[(oxan-4-yl)amino]methyl}-1H-indol-2-yl)prop-2-yn-1-yl]amino}pyridin-2-yl)-2-methylpropanenitrile |
| 168. | 2-methyl-2-(5-{[3-(6-{[(oxan-4-yl)amino]methyl}-3-(2,2,2-trifluoroethyl)-1H-indol-2-yl)prop-2-yn-1-yl]amino}pyridin-2-yl)propanenitrile |
| 169. | 2-(5-{[3-(1-acetyl-3-ethyl-6-{[(oxan-4-yl)amino]methyl}-1H-indol-2-yl)prop-2-yn-1-yl]amino}pyridin-2-yl)-2-methylpropanenitrile |
| 170. | 2-(5-{[3-(3-ethyl-6-{[(1-methylpiperidin-4-yl)amino]methyl}-1H-indol-2-yl)prop-2-yn-1-yl]amino}pyridin-2-yl)-2-methylpropanenitrile |
| 171. | 2-methyl-2-(5-{[3-(6-{[(1-methylpiperidin-4-yl)amino]methyl}-3-(2,2,2-trifluoroethyl)-1H-indol-2-yl)prop-2-yn-1-yl]amino}pyridin-2-yl)propanenitrile |
| 172. | 2-{5-[(3-{6-chloro-4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile |
| 173. | 2-(3-{[6-(1-cyano-1-methylethyl)pyridin-3-yl]amino}prop-1-yn-1-yl)-6-fluoro-N-(1-methylpiperidin-4-yl)-1-(2,2,2-trifluoroethyl)-1H-indole-4-carboxamide |
| 174. | 2-[5-({3-[6-fluoro-4-(4-methylpiperazine-1-carbonyl)-1-(2,2,2-trifluoroethyl)-1H-indol-2-yl]prop-2-yn-1-yl}amino)pyridin-2-yl]-2-methylpropanenitrile |
| 175. | 6-fluoro-2-{3-[(6-methanesulfonylpyridin-3-yl)amino]prop-1-yn-1-yl}-N-(1-methylpiperidin-4-yl)-1-(2,2,2-trifluoroethyl)-1H-indol-4-amine |
| 176. | 2-{5-[(3-{6-fluoro-4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile |
| 177. | 5-[(3-{6-fluoro-4-[(1-methylpiperidin-4-yl)amino]-1-(2,2,2-trifluoroethyl)-1H-indol-2-yl}prop-2-yn-1-yl)amino]-N-(pyridin-3-yl)pyridine-2-carboxamide |
| 178. | 2-methyl-2-(5-{[3-(5-{[(oxan-4-yl)amino]methyl}-1-(2,2,2-trifluoroethyl)-1H-pyrrolo[2,3-b]pyridin-2-yl)prop-2-yn-1-yl]amino}pyridin-2-yl)propanenitrile |
| 179. | 2-methyl-2-{5-[(3-{4-[(1-methylpiperidin-4-yl)amino]-1-(2,2,2-trifluoroethyl)-1H-pyrrolo[2,3-b]pyridin-2-yl}prop-2-yn-1-yl)amino]pyridin-2-yl}propanenitrile |
| 180. | 2-(5-{[3-(7-chloro-1-ethyl-4-{[4-(pyrrolidin-1-yl)piperidin-1-yl]methyl}-1H-indol-2-yl)prop-2-yn-1-yl]amino}pyridin-2-yl)-2-methylpropanenitrile |
| 181. | 2-(5-{[3-(7-chloro-5-{[(oxan-4-yl)amino]methyl}-1-(2,2,2-trifluoroethyl)-1H-indol-2-yl)prop-2-yn-1-yl]amino}pyridin-2-yl)-2-methylpropanenitrile |
| 182. | 2-(5-{[3-(7-chloro-5-{[(1-methylpiperidin-4-yl)amino]methyl}-1-(2,2,2-trifluoroethyl)-1H-indol-2-yl)prop-2-yn-1-yl]amino}pyridin-2-yl)-2-methylpropanenitrile |
| 183. | 2-{5-[(3-{7-fluoro-4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile |
| 184. | 2-(5-{[3-(7-fluoro-5-{[(oxan-4-yl)amino]methyl}-1-(2,2,2-trifluoroethyl)-1H-indol-2-yl)prop-2-yn-1-yl]amino}pyridin-2-yl)-2-methylpropanenitrile |
| 185. | 2-(5-{[3-(7-fluoro-5-{[(1-methylpiperidin-4-yl)amino]methyl}-1-(2,2,2-trifluoroethyl)-1H-indol-2-yl)prop-2-yn-1-yl]amino}pyridin-2-yl)-2-methylpropanenitrile |
| 186. | 2-methyl-2-(5-{[3-(5-{[(oxan-4-yl)amino]methyl}-1-(2,2,2-trifluoroethyl)-1H-1,3-benzodiazol-2-yl)prop-2-yn-1-yl]amino}pyridin-2-yl)propanenitrile |
| 187. | N-{[2-(2-phenylethynyl)-1-(2,2,2-trifluoroethyl)-1H-1,3-benzodiazol-5-yl]methyl}oxan-4-amine |
| 188. | 2-methyl-2-(5-{[3-(5-{[(oxan-4-yl)amino]methyl}-1-(2,2,2-trifluoroethyl)-1H-pyrrolo[3,2-b]pyridin-2-yl)prop-2-yn-1-yl]amino}pyridin-2-yl)propanenitrile |
| 189. | 2-{3-[(4-methanesulfonylphenyl)amino]prop-1-yn-1-yl}-5-methyl-N-(1-methylpiperidin-4-yl)-1-(2,2,2-trifluoroethyl)-1H-indol-4-amine |

TABLE 7-continued

| Mol # | IUPAC name |
|---|---|
| Alkynyl indole compounds of the disclosure. | |
| 190. | 4-[(2-{3-[(4-methanesulfonylphenyl)amino]prop-1-yn-1-yl}-5-methyl-1-(2,2,2-trifluoroethyl)-1H-indol-4-yl)amino]-1λ$^6$-thiane-1,1-dione |
| 191. | 2-methyl-2-{5-[(3-{5-methyl-4-[(1-methylpiperidin-4-yl)amino]-1-(2,2,2-trifluoroethyl)-1H-indol-2-yl}prop-2-yn-1-yl)amino]pyridin-2-yl}propanenitrile |
| 192. | N-[1-(2-methanesulfonylethyl)piperidin-4-yl]-2-{3-[(4-methanesulfonylphenyl)amino]prop-1-yn-1-yl}-5-methyl-1-(2,2,2-trifluoroethyl)-1H-indol-4-amine |
| 193. | 4-[(3-{5-methyl-4-[(piperidin-4-yl)amino]-1-(2,2,2-trifluoroethyl)-1H-indol-2-yl}prop-2-yn-1-yl)amino]benzene-1-sulfonamide |
| 194. | 2-{3-[(4-methanesulfonylphenyl)amino]prop-1-yn-1-yl}-5-methyl-N-[1-(oxan-4-yl)piperidin-4-yl]-1-(2,2,2-trifluoroethyl)-1H-indol-4-amine |
| 195. | 2-{4-[(2-{3-[(4-methanesulfonylphenyl)amino]prop-1-yn-1-yl}-5-methyl-1-(2,2,2-trifluoroethyl)-1H-indol-4-yl)amino]piperidin-1-yl}ethan-1-ol |
| 196. | 2-[5-({3-[4-(methoxymethyl)-1-(2,2,2-trifluoroethyl)-1H-indol-2-yl]prop-2-yn-1-yl}amino)pyridin-2-yl]-2-methylpropanenitrile |
| 197. | 2-[5-({3-[4-(cyanomethyl)-1-(2,2,2-trifluoroethyl)-1H-indol-2-yl]prop-2-yn-1-yl}amino)pyridin-2-yl]-2-methylpropanenitrile |
| 198. | 2-methyl-2-[5-({3-[5-(morpholine-4-carbonyl)-1-(2,2,2-trifluoroethyl)-1H-indol-2-yl]prop-2-yn-1-yl}amino)pyridin-2-yl]propanenitrile |
| 199. | 2-methyl-2-[5-({3-[5-(4-methylpiperazine-1-carbonyl)-1-(2,2,2-trifluoroethyl)-1H-indol-2-yl]prop-2-yn-1-yl}amino)pyridin-2-yl]propanenitrile |
| 200. | 2-{5-[(3-{5-[4-(dimethylamino)piperidine-1-carbonyl]-1-(2,2,2-trifluoroethyl)-1H-indol-2-yl}prop-2-yn-1-yl)amino]pyridin-2-yl}-2-methylpropanenitrile |
| 201. | 2-(3-{[6-(1-cyano-1-methylethyl)pyridin-3-yl]amino}prop-1-yn-1-yl)-N-{1-[2-(dimethylamino)acetyl]piperidin-4-yl}-1-(2,2,2-trifluoroethyl)-1H-indole-5-carboxamide |
| 202. | 2-(3-{[6-(1-cyano-1-methylethyl)pyridin-3-yl]amino}prop-1-yn-1-yl)-N-(oxan-4-yl)-1-(2,2,2-trifluoroethyl)-1H-indole-5-carboxamide |
| 203. | 2-methyl-2-(5-{[3-(5-{1-[(oxan-4-yl)amino]ethyl}-1-(2,2,2-trifluoroethyl)-1H-indol-2-yl)prop-2-yn-1-yl]amino}pyridin-2-yl)propanenitrile |
| 204. | 2-methyl-2-{5-[(3-{4-[(1-methylpiperidin-4-yl)amino]-1-(2,2,2-trifluoroethyl)-1H-pyrrolo[3,2-c]pyridin-2-yl}prop-2-yn-1-yl)amino]pyridin-2-yl}propanenitrile |
| 205. | 2-methyl-2-[5-({3-[5-(morpholin-4-ylmethyl)-1-(2,2,2-trifluoroethyl)-1H-indol-2-yl]prop-2-yn-1-yl}amino)pyridin-2-yl]propanenitrile |
| 206. | 2-[5-({3-[5-({[1-(2-cyanoethyl)-piperidin-4-yl]amino}methyl)-1-(2,2,2-trifluoroethyl)-1H-indol-2-yl]prop-2-yn-1-yl}amino)pyridin-2-yl]-2-methylpropanenitrile |
| 207. | 2-methyl-2-(5-{[3-(5-{[(1-methylazetidin-3-yl)amino]methyl}-1-(2,2,2-trifluoroethyl)-1H-indol-2-yl)prop-2-yn-1-yl]amino}pyridin-2-yl)propanenitrile |
| 208. | 2-methyl-2-(5-{[3-(5-{[(oxetan-3-yl)amino]methyl}-1-(2,2,2-trifluoroethyl)-1H-indol-2-yl)prop-2-yn-1-yl]amino}pyridin-2-yl)propanenitrile |
| 209. | 2-(5-{[3-(5-{[4-(dimethylamino)-piperidin-1-yl]methyl}-1-(2,2,2-trifluoroethyl)-1H-indol-2-yl)prop-2-yn-1-yl]amino}pyridin-2-yl)-2-methylpropanenitrile |
| 210. | 2-methyl-2-{5-[(3-{5-[({1-[2-(4-methylpiperazin-1-yl)acetyl]piperidin-4-yl}amino)methyl]-1-(2,2,2-trifluoroethyl)-1H-indol-2-yl}prop-2-yn-1-yl)amino]pyridin-2-yl}propanenitrile |
| 211. | 2-(5-{[3-(5-{[(1-methoxypropan-2-yl)amino]methyl}-1-(2,2,2-trifluoroethyl)-1H-indol-2-yl)prop-2-yn-1-yl]amino}pyridin-2-yl)-2-methylpropanenitrile |
| 212. | 2-methyl-2-(5-{[3-(5-{[(pyridin-4-ylmethyl)amino]methyl}-1-(2,2,2-trifluoroethyl)-1H-indol-2-yl)prop-2-yn-1-yl]amino}pyridin-2-yl)propanenitrile |
| 213. | 2-methyl-2-(5-{[3-(5-{[(pyridin-3-ylmethyl)amino]methyl}-1-(2,2,2-trifluoroethyl)-1H-indol-2-yl)prop-2-yn-1-yl]amino}pyridin-2-yl)propanenitrile |
| 214. | 2-[5-({3-[5-({[1-(dimethylamino)-propan-2-yl]amino}methyl)-1-(2,2,2-trifluoroethyl)-1H-indol-2-yl]prop-2-yn-1-yl}amino)pyridin-2-yl]-2-methylpropanenitrile |
| 215. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(oxan-4-yl)acetamide |
| 216. | 2-[5-({3-[5-({[1-(2-methoxyacetyl)-piperidin-4-yl]amino}methyl)-1-(2,2,2-trifluoroethyl)-1H-indol-2-yl]prop-2-yn-1-yl}amino)pyridin-2-yl]-2-methylpropanenitrile |
| 217. | 2-methyl-2-{5-[(3-{5-[({1-[2-(oxan-4-yl)acetyl]piperidin-4-yl}amino)-methyl]-1-(2,2,2-trifluoroethyl)-1H-indol-2-yl}prop-2-yn-1-yl)amino]-pyridin-2-yl}propanenitrile |
| 218. | 2-methyl-2-{5-[(3-{5-[({1-[2-(pyridin-3-yl)acetyl]piperidin-4-yl}amino)-methyl]-1-(2,2,2-trifluoroethyl)-1H-indol-2-yl}prop-2-yn-1-yl)amino]-pyridin-2-yl}propanenitrile |
| 219. | 2-methyl-2-(5-{[3-(5-{[(1-{2-[(oxan-4-yl)amino]acetyl}piperidin-4-yl)amino]methyl}-1-(2,2,2-trifluoroethyl)-1H-indol-2-yl)prop-2-yn-1-yl]amino}pyridin-2-yl)-propanenitrile |
| 220. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-methyl-N-(propan-2-yl)acetamide |
| 221. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(2-methoxyethyl)-N-methylacetamide |
| 222. | 6-methanesulfonyl-N-[3-(5-{[(oxan-4-yl)amino]methyl}-1-(2,2,2-trifluoroethyl)-1H-indol-2-yl)prop-2-yn-1-yl]pyridin-3-amine |
| 223. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N,N-dimethylacetamide |
| 224. | 2-methyl-2-{5-[(3-{5-[({1-[2-oxo-2-(pyrrolidin-1-yl)ethyl]piperidin-4-yl}amino)methyl]-1-(2,2,2-trifluoroethyl)-1H-indol-2-yl}prop-2-yn-1-yl)amino]pyridin-2-yl}propanenitrile |
| 225. | 4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)-N,N-dimethylpiperidine-1-carboxamide |

TABLE 7-continued

Alkynyl indole compounds of the disclosure.

| Mol # | IUPAC name |
|---|---|
| 226. | 2-{5-[(3-{5-[({1-[2-(azetidin-1-yl)-2-oxoethyl]piperidin-4-yl}amino)-methyl]-1-(2,2,2-trifluoroethyl)-1H-indol-2-yl}prop-2-yn-1-yl)amino]-pyridin-2-yl}-2-methylpropanenitrile |
| 227. | 2-methyl-2-{5-[(3-{5-[({1-[2-(pyrrolidin-1-yl)acetyl]piperidin-4-yl}amino)methyl]-1-(2,2,2-trifluoroethyl)-1H-indol-2-yl}prop-2-yn-1-yl)amino]pyridin-2-yl}-propanenitrile |
| 228. | 2-(5-{[3-(5-{[(1-{2-[4-(dimethylamino)piperidin-1-yl]acetyl}piperidin-4-yl)amino]-methyl}-1-(2,2,2-trifluoroethyl)-1H-indol-2-yl)prop-2-yn-1-yl]amino}pyridin-2-yl)-2-methylpropanenitrile |
| 229. | 2-{5-[(3-{5-[({1-[2-(diethylamino)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 230. | 2-methyl-2-(5-{[3-(5-{[(1-{2-[methyl(propan-2-yl)amino]acetyl}piperidin-4-yl)amino]methyl}-1-(2,2,2-trifluoroethyl)-1H-indol-2-yl)prop-2-yn-1-yl]amino}pyridin-2-yl)propanenitrile |
| 231. | 2-methyl-2-{5-[(3-{5-[({1-[2-(pyridin-4-yl)acetyl]piperidin-4-yl}amino)methyl]-1-(2,2,2-trifluoroethyl)-1H-indol-2-yl}prop-2-yn-1-yl)amino]pyridin-2-yl}propanenitrile |
| 232. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(pyridin-4-yl)acetamide |
| 233. | 2-methyl-2-{5-[(3-{5-[({1-[2-(morpholin-4-yl)-2-oxoethyl]piperidin-4-yl}amino)methyl]-1-(2,2,2-trifluoroethyl)-1H-indol-2-yl}prop-2-yn-1-yl)amino]pyridin-2-yl}propanenitrile |
| 234. | 2-methyl-2-{5-[(3-{5-[({1-[2-(4-methylpiperazin-1-yl)-2-oxoethyl]piperidin-4-yl}amino)methyl]-1-(2,2,2-trifluoroethyl)-1H-indol-2-yl}prop-2-yn-1-yl)amino]pyridin-2-yl}propanenitrile |
| 235. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(pyridin-3-yl)acetamide |
| 236. | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(1-methylpiperidin-4-yl)acetamide |
| 237. | 2-methyl-2-[5-({3-[5-({[4-(morpholin-4-yl)cyclohexyl]amino}methyl)-1-(2,2,2-trifluoroethyl)-1H-indol-2-yl]prop-2-yn-1-yl}amino)pyridin-2-yl]propanenitrile |
| 238. | 2-{5-[(3-{5-[({1-[2-(4-hydroxypiperidin-1-yl)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 239. | 2-{5-[(3-{5-[({1-[2-(4-acetylpiperazin-1-yl)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 240. | 2-(5-{[3-(5-{[(1,1-dioxo-1$\lambda^6$-thian-4-yl)amino]methyl}-1-(2,2,2-trifluoroethyl)-1H-indol-2-yl)prop-2-yn-1-yl]amino}pyridin-2-yl)-2-methylpropanenitrile |
| 241. | 2-{5-[(3-{5-[({1-[2-(1,1-dioxo-1$\lambda^6$,4-thiomorpholin-4-yl)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 242. | 2-[5-({3-[5-({[1-(4-acetylpiperazine-1-carbonyl)piperidin-4-yl]amino}methyl)-1-(2,2,2-trifluoroethyl)-1H-indol-2-yl]prop-2-yn-1-yl}amino)pyridin-2-yl]-2-methylpropanenitrile |
| 243. | 2-(5-{[3-(5-{[(1-{2-[bis(2-hydroxyethyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 244. | 2-methyl-2-{5-[(3-{5-[({1-[2-(3-oxopiperazin-1-yl)acetyl]piperidin-4-yl}amino)methyl]-1-(2,2,2-trifluoroethyl)-1H-indol-2-yl}prop-2-yn-1-yl)amino]pyridin-2-yl}propanenitrile |
| 245. | 2-methyl-2-[5-({3-[5-({[1-(morpholine-4-carbonyl)piperidin-4-yl]amino}-methyl)-1-(2,2,2-trifluoroethyl)-1H-indol-2-yl]prop-2-yn-1-yl}amino)pyridin-2-yl]propanenitrile |
| 246. | 2-methyl-2-(5-{[3-(5-{[(1-methylpiperidin-3-yl)amino]methyl}-1-(2,2,2-trifluoroethyl)-1H-indol-2-yl)prop-2-yn-1-yl]amino}pyridin-2-yl)propanenitrile |
| 247. | N-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)-cyclohexyl]acetamide |
| 248. | 2-{5-[(3-{5-[({1-[2-(1H-imidazol-1-yl)acetyl]piperidin-4-yl}amino)-methyl]-1-(2,2,2-trifluoroethyl)-1H-indol-2-yl}prop-2-yn-1-yl)amino]pyridin-2-yl}-2-methylpropanenitrile |
| 249. | 2-(5-{[3-(5-{[(1-{2-[(2-methoxyethyl)(methyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 250. | N-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)-cyclohexyl]methanesulfonamide |
| 251. | 2-methyl-2-(5-{[3-(5-{[(1-methyl-6-oxopiperidin-3-yl)amino]methyl}-1-(2,2,2-trifluoroethyl)-1H-indol-2-yl)prop-2-yn-1-yl]amino}pyridin-2-yl)propanenitrile |
| 252. | 2-[5-({3-[5-({[3-(dimethylamino)cyclohexyl]amino}methyl)-1-(2,2,2-trifluoroethyl)-1H-indol-2-yl]prop-2-yn-1-yl}amino)pyridin-2-yl]-2-methylpropanenitrile |
| 253. | 2-methyl-2-[5-({3-[5-({[1-(4-methylpiperazine-1-carbonyl)piperidin-4-yl]amino}methyl)-1-(2,2,2-trifluoroethyl)-1H-indol-2-yl]prop-2-yn-1-yl}amino)pyridin-2-yl]propanenitrile |
| 254. | 2-{5-[(3-{5-[({1-[4-(dimethylamino)piperidine-1-carbonyl]piperidin-4-yl}amino)-methyl]-1-(2,2,2-trifluoroethyl)-1H-indol-2-yl}prop-2-yn-1-yl)amino]pyridin-2-yl}-2-methylpropanenitrile |
| 255. | 2-{5-[(3-{5-[({1-[2-(3-hydroxypyrrolidin-1-yl)acetyl]-piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 256. | 2-{5-[(3-{5-[({1-[2-(3-methoxypyrrolidin-1-yl)acetyl]-piperidin-4-yl}amino)methyl]-1-(2,2,2-trifluoroethyl)-1H-indol-2-yl}prop-2-yn-1-yl)amino]pyridin-2-yl}-2-methylpropanenitrile |

TABLE 7-continued

| Mol # | IUPAC name |
|---|---|
| | Alkynyl indole compounds of the disclosure. |
| 257. | 2-methyl-2-[5-({3-[5-({[1-(2-{2-oxa-8-azaspiro[4.5]decan-8-yl}acetyl)-piperidin-4-yl]amino}methyl)-1-(2,2,2-trifluoroethyl)-1H-indol-2-yl]prop-2-yn-1-yl}amino)pyridin-2-yl]propanenitrile |
| 258. | 2-{5-[(3-{5-[({1-[2-(4-hydroxy-4-methylpiperidin-1-yl)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile |
| 259. | 2-(5-{[3-(5-{[(1-{2-[bis(2-methoxyethyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 260. | 2-(5-{[3-(5-{[(1-{2-[methoxy(methyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 261. | 2-(5-{[3-(5-{[(1-{2-[(2,3-dihydroxypropyl)(methyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 262. | 2-methyl-2-(5-{[3-(5-{[(1-methyl-2-oxopiperidin-4-yl)amino]methyl}-1-(2,2,2-trifluoroethyl)-1H-indol-2-yl)prop-2-yn-1-yl]amino}pyridin-2-yl)propanenitrile |
| 263. | 2-methyl-2-(5-{[3-(5-{[(1-{2-[methyl(1-methylpiperidin-4-yl)amino]acetyl}piperidin-4-yl)amino]methyl}-1-(2,2,2-trifluoroethyl)-1H-indol-2-yl)prop-2-yn-1-yl]amino}pyridin-2-yl)propanenitrile |
| 264. | 2-methyl-2-[5-({3-[5-({[1-(2-{9-methyl-3,9-diazaspiro[5.5]undecan-3-yl}acetyl)piperidin-4-yl]amino}methyl)-1-(2,2,2-trifluoroethyl)-1H-indol-2-yl]prop-2-yn-1-yl}amino)pyridin-2-yl]propanenitrile |
| 265. | 2-(5-{[3-(5-{[(1-{2-[3-(dimethyl-amino)pyrrolidin-1-yl]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile |
| 266. | N-[3-(5-{[(oxan-4-yl)amino]methyl}-1-(2,2,2-trifluoroethyl)-1H-indol-2-yl)prop-2-yn-1-yl]-6-(pyrrolidine-1-carbonyl)pyridin-3-amine |
| 267. | 6-(morpholine-4-carbonyl)-N-[3-(5-{[(oxan-4-yl)amino]methyl}-1-(2,2,2-trifluoroethyl)-1H-indol-2-yl)prop-2-yn-1-yl]pyridin-3-amine |
| 268. | 2-chloro-N-[3-(5-{[(oxan-4-yl)amino]-methyl}-1-(2,2,2-trifluoroethyl)-1H-indol-2-yl)prop-2-yn-1-yl]pyrimidin-5-amine |
| 269. | 5-{[3-(5-{[(oxan-4-yl)amino]methyl}-1-(2,2,2-trifluoroethyl)-1H-indol-2-yl)prop-2-yn-1-yl]amino}-N-phenylpyridine-2-carboxamide |
| 270. | N-methyl-5-{[3-(5-([(oxan-4-yl)amino]methyl}-1-(2,2,2-trifluoroethyl)-1H-indol-2-yl)prop-2-yn-1-yl]amino]-N-(propan-2-yl)pyridine-2-carboxamide |
| 271. | 5-{[3-(5-{[(oxan-4-yl)amino]methyl}-1-(2,2,2-trifluoroethyl)-1H-indol-2-yl)prop-2-yn-1-yl]amino}-N-(pyridin-4-yl)pyridine-2-carboxamide |
| 272. | 5-{[3-(5-{[(oxan-4-yl)amino]methyl}-1-(2,2,2-trifluoroethyl)-1H-indol-2-yl)prop-2-yn-1-yl]amino}-N-(pyridin-3-yl)pyridine-2-carboxamide |
| 273. | N-(1-methylazetidin-3-yl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 274. | N,N-diethyl-5-{[3-(5-{[(oxan-4-yl)amino]methyl}-1-(2,2,2-trifluoroethyl)-1H-indol-2-yl)prop-2-yn-1-yl]amino}pyridine-2-carboxamide |
| 275. | 5-{[3-(5-{[(oxan-4-yl)amino]methyl}-1-(2,2,2-trifluoroethyl)-1H-indol-2-yl)prop-2-yn-1-yl]amino}-N-(oxetan-3-yl)pyridine-2-carboxamide |
| 276. | 1-(4-{[(2-{3-[(2-tert-butylpyrimidin-5-yl)amino]prop-1-yn-1-yl}-1-(2,2,2-trifluoroethyl)-1H-indol-5-yl)methyl]amino}piperidin-1-yl)-2-(dimethylamino)ethan-1-one |
| 277. | 1-(4-{[(2-{3-[(6-chloropyridin-3-yl)amino]prop-1-yn-1-yl}-1-(2,2,2-trifluoroethyl)-1H-indol-5-yl)methyl]amino}piperidin-1-yl)-2-(dimethylamino)ethan-1-one |
| 278. | 5-[(3-{5-[({1-[2-(dimethylamino)-acetyl]piperidin-4-yl}amino)methyl]-1-(2,2,2-trifluoroethyl)-1H-indol-2-yl}prop-2-yn-1-yl)amino]-N-(1-methylpiperidin-4-yl)pyridine-2-carboxamide |
| 279. | 1-(4-{[(2-{3-[(4-chloro-3-fluorophenyl)amino]prop-1-yn-1-yl}-1-(2,2,2-trifluoroethyl)-1H-indol-5-yl)methyl]amino}piperidin-1-yl)-2-(dimethylamino)ethan-1-one |
| 280. | 2-(dimethylamino)-1-(4-{[(2-{3-[(6-methylpyridin-3-yl)amino]prop-1-yn-1-yl}-1-(2,2,2-trifluoroethyl)-1H-indol-5-yl)methyl]amino}piperidin-1-yl)ethan-1-one |
| 281. | 1-(4-{[(2-{3-[(6-tert-butylpyridin-3-yl)amino]prop-1-yn-1-yl}-1-(2,2,2-trifluoroethyl)-1H-indol-5-yl)methyl]amino}piperidin-1-yl)-2-(dimethylamino)ethan-1-one |
| 282. | N-[6-(1-cyano-1-methylethyl)pyridin-3-yl]-3-[1-(2-fluoroethyl)-5-{[(1-methylpiperidin-4-yl)amino]methyl}-1H-indol-2-yl]prop-2-ynamide |
| 283. | 2-{5-[(3-{5-[({1-[2-(dimethylamino)acetyl]piperidin-4-yl}amino)methyl]-1-ethyl-1H-indol-2-yl}prop-2-yn-1-yl)amino]pyridin-2-yl}-2-methylpropanenitrile |
| 284. | 2-[5-({3-[1-(2,2-difluoroethyl)-5-[({1-[2-(dimethylamino)acetyl]piperidin-4-yl}amino)methyl]-1H-indol-2-yl]prop-2-yn-1-yl}amino)pyridin-2-yl]-2-methylpropanenitrile |
| 285. | 2-{5-[(3-{5-[({1-[2-(dimethylamino)acetyl]piperidin-4-yl}amino)methyl]-1-(2-fluoroethyl)-1H-indol-2-yl}prop-2-yn-1-yl)amino]pyridin-2-yl}-2-methylpropanenitrile |
| 286. | N-(6-chloropyridin-3-yl)-3-(5-{[(1-methylpiperidin-4-yl)amino]methyl}-1-(2,2,2-trifluoroethyl)-1H-indol-2-yl)prop-2-ynamide |
| 287. | 2-(5-{[3-(5-{[(1-acetylpiperidin-4-yl)amino]methyl}-1-(oxiran-2-ylmethyl)-1H-indol-2-yl)prop-2-yn-1-yl]amino}pyridin-2-yl)-2-methylpropanenitrile |
| 288. | 2-methyl-2-{5-[(3-{5-[(oxan-4-yl)amino]-1-(2,2,2-trifluoroethyl)-1H-indol-2-yl}prop-2-yn-1-yl)amino]pyridin-2-yl}propanenitrile |
| 289. | 2-{5-[(3-{4-[(1-acetylpiperidin-4-yl)amino]-1-(2,2,2-trifluoroethyl)-1H-indol-2-yl}prop-2-yn-1-yl)amino]pyridin-2-yl}-2-methylpropanenitrile |

TABLE 7-continued

Alkynyl indole compounds of the disclosure.

| Mol # | IUPAC name |
|---|---|
| 290. | 2-methyl-2-{5-[(3-{4-[(propan-2-yl)amino]-1-(2,2,2-trifluoroethyl)-1H-indol-2-yl}prop-2-yn-1-yl)amino]pyridin-2-yl}propanenitrile |
| 291. | 2-methyl-2-{5-[(3-{4-[(piperidin-4-yl)amino]-1-(2,2,2-trifluoroethyl)-1H-indol-2-yl}prop-2-yn-1-yl)amino]pyridin-2-yl}propanenitrile |
| 292. | 2-(5-{[3-(4-{[1-(2-methoxyethyl)-piperidin-4-yl]amino}-1-(2,2,2-trifluoroethyl)-1H-indol-2-yl)prop-2-yn-1-yl]amino}pyridin-2-yl)-2-methylpropanenitrile |
| 293. | 2-{5-[(3-{4-[(1,1-dioxo-1λ$^6$-thian-4-yl)amino]-1-(2,2,2-trifluoroethyl)-1H-indol-2-yl}prop-2-yn-1-yl)amino]pyridin-2-yl}-2-methylpropanenitrile |
| 294. | 3-[2-(3-{[6-(1-cyano-1-methylethyl)-pyridin-3-yl]amino}prop-1-yn-1-yl)-1-(2,2,2-trifluoroethyl)-1H-indol-4-yl]-1-(oxan-4-yl)urea |
| 295. | 3-[2-(3-{[6-(1-cyano-1-methylethyl)-pyridin-3-yl]amino}prop-1-yn-1-yl)-1-(2,2,2-trifluoroethyl)-1H-indol-4-yl]-1-(1-methylpiperidin-4-yl)urea |
| 296. | 2-(4-{[2-(3-{[6-(1-cyano-1-methylethyl)-pyridin-3-yl]amino}prop-1-yn-1-yl)-1-(2,2,2-trifluoroethyl)-1H-indol-4-yl]amino}piperidin-1-yl)-N,N-dimethylacetamide |
| 297. | 2-methyl-2-(5-{[3-(4-{[1-(propan-2-yl)piperidin-4-yl]amino}-1-(2,2,2-trifluoroethyl)-1H-indol-2-yl)prop-2-yn-1-yl]amino}pyridin-2-yl)propanenitrile |
| 298. | 2-methyl-2-(5-{[3-(4-{[1-(1-methylpiperidin-4-yl)piperidin-4-yl]amino}-1-(2,2,2-trifluoroethyl)-1H-indol-2-yl)prop-2-yn-1-yl]amino}pyridin-2-yl)propanenitrile |
| 299. | 4-{[2-(3-{[6-(1-cyano-1-methylethyl)-pyridin-3-yl]amino}prop-1-yn-1-yl)-1-(2,2,2-trifluoroethyl)-1H-indol-4-yl]amino}-N,N-dimethylpiperidine-1-carboxamide |
| 300. | N-[2-(3-{[6-(1-cyano-1-methylethyl)-pyridin-3-yl]amino}prop-1-yn-1-yl)-1-(2,2,2-trifluoroethyl)-1H-indol-4-yl]-4-methylpiperazine-1-carboxamide |
| 301. | 1-[2-(3-{[6-(1-cyano-1-methylethyl)pyridin-3-yl]amino}prop-1-yn-1-yl)-1-(2,2,2-trifluoroethyl)-1H-indol-4-yl]-3,3-dimethylurea |
| 302. | N-[2-(3-{[6-(1-cyano-1-methylethyl)-pyridin-3-yl]amino}prop-1-yn-1-yl)-1-(2,2,2-trifluoroethyl)-1H-indol-4-yl]morpholine-4-carboxamide |
| 303. | 2-{5-[(3-{4-[(4-hydroxycyclohexyl)-amino]-1-(2,2,2-trifluoroethyl)-1H-indol-2-yl}prop-2-yn-1-yl)amino]pyridin-2-yl}-2-methylpropanenitrile |
| 304. | 2-methyl-2-[5-({3-[4-({1-[2-(4-methylpiperazin-1-yl)-2-oxoethyl]-piperidin-4-yl}amino)-1-(2,2,2-trifluoroethyl)-1H-indol-2-yl]prop-2-yn-1-yl}amino)pyridin-2-yl]propanenitrile |
| 305. | 2-methyl-2-{5-[(3-{4-[(oxan-4-ylmethyl)amino]-1-(2,2,2-trifluoroethyl)-1H-indol-2-yl}prop-2-yn-1-yl)amino]pyridin-2-yl}propanenitrile |
| 306. | 2-{5-[(3-{4-[(1-ethylpiperidin-4-yl)amino]-1-(2,2,2-trifluoroethyl)-1H-indol-2-yl}prop-2-yn-1-yl)amino]pyridin-2-yl}-2-methylpropanenitrile |
| 307. | 2-(5-{[3-(4-{[1-(2-hydroxyethyl)piperidin-4-yl]amino}-1-(2,2,2-trifluoroethyl)-1H-indol-2-yl)prop-2-yn-1-yl]amino}pyridin-2-yl)-2-methylpropanenitrile |
| 308. | 2-{5-[(3-{4-[(1-methanesulfonylpiperidin-4-yl)amino]-1-(2,2,2-trifluoroethyl)-1H-indol-2-yl}prop-2-yn-1-yl)amino]pyridin-2-yl}-2-methylpropanenitrile |
| 309. | 2-(5-{[3-(4-{[1-(2-methanesulfonyl-ethyl)piperidin-4-yl]amino}-1-(2,2,2-trifluoroethyl)-1H-indol-2-yl)prop-2-yn-1-yl]amino}pyridin-2-yl)-2-methylpropanenitrile |
| 310. | 2-methyl-2-(5-{[3-(4-{[(1R,4R)-4-hydroxycyclohexyl]amino]-1-(2,2,2-trifluoroethyl)-1H-indol-2-yl)prop-2-yn-1-yl]amino}pyridin-2-yl)propanenitrile |
| 311. | 2-methyl-2-(5-{[3-(4-{[(1S,4S)-4-hydroxycyclohexyl]amino]-1-(2,2,2-trifluoroethyl)-1H-indol-2-yl)prop-2-yn-1-yl]amino}pyridin-2-yl)propanenitrile |
| 312. | 2-methyl-2-[5-({3-[4-({1-[2-(morpholin-4-yl)-2-oxoethyl]piperidin-4-yl}amino)-1-(2,2,2-trifluoroethyl)-1H-indol-2-yl]prop-2-yn-1-yl}amino)pyridin-2-yl]propanenitrile |
| 313. | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)-N,N-bis(2-methoxyethyl)acetamide |
| 314. | 2-methyl-2-{5-[(3-{4-[(pyrrolidin-3-yl)amino]-1-(2,2,2-trifluoroethyl)-1H-indol-2-yl}prop-2-yn-1-yl)amino]pyridin-2-yl}propanenitrile |
| 315. | 2-methyl-2-{5-[(3-{4-[(1-methylpyrrolidin-3-yl)amino]-1-(2,2,2-trifluoroethyl)-1H-indol-2-yl}prop-2-yn-1-yl)amino]pyridin-2-yl}propanenitrile |
| 316. | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)acetamide |
| 317. | methyl 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)acetate |
| 318. | 2-[5-({3-[4-({1-[2-(4-hydroxypiperidin-1-yl)-2-oxoethyl]piperidin-4-yl}amino)-1-(2,2,2-trifluoroethyl)-1H-indol-2-yl]prop-2-yn-1-yl}amino)pyridin-2-yl]-2-methylpropanenitrile |
| 319. | 2-methyl-2-{5-[(3-{4-[(2-methylpiperidin-4-yl)amino]-1-(2,2,2-trifluoroethyl)-1H-indol-2-yl}prop-2-yn-1-yl)amino]pyridin-2-yl}propanenitrile |
| 320. | 2-{5-[(3-{4-[(1,1-dioxo-1λ$^6$-thiolan-3-yl)amino]-1-(2,2,2-trifluoroethyl)-1H-indol-2-yl}prop-2-yn-1-yl)amino]pyridin-2-yl}-2-methylpropanenitrile |
| 321. | 2-methyl-2-[5-({3-[4-({1-[2-oxo-2-(pyrrolidin-1-yl)ethyl]piperidin-4-yl}amino)-1-(2,2,2-trifluoroethyl)-1H-indol-2-yl]prop-2-yn-1-yl}amino)pyridin-2-yl]propanenitrile |
| 322. | 2-{5-[(3-{4-[(1-{2-[4-(dimethylamino)piperidin-1-yl]-2-oxoethyl}piperidin-4-yl)amino]-1-(2,2,2-trifluoroethyl)-1H-indol-2-yl}prop-2-yn-1-yl)amino]pyridin-2-yl}-2-methylpropanenitrile |
| 323. | 2-[5-({3-[4-({1-[2-(dimethylamino)acetyl]piperidin-4-yl}amino)-1-(2,2,2-trifluoroethyl)-1H-indol-2-yl]prop-2-yn-1-yl}amino)pyridin-2-yl]-2-methylpropanenitrile |
| 324. | 2-(5-{[3-(4-{[1-(1,1-dioxo-1λ$^6$-thian-4-yl)piperidin-4-yl]amino}-1-(2,2,2-trifluoroethyl)-1H-indol-2-yl)prop-2-yn-1-yl]amino}pyridin-2-yl)-2-methylpropanenitrile |
| 325. | 2-(5-{[3-(4-{[1-(cyanomethyl)piperidin-4-yl]amino}-1-(2,2,2-trifluoroethyl)-1H-indol-2-yl)prop-2-yn-1-yl]amino}pyridin-2-yl)-2-methylpropanenitrile |
| 326. | 2-methyl-2-[5-({3-[1-(2,2,2-trifluoroethyl)-4-{[1-(2,2,2-trifluoroethyl)piperidin-4-yl]amino}-1H-indol-2-yl]prop-2-yn-1-yl}amino)pyridin-2-yl]propanenitrile |

TABLE 7-continued

| Mol # | IUPAC name |
|---|---|
| | Alkynyl indole compounds of the disclosure. |
| 327. | 2-{5-[(3-{4-[(1-{2-[4-(2-methanesulfonylethyl)piperazin-1-yl]-2-oxoethyl}piperidin-4-yl)amino]-1-(2,2,2-trifluoroethyl)-1H-indol-2-yl}prop-2-yn-1-yl)amino]pyridin-2-yl}-2-methylpropanenitrile |
| 328. | 2-[5-({3-[4-({1-[2-(1,1-dioxo-1λ$^6$,4-thiomorpholin-4-yl)-2-oxoethyl]piperidin-4-yl}amino)-1-(2,2,2-trifluoroethyl)-1H-indol-2-yl]prop-2-yn-1-yl}amino)pyridin-2-yl]-2-methylpropanenitrile |
| 329. | 2-(5-{[3-(4-{[1-(1-methanesulfonylpiperidin-4-yl)piperidin-4-yl]amino}-1-(2,2,2-trifluoroethyl)-1H-indol-2-yl)prop-2-yn-1-yl]amino}pyridin-2-yl)-2-methylpropanenitrile |
| 330. | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)-N-(2,3-dihydroxypropyl)-N-methylacetamide |
| 331. | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)-N-(2,3-dihydroxypropyl)acetamide |
| 332. | 2-[5-({3-[4-({1-[2-(4-methanesulfonylpiperazin-1-yl)-2-oxoethyl]piperidin-4-yl}amino)-1-(2,2,2-trifluoroethyl)-1H-indol-2-yl]prop-2-yn-1-yl}amino)pyridin-2-yl]-2-methylpropanenitrile |
| 333. | 2-{5-[(3-{4-[(1-{2-[4-(2-hydroxyethyl)piperazin-1-yl]-2-oxoethyl}piperidin-4-yl)amino]-1-(2,2,2-trifluoroethyl)-1H-indol-2-yl}prop-2-yn-1-yl)amino]pyridin-2-yl}-2-methylpropanenitrile |
| 334. | 2-methyl-2-(5-{[3-(4-{[1-(oxan-4-yl)piperidin-4-yl]amino}-1-(2,2,2-trifluoroethyl)-1H-indol-2-yl)prop-2-yn-1-yl]amino}pyridin-2-yl)propanenitrile |
| 335. | 2-[5-({3-[4-({1-[1-(2-methanesulfonylethyl)piperidin-4-yl]piperidin-4-yl}amino)-1-(2,2,2-trifluoroethyl)-1H-indol-2-yl]prop-2-yn-1-yl}amino)pyridin-2-yl]-2-methylpropanenitrile |
| 336. | 2-[5-({3-[4-({1-[1-(2-methoxyethyl)piperidin-4-yl]piperidin-4-yl}amino)-1-(2,2,2-trifluoroethyl)-1H-indol-2-yl]prop-2-yn-1-yl}amino)pyridin-2-yl]-2-methylpropanenitrile |
| 337. | 2-[5-({3-[4-({1-[1-(2-hydroxyethyl)piperidin-4-yl]piperidin-4-yl}amino)-1-(2,2,2-trifluoroethyl)-1H-indol-2-yl]prop-2-yn-1-yl}amino)pyridin-2-yl]-2-methylpropanenitrile |
| 338. | 2-[5-({3-[4-({1-[2-(dimethylamino)ethyl]piperidin-4-yl}amino)-1-(2,2,2-trifluoroethyl)-1H-indol-2-yl]prop-2-yn-1-yl}amino)pyridin-2-yl]-2-methylpropanenitrile |
| 339. | 2-(5-{[3-(4-{[1-(1-acetylpiperidin-4-yl)piperidin-4-yl]amino}-1-(2,2,2-trifluoroethyl)-1H-indol-2-yl)prop-2-yn-1-yl]amino}pyridin-2-yl)-2-methylpropanenitrile |
| 340. | 2-methyl-2-[5-({3-[4-({1-[(1R,4R)-4-hydroxycyclohexyl]piperidin-4-yl}amino)-1-(2,2,2-trifluoroethyl)-1H-indol-2-yl]prop-2-yn-1-yl}amino)pyridin-2-yl]propanenitrile |
| 341. | 2-methyl-2-[5-({3-[4-({1-[(1S,4S)-4-hydroxycyclohexyl]piperidin-4-yl}amino)-1-(2,2,2-trifluoroethyl)-1H-indol-2-yl]prop-2-yn-1-yl}amino)pyridin-2-yl]propanenitrile |
| 342. | N-(1-methylpiperidin-4-yl)-2-{3-[(6-methylpyridin-3-yl)amino]prop-1-yn-1-yl}-1-(2,2,2-trifluoroethyl)-1H-indol-4-amine |
| 343. | 2-methyl-2-{5-[(3-{4-[(1-methylpiperidin-4-yl)amino]-1-(2,2,2-trifluoroethyl)-1H-indol-2-yl}prop-2-yn-1-yl)amino]pyridin-2-yl}propanenitrile |
| 344. | 5-[(3-{4-[(1-methylpiperidin-4-yl)amino]-1-(2,2,2-trifluoroethyl)-1H-indol-2-yl}prop-2-yn-1-yl)amino]-N-(pyridin-3-yl)pyridine-2-carboxamide |
| 345. | 5-[(3-{4-[(1-methylpiperidin-4-yl)amino]-1-(2,2,2-trifluoroethyl)-1H-indol-2-yl}prop-2-yn-1-yl)amino]pyridine-2-carbonitrile |
| 346. | N-[6-(1-cyano-1-methylethyl)pyridin-3-yl]-3-{4-[(1-methylpiperidin-4-yl)amino]-1-(2,2,2-trifluoroethyl)-1H-indol-2-yl}prop-2-ynamide |
| 347. | 2-{3-[(2-fluorophenyl)amino]prop-1-yn-1-yl}-N-(1-methylpiperidin-4-yl)-1-(2,2,2-trifluoroethyl)-1H-indol-4-amine |
| 348. | 2-{3-[(3-fluorophenyl)amino]prop-1-yn-1-yl}-N-(1-methylpiperidin-4-yl)-1-(2,2,2-trifluoroethyl)-1H-indol-4-amine |
| 349. | 4-amino-N-(3-{4-[(1-methylpiperidin-4-yl)amino]-1-(2,2,2-trifluoroethyl)-1H-indol-2-yl}prop-2-yn-1-yl)benzene-1-sulfonamide |
| 350. | 2-{3-[(6-tert-butylpyridin-3-yl)amino]prop-1-yn-1-yl}-N-(1-methylpiperidin-4-yl)-1-(2,2,2-trifluoroethyl)-1H-indol-4-amine |
| 351. | 2-{3-[(4-fluorophenyl)amino]prop-1-yn-1-yl}-N-(1-methylpiperidin-4-yl)-1-(2,2,2-trifluoroethyl)-1H-indol-4-amine |
| 352. | N,N-dimethyl-5-[(3-{4-[(1-methylpiperidin-4-yl)amino]-1-(2,2,2-trifluoroethyl)-1H-indol-2-yl}prop-2-yn-1-yl)amino]pyridine-2-carboxamide |
| 353. | 5-[(3-{4-[(1-methylpiperidin-4-yl)amino]-1-(2,2,2-trifluoroethyl)-1H-indol-2-yl}prop-2-yn-1-yl)amino]-N-(propan-2-yl)pyridine-2-carboxamide |
| 354. | N-(pyridin-3-yl)-5-{[3-(4-{[(1R,4R)-4-(dimethylamino)cyclohexyl]amino}-1-(2,2,2-trifluoroethyl)-1H-indol-2-yl)prop-2-yn-1-yl]amino}pyridine-2-carboxamide |
| 355. | N-(pyridin-3-yl)-5-{[3-(4-{[(1S,4S)-4-(dimethylamino)cyclohexyl]amino}-1-(2,2,2-trifluoroethyl)-1H-indol-2-yl)prop-2-yn-1-yl]amino}pyridine-2-carboxamide |
| 356. | 2-{3-[(6-methanesulfonylpyridin-3-yl)amino]prop-1-yn-1-yl}-N-(1-methylpiperidin-4-yl)-1-(2,2,2-trifluoroethyl)-1H-indol-4-amine |
| 357. | 6-tert-butyl-N-(3-{4-[(1-methylpiperidin-4-yl)amino]-1-(2,2,2-trifluoroethyl)-1H-indol-2-yl}prop-2-yn-1-yl)pyridine-3-carboxamide |
| 358. | 2-{3-[(6-chloropyridin-3-yl)amino]prop-1-yn-1-yl}-N-(1-methylpiperidin-4-yl)-1-(2,2,2-trifluoroethyl)-1H-indol-4-amine |
| 359. | 2-{4-[(3-{4-[(1-methylpiperidin-4-yl)amino]-1-(2,2,2-trifluoroethyl)-1H-indol-2-yl}prop-2-yn-1-yl)amino]phenyl}propan-2-ol |
| 360. | 6-methyl-N-(3-{4-[(1-methylpiperidin-4-yl)amino]-1-(2,2,2-trifluoroethyl)-1H-indol-2-yl}prop-2-yn-1-yl)pyridine-3-carboxamide |
| 361. | N-(1-methylpiperidin-4-yl)-1-(2,2,2-trifluoroethyl)-2-(3-{[6-(trifluoromethyl)pyridin-3-yl]amino}prop-1-yn-1-yl)-1H-indol-4-amine |

TABLE 7-continued

| Mol # | IUPAC name |
|---|---|
| | Alkynyl indole compounds of the disclosure. |
| 362. | 3-(3-{4-[(1-methylpiperidin-4-yl)amino]-1-(2,2,2-trifluoroethyl)-1H-indol-2-yl}prop-2-yn-1-yl)-1-phenylurea |
| 363. | 2-{3-[(4-tert-butyl-2-fluorophenyl)-amino]prop-1-yn-1-yl}-N-(1-methylpiperidin-4-yl)-1-(2,2,2-trifluoroethyl)-1H-indol-4-amine |
| 364. | 2-{3-fluoro-4-[(3-{4-[(1-methylpiperidin-4-yl)amino]-1-(2,2,2-trifluoroethyl)-1H-indol-2-yl}prop-2-yn-1-yl)amino]phenyl}-2-methylpropanenitrile |
| 365. | 4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 366. | 2-{3-[(2,6-difluoro-4-methane-sulfonylphenyl)amino]prop-1-yn-1-yl}-N-(1-methylpiperidin-4-yl)-1-(2,2,2-trifluoroethyl)-1H-indol-4-amine |
| 367. | N-methyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 368. | 2-{3-[(4-methanesulfonyl-3-methoxyphenyl)amino]prop-1-yn-1-yl}-N-(1-methylpiperidin-4-yl)-1-(2,2,2-trifluoroethyl)-1H-indol-4-amine |
| 369. | 2-{3-[(4-methanesulfonyl-2-methoxyphenyl)amino]prop-1-yn-1-yl}-N-(1-methylpiperidin-4-yl)-1-(2,2,2-trifluoroethyl)-1H-indol-4-amine |
| 370. | 2-{3-[(5-methanesulfonylpyridin-2-yl)amino]prop-1-yn-1-yl}-N-(1-methylpiperidin-4-yl)-1-(2,2,2-trifluoroethyl)-1H-indol-4-amine |
| 371. | 2-{3-[(4-methanesulfonyl-2-methylphenyl)amino]prop-1-yn-1-yl}-N-(1-methylpiperidin-4-yl)-1-(2,2,2-trifluoroethyl)-1H-indol-4-amine |
| 372. | methyl 3-methoxy-4-[(3-{4-[(1-methylpiperidin-4-yl)amino]-1-(2,2,2-trifluoroethyl)-1H-indol-2-yl}prop-2-yn-1-yl)amino]benzoate |
| 373. | N-{3-methoxy-4-[(3-{4-[(1-methylpiperidin-4-yl)amino]-1-(2,2,2-trifluoroethyl)-1H-indol-2-yl}prop-2-yn-1-yl)amino]phenyl}methanesulfonamide |
| 374. | 3-methoxy-4-[(3-{4-[(1-methylpiperidin-4-yl)amino]-1-(2,2,2-trifluoroethyl)-1H-indol-2-yl}prop-2-yn-1-yl)amino]benzonitrile |
| 375. | 3-methoxy-4-[(3-{4-[(1-methylpiperidin-4-yl)amino]-1-(2,2,2-trifluoroethyl)-1H-indol-2-yl}prop-2-yn-1-yl)amino]benzoic acid |
| 376. | 2-{3-[(2,4-dimethoxyphenyl)amino]prop-1-yn-1-yl}-N-(1-methylpiperidin-4-yl)-1-(2,2,2-trifluoroethyl)-1H-indol-4-amine |
| 377. | 2-{3-[(2-methoxypyridin-3-yl)amino]prop-1-yn-1-yl}-N-(1-methylpiperidin-4-yl)-1-(2,2,2-trifluoroethyl)-1H-indol-4-amine |
| 378. | 2-{3-[(5-fluoro-2-methoxyphenyl)-amino]prop-1-yn-1-yl}-N-(1-methylpiperidin-4-yl)-1-(2,2,2-trifluoroethyl)-1H-indol-4-amine |
| 379. | 2-{3-[(2-ethoxy-4-methane-sulfonylphenyl)amino]prop-1-yn-1-yl}-N-(1-methylpiperidin-4-yl)-1-(2,2,2-trifluoroethyl)-1H-indol-4-amine |
| 380. | 2-{3-[(3-fluoro-2-methoxyphenyl)-amino]prop-1-yn-1-yl}-N-(1-methylpiperidin-4-yl)-1-(2,2,2-trifluoroethyl)-1H-indol-4-amine |
| 381. | 3-methoxy-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 382. | 2-{3-[(4-fluoro-2-methoxyphenyl)-amino]prop-1-yn-1-yl}-N-(1-methylpiperidin-4-yl)-1-(2,2,2-trifluoroethyl)-1H-indol-4-amine |
| 383. | 3-methoxy-4-[(3-{4-[(1-methylpiperidin-4-yl)amino]-1-(2,2,2-trifluoroethyl)-1H-indol-2-yl}prop-2-yn-1-yl)amino]-benzamide |
| 384. | 2-{3-[(2-fluoro-6-methoxyphenyl)-amino]prop-1-yn-1-yl}-N-(1-methylpiperidin-4-yl)-1-(2,2,2-trifluoroethyl)-1H-indol-4-amine |
| 385. | 2-{3-[(4-tert-butyl-2-methoxyphenyl)-amino]prop-1-yn-1-yl}-N-(1-methylpiperidin-4-yl)-1-(2,2,2-trifluoroethyl)-1H-indol-4-amine |
| 386. | 4-methoxy-3-[(3-{4-[(1-methylpiperidin-4-yl)amino]-1-(2,2,2-trifluoroethyl)-1H-indol-2-yl}prop-2-yn-1-yl)amino]-benzonitrile |
| 387. | 2-{3-[(5-tert-butyl-2-methoxyphenyl)-amino]prop-1-yn-1-yl}-N-(1-methylpiperidin-4-yl)-1-(2,2,2-trifluoroethyl)-1H-indol-4-amine |
| 388. | N-(1-methylpiperidin-4-yl)-2-[3-(phenylamino)prop-1-yn-1-yl]-1-(2,2,2-trifluoroethyl)-1H-indol-4-amine |
| 389. | 5-methanesulfonyl-2-[(3-{4-[(1-methylpiperidin-4-yl)amino]-1-(2,2,2-trifluoroethyl)-1H-indol-2-yl}prop-2-yn-1-yl)amino]benzonitrile |
| 390. | 2-(3-{[2-(2-fluoroethoxy)-4-methanesulfonylphenyl]amino}prop-1-yn-1-yl)-N-(1-methylpiperidin-4-yl)-1-(2,2,2-trifluoroethyl)-1H-indol-4-amine |
| 391. | 2-{3-[(3-methoxypyridin-4-yl)amino]prop-1-yn-1-yl}-N-(1-methylpiperidin-4-yl)-1-(2,2,2-trifluoroethyl)-1H-indol-4-amine |
| 392. | 2-{3-[(2-chloro-4-methanesulfonyl-phenyl)amino]prop-1-yn-1-yl}-N-(1-methylpiperidin-4-yl)-1-(2,2,2-trifluoroethyl)-1H-indol-4-amine |
| 393. | 2-{3-[(4-methoxyphenyl)amino]prop-1-yn-1-yl}-N-(1-methylpiperidin-4-yl)-1-(2,2,2-trifluoroethyl)-1H-indol-4-amine |
| 394. | 2-(3-{[4-methanesulfonyl-2-(2-methoxyethoxy)phenyl]amino}prop-1-yn-1-yl)-N-(1-methylpiperidin-4-yl)-1-(2,2,2-trifluoroethyl)-1H-indol-4-amine |
| 395. | 5-[(3-{4-[(1,1-dioxo-1λ$^6$-thian-4-yl)amino]-1-(2,2,2-trifluoroethyl)-1H-indol-2-yl}prop-2-yn-1-yl)amino]pyridine-2-carbonitrile |
| 396. | 4-{[2-(3-{[6-(morpholine-4-carbonyl)pyridin-3-yl]amino}prop-1-yn-1-yl)-1-(2,2,2-trifluoroethyl)-1H-indol-4-yl]amino}-1λ$^6$-thiane-1,1-dione |
| 397. | 4-{[2-(3-{[6-(4-methylpiperazine-1-carbonyl)pyridin-3-yl]amino}prop-1-yn-1-yl)-1-(2,2,2-trifluoroethyl)-1H-indol-4-yl]amino}-1λ$^6$-thiane-1,1-dione |
| 398. | 4-[(2-{3-[(quinolin-3-yl)amino]prop-1-yn-1-yl}-1-(2,2,2-trifluoroethyl)-1H-indol-4-yl)amino]-1λ$^6$-thiane-1,1-dione |
| 399. | 4-[(2-{3-[(quinoxalin-6-yl)amino]prop-1-yn-1-yl}-1-(2,2,2-trifluoroethyl)-1H-indol-4-yl)amino]-1λ$^6$-thiane-1,1-dione |

TABLE 7-continued

Alkynyl indole compounds of the disclosure.

| Mol # | IUPAC name |
|---|---|
| 400. | 4-[(2-{3-[(4-methanesulfonylphenyl)-amino]prop-1-yn-1-yl}-1-(2,2,2-trifluoroethyl)-1H-indol-4-yl)amino]-1λ6-thiane-1,1-dione |
| 401. | 5-[(3-{4-[(1,1-dioxo-1λ6-thian-4-yl)amino]-1-(2,2,2-trifluoroethyl)-1H-indol-2-yl}prop-2-yn-1-yl)amino]pyridine-2-carboxamide |
| 402. | 4-[(2-{3-[(6-methoxypyridin-3-yl)amino]prop-1-yn-1-yl}-1-(2,2,2-trifluoroethyl)-1H-indol-4-yl)amino]-1λ6-thiane-1,1-dione |
| 403. | 4-{[2-(3-{[6-(4-hydroxypiperidine-1-carbonyl)pyridin-3-yl]amino}prop-1-yn-1-yl)-1-(2,2,2-trifluoroethyl)-1H-indol-4-yl]amino}-1λ6-thiane-1,1-dione |
| 404. | 4-[(2-{3-[(1-methyl-2-oxo-1,2-dihydropyridin-4-yl)amino]prop-1-yn-1-yl}-1-(2,2,2-trifluoroethyl)-1H-indol-4-yl)amino]-1λ6-thiane-1,1-dione |
| 405. | 4-[(2-{3-[(2-methoxypyridin-4-yl)amino]prop-1-yn-1-yl}-1-(2,2,2-trifluoroethyl)-1H-indol-4-yl)amino]-1λ6-thiane-1,1-dione |
| 406. | 2-{4-[(3-{4-[(1,1-dioxo-1λ6-thian-4-yl)amino]-1-(2,2,2-trifluoroethyl)-1H-indol-2-yl}prop-2-yn-1-yl)amino]-3-fluorophenyl}-2-methylpropanenitrile |
| 407. | 5-[(3-{4-[(1,1-dioxo-1λ6-thian-4-yl)amino]-1-(2,2,2-trifluoroethyl)-1H-indol-2-yl}prop-2-yn-1-yl)amino]-N-(1-methylpiperidin-4-yl)pyridine-2-carboxamide |
| 408. | 4-[(2-{3-[(2-fluoro-4-methanesulfonyl-phenyl)amino]prop-1-yn-1-yl}-1-(2,2,2-trifluoroethyl)-1H-indol-4-yl)amino]-1λ6-thiane-1,1-dione |
| 409. | 4-{[2-(3-{[4-(ethanesulfonyl)-phenyl]amino}prop-1-yn-1-yl)-1-(2,2,2-trifluoroethyl)-1H-indol-4-yl]amino}-1λ6-thiane-1,1-dione |
| 410. | 4-[(2-{3-[(2-tert-butylpyrimidin-5-yl)amino]prop-1-yn-1-yl}-1-(2,2,2-trifluoroethyl)-1H-indol-4-yl)amino]-1λ6-thiane-1,1-dione |
| 411. | 3-{4-[(1,1-dioxo-1λ6-thian-4-yl)amino]-1-(2,2,2-trifluoroethyl)-1H-indol-2-yl}-N-(4-methanesulfonyl-phenyl)-prop-2-ynamide |
| 412. | 5-[(3-{4-[(1,1-dioxo-1λ6-thian-4-yl)amino]-1-(2,2,2-trifluoroethyl)-1H-indol-2-yl}prop-2-yn-1-yl)amino]-N-(oxan-4-yl)pyridine-2-carboxamide |
| 413. | 5-[(3-{4-[(1,1-dioxo-1λ6-thian-4-yl)amino]-1-(2,2,2-trifluoroethyl)-1H-indol-2-yl}prop-2-yn-1-yl)amino]-N-(pyridin-3-yl)pyridine-2-carboxamide |
| 414. | 5-[(3-{4-[(1,1-dioxo-1λ6-thian-4-yl)amino]-1-(2,2,2-trifluoroethyl)-1H-indol-2-yl}prop-2-yn-1-yl)amino]-N-methylpyridine-2-carboxamide |
| 415. | 4-[(2-{3-[(3-chloro-4-methanesulfonylphenyl)amino]prop-1-yn-1-yl}-1-(2,2,2-trifluoroethyl)-1H-indol-4-yl)amino]-1λ6-thiane-1,1-dione |
| 416. | N-(2,3-dihydroxypropyl)-5-[(3-{4-[(1,1-dioxo-1λ6-thian-4-yl)amino]-1-(2,2,2-trifluoroethyl)-1H-indol-2-yl}prop-2-yn-1-yl)amino]pyridine-2-carboxamide |
| 417. | 5-[(3-{4-[(1,1-dioxo-1λ6-thian-4-yl)amino]-1-(2,2,2-trifluoroethyl)-1H-indol-2-yl}prop-2-yn-1-yl)amino]-N-hydroxypyridine-2-carboxamide |
| 418. | 5-[(3-{4-[(1,1-dioxo-1λ6-thian-4-yl)amino]-1-(2,2,2-trifluoroethyl)-1H-indol-2-yl}prop-2-yn-1-yl)amino]-N-(2-hydroxyethyl)pyridine-2-carboxamide |
| 419. | 5-[(3-{4-[(1,1-dioxo-1λ6-thian-4-yl)amino]-1-(2,2,2-trifluoroethyl)-1H-indol-2-yl}prop-2-yn-1-yl)amino]-N-hydroxy-N-methylpyridine-2-carboxamide |
| 420. | 4-amino-N-(3-{4-[(1,1-dioxo-1λ6-thian-4-yl)amino]-1-(2,2,2-trifluoroethyl)-1H-indol-2-yl}prop-2-yn-1-yl)benzene-1-sulfonamide |
| 421. | 4-({2-[3-({pyrido[2,3-b]pyrazin-7-yl}amino)prop-1-yn-1-yl]-1-(2,2,2-trifluoroethyl)-1H-indol-4-yl}amino)-1λ6-thiane-1,1-dione |
| 422. | 4-[(3-{4-[(1,1-dioxo-1λ6-thian-4-yl)amino]-1-(2,2,2-trifluoroethyl)-1H-indol-2-yl}prop-2-yn-1-yl)amino]-benzamide |
| 423. | 4-{[2-(3-{[2-(methylsulfanyl)pyrimidin-5-yl]amino}prop-1-yn-1-yl)-1-(2,2,2-trifluoroethyl)-1H-indol-4-yl]amino}-1λ6-thiane-1,1-dione |
| 424. | 4-[(3-{4-[(1,1-dioxo-1λ6-thian-4-yl)amino]-1-(2,2,2-trifluoroethyl)-1H-indol-2-yl}prop-2-yn-1-yl)amino]benzene-1-sulfonamide |
| 425. | 4-{[2-(3-{[4-(2-methylpropane-2-sulfonyl)phenyl]amino}prop-1-yn-1-yl)-1-(2,2,2-trifluoroethyl)-1H-indol-4-yl]amino}-1λ6-thiane-1,1-dione |
| 426. | 4-[(3-{4-[(1,1-dioxo-1λ6-thian-4-yl)amino]-1-(2,2,2-trifluoroethyl)-1H-indol-2-yl}prop-2-yn-1-yl)amino]-N,N-dimethylbenzene-1-sulfonamide |
| 427. | 4-{[1-(2,2,2-trifluoroethyl)-2-[2-(trimethylsilyl)ethynyl]-1H-indol-4-yl]amino}-1λ6-thiane-1,1-dione |
| 428. | 4-[(2-{3-[(5-methanesulfonylpyridin-2-yl)amino]prop-1-yn-1-yl}-1-(2,2,2-trifluoroethyl)-1H-indol-4-yl)amino]-1λ6-thiane-1,1-dione |
| 429. | 4-[(2-{3-[(4-methanesulfonyl-2-methoxyphenyl)amino]prop-1-yn-1-yl}-1-(2,2,2-trifluoroethyl)-1H-indol-4-yl)amino]-1λ6-thiane-1,1-dione |
| 430. | 4-[(3-{4-[(1,1-dioxo-1λ6-thian-4-yl)amino]-1-(2,2,2-trifluoroethyl)-1H-indol-2-yl}prop-2-yn-1-yl)amino]-N-methylbenzene-1-sulfonamide |
| 431. | 4-{[2-ethynyl-1-(2,2,2-trifluoroethyl)-1H-indol-4-yl]amino}-1λ6-thiane-1,1-dione |
| 432. | N-{4-[(3-{4-[(1,1-dioxo-1λ6-thian-4-yl)amino]-1-(2,2,2-trifluoroethyl)-1H-indol-2-yl}prop-2-yn-1-yl)amino]-3-methoxyphenyl}methanesulfonamide |
| 433. | 4-[(3-{4-[(1,1-dioxo-1λ6-thian-4-yl)amino]-1-(2,2,2-trifluoroethyl)-1H-indol-2-yl}prop-2-yn-1-yl)amino]-3-methoxybenzoic acid |
| 434. | 4-[(3-{4-[(1,1-dioxo-1λ6-thian-4-yl)amino]-1-(2,2,2-trifluoroethyl)-1H-indol-2-yl}prop-2-yn-1-yl)amino]-3-methoxybenzonitrile |
| 435. | 4-[(2-{3-[(5-fluoro-2-methoxyphenyl)amino]prop-1-yn-1-yl}-1-(2,2,2-trifluoroethyl)-1H-indol-4-yl)amino]-1λ6-thiane-1,1-dione |
| 436. | 4-[(2-{3-[(2-methoxy-6-methylpyridin-3-yl)amino]prop-1-yn-1-yl}-1-(2,2,2-trifluoroethyl)-1H-indol-4-yl)amino]-1λ6-thiane-1,1-dione |
| 437. | 4-[(2-{3-[(2-hydroxy-6-methylpyridin-3-yl)amino]prop-1-yn-1-yl}-1-(2,2,2-trifluoroethyl)-1H-indol-4-yl)amino]-1λ6-thiane-1,1-dione |

TABLE 7-continued

Alkynyl indole compounds of the disclosure.

| Mol # | IUPAC name |
|---|---|
| 438. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxybenzamide |
| 439. | 4-[(2-{3-[(2-methoxypyridin-3-yl)amino]prop-1-yn-1-yl}-1-(2,2,2-trifluoroethyl)-1H-indol-4-yl)amino]-1$\lambda^6$-thiane-1,1-dione |
| 440. | 4-[(2-{3-[(4-fluoro-2-methoxyphenyl)amino]prop-1-yn-1-yl}-1-(2,2,2-trifluoroethyl)-1H-indol-4-yl)amino]-1$\lambda^6$-thiane-1,1-dione |
| 441. | 4-[(2-{3-[(5-tert-butyl-2-methoxyphenyl)amino]prop-1-yn-1-yl}-1-(2,2,2-trifluoroethyl)-1H-indol-4-yl)amino]-1$\lambda^6$-thiane-1,1-dione |
| 442. | 4-[(2-{3-[(2-ethoxy-4-methanesulfonylphenyl)amino]prop-1-yn-1-yl}-1-(2,2,2-trifluoroethyl)-1H-indol-4-yl)amino]-1$\lambda^6$-thiane-1,1-dione |
| 443. | 4-[(2-{3-[(3-fluoro-2-methoxyphenyl)-amino]prop-1-yn-1-yl}-1-(2,2,2-trifluoroethyl)-1H-indol-4-yl)amino]-1$\lambda^6$-thiane-1,1-dione |
| 444. | 4-({2-[3-(methylamino)prop-1-yn-1-yl]-1-(2,2,2-trifluoroethyl)-1H-indol-4-yl}amino)-1$\lambda^6$-thiane-1,1-dione |
| 445. | 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxybenzene-1-sulfonamide |
| 446. | 4-[(2-{3-[(2-fluoro-6-methoxyphenyl)-amino]prop-1-yn-1-yl}-1-(2,2,2-trifluoroethyl)-1H-indol-4-yl)amino]-1$\lambda^6$-thiane-1,1-dione |
| 447. | 3-[(3-{4-[(1,1-dioxo-1$\lambda^6$-thian-4-yl)amino]-1-(2,2,2-trifluoroethyl)-1H-indol-2-yl}prop-2-yn-1-yl)amino]-4-methoxybenzonitrile |
| 448. | 4-[(2-{3-[(4-tert-butyl-2-methoxy-phenyl)amino]prop-1-yn-1-yl}-1-(2,2,2-trifluoroethyl)-1H-indol-4-yl)amino]-1$\lambda^6$-thiane-1,1-dione |
| 449. | 4-({2-[3-(phenylamino)prop-1-yn-1-yl]-1-(2,2,2-trifluoroethyl)-1H-indol-4-yl}amino)-1$\lambda^6$-thiane-1,1-dione |
| 450. | 4-{[2-(3-{[2-(2-fluoroethoxy)-4-methanesulfonylphenyl]amino}prop-1-yn-1-yl)-1-(2,2,2-trifluoroethyl)-1H-indol-4-yl]amino}-1$\lambda^6$-thiane-1,1-dione |
| 451. | 2-[(3-{4-[(1,1-dioxo-1$\lambda^6$-thian-4-yl)amino]-1-(2,2,2-trifluoroethyl)-1H-indol-2-yl}prop-2-yn-1-yl)amino]-5-methanesulfonylbenzonitrile |
| 452. | 4-[(2-{3-[(2-chloro-4-methanesulfonyl-phenyl)amino]prop-1-yn-1-yl}-1-(2,2,2-trifluoroethyl)-1H-indol-4-yl)amino]-1$\lambda^6$-thiane-1,1-dione |
| 453. | 4-[(2-{3-[(4-methoxyphenyl)amino]prop-1-yn-1-yl}-1-(2,2,2-trifluoroethyl)-1H-indol-4-yl)amino]-1$\lambda^6$-thiane-1,1-dione |
| 454. | 4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}-1$\lambda^6$-thiane-1,1-dione |
| 455. | 2-{4-[(2-{3-[(4-methanesulfonylphenyl)amino]prop-1-yn-1-yl}-1-(2,2,2-trifluoroethyl)-1H-indol-4-yl)amino]piperidin-1-yl}-N,N-dimethylacetamide |
| 456. | 2-methyl-2-(5-{[3-(4-{[(1R,4R)-4-(dimethylamino)cyclohexyl]amino}-1-(2,2,2-trifluoroethyl)-1H-indol-2-yl)prop-2-yn-1-yl]amino}pyridin-2-yl)propanenitrile |
| 457. | 2-(5-((3-(4-(((1S,4S)-4-(dimethylamino)-cyclohexyl)amino)-1-(2,2,2-trifluoroethyl)-1H-indol-2-yl)prop-2-yn-1-yl)amino)pyridin-2-yl)-2-methylpropanenitrile |
| 458. | N-[1-(2-methanesulfonylethyl)piperidin-4-yl]-2-{3-[(4-methanesulfonylphenyl)-amino]prop-1-yn-1-yl}-1-(2,2,2-trifluoroethyl)-1H-indol-4-amine |
| 459. | 5-({3-[4-({1-[(dimethylcarbamoyl)methyl]piperidin-4-yl}amino)-1-(2,2,2-trifluoroethyl)-1H-indol-2-yl]prop-2-yn-1-yl}amino)pyridine-2-carboxamide |
| 460. | 5-{[3-(4-{[1-(2-methanesulfonylethyl)piperidin-4-yl]amino}-1-(2,2,2-trifluoroethyl)-1H-indol-2-yl)prop-2-yn-1-yl]amino}pyridine-2-carboxamide |
| 461. | 5-[(3-{4-[(piperidin-4-yl)amino]-1-(2,2,2-trifluoroethyl)-1H-indol-2-yl}prop-2-yn-1-yl)amino]pyridine-2-carboxamide |
| 462. | 5-{[3-(4-{[1-(carbamoylmethyl)piperidin-4-yl]amino}-1-(2,2,2-trifluoroethyl)-1H-indol-2-yl)prop-2-yn-1-yl]amino}pyridine-2-carboxamide |
| 463. | 5-{[3-(4-{[1-(2-hydroxyethyl)piperidin-4-yl]amino}-1-(2,2,2-trifluoroethyl)-1H-indol-2-yl)prop-2-yn-1-yl]amino}pyridine-2-carboxamide |
| 464. | 5-{[3-(4-{[1-(oxan-4-yl)piperidin-4-yl]amino}-1-(2,2,2-trifluoroethyl)-1H-indol-2-yl)prop-2-yn-1-yl]amino}pyridine-2-carboxamide |
| 465. | 5-{[3-(4-{[(1R,4R)-4-(dimethylamino)-cyclohexyl]amino}-1-(2,2,2-trifluoroethyl)-1H-indol-2-yl)prop-2-yn-1-yl]amino}pyridine-2-carboxamide |
| 466. | 4-{[3-(4-{[1-(2-methanesulfonyl-ethyl)piperidin-4-yl]amino}-1-(2,2,2-trifluoroethyl)-1H-indol-2-yl)prop-2-yn-1-yl]amino}benzene-1-sulfonamide |
| 467. | 4-{[3-(4-{[1-(2-methoxyethyl)piperidin-4-yl]amino}-1-(2,2,2-trifluoroethyl)-1H-indol-2-yl)prop-2-yn-1-yl]amino}benzene-1-sulfonamide |
| 468. | 5-{[3-(4-{[(1S,4S)-4-(dimethylamino)-cyclohexyl]amino}-1-(2,2,2-trifluoroethyl)-1H-indol-2-yl)prop-2-yn-1-yl]amino}pyridine-2-carboxamide |
| 469. | N,N-dimethyl-4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide |
| 470. | 4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide |
| 471. | 2-{4-[(2-{3-[(4-sulfamoylphenyl)-amino]prop-1-yn-1-yl}-1-(2,2,2-trifluoroethyl)-1H-indol-4-yl)amino]-piperidin-1-yl}acetamide |
| 472. | 4-{[3-(4-{[1-(2-methoxyethyl)piperidin-4-yl]amino}-1-(2,2,2-trifluoroethyl)-1H-indol-2-yl)prop-2-yn-1-yl]amino}-N,N-dimethylbenzene-1-sulfonamide |
| 473. | 4-[(3-{4-[(oxan-4-yl)amino]-1-(2,2,2-trifluoroethyl)-1H-indol-2-yl}prop-2-yn-1-yl)amino]benzene-1-sulfonamide |
| 474. | 4-{[3-(4-{[1-(2-hydroxypropyl)piperidin-4-yl]amino}-1-(2,2,2-trifluoroethyl)-1H-indol-2-yl)prop-2-yn-1-yl]amino}benzene-1-sulfonamide |
| 475. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}benzene-1-sulfonamide |

TABLE 7-continued

| Mol # | IUPAC name |
|---|---|
| | Alkynyl indole compounds of the disclosure. |
| 476. | 4-({3-[4-({1-[2-(morpholin-4-yl)-2-oxoethyl]piperidin-4-yl}amino)-1-(2,2,2-trifluoroethyl)-1H-indol-2-yl]prop-2-yn-1-yl}amino)benzene-1-sulfonamide |
| 477. | methyl 2-{4-[(2-{3-[(4-sulfamoylphenyl)-amino]prop-1-yn-1-yl}-1-(2,2,2-trifluoro-ethyl)-1H-indol-4-yl)amino]piperidin-1-yl}acetate |
| 478. | 4-{[3-(4-{[1-(2-hydroxyethyl)piperidin-4-yl]amino}-1-(2,2,2-trifluoroethyl)-1H-indol-2-yl)prop-2-yn-1-yl]amino}benzene-1-sulfonamide |
| 479. | 4-({3-[4-({1-[2-(2-hydroxyethoxy)ethyl]piperidin-4-yl}amino)-1-(2,2,2-trifluoroethyl)-1H-indol-2-yl]prop-2-yn-1-yl}amino)benzene-1-sulfonamide |
| 480. | N,N-dimethyl-2-{4-[(2-{3-[(4-sulfamoylphenyl)amino]prop-1-yn-1-yl}-1-(2,2,2-trifluoroethyl)-1H-indol-4-yl)amino]piperidin-1-yl}acetamide |
| 481. | 4-({3-[4-({1-[2-(4-hydroxypiperidin-1-yl)-2-oxoethyl]piperidin-4-yl}amino)-1-(2,2,2-trifluoroethyl)-1H-indol-2-yl]prop-2-yn-1-yl}amino)benzene-1-sulfonamide |
| 482. | 2-{4-[(2-{3-[(4-sulfamoylphenyl)amino]prop-1-yn-1-yl}-1-(2,2,2-trifluoroethyl)-1H-indol-4-yl)amino]piperidin-1-yl}acetic acid |
| 483. | 4-({3-[4-({1-[2-(4-methylpiperazin-1-yl)-2-oxoethyl]piperidin-4-yl}amino)-1-(2,2,2-trifluoroethyl)-1H-indol-2-yl]prop-2-yn-1-yl}amino)benzene-1-sulfonamide |
| 484. | N-methyl-2-{4-[(2-{3-[(4-sulfamoylphenyl)amino]prop-1-yn-1-yl}-1-(2,2,2-trifluoroethyl)-1H-indol-4-yl)amino]piperidin-1-yl}acetamide |
| 485. | N-methyl-4-[(3-{4-[(oxan-4-yl)amino]-1-(2,2,2-trifluoroethyl)-1H-indol-2-yl}prop-2-yn-1-yl)amino]benzene-1-sulfonamide |
| 486. | 4-{[3-(4-{[1-(2-methoxyethyl)piperidin-4-yl]amino}-1-(2,2,2-trifluoroethyl)-1H-indol-2-yl)prop-2-yn-1-yl]amino}-N-methylbenzene-1-sulfonamide |
| 487. | N-methyl-4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide |
| 488. | 2-(dimethylamino)ethyl 2-{4-[(2-{3-[(4-methanesulfonylphenyl)-amino]prop-1-yn-1-yl}-1-(2,2,2-trifluoroethyl)-1H-indol-4-yl)amino]piperidin-1-yl}acetate |
| 489. | 2-methoxy-4-[(3-{4-[(oxan-4-yl)amino]-1-(2,2,2-trifluoroethyl)-1H-indol-2-yl}prop-2-yn-1-yl)amino]benzene-1-sulfonamide |
| 490. | 2-chloro-4-[(3-{4-[(oxan-4-yl)amino]-1-(2,2,2-trifluoroethyl)-1H-indol-2-yl}prop-2-yn-1-yl)amino]benzene-1-sulfonamide |
| 491. | 3-methoxy-4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide |
| 492. | 4-{[3-(4-{[1-(2,3-dihydroxypropyl)-piperidin-4-yl]amino}-1-(2,2,2-trifluoro-ethyl)-1H-indol-2-yl)prop-2-yn-1-yl]amino}-3-methoxybenzene-1-sulfonamide |
| 493. | 3-methoxy-4-[(3-{4-[(piperidin-4-yl)amino]-1-(2,2,2-trifluoroethyl)-1H-indol-2-yl}prop-2-yn-1-yl)amino]benzene-1-sulfonamide |
| 494. | 3-methoxy-4-[(3-{4-[(oxan-4-yl)amino]-1-(2,2,2-trifluoroethyl)-1H-indol-2-yl}prop-2-yn-1-yl)amino]benzene-1-sulfonamide |
| 495. | 3-methoxy-4-[(3-{4-[(oxan-4-yl)amino]-1-(2,2,2-trifluoroethyl)-1H-indol-2-yl}prop-2-yn-1-yl)amino]benzamide |
| 496. | 3-methoxy-4-{[3-(4-{[1-(oxan-4-yl)piperidin-4-yl]amino}-1-(2,2,2-trifluoroethyl)-1H-indol-2-yl)prop-2-yn-1-yl]amino}benzamide |
| 497. | 4-{[3-(4-{[1-(2,3-dihydroxypropyl)-piperidin-4-yl]amino}-1-(2,2,2-trifluoroethyl)-1H-indol-2-yl)prop-2-yn-1-yl]amino}-3-methoxybenzamide |
| 498. | 2-[5-({3-[1-(cyanomethyl)-4-[(1-methylpiperidin-4-yl)amino]-1H-indol-2-yl]prop-2-yn-1-yl}amino)pyridin-2-yl]-2-methylpropanenitrile |
| 499. | 2-[5-({3-[1-(3-methoxypropyl)-4-[(1-methylpiperidin-4-yl)amino]-1H-indol-2-yl]prop-2-yn-1-yl}amino)pyridin-2-yl]-2-methylpropanenitrile |
| 500. | 2-[5-({3-[1-(2-chloroethyl)-4-[(1-methylpiperidin-4-yl)amino]-1H-indol-2-yl]prop-2-yn-1-yl}amino)pyridin-2-yl]-2-methylpropanenitrile |
| 501. | 2-methyl-2-{5-[(3-{4-[(1-methylpiperidin-4-yl)amino]-1-(propan-2-yl)-1H-indol-2-yl}prop-2-yn-1-yl)amino]pyridin-2-yl}propanenitrile |
| 502. | 2-{5-[(3-{1-cyclopentyl-4-[(1-methylpiperidin-4-yl)amino]-1H-indol-2-yl}prop-2-yn-1-yl)amino]pyridin-2-yl}-2-methylpropanenitrile |
| 503. | 2-methyl-2-{5-[(3-{4-[(1-methylpiperidin-4-yl)amino]-1-(3,3,3-trifluoropropyl)-1H-indol-2-yl}prop-2-yn-1-yl)amino]pyridin-2-yl}propanenitrile |
| 504. | 1-(2-chloroethyl)-N-(1-methylpiperidin-4-yl)-2-{3-[(6-methylpyridin-3-yl)amino]-prop-1-yn-1-yl}-1H-indol-4-amine |
| 505. | 1-(2-chloroethyl)-N-(1-methylpiperidin-4-yl)-2-{3-[(6-methylpyridin-3-yl)amino]-prop-1-yn-1-yl}-1H-indol-4-amine |
| 506. | 1-(2-chloroethyl)-2-{3-[(4-chlorophenyl)-amino]prop-1-yn-1-yl}-N-(1-methylpiperidin-4-yl)-1H-indol-4-amine |
| 507. | 2-[5-({3-[1-(1-cyanoethyl)-4-[(1-methylpiperidin-4-yl)amino]-1H-indol-2-yl]prop-2-yn-1-yl}amino)pyridin-2-yl]-2-methylpropanenitrile |
| 508. | 2-[5-({3-[1-(cyanomethyl)-4-[(1,1-dioxo-1λ$^6$-thian-4-yl)amino]-1H-indol-2-yl]prop-2-yn-1-yl}amino)pyridin-2-yl]-2-methylpropanenitrile |
| 509. | 4-[(2-{3-[(4-methanesulfonylphenyl)amino]prop-1-yn-1-yl}-1-(oxiran-2-ylmethyl)-1H-indol-4-yl)amino]-1λ$^6$-thiane-1,1-dione |
| 510. | 2-{3-[(4-methanesulfonylphenyl)-amino]prop-1-yn-1-yl}-N-[1-(oxan-4-yl)piperidin-4-yl]-1-(oxiran-2-ylmethyl)-1H-indol-4-amine |
| 511. | 4-[(2-{3-[(4-methanesulfonyl-2-methoxyphenyl)amino]prop-1-yn-1-yl}-1-(oxiran-2-ylmethyl)-1H-indol-4-yl)amino]-1λ$^6$-thiane-1,1-dione |
| 512. | 2-{3-[(4-methanesulfonyl-2-methoxy-phenyl)amino]prop-1-yn-1-yl}-N-[1-(oxan-4-yl)piperidin-4-yl]-1-(oxiran-2-ylmethyl)-1H-indol-4-amine |
| 513. | 1-[6-(1-cyano-1-methylethyl)pyridin-3-yl]-3-(3-{4-[(1-methylpiperidin-4-yl)amino]-1-(2,2,2-trifluoroethyl)-1H-indol-2-yl}prop-2-yn-1-yl)urea |

TABLE 7-continued

| Mol # | IUPAC name |
|---|---|
| | Alkynyl indole compounds of the disclosure. |
| 514. | 1-(6-methanesulfonylpyridin-3-yl)-3-(3-{4-[(1-methylpiperidin-4-yl)amino]-1-(2,2,2-trifluoroethyl)-1H-indol-2-yl}prop-2-yn-1-yl)urea |
| 515. | 1-[6-(1-cyano-1-methylethyl)pyridin-3-yl]-3-(3-{4-[(1,1-dioxo-1$\lambda^6$-thian-4-yl)amino]-1-(2,2,2-trifluoroethyl)-1H-indol-2-yl}prop-2-yn-1-yl)urea |
| 516. | 3-(3-{4-[(1,1-dioxo-1$\lambda^6$-thian-4-yl)amino]-1-(2,2,2-trifluoroethyl)-1H-indol-2-yl}prop-2-yn-1-yl)-1-(6-methanesulfonylpyridin-3-yl)urea |
| 517. | 1-(6-cyanopyridin-3-yl)-3-(3-{4-[(1-methylpiperidin-4-yl)amino]-1-(2,2,2-trifluoroethyl)-1H-indol-2-yl}prop-2-yn-1-yl)urea |
| 518. | 1-(6-cyanopyridin-3-yl)-3-(3-{4-[(1,1-dioxo-1$\lambda^6$-thian-4-yl)amino]-1-(2,2,2-trifluoroethyl)-1H-indol-2-yl}prop-2-yn-1-yl)urea |
| 519. | 3-(3-{4-[(1,1-dioxo-1$\lambda^6$-thian-4-yl)amino]-1-(2,2,2-trifluoroethyl)-1H-indol-2-yl}prop-2-yn-1-yl)-1-(quinoxalin-6-yl)urea |
| 520. | N-(3-{4-[(1,1-dioxo-1$\lambda^6$-thian-4-yl)amino]-1-(2,2,2-trifluoroethyl)-1H-indol-2-yl}prop-2-yn-1-yl)-4-methylpiperazine-1-carboxamide |
| 521. | N-(3-{4-[(1,1-dioxo-1$\lambda^6$-thian-4-yl)amino]-1-(2,2,2-trifluoroethyl)-1H-indol-2-yl}prop-2-yn-1-yl)morpholine-4-carboxamide |
| 522. | 4-[(2-{3-[(6-methanesulfonylpyridin-3-yl)amino]prop-1-yn-1-yl}-1-(2,2,2-trifluoroethyl)-1H-indol-4-yl)amino]-1$\lambda^6$-thiane-1,1-dione |
| 523. | 2-{4-[(2-{3-[(6-methanesulfonylpyridin-3-yl)amino]prop-1-yn-1-yl}-1-(2,2,2-trifluoroethyl)-1H-indol-4-yl)amino]piperidin-1-yl}-N,N-dimethylacetamide |
| 524. | N-(1-ethylpiperidin-4-yl)-2-{3-[(6-methanesulfonylpyridin-3-yl)amino]prop-1-yn-1-yl}-1-(2,2,2-trifluoroethyl)-1H-indol-4-amine |
| 525. | N-[1-(2-methanesulfonylethyl)piperidin-4-yl]-2-{3-[(6-methanesulfonylpyridin-3-yl)amino]prop-1-yn-1-yl}-1-(2,2,2-trifluoroethyl)-1H-indol-4-amine |
| 526. | 2-{3-[(6-methanesulfonylpyridin-3-yl)amino]prop-1-yn-1-yl}-N-[1-(1-methylpiperidin-4-yl)piperidin-4-yl]-1-(2,2,2-trifluoroethyl)-1H-indol-4-amine |
| 527. | 2-{4-[(2-{3-[(6-methanesulfonylpyridin-3-yl)amino]prop-1-yn-1-yl}-1-(2,2,2-trifluoroethyl)-1H-indol-4-yl)amino]piperidin-1-yl}ethan-1-ol |
| 528. | 4-{4-[(2-{3-[(6-methanesulfonylpyridin-3-yl)amino]prop-1-yn-1-yl}-1-(2,2,2-trifluoroethyl)-1H-indol-4-yl)amino]piperidin-1-yl}-1$\lambda^6$-thiane-1,1-dione |
| 529. | 2-{4-[(2-{3-[(6-methanesulfonylpyridin-3-yl)amino]prop-1-yn-1-yl}-1-(2,2,2-trifluoroethyl)-1H-indol-4-yl)amino]piperidin-1-yl}-1-(4-methylpiperazin-1-yl)ethan-1-one |
| 530. | 2-{3-[(4-methanesulfonylphenyl)amino]prop-1-yn-1-yl}-N-(oxan-4-yl)-1-(2,2,2-trifluoroethyl)-1H-indol-4-amine |
| 531. | 2-{4-[(2-{3-[(4-methanesulfonylphenyl)amino]prop-1-yn-1-yl}-1-(2,2,2-trifluoroethyl)-1H-indol-4-yl)amino]piperidin-1-yl}ethan-1-ol |
| 532. | 2-{4-[(2-{3-[(4-methanesulfonylphenyl)amino]prop-1-yn-1-yl}-1-(2,2,2-trifluoroethyl)-1H-indol-4-yl)amino]piperidin-1-yl}-1-(4-methylpiperazin-1-yl)ethan-1-one |
| 533. | 2-{3-[(4-methanesulfonylphenyl)amino]prop-1-yn-1-yl}-N-[1-(1-methylpiperidin-4-yl)piperidin-4-yl]-1-(2,2,2-trifluoroethyl)-1H-indol-4-amine |
| 534. | N-(2,3-dihydroxypropyl)-2-{4-[(2-{3-[(4-methanesulfonylphenyl)-amino]prop-1-yn-1-yl}-1-(2,2,2-trifluoroethyl)-1H-indol-4-yl)amino]piperidin-1-yl}-N-methylacetamide |
| 535. | 4-N-(2-{3-[(4-methanesulfonylphenyl)-amino]prop-1-yn-1-yl}-1-(2,2,2-trifluoroethyl)-1H-indol-4-yl)-1-N,1-N-dimethylcyclohexane-1,4-diamine |
| 536. | (1S,4S)-4-N-(2-{3-[(4-methanesulfonyl-phenyl)amino]prop-1-yn-1-yl}-1-(2,2,2-trifluoroethyl)-1H-indol-4-yl)-1-N,1-N-dimethylcyclohexane-1,4-diamine |
| 537. | 2-{3-[(4-methanesulfonylphenyl)-amino]prop-1-yn-1-yl}-N-[1-(oxan-4-yl)piperidin-4-yl]-1-(2,2,2-trifluoroethyl)-1H-indol-4-amine |
| 538. | 2-{4-[(2-{3-[(4-methanesulfonylphenyl)amino]prop-1-yn-1-yl}-1-(2,2,2-trifluoroethyl)-1H-indol-4-yl)amino]piperidin-1-yl}-1-(morpholin-4-yl)ethan-1-one |
| 539. | 1-(4-hydroxypiperidin-1-yl)-2-{4-[(2-{3-[(4-methanesulfonylphenyl)-amino]prop-1-yn-1-yl}-1-(2,2,2-trifluoroethyl)-1H-indol-4-yl)amino]piperidin-1-yl}ethan-1-one |
| 540. | 2-{3-[(4-methanesulfonylphenyl)-amino]prop-1-yn-1-yl}-N-(piperidin-4-yl)-1-(2,2,2-trifluoroethyl)-1H-indol-4-amine |
| 541. | N-{1-[1-(2-methanesulfonylethyl)piperidin-4-yl]piperidin-4-yl}-2-{3-[(4-methanesulfonylphenyl)amino]prop-1-yn-1-yl}-1-(2,2,2-trifluoroethyl)-1H-indol-4-amine |
| 542. | 2-{3-[(4-methanesulfonylphenyl)-amino]prop-1-yn-1-yl}-N-[1-(2-methoxyethyl)piperidin-4-yl]-1-(2,2,2-trifluoroethyl)-1H-indol-4-amine |
| 543. | 3-{4-[(2-{3-[(4-methane-sulfonylphenyl)-amino]prop-1-yn-1-yl}-1-(2,2,2-trifluoroethyl)-1H-indol-4-yl)amino]piperidin-1-yl}propanenitrile |
| 544. | 2-{3-[(4-methanesulfonylphenyl)-amino]prop-1-yn-1-yl}-N-(1-methylpiperidin-4-yl)-1-(2,2,2-trifluoroethyl)-1H-indol-4-amine |
| 545. | 2-{4-[(2-{3-[(4-methane-sulfonylphenyl)-amino]prop-1-yn-1-yl}-1-(2,2,2-trifluoroethyl)-1H-indol-4-yl)amino]piperidin-1-yl}acetamide |
| 546. | 4-{4-[(2-{3-[(4-methane-sulfonylphenyl)-amino]prop-1-yn-1-yl}-1-(2,2,2-trifluoroethyl)-1H-indol-4-yl)amino]piperidin-1-yl}-1$\lambda^6$-thiane-1,1-dione |
| 547. | 2-{4-[(2-{3-[(4-methane-sulfonylphenyl)amino]prop-1-yn-1-yl}-1-(2,2,2-trifluoroethyl)-1H-indol-4-yl)amino]piperidin-1-yl}-N-methylacetamide |
| 548. | 2-(3-{[4-(ethanesulfonyl)phenyl]amino}prop-1-yn-1-yl)-N-(1-methylpiperidin-4-yl)-1-(2,2,2-trifluoroethyl)-1H-indol-4-amine |
| 549. | 2-{4-[(2-{3-[(2-fluoro-4-methanesulfonylphenyl)amino]prop-1-yn-1-yl}-1-(2,2,2-trifluoroethyl)-1H-indol-4-yl)amino]piperidin-1-yl}ethan-1-ol |
| 550. | 2-{3-[(2-fluoro-4-methane-sulfonylphenyl)-amino]prop-1-yn-1-yl}-N-[1-(2-methanesulfonylethyl)-piperidin-4-yl]-1-(2,2,2-trifluoroethyl)-1H-indol-4-amine |

TABLE 7-continued

| Mol # | IUPAC name |
|---|---|
| | Alkynyl indole compounds of the disclosure. |
| 551. | 2-{4-[(2-{3-[(2-fluoro-4-methanesulfonylphenyl)amino]prop-1-yn-1-yl}-1-(2,2,2-trifluoroethyl)-1H-indol-4-yl)amino]piperidin-1-yl}acetamide |
| 552. | 2-{3-[(2-fluoro-4-methane-sulfonylphenyl)-amino]prop-1-yn-1-yl}-N-(1-methylpiperidin-4-yl)-1-(2,2,2-trifluoroethyl)-1H-indol-4-amine |
| 553. | 1-{4-[(2-{3-[(4-methanesulfonyl-phenyl)amino]prop-1-yn-1-yl}-1-(2,2,2-trifluoroethyl)-1H-indol-4-yl)amino]piperidin-1-yl}-2-methoxyethan-1-one |
| 554. | 2-{3-[(4-methanesulfonyl-phenyl)amino]prop-1-yn-1-yl}-N-(1-methylpyrrolidin-3-yl)-1-(2,2,2-trifluoroethyl)-1H-indol-4-amine |
| 555. | N-hydroxy-2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetamide |
| 556. | 3-{4-[(2-{3-[(4-methanesulfonyl-phenyl)amino]prop-1-yn-1-yl}-1-(2,2,2-trifluoroethyl)-1H-indol-4-yl)amino]piperidin-1-yl}propane-1,2-diol |
| 557. | 2-{3-[(2-fluoro-4-methanesulfonyl-phenyl)amino]prop-1-yn-1-yl}-N-[1-(1-methylpiperidin-4-yl)piperidin-4-yl]-1-(2,2,2-trifluoroethyl)-1H-indol-4-amine |
| 558. | 2-(3-{[4-(ethanesulfonyl)phenyl]amino}prop-1-yn-1-yl)-N-[1-(1-methylpiperidin-4-yl)piperidin-4-yl]-1-(2,2,2-trifluoroethyl)-1H-indol-4-amine |
| 559. | 2-{3-[(2-fluoro-4-methanesulfonyl-phenyl)amino]prop-1-yn-1-yl}-N-(oxan-4-yl)-1-(2,2,2-trifluoroethyl)-1H-indol-4-amine |
| 560. | 2-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)ethan-1-ol |
| 561. | 1-{4-[(2-{3-[(4-methanesulfonyl-phenyl)amino]prop-1-yn-1-yl}-1-(2,2,2-trifluoroethyl)-1H-indol-4-yl)amino]piperidin-1-yl}propan-2-ol |
| 562. | 2-(3-{[4-(ethanesulfonyl)-phenyl]amino}prop-1-yn-1-yl)-N-[1-(2-methanesulfonylethyl)piperidin-4-yl]-1-(2,2,2-trifluoroethyl)-1H-indol-4-amine |
| 563. | 4-{[1-(2,2,2-trifluoroethyl)-2-{3-[(4-trifluoromethanesulfonylphenyl)amino]prop-1-yn-1-yl}-1H-indol-4-yl]amino}-1$\lambda^6$-thiane-1,1-dione |
| 564. | 2-(4-{[1-(2,2,2-trifluoroethyl)-2-{3-[(4-trifluoromethanesulfonylphenyl)amino]prop-1-yn-1-yl}-1H-indol-4-yl]amino}piperidin-1-yl)ethan-1-ol |
| 565. | N-(1-methylpiperidin-4-yl)-1-(2,2,2-trifluoroethyl)-2-{3-[(4-trifluoromethanesulfonylphenyl)amino]prop-1-yn-1-yl}-1H-indol-4-amine |
| 566. | 2-{3-[(4-methanesulfonyl-phenyl)amino]prop-1-yn-1-yl}-N-[1-(1-methylpyrrolidin-3-yl)piperidin-4-yl]-1-(2,2,2-trifluoroethyl)-1H-indol-4-amine |
| 567. | 2-{3-[(4-methanesulfonyl-phenyl)amino]prop-1-yn-1-yl}-N-[1-(3-methanesulfonylpropyl)piperidin-4-yl]-1-(2,2,2-trifluoroethyl)-1H-indol-4-amine |
| 568. | 2-(3-{[4-(ethanesulfonyl)-phenyl]amino}prop-1-yn-1-yl)-N-[1-(2-methoxyethyl)piperidin-4-yl]-1-(2,2,2-trifluoroethyl)-1H-indol-4-amine |
| 569. | 4-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)-1$\lambda^6$-thiane-1,1-dione |
| 570. | 2-(3-{[4-(ethanesulfonyl)-phenyl]amino}prop-1-yn-1-yl)-N-[1-(oxan-4-yl)piperidin-4-yl]-1-(2,2,2-trifluoroethyl)-1H-indol-4-amine |
| 571. | N-[1-(2-methanesulfonylethyl)-piperidin-4-yl]-1-(2,2,2-trifluoroethyl)-2-{3-[(4-trifluoromethane-sulfonylphenyl)amino]prop-1-yn-1-yl}-1H-indol-4-amine |
| 572. | N-[1-(oxan-4-yl)piperidin-4-yl]-1-(2,2,2-trifluoroethyl)-2-{3-[(4-trifluoromethanesulfonylphenyl)amino]prop-1-yn-1-yl}-1H-indol-4-amine |
| 573. | N-[1-(1-methylpiperidin-4-yl)piperidin-4-yl]-1-(2,2,2-trifluoroethyl)-2-{3-[(4-trifluoromethanesulfonylphenyl)amino]prop-1-yn-1-yl}-1H-indol-4-amine |
| 574. | 2-{3-[(2-fluoro-4-methanesulfonyl-phenyl)amino]prop-1-yn-1-yl}-N-[1-(oxan-4-yl)piperidin-4-yl]-1-(2,2,2-trifluoroethyl)-1H-indol-4-amine |
| 575. | 2-{4-[(2-{3-[(4-methanesulfonyl-phenyl)amino]prop-1-yn-1-yl}-1-(2,2,2-trifluoroethyl)-1H-indol-4-yl)amino]piperidin-1-yl}acetonitrile |
| 576. | 2-{3-[(2-fluoro-4-methanesulfonylphenyl)amino]prop-1-yn-1-yl}-N-[1-(2-methoxyethyl)piperidin-4-yl]-1-(2,2,2-trifluoroethyl)-1H-indol-4-amine |
| 577. | 2-{3-[(3-chloro-4-methanesulfonylphenyl)amino]prop-1-yn-1-yl}-N-[1-(oxan-4-yl)piperidin-4-yl]-1-(2,2,2-trifluoroethyl)-1H-indol-4-amine |
| 578. | 2-{3-[(2,6-difluoro-4-methanesulfonyl-phenyl)amino]prop-1-yn-1-yl}-N-[1-(oxan-4-yl)piperidin-4-yl]-1-(2,2,2-trifluoroethyl)-1H-indol-4-amine |
| 579. | 2-{3-[(3-chloro-4-methanesulfonyl-phenyl)amino]prop-1-yn-1-yl}-N-[1-(2-methoxyethyl)piperidin-4-yl]-1-(2,2,2-trifluoroethyl)-1H-indol-4-amine |
| 580. | 2-{4-[(2-{3-[(3-chloro-4-methanesulfonylphenyl)amino]prop-1-yn-1-yl}-1-(2,2,2-trifluoroethyl)-1H-indol-4-yl)amino]piperidin-1-yl}ethan-1-ol |
| 581. | (2S)-3-{4-[(2-{3-[(4-methanesulfonyl-phenyl)amino]prop-1-yn-1-yl}-1-(2,2,2-trifluoroethyl)-1H-indol-4-yl)amino]piperidin-1-yl}propane-1,2-diol |
| 582. | N-(5-aminopentyl)-2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetamide |
| 583. | 2-{3-[(2,6-difluoro-4-methanesulfonyl-phenyl)amino]prop-1-yn-1-yl}-N-[1-(2-methoxyethyl)piperidin-4-yl]-1-(2,2,2-trifluoroethyl)-1H-indol-4-amine |
| 584. | 2-(3-{[4-(ethanesulfonyl)phenyl]-amino}prop-1-yn-1-yl)-N-(oxan-4-yl)-1-(2,2,2-trifluoroethyl)-1H-indol-4-amine |
| 585. | 2-(4-{[2-(3-{[4-(ethanesulfonyl)phenyl]amino}prop-1-yn-1-yl)-1-(2,2,2-trifluoroethyl)-1H-indol-4-yl]amino}piperidin-1-yl)acetonitrile |
| 586. | 2-(3-{[4-(2-methylpropane-2-sulfonyl)phenyl]amino}prop-1-yn-1-yl)-N-[1-(oxan-4-yl)piperidin-4-yl]-1-(2,2,2-trifluoroethyl)-1H-indol-4-amine |
| 587. | 2-(2-{4-[(2-{3-[(4-methanesulfonyl-phenyl)amino]prop-1-yn-1-yl}-1-(2,2,2-trifluoroethyl)-1H-indol-4-yl)amino]piperidin-1-yl}ethoxy)ethan-1-ol |
| 588. | 1-{4-[(2-{3-[(2-fluoro-4-methane-sulfonylphenyl)amino]prop-1-yn-1-yl}-1-(2,2,2-trifluoroethyl)-1H-indol-4-yl)amino]piperidin-1-yl}propan-2-ol |

TABLE 7-continued

Alkynyl indole compounds of the disclosure.

| Mol # | IUPAC name |
|---|---|
| 589. | 3-{4-[(2-{3-[(2-fluoro-4-methanesulfonylphenyl)amino]prop-1-yn-1-yl}-1-(2,2,2-trifluoroethyl)-1H-indol-4-yl)amino]piperidin-1-yl}propane-1,2-diol |
| 590. | (1S,4S)-4-N-(2-{3-[(2-fluoro-4-methanesulfonylphenyl)amino]prop-1-yn-1-yl}-1-(2,2,2-trifluoroethyl)-1H-indol-4-yl)-1-N,1-N-dimethylcyclohexane-1,4-diamine |
| 591. | 3-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)propane-1,2-diol |
| 592. | 2-(3-{[4-(ethanesulfonyl)-phenyl]amino}prop-1-yn-1-yl)-N-[1-(3-methanesulfonylpropyl)-piperidin-4-yl]-1-(2,2,2-trifluoroethyl)-1H-indol-4-amine |
| 593. | 1-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)propan-2-ol |
| 594. | 2-[2-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)ethoxy]ethan-1-ol |
| 595. | (1R,4R)-4-N-(2-{3-[(2-fluoro-4-methanesulfonylphenyl)amino]prop-1-yn-1-yl}-1-(2,2,2-trifluoroethyl)-1H-indol-4-yl)-1-N,1-N-dimethyl-cyclohexane-1,4-diamine |
| 596. | 2-{3-[(2,6-difluoro-4-methanesulfonylphenyl)amino]prop-1-yn-1-yl}-N-[1-(2-methanesulfonylethyl)piperidin-4-yl]-1-(2,2,2-trifluoroethyl)-1H-indol-4-amine |
| 597. | 4-{4-[(2-{3-[(2,6-difluoro-4-methanesulfonylphenyl)amino]prop-1-yn-1-yl}-1-(2,2,2-trifluoroethyl)-1H-indol-4-yl)amino]piperidin-1-yl}-1$\lambda^6$-thiane-1,1-dione |
| 598. | 2-{3-[(4-methanesulfonyl-3-methoxyphenyl)amino]prop-1-yn-1-yl}-N-[1-(oxan-4-yl)piperidin-4-yl]-1-(2,2,2-trifluoroethyl)-1H-indol-4-amine |
| 599. | 2-{3-[(4-methanesulfonyl-3-methoxyphenyl)amino]prop-1-yn-1-yl}-N-[1-(2-methoxyethyl)piperidin-4-yl]-1-(2,2,2-trifluoroethyl)-1H-indol-4-amine |
| 600. | 4-N-(2-{3-[(2-fluoro-4-methanesulfonylphenyl)amino]prop-1-yn-1-yl}-1-(2,2,2-trifluoroethyl)-1H-indol-4-yl)-1-N,1-N-dimethylcyclohexane-1,4-diamine |
| 601. | 2-{4-[(2-{3-[(4-methanesulfonyl-phenyl)amino]prop-1-yn-1-yl}-1-(2,2,2-trifluoroethyl)-1H-indol-4-yl)amino]piperidin-1-yl}acetic acid |
| 602. | 2-hydroxyethyl 2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetate |
| 603. | 2-{3-[(4-methanesulfonylphenyl)-amino]prop-1-yn-1-yl}-N-(2-methylpiperidin-4-yl)-1-(2,2,2-trifluoroethyl)-1H-indol-4-amine |
| 604. | 2-{4-[(2-{3-[(4-methanesulfonyl-3-methoxyphenyl)amino]prop-1-yn-1-yl}-1-(2,2,2-trifluoroethyl)-1H-indol-4-yl)amino]piperidin-1-yl}ethan-1-ol |
| 605. | (2S)-2-(2-{4-[(2-{3-[(4-methane-sulfonylphenyl)amino]prop-1-yn-1-yl}-1-(2,2,2-trifluoroethyl)-1H-indol-4-yl)amino]piperidin-1-yl}acetamido)pentanedioic acid |
| 606. | 1,5-dimethyl (2S)-2-(2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetamido)pentanedioate |
| 607. | N-(4-carbamimidamidobutyl)-2-{4-[(2-{3-[(4-methanesulfonylphenyl)-amino]prop-1-yn-1-yl}-1-(2,2,2-trifluoroethyl)-1H-indol-4-yl)amino]piperidin-1-yl}acetamide |
| 608. | 2-{3-[(4-methanesulfonyl-2-methoxyphenyl)amino]prop-1-yn-1-yl}-N-(oxan-4-yl)-1-(2,2,2-trifluoroethyl)-1H-indol-4-amine |
| 609. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethan-1-ol |
| 610. | 2-{3-[(5-methanesulfonylpyridin-2-yl)amino]prop-1-yn-1-yl}-N-(oxan-4-yl)-1-(2,2,2-trifluoroethyl)-1H-indol-4-amine |
| 611. | 3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propane-1,2-diol |
| 612. | 4-[(2-{3-[(2,4-dimethoxyphenyl)-amino]prop-1-yn-1-yl}-1-(2,2,2-trifluoroethyl)-1H-indol-4-yl)amino]-1$\lambda^6$-thiane-1,1-dione |
| 613. | methyl 4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxybenzoate |
| 614. | 2-{3-[(4-methanesulfonyl-2-methoxyphenyl)amino]prop-1-yn-1-yl}-N-[1-(2-methanesulfonylethyl)-piperidin-4-yl]-1-(2,2,2-trifluoroethyl)-1H-indol-4-amine |
| 615. | 2-{3-[(4-methanesulfonyl-2-methoxyphenyl)amino]prop-1-yn-1-yl}-N-[1-(2-methoxyethyl)piperidin-4-yl]-1-(2,2,2-trifluoroethyl)-1H-indol-4-amine |
| 616. | (1S,4S)-4-N-(2-{3-[(4-methanesulfonyl-2-methoxyphenyl)amino]prop-1-yn-1-yl}-1-(2,2,2-trifluoroethyl)-1H-indol-4-yl)-1-N,1-N-dimethylcyclohexane-1,4-diamine |
| 617. | (1R,4R)-4-N-(2-{3-[(4-methanesulfonyl-2-methoxyphenyl)amino]prop-1-yn-1-yl}-1-(2,2,2-trifluoroethyl)-1H-indol-4-yl)-1-N,1-N-dimethylcyclohexane-1,4-diamine |
| 618. | 2-{3-[(4-methanesulfonyl-2-methoxyphenyl)amino]prop-1-yn-1-yl}-N-[1-(oxan-4-yl)piperidin-4-yl]-1-(2,2,2-trifluoroethyl)-1H-indol-4-amine |
| 619. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-o |
| 620. | 2-{3-[(4-methanesulfonyl-2-methoxyphenyl)amino]prop-1-yn-1-yl}-N-[1-(1-methylpyrrolidin-3-yl)piperidin-4-yl]-1-(2,2,2-trifluoroethyl)-1H-indol-4-amine |
| 621. | 2-{3-[(4-methanesulfonyl-2-methoxyphenyl)amino]prop-1-yn-1-yl}-N-(2-methylpiperidin-4-yl)-1-(2,2,2-trifluoroethyl)-1H-indol-4-amine |
| 622. | 2-{3-[(4-methanesulfonyl-2-methoxyphenyl)amino]prop-1-yn-1-yl}-N-(piperidin-4-yl)-1-(2,2,2-trifluoroethyl)-1H-indol-4-amine |
| 623. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-1-(4-methylpiperazin-1-yl)ethan-1-one |
| 624. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}acetamide |
| 625. | 2-{3-[(4-methanesulfonyl-2-methoxyphenyl)amino]prop-1-yn-1-yl}-N-[1-(1-methylpiperidin-4-yl)piperidin-4-yl]-1-(2,2,2-trifluoroethyl)-1H-indol-4-amine |

TABLE 7-continued

Alkynyl indole compounds of the disclosure.

| Mol # | IUPAC name |
|---|---|
| 626. | 1-{4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl}piperidin-4-ol |
| 627. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-1-(morpholin-4-yl)ethan-1-one |
| 628. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-N,N-dimethylacetamide |
| 629. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}acetonitrile |
| 630. | methyl 2-{4-[(2-{3-[(4-methane-sulfonyl-2-methoxyphenyl)amino]prop-1-yn-1-yl}-1-(2,2,2-trifluoroethyl)-1H-indol-4-yl)amino]piperidin-1-yl}acetate |
| 631. | 1-(4-hydroxypiperidin-1-yl)-2-{4-[(2-{3-[(4-methanesulfonyl-2-methoxy-phenyl)amino]prop-1-yn-1-yl}-1-(2,2,2-trifluoroethyl)-1H-indol-4-yl)amino]piperidin-1-yl}ethan-1-one |
| 632. | 2-(2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethoxy)ethan-1-ol |
| 633. | -[(1R,4R)-4-[(2-{3-[(4-methane-sulfonyl-2-methoxyphenyl)amino]prop-1-yn-1-yl}-1-(2,2,2-trifluoroethyl)-1H-indol-4-yl)amino]cyclohexyl]piperidin-4-ol |
| 634. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}acetic acid |
| 635. | (1R,4R)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol |
| 636. | (1S,4S)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol |
| 637. | 2-{3-[(4-methanesulfonyl-2-methoxyphenyl)amino]prop-1-yn-1-yl}-1-(2,2,2-trifluoroethyl)-1H-indol-4-amine |
| 638. | 1-{4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl}-3-methylpyrrolidin-3-ol |
| 639. | (3R,4R)-1-{4-[(2-{3-[(4-methane-sulfonyl-2-methoxyphenyl)amino]prop-1-yn-1-yl}-1-(2,2,2-trifluoroethyl)-1H-indol-4-yl)amino]cyclohexyl}-pyrrolidine-3,4-diol |
| 640. | 4-[(2-{3-[(4-methanesulfonyl-2-methoxyphenyl)amino]prop-1-yn-1-yl}-1-(2,2,2-trifluoroethyl)-1H-indol-4-yl)amino]piperidine-1-carboximidamide |
| 641. | 1-[(1S,4S)-4-[(2-{3-[(4-methane-sulfonyl-2-methoxyphenyl)amino]prop-1-yn-1-yl}-1-(2,2,2-trifluoroethyl)-1H-indol-4-yl)amino]cyclohexyl]piperidin-4-ol |
| 642. | 4-[(2-{3-[(3-methoxypyridin-4-yl)amino]prop-1-yn-1-yl}-1-(2,2,2-trifluoroethyl)-1H-indol-4-yl)amino]-1$\lambda^6$-thiane-1,1-dione |
| 643. | 2-{3-[(4-methanesulfonyl-2-methoxyphenyl)amino]prop-1-yn-1-yl}-N-[(1S,4S)-4-(morpholin-4-yl)cyclohexyl]-1-(2,2,2-trifluoroethyl)-1H-indol-4-amine |
| 644. | 2-{3-[(4-methanesulfonyl-2-methoxyphenyl)amino]prop-1-yn-1-yl}-N-[(1R,4R)-4-(morpholin-4-yl)cyclohexyl]-1-(2,2,2-trifluoroethyl)-1H-indol-4-amine |
| 645. | 2-(3-{[2-(2-fluoroethoxy)-4-methanesulfonylphenyl]amino}prop-1-yn-1-yl)-N-[1-(oxan-4-yl)piperidin-4-yl]-1-(2,2,2-trifluoroethyl)-1H-indol-4-amine |
| 646. | 4-{[2-(3-{[4-methanesulfonyl-2-(trifluoromethyl)phenyl]amino}prop-1-yn-1-yl)-1-(2,2,2-trifluoroethyl)-1H-indol-4-yl]amino}-1$\lambda^6$-thiane-1,1-dione |
| 647. | 2-(3-{[4-methanesulfonyl-2-(trifluoromethyl)phenyl]amino}prop-1-yn-1-yl)-N-(1-methylpiperidin-4-yl)-1-(2,2,2-trifluoroethyl)-1H-indol-4-amine |
| 648. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethan-1-one |
| 649. | 3-methoxy-4-{[3-(4-{[1-(1-methylpiperidin-4-yl)piperidin-4-yl]amino}-1-(2,2,2-trifluoroethyl)-1H-indol-2-yl)prop-2-yn-1-yl]amino}benzene-1-sulfonamide |
| 650. | 3-methoxy-4-[(3-{4-[(piperidin-4-yl)amino]-1-(2,2,2-trifluoroethyl)-1H-indol-2-yl}prop-2-yn-1-yl)amino]-benzamide |
| 651. | 3-methoxy-4-{[3-(4-{[1-(1-methylpiperidin-4-yl)piperidin-4-yl]amino}-1-(2,2,2-trifluoroethyl)-1H-indol-2-yl)prop-2-yn-1-yl]amino}benzamide |
| 652. | 3-(4-{[2-(3-{[2-(2-fluoroethoxy)-4-methanesulfonylphenyl]amino}prop-1-yn-1-yl)-1-(2,2,2-trifluoroethyl)-1H-indol-4-yl]amino}piperidin-1-yl)propane-1,2-diol |
| 653. | 3-(4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}piperidin-1-yl)propane-1,2-diol |
| 654. | 2-(4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}piperidin-1-yl)acetamide |
| 655. | 2-(4-{[2-(3-{[2-(2-fluoroethoxy)-4-methanesulfonylphenyl]amino}prop-1-yn-1-yl)-1-(2,2,2-trifluoroethyl)-1H-indol-4-yl]amino}piperidin-1-yl)-1-(4-methylpiperazin-1-yl)ethan-1-one |
| 656. | 2-(3-{[2-(2-fluoroethoxy)-4-methanesulfonylphenyl]amino}prop-1-yn-1-yl)-N-(oxan-4-yl)-1-(2,2,2-trifluoroethyl)-1H-indol-4-amine |
| 657. | 2-(3-{[2-(2-fluoroethoxy)-4-methanesulfonylphenyl]amino}prop-1-yn-1-yl)-N-[1-(1-methylpiperidin-4-yl)piperidin-4-yl]-1-(2,2,2-trifluoroethyl)-1H-indol-4-amine |
| 658. | 4-[(2-{3-[(4-methoxypyridin-3-yl)amino]prop-1-yn-1-yl}-1-(2,2,2-trifluoroethyl)-1H-indol-4-yl)amino]-1$\lambda^6$-thiane-1,1-dione |
| 659. | S-{4-[(3-{4-[(1,1-dioxo-1$\lambda^6$-thian-4-yl)amino]-1-(2,2,2-trifluoroethyl)-1H-indol-2-yl}prop-2-yn-1-yl)amino]-3-methoxyphenyl}-2-hydroxyethane-1-sulfonamido |
| 660. | 2-hydroxy-S-{3-methoxy-4-[(3-{4-[(1-methylpiperidin-4-yl)amino]-1-(2,2,2-trifluoroethyl)-1H-indol-2-yl}prop-2-yn-1-yl)amino]phenyl}ethane-1-sulfonamido |
| 661. | 2-methyl-2-[5-({3-[4-(morpholin-4-yl)-1-(2,2,2-trifluoroethyl)-1H-indol-2-yl]prop-2-yn-1-yl}amino)pyridin-2-yl]propanenitrile |

TABLE 7-continued

| Alkynyl indole compounds of the disclosure. | |
|---|---|
| Mol # | IUPAC name |
| 662. | -{4-[(2-{3-[(4-methanesulfonylphenyl)amino]prop-1-yn-1-yl}-1-(2,2,2-trifluoroethyl)-1H-indol-4-yl)amino]piperidin-1-yl}-N-[5-(2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetamido)pentyl]acetamide |
| 663. | 6-[(2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetyl)oxy]hexyl 2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetate |
| 664. | 3-methoxy-4-({3-[4-({1-[2-(4-methylpiperazin-1-yl)-2-oxoethyl]piperidin-4-yl}amino)-1-(2,2,2-trifluoroethyl)-1H-indol-2-yl]prop-2-yn-1-yl}amino)benzene-1-sulfonamide |
| 665. | 2-{5-methanesulfonyl-2-[(3-{4-[(1-methylpiperidin-4-yl)amino]-1-(2,2,2-trifluoroethyl)-1H-indol-2-yl}prop-2-yn-1-yl)amino]phenoxy}acetamide |
| 666. | 2-(3-{[4-methanesulfonyl-2-(2-methoxyethoxy)phenyl]amino}prop-1-yn-1-yl)-N-[l-(oxan-4-yl)piperidin-4-yl]-1-(2,2,2-trifluoroethyl)-1H-indol-4-amine |
| 667. | 2-(4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}piperidin-1-yl)ethan-1-ol |
| 668. | 3-methoxy-4-[(3-{4-[(oxan-4-yl)amino]-1-(2,2,2-trifluoroethyl)-1H-indol-2-yl}prop-2-yn-1-yl)amino]benzoic acid |
| 669. | 2-{2-[(3-{4-[(1,1-dioxo-1λ$^6$-thian-4-yl)amino]-1-(2,2,2-trifluoroethyl)-1H-indol-2-yl}prop-2-yn-1-yl)amino]-5-methanesulfonylphenoxy}acetamide |
| 670. | 4-[(2-{3-[(4-methanesulfonyl-2-methoxyphenyl)amino]prop-1-yn-1-yl}-1-(2,2,2-trifluoroethyl)-1H-indol-4-yl)amino]piperidine-1-carboxamide |
| 671. | 2-{3-[(4-methoxypyridin-3-yl)amino]prop-1-yn-1-yl}-N-(1-methylpiperidin-4-yl)-1-(2,2,2-trifluoroethyl)-1H-indol-4-amine |
| 672. | 4-[(2-{3-[(4-methanesulfonyl-2-methoxyphenyl)amino]prop-1-yn-1-yl}-1-(2,2,2-trifluoroethyl)-1H-indol-4-yl)amino]piperidine-1-carbothioamide |
| 673. | 4-[(2-{3-[(6-methanesulfonyl-4-methoxypyridin-3-yl)amino]prop-1-yn-1-yl}-1-(2,2,2-trifluoroethyl)-1H-indol-4-yl)amino]-1λ$^6$-thiane-1,1-dione |
| 674. | 3-methoxy-4-{[3-(4-{[1-(2-methoxyethyl)piperidin-4-yl]amino}-1-(2,2,2-trifluoroethyl)-1H-indol-2-yl)prop-2-yn-1-yl]amino}benzene-1-sulfonamide |
| 675. | 4-{[2-(3-{[4-(ethanesulfonyl)-2-methoxyphenyl]amino}prop-1-yn-1-yl)-1-(2,2,2-trifluoroethyl)-1H-indol-4-yl]amino}-1λ$^6$-thiane-1,1-dione |
| 676. | 2-(3-{[4-(ethanesulfonyl)-2-methoxyphenyl]amino}prop-1-yn-1-yl)-N-[1-(oxan-4-yl)piperidin-4-yl]-1-(2,2,2-trifluoroethyl)-1H-indol-4-amine |
| 677. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxybenzoic acid |
| 678. | methyl 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxybenzoate |
| 679. | methyl 3-methoxy-4-[(3-{4-[(oxan-4-yl)amino]-1-(2,2,2-trifluoroethyl)-1H-indol-2-yl}prop-2-yn-1-yl)amino]benzoate |
| 680. | 3-methoxy-4-({3-[4-({1-[2-(4-methylpiperazin-1-yl)-2-oxoethyl]piperidin-4-yl}amino)-1-(2,2,2-trifluoroethyl)-1H-indol-2-yl]prop-2-yn-1-yl}amino)benzamide |
| 681. | 4-[(2-{3-[(4-methanesulfonyl-2-methoxyphenyl)amino]prop-1-yn-1-yl}-1-(2,2,2-trifluoroethyl)-1H-indol-4-yl)amino]-N-methylpiperidine-1-carboximidamide |
| 682. | 2-{3-[(6-methanesulfonyl-4-methoxypyridin-3-yl)amino]prop-1-yn-1-yl}-N-(1-methylpiperidin-4-yl)-1-(2,2,2-trifluoroethyl)-1H-indol-4-amine |
| 683. | 2-{3-[(4-methanesulfonyl-2-methoxyphenyl)amino]prop-1-yn-1-yl}-N-[1-(pyridin-4-yl)piperidin-4-yl]-1-(2,2,2-trifluoroethyl)-1H-indol-4-amine |
| 684. | 3-(4-{[2-(3-{[4-(ethanesulfonyl)-2-methoxyphenyl]amino}prop-1-yn-1-yl)-1-(2,2,2-trifluoroethyl)-1H-indol-4-yl]amino}piperidin-1-yl)propane-1,2-diol |
| 685. | 2-(3-{[4-(ethanesulfonyl)-2-methoxyphenyl]amino}prop-1-yn-1-yl)-N-(1-methylpiperidin-4-yl)-1-(2,2,2-trifluoroethyl)-1H-indol-4-amine |
| 686. | 2-hydroxy-S-{3-methoxy-4-[(3-{4-[(oxan-4-yl)amino]-1-(2,2,2-trifluoroethyl)-1H-indol-2-yl}prop-2-yn-1-yl)amino]phenyl}ethane-1-sulfonamido |
| 687. | 2-(3-{[4-methanesulfonyl-2-(2,2,2-trifluoroethoxy)phenyl]amino}prop-1-yn-1-yl)-N-(1-methylpiperidin-4-yl)-1-(2,2,2-trifluoroethyl)-1H-indol-4-amine |
| 688. | 4-{[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]amino}-1λ$^6$-thiane-1,1-dione |
| 689. | 2-hydroxy-S-(3-methoxy-4-{[3-(4-{[1-(oxan-4-yl)piperidin-4-yl]amino}-1-(2,2,2-trifluoroethyl)-1H-indol-2-yl)prop-2-yn-1-yl]amino}phenyl)ethane-1-sulfonamido |
| 690. | S-(4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxyphenyl)-2-hydroxyethane-1-sulfonamido |
| 691. | 2-{3-methoxy-4-[(3-{4-[(1-methylpiperidin-4-yl)amino]-1-(2,2,2-trifluoroethyl)-1H-indol-2-yl}prop-2-yn-1-yl)amino]phenyl}-2-methylpropanenitrile |
| 692. | 3-methoxy-4-{[3-(4-{[(1S,4S)-4-[(3R,4R)-3,4-dihydroxypyrrolidin-1-yl]cyclohexyl]amino}-1-(2,2,2-trifluoroethyl)-1H-indol-2-yl)prop-2-yn-1-yl]amino}benzene-1-sulfonamide |
| 693. | 3-methoxy-4-{[3-(4-{[(1R,4R)-4-[(3R,4R)-3,4-dihydroxypyrrolidin-1-yl]cyclohexyl]amino}-1-(2,2,2-trifluoroethyl)-1H-indol-2-yl)prop-2-yn-1-yl]amino}benzene-1-sulfonamide |
| 694. | 3-methoxy-4-{[3-(4-{[(1S,4S)-4-(4-hydroxypiperidin-1-yl)cyclohexyl]amino}-1-(2,2,2-trifluoroethyl)-1H-indol-2-yl)prop-2-yn-1-yl]amino}benzene-1-sulfonamide |
| 695. | 3-methoxy-4-{[3-(4-{[(1R,4R)-4-(4-hydroxypiperidin-1-yl)cyclohexyl]amino}-1-(2,2,2-trifluoroethyl)-1H-indol-2-yl)prop-2-yn-1-yl]amino}benzene-1-sulfonamide |
| 696. | 2-{4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxyphenyl}-2-methylpropanenitrile |

TABLE 7-continued

Alkynyl indole compounds of the disclosure.

| Mol # | IUPAC name |
|---|---|
| 697. | 3-methoxy-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzene-1-sulfonamide |
| 698. | 3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide |
| 699. | (3S,4S)-1-[(1S,4S)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]pyrrolidine-3,4-diol |
| 700. | 3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 701. | 3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 702. | 2-{3-[(4-methanesulfonyl-2-methoxyphenyl)amino]prop-1-yn-1-yl}-N,N-dimethyl-1-(2,2,2-trifluoroethyl)-1H-indol-4-amine |
| 703. | 3-methoxy-4-[(3-{4-[(2-methoxyethyl)amino]-1-(2,2,2-trifluoroethyl)-1H-indol-2-yl}prop-2-yn-1-yl)amino]benzene-1-sulfonamide |
| 704. | 2-[(2-{3-[(2-methoxy-4-sulfamoylphenyl)amino]prop-1-yn-1-yl}-1-(2,2,2-trifluoroethyl)-1H-indol-4-yl)amino]acetamide |
| 705. | 4-[(3-{4-[(1,5-dihydroxypentan-3-yl)amino]-1-(2,2,2-trifluoroethyl)-1H-indol-2-yl}prop-2-yn-1-yl)amino]-3-methoxybenzene-1-sulfonamide |
| 706. | N-(2-{3-[(4-methanesulfonyl-2-methoxyphenyl)amino]prop-1-yn-1-yl}-1-(2,2,2-trifluoroethyl)-1H-indol-4-yl)acetamide |
| 707. | 3-(2-{3-[(4-methanesulfonyl-2-methoxyphenyl)amino]prop-1-yn-1-yl}-1-(2,2,2-trifluoroethyl)-1H-indol-4-yl)-1-(1-methylpiperidin-4-yl)urea |
| 708. | 3-methoxy-4-{[3-(4-{[(1-methylpiperidin-4-yl)carbamoyl]amino}-1-(2,2,2-trifluoroethyl)-1H-indol-2-yl)prop-2-yn-1-yl]amino}benzamide |
| 709. | N-(2-{3-[(4-methanesulfonyl-2-methoxyphenyl)amino]prop-1-yn-1-yl}-1-(2,2,2-trifluoroethyl)-1H-indol-4-yl)-4-methylpiperazine-1-carboxamide |
| 710. | N-(2-{3-[(4-carbamoyl-2-methoxyphenyl)amino]prop-1-yn-1-yl}-1-(2,2,2-trifluoroethyl)-1H-indol-4-yl)-4-methylpiperazine-1-carboxamide |
| 711. | 3-(2-{3-[(4-methanesulfonyl-2-methoxyphenyl)amino]prop-1-yn-1-yl}-1-(2,2,2-trifluoroethyl)-1H-indol-4-yl)-1-[(1S,4S)-4-(dimethylamino)cyclohexyl]urea |
| 712. | 1-(2-(3-((2-methoxy-4-(methylsulfonyl)phenyl)amino)prop-1-yn-1-yl)-1-(2,2,2-trifluoroethyl)-1H-indol-4-yl)-3-(pyridin-4-yl)urea |
| 713. | 3-(2-{3-[(4-methanesulfonyl-2-methoxyphenyl)amino]prop-1-yn-1-yl}-1-(2,2,2-trifluoroethyl)-1H-indol-4-yl)-1-[(1R,4R)-4-(dimethylamino)cyclohexyl]urea |
| 714. | 3-(2-{3-[(4-methanesulfonyl-2-methoxyphenyl)amino]prop-1-yn-1-yl}-1-(2,2,2-trifluoroethyl)-1H-indol-4-yl)-1-[1-(2-methoxyethyl)piperidin-4-yl]urea |
| 715. | 3-(2-{3-[(4-methanesulfonyl-2-methoxyphenyl)amino]prop-1-yn-1-yl}-1-(2,2,2-trifluoroethyl)-1H-indol-4-yl)-1-[1-(oxan-4-yl)piperidin-4-yl]urea |
| 716. | 1-[1-(2,3-dihydroxypropyl)piperidin-4-yl]-3-(2-{3-[(4-methanesulfonyl-2-methoxyphenyl)amino]prop-1-yn-1-yl}-1-(2,2,2-trifluoroethyl)-1H-indol-4-yl)urea |
| 717. | 2-(4-{[(2-{3-[(4-methanesulfonyl-2-methoxyphenyl)amino]prop-1-yn-1-yl}-1-(2,2,2-trifluoroethyl)-1H-indol-4-yl)carbamoyl]amino}piperidin-1-yl)acetamide |
| 718. | 3-methoxy-4-({3-[4-({2-oxaspiro[3.3]heptan-6-yl}amino)-1-(2,2,2-trifluoroethyl)-1H-indol-2-yl]prop-2-yn-1-yl}amino)benzene-1-sulfonamide |
| 719. | [1-(chloromethyl)-3-[(2-{3-[(4-methanesulfonyl-2-methoxyphenyl)amino]prop-1-yn-1-yl}-1-(2,2,2-trifluoroethyl)-1H-indol-4-yl)amino]cyclobutyl]methanol |
| 720. | 2-{3-[(4-methanesulfonyl-2-methoxyphenyl)amino]prop-1-yn-1-yl}-N-{2-oxaspiro[3.3]heptan-6-yl}-1-(2,2,2-trifluoroethyl)-1H-indol-4-amine |
| 721. | 4-({3-[4-({2-azaspiro[3.3]heptan-6-yl}amino)-1-(2,2,2-trifluoroethyl)-1H-indol-2-yl]prop-2-yn-1-yl}amino)-3-methoxybenzene-1-sulfonamide |
| 722. | N-{2-azaspiro[3.3]heptan-6-yl}-2-{3-[(4-methanesulfonyl-2-methoxyphenyl)amino]prop-1-yn-1-yl}-1-(2,2,2-trifluoroethyl)-1H-indol-4-amine |
| 723. | 3-methoxy-N-methyl-4-{[3-(4-{[(1R,4R)-4-(methylamino)cyclohexyl]amino}-1-(2,2,2-trifluoroethyl)-1H-indol-2-yl)prop-2-yn-1-yl]amino}benzamide |
| 724. | 3-methoxy-N-methyl-4-{[3-(4-{[(1R,4R)-4-aminocyclohexyl]amino}-1-(2,2,2-trifluoroethyl)-1H-indol-2-yl)prop-2-yn-1-yl]amino}benzamide |
| 725. | 3-methoxy-N-methyl-4-{[3-(4-{[(1S,4S)-4-aminocyclohexyl]amino}-1-(2,2,2-trifluoroethyl)-1H-indol-2-yl)prop-2-yn-1-yl]amino}benzamide |
| 726. | rel-(1R,3R)-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,3-diamine |
| 727. | rac-(1R,3S)-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,3-diamine |
| 728. | (1R,2S)-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,2-diamineQ |
| 729. | rac-(1R,2S)-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,2-diamine |
| 730. | rel-(1R,3S)-3-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol |
| 731. | 3-methoxy-N-methyl-4-{[3-(4-{[(1R,4R)-4-hydroxy-4-methylcyclohexyl]amino}-1-(2,2,2-trifluoroethyl)-1H-indol-2-yl)prop-2-yn-1-yl]amino}benzamide |
| 732. | 3-methoxy-N-methyl-4-{[3-(4-{[(1S,4S)-4-hydroxy-4-methylcyclohexyl]amino}-1-(2,2,2-trifluoroethyl)-1H-indol-2-yl)prop-2-yn-1-yl]amino}benzamide |
| 733. | 4-[(3-{4-[(4-cyanocyclohexyl)amino]-1-(2,2,2-trifluoroethyl)-1H-indol-2-yl}prop-2-yn-1-yl)amino]-3-methoxy-N-methylbenzamide |
| 734. | 3-methoxy-N-methyl-4-{[3-(4-{[(1R,4R)-4-cyanocyclohexyl]amino}-1-(2,2,2-trifluoroethyl)-1H-indol-2-yl)prop-2-yn-1-yl]amino}benzamide |

TABLE 7-continued

| Mol # | IUPAC name |
|---|---|
| | Alkynyl indole compounds of the disclosure. |
| 735. | 3-methoxy-N-methyl-4-{[3-(4-{[(1S,4S)-4-cyanocyclohexyl]amino}-1-(2,2,2-trifluoroethyl)-1H-indol-2-yl)prop-2-yn-1-yl]amino}benzamide |
| 736. | 3-[(2-{3-[(4-methanesulfonyl-2-methoxyphenyl)amino]prop-1-yn-1-yl}-1-(2,2,2-trifluoroethyl)-1H-indol-4-yl)amino]cyclohexane-1-carboxylic acid |
| 737. | 2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine |
| 738. | (1R,2R,4S)-2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine |
| 739. | 2-fluoro-$N^1$-(2-{3-[(4-methanesulfonyl-2-methoxyphenyl)amino]prop-1-yn-1-yl}-1-(2,2,2-trifluoroethyl)-1H-indol-4-yl)-$N^4$-methylcyclohexane-1,4-diamine |
| 740. | (1R,2R,4S)-2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)-$N^4$-methylcyclohexane-1,4-diamine |
| 741. | 2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 742. | (1R,2R,4S)-2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 743. | (3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol |
| 744. | 3-methoxy-4-{[3-(4-{[(1R,4R)-4-[bis(2-hydroxyethyl)amino]cyclohexyl]amino}-1-(2,2,2-trifluoroethyl)-1H-indol-2-yl)prop-2-yn-1-yl]amino}benzene-1-sulfonamide |
| 745. | 3-methoxy-4-{[3-(4-{[(1S,4S)-4-[bis(2-hydroxyethyl)amino]cyclohexyl]amino}-1-(2,2,2-trifluoroethyl)-1H-indol-2-yl)prop-2-yn-1-yl]amino}benzene-1-sulfonamide |
| 746. | 4-((3-(4-(((1R,4R)-4-(dimethylamino)cyclohexyl)amino)-1-(2,2,2-trifluoroethyl)-1H-indol-2-yl)prop-2-yn-1-yl)amino)-3-methoxybenzenesulfonamide |
| 747. | 4-((3-(4-(((1S,4S)-4-(dimethylamino)cyclohexyl)amino)-1-(2,2,2-trifluoroethyl)-1H-indol-2-yl)prop-2-yn-1-yl)amino)-3-methoxybenzenesulfonamide |
| 748. | 3-methoxy-N-(1,2-oxazol-3-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 749. | 3-methoxy-N-(oxan-4-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 750. | 3-methoxy-N-(1,2-oxazol-3-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 751. | 3-methoxy-N-(oxan-4-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 752. | N-(3-(4-(((1S,4S)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 753. | N-(3-(4-(((1R,4R)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 754. | 3-methoxy-N-(5-methyl-1,2-oxazol-3-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 755. | 3-methoxy-N-(5-methyl-1,2-oxazol-3-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 756. | (1S,4S)-$N^4$-(2-{3-[(4-methanesulfonyl-2-methoxyphenyl)amino]prop-1-yn-1-yl}-1-(2,2,2-trifluoroethyl)-1H-indol-4-yl)-$N^1$-(2-methoxyethyl)-$N^1$-methylcyclohexane-1,4-diamine |
| 757. | (1R,4R)-$N^4$-(2-{3-[(4-methanesulfonyl-2-methoxyphenyl)amino]prop-1-yn-1-yl}-1-(2,2,2-trifluoroethyl)-1H-indol-4-yl)-$N^1$-(2-methoxyethyl)-$N^1$-methylcyclohexane-1,4-diamine |
| 758. | 3-methoxy-4-{[3-(4-{[(1S,4S)-4-[(3S,4S)-3,4-dihydroxypyrrolidin-1-yl]cyclohexyl]amino}-1-(2,2,2-trifluoroethyl)-1H-indol-2-yl)prop-2-yn-1-yl]amino}benzene-1-sulfonamide |
| 759. | 4-((3-(4-(((1R,4R)-4-((3R,4R)-3,4-dihydroxypyrrolidin-1-yl)cyclohexyl)amino)-1-(2,2,2-trifluoroethyl)-1H-indol-2-yl)prop-2-yn-1-yl)amino)-3-methoxybenzenesulfonamide |
| 760. | 4-((3-(4-(((1R,4S)-4-((3S,4S)-3,4-dihydroxypyrrolidin-1-yl)cyclohexyl)amino)-1-(2,2,2-trifluoroethyl)-1H-indol-2-yl)prop-2-yn-1-yl)amino)-3-methoxybenzenesulfonamide |
| 761. | 3-methoxy-4-{[3-(4-{[(1R,4R)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 762. | 3-methoxy-4-{[3-(4-{[(1S,4S)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 763. | 4-({3-[4-({1,4-dioxaspiro[4.5]decan-8-yl}amino)-1-(2,2,2-trifluoroethyl)-1H-indol-2-yl]prop-2-yn-1-yl}amino)-3-methoxybenzene-1-sulfonamide |
| 764. | N-{1,4-dioxaspiro[4.5]decan-8-yl}-2-{3-[(4-methanesulfonyl-2-methoxyphenyl)amino]prop-1-yn-1-yl}-1-(2,2,2-trifluoroethyl)-1H-indol-4-amine |
| 765. | 3-methoxy-4-[(3-{4-[(4-oxocyclohexyl)amino]-1-(2,2,2-trifluoroethyl)-1H-indol-2-yl}prop-2-yn-1-yl)amino]benzene-1-sulfonamide |
| 766. | 4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-one |
| 767. | (1R,4R)-$N^4$-[2-(3-{[2-methoxy-4-(morpholine-4-sulfonyl)phenyl]amino}prop-1-yn-1-yl)-1-(2,2,2-trifluoroethyl)-1H-indol-4-yl]-$N^1$,$N^1$-dimethylcyclohexane-1,4-diamine |
| 768. | (1S,4S)-$N^4$-[2-(3-{[2-methoxy-4-(morpholine-4-sulfonyl)phenyl]amino}prop-1-yn-1-yl)-1-(2,2,2-trifluoroethyl)-1H-indol-4-yl]-$N^1$,$N^1$-dimethylcyclohexane-1,4-diamine |

TABLE 7-continued

Alkynyl indole compounds of the disclosure.

| Mol # | IUPAC name |
|---|---|
| 769. | N,N-bis(2-hydroxyethyl)-3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 770. | N,N-bis(2-hydroxyethyl)-3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 771. | 3-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 772. | 3-methoxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 773. | 3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 774. | 3-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 775. | 3-methoxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 776. | (1R,4R)-$N^4$-{2-[3-({2-methoxy-4-[(4-methylpiperazin-1-yl)sulfonyl]phenyl}amino)prop-1-yn-1-yl]-1-(2,2,2-trifluoroethyl)-1H-indol-4-yl}-$N^1$,$N^1$-dimethylcyclohexane-1,4-diamine |
| 777. | (1R,4R)-$N^4$-(2-{3-[(4-methanesulfonyl-2-methoxyphenyl)amino]prop-1-yn-1-yl}-1-[(oxiran-2-yl)methyl]-1H-indol-4-yl)-$N^1$,$N^1$-dimethylcyclohexane-1,4-diamine |
| 778. | 2-[(2-{3-[(4-methanesulfonyl-2-methoxyphenyl)amino]prop-1-yn-1-yl}-4-{[(1R,4R)-4-(dimethylamino)cyclohexyl]amino}-1H-indol-1-yl)methyl]prop-2-enenitrile |
| 779. | 5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenol |
| 780. | 5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenol |
| 781. | 2-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenoxy)acetonitrile |
| 782. | 2-(5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenoxy)acetonitrile |
| 783. | N-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzenesulfonyl)acetamide |
| 784. | N-(3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzenesulfonyl)acetamide |
| 785. | N-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzenesulfonyl)propanamide |
| 786. | N-(3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzenesulfonyl)propanamide |
| 787. | 2-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenoxy)ethan-1-ol |
| 788. | 2-(5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenoxy)ethan-1-ol |
| 789. | (1R,4R)-$N^4$-[2-(3-{[4-methanesulfonyl-2-(2-methoxyethoxy)phenyl]amino}prop-1-yn-1-yl)-1-(2,2,2-trifluoroethyl)-1H-indol-4-yl]-$N^1$,$N^1$-dimethylcyclohexane-1,4-diamine |
| 790. | N-(3-(4-(((1R,4R)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide |
| 791. | N-(3-(4-(((1S,4S)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide |
| 792. | (1R,4R)-$N^4$-[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]-$N^1$,$N^1$-dimethylcyclohexane-1,4-diamine |
| 793. | (1S,4S)-$N^4$-[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]-$N^1$,$N^1$-dimethylcyclohexane-1,4-diamine |
| 794. | (1S,4S)-$N^4$-{2-[3-(2-amino-4-methanesulfonylphenoxy)prop-1-yn-1-yl]-1-(2,2,2-trifluoroethyl)-1H-indol-4-yl}-$N^1$,$N^1$-dimethylcyclohexane-1,4-diamine |
| 795. | (1R,4R)-$N^4$-(2-{3-[(2-ethoxy-4-methanesulfonylphenyl)amino]prop-1-yn-1-yl}-1-(2,2,2-trifluoroethyl)-1H-indol-4-yl)-$N^1$,$N^1$-dimethylcyclohexane-1,4-diamine |
| 796. | (1S,4S)-$N^4$-(2-{3-[(2-ethoxy-4-methanesulfonylphenyl)amino]prop-1-yn-1-yl}-1-(2,2,2-trifluoroethyl)-1H-indol-4-yl)-$N^1$,$N^1$-dimethylcyclohexane-1,4-diamine |
| 797. | 3-hydroxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 798. | 3-hydroxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 799. | 3-(2-methoxyethoxy)-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 800. | (1R,4R)-$N^4$-{2-[3-(2-amino-4-methanesulfonylphenoxy)prop-1-yn-1-yl]-1-(2,2,2-trifluoroethyl)-1H-indol-4-yl}-$N^1$,$N^1$-dimethylcyclohexane-1,4-diamine |
| 801. | N-ethyl-3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 802. | N-ethyl-3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 803. | 3-(2-methoxyethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |

TABLE 7-continued

| Mol # | IUPAC name |
|---|---|
| | Alkynyl indole compounds of the disclosure. |
| 804. | 3-(2-fluoroethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 805. | 3-(2-fluoroethoxy)-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 806. | 3-(fluoromethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 807. | 3-(fluoromethoxy)-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 808. | (1S,4S)-$N^4$-(2-{3-[4-methanesulfonyl-2-(methylamino)phenoxy]prop-1-yn-1-yl}-1-(2,2,2-trifluoroethyl)-1H-indol-4-yl)-$N^1$,$N^1$-dimethylcyclohexane-1,4-diamine |
| 809. | (1R,4R)-$N^4$-(2-{3-[4-methanesulfonyl-2-(methylamino)phenoxy]prop-1-yn-1-yl}-1-(2,2,2-trifluoroethyl)-1H-indol-4-yl)-$N^1$,$N^1$-dimethylcyclohexane-1,4-diamine |
| 810. | 3-methoxy-N-methyl-4-{[3-(4-{[(1S,4S)-4-(methylamino)cyclohexyl]amino}-1-(2,2,2-trifluoroethyl)-1H-indol-2-yl)prop-2-yn-1-yl]amino}benzamide |
| 811. | (1S,4S)-$N^4$-(2-{3-[2-(dimethylamino)-4-methanesulfonylphenoxy]prop-1-yn-1-yl}-1-(2,2,2-trifluoroethyl)-1H-indol-4-yl)-$N^1$,$N^1$-dimethylcyclohexane-1,4-diamine |
| 812. | (1R,4R)-$N^4$-(2-{3-[2-(dimethylamino)-4-methanesulfonylphenoxy]prop-1-yn-1-yl}-1-(2,2,2-trifluoroethyl)-1H-indol-4-yl)-$N^1$,$N^1$-dimethylcyclohexane-1,4-diamine |
| 813. | 3-(cyanomethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 814. | 3-(2-cyanoethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 815. | N-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]oxy}phenyl)acetamide |
| 816. | N-(2-((3-(4-(((1S,4S)-4-(dimethylamino)cyclohexyl)amino)-1-(2,2,2-trifluoroethyl)-1H-indol-2-yl)prop-2-yn-1-yl)oxy)-5-(methylsulfonyl)phenyl)acetamide |
| 817. | (1R,4R)-$N^1$-(2-(3-((2-(fluoromethoxy)-4-(methylsulfonyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 818. | (1S,4S)-$N^1$-(2-(3-((2-(fluoromethoxy)-4-(methylsulfonyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 819. | (1R,4R)-$N^4$-[2-(3-{[4-(ethanesulfonyl)-2-methoxyphenyl]amino}prop-1-yn-1-yl)-1-(2,2,2-trifluoroethyl)-1H-indol-4-yl]-$N^1$,$N^1$-dimethylcyclohexane-1,4-diamine |
| 820. | (1S,4S)-$N^4$-[2-(3-{[4-(ethanesulfonyl)-2-methoxyphenyl]amino}prop-1-yn-1-yl)-1-(2,2,2-trifluoroethyl)-1H-indol-4-yl]-$N^1$,$N^1$-dimethylcyclohexane-1,4-diamine |
| 821. | 2-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}phenyl)-2-methylpropanenitrile |
| 822. | 2-(4-((3-(4-(((1S,4S)-4-(dimethylamino)cyclohexyl)amino)-1-(2,2,2-trifluoroethyl)-1H-indol-2-yl)prop-2-yn-1-yl)amino)-3-methoxyphenyl)-2-methylpropanenitrile |
| 823. | 3-(cyanomethoxy)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 824. | 3-(cyanomethoxy)-4-((3-(4-(((1S,4S)-4-(dimethylamino)cyclohexyl)amino)-1-(2,2,2-trifluoroethyl)-1H-indol-2-yl)prop-2-yn-1-yl)amino)benzenesulfonamide |
| 825. | 3-(3-(4-(((1R,4R)-4-(dimethylamino)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 826. | 3-(3-(4-(((1S,4S)-4-(dimethylamino)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 827. | 3-methoxy-N,N-dimethyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 828. | (1R,4R)-$N^1$-(2-(3-(((3S,4R)-3-methoxytetrahydro-2H-pyran-4-yl)amino)prop-1-yn-1-yl)-1-(2,2,2-trifluoroethyl)-1H-indol-4-yl)-$N^4$,$N^4$-dimethylcyclohexane-1,4-diamine |
| 829. | (1S,4S)-$N^1$-(2-(3-(((3S,4R)-3-methoxytetrahydro-2H-pyran-4-yl)amino)prop-1-yn-1-yl)-1-(2,2,2-trifluoroethyl)-1H-indol-4-yl)-$N^4$,$N^4$-dimethylcyclohexane-1,4-diamine |
| 830. | (1R,4R)-$N^4$-(2-{3-[(4-chloro-2-methoxyphenyl)amino]prop-1-yn-1-yl}-1-(2,2,2-trifluoroethyl)-1H-indol-4-yl)-$N^1$,$N^1$-dimethylcyclohexane-1,4-diamine |
| 831. | (1S,4S)-$N^1$-(2-(3-((4-chloro-2-methoxyphenyl)amino)prop-1-yn-1-yl)-1-(2,2,2-trifluoroethyl)-1H-indol-4-yl)-$N^4$,$N^4$-dimethylcyclohexane-1,4-diamine |
| 832. | 4-((3-(4-(((1R,4R)-4-(dimethylamino)cyclohexyl)amino)-1-(2,2,2-trifluoroethyl)-1H-indol-2-yl)prop-2-yn-1-yl)amino)-2-fluoro-5-methoxybenzamide |
| 833. | 4-((3-(4-(((1S,4S)-4-(dimethylamino)cyclohexyl)amino)-1-(2,2,2-trifluoroethyl)-1H-indol-2-yl)prop-2-yn-1-yl)amino)-2-fluoro-5-methoxybenzamide |
| 834. | (1R,4R)-$N^4$-[2-(3-{[2-methoxy-4-(trifluoromethyl)phenyl]amino}prop-1-yn-1-yl)-1-(2,2,2-trifluoroethyl)-1H-indol-4-yl]-$N^1$,$N^1$-dimethylcyclohexane-1,4-diamine |
| 835. | (1S,4S)-$N^1$-(2-(3-((2-methoxy-4-(trifluoromethyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 836. | 2-fluoro-5-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 837. | 4-((3-(4-(((1S,4S)-4-(dimethylamino)cyclohexyl)amino)-1-(2,2,2-trifluoroethyl)-1H-indol-2-yl)prop-2-yn-1-yl)amino)-2-fluoro-5-methoxy-N-methylbenzamide |
| 838. | (1S,4S)-$N^4$-[2-(3-{[4-methanesulfonyl-2-(trifluoromethyl)phenyl]amino}prop-1-yn-1-yl)-1-(2,2,2-trifluoroethyl)-1H-indol-4-yl]-$N^1$,$N^1$-dimethylcyclohexane-1,4-diamine |
| 839. | (1R,4R)-$N^4$-[2-(3-{[4-methanesulfonyl-2-(trifluoromethyl)phenyl]amino}prop-1-yn-1-yl)-1-(2,2,2-trifluoroethyl)-1H-indol-4-yl]-$N^1$,$N^1$-dimethylcyclohexane-1,4-diamine |
| 840. | (1R,4R)-$N^4$-(2-{3-[(4-methanesulfonyl-2-methylphenyl)amino]prop-1-yn-1-yl}-1-(2,2,2-trifluoroethyl)-1H-indol-4-yl)-$N^1$,$N^1$-dimethylcyclohexane-1,4-diamine |
| 841. | (1S,4S)-$N^1$,$N^1$-dimethyl-$N^4$-(2-(3-((2-methyl-4-(methylsulfonyl)phenyl)amino)prop-1-yn-1-yl)-1-(2,2,2-trifluoroethyl)-1H-indol-4-yl)cyclohexane-1,4-diamine |

TABLE 7-continued

Alkynyl indole compounds of the disclosure.

| Mol # | IUPAC name |
|---|---|
| 842. | (1R,4R)-$N^4$-[2-(3-{[4-methanesulfonyl-2-(trifluoromethoxy)phenyl]amino}prop-1-yn-1-yl)-1-(2,2,2-trifluoroethyl)-1H-indol-4-yl]-$N^1$,$N^1$-dimethylcyclohexane-1,4-diamine |
| 843. | (1S,4S)-$N^1$,$N^1$-dimethyl-$N^4$-(2-(3-((4-(methylsulfonyl)-2-(trifluoromethoxy)phenyl)amino)prop-1-yn-1-yl)-1-(2,2,2-trifluoroethyl)-1H-indol-4-yl)cyclohexane-1,4-diamine |
| 844. | 3-methoxy-N-methyl-4-{[3-(4-{[(1R,4R)-4-(diethylamino)cyclohexyl]amino}-1-(2,2,2-trifluoroethyl)-1H-indol-2-yl)prop-2-yn-1-yl]amino}benzamide |
| 845. | 4-((3-(4-(((1S,4S)-4-(diethylamino)cyclohexyl)amino)-1-(2,2,2-trifluoroethyl)-1H-indol-2-yl)prop-2-yn-1-yl)amino)-3-methoxy-N-methylbenzamide |
| 846. | 3-methoxy-4-{[3-(4-{[(1R,4R)-4-(diethylamino)cyclohexyl]amino}-1-(2,2,2-trifluoroethyl)-1H-indol-2-yl)prop-2-yn-1-yl]amino}benzene-1-sulfonamide |
| 847. | 4-((3-(4-(((1S,4S)-4-(diethylamino)cyclohexyl)amino)-1-(2,2,2-trifluoroethyl)-1H-indol-2-yl)prop-2-yn-1-yl)amino)-3-methoxybenzenesulfonamide |
| 848. | 3-methoxy-N-methyl-4-{[3-(4-{[(1R,4R)-4-(diethylamino)cyclohexyl]amino}-1-(2,2,2-trifluoroethyl)-1H-indol-2-yl)prop-2-yn-1-yl]amino}benzene-1-sulfonamide |
| 849. | 2-(5-methanesulfonyl-2-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}phenoxy)acetonitrile |
| 850. | 2-(5-methanesulfonyl-2-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}phenoxy)acetonitrile |
| 851. | 3-methoxy-N-methyl-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 852. | 3-methoxy-N-methyl-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 853. | N-ethyl-3-methoxy-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 854. | N-ethyl-3-methoxy-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)benzamide |
| 855. | (1R,4R)-$N^1$-(2-(3-((2-(fluoromethoxy)-4-(methylsulfonyl)phenyl)amino)prop-1-yn-1-yl)-1-(2,2,2-trifluoroethyl)-1H-indol-4-yl)-$N^4$-(2-methoxyethyl)-$N^4$-methylcyclohexane-1,4-diamine |
| 856. | (1S,4S)-$N^1$-(2-(3-((2-(fluoromethoxy)-4-(methylsulfonyl)phenyl)amino)prop-1-yn-1-yl)-1-(2,2,2-trifluoroethyl)-1H-indol-4-yl)-$N^4$-(2-methoxyethyl)-$N^4$-methylcyclohexane-1,4-diamine |
| 857. | 3-(fluoromethoxy)-N-methyl-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 858. | 3-(fluoromethoxy)-N-methyl-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 859. | 3-(fluoromethoxy)-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)-N-methylbenzamide |
| 860. | 3-methoxy-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 861. | 3-methoxy-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)benzenesulfonamide |
| 862. | (1R,4R)-$N^1$,$N^1$-diethyl-$N^4$-(2-{3-[(4-methanesulfonyl-2-methoxyphenyl)amino]prop-1-yn-1-yl}-1-(2,2,2-trifluoroethyl)-1H-indol-4-yl)cyclohexane-1,4-diamine |
| 863. | (1S,4S)-$N^1$,$N^1$-diethyl-$N^4$-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine |
| 864. | 3-(cyanomethoxy)-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 865. | 3-(cyanomethoxy)-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 866. | 3-(fluoromethoxy)-4-{[3-(4-{[(1R,4R)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 867. | 3-(fluoromethoxy)-4-{[3-(4-{[(1S,4S)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 868. | 3-(fluoromethoxy)-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 869. | 3-(fluoromethoxy)-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 870. | 3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide |
| 871. | 3-methoxy-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzamide |

TABLE 7-continued

| Mol # | IUPAC name |
|---|---|
| Alkynyl indole compounds of the disclosure. | |
| 872. | 3-methoxy-N-methyl-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide |
| 873. | 3-methoxy-N-methyl-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzamide |
| 874. | 2-(2-{3-[(4-methanesulfonyl-2-methoxyphenyl)amino]prop-1-yn-1-yl}-4-{[(1R,4R)-4-(morpholin-4-yl)cyclohexyl]amino}-1H-indol-1-yl)acetonitrile |
| 875. | 4-({3-[1-(2-fluoroethyl)-4-{[(1R,4R)-4-(morpholin-4-yl)cyclohexyl]amino}-1H-indol-2-yl]prop-2-yn-1-yl}amino)-3-methoxy-N-methylbenzamide |
| 876. | 1-(2-fluoroethyl)-2-{3-[(4-methanesulfonyl-2-methoxyphenyl)amino]prop-1-yn-1-yl}-N-[(1R,4R)-4-(morpholin-4-yl)cyclohexyl]-1H-indol-4-amine |
| 877. | 4-({3-[1-(cyanomethyl)-4-{[(1R,4R)-4-(morpholin-4-yl)cyclohexyl]amino}-1H-indol-2-yl]prop-2-yn-1-yl}amino)-3-methoxy-N-methylbenzamide |
| 878. | 2-{3-[(4-methanesulfonyl-2-methoxyphenyl)amino]prop-1-yn-1-yl}-1-propyl-N-[(1R,4R)-4-(morpholin-4-yl)cyclohexyl]-1H-indol-4-amine |
| 879. | 2-{3-[(4-methanesulfonyl-2-methoxyphenyl)amino]prop-1-yn-1-yl}-1-(2-methylpropyl)-N-[(1R,4R)-4-(morpholin-4-yl)cyclohexyl]-1H-indol-4-amine |
| 880. | 1-(2,2-difluoroethyl)-2-{3-[(4-methanesulfonyl-2-methoxyphenyl)amino]prop-1-yn-1-yl}-N-[(1R,4R)-4-(morpholin-4-yl)cyclohexyl]-1H-indol-4-amine |
| 881. | 3-methoxy-4-((3-(4-(((1R,4R)-4-morpholinocyclohexyl)amino)-1-(2,2,2-trifluoroethyl)-1H-indol-2-yl)prop-2-yn-1-yl)amino)benzenesulfonamide |
| 882. | 3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzenesulfonamide |
| 883. | N-ethyl-3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide |
| 884. | N-ethyl-3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzamide |
| 885. | 2-(5-methanesulfonyl-2-{[3-(4-{[(1R,4R)-4-(morpholin-4-yl)cyclohexyl]amino}-1-(2,2,2-trifluoroethyl)-1H-indol-2-yl)prop-2-yn-1-yl]amino}phenoxy)acetonitrile |
| 886. | 2-(5-methanesulfonyl-2-{[3-(4-{[(1S,4S)-4-(morpholin-4-yl)cyclohexyl]amino}-1-(2,2,2-trifluoroethyl)-1H-indol-2-yl)prop-2-yn-1-yl]amino}phenoxy)acetonitrile |
| 887. | 3-methoxy-N-methyl-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide |
| 888. | 2-{3-[(4-methanesulfonyl-2-methoxyphenyl)amino]prop-1-yn-1-yl}-N-[(1R,4R)-4-(3-methanesulfonylazetidin-1-yl)cyclohexyl]-1-(2,2,2-trifluoroethyl)-1H-indol-4-amine |
| 889. | 2-(3-((2-methoxy-4-(methylsulfonyl)phenyl)amino)prop-1-yn-1-yl)-N-((1S,4S)-4-(3-(methylsulfonyl)azetidin-1-yl)cyclohexyl)-1-(2,2,2-trifluoroethyl)-1H-indol-4-amine |
| 890. | 3-methoxy-4-{[3-(4-{[(1R,4R)-4-(3-methanesulfonylazetidin-1-yl)cyclohexyl]amino}-1-(2,2,2-trifluoroethyl)-1H-indol-2-yl)prop-2-yn-1-yl]amino}benzene-1-sulfonamide |
| 891. | 3-methoxy-4-((3-(4-(((1S,4S)-4-(3-(methylsulfonyl)azetidin-1-yl)cyclohexyl)amino)-1-(2,2,2-trifluoroethyl)-1H-indol-2-yl)prop-2-yn-1-yl)amino)benzenesulfonamide |
| 892. | 3-methoxy-N-methyl-4-{[3-(4-{[(1R,4R)-4-(3-methanesulfonylazetidin-1-yl)cyclohexyl]amino}-1-(2,2,2-trifluoroethyl)-1H-indol-2-yl)prop-2-yn-1-yl]amino}benzamide |
| 893. | 3-methoxy-N-methyl-4-((3-(4-(((1S,4S)-4-(3-(methylsulfonyl)azetidin-1-yl)cyclohexyl)amino)-1-(2,2,2-trifluoroethyl)-1H-indol-2-yl)prop-2-yn-1-yl)amino)benzamide |
| 894. | 2-{3-[(4-methanesulfonyl-2-methoxyphenyl)amino]prop-1-yn-1-yl}-N-[(1R,4R)-4-{2-azaspiro[3.3]heptan-2-yl}cyclohexyl]-1-(2,2,2-trifluoroethyl)-1H-indol-4-amine |
| 895. | N-((1S,4S)-4-(2-azaspiro[3.3]heptan-2-yl)cyclohexyl)-2-(3-((2-methoxy-4-(methylsulfonyl)phenyl)amino)prop-1-yn-1-yl)-1-(2,2,2-trifluoroethyl)-1H-indol-4-amine |
| 896. | 3-methoxy-N-methyl-4-{[3-(4-{[(1R,4R)-4-{2-azaspiro[3.3]heptan-2-yl}cyclohexyl]amino}-1-(2,2,2-trifluoroethyl)-1H-indol-2-yl)prop-2-yn-1-yl]amino}benzamide |
| 897. | 4-((3-(4-(((1S,4S)-4-(2-azaspiro[3.3]heptan-2-yl)cyclohexyl)amino)-1-(2,2,2-trifluoroethyl)-1H-indol-2-yl)prop-2-yn-1-yl)amino)-3-methoxy-N-methylbenzamide |
| 898. | 3-methoxy-4-{[3-(4-{[(1R,4R)-4-{2-azaspiro[3.3]heptan-2-yl}cyclohexyl]amino}-1-(2,2,2-trifluoroethyl)-1H-indol-2-yl)prop-2-yn-1-yl]amino}benzene-1-sulfonamide |
| 899. | 4-((3-(4-(((1S,4S)-4-(2-azaspiro[3.3]heptan-2-yl)cyclohexyl)amino)-1-(2,2,2-trifluoroethyl)-1H-indol-2-yl)prop-2-yn-1-yl)amino)-3-methoxybenzenesulfonamide |
| 900. | 2-(3-((2-methoxy-4-(methylsulfonyl)phenyl)amino)prop-1-yn-1-yl)-N-(2-azaspiro[3.3]heptan-6-yl)-1-(2,2,2-trifluoroethyl)-1H-indol-4-amine |
| 901. | 4-((3-(4-((2-azaspiro[3.3]heptan-6-yl)amino)-1-(2,2,2-trifluoroethyl)-1H-indol-2-yl)prop-2-yn-1-yl)amino)-3-methoxybenzenesulfonamide |
| 902. | 2-{3-[(4-methanesulfonyl-2-methoxyphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 903. | 2-{3-[(4-methanesulfonyl-2-methoxyphenyl)amino]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine |
| 904. | 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 905. | 3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 906. | N-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)propanamide |

TABLE 7-continued

Alkynyl indole compounds of the disclosure.

| Mol # | IUPAC name |
|---|---|
| 907. | N-(3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)propanamide |
| 908. | N-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)acetamide |
| 909. | N-(3-methoxy-4-{[3-(4-{[(1S,4S)-4-}2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)acetamide |
| 910. | N-((1R,4R)-4-(2-oxa-6-azaspiro[3.3]heptan-6-yl)cyclohexyl)-2-(3-((2-(2-fluoroethoxy)-4-(methylsulfonyl)phenyl)amino)prop-1-yn-1-yl)-1-(2,2,2-trifluoroethyl)-1H-indol-4-amine |
| 911. | N-((1S,4S)-4-(2-oxa-6-azaspiro[3.3]heptan-6-yl)cyclohexyl)-2-(3-((2-(2-fluoroethoxy)-4-(methylsulfonyl)phenyl)amino)prop-1-yn-1-yl)-1-(2,2,2-trifluoroethyl)-1H-indol-4-amine |
| 912. | 3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 913. | 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 914. | 5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenol |
| 915. | 5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenol |
| 916. | N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 917. | N-(3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 918. | N-(2-hydroxy-4-methanesulfonylphenyl)-2-methyl-N-[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]propanamide |
| 919. | N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide |
| 920. | 2-(3-{[4-methanesulfonyl-2-(2-methoxyethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 921. | 2-(3-{[4-methanesulfonyl-2-(2-methoxyethoxy)phenyl]amino}prop-1-yn-1-yl)-N-[(1S,4S)-4-{2-oxa-6-azaspiro[3.3]heptan-6-yl}cyclohexyl]-1-(2,2,2-trifluoroethyl)-1H-indol-4-amine |
| 922. | 2-(5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)acetonitrile |
| 923. | 2-(5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)acetonitrile |
| 924. | 5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl 2-methylpropanoate |
| 925. | 2-(5-methanesulfonyl-2-([3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)ethan-1-ol |
| 926. | 2-(5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)ethan-1-ol |
| 927. | N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)acetamide |
| 928. | 5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl 2-methylpropanoate |
| 929. | 3-methoxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 930. | 3-methoxy-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 931. | 2-(3-{[4-methanesulfonyl-2-(2,2,2-trifluoroethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 932. | 2-(3-{[4-methanesulfonyl-2-(2,2,2-trifluoroethoxy)phenyl]amino}prop-1-yn-1-yl)-N-[(1S,4S)-4-{2-oxa-6-azaspiro[3.3]heptan-6-yl}cyclohexyl]-1-(2,2,2-trifluoroethyl)-1H-indol-4-amine |
| 933. | 2-[3-(2-amino-4-methanesulfonylphenoxy)prop-1-yn-1-yl]-N-[(1S,4S)-4-{2-oxa-6-azaspiro[3.3]heptan-6-yl}cyclohexyl]-1-(2,2,2-trifluoroethyl)-1H-indol-4-amine |

TABLE 7-continued

Alkynyl indole compounds of the disclosure.

| Mol # | IUPAC name |
|---|---|
| 934. | 2-{3-[(2-ethoxy-4-methanesulfonylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 935. | 2-{3-[(2-ethoxy-4-methanesulfonylphenyl)amino]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine |
| 936. | 3-(2-methoxyethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 937. | 3-(2-methoxyethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 938. | N-ethyl-3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 939. | N-ethyl-3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 940. | 3-(2-fluoroethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 941. | 3-(2-fluoroethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 942. | 3-(cyanomethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 943. | 3-(cyanomethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 944. | 2-{3-[4-methanesulfonyl-2-(methylamino)phenoxy]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine |
| 945. | 2-{3-[4-methanesulfonyl-2-(methylamino)phenoxy]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 946. | 2-[3-(2-amino-4-methanesulfonylphenoxy)prop-1-yn-1-yl]-N-[(1R,4R)-4-{2-oxa-6-azaspiro[3.3]heptan-6-yl}cyclohexyl]-1-(2,2,2-trifluoroethyl)-1H-indol-4-amine |
| 947. | N-((1R,4R)-4-(2-oxa-6-azaspiro[3.3]heptan-6-yl)cyclohexyl)-2-(3-(2-amino-4-(methylsulfonyl)phenoxy)prop-1-yn-1-yl)-1-(2,2,2-trifluoroethyl)-1H-indol-4-amine |
| 948. | 3-hydroxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 949. | 3-methoxy-4-[(3-{4-[(4-{2-oxa-6-azaspiro[3.3]heptan-6-yl}cyclohexyl)amino]-1-(2,2,2-trifluoroethyl)-1H-indol-2-yl}prop-2-yn-1-yl)amino]benzonitrile |
| 950. | 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzonitrile |
| 951. | 2-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl)-2-methylpropanenitrile |
| 952. | 2-(4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxyphenyl)-2-methylpropanenitrile |
| 953. | 3-(fluoromethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 954. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(fluoromethoxy)-N-methylbenzamide |
| 955. | 3-(2-cyanoethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 956. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(2-cyanoethoxy)-N-methylbenzamide |
| 957. | 2-(3-{[2-(fluoromethoxy)-4-methanesulfonylphenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 958. | N-((1S,4S)-4-(2-oxa-6-azaspiro[3.3]heptan-6-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine |
| 959. | 3-(cyanomethoxy)-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 960. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(cyanomethoxy)benzenesulfonamide |
| 961. | 3-(fluoromethoxy)-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |

TABLE 7-continued

Alkynyl indole compounds of the disclosure.

| Mol # | IUPAC name |
|---|---|
| 962. | 3-(fluoromethoxy)-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 963. | 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N-methylbenzenesulfonamide |
| 964. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N-methylbenzenesulfonamide |
| 965. | N-((1R,4R)-4-(2-oxa-6-azaspiro[3.3]heptan-6-yl)cyclohexyl)-2-(3-((4-chloro-2-methoxyphenyl)amino)prop-1-yn-1-yl)-1-(2,2,2-trifluoroethyl)-1H-indol-4-amine |
| 966. | N-((1S,4S)-4-(2-oxa-6-azaspiro[3.3]heptan-6-yl)cyclohexyl)-2-(3-((4-chloro-2-methoxyphenyl)amino)prop-1-yn-1-yl)-1-(2,2,2-trifluoroethyl)-1H-indol-4-amine |
| 967. | 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N,N-dimethylbenzenesulfonamide |
| 968. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N,N-dimethylbenzenesulfonamide |
| 969. | N-((1R,4R)-4-(2-oxa-6-azaspiro[3.3]heptan-6-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 970. | N-((1S,4S)-4-(2-oxa-6-azaspiro[3.3]heptan-6-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 971. | N-((1R,4R)-4-(2-oxa-6-azaspiro[3.3]heptan-6-yl)cyclohexyl)-2-(3-(((3S,4R)-3-methoxytetrahydro-2H-pyran-4-yl)amino)prop-1-yn-1-yl)-1-(2,2,2-trifluoroethyl)-1H-indol-4-amine |
| 972. | N-((1S,4S)-4-(2-oxa-6-azaspiro[3.3]heptan-6-yl)cyclohexyl)-2-(3-(((3S,4R)-3-methoxytetrahydro-2H-pyran-4-yl)amino)prop-1-yn-1-yl)-1-(2,2,2-trifluoroethyl)-1H-indol-4-amine |
| 973. | 2-fluoro-5-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 974. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxybenzamide |
| 975. | 2-fluoro-5-methoxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 976. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxy-N-methylbenzamide |
| 977. | 2-(3-{[2-methoxy-4-(trifluoromethyl)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 978. | N-((1S,4S)-4-(2-oxa-6-azaspiro[3.3]heptan-6-yl)cyclohexyl)-2-(3-((2-methoxy-4-(trifluoromethyl)phenyl)amino)prop-1-yn-1-yl)-1-(2,2,2-trifluoroethyl)-1H-indol-4-amine |
| 979. | 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxybenzoic acid |
| 980. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxybenzoic acid |
| 981. | 2-fluoro-5-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzoic acid |
| 982. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxybenzoic acid |
| 983. | 2-{3-[(4-methanesulfonyl-2-methylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 984. | N-((1S,4S)-4-(2-oxa-6-azaspiro[3.3]heptan-6-yl)cyclohexyl)-2-(3-((2-methyl-4-(methylsulfonyl)phenyl)amino)prop-1-yn-1-yl)-1-(2,2,2-trifluoroethyl)-1H-indol-4-amine |
| 985. | 2-(3-{[4-methanesulfonyl-2-(trifluoromethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 986. | N-((1S,4S)-4-(2-oxa-6-azaspiro[3.3]heptan-6-yl)cyclohexyl)-2-(3-((4-(methylsulfonyl)-2-(trifluoromethoxy)phenyl)amino)prop-1-yn-1-yl)-1-(2,2,2-trifluoroethyl)-1H-indol-4-amine |
| 987. | 2-(3-{[4-methanesulfonyl-2-(trifluoromethyl)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 988. | N-((1S,4S)-4-(2-oxa-6-azaspiro[3.3]heptan-6-yl)cyclohexyl)-2-(3-((4-(methylsulfonyl)-2-(trifluoromethyl)phenyl)amino)prop-1-yn-1-yl)-1-(2,2,2-trifluoroethyl)-1H-indol-4-amine |
| 989. | 2-{3-[(2-chloro-4-methanesulfonylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 990. | N-((1S,4S)-4-(2-oxa-6-azaspiro[3.3]heptan-6-yl)cyclohexyl)-2-(3-((2-chloro-4-(methylsulfonyl)phenyl)amino)prop-1-yn-1-yl)-1-(2,2,2-trifluoroethyl)-1H-indol-4-amine |
| 991. | 3-(3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)-6-(methylsulfonyl)benzo[d]oxazol-2(3H)-one |

TABLE 7-continued

Alkynyl indole compounds of the disclosure.

| Mol # | IUPAC name |
|---|---|
| 992. | 3-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 993. | 2-{3-[(4-methanesulfonyl-2-methoxyphenyl)amino]prop-1-yn-1-yl}-N-[(1S,4S)-4-{7-oxa-2-azaspiro[3.5]nonan-2-yl]cyclohexyl]-1-(2,2,2-trifluoroethyl)-1H-indol-4-amine |
| 994. | 2-{3-[(4-methanesulfonyl-2-methoxyphenyl)amino]prop-1-yn-1-yl}-N-[(1R,4R)-4-{7-oxa-2-azaspiro[3.5]nonan-2-yl]cyclohexyl]-1-(2,2,2-trifluoroethyl)-1H-indol-4-amine |
| 995. | 3-methoxy-N-methyl-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 996. | 3-methoxy-N-methyl-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 997. | 3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 998. | 3-methoxy-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 999. | 3-(cyanomethoxy)-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1000. | 3-(cyanomethoxy)-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1001. | 2-(3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenyl)-2-methylpropanenitrile |
| 1002. | 2-(4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)-2-methylpropanenitrile |
| 1003. | 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetonitrile |
| 1004. | 2-(5-methanesulfonyl-2-{[3-(4-([(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetonitrile |
| 1005. | N-((4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)acetamide |
| 1006. | N-((4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)acetamide |
| 1007. | N-((4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)-2-aminoacetamide |
| 1008. | N-((4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)-2-aminoacetamide |
| 1009. | methyl 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetate |
| 1010. | methyl 2-(2-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetate |
| 1011. | 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetic acid |
| 1012. | 2-(2-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetic acid |
| 1013. | 2-{3-[(4-methanesulfonyl-2-methoxyphenyl)amino]prop-1-yn-1-yl}-N-[(1R,4R)-4-{2-oxa-7-azaspiro[3.5]nonan-7-yl}cyclohexyl]-1-(2,2,2-trifluoroethyl)-1H-indol-4-amine |
| 1014. | 2-(3-{[4-(ethanesulfonyl)-2-methoxyphenyl]amino}prop-1-yn-1-yl)-N-[(1R,4R)-4-{7-oxa-2-azaspiro[3.5]nonan-2-yl}cyclohexyl]-1-(2,2,2-trifluoroethyl)-1H-indol-4-amine |
| 1015. | 2-(3-{[4-(ethanesulfonyl)-2-methoxyphenyl]amino}prop-1-yn-1-yl)-N-[(1S,4S)-4-{7-oxa-2-azaspiro[3.5]nonan-2-yl}cyclohexyl]-1-(2,2,2-trifluoroethyl)-1H-indol-4-amine |
| 1016. | 3-(fluoromethoxy)-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1017. | 3-(fluoromethoxy)-4-{[3-(4-{[(1S,4S)-4-{7-oxa-2-azaspiro[3,5]nonan-2-yl}cyclohexyl]amino}-1-(2,2,2-trifluoroethyl)-1H-indol-2-yl)prop-2-yn-1-yl]amino}benzene-1-sulfonamide |
| 1018. | 3-methoxy-N-methyl-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1019. | 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzamide |

TABLE 7-continued

Alkynyl indole compounds of the disclosure.

| Mol # | IUPAC name |
|---|---|
| 1020. | 3-methoxy-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1021. | 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzenesulfonamide |
| 1022. | 2-{3-[(4-methanesulfonyl-2-methoxyphenyl)amino]prop-1-yn-1-yl}-N-[(1R,4R)-4-{6-oxa-2-azaspiro[3.5]nonan-2-yl}cyclohexyl]-1-(2,2,2-trifluoroethyl)-1H-indol-4-amine |
| 1023. | N-((1S,4S)-4-(6-oxa-2-azaspiro[3.5]nonan-2-yl)cyclohexyl)-2-(3-((2-methoxy-4-(methylsulfonyl)phenyl)amino)prop-1-yn-1-yl)-1-(2,2,2-trifluoroethyl)-1H-indol-4-amine |
| 1024. | N-((1R,4R)-4-(7-oxa-2-azaspiro[3.5]nonan-2-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine |
| 1025. | N-((1S,4S)-4-(7-oxa-2-azaspiro[3.5]nonan-2-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine |
| 1026. | 4-(3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)-7-(methylsulfonyl)-2H-benzo[b][1,4]oxazin-3(4H)-one |
| 1027. | 4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzenesulfonamide |
| 1028. | 4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzenesulfonamide |
| 1029. | N-((1R,4R)-4-(7-oxa-2-azaspiro[3.5]nonan-2-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine |
| 1030. | N-((1S,4S)-4-(7-oxa-2-azaspiro[3.5]nonan-2-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine |
| 1031. | 3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1032. | 4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzamide |
| 1033. | 3-methoxy-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1034. | 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzamide |
| 1035. | 2-fluoro-5-methoxy-N-methyl-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1036. | 2-(3-((2-methoxy-4-(methylsulfonyl)phenyl)amino)prop-1-yn-1-yl)-N-((1R,4R)-4-(3-methoxypyrrolidin-1-yl)cyclohexyl)-1-(2,2,2-trifluoroethyl)-1H-indol-4-amine |
| 1037. | 2-(3-((2-methoxy-4-(methylsulfonyl)phenyl)amino)prop-1-yn-1-yl)-N-((1S,4S)-4-(3-methoxypyrrolidin-1-yl)cyclohexyl)-1-(2,2,2-trifluoroethyl)-1H-indol-4-amine |
| 1038. | 3-methoxy-4-((3-(4-(((1R,4R)-4-(3-methoxypyrrolidin-1-yl)cyclohexyl)amino)-1-(2,2,2-trifluoroethyl)-1H-indol-2-yl)prop-2-yn-1-yl)amino)benzenesulfonamide |
| 1039. | 3-methoxy-4-((3-(4-(((1S,4S)-4-(3-methoxypyrrolidin-1-yl)cyclohexyl)amino)-1-(2,2,2-trifluoroethyl)-1H-indol-2-yl)prop-2-yn-1-yl)amino)benzenesulfonamide |
| 1040. | 2-(3-{[2-(fluoromethoxy)-4-methanesulfonylphenyl]amino}prop-1-yn-1-yl)-N-[(1R,4R)-4-(morpholin-4-yl)cyclohexyl]-1-(2,2,2-trifluoroethyl)-1H-indol-4-amine |
| 1041. | 2-(3-{[2-(fluoromethoxy)-4-methanesulfonylphenyl]amino}prop-1-yn-1-yl)-N-[(1S,4S)-4-(morpholin-4-yl)cyclohexyl]-1-(2,2,2-trifluoroethyl)-1H-indol-4-amine |
| 1042. | 3-(cyanomethoxy)-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1043. | 3-(cyanomethoxy)-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1044. | 3-(fluoromethoxy)-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1045. | 3-(fluoromethoxy)-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1046. | 2-(3-((2-ethoxy-4-(methylsulfonyl)phenyl)amino)prop-1-yn-1-yl)-N-((1R,4R)-4-morpholinocyclohexyl)-1-(2,2,2-trifluoroethyl)-1H-indol-4-amine |
| 1047. | 2-(3-((2-ethoxy-4-(methylsulfonyl)phenyl)amino)prop-1-yn-1-yl)-N-((1S,4S)-4-morpholinocyclohexyl)-1-(2,2,2-trifluoroethyl)-1H-indol-4-amine |
| 1048. | 2-{3-[(4-methanesulfonyl-2-methoxyphenyl)amino]prop-1-yn-1-yl}-N-[(1R,4R)-4-(3-methoxypiperidin-1-yl)cyclohexyl]-1-(2,2,2-trifluoroethyl)-1H-indol-4-amine |
| 1049. | 2-(3-((2-methoxy-4-(methylsulfonyl)phenyl)amino)prop-1-yn-1-yl)-N-((1S,4S)-4-(3-methoxypiperidin-1-yl)cyclohexyl)-1-(2,2,2-trifluoroethyl)-1H-indol-4-amine |
| 1050. | 2-{3-[(4-methanesulfonyl-2-methoxyphenyl)amino]prop-1-yn-1-yl}-N-[(1R,4R)-4-(4-methoxypiperidin-1-yl)cyclohexyl]-1-(2,2,2-trifluoroethyl)-1H-indol-4-amine |
| 1051. | 2-(3-((2-methoxy-4-(methylsulfonyl)phenyl)amino)prop-1-yn-1-yl)-N-((1S,4S)-4-(4-methoxypiperidin-1-yl)cyclohexyl)-1-(2,2,2-trifluoroethyl)-1H-indol-4-amine |
| 1052. | 3-methoxy-N-methyl-4-{[3-(4-{[(1R,4R)-4-(4-methoxypiperidin-1-yl)cyclohexyl]amino}-1-(2,2,2-trifluoroethyl)-1H-indol-2-yl)prop-2-yn-1-yl]amino}benzamide |
| 1053. | 3-methoxy-4-((3-(4-(((1S,4S)-4-(4-methoxypiperidin-1-yl)cyclohexyl)amino)-1-(2,2,2-trifluoroethyl)-1H-indol-2-yl)prop-2-yn-1-yl)amino)-N-methylbenzamide |
| 1054. | 3-methoxy-4-{[3-(4-{[(1R,4R)-4-(4-methoxypiperidin-1-yl)cyclohexyl]amino}-1-(2,2,2-trifluoroethyl)-1H-indol-2-yl)prop-2-yn-1-yl]amino}benzene-1-sulfonamide |

TABLE 7-continued

Alkynyl indole compounds of the disclosure.

| Mol # | IUPAC name |
|---|---|
| 1055. | 3-methoxy-4-((3-(4-(((1S,4S)-4-(4-methoxypiperidin-1-yl)cyclohexyl)amino)-1-(2,2,2-trifluoroethyl)-1H-indol-2-yl)prop-2-yn-1-yl)amino)benzenesulfonamide |
| 1056. | 3-methoxy-N-methyl-4-{[3-(4-{[(1R,4R)-4-(3-methoxypiperidin-1-yl)cyclohexyl]amino}-1-(2,2,2-trifluoroethyl)-1H-indol-2-yl)prop-2-yn-1-yl]amino}benzamide |
| 1057. | 3-methoxy-4-((3-(4-(((1S,4S)-4-(3-methoxypiperidin-1-yl)cyclohexyl)amino)-1-(2,2,2-trifluoroethyl)-1H-indol-2-yl)prop-2-yn-1-yl)amino)-N-methylbenzamide |
| 1058. | 3-methoxy-4-{[3-(4-{[(1R,4R)-4-(3-methoxypiperidin-1-yl)cyclohexyl]amino}-1-(2,2,2-trifluoroethyl)-1H-indol-2-yl)prop-2-yn-1-yl]amino}benzene-1-sulfonamide |
| 1059. | 3-methoxy-4-((3-(4-(((1S,4S)-4-(3-methoxypiperidin-1-yl)cyclohexyl)amino)-1-(2,2,2-trifluoroethyl)-1H-indol-2-yl)prop-2-yn-1-yl)amino)benzenesulfonamide |
| 1060. | 3-methoxy-4-((3-(4-(((1R,4R)-4-morpholinocyclohexyl)amino)-1-(2,2,2-trifluoroethyl)-1H-indol-2-yl)prop-2-yn-1-yl)amino)benzenesulfonamide |
| 1061. | 3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzenesulfonamide |
| 1062. | 4-[(1R,4R)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1$\lambda^6$-thiomorpholine-1,1-dione |
| 1063. | 4-((1S,4S)-4-((2-(3-((2-methoxy-4-(methylsulfonyl)phenyl)amino)prop-1-yn-1-yl)-1-(2,2,2-trifluoroethyl)-1H-indol-4-yl)amino)cyclohexyl)thiomorpholine 1,1-dioxide |
| 1064. | 4-[(1R,4R)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1$\lambda^4$-thiomorpholin-1-one |
| 1065. | 4-[(1S,4S)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1$\lambda^4$-thiomorpholin-1-one |
| 1066. | 4-((3-(4-(((1R,4R)-4-(1,1-dioxidothiomorpholino)cyclohexyl)amino)-1-(2,2,2-trifluoroethyl)-1H-indol-2-yl)prop-2-yn-1-yl)amino)-3-methoxy-N-methylbenzamide |
| 1067. | 4-((3-(4-(((1S,4S)-4-(1,1-dioxidothiomorpholino)cyclohexyl)amino)-1-(2,2,2-trifluoroethyl)-1H-indol-2-yl)prop-2-yn-1-yl)amino)-3-methoxy-N-methylbenzamide |
| 1068. | 4-((1S,4S)-4-((2-(3-((2-methoxy-4-(methylsulfonyl)phenyl)amino)prop-1-yn-1-yl)-1-(2,2,2-trifluoroethyl)-1H-indol-4-yl)amino)cyclohexyl)thiomorpholine 1-oxide |
| 1069. | 3-methoxy-N-methyl-4-{[3-(4-{[(1R,4R)-4-(1-oxo-1$\lambda^4$-thiomorpholin-4-yl)cyclohexyl]amino}-1-(2,2,2-trifluoroethyl)-1H-indol-2-yl)prop-2-yn-1-yl]amino}benzamide |
| 1070. | 3-methoxy-4-{[3-(4-{[(1R,4R)-4-(1-oxo-1$\lambda^4$-thiomorpholin-4-yl)cyclohexyl]amino}-1-(2,2,2-trifluoroethyl)-1H-indol-2-yl)prop-2-yn-1-yl]amino}benzene-1-sulfonamide |
| 1071. | 3-methoxy-4-((3-(4-(((1S,4S)-4-(1-oxidothiomorpholino)cyclohexyl)amino)-1-(2,2,2-trifluoroethyl)-1H-indol-2-yl)prop-2-yn-1-yl)amino)benzenesulfonamide |
| 1072. | 3-methoxy-4-{[3-(4-{[(1R,4R)-4-(1,1-dioxo-1$\lambda^6$-thiomorpholin-4-yl)cyclohexyl]amino}-1-(2,2,2-trifluoroethyl)-1H-indol-2-yl)prop-2-yn-1-yl]amino}benzene-1-sulfonamide |
| 1073. | 4-((3-(4-(((1S,4S)-4-(1,1-dioxidothiomorpholino)cyclohexyl)amino)-1-(2,2,2-trifluoroethyl)-1H-indol-2-yl)prop-2-yn-1-yl)amino)-3-methoxybenzenesulfonamide |
| 1074. | 2-{3-[(4-methanesulfonyl-2-methoxyphenyl)amino]prop-1-yn-1-yl}-N-[(1S,4S)-4-{2-oxa-7-azaspiro[3.5]nonan-7-yl}cyclohexyl]-1-(2,2,2-trifluoroethyl)-1H-indol-4-amine |
| 1075. | 3-methoxy-N-methyl-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzamide |
| 1076. | 3-methoxy-N-methyl-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzamide |
| 1077. | 3-methoxy-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1078. | 4-((3-(4-(((1S,4S)-4-(2-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxybenzenesulfonamide |
| 1079. | 3-(cyanomethoxy)-4-][3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1080. | 3-(cyanomethoxy)-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1081. | 3-(fluoromethoxy)-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1082. | 3-(fluoromethoxy)-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1083. | 2-{3-[(4-methanesulfonyl-2-methoxyphenyl)amino]prop-1-yn-1-yl}-N-[(1R,4R)-4-{1-oxa-7-azaspiro[3.5]nonan-7-yl}cyclohexyl]-1-(2,2,2-trifluoroethyl)-1H-indol-4-amine |
| 1084. | N-((1S,4S)-4-(1-oxa-7-azaspiro[3.5]nonan-7-yl)cyclohexyl)-2-(3-((2-methoxy-4-(methylsulfonyl)phenyl)amino)prop-1-yn-1-yl)-1-(2,2,2-trifluoroethyl)-1H-indol-4-amine |
| 1085. | 3-methoxy-N-methyl-4-{[3-(4-{[(1R,4R)-4-{1-oxa-7-azaspiro[3.5]nonan-7-yl}cyclohexyl]amino}-1-(2,2,2-trifluoroethyl)-1H-indol-2-yl)prop-2-yn-1-yl]amino}benzamide |
| 1086. | 4-((3-(4-(((1S,4S)-4-(1-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxy-N-methylbenzamide |
| 1087. | 3-methoxy-4-{[3-(4-{[(1R,4R)-4-{1-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |

TABLE 7-continued

| Mol # | IUPAC name |
| --- | --- |
| | Alkynyl indole compounds of the disclosure. |
| 1088. | 4-((3-(4-(((1S,4S)-4-(1-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxybenzenesulfonamide |
| 1089. | 2-(5-methanesulfonyl-2-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}phenoxy)acetonitrile |
| 1090. | 2-(5-methanesulfonyl-2-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}phenoxy)acetonitrile |
| 1091. | 2-(3-{[2-(fluoromethoxy)-4-methanesulfonylphenyl]amino}prop-1-yn-1-yl)-N-[(1R,4R)-4-{2-oxa-7-azaspiro[3.5]nonan-7-yl}cyclohexyl]-1-(2,2,2-trifluoroethyl)-1H-indol-4-amine |
| 1092. | 2-(3-{[2-(fluoromethoxy)-4-methanesulfonylphenyl]amino}prop-1-yn-1-yl)-N-[(1S,4S)-4-{2-oxa-7-azaspiro[3.5]nonan-7-yl}cyclohexyl]-1-(2,2,2-trifluoroethyl)-1H-indol-4-amine |
| 1093. | N-((1R,4R)-4-(2-oxa-7-azaspiro[3.5]nonan-7-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine |
| 1094. | N-((1S,4S)-4-(2-oxa-7-azaspiro[3.5]nonan-7-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine |
| 1095. | 3-methoxy-N-methyl-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1096. | N-((1R,4R)-4-(2-oxa-7-azaspiro[3.5]nonan-7-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 1097. | N-((1S,4S)-4-(2-oxa-7-azaspiro[3.5]nonan-7-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 1098. | 2-{3-[(4-methanesulfonyl-2-methoxyphenyl)amino]prop-1-yn-1-yl}-N-[(1R,4R)-4-{6-oxa-3-azabicyclo[3.1.1]heptan-3-yl}cyclohexyl]-1-(2,2,2-trifluoroethyl)-1H-indol-4-amine |
| 1099. | 2-{3-[(4-methanesulfonyl-2-methoxyphenyl)amino]prop-1-yn-1-yl}-N-[(1S,4S)-4-{6-oxa-3-azabicyclo[3.1.1]heptan-3-yl}cyclohexyl]-1-(2,2,2-trifluoroethyl)-1H-indol-4-amine |
| 1100. | 3-methoxy-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzene-1-sulfonamide |
| 1101. | 3-methoxy-4-{[3-(4-{[(1S,4S)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzene-1-sulfonamide |
| 1102. | 3-methoxy-N-methyl-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide |
| 1103. | 3-methoxy-N-methyl-4-{[3-(4-{[(1S,4S)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide |
| 1104. | 2-{3-[(2-ethoxy-4-methanesulfonylphenyl)amino]prop-1-yn-1-yl}-N-[(1R,4R)-4-{6-oxa-3-azabicyclo[3.1.1]heptan-3-yl}cyclohexyl]-1-(2,2,2-trifluoroethyl)-1H-indol-4-amine |
| 1105. | 2-{3-[(2-ethoxy-4-methanesulfonylphenyl)amino]prop-1-yn-1-yl}-N-[(1S,4S)-4-{6-oxa-3-azabicyclo[3.1.1]heptan-3-yl}cyclohexyl]-1-(2,2,2-trifluoroethyl)-1H-indol-4-amine |
| 1106. | N-ethyl-3-methoxy-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide |
| 1107. | 2-(5-methanesulfonyl-2-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}phenoxy)acetonitrile |
| 1108. | 2-(2-((3-(4-(((1S,4S)-4-(6-oxa-3-azabicyclo[3.1.1]heptan-3-yl)cyclohexyl)amino)-1-(2,2,2-trifluoroethyl)-1H-indol-2-yl)prop-2-yn-1-yl)amino)-5-(methylsulfonyl)phenoxy)acetonitrile |
| 1109. | 3-methoxy-N-methyl-4-{[3-(4-{[(1R,4R)-4-[2-oxa-8-azaspiro[4.5]decan-8-yl}cyclohexyl]amino}-1-(2,2,2-trifluoroethyl)-1H-indol-2-yl)prop-2-yn-1-yl]amino}benzamide |
| 1110. | 2-{3-[(4-methanesulfonyl-2-methoxyphenyl)amino]prop-1-yn-1-yl}-N-[(1R,4R)-4-{2-oxa-8-azaspiro[4.5]decan-8-yl}cyclohexyl]-1-(2,2,2-trifluoroethyl)-1H-indol-4-amine |
| 1111. | 3-methoxy-4-{[3-(4-{[(1R,4R)-4-{2-oxa-8-azaspiro[4.5]decan-8-yl}cyclohexyl]amino}-1-(2,2,2-trifluoroethyl)-1H-indol-2-yl)prop-2-yn-1-yl]amino}benzene-1-sulfonamide |
| 1112. | 4-((3-(4-(((1R,4R)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxybenzenesulfonamide |
| 1113. | 4-((3-(4-(((1S,4S)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxybenzenesulfonamide |
| 1114. | 2-{3-[(4-methanesulfonyl-2-methoxyphenyl)amino]prop-1-yn-1-yl}-N-[(1R,4R)-4-{3-oxa-9-azaspiro[5.5]undecan-9-yl}cyclohexyl]-1-(2,2,2-trifluoroethyl)-1H-indol-4-amine |
| 1115. | N-((1S,4S)-4-(3-oxa-9-azaspiro[5.5]undecan-9-yl)cyclohexyl)-2-(3-((2-methoxy-4-(methylsulfonyl)phenyl)amino)prop-1-yn-1-yl)-1-(2,2,2-trifluoroethyl)-1H-indol-4-amine |
| 1116. | 3-methoxy-N-methyl-4-{[3-(4-{[(1R,4R)-4-{3-oxa-9-azaspiro[5.5]undecan-9-yl}cyclohexyl]amino}-1-(2,2,2-trifluoroethyl)-1H-indol-2-yl)prop-2-yn-1-yl]amino}benzamide |

TABLE 7-continued

| Mol # | IUPAC name |
| --- | --- |
| | Alkynyl indole compounds of the disclosure. |
| 1117. | 4-((3-(4-(((1S,4S)-4-(3-oxa-9-azaspiro[5.5]undecan-9-yl)cyclohexyl)amino)-1-(2,2,2-trifluoroethyl)-1H-indol-2-yl)prop-2-yn-1-yl)amino)-3-methoxy-N-methylbenzamide |
| 1118. | 3-methoxy-4-{[3-(4-{[(1R,4R)-4-{3-oxa-9-azaspiro[5.5]undecan-9-yl}cyclohexyl]amino}-1-(2,2,2-trifluoroethyl)-1H-indol-2-yl)prop-2-yn-1-yl]amino}benzene-1-sulfonamide |
| 1119. | 4-((3-(4-(((1S,4S)-4-(3-oxa-9-azaspiro[5.5]undecan-9-yl)cyclohexyl)amino)-1-(2,2,2-trifluoroethyl)-1H-indol-2-yl)prop-2-yn-1-yl)amino)-3-methoxybenzenesulfonamide |
| 1120. | 3-methoxy-N-methyl-4-{[3-(4-{[(1R,4R)-4-(pyrrolidin-1-yl)cyclohexyl]amino}-1-(2,2,2-trifluoroethyl)-1H-indol-2-yl)prop-2-yn-1-yl]amino}benzamide |
| 1121. | 3-methoxy-N-methyl-4-((3-(4-(((1S,4S)-4-(pyrrolidin-1-yl)cyclohexyl)amino)-1-(2,2,2-trifluoroethyl)-1H-indol-2-yl)prop-2-yn-1-yl)amino)benzamide |
| 1122. | 3-methoxy-4-{[3-(4-{[(1R,4R)-4-(pyrrolidin-1-yl)cyclohexyl]amino}-1-(2,2,2-trifluoroethyl)-1H-indol-2-yl)prop-2-yn-1-yl]amino}benzene-1-sulfonamide |
| 1123. | 3-methoxy-4-((3-(4-(((1S,4S)-4-(pyrrolidin-1-yl)cyclohexyl)amino)-1-(2,2,2-trifluoroethyl)-1H-indol-2-yl)prop-2-yn-1-yl)amino)benzenesulfonamide |
| 1124. | 2-{3-[(4-methanesulfonyl-2-methoxyphenyl)amino]prop-1-yn-1-yl}-N-[(1R,4R)-4-(pyrrolidin-1-yl)cyclohexyl]-1-(2,2,2-trifluoroethyl)-1H-indol-4-amine |
| 1125. | 2-(3-((2-methoxy-4-(methylsulfonyl)phenyl)amino)prop-1-yn-1-yl)-N-((1S,4S)-4-(pyrrolidin-1-yl)cyclohexyl)-1-(2,2,2-trifluoroethyl)-1H-indol-4-amine |
| 1126. | -{3-[(4-methanesulfonyl-2-methoxyphenyl)amino]prop-1-yn-1-yl}-N-[(1R,4R)-4-(3-methoxypyrrolidin-1-yl)cyclohexyl]-1-(2,2,2-trifluoroethyl)-1H-indol-4-amine |
| 1127. | 3-methoxy-4-{[3-(4-{[(1R,4R)-4-(3-methoxypyrrolidin-1-yl)cyclohexyl]amino}-1-(2,2,2-trifluoroethyl)-1H-indol-2-yl)prop-2-yn-1-yl]amino}benzene-1-sulfonamide |
| 1128. | 3-methoxy-N-methyl-4-{[3-(4-{[(1R,4R)-4-(3-methoxypyrrolidin-1-yl)cyclohexyl]amino}-1-(2,2,2-trifluoroethyl)-1H-indol-2-yl)prop-2-yn-1-yl]amino}benzamide |
| 1129. | 3-methoxy-4-((3-(4-(((1S,4S)-4-(3-methoxypyrrolidin-1-yl)cyclohexyl)amino)-1-(2,2,2-trifluoroethyl)-1H-indol-2-yl)prop-2-yn-1-yl)amino)-N-methylbenzamide |
| 1130. | 3-methoxy-4-{[3-(4-{[(1R,4R)-4-{hexahydro-1H-furo[3,4-c]pyrrol-5-yl}cyclohexyl]amino}-1-(2,2,2-trifluoroethyl)-1H-indol-2-yl)prop-2-yn-1-yl]amino}benzene-1-sulfonamide |
| 1131. | 3-methoxy-4-((3-(4-(((1S,4S)-4-(tetrahydro-1H-furo[3,4-c]pyrrol-5(3H)-yl)cyclohexyl)amino)-1-(2,2,2-trifluoroethyl)-1H-indol-2-yl)prop-2-yn-1-yl)amino)benzenesulfonamide |
| 1132. | 2-{3-[(4-methanesulfonyl-2-methoxyphenyl)amino]prop-1-yn-1-yl}-N-[(1R,4R)-4-{hexahydro-1H-furo[3,4-c]pyrrol-5-yl}cyclohexyl]-1-(2,2,2-trifluoroethyl)-1H-indol-4-amine |
| 1133. | 2-(3-((2-methoxy-4-(methylsulfonyl)phenyl)amino)prop-1-yn-1-yl)-N-((1R,4R)-4-(tetrahydro-1H-furo[3,4-c]pyrrol-5(3H)-yl)cyclohexyl)-1-(2,2,2-trifluoroethyl)-1H-indol-4-amine |
| 1134. | 3-methoxy-N-methyl-4-{[3-(4-{[(1R,4R)-4-{hexahydro-1H-furo[3,4-c]pyrrol-5-yl}cyclohexyl]amino}-1-(2,2,2-trifluoroethyl)-1H-indol-2-yl)prop-2-yn-1-yl]amino}benzamide |
| 1135. | 3-methoxy-N-methyl-4-((3-(4-(((1S,4S)-4-(tetrahydro-1H-furo[3,4-c]pyrrol-5(3H)-yl)cyclohexyl)amino)-1-(2,2,2-trifluoroethyl)-1H-indol-2-yl)prop-2-yn-1-yl)amino)benzamide |
| 1136. | 2-{3-[(4-methanesulfonyl-2-methoxyphenyl)amino]prop-1-yn-1-yl}-N-[(1R,4R)-4-[4-(trifluoromethyl)piperidin-1-yl]cyclohexyl]-1-(2,2,2-trifluoroethyl)-1H-indol-4-amine |
| 1137. | 2-(3-((2-methoxy-4-(methylsulfonyl)phenyl)amino)prop-1-yn-1-yl)-1-(2,2,2-trifluoroethyl)-N-((1S,4S)-4-(4-(trifluoromethyl)piperidin-1-yl)cyclohexyl)-1H-indol-4-amine |
| 1138. | 3-methoxy-N-methyl-4-{[3-(4-{[(1R,4R)-4-[4-(trifluoromethyl)piperidin-1-yl]cyclohexyl]amino}-1-(2,2,2-trifluoroethyl)-1H-indol-2-yl)prop-2-yn-1-yl]amino}benzamide |
| 1139. | 3-methoxy-N-methyl-4-((3-(1-(2,2,2-trifluoroethyl)-4-(((1S,4S)-4-(4-(trifluoromethyl)piperidin-1-yl)cyclohexyl)amino)-1H-indol-2-yl)prop-2-yn-1-yl)amino)benzamide |
| 1140. | 3-methoxy-4-{[3-(4-{[(1R,4R)-4-[4-(trifluoromethyl)piperidin-1-yl]cyclohexyl]amino}-1-(2,2,2-trifluoroethyl)-1H-indol-2-yl)prop-2-yn-1-yl]amino}benzene-1-sulfonamide |
| 1141. | 3-methoxy-4-((3-(1-(2,2,2-trifluoroethyl)-4-(((1S,4S)-4-(4-(trifluoromethyl)piperidin-1-yl)cyclohexyl)amino)-1H-indol-2-yl)prop-2-yn-1-yl)amino)benzenesulfonamide |
| 1142. | 2-{3-[(4-methanesulfonyl-2-methoxyphenyl)amino]prop-1-yn-1-yl}-N-[(1R,4R)-4-(4-methanesulfonylpiperidin-1-yl)cyclohexyl]-1-(2,2,2-trifluoroethyl)-1H-indol-4-amine |
| 1143. | 2-(3-((2-methoxy-4-(methylsulfonyl)phenyl)amino)prop-1-yn-1-yl)-N-((1S,4S)-4-(4-(methylsulfonyl)piperidin-1-yl)cyclohexyl)-1-(2,2,2-trifluoroethyl)-1H-indol-4-amine |
| 1144. | 3-methoxy-N-methyl-4-{[3-(4-{[(1R,4R)-4-(4-methanesulfonylpiperidin-1-yl)cyclohexyl]amino}-1-(2,2,2-trifluoroethyl)-1H-indol-2-yl)prop-2-yn-1-yl]amino}benzamide |
| 1145. | 3-methoxy-N-methyl-4-((3-(4-(((1S,4S)-4-(4-(methylsulfonyl)piperidin-1-yl)cyclohexyl)amino)-1-(2,2,2-trifluoroethyl)-1H-indol-2-yl)prop-2-yn-1-yl)amino)benzamide |
| 1146. | 3-methoxy-4-{[3-(4-{[(1R,4R)-4-(4-methanesulfonylpiperidin-1-yl)cyclohexyl]amino}-1-(2,2,2-trifluoroethyl)-1H-indol-2-yl)prop-2-yn-1-yl]amino}benzene-1-sulfonamide |
| 1147. | 3-methoxy-4-((3-(4-(((1S,4S)-4-(4-(methylsulfonyl)piperidin-1-yl)cyclohexyl)amino)-1-(2,2,2-trifluoroethyl)-1H-indol-2-yl)prop-2-yn-1-yl)amino)benzenesulfonamide |

TABLE 7-continued

Alkynyl indole compounds of the disclosure.

| Mol # | IUPAC name |
|---|---|
| 1148. | 1-[(1S,3R)-3-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-4,5-dihydro-1H-1,2,3,4-tetrazol-5-one |
| 1149. | 2-(3-((2-methoxy-4-(methylsulfonyl)phenyl)amino)prop-1-yn-1-yl)-N-((1R,4R)-4-morpholinocyclohexyl)-1-(oxiran-2-ylmethyl)-1H-indol-4-amine |
| 1150. | 2-((2-(3-((2-methoxy-4-(methylsulfonyl)phenyl)amino)prop-1-yn-1-yl)-4-(((1R,4R)-4-morpholinocyclohexyl)amino)-1H-indol-1-yl)methyl)acrylonitrile |
| 1151. | N-((1R,4R)-4-(2-oxa-8-azaspiro[4.5]decan-8-yl)cyclohexyl)-2-(3-((2-methoxy-4-(methylsulfonyl)phenyl)amino)prop-1-yn-1-yl)-1-(2,2,2-trifluoroethyl)-1H-benzo[d]imidazol-4-amine |
| 1152. | N-((1S,4S)-4-(2-oxa-8-azaspiro[4.5]decan-8-yl)cyclohexyl)-2-(3-((2-methoxy-4-(methylsulfonyl)phenyl)amino)prop-1-yn-1-yl)-1-(2,2,2-trifluoroethyl)-1H-benzo[d]imidazol-4-amine |
| 1153. | 4-((3-(4-(((1R,4R)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxy-N-methylbenzamide |
| 1154. | 4-((3-(4-(((1S,4S)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxy-N-methylbenzamide |
| 1155. | 1-[1-(2-hydroxyethyl)piperidin-4-yl]-3-(2-{3-[(4-methanesulfonyl-2-methoxyphenyl)amino]prop-1-yn-1-yl}-1-(2,2,2-trifluoroethyl)-1H-indol-4-yl)urea |
| 1156. | 3-methoxy-4-({3-[4-({2-oxaspiro[3.3]heptan-6-yl}amino)-1-(2,2,2-trifluoroethyl)-1H-indol-2-yl]prop-2-yn-1-yl}amino)benzene-1-sulfonamide |
| 1157. | [1-(chloromethyl)-3-[(2-{3-[(4-methanesulfonyl-2-methoxyphenyl)amino]prop-1-yn-1-yl}-1-(2,2,2-trifluoroethyl)-1H-indol-4-yl)amino]cyclobutyl]methanol |
| 1158. | 2-{3-[(4-methanesulfonyl-2-methoxyphenyl)amino]prop-1-yn-1-yl}-N-{2-oxaspiro[3.3]heptan-6-yl}-1-(2,2,2-trifluoroethyl)-1H-indol-4-amine |
| 1159. | 4-({3-[4-({2-azaspiro[3.3]heptan-6-yl}amino)-1-(2,2,2-trifluoroethyl)-1H-indol-2-yl]prop-2-yn-1-yl}amino)-3-methoxybenzene-1-sulfonamide |
| 1160. | N-{2-azaspiro[3.3]heptan-6-yl}-2-{3-[(4-methanesulfonyl-2-methoxyphenyl)amino]prop-1-yn-1-yl}-1-(2,2,2-trifluoroethyl)-1H-indol-4-amine |
| 1161. | 3-methoxy-N-methyl-4-{[3-(4-{[(1R,4R)-4-(methylamino)cyclohexyl]amino}-1-(2,2,2-trifluoroethyl)-1H-indol-2-yl)prop-2-yn-1-yl]amino}benzamide |
| 1162. | 3-methoxy-N-methyl-4-{[3-(4-{[(1R,4R)-4-aminocyclohexyl]amino}-1-(2,2,2-trifluoroethyl)-1H-indol-2-yl)prop-2-yn-1-yl]amino}benzamide |
| 1163. | 3-methoxy-N-methyl-4-{[3-(4-{[(1S,4S)-4-aminocyclohexyl]amino}-1-(2,2,2-trifluoroethyl)-1H-indol-2-yl)prop-2-yn-1-yl]amino}benzamide |
| 1164. | rel-(1R,3R)-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,3-diamine |
| 1165. | rac-(1R,3S)-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,3-diamine |
| 1166. | (1R,2S)-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,2-diamine |
| 1167. | rac-(1R,2S)-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,2-diamine |
| 1168. | rel-(1R,3S)-3-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol |
| 1169. | 3-methoxy-N-methyl-4-{[3-(4-{[(1R,4R)-4-hydroxy-4-methylcyclohexyl]amino}-1-(2,2,2-trifluoroethyl)-1H-indol-2-yl)prop-2-yn-1-yl]amino}benzamide |
| 1170. | 3-methoxy-N-methyl-4-{[3-(4-{[(1S,4S)-4-hydroxy-4-methylcyclohexyl]amino}-1-(2,2,2-trifluoroethyl)-1H-indol-2-yl)prop-2-yn-1-yl]amino}benzamide |
| 1171. | 4-[(3-{4-[(4-cyanocyclohexyl)amino]-1-(2,2,2-trifluoroethyl)-1H-indol-2-yl}prop-2-yn-1-yl)amino]-3-methoxy-N-methylbenzamide |
| 1172. | 3-methoxy-N-methyl-4-{[3-(4-{[(1R,4R)-4-cyanocyclohexyl]amino}-1-(2,2,2-trifluoroethyl)-1H-indol-2-yl)prop-2-yn-1-yl]amino}benzamide |
| 1173. | 3-methoxy-N-methyl-4-{[3-(4-{[(1S,4S)-4-cyanocyclohexyl]amino}-1-(2,2,2-trifluoroethyl)-1H-indol-2-yl)prop-2-yn-1-yl]amino}benzamide |
| 1174. | 3-[(2-{3-[(4-methanesulfonyl-2-methoxyphenyl)amino]prop-1-yn-1-yl}-1-(2,2,2-trifluoroethyl)-1H-indol-4-yl)amino]cyclohexane-1-carboxylic acid |
| 1175. | 2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine |
| 1176. | (1R,2R,4S)-2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine |
| 1177. | 2-fluoro-$N^1$-(2-{3-[(4-methanesulfonyl-2-methoxyphenyl)amino]prop-1-yn-1-yl}-1-(2,2,2-trifluoroethyl)-1H-indol-4-yl)-$N^4$-methylcyclohexane-1,4-diamine |
| 1178. | (1R,2R,4S)-2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)-$N^4$-methylcyclohexane-1,4-diamine |
| 1179. | 2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 1180. | (1R,2R,4S)-2-fluoro-$N^1$-(2-(3-((2-methoxy-4-(methylsulfonyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 1181. | (3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol |
| 1182. | 3-methoxy-4-{[3-(4-{[(1R,4R)-4-[bis(2-hydroxyethyl)amino]cyclohexyl]amino}-1-(2,2,2-trifluoroethyl)-1H-indol-2-yl)prop-2-yn-1-yl]amino}benzene-1-sulfonamide |

TABLE 7-continued

| Mol # | IUPAC name |
|---|---|
| | Alkynyl indole compounds of the disclosure. |
| 1183. | 3-methoxy-4-{[3-(4-{[(1S,4S)-4-[bis(2-hydroxyethyl)amino]cyclohexyl]amino}-1-(2,2,2-trifluoroethyl)-1H-indol-2-yl)prop-2-yn-1-yl]amino}benzene-1-sulfonamide |
| 1184. | 4-((3-(4-(((1R,4R)-4-(dimethylamino)cyclohexyl)amino)-1-(2,2,2-trifluoroethyl)-1H-indol-2-yl)prop-2-yn-1-yl)amino)-3-methoxybenzenesulfonamide |
| 1185. | 4-((3-(4-(((1S,4S)-4-(dimethylamino)cyclohexyl)amino)-1-(2,2,2-trifluoroethyl)-1H-indol-2-yl)prop-2-yn-1-yl)amino)-3-methoxybenzenesulfonamide |
| 1186. | 3-methoxy-N-(1,2-oxazol-3-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 1187. | 3-methoxy-N-(oxan-4-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 1188. | 3-methoxy-N-(1,2-oxazol-3-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 1189. | 3-methoxy-N-(oxan-4-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 1190. | N-(3-(4-(((1S,4S)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 1191. | N-(3-(4-(((1R,4R)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 1192. | 3-methoxy-N-(5-methyl-1,2-oxazol-3-yl)-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 1193. | 3-methoxy-N-(5-methyl-1,2-oxazol-3-yl)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 1194. | (1S,4S)-$N^4$-(2-{3-[(4-methanesulfonyl-2-methoxyphenyl)amino]prop-1-yn-1-yl}-1-(2,2,2-trifluoroethyl)-1H-indol-4-yl)-$N^1$-(2-methoxyethyl)-$N^1$-methylcyclohexane-1,4-diamine |
| 1195. | (1R,4R)-$N^4$-(2-{3-[(4-methanesulfonyl-2-methoxyphenyl)amino]prop-1-yn-1-yl}-1-(2,2,2-trifluoroethyl)-1H-indol-4-yl)-$N^1$-(2-methoxyethyl)-$N^1$-methylcyclohexane-1,4-diamine |
| 1196. | 3-methoxy-4-{[3-(4-{[(1S,4S)-4-[(3S,4S)-3,4-dihydroxypyrrolidin-1-yl]cyclohexyl]amino}-1-(2,2,2-trifluoroethyl)-1H-indol-2-yl)prop-2-yn-1-yl]amino}benzene-1-sulfonamide |
| 1197. | 4-((3-(4-(((1R,4R)-4-((3R,4R)-3,4-dihydroxypyrrolidin-1-yl)cyclohexyl)amino)-1-(2,2,2-trifluoroethyl)-1H-indol-2-yl)prop-2-yn-1-yl)amino)-3-methoxybenzenesulfonamide |
| 1198. | 4-((3-(4-(((1R,4S)-4-((3S,4S)-3,4-dihydroxypyrrolidin-1-yl)cyclohexyl)amino)-1-(2,2,2-trifluoroethyl)-1H-indol-2-yl)prop-2-yn-1-yl)amino)-3-methoxybenzenesulfonamide |
| 1199. | 3-methoxy-4-{[3-(4-{[(1R,4R)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 1200. | 3-methoxy-4-{[3-(4-{[(1S,4S)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 1201. | 4-({3-[4-({1,4-dioxaspiro[4.5]decan-8-yl}amino)-1-(2,2,2-trifluoroethyl)-1H-indol-2-yl]prop-2-yn-1-yl}amino)-3-methoxybenzene-1-sulfonamide |
| 1202. | N-{1,4-dioxaspiro[4.5]decan-8-yl}-2-{3-[(4-methanesulfonyl-2-methoxyphenyl)amino]prop-1-yn-1-yl}-1-(2,2,2-trifluoroethyl)-1H-indol-4-amine |
| 1203. | 3-methoxy-4-[(3-{4-[(4-oxocyclohexyl)amino]-1-(2,2,2-trifluoroethyl)-1H-indol-2-yl}prop-2-yn-1-yl)amino]benzene-1-sulfonamide |
| 1204. | 4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-one |
| 1205. | (1R,4R)-$N^4$-[2-(3-{[2-methoxy-4-(morpholine-4-sulfonyl)phenyl]amino}prop-1-yn-1-yl)-1-(2,2,2-trifluoroethyl)-1H-indol-4-yl]-$N^1$,$N^1$-dimethylcyclohexane-1,4-diamine |
| 1206. | (1S,4S)-$N^4$-[2-(3-{[2-methoxy-4-(morpholine-4-sulfonyl)phenyl]amino}prop-1-yn-1-yl)-1-(2,2,2-trifluoroethyl)-1H-indol-4-yl]-$N^1$,$N^1$-dimethylcyclohexane-1,4-diamine |
| 1207. | N,N-bis(2-hydroxyethyl)-3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 1208. | N,N-bis(2-hydroxyethyl)-3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 1209. | 3-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 1210. | 3-methoxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzene-1-sulfonamide |
| 1211. | 3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1212. | 3-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1213. | 3-methoxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1214. | (1R,4R)-$N^4$-{2-[3-({2-methoxy-4-[(4-methylpiperazin-1-yl)sulfonyl]phenyl}amino)prop-1-yn-1-yl]-1-(2,2,2-trifluoroethyl)-1H-indol-4-yl}-$N^1$,$N^1$-dimethylcyclohexane-1,4-diamine |
| 1215. | (1R,4R)-$N^4$-(2-{3-[(4-methanesulfonyl-2-methoxyphenyl)amino]prop-1-yn-1-yl}-1-[(oxiran-2-yl)methyl]-1H-indol-4-yl)-$N^1$,$N^1$-dimethylcyclohexane-1,4-diamine |

TABLE 7-continued

| Alkynyl indole compounds of the disclosure. | |
|---|---|
| Mol # | IUPAC name |
| 1216. | 2-[(2-{3-[(4-methanesulfonyl-2-methoxyphenyl)amino]prop-1-yn-1-yl}-4-{[(1R,4R)-4-(dimethylamino)cyclohexyl]amino}-1H-indol-1-yl)methyl]prop-2-enenitrile |
| 1217. | 5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenol |
| 1218. | 5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenol |
| 1219. | 2-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenoxy)acetonitrile |
| 1220. | 2-(5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenoxy)acetonitrile |
| 1221. | N-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzenesulfonyl)acetamide |
| 1222. | N-(3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzenesulfonyl)acetamide |
| 1223. | N-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzenesulfonyl)propanamide |
| 1224. | N-(3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzenesulfonyl)propanamide |
| 1225. | 2-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]amino}phenoxy)ethan-1-ol |
| 1226. | 2-(5-methanesulfonyl-2-{[3-(4-{[(1S,4S)-4-(dimethylamino)cyclohexyl]amino}-1-(2,2,2-trifluoroethyl)-1H-indol-2-yl)prop-2-yn-1-yl]amino}phenoxy)ethan-1-ol |
| 1227. | (1R,4R)-$N^4$-[2-(3-{[4-methanesulfonyl-2-(2-methoxyethoxy)phenyl]amino}prop-1-yn-1-yl)-1-(2,2,2-trifluoroethyl)-1H-indol-4-yl]-$N^1$,$N^1$-dimethylcyclohexane-1,4-diamine |
| 1228. | N-(3-(4-(((1R,4R)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide |
| 1229. | N-(3-(4-(((1S,4S)-4-(dimethylamino)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide |
| 1230. | (1R,4R)-$N^4$-[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]-$N^1$,$N^1$-dimethylcyclohexane-1,4-diamine |
| 1231. | (1S,4S)-$N^4$-[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]-$N^1$,$N^1$-dimethylcyclohexane-1,4-diamine |
| 1232. | (1S,4S)-$N^4$-{2-[3-(2-amino-4-methanesulfonylphenoxy)prop-1-yn-1-yl]-1-(2,2,2-trifluoroethyl)-1H-indol-4-yl}-$N^1$,$N^1$-dimethylcyclohexane-1,4-diamine |
| 1233. | (1R,4R)-$N^4$-(2-{3-[(2-ethoxy-4-methanesulfonylphenyl)amino]prop-1-yn-1-yl}-1-(2,2,2-trifluoroethyl)-1H-indol-4-yl)-$N^1$,$N^1$-dimethylcyclohexane-1,4-diamine |
| 1234. | (1S,4S)-$N^4$-(2-{3-[(2-ethoxy-4-methanesulfonylphenyl)amino]prop-1-yn-1-yl}-1-(2,2,2-trifluoroethyl)-1H-indol-4-yl)-$N^1$,$N^1$-dimethylcyclohexane-1,4-diamine |
| 1235. | 3-hydroxy-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1236. | 3-hydroxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1237. | 3-(2-methoxyethoxy)-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1238. | (1R,4R)-$N^4$-{2-[3-(2-amino-4-methanesulfonylphenoxy)prop-1-yn-1-yl]-1-(2,2,2-trifluoroethyl)-1H-indol-4-yl}-$N^1$,$N^1$-dimethylcyclohexane-1,4-diamine |
| 1239. | N-ethyl-3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1240. | N-ethyl-3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1241. | 3-(2-methoxyethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1242. | 3-(2-fluoroethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1243. | 3-(2-fluoroethoxy)-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1244. | 3-(fluoromethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1245. | 3-(fluoromethoxy)-N-methyl-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1246. | (1S,4S)-$N^4$-(2-{3-[4-methanesulfonyl-2-(methylamino)phenoxy]prop-1-yn-1-yl}-1-(2,2,2-trifluoroethyl)-1H-indol-4-yl)-$N^1$,$N^1$-dimethylcyclohexane-1,4-diamine |
| 1247. | (1R,4R)-$N^4$-(2-{3-[4-methanesulfonyl-2-(methylamino)phenoxy]prop-1-yn-1-yl}-1-(2,2,2-trifluoroethyl)-1H-indol-4-yl)-$N^1$,$N^1$-dimethylcyclohexane-1,4-diamine |
| 1248. | 3-methoxy-N-methyl-4-{[3-(4-{[(1S,4S)-4-(methylamino)cyclohexyl]amino}-1-(2,2,2-trifluoroethyl)-1H-indol-2-yl)prop-2-yn-1-yl]amino}benzamide |
| 1249. | (1S,4S)-$N^4$-(2-{3-[2-(dimethylamino)-4-methanesulfonylphenoxy]prop-1-yn-1-yl}-1-(2,2,2-trifluoroethyl)-1H-indol-4-yl)-$N^1$,$N^1$-dimethylcyclohexane-1,4-diamine |
| 1250. | (1R,4R)-$N^4$-(2-{3-[2-(dimethylamino)-4-methanesulfonylphenoxy]prop-1-yn-1-yl}-1-(2,2,2-trifluoroethyl)-1H-indol-4-yl)-$N^1$,$N^1$-dimethylcyclohexane-1,4-diamine |
| 1251. | 3-(cyanomethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1252. | 3-(2-cyanoethoxy)-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |

TABLE 7-continued

| Mol # | IUPAC name |
|---|---|
| Alkynyl indole compounds of the disclosure. | |
| 1253. | N-(5-methanesulfonyl-2-{[3-(4-{[(1R,4R)-4-(dimethylamino)cyclohexyl]amino}-1-(2,2,2-trifluoroethyl)-1H-indol-2-yl)prop-2-yn-1-yl]oxy}phenyl)acetamide |
| 1254. | N-(2-((3-(4-(((1S,4S)-4-(dimethylamino)cyclohexyl)amino)-1-(2,2,2-trifluoroethyl)-1H-indol-2-yl)prop-2-yn-1-yl)oxy)-5-(methylsulfonyl)phenyl)acetamide |
| 1255. | (1R,4R)-$N^1$-(2-(3-((2-(fluoromethoxy)-4-(methylsulfonyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 1256. | (1S,4S)-$N^1$-(2-(3-((2-(fluoromethoxy)-4-(methylsulfonyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 1257. | (1R,4R)-$N^4$-[2-(3-{[4-(ethanesulfonyl)-2-methoxyphenyl]amino}prop-1-yn-1-yl)-1-(2,2,2-trifluoroethyl)-1H-indol-4-yl]-$N^1$,$N^1$-dimethylcyclohexane-1,4-diamine |
| 1258. | (1S,4S)-$N^4$-[2-(3-{[4-(ethanesulfonyl)-2-methoxyphenyl]amino}prop-1-yn-1-yl)-1-(2,2,2-trifluoroethyl)-1H-indol-4-yl]-$N^1$,$N^1$-dimethylcyclohexane-1,4-diamine |
| 1259. | 2-(3-methoxy-4-{[3-(4-{[(1R,4R)-4-(dimethylamino)cyclohexyl]amino}-1-(2,2,2-trifluoroethyl)-1H-indol-2-yl)prop-2-yn-1-yl]amino}phenyl)-2-methylpropanenitrile |
| 1260. | 2-(4-((3-(4-(((1S,4S)-4-(dimethylamino)cyclohexyl)amino)-1-(2,2,2-trifluoroethyl)-1H-indol-2-yl)prop-2-yn-1-yl)amino)-3-methoxyphenyl)-2-methylpropanenitrile |
| 1261. | 3-(cyanomethoxy)-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 1262. | 3-(cyanomethoxy)-4-((3-(4-(((1S,4S)-4-(dimethylamino)cyclohexyl)amino)-1-(2,2,2-trifluoroethyl)-1H-indol-2-yl)prop-2-yn-1-yl)amino)benzenesulfonamide |
| 1263. | 3-(3-(4-(((1R,4R)-4-(dimethylamino)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 1264. | 3-(3-(4-(((1S,4S)-4-(dimethylamino)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 1265. | 3-methoxy-N,N-dimethyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzene-1-sulfonamide |
| 1266. | (1R,4R)-$N^1$-(2-(3-(((3S,4R)-3-methoxytetrahydro-2H-pyran-4-yl)amino)prop-1-yn-1-yl)-1-(2,2,2-trifluoroethyl)-1H-indol-4-yl)-$N^4$,$N^4$-dimethylcyclohexane-1,4-diamine |
| 1267. | (1S,4S)-$N^1$-(2-(3-(((3S,4R)-3-methoxytetrahydro-2H-pyran-4-yl)amino)prop-1-yn-1-yl)-1-(2,2,2-trifluoroethyl)-1H-indol-4-yl)-$N^4$,$N^4$-dimethylcyclohexane-1,4-diamine |
| 1268. | (1R,4R)-$N^4$-(2-{3-[(4-chloro-2-methoxyphenyl)amino]prop-1-yn-1-yl}-1-(2,2,2-trifluoroethyl)-1H-indol-4-yl)-$N^1$,$N^1$-dimethylcyclohexane-1,4-diamine |
| 1269. | (1S,4S)-$N^1$-(2-(3-((4-chloro-2-methoxyphenyl)amino)prop-1-yn-1-yl)-1-(2,2,2-trifluoroethyl)-1H-indol-4-yl)-$N^4$,$N^4$-dimethylcyclohexane-1,4-diamine |
| 1270. | 4-((3-(4-(((1R,4R)-4-(dimethylamino)cyclohexyl)amino)-1-(2,2,2-trifluoroethyl)-1H-indol-2-yl)prop-2-yn-1-yl)amino)-2-fluoro-5-methoxybenzamide |
| 1271. | 4-((3-(4-(((1S,4S)-4-(dimethylamino)cyclohexyl)amino)-1-(2,2,2-trifluoroethyl)-1H-indol-2-yl)prop-2-yn-1-yl)amino)-2-fluoro-5-methoxybenzamide |
| 1272. | (1R,4R)-$N^4$-[2-(3-{[2-methoxy-4-(trifluoromethyl)phenyl]amino}prop-1-yn-1-yl)-1-(2,2,2-trifluoroethyl)-1H-indol-4-yl]-$N^1$,$N^1$-dimethylcyclohexane-1,4-diamine |
| 1273. | (1S,4S)-$N^1$-(2-(3-((2-methoxy-4-(trifluoromethyl)phenyl)amino)prop-1-yn-1-yl)-1-(2,2,2-trifluoroethyl)-1H-indol-4-yl)-$N^4$,$N^4$-dimethylcyclohexane-1,4-diamine |
| 1274. | 2-fluoro-5-methoxy-N-methyl-4-{[3-(4-{[(1R,4R)-4-(dimethylamino)cyclohexyl]amino}-1-(2,2,2-trifluoroethyl)-1H-indol-2-yl)prop-2-yn-1-yl]amino}benzamide |
| 1275. | 4-((3-(4-(((1S,4S)-4-(dimethylamino)cyclohexyl)amino)-1-(2,2,2-trifluoroethyl)-1H-indol-2-yl)prop-2-yn-1-yl)amino)-2-fluoro-5-methoxy-N-methylbenzamide |
| 1276. | (1S,4S)-$N^4$-[2-(3-{[4-methanesulfonyl-2-(trifluoromethyl)phenyl]amino}prop-1-yn-1-yl)-1-(2,2,2-trifluoroethyl)-1H-indol-4-yl]-$N^1$,$N^1$-dimethylcyclohexane-1,4-diamine |
| 1277. | (1R,4R)-$N^4$-[2-(3-{[4-methanesulfonyl-2-(trifluoromethyl)phenyl]amino}prop-1-yn-1-yl)-1-(2,2,2-trifluoroethyl)-1H-indol-4-yl]-$N^1$,$N^1$-dimethylcyclohexane-1,4-diamine |
| 1278. | (1R,4R)-$N^4$-(2-{3-[(4-methanesulfonyl-2-methylphenyl)amino]prop-1-yn-1-yl}-1-(2,2,2-trifluoroethyl)-1H-indol-4-yl)-$N^1$,$N^1$-dimethylcyclohexane-1,4-diamine |
| 1279. | (1S,4S)-$N^1$,$N^1$-dimethyl-$N^4$-(2-(3-((2-methyl-4-(methylsulfonyl)phenyl)amino)prop-1-yn-1-yl)-1-(2,2,2-trifluoroethyl)-1H-indol-4-yl)cyclohexane-1,4-diamine |
| 1280. | (1R,4R)-$N^4$-[2-(3-{[4-methanesulfonyl-2-(trifluoromethoxy)phenyl]amino}prop-1-yn-1-yl)-1-(2,2,2-trifluoroethyl)-1H-indol-4-yl]-$N^1$,$N^1$-dimethylcyclohexane-1,4-diamine |
| 1281. | (1S,4S)-$N^1$,$N^1$-dimethyl-$N^4$-(2-(3-((4-(methylsulfonyl)-2-(trifluoromethoxy)phenyl)amino)prop-1-yn-1-yl)-1-(2,2,2-trifluoroethyl)-1H-indol-4-yl)cyclohexane-1,4-diamine |
| 1282. | 3-methoxy-N-methyl-4-{[3-(4-{[(1R,4R)-4-(diethylamino)cyclohexyl]amino}-1-(2,2,2-trifluoroethyl)-1H-indol-2-yl)prop-2-yn-1-yl]amino}benzamide |
| 1283. | 4-((3-(4-(((1S,4S)-4-(diethylamino)cyclohexyl)amino)-1-(2,2,2-trifluoroethyl)-1H-indol-2-yl)prop-2-yn-1-yl)amino)-3-methoxy-N-methylbenzamide |
| 1284. | 3-methoxy-4-{[3-(4-{[(1R,4R)-4-(diethylamino)cyclohexyl]amino}-1-(2,2,2-trifluoroethyl)-1H-indol-2-yl)prop-2-yn-1-yl]amino}benzene-1-sulfonamide |
| 1285. | 4-((3-(4-(((1S,4S)-4-(diethylamino)cyclohexyl)amino)-1-(2,2,2-trifluoroethyl)-1H-indol-2-yl)prop-2-yn-1-yl)amino)-3-methoxybenzenesulfonamide |
| 1286. | 3-methoxy-N-methyl-4-{[3-(4-{[(1R,4R)-4-(diethylamino)cyclohexyl]amino}-1-(2,2,2-trifluoroethyl)-1H-indol-2-yl)prop-2-yn-1-yl]amino}benzene-1-sulfonamide |
| 1287. | 2-(5-methanesulfonyl-2-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}phenoxy)acetonitrile |
| 1288. | 2-(5-methanesulfonyl-2-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}phenoxy)acetonitrile |

TABLE 7-continued

| Mol # | IUPAC name |
|---|---|
| | Alkynyl indole compounds of the disclosure. |
| 1289. | 3-methoxy-N-methyl-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 1290. | 3-methoxy-N-methyl-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 1291. | N-ethyl-3-methoxy-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 1292. | N-ethyl-3-methoxy-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)benzamide |
| 1293. | (1R,4R)-$N^1$-(2-(3-((2-(fluoromethoxy)-4-(methylsulfonyl)phenyl)amino)prop-1-yn-1-yl)-1-(2,2,2-trifluoroethyl)-1H-indol-4-yl)-$N^4$-(2-methoxyethyl)-$N^4$-methylcyclohexane-1,4-diamine |
| 1294. | (1S,4S)-$N^1$-(2-(3-((2-(fluoromethoxy)-4-(methylsulfonyl)phenyl)amino)prop-1-yn-1-yl)-1-(2,2,2-trifluoroethyl)-1H-indol-4-yl)-$N^4$-(2-methoxyethyl)-$N^4$-methylcyclohexane-1,4-diamine |
| 1295. | 3-(fluoromethoxy)-N-methyl-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 1296. | 3-(fluoromethoxy)-N-methyl-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzamide |
| 1297. | 3-(fluoromethoxy)-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)-N-methylbenzamide |
| 1298. | 3-methoxy-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 1299. | 3-methoxy-4-((3-(4-(((1S,4S)-4-((2-methoxyethyl)(methyl)amino)cyclohexyl)amino)-1-(2,2,2-trifluoroethyl)-1H-indol-2-yl)prop-2-yn-1-yl)amino)benzenesulfonamide |
| 1300. | (1R,4R)-$N^1$,$N^1$-diethyl-$N^4$-(2-{3-[(4-methanesulfonyl-2-methoxyphenyl)amino]prop-1-yn-1-yl}-1-(2,2,2-trifluoroethyl)-1H-indol-4-yl)cyclohexane-1,4-diamine |
| 1301. | (1S,4S)-$N^1$,$N^1$-diethyl-$N^4$-(2-(3-((2-methoxy-4-(methylsulfonyl)phenyl)amino)prop-1-yn-1-yl)-1-(2,2,2-trifluoroethyl)-1H-indol-4-yl)cyclohexane-1,4-diamine |
| 1302. | 3-(cyanomethoxy)-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 1303. | 3-(cyanomethoxy)-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 1304. | 3-(fluoromethoxy)-4-{[3-(4-{[(1R,4R)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 1305. | 3-(fluoromethoxy)-4-{[3-(4-{[(1S,4S)-4-[bis(2-methoxyethyl)amino]cyclohexyl]amino}-1-(2,2,2-trifluoroethyl)-1H-indol-2-yl)prop-2-yn-1-yl]amino}benzene-1-sulfonamide |
| 1306. | 3-(fluoromethoxy)-4-{[3-(4-{[(1R,4R)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 1307. | 3-(fluoromethoxy)-4-{[3-(4-{[(1S,4S)-4-[(2-methoxyethyl)(methyl)amino]cyclohexyl]amino}-1-(2,2,2-trifluoroethyl)-1H-indol-2-yl)prop-2-yn-1-yl]amino}benzene-1-sulfonamide |
| 1308. | 3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide |
| 1309. | 3-methoxy-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzamide |
| 1310. | 3-methoxy-N-methyl-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide |
| 1311. | 3-methoxy-N-methyl-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzamide |
| 1312. | 2-(2-{3-[(4-methanesulfonyl-2-methoxyphenyl)amino]prop-1-yn-1-yl}-4-{[(1R,4R)-4-(morpholin-4-yl)cyclohexyl]amino}-1H-indol-1-yl)acetonitrile |
| 1313. | 4-({3-[1-(2-fluoroethyl)-4-{[(1R,4R)-4-(morpholin-4-yl)cyclohexyl]amino}-1H-indol-2-yl]prop-2-yn-1-yl}amino)-3-methoxy-N-methylbenzamide |
| 1314. | 1-(2-fluoroethyl)-2-{3-[(4-methanesulfonyl-2-methoxyphenyl)amino]prop-1-yn-1-yl}-N-[(1R,4R)-4-(morpholin-4-yl)cyclohexyl]-1H-indol-4-amine |
| 1315. | 4-({3-[1-(cyanomethyl)-4-{[(1R,4R)-4-(morpholin-4-yl)cyclohexyl]amino}-1H-indol-2-yl]prop-2-yn-1-yl}amino)-3-methoxy-N-methylbenzamide |
| 1316. | 2-{3-[(4-methanesulfonyl-2-methoxyphenyl)amino]prop-1-yn-1-yl}-1-propyl-N-[(1R,4R)-4-(morpholin-4-yl)cyclohexyl]-1H-indol-4-amine |
| 1317. | 2-{3-[(4-methanesulfonyl-2-methoxyphenyl)amino]prop-1-yn-1-yl}-1-(2-methylpropyl)-N-[(1R,4R)-4-(morpholin-4-yl)cyclohexyl]-1H-indol-4-amine |
| 1318. | 1-(2,2-difluoroethyl)-2-{3-[(4-methanesulfonyl-2-methoxyphenyl)amino]prop-1-yn-1-yl}-N-[(1R,4R)-4-(morpholin-4-yl)cyclohexyl]-1H-indol-4-amine |
| 1319. | 3-methoxy-4-((3-(4-(((1R,4R)-4-morpholinocyclohexyl)amino)-1-(2,2,2-trifluoroethyl)-1H-indol-2-yl)prop-2-yn-1-yl)amino)benzenesulfonamide |

TABLE 7-continued

Alkynyl indole compounds of the disclosure.

| Mol # | IUPAC name |
|---|---|
| 1320. | 3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzenesulfonamide |
| 1321. | N-ethyl-3-methoxy-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzamide |
| 1322. | N-ethyl-3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzamide |
| 1323. | 2-(5-methanesulfonyl-2-{[3-(4-{[(1R,4R)-4-(morpholin-4-yl)cyclohexyl]amino}-1-(2,2,2-trifluoroethyl)-1H-indol-2-yl)prop-2-yn-1-yl]amino}phenoxy)acetonitrile |
| 1324. | 2-(5-methanesulfonyl-2-{[3-(4-{[(1S,4S)-4-(morpholin-4-yl)cyclohexyl]amino}-1-(2,2,2-trifluoroethyl)-1H-indol-2-yl)prop-2-yn-1-yl]amino}phenoxy)acetonitrile |
| 1325. | 3-methoxy-N-methyl-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1326. | 2-{3-[(4-methanesulfonyl-2-methoxyphenyl)amino]prop-1-yn-1-yl}-N-[(1R,4R)-4-(3-methanesulfonylazetidin-1-yl)cyclohexyl]-1-(2,2,2-trifluoroethyl)-1H-indol-4-amine |
| 1327. | 2-(3-((2-methoxy-4-(methylsulfonyl)phenyl)amino)prop-1-yn-1-yl)-N-((1S,4S)-4-(3-(methylsulfonyl)azetidin-1-yl)cyclohexyl)-1-(2,2,2-trifluoroethyl)-1H-indol-4-amine |
| 1328. | 3-methoxy-4-{[3-(4-{[(1R,4R)-4-(3-methanesulfonylazetidin-1-yl)cyclohexyl]amino}-1-(2,2,2-trifluoroethyl)-1H-indol-2-yl)prop-2-yn-1-yl]amino}benzene-1-sulfonamide |
| 1329. | 3-methoxy-4-((3-(4-(((1S,4S)-4-(3-(methylsulfonyl)azetidin-1-yl)cyclohexyl)amino)-1-(2,2,2-trifluoroethyl)-1H-indol-2-yl)prop-2-yn-1-yl)amino)benzenesulfonamide |
| 1330. | 3-methoxy-N-methyl-4-{[3-(4-{[(1R,4R)-4-(3-methanesulfonylazetidin-1-yl)cyclohexyl]amino}-1-(2,2,2-trifluoroethyl)-1H-indol-2-yl)prop-2-yn-1-yl]amino}benzamide |
| 1331. | 3-methoxy-N-methyl-4-((3-(4-(((1S,4S)-4-(3-(methylsulfonyl)azetidin-1-yl)cyclohexyl)amino)-1-(2,2,2-trifluoroethyl)-1H-indol-2-yl)prop-2-yn-1-yl)amino)benzamide |
| 1332. | 2-{3-[(4-methanesulfonyl-2-methoxyphenyl)amino]prop-1-yn-1-yl}-N-[(1R,4R)-4-{2-azaspiro[3.3]heptan-2-yl}cyclohexyl]-1-(2,2,2-trifluoroethyl)-1H-indol-4-amine |
| 1333. | N-((1S,4S)-4-(2-azaspiro[3.3]heptan-2-yl)cyclohexyl)-2-(3-((2-methoxy-4-(methylsulfonyl)phenyl)amino)prop-1-yn-1-yl)-1-(2,2,2-trifluoroethyl)-1H-indol-4-amine |
| 1334. | 3-methoxy-N-methyl-4-{[3-(4-{[(1R,4R)-4-{2-azaspiro[3.3]heptan-2-yl}cyclohexyl]amino}-1-(2,2,2-trifluoroethyl)-1H-indol-2-yl)prop-2-yn-1-yl]amino}benzamide |
| 1335. | 4-((3-(4-(((1S,4S)-4-(2-azaspiro[3.3]heptan-2-yl)cyclohexyl)amino)-1-(2,2,2-trifluoroethyl)-1H-indol-2-yl)prop-2-yn-1-yl)amino)-3-methoxy-N-methylbenzamide |
| 1336. | 3-methoxy-4-{[3-(4-{[(1R,4R)-4-{2-azaspiro[3.3]heptan-2-yl}cyclohexyl]amino}-1-(2,2,2-trifluoroethyl)-1H-indol-2-yl)prop-2-yn-1-yl]amino}benzene-1-sulfonamide |
| 1337. | 4-((3-(4-(((1S,4S)-4-(2-azaspiro[3.3]heptan-2-yl)cyclohexyl)amino)-1-(2,2,2-trifluoroethyl)-1H-indol-2-yl)prop-2-yn-1-yl)amino)-3-methoxybenzenesulfonamide |
| 1338. | 2-(3-((2-methoxy-4-(methylsulfonyl)phenyl)amino)prop-1-yn-1-yl)-N-(2-azaspiro[3.3]heptan-6-yl)-1-(2,2,2-trifluoroethyl)-1H-indol-4-amine |
| 1339. | 4-((3-(4-((2-azaspiro[3.3]heptan-6-yl)amino)-1-(2,2,2-trifluoroethyl)-1H-indol-2-yl)prop-2-yn-1-yl)amino)-3-methoxybenzenesulfonamide |
| 1340. | 2-{3-[(4-methanesulfonyl-2-methoxyphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 1341. | 2-{3-[(4-methanesulfonyl-2-methoxyphenyl)amino]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine |
| 1342. | 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 1343. | 3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 1344. | N-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)propanamide |
| 1345. | N-(3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)propanamide |
| 1346. | N-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)acetamide |
| 1347. | N-(3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzenesulfonyl)acetamide |
| 1348. | N-((1R,4R)-4-(2-oxa-6-azaspiro[3.3]heptan-6-yl)cyclohexyl)-2-(3-((2-(2-fluoroethoxy)-4-(methylsulfonyl)phenyl)amino)prop-1-yn-1-yl)-1-(2,2,2-trifluoroethyl)-1H-indol-4-amine |
| 1349. | N-((1S,4S)-4-(2-oxa-6-azaspiro[3.3]heptan-6-yl)cyclohexyl)-2-(3-((2-(2-fluoroethoxy)-4-(methylsulfonyl)phenyl)amino)prop-1-yn-1-yl)-1-(2,2,2-trifluoroethyl)-1H-indol-4-amine |
| 1350. | 3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1351. | 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1352. | 5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenol |

TABLE 7-continued

| Alkynyl indole compounds of the disclosure. | |
|---|---|
| Mol # | IUPAC name |
| 1353. | 5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenol |
| 1354. | N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 1355. | N-(3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)propionamide |
| 1356. | N-(2-hydroxy-4-methanesulfonylphenyl)-2-methyl-N-[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]propanamide |
| 1357. | N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)isobutyramide |
| 1358. | 2-(3-{[4-methanesulfonyl-2-(2-methoxyethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 1359. | 2-(3-{[4-methanesulfonyl-2-(2-methoxyethoxy)phenyl]amino}prop-1-yn-1-yl)-N-[(1S,4S)-4-{2-oxa-6-azaspiro[3.3]heptan-6-yl}cyclohexyl]-1-(2,2,2-trifluoroethyl)-1H-indol-4-amine |
| 1360. | 2-(5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)acetonitrile |
| 1361. | 2-(5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)acetonitrile |
| 1362. | 5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl 2-methylpropanoate |
| 1363. | 2-(5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)ethan-1-ol |
| 1364. | 2-(5-methanesulfonyl-2-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenoxy)ethan-1-ol |
| 1365. | N-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-N-(2-hydroxy-4-(methylsulfonyl)phenyl)acetamide |
| 1366. | 5-methanesulfonyl-2-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl 2-methylpropanoate |
| 1367. | 3-methoxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1368. | 3-methoxy-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1369. | 2-(3-{[4-methanesulfonyl-2-(2,2,2-trifluoroethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 1370. | 2-(3-{[4-methanesulfonyl-2-(2,2,2-trifluoroethoxy)phenyl]amino}prop-1-yn-1-yl)-N-[(1S,4S)-4-{2-oxa-6-azaspiro[3.3]heptan-6-yl}cyclohexyl]-1-(2,2,2-trifluoroethyl)-1H-indol-4-amine |
| 1371. | 2-[3-(2-amino-4-methanesulfonylphenoxy)prop-1-yn-1-yl]-N-[(1S,4S)-4-{2-oxa-6-azaspiro[3.3]heptan-6-yl}cyclohexyl]-1-(2,2,2-trifluoroethyl)-1H-indol-4-amine |
| 1372. | 2-{3-[(2-ethoxy-4-methanesulfonylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 1373. | 2-{3-[(2-ethoxy-4-methanesulfonylphenyl)amino]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine |
| 1374. | 3-(2-methoxyethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1375. | 3-(2-methoxyethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1376. | N-ethyl-3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1377. | N-ethyl-3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1378. | 3-(2-fluoroethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |

TABLE 7-continued

| Alkynyl indole compounds of the disclosure. | |
|---|---|
| Mol # | IUPAC name |
| 1379. | 3-(2-fluoroethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1380. | 3-(cyanomethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1381. | 3-(cyanomethoxy)-N-methyl-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1382. | 2-{3-[4-methanesulfonyl-2-(methylamino)phenoxy]prop-1-yn-1-yl}-N-[(1S,4S)-4-{2-oxa-6-azaspiro[3.3]heptan-6-yl}cyclohexyl]-1-(2,2,2-trifluoroethyl)-1H-indol-4-amine |
| 1383. | 2-{3-[4-methanesulfonyl-2-(methylamino)phenoxy]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 1384. | 2-[3-(2-amino-4-methanesulfonylphenoxy)prop-1-yn-1-yl]-N-[(1R,4R)-4-{2-oxa-6-azaspiro[3.3]heptan-6-yl}cyclohexyl]-1-(2,2,2-trifluoroethyl)-1H-indol-4-amine |
| 1385. | N-((1R,4R)-4-(2-oxa-6-azaspiro[3.3]heptan-6-yl)cyclohexyl)-2-(3-(2-amino-4-(methylsulfonyl)phenoxy)prop-1-yn-1-yl)-1-(2,2,2-trifluoroethyl)-1H-indol-4-amine |
| 1386. | 3-hydroxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1387. | 3-methoxy-4-[(3-{4-[(4-{2-oxa-6-azaspiro[3.3]heptan-6-yl}cyclohexyl)amino]-1-(2,2,2-trifluoroethyl)-1H-indol-2-yl}prop-2-yn-1-yl)amino]benzonitrile |
| 1388. | 3-methoxy-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzonitrile |
| 1389. | 2-(3-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}phenyl)-2-methylpropanenitrile |
| 1390. | 2-(4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxyphenyl)-2-methylpropanenitrile |
| 1391. | 3-(fluoromethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1392. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(fluoromethoxy)-N-methylbenzamide |
| 1393. | 3-(2-cyanoethoxy)-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1394. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(2-cyanoethoxy)-N-methylbenzamide |
| 1395. | 2-(3-{[2-(fluoromethoxy)-4-methanesulfonylphenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 1396. | N-((1S,4S)-4-(2-oxa-6-azaspiro[3.3]heptan-6-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine |
| 1397. | 3-(cyanomethoxy)-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 1398. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-(cyanomethoxy)benzenesulfonamide |
| 1399. | 3-(fluoromethoxy)-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 1400. | 3-(fluoromethoxy)-4-{[3-(4-{[(1S,4S)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzene-1-sulfonamide |
| 1401. | 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N-methylbenzenesulfonamide |
| 1402. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N-methylbenzenesulfonamide |
| 1403. | N-((1R,4R)-4-(2-oxa-6-azaspiro[3.3]heptan-6-yl)cyclohexyl)-2-(3-((4-chloro-2-methoxyphenyl)amino)prop-1-yn-1-yl)-1-(2,2,2-trifluoroethyl)-1H-indol-4-amine |
| 1404. | N-((1S,4S)-4-(2-oxa-6-azaspiro[3.3]heptan-6-yl)cyclohexyl)-2-(3-((4-chloro-2-methoxyphenyl)amino)prop-1-yn-1-yl)-1-(2,2,2-trifluoroethyl)-1H-indol-4-amine |
| 1405. | 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N,N-dimethylbenzenesulfonamide |
| 1406. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxy-N,N-dimethylbenzenesulfonamide |

TABLE 7-continued

| Mol # | IUPAC name |
|---|---|
| Alkynyl indole compounds of the disclosure. | |
| 1407. | N-((1R,4R)-4-(2-oxa-6-azaspiro[3.3]heptan-6-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 1408. | N-((1S,4S)-4-(2-oxa-6-azaspiro[3.3]heptan-6-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 1409. | N-((1R,4R)-4-(2-oxa-6-azaspiro[3.3]heptan-6-yl)cyclohexyl)-2-(3-(((3S,4R)-3-methoxytetrahydro-2H-pyran-4-yl)amino)prop-1-yn-1-yl)-1-(2,2,2-trifluoroethyl)-1H-indol-4-amine |
| 1410. | N-((1S,4S)-4-(2-oxa-6-azaspiro[3.3]heptan-6-yl)cyclohexyl)-2-(3-(((3S,4R)-3-methoxytetrahydro-2H-pyran-4-yl)amino)prop-1-yn-1-yl)-1-(2,2,2-trifluoroethyl)-1H-indol-4-amine |
| 1411. | 2-fluoro-5-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1412. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxybenzamide |
| 1413. | 2-fluoro-5-methoxy-N-methyl-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzamide |
| 1414. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxy-N-methylbenzamide |
| 1415. | 2-(3-{[2-methoxy-4-(trifluoromethyl)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 1416. | N-((1S,4S)-4-(2-oxa-6-azaspiro[3.3]heptan-6-yl)cyclohexyl)-2-(3-((2-methoxy-4-(trifluoromethyl)phenyl)amino)prop-1-yn-1-yl)-1-(2,2,2-trifluoroethyl)-1H-indol-4-amine |
| 1417. | 4-((3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxybenzoic acid |
| 1418. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-3-methoxybenzoic acid |
| 1419. | 2-fluoro-5-methoxy-4-{[3-(4-{[(1R,4R)-4-{2-oxa-6-azaspiro[3.3]heptan-6-yl}cyclohexyl]amino}-1-(2,2,2-trifluoroethyl)-1H-indol-2-yl)prop-2-yn-1-yl]amino}benzoic acid |
| 1420. | 4-((3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)amino)-2-fluoro-5-methoxybenzoic acid |
| 1421. | 2-{3-[(4-methanesulfonyl-2-methylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 1422. | N-((1S,4S)-4-(2-oxa-6-azaspiro[3.3]heptan-6-yl)cyclohexyl)-2-(3-((2-methyl-4-(methylsulfonyl)phenyl)amino)prop-1-yn-1-yl)-1-(2,2,2-trifluoroethyl)-1H-indol-4-amine |
| 1423. | 2-(3-{[4-methanesulfonyl-2-(trifluoromethoxy)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 1424. | N-((1S,4S)-4-(2-oxa-6-azaspiro[3.3]heptan-6-yl)cyclohexyl)-2-(3-((4-(methylsulfonyl)-2-(trifluoromethoxy)phenyl)amino)prop-1-yn-1-yl)-1-(2,2,2-trifluoroethyl)-1H-indol-4-amine |
| 1425. | 2-(3-{[4-methanesulfonyl-2-(trifluoromethyl)phenyl]amino}prop-1-yn-1-yl)-N-[(1R,4R)-4-{2-oxa-6-azaspiro[3.3]heptan-6-yl}cyclohexyl]-1-(2,2,2-trifluoroethyl)-1H-indol-4-amine |
| 1426. | N-((1S,4S)-4-(2-oxa-6-azaspiro[3.3]heptan-6-yl)cyclohexyl)-2-(3-((4-(methylsulfonyl)-2-(trifluoromethyl)phenyl)amino)prop-1-yn-1-yl)-1-(2,2,2-trifluoroethyl)-1H-indol-4-amine |
| 1427. | 2-{3-[(2-chloro-4-methanesulfonylphenyl)amino]prop-1-yn-1-yl}-N-[(1R,4R)-4-{2-oxa-6-azaspiro[3.3]heptan-6-yl}cyclohexyl]-1-(2,2,2-trifluoroethyl)-1H-indol-4-amine |
| 1428. | N-((1S,4S)-4-(2-oxa-6-azaspiro[3.3]heptan-6-yl)cyclohexyl)-2-(3-((2-chloro-4-(methylsulfonyl)phenyl)amino)prop-1-yn-1-yl)-1-(2,2,2-trifluoroethyl)-1H-indol-4-amine |
| 1429. | 3-(3-(4-(((1R,4R)-4-(2-oxa-6-azaspiro[3.3]heptan-6-yl)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 1430. | 3-(3-(4-(((1S,4S)-4-(2-oxa-6-azaspiro[3.3]heptan-6-yl)cyclohexyl)amino)-1-(2,2,2-trifluoroethyl)-1H-indol-2-yl)prop-2-yn-1-yl)-6-(methylsulfonyl)benzo[d]oxazol-2(3H)-one |
| 1431. | 2-{3-[(4-methanesulfonyl-2-methoxyphenyl)amino]prop-1-yn-1-yl}-N-[(1S,4S)-4-{7-oxa-2-azaspiro[3.5]nonan-2-yl}cyclohexyl]-1-(2,2,2-trifluoroethyl)-1H-indol-4-amine |
| 1432. | 2-{3-[(4-methanesulfonyl-2-methoxyphenyl)amino]prop-1-yn-1-yl}-N-[(1R,4R)-4-{7-oxa-2-azaspiro[3.5]nonan-2-yl}cyclohexyl]-1-(2,2,2-trifluoroethyl)-1H-indol-4-amine |
| 1433. | 3-methoxy-N-methyl-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1434. | 3-methoxy-N-methyl-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1435. | 3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1436. | 3-methoxy-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1437. | 3-(cyanomethoxy)-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |

TABLE 7-continued

| Mol # | IUPAC name |
|---|---|
| Alkynyl indole compounds of the disclosure. | |
| 1438. | 3-(cyanomethoxy)-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1439. | 2-(3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenyl)-2-methylpropanenitrile |
| 1440. | 2-(4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)-2-methylpropanenitrile |
| 1441. | 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetonitrile |
| 1442. | 2-(5-methanesulfonyl-2-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetonitrile |
| 1443. | N-((4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)acetamide |
| 1444. | N-((4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)acetamide |
| 1445. | N-((4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)-2-aminoacetamide |
| 1446. | N-((4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxyphenyl)sulfonyl)-2-aminoacetamide |
| 1447. | methyl 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetate |
| 1448. | methyl 2-(2-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetate |
| 1449. | 2-(5-methanesulfonyl-2-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}phenoxy)acetic acid |
| 1450. | 2-(2-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-5-(methylsulfonyl)phenoxy)acetic acid |
| 1451. | 2-{3-[(4-methanesulfonyl-2-methoxyphenyl)amino]prop-1-yn-1-yl}-N-[(1R,4R)-4-{2-oxa-7-azaspiro[3.5]nonan-7-yl}cyclohexyl]-1-(2,2,2-trifluoroethyl)-1H-indol-4-amine |
| 1452. | 2-(3-{[4-(ethanesulfonyl)-2-methoxyphenyl]amino}prop-1-yn-1-yl)-N-[(1R,4R)-4-{7-oxa-2-azaspiro[3.5]nonan-2-yl}cyclohexyl]-1-(2,2,2-trifluoroethyl)-1H-indol-4-amine |
| 1453. | 2-(3-{[4-(ethanesulfonyl)-2-methoxyphenyl]amino}prop-1-yn-1-yl)-N-[(1S,4S)-4-{7-oxa-2-azaspiro[3.5]nonan-2-yl}cyclohexyl]-1-(2,2,2-trifluoroethyl)-1H-indol-4-amine |
| 1454. | 3-(fluoromethoxy)-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1455. | 3-(fluoromethoxy)-4-{[3-(4-{[(1S,4S)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1456. | 3-methoxy-N-methyl-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1457. | 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzamide |
| 1458. | 3-methoxy-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzene-1-sulfonamide |
| 1459. | 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzenesulfonamide |
| 1460. | 2-{3-[(4-methanesulfonyl-2-methoxyphenyl)amino]prop-1-yn-1-yl}-N-[(1R,4R)-4-{6-oxa-2-azaspiro[3.5]nonan-2-yl}cyclohexyl]-1-(2,2,2-trifluoroethyl)-1H-indol-4-amine |
| 1461. | N-((1S,4S)-4-(6-oxa-2-azaspiro[3.5]nonan-2-yl)cyclohexyl)-2-(3-((2-methoxy-4-(methylsulfonyl)phenyl)amino)prop-1-yn-1-yl)-1-(2,2,2-trifluoroethyl)-1H-indol-4-amine |
| 1462. | N-((1R,4R)-4-(7-oxa-2-azaspiro[3.5]nonan-2-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine |
| 1463. | N-((1S,4S)-4-(7-oxa-2-azaspiro[3.5]nonan-2-yl)cyclohexyl)-2-(3-((2-(fluoromethoxy)-4-(methylsulfonyl)phenyl)amino)prop-1-yn-1-yl)-1-(2,2,2-trifluoroethyl)-1H-indol-4-amine |
| 1464. | 4-(3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)-7-(methylsulfonyl)-2H-benzo[b][1,4]oxazin-3(4H)-one |
| 1465. | 4-((3-(4-(((1R,4R)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzenesulfonamide |

TABLE 7-continued

Alkynyl indole compounds of the disclosure.

| Mol # | IUPAC name |
|---|---|
| 1466. | 4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxy-N-methylbenzenesulfonamide |
| 1467. | N-((1R,4R)-4-(7-oxa-2-azaspiro[3.5]nonan-2-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine |
| 1468. | N-((1S,4S)-4-(7-oxa-2-azaspiro[3.5]nonan-2-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine |
| 1469. | 3-methoxy-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1470. | 4-((3-(4-(((1S,4S)-4-(7-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzamide |
| 1471. | 3-methoxy-4-{[3-(4-{[(1R,4R)-4-{6-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1472. | 4-((3-(4-(((1S,4S)-4-(6-oxa-2-azaspiro[3.5]nonan-2-yl)cyclohexyl)amino)-1-(2,2,2-trifluoroethyl)-1H-indol-2-yl)prop-2-yn-1-yl)amino)-3-methoxybenzamide |
| 1473. | 2-fluoro-5-methoxy-N-methyl-4-{[3-(4-{[(1R,4R)-4-{7-oxa-2-azaspiro[3.5]nonan-2-yl}cyclohexyl]amino}-1-(2,2,2-trifluoroethyl)-1H-indol-2-yl)prop-2-yn-1-yl]amino}benzamide |
| 1474. | 2-(3-((2-methoxy-4-(methylsulfonyl)phenyl)amino)prop-1-yn-1-yl)-N-((1R,4R)-4-(3-methoxypyrrolidin-1-yl)cyclohexyl)-1-(2,2,2-trifluoroethyl)-1H-indol-4-amine |
| 1475. | 2-(3-((2-methoxy-4-(methylsulfonyl)phenyl)amino)prop-1-yn-1-yl)-N-((1S,4S)-4-(3-methoxypyrrolidin-1-yl)cyclohexyl)-1-(2,2,2-trifluoroethyl)-1H-indol-4-amine |
| 1476. | 3-methoxy-4-((3-(4-(((1R,4R)-4-(3-methoxypyrrolidin-1-yl)cyclohexyl)amino)-1-(2,2,2-trifluoroethyl)-1H-indol-2-yl)prop-2-yn-1-yl)amino)benzenesulfonamide |
| 1477. | 3-methoxy-4-((3-(4-(((1S,4S)-4-(3-methoxypyrrolidin-1-yl)cyclohexyl)amino)-1-(2,2,2-trifluoroethyl)-1H-indol-2-yl)prop-2-yn-1-yl)amino)benzenesulfonamide |
| 1478. | 2-(3-{[2-(fluoromethoxy)-4-methanesulfonylphenyl]amino}prop-1-yn-1-yl)-N-[(1R,4R)-4-(morpholin-4-yl)cyclohexyl]-1-(2,2,2-trifluoroethyl)-1H-indol-4-amine |
| 1479. | 2-(3-{[2-(fluoromethoxy)-4-methanesulfonylphenyl]amino}prop-1-yn-1-yl)-N-[(1S,4S)-4-(morpholin-4-yl)cyclohexyl]-1-(2,2,2-trifluoroethyl)-1H-indol-4-amine |
| 1480. | 3-(cyanomethoxy)-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1481. | 3-(cyanomethoxy)-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1482. | 3-(fluoromethoxy)-4-{[3-(4-{[(1R,4R)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1483. | 3-(fluoromethoxy)-4-{[3-(4-{[(1S,4S)-4-(morpholin-4-yl)cyclohexyl]amino}-1-(2,2,2-trifluoroethyl)-1H-indol-2-yl)prop-2-yn-1-yl]amino}benzene-1-sulfonamide |
| 1484. | 2-(3-((2-ethoxy-4-(methylsulfonyl)phenyl)amino)prop-1-yn-1-yl)-N-((1R,4R)-4-morpholinocyclohexyl)-1-(2,2,2-trifluoroethyl)-1H-indol-4-amine |
| 1485. | 2-(3-((2-ethoxy-4-(methylsulfonyl)phenyl)amino)prop-1-yn-1-yl)-N-((1S,4S)-4-morpholinocyclohexyl)-1-(2,2,2-trifluoroethyl)-1H-indol-4-amine |
| 1486. | 2-{3-[(4-methanesulfonyl-2-methoxyphenyl)amino]prop-1-yn-1-yl}-N-[(1R,4R)-4-(3-methoxypiperidin-1-yl)cyclohexyl]-1-(2,2,2-trifluoroethyl)-1H-indol-4-amine |
| 1487. | 2-(3-((2-methoxy-4-(methylsulfonyl)phenyl)amino)prop-1-yn-1-yl)-N-((1S,4S)-4-(3-methoxypiperidin-1-yl)cyclohexyl)-1-(2,2,2-trifluoroethyl)-1H-indol-4-amine |
| 1488. | 2-{3-[(4-methanesulfonyl-2-methoxyphenyl)amino]prop-1-yn-1-yl}-N-[(1R,4R)-4-(4-methoxypiperidin-1-yl)cyclohexyl]-1-(2,2,2-trifluoroethyl)-1H-indol-4-amine |
| 1489. | 2-(3-((2-methoxy-4-(methylsulfonyl)phenyl)amino)prop-1-yn-1-yl)-N-((1S,4S)-4-(4-methoxypiperidin-1-yl)cyclohexyl)-1-(2,2,2-trifluoroethyl)-1H-indol-4-amine |
| 1490. | 3-methoxy-N-methyl-4-{[3-(4-{[(1R,4R)-4-(4-methoxypiperidin-1-yl)cyclohexyl]amino}-1-(2,2,2-trifluoroethyl)-1H-indol-2-yl)prop-2-yn-1-yl]amino}benzamide |
| 1491. | 3-methoxy-4-((3-(4-(((1S,4S)-4-(4-methoxypiperidin-1-yl)cyclohexyl)amino)-1-(2,2,2-trifluoroethyl)-1H-indol-2-yl)prop-2-yn-1-yl)amino)-N-methylbenzamide |
| 1492. | 3-methoxy-4-{[3-(4-{[(1R,4R)-4-(4-methoxypiperidin-1-yl)cyclohexyl]amino}-1-(2,2,2-trifluoroethyl)-1H-indol-2-yl)prop-2-yn-1-yl]amino}benzene-1-sulfonamide |
| 1493. | 3-methoxy-4-((3-(4-(((1S,4S)-4-(4-methoxypiperidin-1-yl)cyclohexyl)amino)-1-(2,2,2-trifluoroethyl)-1H-indol-2-yl)prop-2-yn-1-yl)amino)benzenesulfonamide |
| 1494. | 3-methoxy-N-methyl-4-{[3-(4-{[(1R,4R)-4-(3-methoxypiperidin-1-yl)cyclohexyl]amino}-1-(2,2,2-trifluoroethyl)-1H-indol-2-yl)prop-2-yn-1-yl]amino}benzamide |
| 1495. | 3-methoxy-4-((3-(4-(((1S,4S)-4-(3-methoxypiperidin-1-yl)cyclohexyl)amino)-1-(2,2,2-trifluoroethyl)-1H-indol-2-yl)prop-2-yn-1-yl)amino)-N-methylbenzamide |
| 1496. | 3-methoxy-4-{[3-(4-{[(1R,4R)-4-(3-methoxypiperidin-1-yl)cyclohexyl]amino}-1-(2,2,2-trifluoroethyl)-1H-indol-2-yl)prop-2-yn-1-yl]amino}benzene-1-sulfonamide |
| 1497. | 3-methoxy-4-((3-(4-(((1S,4S)-4-(3-methoxypiperidin-1-yl)cyclohexyl)amino)-1-(2,2,2-trifluoroethyl)-1H-indol-2-yl)prop-2-yn-1-yl)amino)benzenesulfonamide |
| 1498. | 3-methoxy-4-((3-(4-(((1R,4R)-4-morpholinocyclohexyl)amino)-1-(2,2,2-trifluoroethyl)-1H-indol-2-yl)prop-2-yn-1-yl)amino)benzenesulfonamide |
| 1499. | 3-methoxy-4-((3-(4-(((1S,4S)-4-morpholinocyclohexyl)amino)-1-(2,2,2-trifluoroethyl)-1H-indol-2-yl)prop-2-yn-1-yl)amino)benzenesulfonamide |
| 1500. | 4-[(1R,4R)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1$\lambda^6$-thiomorpholine-1,1-dione |
| 1501. | 4-((1S,4S)-4-((2-(3-((2-methoxy-4-(methylsulfonyl)phenyl)amino)prop-1-yn-1-yl)-1-(2,2,2-trifluoroethyl)-1H-indol-4-yl)amino)cyclohexyl)thiomorpholine 1,1-dioxide |

TABLE 7-continued

Alkynyl indole compounds of the disclosure.

| Mol # | IUPAC name |
|---|---|
| 1502. | 4-[(1R,4R)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1λ$^4$-thiomorpholin-1-one |
| 1503. | 4-[(1S,4S)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-1λ$^4$-thiomorpholin-1-one |
| 1504. | 4-((3-(4-(((1R,4R)-4-(1,1-dioxidothiomorpholino)cyclohexyl)amino)-1-(2,2,2-trifluoroethyl)-1H-indol-2-yl)prop-2-yn-1-yl)amino)-3-methoxy-N-methylbenzamide |
| 1505. | 4-((3-(4-(((1S,4S)-4-(1,1-dioxidothiomorpholino)cyclohexyl)amino)-1-(2,2,2-trifluoroethyl)-1H-indol-2-yl)prop-2-yn-1-yl)amino)-3-methoxy-N-methylbenzamide |
| 1506. | 4-((1S,4S)-4-((2-(3-((2-methoxy-4-(methylsulfonyl)phenyl)amino)prop-1-yn-1-yl)-1-(2,2,2-trifluoroethyl)-1H-indol-4-yl)amino)cyclohexyl)thiomorpholine 1-oxide |
| 1507. | 3-methoxy-N-methyl-4-{[3-(4-{[(1R,4R)-4-(1-oxo-1λ$^4$-thiomorpholin-4-yl)cyclohexyl]amino}-1-(2,2,2-trifluoroethyl)-1H-indol-2-yl)prop-2-yn-1-yl]amino}benzamide |
| 1508. | 3-methoxy-4-{[3-(4-{[(1R,4R)-4-(1-oxo-1λ$^4$-thiomorpholin-4-yl)cyclohexyl]amino}-1-(2,2,2-trifluoroethyl)-1H-indol-2-yl)prop-2-yn-1-yl]amino}benzene-1-sulfonamide |
| 1509. | 3-methoxy-4-((3-(4-(((1S,4S)-4-(1-oxidothiomorpholino)cyclohexyl)amino)-1-(2,2,2-trifluoroethyl)-1H-indol-2-yl)prop-2-yn-1-yl)amino)benzenesulfonamide |
| 1510. | 3-methoxy-4-{[3-(4-{[(1R,4R)-4-(1,1-dioxo-1λ$^6$-thiomorpholin-4-yl)cyclohexyl]amino}-1-(2,2,2-trifluoroethyl)-1H-indol-2-yl)prop-2-yn-1-yl]amino}benzene-1-sulfonamide |
| 1511. | 4-((3-(4-(((1S,4S)-4-(1,1-dioxidothiomorpholino)cyclohexyl)amino)-1-(2,2,2-trifluoroethyl)-1H-indol-2-yl)prop-2-yn-1-yl)amino)-3-methoxybenzenesulfonamide |
| 1512. | 2-{3-[(4-methanesulfonyl-2-methoxyphenyl)amino]prop-1-yn-1-yl}-N-[(1S,4S)-4-{2-oxa-7-azaspiro[3.5]nonan-7-yl}cyclohexyl]-1-(2,2,2-trifluoroethyl)-1H-indol-4-amine |
| 1513. | 3-methoxy-N-methyl-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzamide |
| 1514. | 3-methoxy-N-methyl-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzamide |
| 1515. | 3-methoxy-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1516. | 4-((3-(4-(((1S,4S)-4-(2-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxybenzenesulfonamide |
| 1517. | 3-(cyanomethoxy)-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1518. | 3-(cyanomethoxy)-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1519. | 3-(fluoromethoxy)-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1520. | 3-(fluoromethoxy)-4-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1521. | 2-{3-[(4-methanesulfonyl-2-methoxyphenyl)amino]prop-1-yn-1-yl}-N-[(1R,4R)-4-{1-oxa-7-azaspiro[3.5]nonan-7-yl}cyclohexyl]-1-(2,2,2-trifluoroethyl)-1H-indol-4-amine |
| 1522. | N-((1S,4S)-4-(1-oxa-7-azaspiro[3.5]nonan-7-yl)cyclohexyl)-2-(3-((2-methoxy-4-(methylsulfonyl)phenyl)amino)prop-1-yn-1-yl)-1-(2,2,2-trifluoroethyl)-1H-indol-4-amine |
| 1523. | 3-methoxy-N-methyl-4-{[3-(4-{[(1R,4R)-4-{1-oxa-7-azaspiro[3.5]nonan-7-yl}cyclohexyl]amino}-1-(2,2,2-trifluoroethyl)-1H-indol-2-yl)prop-2-yn-1-yl]amino}benzamide |
| 1524. | 4-((3-(4-(((1S,4S)-4-(1-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxy-N-methylbenzamide |
| 1525. | 3-methoxy-4-{[3-(4-{[(1R,4R)-4-{1-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1526. | 4-((3-(4-(((1S,4S)-4-(1-oxa-7-azaspiro[3.5]nonan-7-yl)cyclohexyl)amino)-1-(2,2,2-trifluoroethyl)-1H-indol-2-yl)prop-2-yn-1-yl)amino)-3-methoxybenzenesulfonamide |
| 1527. | 2-(5-methanesulfonyl-2-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}phenoxy)acetonitrile |
| 1528. | 2-(5-methanesulfonyl-2-{[3-(4-{[(1S,4S)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}phenoxy)acetonitrile |
| 1529. | 2-(3-{[2-(fluoromethoxy)-4-methanesulfonylphenyl]amino}prop-1-yn-1-yl)-N-[(1R,4R)-4-{2-oxa-7-azaspiro[3.5]nonan-7-yl}cyclohexyl]-1-(2,2,2-trifluoroethyl)-1H-indol-4-amine |
| 1530. | 2-(3-{[2-(fluoromethoxy)-4-methanesulfonylphenyl]amino}prop-1-yn-1-yl)-N-[(1S,4S)-4-{2-oxa-7-azaspiro[3.5]nonan-7-yl}cyclohexyl]-1-(2,2,2-trifluoroethyl)-1H-indol-4-amine |
| 1531. | N-((1R,4R)-4-(2-oxa-7-azaspiro[3.5]nonan-7-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine |
| 1532. | N-((1S,4S)-4-(2-oxa-7-azaspiro[3.5]nonan-7-yl)cyclohexyl)-2-(3-((2-ethoxy-4-(methylsulfonyl)phenyl)amino)prop-1-yn-1-yl)-1-(2,2,2-trifluoroethyl)-1H-indol-4-amine |

TABLE 7-continued

Alkynyl indole compounds of the disclosure.

| Mol # | IUPAC name |
|---|---|
| 1533. | 3-methoxy-N-methyl-4-{[3-(4-{[(1R,4R)-4-{2-oxa-7-azaspiro[3.5]nonan-7-yl}cyclohexyl]amino}-1-(2,2,2-trifluoroethyl)-1H-indol-2-yl)prop-2-yn-1-yl]amino}benzene-1-sulfonamide |
| 1534. | N-((1R,4R)-4-(2-oxa-7-azaspiro[3.5]nonan-7-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 1535. | N-((1S,4S)-4-(2-oxa-7-azaspiro[3.5]nonan-7-yl)cyclohexyl)-2-(3-((4-(ethylsulfonyl)-2-methoxyphenyl)amino)prop-1-yn-1-yl)-1-(2,2,2-trifluoroethyl)-1H-indol-4-amine |
| 1536. | 2-{3-[(4-methanesulfonyl-2-methoxyphenyl)amino]prop-1-yn-1-yl}-N-[(1R,4R)-4-{6-oxa-3-azabicyclo[3.1.1]heptan-3-yl}cyclohexyl]-1-(2,2,2-trifluoroethyl)-1H-indol-4-amine |
| 1537. | 2-{3-[(4-methanesulfonyl-2-methoxyphenyl)amino]prop-1-yn-1-yl}-N-[(1S,4S)-4-{6-oxa-3-azabicyclo[3.1.1]heptan-3-yl}cyclohexyl]-1-(2,2,2-trifluoroethyl)-1H-indol-4-amine |
| 1538. | 3-methoxy-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzene-1-sulfonamide |
| 1539. | 3-methoxy-4-{[3-(4-{[(1S,4S)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzene-1-sulfonamide |
| 1540. | 3-methoxy-N-methyl-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide |
| 1541. | 3-methoxy-N-methyl-4-{[3-(4-{[(1S,4S)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide |
| 1542. | 2-{3-[(2-ethoxy-4-methanesulfonylphenyl)amino]prop-1-yn-1-yl}-N-[(1R,4R)-4-{6-oxa-3-azabicyclo[3.1.1]heptan-3-yl}cyclohexyl]-1-(2,2,2-trifluoroethyl)-1H-indol-4-amine |
| 1543. | 2-{3-[(2-ethoxy-4-methanesulfonylphenyl)amino]prop-1-yn-1-yl}-N-[(1S,4S)-4-{6-oxa-3-azabicyclo[3.1.1]heptan-3-yl}cyclohexyl]-1-(2,2,2-trifluoroethyl)-1H-indol-4-amine |
| 1544. | N-ethyl-3-methoxy-4-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}benzamide |
| 1545. | 2-(5-methanesulfonyl-2-{[3-(4-{[(1R,4R)-4-{6-oxa-3-azabicyclo[3.1.1]heptan-3-yl}cyclohexyl]amino}-1-(2,2,2-trifluoroethyl)-1H-indol-2-yl)prop-2-yn-1-yl]amino}phenoxy)acetonitrile |
| 1546. | 2-(2-((3-(4-(((1S,4S)-4-(6-oxa-3-azabicyclo[3.1.1]heptan-3-yl)cyclohexyl)amino)-1-(2,2,2-trifluoroethyl)-1H-indol-2-yl)prop-2-yn-1-yl)amino)-5-(methylsulfonyl)phenoxy)acetonitrile |
| 1547. | 3-methoxy-N-methyl-4-{[3-(4-{[(1R,4R)-4-{2-oxa-8-azaspiro[4.5]decan-8-yl}cyclohexyl]amino}-1-(2,2,2-trifluoroethyl)-1H-indol-2-yl)prop-2-yn-1-yl]amino}benzamide |
| 1548. | 2-{3-[(4-methanesulfonyl-2-methoxyphenyl)amino]prop-1-yn-1-yl}-N-[(1R,4R)-4-{2-oxa-8-azaspiro[4.5]decan-8-yl}cyclohexyl]-1-(2,2,2-trifluoroethyl)-1H-indol-4-amine |
| 1549. | 3-methoxy-4-{[3-(4-{[(1R,4R)-4-{2-oxa-8-azaspiro[4.5]decan-8-yl}cyclohexyl]amino}-1-(2,2,2-trifluoroethyl)-1H-indol-2-yl)prop-2-yn-1-yl]amino}benzene-1-sulfonamide |
| 1550. | 4-((3-(4-(((1R,4R)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxybenzenesulfonamide |
| 1551. | 4-((3-(4-(((1S,4S)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxybenzenesulfonamide |
| 1552. | 2-{3-[(4-methanesulfonyl-2-methoxyphenyl)amino]prop-1-yn-1-yl}-N-[(1R,4R)-4-{3-oxa-9-azaspiro[5.5]undecan-9-yl}cyclohexyl]-1-(2,2,2-trifluoroethyl)-1H-indol-4-amine |
| 1553. | N-((1S,4S)-4-(3-oxa-9-azaspiro[5.5]undecan-9-yl)cyclohexyl)-2-(3-((2-methoxy-4-(methylsulfonyl)phenyl)amino)prop-1-yn-1-yl)-1-(2,2,2-trifluoroethyl)-1H-indol-4-amine |
| 1554. | 3-methoxy-N-methyl-4-{[3-(4-{[(1R,4R)-4-{3-oxa-9-azaspiro[5.5]undecan-9-yl}cyclohexyl]amino}-1-(2,2,2-trifluoroethyl)-1H-indol-2-yl)prop-2-yn-1-yl]amino}benzamide |
| 1555. | 4-((3-(4-(((1S,4S)-4-(3-oxa-9-azaspiro[5.5]undecan-9-yl)cyclohexyl)amino)-1-(2,2,2-trifluoroethyl)-1H-indol-2-yl)prop-2-yn-1-yl)amino)-3-methoxy-N-methylbenzamide |
| 1556. | 3-methoxy-4-{[3-(4-{[(1R,4R)-4-{3-oxa-9-azaspiro[5.5]undecan-9-yl}cyclohexyl]amino}-1-(2,2,2-trifluoroethyl)-1H-indol-2-yl)prop-2-yn-1-yl]amino}benzene-1-sulfonamide |
| 1557. | 4-((3-(4-(((1S,4S)-4-(3-oxa-9-azaspiro[5.5]undecan-9-yl)cyclohexyl)amino)-1-(2,2,2-trifluoroethyl)-1H-indol-2-yl)prop-2-yn-1-yl)amino)-3-methoxybenzenesulfonamide |
| 1558. | 3-methoxy-N-methyl-4-{[3-(4-{[(1R,4R)-4-(pyrrolidin-1-yl)cyclohexyl]amino}-1-(2,2,2-trifluoroethyl)-1H-indol-2-yl)prop-2-yn-1-yl]amino}benzamide |
| 1559. | 3-methoxy-N-methyl-4-((3-(4-(((1S,4S)-4-(pyrrolidin-1-yl)cyclohexyl]amino)-1-(2,2,2-trifluoroethyl)-1H-indol-2-yl)prop-2-yn-1-yl)amino)benzamide |
| 1560. | 3-methoxy-4-{[3-(4-{[(1R,4R)-4-(pyrrolidin-1-yl)cyclohexyl]amino}-1-(2,2,2-trifluoroethyl)-1H-indol-2-yl)prop-2-yn-1-yl]amino}benzene-1-sulfonamide |
| 1561. | 3-methoxy-4-((3-(4-(((1S,4S)-4-(pyrrolidin-1-yl)cyclohexyl]amino)-1-(2,2,2-trifluoroethyl)-1H-indol-2-yl)prop-2-yn-1-yl)amino)benzenesulfonamide |
| 1562. | 2-{3-[(4-methanesulfonyl-2-methoxyphenyl)amino]prop-1-yn-1-yl}-N-[(1R,4R)-4-(pyrrolidin-1-yl)cyclohexyl]-1-(2,2,2-trifluoroethyl)-1H-indol-4-amine |

TABLE 7-continued

| Alkynyl indole compounds of the disclosure. | |
|---|---|
| Mol # | IUPAC name |
| 1563. | 2-(3-((2-methoxy-4-(methylsulfonyl)phenyl)amino)prop-1-yn-1-yl)-N-((1S,4S)-4-(pyrrolidin-1-yl)cyclohexyl)-1-(2,2,2-trifluoroethyl)-1H-indol-4-amine |
| 1564. | 2-{3-[(4-methanesulfonyl-2-methoxyphenyl)amino]prop-1-yn-1-yl}-N-[(1R,4R)-4-(3-methoxypyrrolidin-1-yl)cyclohexyl]-1-(2,2,2-trifluoroethyl)-1H-indol-4-amine |
| 1565. | 3-methoxy-4-{[3-(4-{[(1R,4R)-4-(3-methoxypyrrolidin-1-yl)cyclohexyl]amino}-1-(2,2,2-trifluoroethyl)-1H-indol-2-yl)prop-2-yn-1-yl]amino}benzene-1-sulfonamide |
| 1566. | 3-methoxy-N-methyl-4-{[3-(4-{[(1R,4R)-4-(3-methoxypyrrolidin-1-yl)cyclohexyl]amino}-1-(2,2,2-trifluoroethyl)-1H-indol-2-yl)prop-2-yn-1-yl]amino}benzamide |
| 1567. | 3-methoxy-4-((3-(4-(((1S,4S)-4-(3-methoxypyrrolidin-1-yl)cyclohexyl)amino)-1-(2,2,2-trifluoroethyl)-1H-indol-2-yl)prop-2-yn-1-yl)amino)-N-methylbenzamide |
| 1568. | 3-methoxy-4-{[3-(4-{[(1R,4R)-4-{hexahydro-1H-furo[3,4-c]pyrrol-5-yl}cyclohexyl]amino}-1-(2,2,2-trifluoroethyl)-1H-indol-2-yl)prop-2-yn-1-yl]amino}benzene-1-sulfonamide |
| 1569. | 3-methoxy-4-((3-(4-(((1S,4S)-4-(tetrahydro-1H-furo[3,4-c]pyrrol-5(3H)-yl)cyclohexyl)amino)-1-(2,2,2-trifluoroethyl)-1H-indol-2-yl)prop-2-yn-1-yl)amino)benzenesulfonamide |
| 1570. | 2-{3-[(4-methanesulfonyl-2-methoxyphenyl)amino]prop-1-yn-1-yl}-N-[(1R,4R)-4-{hexahydro-1H-furo[3,4-c]pyrrol-5-yl}cyclohexyl]-1-(2,2,2-trifluoroethyl)-1H-indol-4-amine |
| 1571. | 2-(3-((2-methoxy-4-(methylsulfonyl)phenyl)amino)prop-1-yn-1-yl)-N-((1R,4R)-4-(tetrahydro-1H-furo[3,4-c]pyrrol-5(3H)-yl)cyclohexyl)-1-(2,2,2-trifluoroethyl)-1H-indol-4-amine |
| 1572. | 3-methoxy-N-methyl-4-{[3-(4-{[(1R,4R)-4-{hexahydro-1H-furo[3,4-c]pyrrol-5-yl}cyclohexyl]amino}-1-(2,2,2-trifluoroethyl)-1H-indol-2-yl)prop-2-yn-1-yl]amino}benzamide |
| 1573. | 3-methoxy-N-methyl-4-((3-(4-(((1S,4S)-4-(tetrahydro-1H-furo[3,4-c]pyrrol-5(3H)-yl)cyclohexyl)amino)-1-(2,2,2-trifluoroethyl)-1H-indol-2-yl)prop-2-yn-1-yl)amino)benzamide |
| 1574. | 2-{3-[(4-methanesulfonyl-2-methoxyphenyl)amino]prop-1-yn-1-yl}-N-[(1R,4R)-4-[4-(trifluoromethyl)piperidin-1-yl]cyclohexyl]-1-(2,2,2-trifluoroethyl)-1H-indol-4-amine |
| 1575. | 2-(3-((2-methoxy-4-(methylsulfonyl)phenyl)amino)prop-1-yn-1-yl)-1-(2,2,2-trifluoroethyl)-N-((1S,4S)-4-(4-(trifluoromethyl)piperidin-1-yl)cyclohexyl)-1H-indol-4-amine |
| 1576. | 3-methoxy-N-methyl-4-{[3-(4-{[(1R,4R)-4-[4-(trifluoromethyl)piperidin-1-yl]cyclohexyl]amino}-1-(2,2,2-trifluoroethyl)-1H-indol-2-yl)prop-2-yn-1-yl]amino}benzamide |
| 1577. | 3-methoxy-N-methyl-4-((3-(1-(2,2,2-trifluoroethyl)-4-(((1S,4S)-4-(4-(trifluoromethyl)piperidin-1-yl)cyclohexyl)amino)-1H-indol-2-yl)prop-2-yn-1-yl)amino)benzamide |
| 1578. | 3-methoxy-4-{[3-(4-{[(1R,4R)-4-[4-(trifluoromethyl)piperidin-1-yl]cyclohexyl]amino}-1-(2,2,2-trifluoroethyl)-1H-indol-2-yl)prop-2-yn-1-yl]amino}benzene-1-sulfonamide |
| 1579. | 3-methoxy-4-((3-(1-(2,2,2-trifluoroethyl)-4-(((1S,4S)-4-(4-(trifluoromethyl)piperidin-1-yl)cyclohexyl)amino)-1H-indol-2-yl)prop-2-yn-1-yl)amino)benzenesulfonamide |
| 1580. | 2-{3-[(4-methanesulfonyl-2-methoxyphenyl)amino]prop-1-yn-1-yl}-N-[(1R,4R)-4-(4-methanesulfonylpiperidin-1-yl)cyclohexyl]-1-(2,2,2-trifluoroethyl)-1H-indol-4-amine |
| 1581. | 2-(3-((2-methoxy-4-(methylsulfonyl)phenyl)amino)prop-1-yn-1-yl)-N-((1S,4S)-4-(4-(methylsulfonyl)piperidin-1-yl)cyclohexyl)-1-(2,2,2-trifluoroethyl)-1H-indol-4-amine |
| 1582. | 3-methoxy-N-methyl-4-{[3-(4-{[(1R,4R)-4-(4-methanesulfonylpiperidin-1-yl)cyclohexyl]amino}-1-(2,2,2-trifluoroethyl)-1H-indol-2-yl)prop-2-yn-1-yl]amino}benzamide |
| 1583. | 3-methoxy-N-methyl-4-((3-(4-(((1S,4S)-4-(4-(methylsulfonyl)piperidin-1-yl)cyclohexyl)amino)-1-(2,2,2-trifluoroethyl)-1H-indol-2-yl)prop-2-yn-1-yl)amino)benzamide |
| 1584. | 3-methoxy-4-{[3-(4-{[(1R,4R)-4-(4-methanesulfonylpiperidin-1-yl)cyclohexyl]amino}-1-(2,2,2-trifluoroethyl)-1H-indol-2-yl)prop-2-yn-1-yl]amino}benzene-1-sulfonamide |
| 1585. | 3-methoxy-4-((3-(4-(((1S,4S)-4-(4-(methylsulfonyl)piperidin-1-yl)cyclohexyl)amino)-1-(2,2,2-trifluoroethyl)-1H-indol-2-yl)prop-2-yn-1-yl)amino)benzenesulfonamide |
| 1586. | 1-[(1S,3R)-3-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]-4,5-dihydro-1H-1,2,3,4-tetrazol-5-one |
| 1587. | 2-((2-(3-((2-methoxy-4-(methylsulfonyl)phenyl)amino)prop-1-yn-1-yl)-4-(((1R,4R)-4-morpholinocyclohexyl)amino)-1H-indol-1-yl)methyl)acrylonitrile |
| 1588. | N-((1R,4R)-4-(2-oxa-8-azaspiro[4.5]decan-8-yl)cyclohexyl)-2-(3-((2-methoxy-4-(methylsulfonyl)phenyl)amino)prop-1-yn-1-yl)-1-(2,2,2-trifluoroethyl)-1H-benzo[d]imidazol-4-amine |
| 1589. | N-((1S,4S)-4-(2-oxa-8-azaspiro[4.5]decan-8-yl)cyclohexyl)-2-(3-((2-methoxy-4-(methylsulfonyl)phenyl)amino)prop-1-yn-1-yl)-1-(2,2,2-trifluoroethyl)-1H-benzo[d]imidazol-4-amine |
| 1590. | 4-((3-(4-(((1R,4R)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxy-N-methylbenzamide |
| 1591. | 4-((3-(4-(((1S,4S)-4-(2-oxa-8-azaspiro[4.5]decan-8-yl)cyclohexyl)amino)-1-(2,2,2-trifluoroethyl)-1H-benzo[d]imidazol-2-yl)prop-2-yn-1-yl)amino)-3-methoxy-N-methylbenzamide |

TABLE 7-continued

Alkynyl indole compounds of the disclosure.

| Mol # | IUPAC name |
|---|---|
| 1592. | 1-{3-[(2-{3-[(4-methanesulfonyl-2-methoxyphenyl)amino]prop-1-yn-1-yl}-1-(2,2,2-trifluoroethyl)-1H-indol-4-yl)amino]pyrrolidin-1-yl}-3-methoxypropan-2-ol |
| 1593. | N-[3-(4-{[1-(2-hydroxy-3-methoxypropyl)pyrrolidin-3-yl]amino}-1-(2,2,2-trifluoroethyl)-1H-indol-2-yl)prop-2-yn-1-yl]benzamide |
| 1594. | 1-{3-[(2-{3-[(4-methanesulfonylphenyl)amino]prop-1-yn-1-yl}-1-(2,2,2-trifluoroethyl)-1H-indol-4-yl)amino]pyrrolidin-1-yl}-3-methoxypropan-2-ol |
| 1595. | 2-{3-[(4-methanesulfonyl-2-methoxyphenyl)amino]prop-1-yn-1-yl}-N-[1-(oxan-4-yl)pyrrolidin-3-yl]-1-(2,2,2-trifluoroethyl)-1H-indol-4-amine |
| 1596. | 2-(3-{[2-methoxy-4-(morpholine-4-sulfonyl)phenyl]amino}prop-1-yn-1-yl)-N-(piperidin-4-yl)-1-(2,2,2-trifluoroethyl)-1H-indol-4-amine |
| 1597. | 3-methoxy-N,N-dimethyl-4-[(3-{4-[(piperidin-4-yl)amino]-1-(2,2,2-trifluoroethyl)-1H-indol-2-yl}prop-2-yn-1-yl)amino]benzene-1-sulfonamide |
| 1598. | 2-{5-methanesulfonyl-2-[(3-{4-[(piperidin-4-yl)amino]-1-(2,2,2-trifluoroethyl)-1H-indol-2-yl}prop-2-yn-1-yl)amino]phenoxy}acetonitrile |
| 1599. | 3-methoxy-4-((3-(4-(piperidin-4-ylamino)-1-(2,2,2-trifluoroethyl)-1H-indol-2-yl)prop-2-yn-1-yl)amino)benzamide |
| 1600. | 2-{3-[(4-methanesulfonyl-2-methoxyphenyl)amino]prop-1-yn-1-yl}-N-[(3R)-piperidin-3-yl]-1-(2,2,2-trifluoroethyl)-1H-indol-4-amine |
| 1601. | 3-methoxy-4-{[3-(4-{[(2S,4S)-2-methylpiperidin-4-yl]amino}-1-(2,2,2-trifluoroethyl)-1H-indol-2-yl)prop-2-yn-1-yl]amino}benzene-1-sulfonamide |
| 1602. | 3-methoxy-4-((3-(4-((1-methylpiperidin-4-yl)amino)-1-(2,2,2-trifluoroethyl)-1H-indol-2-yl)prop-2-yn-1-yl)amino)benzenesulfonamide |
| 1603. | 2-(3-{[4-methanesulfonyl-2-(trifluoromethoxy)phenyl]amino}prop-1-yn-1-yl)-N-(1-methylpiperidin-4-yl)-1-(2,2,2-trifluoroethyl)-1H-indol-4-amine |
| 1604. | N-(1-methylpiperidin-4-yl)-2-(3-((4-(methylsulfonyl)-2-(2,2,2-trifluoroethoxy)phenyl)amino)prop-1-yn-1-yl)-1-(2,2,2-trifluoroethyl)-1H-indol-4-amine |
| 1605. | 2-{4-methoxy-5-[(3-{4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile |
| 1606. | 3-methoxy-4-[(3-{4-[(1-methylpiperidin-4-yl)amino]-1-(2,2,2-trifluoroethyl)-1H-indol-2-yl}prop-2-yn-1-yl)amino]-N-(1,2-oxazol-3-yl)benzene-1-sulfonamide |
| 1607. | 3-methoxy-4-[(3-{4-[(1-methylpiperidin-4-yl)amino]-1-(2,2,2-trifluoroethyl)-1H-indol-2-yl}prop-2-yn-1-yl)amino]-N-(oxan-4-yl)benzene-1-sulfonamide |
| 1608. | 3-methoxy-N-(5-methyl-1,2-oxazol-3-yl)-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 1609. | N-(2-hydroxyethyl)-3-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 1610. | 3-methoxy-N,N-dimethyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 1611. | 4-[(3-{6-fluoro-4-[(1-methylpiperidin-4-yl)amino]-1-(2,2,2-trifluoroethyl)-1H-indol-2-yl}prop-2-yn-1-yl)amino]-3-methoxybenzene-1-sulfonamide |
| 1612. | 6-fluoro-2-{3-[(4-methanesulfonyl-2-methoxyphenyl)amino]prop-1-yn-1-yl}-N-(1-methylpiperidin-4-yl)-1-(2,2,2-trifluoroethyl)-1H-indol-4-amine |
| 1613. | 2-(3-((4-methoxy-6-(methylsulfonyl)pyridin-3-yl)amino)prop-1-yn-1-yl)-N-(1-methylpiperidin-4-yl)-1-(2,2,2-trifluoroethyl)-1H-indol-4-amine |
| 1614. | 3-methoxy-N-(2-methoxyethyl)-N-methyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 1615. | 2-{3-[(4-methanesulfonyl-2-methoxyphenyl)(methyl)amino]prop-1-yn-1-yl}-N-(1-methylpiperidin-4-yl)-1-(2,2,2-trifluoroethyl)-1H-indol-4-amine |
| 1616. | 1-(4-{3-methoxy-4-[(3-{4-[(1-methylpiperidin-4-yl)amino]-1-(2,2,2-trifluoroethyl)-1H-indol-2-yl}prop-2-yn-1-yl)amino]benzenesulfonyl}piperazin-1-yl)ethan-1-one |
| 1617. | 2-(3-{[2-methoxy-4-(morpholine-4-sulfonyl)phenyl]amino}prop-1-yn-1-yl)-N-(1-methylpiperidin-4-yl)-1-(2,2,2-trifluoroethyl)-1H-indol-4-amine |
| 1618. | 3-methoxy-4-((3-(4-((1-methylpiperidin-4-yl)amino)-1-(2,2,2-trifluoroethyl)-1H-indol-2-yl)prop-2-yn-1-yl)amino)benzoic acid |
| 1619. | 3-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzamide |
| 1620. | N,N-bis(2-hydroxyethyl)-3-methoxy-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 1621. | 3-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide |
| 1622. | 2-[3-({2-methoxy-4-[(4-methylpiperazin-1-yl)sulfonyl]phenyl}amino)prop-1-yn-1-yl]-N-(1-methylpiperidin-4-yl)-1-(2,2,2-trifluoroethyl)-1H-indol-4-amine |
| 1623. | 5-methanesulfonyl-2-[(3-{4-[(1-methylpiperidin-4-yl)amino]-1-(2,2,2-trifluoroethyl)-1H-indol-2-yl}prop-2-yn-1-yl)amino]phenol |
| 1624. | 2-{3-[(4-methanesulfonyl-2-methoxyphenyl)amino]prop-1-yn-1-yl}-6-methoxy-N-(1-methylpiperidin-4-yl)-1-(2,2,2-trifluoroethyl)-1H-indol-4-amine |
| 1625. | 2-{3-[2-(dimethylamino)-4-methanesulfonylphenoxy]prop-1-yn-1-yl}-N-(1-methylpiperidin-4-yl)-1-(2,2,2-trifluoroethyl)-1H-indol-4-amine |
| 1626. | 2-{5-methanesulfonyl-2-[(3-{4-[(1-methylpiperidin-4-yl)amino]-1-(2,2,2-trifluoroethyl)-1H-indol-2-yl}prop-2-yn-1-yl)amino]phenoxy}acetonitrile |
| 1627. | 2-(3-{[2-(fluoromethoxy)-4-methanesulfonylphenyl]amino}prop-1-yn-1-yl)-N-(1-methylpiperidin-4-yl)-1-(2,2,2-trifluoroethyl)-1H-indol-4-amine |
| 1628. | 2-(3-{[2-methoxy-4-(morpholine-4-carbonyl)phenyl]amino}prop-1-yn-1-yl)-N-(1-methylpiperidin-4-yl)-1-(2,2,2-trifluoroethyl)-1H-indol-4-amine |
| 1629. | 1-{3-methoxy-4-[(3-{4-[(1-methylpiperidin-4-yl)amino]-1-(2,2,2-trifluoroethyl)-1H-indol-2-yl}prop-2-yn-1-yl)amino]benzoyl}piperidin-4-ol |

TABLE 7-continued

Alkynyl indole compounds of the disclosure.

| Mol # | IUPAC name |
|---|---|
| 1630. | 3-(3-(4-((1-methylpiperidin-4-yl)amino)-1-(2,2,2-trifluoroethyl)-1H-indol-2-yl)prop-2-yn-1-yl)-6-(methylsulfonyl)benzo[d]oxazol-2(3H)-one |
| 1631. | 2-(3-{[2-methoxy-4-(5-methoxypyridin-3-yl)phenyl]amino}prop-1-yn-1-yl)-N-(1-methylpiperidin-4-yl)-1-(2,2,2-trifluoroethyl)-1H-indol-4-amine |
| 1632. | 2-{3-[(5-methanesulfonyl-2-methoxyphenyl)amino]prop-1-yn-1-yl}-N-(1-methylpiperidin-4-yl)-1-(2,2,2-trifluoroethyl)-1H-indol-4-amine |
| 1633. | N-(2-hydroxyethyl)-3-methoxy-4-[(3-{4-[(1-methylpiperidin-4-yl)amino]-1-(2,2,2-trifluoroethyl)-1H-indol-2-yl}prop-2-yn-1-yl)amino]benzamide |
| 1634. | 3-methoxy-N-(2-methoxyethyl)-4-[(3-{4-[(1-methylpiperidin-4-yl)amino]-1-(2,2,2-trifluoroethyl)-1H-indol-2-yl}prop-2-yn-1-yl)amino]benzamide |
| 1635. | 3-methoxy-N-(1-methylpiperidin-4-yl)-4-[(3-{4-[(1-methylpiperidin-4-yl)amino]-1-(2,2,2-trifluoroethyl)-1H-indol-2-yl}prop-2-yn-1-yl)amino]benzamide |
| 1636. | 2-[3-({4-[4-(dimethylamino)piperidine-1-carbonyl]-2-methoxyphenyl}amino)prop-1-yn-1-yl]-N-(1-methylpiperidin-4-yl)-1-(2,2,2-trifluoroethyl)-1H-indol-4-amine |
| 1637. | 3-methoxy-4-[(3-{4-[(1-methylpiperidin-4-yl)amino]-1-(2,2,2-trifluoroethyl)-1H-indol-2-yl}prop-2-yn-1-yl)amino]-N-(oxan-4-yl)benzamide |
| 1638. | 2-(3-{[2-methoxy-4-(4-methylpiperazine-1-carbonyl)phenyl]amino}prop-1-yn-1-yl)-N-(1-methylpiperidin-4-yl)-1-(2,2,2-trifluoroethyl)-1H-indol-4-amine |
| 1639. | 2-{3-[(2-methoxy-4-{2-oxa-6-azaspiro[3.3]heptane-6-carbonyl}phenyl)amino]prop-1-yn-1-yl}-N-(1-methylpiperidin-4-yl)-1-(2,2,2-trifluoroethyl)-1H-indol-4-amine |
| 1640. | 2-(3-{[2-methoxy-4-(pyridin-3-yl)phenyl]amino}prop-1-yn-1-yl)-N-(1-methylpiperidin-4-yl)-1-(2,2,2-trifluoroethyl)-1H-indol-4-amine |
| 1641. | 2-(3-{[2-methoxy-4-(pyridin-4-yl)phenyl]amino}prop-1-yn-1-yl)-N-(1-methylpiperidin-4-yl)-1-(2,2,2-trifluoroethyl)-1H-indol-4-amine |
| 1642. | N-(3-{4-[(1-methylpiperidin-4-yl)amino]-1-(2,2,2-trifluoroethyl)-1H-indol-2-yl}prop-2-yn-1-yl)pyridine-3-carboxamide |
| 1643. | 2-(3-{[2-methoxy-4-(1,3-oxazol-2-yl)phenyl]amino}prop-1-yn-1-yl)-N-(1-methylpiperidin-4-yl)-1-(2,2,2-trifluoroethyl)-1H-indol-4-amine |
| 1644. | 2-{3-[(3-methanesulfonylphenyl)amino]prop-1-yn-1-yl}-N-(1-methylpiperidin-4-yl)-1-(2,2,2-trifluoroethyl)-1H-indol-4-amine |
| 1645. | N-(1-methylpiperidin-4-yl)-2-[3-({4-[(morpholin-4-yl)methyl]phenyl}amino)prop-1-yn-1-yl]-1-(2,2,2-trifluoroethyl)-1H-indol-4-amine |
| 1646. | 2-(3-{[2-methoxy-4-(1,3-thiazol-2-yl)phenyl]amino}prop-1-yn-1-yl)-N-(1-methylpiperidin-4-yl)-1-(2,2,2-trifluoroethyl)-1H-indol-4-amine |
| 1647. | 2-[3-({2-methoxy-4-[1-(2-methoxyethyl)-1H-pyrazol-4-yl]phenyl}amino)prop-1-yn-1-yl]-N-(1-methylpiperidin-4-yl)-1-(2,2,2-trifluoroethyl)-1H-indol-4-amine |
| 1648. | 2-{3-[(2-methoxy-4-{7-oxa-2-azaspiro[3.5]nonane-2-carbonyl}phenyl)amino]prop-1-yn-1-yl}-N-(1-methylpiperidin-4-yl)-1-(2,2,2-trifluoroethyl)-1H-indol-4-amine |
| 1649. | 2-{3-[(4-chloro-2-methoxyphenyl)amino]prop-1-yn-1-yl}-N-(1-methylpiperidin-4-yl)-1-(2,2,2-trifluoroethyl)-1H-indol-4-amine |
| 1650. | 2-(3-(((3S,4R)-3-methoxytetrahydro-2H-pyran-4-yl)amino)prop-1-yn-1-yl)-N-(1-methylpiperidin-4-yl)-1-(2,2,2-trifluoroethyl)-1H-indol-4-amine |
| 1651. | 2-fluoro-5-methoxy-4-[(3-{4-[(1-methylpiperidin-4-yl)amino]-1-(2,2,2-trifluoroethyl)-1H-indol-2-yl}prop-2-yn-1-yl)amino]benzamide |
| 1652. | 2-(3-{[2-methoxy-4-(trifluoromethyl)phenyl]amino}prop-1-yn-1-yl)-N-(1-methylpiperidin-4-yl)-1-(2,2,2-trifluoroethyl)-1H-indol-4-amine |
| 1653. | 2-fluoro-5-methoxy-N-methyl-4-[(3-{4-[(1-methylpiperidin-4-yl)amino]-1-(2,2,2-trifluoroethyl)-1H-indol-2-yl}prop-2-yn-1-yl)amino]benzamide |
| 1654. | 2-{3-[(4-methanesulfonyl-2-methoxyphenyl)amino]prop-1-yn-1-yl}-N-(1-methylpiperidin-4-yl)-1-[(oxiran-2-yl)methyl]-1H-indol-4-amine |
| 1655. | 2-(3-((2-ethoxy-4-(methylsulfonyl)phenyl)amino)prop-1-yn-1-yl)-N-(1-methylpiperidin-4-yl)-1-(2,2,2-trifluoroethyl)-1H-indol-4-amine |
| 1656. | 2-{3-[(2-fluoro-4-methanesulfonyl-6-methoxyphenyl)amino]prop-1-yn-1-yl}-N-(1-methylpiperidin-4-yl)-1-(2,2,2-trifluoroethyl)-1H-indol-4-amine |
| 1657. | 2-{3-[(4-methanesulfonyl-2-methoxyphenyl)amino]prop-1-yn-1-yl}-3-methyl-N-(1-methylpiperidin-4-yl)-1-(2,2,2-trifluoroethyl)-1H-indol-4-amine |
| 1658. | 2-(3-(((3R,4R)-3-methoxytetrahydro-2H-pyran-4-yl)amino)prop-1-yn-1-yl)-N-(1-methylpiperidin-4-yl)-1-(2,2,2-trifluoroethyl)-1H-indol-4-amine |
| 1659. | 2-{3-[(5-fluoro-4-methanesulfonyl-2-methoxyphenyl)amino]prop-1-yn-1-yl}-N-(1-methylpiperidin-4-yl)-1-(2,2,2-trifluoroethyl)-1H-indol-4-amine |
| 1660. | 2-{3-[(5-methanesulfonylthiophen-2-yl)amino]prop-1-yn-1-yl}-N-(1-methylpiperidin-4-yl)-1-(2,2,2-trifluoroethyl)-1H-indol-4-amine |
| 1661. | N-methyl-5-[(3-{4-[(1-methylpiperidin-4-yl)amino]-1-(2,2,2-trifluoroethyl)-1H-indol-2-yl}prop-2-yn-1-yl)amino]thiophene-2-carboxamide |
| 1662. | N,N-dimethyl-5-[(3-{4-[(1-methylpiperidin-4-yl)amino]-1-(2,2,2-trifluoroethyl)-1H-indol-2-yl}prop-2-yn-1-yl)amino]thiophene-2-carboxamide |
| 1663. | 5-[(3-{4-[(1-methylpiperidin-4-yl)amino]-1-(2,2,2-trifluoroethyl)-1H-indol-2-yl}prop-2-yn-1-yl)amino]thiophene-2-carboxylic acid |
| 1664. | 2-(3-((4-methoxypyridin-3-yl)amino)prop-1-yn-1-yl)-N-(1-methylpiperidin-4-yl)-1-(2,2,2-trifluoroethyl)-1H-indol-4-amine |
| 1665. | 2-(2-((3-(4-((1-methylpiperidin-4-yl)amino)-1-(2,2,2-trifluoroethyl)-1H-indol-2-yl)prop-2-yn-1-yl)amino)-5-(methylsulfonyl)phenoxy)acetamide |
| 1666. | N-(2-hydroxyethyl)-3-methoxy-4-((3-(4-((1-methylpiperidin-4-yl)amino)-1-(2,2,2-trifluoroethyl)-1H-indol-2-yl)prop-2-yn-1-yl)amino)benzenesulfonamide |
| 1667. | 4-((2-(3-((2-methoxy-4-(methylsulfonyl)phenyl)amino)prop-1-yn-1-yl)-1-(2,2,2-trifluoroethyl)-1H-indol-4-yl)amino)-1-methylpiperidin-2-one |

TABLE 7-continued

Alkynyl indole compounds of the disclosure.

| Mol # | IUPAC name |
|---|---|
| 1668. | 2-{3-[(4-methanesulfonyl-2-methoxyphenyl)amino]prop-1-yn-1-yl}-N-[(3R,4S)-3-methoxy-1-methylpiperidin-4-yl]-1-(2,2,2-trifluoroethyl)-1H-indol-4-amine |
| 1669. | 2-{3-[(4-methanesulfonyl-2-methoxyphenyl)amino]prop-1-yn-1-yl}-N-[(3S,4R)-3-methoxy-1-methylpiperidin-4-yl]-1-(2,2,2-trifluoroethyl)-1H-indol-4-amine |
| 1670. | 2-{3-[(4-methanesulfonyl-2-methoxyphenyl)amino]prop-1-yn-1-yl}-N-[(3S,4R)-3-methoxy-1-methylpiperidin-4-yl]-N-methyl-1-(2,2,2-trifluoroethyl)-1H-indol-4-amine |
| 1671. | N-(1-ethylpiperidin-4-yl)-2-(3-{[2-(fluoromethoxy)-4-methanesulfonylphenyl]amino}prop-1-yn-1-yl)-1-(2,2,2-trifluoroethyl)-1H-indol-4-amine |
| 1672. | 4-[(3-{4-[(1-ethylpiperidin-4-yl)amino]-1-(2,2,2-trifluoroethyl)-1H-indol-2-yl}prop-2-yn-1-yl)amino]-3-methoxy-N-methylbenzamide |
| 1673. | 2-{2-[(3-{4-[(1-ethylpiperidin-4-yl)amino]-1-(2,2,2-trifluoroethyl)-1H-indol-2-yl}prop-2-yn-1-yl)amino]-5-methanesulfonylphenoxy}acetonitrile |
| 1674. | N-(1-ethylpiperidin-4-yl)-2-{3-[(4-methanesulfonyl-2-methoxyphenyl)amino]prop-1-yn-1-yl}-1-(2,2,2-trifluoroethyl)-1H-indol-4-amine |
| 1675. | 4-[(3-{4-[(1-ethylpiperidin-4-yl)amino]-1-(2,2,2-trifluoroethyl)-1H-indol-2-yl}prop-2-yn-1-yl)amino]-3-methoxybenzene-1-sulfonamide |
| 1676. | 3-methoxy-N-methyl-4-{[3-(4-{[1-(propan-2-yl)piperidin-4-yl]amino}-1-(2,2,2-trifluoroethyl)-1H-indol-2-yl)prop-2-yn-1-yl]amino}benzamide |
| 1677. | 2-(5-methanesulfonyl-2-{[3-(4-{[1-(propan-2-yl)piperidin-4-yl]amino}-1-(2,2,2-trifluoroethyl)-1H-indol-2-yl)prop-2-yn-1-yl]amino}phenoxy)acetonitrile |
| 1678. | 2-(3-{[2-(fluoromethoxy)-4-methanesulfonylphenyl]amino}prop-1-yn-1-yl)-N-[1-(propan-2-yl)piperidin-4-yl]-1-(2,2,2-trifluoroethyl)-1H-indol-4-amine |
| 1679. | 2-{3-[(4-methanesulfonyl-2-methoxyphenyl)amino]prop-1-yn-1-yl}-N-[1-(propan-2-yl)piperidin-4-yl]-1-(2,2,2-trifluoroethyl)-1H-indol-4-amine |
| 1680. | 3-methoxy-4-{[3-(4-{[1-(propan-2-yl)piperidin-4-yl]amino}-1-(2,2,2-trifluoroethyl)-1H-indol-2-yl)prop-2-yn-1-yl]amino}benzene-1-sulfonamide |
| 1681. | 2-[2-(2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethoxy)ethoxy]ethan-1-ol |
| 1682. | 4-({4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}methyl)-1,3-dioxolan-2-one |
| 1683. | 3-methoxy-4-({3-[4-({1-[(2-oxo-1,3-dioxolan-4-yl)methyl]piperidin-4-yl}amino)-1-(2,2,2-trifluoroethyl)-1H-indol-2-yl]prop-2-yn-1-yl}amino)benzene-1-sulfonamide |
| 1684. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-(1,2-oxazol-3-yl)benzene-1-sulfonamide |
| 1685. | 4-((3-(4-((1-(2,3-dihydroxypropyl)piperidin-4-yl)amino)-1-(2,2,2-trifluoroethyl)-1H-indol-2-yl)prop-2-yn-1-yl)amino)-3-methoxybenzenesulfonamide |
| 1686. | 4-({3-[4-({1-[(2S)-2,3-dihydroxypropyl]piperidin-4-yl}amino)-1-(2,2,2-trifluoroethyl)-1H-indol-2-yl]prop-2-yn-1-yl}amino)-3-methoxybenzene-1-sulfonamide |
| 1687. | 4-({3-[4-({1-[(2R)-2,3-dihydroxypropyl]piperidin-4-yl}amino)-1-(2,2,2-trifluoroethyl)-1H-indol-2-yl]prop-2-yn-1-yl}amino)-3-methoxybenzene-1-sulfonamide |
| 1688. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-(5-methyl-1,2-oxazol-3-yl)benzene-1-sulfonamide |
| 1689. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-(oxan-4-yl)benzene-1-sulfonamide |
| 1690. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-N-(2-hydroxyethyl)-3-methoxy-N-methylbenzene-1-sulfonamide |
| 1691. | 2-(5-{[3-(4-{[1-(2,3-dihydroxypropyl)piperidin-4-yl]amino}-1-(2,2,2-trifluoroethyl)-1H-indol-2-yl)prop-2-yn-1-yl]amino}-4-methoxypyridin-2-yl)-2-methylpropanenitrile |
| 1692. | N-(2-hydroxyethyl)-3-methoxy-N-methyl-4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide |
| 1693. | 3-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)propane-1,2-diol |
| 1694. | (2R)-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propane-1,2-diol |
| 1695. | (2S)-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propane-1,2-diol |
| 1696. | 3-[4-({2-[3-({2-methoxy-4-[(4-methylpiperazin-1-yl)sulfonyl]phenyl}amino)prop-1-yn-1-yl]-1-(2,2,2-trifluoroethyl)-1H-indol-4-yl}amino)piperidin-1-yl]propane-1,2-diol |
| 1697. | 4-((3-(4-((1-(2,3-dihydroxypropyl)piperidin-4-yl)amino)-1-(2,2,2-trifluoroethyl)-1H-indol-2-yl)prop-2-yn-1-yl)amino)-3-methoxybenzoic acid |
| 1698. | methyl 4-((3-(4-((1-(2,3-dihydroxypropyl)piperidin-4-yl)amino)-1-(2,2,2-trifluoroethyl)-1H-indol-2-yl)prop-2-yn-1-yl)amino)-3-methoxybenzoate |
| 1699. | 3-methoxy-4-[(3-{4-[(1-{[(4R)-2-oxo-1,3-dioxolan-4-yl]methyl}piperidin-4-yl)amino]-1-(2,2,2-trifluoroethyl)-1H-indol-2-yl}prop-2-yn-1-yl)amino]benzene-1-sulfonamide |
| 1700. | (4R)-4-({4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}methyl)-1,3-dioxolan-2-one |
| 1701. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N,N-dimethylbenzene-1-sulfonamide |
| 1702. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}EtOAc |
| 1703. | N-(1-{[(4R)-2,2-dimethyl-1,3-dioxolan-4-yl]methyl}piperidin-4-yl)-2-{3-[(4-methanesulfonyl-2-methoxyphenyl)amino]prop-1-yn-1-yl}-1-(2,2,2-trifluoroethyl)-1H-indol-4-amine |

TABLE 7-continued

| Mol # | IUPAC name |
| --- | --- |
| | Alkynyl indole compounds of the disclosure. |
| 1704. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl acetate |
| 1705. | 4-[(3-{4-[(1-{[(4R)-2,2-dimethyl-1,3-dioxolan-4-yl]methyl}piperidin-4-yl)amino]-1-(2,2,2-trifluoroethyl)-1H-indol-2-yl}prop-2-yn-1-yl)amino]-3-methoxybenzene-1-sulfonamide |
| 1706. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 1707. | 1-(4-((2-(3-((4-(ethylsulfonyl)-2-methoxyphenyl)amino)prop-1-yn-1-yl)-1-(2,2,2-trifluoroethyl)-1H-indol-4-yl)amino)piperidin-1-yl)-3-methoxypropan-2-ol |
| 1708. | 1-ethoxy-3-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)propan-2-ol |
| 1709. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-(2-methoxyethyl)-N-methylbenzene-1-sulfonamide |
| 1710. | 1-(acetyloxy)-3-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl acetate |
| 1711. | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzene-1-sulfonamide |
| 1712. | 3-methoxy-4-{[3-(4-{[1-(2-methoxyacetyl)piperidin-4-yl]amino}-1-(2,2,2-trifluoroethyl)-1H-indol-2-yl)prop-2-yn-1-yl]amino}benzene-1-sulfonamide |
| 1713. | 1-(4-(N-(2-(3-((2-methoxy-4-(methylsulfonyl)phenyl)amino)prop-1-yn-1-yl)-1-(2,2,2-trifluoroethyl)-1H-indol-4-yl)acetamido)piperidin-1-yl)propan-2-yl acetate |
| 1714. | 1-[4-(4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxybenzenesulfonyl)piperazin-1-yl]ethan-1-one |
| 1715. | (4S)-4-({4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}methyl)-1,3-dioxolan-2-one |
| 1716. | 1-(acetyloxy)-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl acetate |
| 1717. | N-[1-(2,3-dimethoxypropyl)piperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1718. | 4-{[3-(4-{[1-(2,3-dimethoxypropyl)piperidin-4-yl]amino}-1-(2,2,2-trifluoroethyl)-1H-indol-2-yl)prop-2-yn-1-yl]amino}-3-methoxybenzene-1-sulfonamide |
| 1719. | 3-(4-{[2-(3-{[2-methoxy-4-(morpholine-4-sulfonyl)phenyl]amino}prop-1-yn-1-yl)-1-(2,2,2-trifluoroethyl)-1H-indol-4-yl]amino}piperidin-1-yl)propane-1,2-diol |
| 1720. | 4-({3-[4-({1-[(2R)-2,3-dihydroxypropyl]piperidin-4-yl}amino)-1-(2,2,2-trifluoroethyl)-1H-indol-2-yl]prop-2-yn-1-yl}amino)-3-methoxybenzamide |
| 1721. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethyl 2-methylpropanoate |
| 1722. | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethyl propanoate |
| 1723. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-(propanoyloxy)propan-2-yl propanoate |
| 1724. | 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}-3-(propanoyloxy)propan-2-yl propanoate |
| 1725. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-[(2-methylpropanoyl)oxy]propan-2-yl 2-methylpropanoate |
| 1726. | 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}-3-[(2-methylpropanoyl)oxy]propan-2-yl 2-methylpropanoate |
| 1727. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl propanoate |
| 1728. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-yl 2-methylpropanoate |
| 1729. | 2-hydroxy-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propyl 2-methylpropanoate |
| 1730. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl acetate |
| 1731. | 2-hydroxy-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propyl propanoate |
| 1732. | N,N-bis(2-hydroxyethyl)-4-{[3-(4-{[1-(2-hydroxypropyl)piperidin-4-yl]amino}-1-(2,2,2-trifluoroethyl)-1H-indol-2-yl)prop-2-yn-1-yl]amino}-3-methoxybenzene-1-sulfonamide |
| 1733. | 4-{[3-(4-{[1-(2-hydroxypropyl)piperidin-4-yl]amino}-1-(2,2,2-trifluoroethyl)-1H-indol-2-yl)prop-2-yn-1-yl]amino}-3-methoxy-N-methylbenzamide |
| 1734. | (S)-4-((3-(4-((1-(2-hydroxy-3-methoxypropyl)piperidin-4-yl)amino)-1-(2,2,2-trifluoroethyl)-1H-indol-2-yl)prop-2-yn-1-yl)amino)-3-methoxy-N-methylbenzamide |
| 1735. | 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl 2-methylpropanoate |
| 1736. | 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl acetate |
| 1737. | 2-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}ethyl 2-methylpropanoate |

TABLE 7-continued

| Mol # | IUPAC name |
|---|---|
| | Alkynyl indole compounds of the disclosure. |
| 1738. | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxy-N-methylbenzamide |
| 1739. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl propanoate |
| 1740. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl 2-methylpropanoate |
| 1741. | 1-methoxy-3-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl 2-methylpropanoate |
| 1742. | 1-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl propanoate |
| 1743. | N-(4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzenesulfonyl)acetamide |
| 1744. | N-(4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzenesulfonyl)propanamide |
| 1745. | 2-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}ethyl propanoate |
| 1746. | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxy-N-methylbenzene-1-sulfonamide |
| 1747. | 1-methoxy-3-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl propanoate |
| 1748. | (2R)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 1749. | (2S)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 1750. | 3-methoxy-4-{[3-(4-{[(1S,4S)-4-(dimethylamino)cyclohexyl]amino}-1-(2,2,2-trifluoroethyl)-1H-indol-2-yl)prop-2-yn-1-yl]amino}benzamide |
| 1751. | 3-methoxy-4-((3-(4-((1-(2-methoxyethyl)piperidin-4-yl)amino)-1-(2,2,2-trifluoroethyl)-1H-indol-2-yl)prop-2-yn-1-yl)amino)benzenesulfonamide |
| 1752. | 2-(3-((2-methoxy-4-(methylsulfonyl)phenyl)amino)prop-1-yn-1-yl)-N-(1-(2-methoxyethyl)piperidin-4-yl)-1-(2,2,2-trifluoroethyl)-1H-indol-4-amine |
| 1753. | 3-methoxy-4-{[3-(4-{[1-(2-methoxyethyl)piperidin-4-yl]amino}-1-(2,2,2-trifluoroethyl)-1H-indol-2-yl)prop-2-yn-1-yl]amino}-N-methylbenzamide |
| 1754. | 3-methoxy-4-{[3-(4-{[1-(2-methoxyethyl)piperidin-4-yl]amino}-1-(2,2,2-trifluoroethyl)-1H-indol-2-yl)prop-2-yn-1-yl]amino}-N-methylbenzene-1-sulfonamide |
| 1755. | 2-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}EtOAc |
| 1756. | 1-methoxy-3-{4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl}propan-2-yl acetate |
| 1757. | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzamide |
| 1758. | 2-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-5-methanesulfonylphenol |
| 1759. | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxy-N,N-dimethylbenzene-1-sulfonamide |
| 1760. | 4-({3-[4-({1-[(2R)-3-hydroxy-2-methoxypropyl]piperidin-4-yl}amino)-1-(2,2,2-trifluoroethyl)-1H-indol-2-yl]prop-2-yn-1-yl}amino)-3-methoxybenzene-1-sulfonamide |
| 1761. | N-(4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzenesulfonyl)-N-methylpropanamide |
| 1762. | 1-(4-{[2-(3-{[2-(2-fluoroethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol |
| 1763. | 1-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)tetradecan-1-one |
| 1764. | 1-methoxy-3-(4-{[2-(3-{[2-methoxy-4-(propanamidosulfonyl)phenyl]amino}prop-1-yn-1-yl)-1-(2,2,2-trifluoroethyl)-1H-indol-4-yl]amino}piperidin-1-yl)propan-2-yl propanoate |
| 1765. | 1-(4-{[2-(3-{[2-methoxy-4-(propanamidosulfonyl)phenyl]amino}prop-1-yn-1-yl)-1-(2,2,2-trifluoroethyl)-1H-indol-4-yl]amino}piperidin-1-yl)-3-(propanoyloxy)propan-2-yl propanoate |
| 1766. | (2R)-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-2-methoxypropan-1-ol |
| 1767. | (2S)-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-2-methoxypropan-1-ol |
| 1768. | 1-{4-[(2-{3-[(2-ethoxy-4-methanesulfonylphenyl)amino]prop-1-yn-1-yl}-1-(2,2,2-trifluoroethyl)-1H-indol-4-yl)amino]piperidin-1-yl}-3-methoxypropan-2-ol |
| 1769. | 4-({3-[4-({1-[(2S)-3-hydroxy-2-methoxypropyl]piperidin-4-yl}amino)-1-(2,2,2-trifluoroethyl)-1H-indol-2-yl]prop-2-yn-1-yl}amino)-3-methoxybenzene-1-sulfonamide |
| 1770. | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxy-N-(propan-2-yl)benzamide |
| 1771. | 3-hydroxy-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}benzene-1-sulfonamide |
| 1772. | (2R)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl 2-methylpropanoate |

TABLE 7-continued

| Mol # | IUPAC name |
| --- | --- |
| | Alkynyl indole compounds of the disclosure. |
| 1773. | N-(3-(4-((1-(2-hydroxy-3-methoxypropyl)piperidin-4-yl)amino)-1-(2,2,2-trifluoroethyl)-1H-indol-2-yl)prop-2-yn-1-yl)-N-(2-hydroxy-4-(N-propionylsulfamoyl)phenyl)propionamide |
| 1774. | 1-(4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}piperidin-1-yl)-3-methoxypropan-2-ol |
| 1775. | (2S)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl 2-methylpropanoate |
| 1776. | N-(3-(4-((1-(2-hydroxy-3-methoxypropyl)piperidin-4-yl)amino)-1-(2,2,2-trifluoroethyl)-1H-indol-2-yl)prop-2-yn-1-yl)-N-(2-hydroxy-4-(methylsulfonyl)phenyl)acetamide |
| 1777. | N-(3-(4-((1-(2-hydroxy-3-methoxypropyl)piperidin-4-yl)amino)-1-(2,2,2-trifluoroethyl)-1H-indol-2-yl)prop-2-yn-1-yl)-N-(2-hydroxy-4-(methylsulfonyl)phenyl)propionamide |
| 1778. | N-(3-(4-((1-(2-hydroxy-3-methoxypropyl)piperidin-4-yl)amino)-1-(2,2,2-trifluoroethyl)-1H-indol-2-yl)prop-2-yn-1-yl)-N-(2-hydroxy-4-(methylsulfonyl)phenyl)isobutyramide |
| 1779. | 2-(2-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-5-methanesulfonylphenoxy)acetonitrile |
| 1780. | 1-{4-[(2-{3-[(4-methanesulfonyl-2-methoxyphenyl)amino]prop-1-yn-1-yl}-5-methoxy-1-(2,2,2-trifluoroethyl)-1H-indol-4-yl)amino]piperidin-1-yl}-3-methoxypropan-2-ol |
| 1781. | 1-(4-{[2-(3-{[2-(2-hydroxyethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol |
| 1782. | 1-(4-{[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]amino}piperidin-1-yl)-3-methoxypropan-2-ol |
| 1783. | 1-[4-({2-[3-(2-amino-4-methanesulfonylphenoxy)prop-1-yn-1-yl]-1-(2,2,2-trifluoroethyl)-1H-indol-4-yl}amino)piperidin-1-yl]-3-methoxypropan-2-ol |
| 1784. | 4-({3-[4-({1-[(2R)-2-hydroxy-3-methoxypropyl]piperidin-4-yl}amino)-1-(2,2,2-trifluoroethyl)-1H-indol-2-yl]prop-2-yn-1-yl}amino)-3-methoxy-N-methylbenzamide |
| 1785. | 4-({3-[4-({1-[(2S)-2-hydroxy-3-methoxypropyl]piperidin-4-yl}amino)-1-(2,2,2-trifluoroethyl)-1H-indol-2-yl]prop-2-yn-1-yl}amino)-3-methoxy-N-methylbenzamide |
| 1786. | 4-({3-[4-({1-[(2R)-3-hydroxy-2-methoxypropyl]piperidin-4-yl}amino)-1-(2,2,2-trifluoroethyl)-1H-indol-2-yl]prop-2-yn-1-yl}amino)-3-methoxy-N-methylbenzamide |
| 1787. | 4-({3-[4-({1-[(2S)-3-hydroxy-2-methoxypropyl]piperidin-4-yl}amino)-1-(2,2,2-trifluoroethyl)-1H-indol-2-yl]prop-2-yn-1-yl}amino)-3-methoxy-N-methylbenzamide |
| 1788. | 1-{4-[(2-{3-[4-methanesulfonyl-2-(methylamino)phenoxy]prop-1-yn-1-yl}-1-(2,2,2-trifluoroethyl)-1H-indol-4-yl)amino]piperidin-1-yl}-3-methoxypropan-2-ol |
| 1789. | 3-(2-fluoroethoxy)-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-N-methylbenzamide |
| 1790. | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-(2-methoxyethoxy)-N-methylbenzamide |
| 1791. | 3-(cyanomethoxy)-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-N-methylbenzamide |
| 1792. | N-ethyl-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzamide |
| 1793. | 1-(4-{[2-(3-{[2-methoxy-4-(methylcarbamoyl)phenyl]amino}prop-1-yn-1-yl)-1-(2,2,2-trifluoroethyl)-1H-indol-4-yl]amino}piperidin-1-yl)-3-(propanoyloxy)propan-2-yl propanoate |
| 1794. | 1-methoxy-3-(4-{[2-(3-{[2-methoxy-4-(methylcarbamoyl)phenyl]amino}prop-1-yn-1-yl)-1-(2,2,2-trifluoroethyl)-1H-indol-4-yl]amino}piperidin-1-yl)propan-2-yl propanoate |
| 1795. | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxy-N-methylbenzamide |
| 1796. | 3-(2-cyanoethoxy)-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-N-methylbenzamide |
| 1797. | 1-ethoxy-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-ol |
| 1798. | 2-(2-{[3-(4-{[1-(2-hydroxypropyl)piperidin-4-yl]amino}-1-(2,2,2-trifluoroethyl)-1H-indol-2-yl)prop-2-yn-1-yl]amino}-5-methanesulfonylphenoxy)acetonitrile |
| 1799. | 1-(4-{[2-(3-{[4-(ethanesulfonyl)-2-methoxyphenyl]amino}prop-1-yn-1-yl)-1-(2,2,2-trifluoroethyl)-1H-indol-4-yl]amino}piperidin-1-yl)-3-methoxypropan-2-ol |
| 1800. | 3-(fluoromethoxy)-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-N-methylbenzamide |
| 1801. | 1-(4-{[2-(3-{[2-(fluoromethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol |
| 1802. | 2-(4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxyphenyl)-2-methylpropanenitrile |
| 1803. | (2S)-1-(4-{[2-(3-{[2-(fluoromethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol |
| 1804. | (2R)-1-(4-{[2-(3-{[2-(fluoromethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol |
| 1805. | 1-(4-{[2-(3-{[2-(difluoromethoxy)-4-methanesulfonylphenyl]amino}prop-1-yn-1-yl)-1-(2,2,2-trifluoroethyl)-1H-indol-4-yl]amino}piperidin-1-yl)-3-methoxypropan-2-ol |
| 1806. | 3-(2-hydroxy-3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propoxy)propane-1,2-diol |
| 1807. | 1-{4-[(2-{3-[(5-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol |

TABLE 7-continued

Alkynyl indole compounds of the disclosure.

| Mol # | IUPAC name |
|---|---|
| 1808. | 3-(3-(4-((1-(2-hydroxy-3-methoxypropyl)piperidin-4-yl)amino)-1-(2,2,2-trifluoroethyl)-1H-indol-2-yl)prop-2-yn-1-yl)-6-(methylsulfonyl)benzo[d]oxazol-2(3H)-one |
| 1809. | 1-{4-[(2-{3-[(4-methanesulfonylphenyl)amino]prop-1-yn-1-yl}-1-(2,2,2-trifluoroethyl)-1H-indol-4-yl)amino]piperidin-1-yl}-3-methoxypropan-2-ol |
| 1810. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-(2,2,2-trifluoroethoxy)propan-2-ol |
| 1811. | 4-hydroxy-9-[(2-{3-[(4-methanesulfonyl-2-methoxyphenyl)amino]prop-1-yn-1-yl}-1-(2,2,2-trifluoroethyl)-1H-indol-4-yl)amino]-2-oxa-6$\lambda^5$-azaspiro[5.5]undecan-6-ylium |
| 1812. | 2-{3-[(4-methanesulfonyl-2-methoxyphenyl)amino]prop-1-yn-1-yl}-N-[1-(3-methoxypropyl)piperidin-4-yl]-1-(2,2,2-trifluoroethyl)-1H-indol-4-amine |
| 1813. | 1-{4-[(2-{3-[(4-methanesulfonyl-2-methoxyphenyl)amino]prop-1-yn-1-yl}-3-methyl-1-(2,2,2-trifluoroethyl)-1H-indol-4-yl)amino]piperidin-1-yl}-3-methoxypropan-2-ol |
| 1814. | 1-{4-[(2-{3-[(5-fluoro-4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 1815. | 2-{3-[(4-methanesulfonyl-2-methoxyphenyl)amino]prop-1-yn-1-yl}-N-[1-(oxetan-3-yl)piperidin-4-yl]-1-(2,2,2-trifluoroethyl)-1H-indol-4-amine |
| 1816. | 2-(3-((2-methoxy-4-(methylsulfonyl)phenyl)amino)prop-1-yn-1-yl)-N-(1-(tetrahydrofuran-3-yl)piperidin-4-yl)-1-(2,2,2-trifluoroethyl)-1H-indol-4-amine |
| 1817. | (R)-2-(3-((2-methoxy-4-(methylsulfonyl)phenyl)amino)prop-1-yn-1-yl)-N-(1-(tetrahydrofuran-3-yl)piperidin-4-yl)-1-(2,2,2-trifluoroethyl)-1H-indol-4-amine |
| 1818. | (S)-2-(3-((2-methoxy-4-(methylsulfonyl)phenyl)amino)prop-1-yn-1-yl)-N-(1-(tetrahydrofuran-3-yl)piperidin-4-yl)-1-(2,2,2-trifluoroethyl)-1H-indol-4-amine |
| 1819. | 2-(3-((2-methoxy-4-(methylsulfonyl)phenyl)amino)prop-1-yn-1-yl)-N-(1-((tetrahydrofuran-2-yl)methyl)piperidin-4-yl)-1-(2,2,2-trifluoroethyl)-1H-indol-4-amine |
| 1820. | 2-fluoro-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-5-methoxybenzamide |
| 1821. | 1-methoxy-3-(4-((2-(3-(((3S,4R)-3-methoxytetrahydro-2H-pyran-4-yl)amino)prop-1-yn-1-yl)-1-(2,2,2-trifluoroethyl)-1H-indol-4-yl)amino)piperidin-1-yl)propan-2-ol |
| 1822. | 1-(4-{[2-(3-{[4-(cyclopropanesulfonyl)-2-methoxyphenyl]amino}prop-1-yn-1-yl)-1-(2,2,2-trifluoroethyl)-1H-indol-4-yl]amino}piperidin-1-yl)-3-methoxypropan-2-ol |
| 1823. | 3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propanenitrile |
| 1824. | 4-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)butanenitrile |
| 1825. | 2-{3-[(4-methanesulfonyl-2-methoxyphenyl)amino]prop-1-yn-1-yl}-N-{1-[(oxolan-2-yl)methyl]piperidin-4-yl}-1-(2,2,2-trifluoroethyl)-1H-indol-4-amine |
| 1826. | 1-methoxy-3-(4-{[2-(3-{[2-methoxy-4-(trifluoromethyl)phenyl]amino}prop-1-yn-1-yl)-1-(2,2,2-trifluoroethyl)-1H-indol-4-yl]amino}piperidin-1-yl)propan-2-ol |
| 1827. | 2-fluoro-4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-5-methoxy-N-methylbenzamide |
| 1828. | 1-(4-{[2-(3-{[4-(benzenesulfonyl)-2-methoxyphenyl]amino}prop-1-yn-1-yl)-1-(2,2,2-trifluoroethyl)-1H-indol-4-yl]amino}piperidin-1-yl)-3-methoxypropan-2-ol |
| 1829. | 2-{3-[(4-methanesulfonyl-2-methoxyphenyl)amino]prop-1-yn-1-yl}-N-[1-(2-methoxy-2-methylpropyl)piperidin-4-yl]-1-(2,2,2-trifluoroethyl)-1H-indol-4-amine |
| 1830. | 2-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)ethan-1-ol |
| 1831. | 1-methoxy-3-(4-{[2-(3-{[2-methoxy-4-(propane-2-sulfonyl)phenyl]amino}prop-1-yn-1-yl)-1-(2,2,2-trifluoroethyl)-1H-indol-4-yl]amino}piperidin-1-yl)propan-2-ol |
| 1832. | 1-{3-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 1833. | 1-methoxy-3-(4-((2-(3-(((3R,4R)-3-methoxytetrahydro-2H-pyran-4-yl)amino)prop-1-yn-1-yl)-1-(2,2,2-trifluoroethyl)-1H-indol-4-yl)amino)piperidin-1-yl)propan-2-ol |
| 1834. | 1-{4-[(2-{3-[(4-methanesulfonyl-2-methoxyphenyl)amino]prop-1-yn-1-yl}-1-propyl-1H-indol-4-yl)amino]piperidin-1-yl}-3-methoxypropan-2-ol |
| 1835. | 1-(4-{[1-(2-fluoroethyl)-2-{3-[(4-methanesulfonyl-2-methoxyphenyl)amino]prop-1-yn-1-yl}-1H-indol-4-yl]amino}piperidin-1-yl)-3-methoxypropan-2-ol |
| 1836. | 2-(4-{[1-(2-hydroxy-3-methoxypropyl)piperidin-4-yl]amino}-2-{3-[(4-methanesulfonyl-2-methoxyphenyl)amino]prop-1-yn-1-yl}-1H-indol-1-yl)acetonitrile |
| 1837. | 1-(4-{[1-(2-chloroethyl)-2-{3-[(4-methanesulfonyl-2-methoxyphenyl)amino]prop-1-yn-1-yl}-1H-indol-4-yl]amino}piperidin-1-yl)-3-methoxypropan-2-ol |
| 1838. | rac-1-[(3R,4S)-4-[(2-{3-[(4-methanesulfonyl-2-methoxyphenyl)amino]prop-1-yn-1-yl}-1-(2,2,2-trifluoroethyl)-1H-indol-4-yl)amino]-3-methylpiperidin-1-yl]-3-methoxypropan-2-ol |
| 1839. | rac-1-[(3R,4R)-4-[(2-{3-[(4-methanesulfonyl-2-methoxyphenyl)amino]prop-1-yn-1-yl}-1-(2,2,2-trifluoroethyl)-1H-indol-4-yl)amino]-3-methylpiperidin-1-yl]-3-methoxypropan-2-ol |
| 1840. | 1-{4-[(2-{3-[(4-methanesulfonyl-2-methylphenyl)amino]prop-1-yn-1-yl}-1-(2,2,2-trifluoroethyl)-1H-indol-4-yl)amino]piperidin-1-yl}-3-methoxypropan-2-ol |
| 1841. | 1-[4-({1-[(2,2-difluorocyclopropyl)methyl]-2-{3-[(4-methanesulfonyl-2-methoxyphenyl)amino]prop-1-yn-1-yl}-1H-indol-4-yl}amino)piperidin-1-yl]-3-methoxypropan-2-ol |
| 1842. | 4-{[3-(4-{[1-(2-hydroxy-3-methoxypropyl)piperidin-4-yl]amino}-1-(2,2,2-trifluoroethyl)-1H-indol-2-yl)prop-2-yn-1-yl]amino}-3-methoxybenzoic acid |
| 1843. | 2-{3-[(4-methanesulfonyl-2-methoxyphenyl)amino]prop-1-yn-1-yl}-N-[1-(3-methanesulfonylpropyl)piperidin-4-yl]-1-(2,2,2-trifluoroethyl)-1H-indol-4-amine |

TABLE 7-continued

Alkynyl indole compounds of the disclosure.

| Mol # | IUPAC name |
|---|---|
| 1844. | 4-{[3-(4-{[1-(3-methanesulfonylpropyl)piperidin-4-yl]amino}-1-(2,2,2-trifluoroethyl)-1H-indol-2-yl)prop-2-yn-1-yl]amino}-3-methoxybenzoic acid |
| 1845. | 1-(4-{[2-(3-{[4-methanesulfonyl-2-(trifluoromethyl)phenyl]amino}prop-1-yn-1-yl)-1-(2,2,2-trifluoroethyl)-1H-indol-4-yl]amino}piperidin-1-yl)-3-methoxypropan-2-ol |
| 1846. | 1-(4-{[1-(2,2-difluoroethyl)-2-{3-[(4-methanesulfonyl-2-methoxyphenyl)ino]prop-1-yn-1-yl}-1H-indol-4-yl]amino}piperidin-1-yl)-3-methoxypropan-2-ol |
| 1847. | 1-(4-{[2-(3-{[4-methanesulfonyl-2-(trifluoromethoxy)phenyl]amino}prop-1-yn-1-yl)-1-(2,2,2-trifluoroethyl)-1H-indol-4-yl]amino}piperidin-1-yl)-3-methoxypropan-2-ol |
| 1848. | 1-{4-[(2-{3-[(4-methanesulfonyl-2-methoxyphenyl)amino]prop-1-yn-1-yl}-1-(3,3,3-trifluoropropyl)-1H-indol-4-yl)amino]piperidin-1-yl}-3-methoxypropan-2-ol |
| 1849. | 1-(4-{[1-(2,2-difluoropropyl)-2-{3-[(4-methanesulfonyl-2-methoxyphenyl)amino]prop-1-yn-1-yl}-1H-indol-4-yl]amino}piperidin-1-yl)-3-methoxypropan-2-ol |
| 1850. | 1-{4-[(2-{3-[(2-chloro-4-methanesulfonylphenyl)amino]prop-1-yn-1-yl}-1-(2,2,2-trifluoroethyl)-1H-indol-4-yl)amino]piperidin-1-yl}-3-methoxypropan-2-ol |
| 1851. | 1-{4-[(2-{3-[(2-fluoro-4-methanesulfonyl-6-methoxyphenyl)amino]prop-1-yn-1-yl}-1-(2,2,2-trifluoroethyl)-1H-indol-4-yl)amino]piperidin-1-yl}-3-methoxypropan-2-ol |
| 1852. | 1-(4-((2-(3-((4-((6-oxa-3-azabicyclo[3.1.1]heptan-3-yl)sulfonyl)-2-methoxyphenyl)amino)prop-1-yn-1-yl)-1-(2,2,2-trifluoroethyl)-1H-indol-4-yl)amino)piperidin-1-yl)-3-methoxypropan-2-ol |
| 1853. | (2S)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-methoxypropan-2-yl propanoate |
| 1854. | 1-{4-[(2-{3-[(4-chloro-2-methoxyphenyl)amino]prop-1-yn-1-yl}-1-(2,2,2-trifluoroethyl)-1H-indol-4-yl)amino]piperidin-1-yl}-3-methoxypropan-2-ol |
| 1855. | 2-(2-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)ethoxy)ethan-1-ol |
| 1856. | 4-((3-(4-((1-(2,3-dihydroxypropyl)piperidin-4-yl)amino)-1-(2,2,2-trifluoroethyl)-1H-indol-2-yl)prop-2-yn-1-yl)amino)-N-(2-hydroxyethyl)-3-methoxybenzenesulfonamide |
| 1857. | 2-{3-[(4-methanesulfonyl-2-methoxyphenyl)amino]prop-1-yn-1-yl}-N-[1-(4-methyl-1,3-thiazol-2-yl)piperidin-4-yl]-1-(2,2,2-trifluoroethyl)-1H-indol-4-amine |
| 1858. | N-(1-cyclopropylpiperidin-4-yl)-2-{3-[(4-methanesulfonyl-2-methoxyphenyl)amino]prop-1-yn-1-yl}-1-(2,2,2-trifluoroethyl)-1H-indol-4-amine |
| 1859. | 4-[(3-{4-[(1-cyclopropylpiperidin-4-yl)amino]-1-(2,2,2-trifluoroethyl)-1H-indol-2-yl}prop-2-yn-1-yl)amino]-3-methoxybenzoic acid |
| 1860. | 2-{3-[(4-methanesulfonyl-2-methoxyphenyl)amino]prop-1-yn-1-yl}-N-{1-[(3R)-oxolan-3-yl]piperidin-4-yl}-1-(2,2,2-trifluoroethyl)-1H-indol-4-amine |
| 1861. | 2-{3-[(4-methanesulfonyl-2-methoxyphenyl)amino]prop-1-yn-1-yl}-N-{1-[(3S)-oxolan-3-yl]piperidin-4-yl}-1-(2,2,2-trifluoroethyl)-1H-indol-4-amine |
| 1862. | 3-methoxy-4-{[3-(4-{[1-(oxan-4-yl)piperidin-4-yl]amino}-1-(2,2,2-trifluoroethyl)-1H-indol-2-yl)prop-2-yn-1-yl]amino}benzoic acid |
| 1863. | 3-methoxy-4-((3-(4-((1-(tetrahydro-2H-pyran-4-yl)piperidin-4-yl)amino)-1-(2,2,2-trifluoroethyl)-1H-indol-2-yl)prop-2-yn-1-yl)amino)benzamide |
| 1864. | N-(2-hydroxyethyl)-3-methoxy-4-((3-(4-((1-(tetrahydro-2H-pyran-4-yl)piperidin-4-yl)amino)-1-(2,2,2-trifluoroethyl)-1H-indol-2-yl)prop-2-yn-1-yl)amino)benzenesulfonamide |
| 1865. | 3-methoxy-4-((3-(4-((1'-methyl-[1,4'-bipiperidin]-4-yl)amino)-1-(2,2,2-trifluoroethyl)-1H-indol-2-yl)prop-2-yn-1-yl)amino)benzamide |
| 1866. | 3-methoxy-4-((3-(4-((1-(2-(4-methylpiperazin-1-yl)-2-oxoethyl)piperidin-4-yl)amino)-1-(2,2,2-trifluoroethyl)-1H-indol-2-yl)prop-2-yn-1-yl)amino)benzamide |
| 1867. | 2-{2-[(3-{4-[(1-acetylpiperidin-4-yl)amino]-1-(2,2,2-trifluoroethyl)-1H-indol-2-yl}prop-2-yn-1-yl)amino]-5-methanesulfonylphenoxy}acetonitrile |
| 1868. | 4-{[3-(4-{[1-(2-hydroxyacetyl)piperidin-4-yl]amino}-1-(2,2,2-trifluoroethyl)-1H-indol-2-yl)prop-2-yn-1-yl]amino}-3-methoxy-N,N-dimethylbenzene-1-sulfonamide |
| 1869. | 2-hydroxy-1-{4-[(2-{3-[(2-hydroxy-4-methanesulfonylphenyl)amino]prop-1-yn-1-yl}-1-(2,2,2-trifluoroethyl)-1H-indol-4-yl)amino]piperidin-1-yl}ethan-1-one |
| 1870. | 2-hydroxy-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethan-1-one |
| 1871. | N-((3S,4S)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1872. | N-((3R,4R)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1873. | N-((3R,4R)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1874. | N-((3R,4S)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1875. | N-((3S,4R)-1,3-dimethylpiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1876. | 1-(4-((2-(3-((2-methoxy-4-(methylsulfonyl)phenyl)amino)prop-1-yn-1-yl)-1-(2,2,2-trifluoroethyl)-1H-indol-4-yl)amino)-2-methylpiperidin-1-yl)ethan-1-one |
| 1877. | 1-{4-[(2-{3-[(4-methanesulfonyl-2-methoxyphenyl)amino]prop-1-yn-1-yl}-1-(2,2,2-trifluoroethyl)-1H-indol-4-yl)amino]-2-methylpiperidin-1-yl}ethan-1-one |
| 1878. | 4-{[3-(4-{[(2S,4S)-1-acetyl-2-methylpiperidin-4-yl]amino}-1-(2,2,2-trifluoroethyl)-1H-indol-2-yl)prop-2-yn-1-yl]amino}-3-methoxybenzene-1-sulfonamide |
| 1879. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-2-methoxyethan-1-one |
| 1880. | 2-hydroxy-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-1-one |

TABLE 7-continued

| Mol # | IUPAC name |
|---|---|
| | Alkynyl indole compounds of the disclosure. |
| 1881. | 2-methoxy-1-(4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)ethan-1-one |
| 1882. | 3-methoxy-4-((3-(4-((1-(2-methoxyacetyl)piperidin-4-yl)amino)-1-(2,2,2-trifluoroethyl)-1H-indol-2-yl)prop-2-yn-1-yl)amino)benzenesulfonamide |
| 1883. | 4-{[3-(4-{[1-(2-hydroxypropanoyl)piperidin-4-yl]amino}-1-(2,2,2-trifluoroethyl)-1H-indol-2-yl)prop-2-yn-1-yl]amino}-3-methoxybenzene-1-sulfonamide |
| 1884. | 3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-3-oxopropanenitrile |
| 1885. | 4-{[3-(4-{[1-(2-cyanoacetyl)piperidin-4-yl]amino}-1-(2,2,2-trifluoroethyl)-1H-indol-2-yl)prop-2-yn-1-yl]amino}-3-methoxybenzene-1-sulfonamide |
| 1886. | 4-{[3-(4-{[1-(2-hydroxyacetyl)piperidin-4-yl]amino}-1-(2,2,2-trifluoroethyl)-1H-indol-2-yl)prop-2-yn-1-yl]amino}-3-methoxybenzene-1-sulfonamide |
| 1887. | 4-[(3-{4-[(1-acetylpiperidin-4-yl)amino]-1-(2,2,2-trifluoroethyl)-1H-indol-2-yl}prop-2-yn-1-yl)amino]-3-methoxybenzene-1-sulfonamide |
| 1888. | 2-(dimethylamino)-1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethan-1-one |
| 1889. | 4-((3-(4-((1-(dimethylglycyl)piperidin-4-yl)amino)-1-(2,2,2-trifluoroethyl)-1H-indol-2-yl)prop-2-yn-1-yl)amino)-3-methoxybenzenesulfonamide |
| 1890. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-2-methylpropan-1-one |
| 1891. | 3-methoxy-4-{[3-(4-{[1-(2-methylpropanoyl)piperidin-4-yl]amino}-1-(2,2,2-trifluoroethyl)-1H-indol-2-yl)prop-2-yn-1-yl]amino}benzene-1-sulfonamide |
| 1892. | 4-((2-(3-((2-methoxy-4-(methylsulfonyl)phenyl)amino)prop-1-yn-1-yl)-1-(2,2,2-trifluoroethyl)-1H-indol-4-yl)amino)-N,N-dimethylpiperidine-1-carboxamide |
| 1893. | 4-[(3-{4-[(1-acetylpiperidin-4-yl)amino]-1-(2,2,2-trifluoroethyl)-1H-indol-2-yl}prop-2-yn-1-yl)amino]-3-methoxy-N,N-dimethylbenzene-1-sulfonamide |
| 1894. | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-1-one |
| 1895. | 3-methoxy-4-[(3-{4-[(1-propanoylpiperidin-4-yl)amino]-1-(2,2,2-trifluoroethyl)-1H-indol-2-yl}prop-2-yn-1-yl)amino]benzene-1-sulfonamide |
| 1896. | 1-(4-{[2-(3-{[2-methoxy-4-(morpholine-4-sulfonyl)phenyl]amino}prop-1-yn-1-yl)-1-(2,2,2-trifluoroethyl)-1H-indol-4-yl]amino}piperidin-1-yl)ethan-1-one |
| 1897. | 3-methoxy-4-[(3-{4-[(1-{[(4S)-2-oxo-1,3-dioxolan-4-yl]methyl}piperidin-4-yl)amino]-1-(2,2,2-trifluoroethyl)-1H-indol-2-yl}prop-2-yn-1-yl)amino]benzene-1-sulfonamide |
| 1898. | N-((3-methoxy-4-((3-(4-((1-((2-oxo-1,3-dioxolan-4-yl)methyl)piperidin-4-yl)amino)-1-(2,2,2-trifluoroethyl)-1H-indol-2-yl)prop-2-yn-1-yl)amino)phenyl)sulfonyl)propionamide |
| 1899. | N-[3-methoxy-4-({3-[4-({1-[(2-oxo-1,3-dioxolan-4-yl)methyl]piperidin-4-yl}amino)-1-(2,2,2-trifluoroethyl)-1H-indol-2-yl]prop-2-yn-1-yl}amino)benzenesulfonyl]acetamide |
| 1900. | 3-methoxy-N-methyl-4-({3-[4-({1-[(2-oxo-1,3-dioxolan-4-yl)methyl]piperidin-4-yl}amino)-1-(2,2,2-trifluoroethyl)-1H-indol-2-yl]prop-2-yn-1-yl}amino)benzamide |
| 1901. | 2-(3-((2-methoxy-4-(methylsulfonyl)phenyl)amino)prop-1-yn-1-yl)-N-(octahydroindolizin-7-yl)-1-(2,2,2-trifluoroethyl)-1H-indol-4-amine |
| 1902. | N-[(7R,8aS)-octahydroindolizin-7-yl]-2-{3-[(4-methanesulfonyl-2-methoxyphfenyl)amino]prop-1-yn-1-yl}-1-(2,2,2-trifluoroethyl)-1H-indol-4-amine |
| 1903. | N-[(7R,8aR)-octahydroindolizin-7-yl]-2-{3-[(4-methanesulfonyl-2-methoxyphenyl)amino]prop-1-yn-1-yl}-1-(2,2,2-trifluoroethyl)-1H-indol-4-amine |
| 1904. | rac-(3R,4S)-3-[(2-{3-[(4-methanesulfonyl-2-methoxyphenyl)amino]prop-1-yn-1-yl}-1-(2,2,2-trifluoroethyl)-1H-indol-4-yl)amino]-1-methylpiperidin-4-ol |
| 1905. | rac-(3R,4R)-4-[(2-{3-[(4-methanesulfonyl-2-methoxyphenyl)amino]prop-1-yn-1-yl}-1-(2,2,2-trifluoroethyl)-1H-indol-4-yl)amino]-1-methylpiperidin-3-ol |
| 1906. | 3-methoxy-4-((3-(4-((1-(tetrahydro-2H-pyran-4-yl)piperidin-4-yl)amino)-1-(2,2,2-trifluoroethyl)-1H-indol-2-yl)prop-2-yn-1-yl)amino)benzenesulfonamide |
| 1907. | rac-N-[(3R,4S)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1908. | N-((3S,4S)-3-fluoro-1-methylpiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1909. | N-[(3S,4S)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1910. | N-[(3R,4S)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1911. | N-[(3S,4R)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1912. | N-[(3R,4R)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1913. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonamide |
| 1914. | rac-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonamide |
| 1915. | rac-methyl 4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1916. | rac-methyl 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1917. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoic acid |
| 1918. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoic acid |

TABLE 7-continued

| Mol # | IUPAC name |
|---|---|
| | Alkynyl indole compounds of the disclosure. |
| 1919. | 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoic acid |
| 1920. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzamide |
| 1921. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide |
| 1922. | 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxy-N-methylbenzamide |
| 1923. | rac-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide |
| 1924. | 2-fluoro-4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-5-methoxy-N-methylbenzamide |
| 1925. | 2-fluoro-4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-5-methoxy-N-methylbenzamide |
| 1926. | 4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzoic acid |
| 1927. | 4-{[3-(4-{[(3S,4S)-3-fluoro-1-methylpiperidin-4-yl]amino}-1-(2,2,2-trifluoroethyl)-1H-indol-2-yl)prop-2-yn-1-yl]amino}-3-methoxybenzoic acid |
| 1928. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonamide |
| 1929. | 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonamide |
| 1930. | methyl 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1931. | rac-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 1932. | methyl 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1933. | rac-N-[(3R,4S)-3-fluoro-1-(propan-2-yl)piperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1934. | rac-4-{[3-(4-{[(3R,4S)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoic acid |
| 1935. | rac-ethyl 4-{[3-(4-{[(3R,4S)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoate |
| 1936. | rac-ethyl 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1937. | (2R)-1-(acetyloxy)-3-[(3RS,4SR)-3-fluoro-4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl]propan-2-yl acetate |
| 1938. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 1939. | 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzamide |
| 1940. | N-[(3S,4R)-3-fluoro-1-(propan-2-yl)piperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1941. | N-[(3R,4S)-3-fluoro-1-(propan-2-yl)piperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1942. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide |
| 1943. | 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-methylbenzamide |
| 1944. | rac-2-hydroxypropyl 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1945. | 4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-N-isopropyl-3-methoxybenzamide |
| 1946. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(propan-2-yl)benzamide |
| 1947. | 4-{[3-(4-{[(3S,4R)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoic acid |
| 1948. | 4-{[3-(4-{[(3R,4S)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoic acid |
| 1949. | rac-2-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]acetamide |
| 1950. | N-[(3S,4R)-1-ethyl-3-fluoropiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1951. | N-[(3R,4S)-1-ethyl-3-fluoropiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1952. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-(2-methoxyethyl)benzamide |
| 1953. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N,N-dimethylbenzamide |
| 1954. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-N-(2-hydroxy-3-methoxypropyl)-3-methoxybenzamide |
| 1955. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-(propan-2-yl)benzamide |

TABLE 7-continued

| Mol # | IUPAC name |
| --- | --- |
| | Alkynyl indole compounds of the disclosure. |
| 1956. | rac-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxy-N-(oxan-4-yl)benzamide |
| 1957. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(oxan-4-yl)benzamide |
| 1958. | rac-N-[(3R,4S)-1-ethyl-3-fluoropiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1959. | ethyl 4-{[3-(4-{[(3S,4R)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoate |
| 1960. | ethyl 4-((3-(4-(((3R,4S)-1-ethyl-3-fluoropiperidin-4-yl)amino)-1-(2,2,2-trifluoroethyl)-1H-indol-2-yl)prop-2-yn-1-yl)amino)-3-methoxybenzoate |
| 1961. | ethyl 4-{[3-(4-{[(3S,4R)-1-ethyl-3-fluoropiperidin-4-yl]amino}-1-(2,2,2-trifluoroethyl)-1H-indol-2-yl)prop-2-yn-1-yl]amino}-3-methoxybenzoate |
| 1962. | ethyl 4-{[3-(4-{[(3R,4S)-1-ethyl-3-fluoropiperidin-4-yl]amino}-1-(2,2,2-trifluoroethyl)-1H-indol-2-yl)prop-2-yn-1-yl]amino}-3-methoxybenzoate |
| 1963. | ethyl 4-{[3-(4-{[(3R,4S)-3-fluoro-1-(propan-2-yl)piperidin-4-yl]amino}-1-(2,2,2-trifluoroethyl)-1H-indol-2-yl)prop-2-yn-1-yl]amino}-3-methoxybenzoate |
| 1964. | 2-fluoro-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-5-methoxy-N-methylbenzamide |
| 1965. | 2-fluoro-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-5-methoxy-N-methylbenzamide |
| 1966. | 4-{[3-(4-{[(3R,4S)-1-ethyl-3-fluoropiperidin-4-yl]amino}-1-(2,2,2-trifluoroethyl)-1H-indol-2-yl)prop-2-yn-1-yl]amino}-3-methoxybenzoic acid |
| 1967. | 4-{[3-(4-{[(3S,4R)-1-ethyl-3-fluoropiperidin-4-yl]amino}-1-(2,2,2-trifluoroethyl)-1H-indol-2-yl)prop-2-yn-1-yl]amino}-3-methoxybenzoic acid |
| 1968. | rac-N-(2-{bis[(pyridin-2-yl)methyl]amino}ethyl)-4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzamide |
| 1969. | rac-N-[(3R,4S)-3-fluoro-1-methylpiperidin-4-yl]-2-{3-[(4-methanesulfonyl-2-methoxyphenyl)amino]prop-1-yn-1-yl}-N-methyl-1-(2,2,2-trifluoroethyl)-1H-indol-4-amine |
| 1970. | rac-4-((3-(4-(((3R,4S)-3-fluoro-1-methylpiperidin-4-yl)amino)-1-(2,2,2-trifluoroethyl)-1H-indol-2-yl)prop-2-yn-1-yl)amino)-3-methoxybenzoic acid |
| 1971. | rac-4-{[3-(4-{[(3R,4R)-3-fluoro-1-methylpiperidin-4-yl]amino}-1-(2,2,2-trifluoroethyl)-1H-indol-2-yl)prop-2-yn-1-yl]amino}-3-methoxybenzoic acid |
| 1972. | 2-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-5-methanesulfonylphenol |
| 1973. | 2-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-5-methanesulfonylphenol |
| 1974. | rac-6-fluoro-N-[(3R,4S)-3-fluoro-1-methylpiperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1975. | N-(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzenesulfonyl)acetamide |
| 1976. | N-(4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzenesulfonyl)acetamide |
| 1977. | ethyl 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1978. | ethyl 4-{[3-(4-{[(3R,4S)-3-fluoro-1-methylpiperidin-4-yl]amino}-1-(2,2,2-trifluoroethyl)-1H-indol-2-yl)prop-2-yn-1-yl]amino}-3-methoxybenzoate |
| 1979. | N-[(3R,4S)-3-fluoro-1-methylpiperidin-4-yl]-2-(3-{[2-(fluoromethoxy)-4-methanesulfonylphenyl]amino}prop-1-yn-1-yl)-1-(2,2,2-trifluoroethyl)-1H-indol-4-amine |
| 1980. | N-[(3S,4R)-3-fluoro-1-methylpiperidin-4-yl]-2-(3-{[2-(fluoromethoxy)-4-methanesulfonylphenyl]amino}prop-1-yn-1-yl)-1-(2,2,2-trifluoroethyl)-1H-indol-4-amine |
| 1981. | 2-{3-[(2-ethoxy-4-methanesulfonylphenyl)amino]prop-1-yn-1-yl}-N-[(3S,4R)-3-fluoro-1-methylpiperidin-4-yl]-1-(2,2,2-trifluoroethyl)-1H-indol-4-amine |
| 1982. | 2-{3-[(2-ethoxy-4-methanesulfonylphenyl)amino]prop-1-yn-1-yl}-N-[(3R,4S)-3-fluoro-1-methylpiperidin-4-yl]-1-(2,2,2-trifluoroethyl)-1H-indol-4-amine |
| 1983. | 4-{[3-(4-{[(3S,4R)-3-fluoropiperidin-4-yl]amino}-1-(2,2,2-trifluoroethyl)-1H-indol-2-yl)prop-2-yn-1-yl]amino}-3-methoxybenzene-1-sulfonamide |
| 1984. | 4-{[3-(4-{[(3R,4S)-3-fluoropiperidin-4-yl]amino}-1-(2,2,2-trifluoroethyl)-1H-indol-2-yl)prop-2-yn-1-yl]amino}-3-methoxybenzene-1-sulfonamide |
| 1985. | N-((3S,4R)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1986. | N-((3R,4S)-3-fluoropiperidin-4-yl)-2-(3-((2-methoxy-4-(methylsulfonyl)phenyl)amino)prop-1-yn-1-yl)-1-(2,2,2-trifluoroethyl)-1H-indol-4-amine |
| 1987. | 4-{[3-(4-{[(3S,4R)-3-fluoropiperidin-4-yl]amino}-1-(2,2,2-trifluoroethyl)-1H-indol-2-yl)prop-2-yn-1-yl]amino}-3-methoxybenzamide |
| 1988. | 4-((3-(4-(((3R,4S)-3-fluoropiperidin-4-yl)amino)-1-(2,2,2-trifluoroethyl)-1H-indol-2-yl)prop-2-yn-1-yl)amino)-3-methoxybenzamide |
| 1989. | 4-{[3-(4-{[(3R,4S)-3-fluoropiperidin-4-yl]amino}-1-(2,2,2-trifluoroethyl)-1H-indol-2-yl)prop-2-yn-1-yl]amino}-3-methoxy-N-methylbenzamide |
| 1990. | 4-{[3-(4-{[(3R,4S)-3-fluoropiperidin-4-yl]amino}-1-(2,2,2-trifluoroethyl)-1H-indol-2-yl)prop-2-yn-1-yl]amino}-3-methoxybenzoic acid |
| 1991. | 2-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-ol |
| 1992. | 2-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-ol |

TABLE 7-continued

| Mol # | IUPAC name |
|---|---|
| | Alkynyl indole compounds of the disclosure. |
| 1993. | 2-(dimethylamino)-1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one |
| 1994. | 2-(dimethylamino)-1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one |
| 1995. | 4-{[3-(4-{[(3S,4R)-3-fluoropiperidin-4-yl]amino}-1-(2,2,2-trifluoroethyl)-1H-indol-2-yl)prop-2-yn-1-yl]amino}-3-methoxy-N-methylbenzamide |
| 1996. | 4-{[3-(4-{[(3S,4R)-3-fluoropiperidin-4-yl]amino}-1-(2,2,2-trifluoroethyl)-1H-indol-2-yl)prop-2-yn-1-yl]amino}-3-methoxybenzoic acid |
| 1997. | N-[(3S,4R)-3-fluoro-1-(2-methoxyethyl)piperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1998. | N-[(3R,4S)-3-fluoro-1-(2-methoxyethyl)piperidin-4-yl]-2-{3-[(4-methanesulfonyl-2-methoxyphenyl)amino]prop-1-yn-1-yl}-1-(2,2,2-trifluoroethyl)-1H-indol-4-amine |
| 1999. | 4-{[3-(4-{[(3S,4R)-3-fluoro-1-[(2R)-2-hydroxy-3-methoxypropyl]piperidin-4-yl]amino}-1-(2,2,2-trifluoroethyl)-1H-indol-2-yl)prop-2-yn-1-yl]amino}-3-methoxybenzene-1-sulfonamide |
| 2000. | 1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one |
| 2001. | 1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one |
| 2002. | 1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]propan-1-one |
| 2003. | 1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]propan-1-one |
| 2004. | 1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]-2-methoxyethan-1-one |
| 2005. | 1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]-2-methoxyethan-1-one |
| 2006. | 4-{[3-(4-{[(3R,4S)-3-fluoropiperidin-4-yl]amino}-1-(2,2,2-trifluoroethyl)-1H-indol-2-yl)prop-2-yn-1-yl]amino}-3-methoxybenzamide |
| 2007. | 4-{[3-(4-{[(3R,4S)-3-fluoro-1-[(2R)-2-hydroxy-3-methoxypropyl]piperidin-4-yl]amino}-1-(2,2,2-trifluoroethyl)-1H-indol-2-yl)prop-2-yn-1-yl]amino}-3-methoxybenzene-1-sulfonamide |
| 2008. | N-[(7S,8R)-7-fluoro-1,4-dioxaspiro[4.5]decan-8-yl]-2-{3-[(4-methanesulfonyl-2-methoxyphenyl)amino]prop-1-yn-1-yl}-1-(2,2,2-trifluoroethyl)-1H-indol-4-amine |
| 2009. | 1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]propan-2-ol |
| 2010. | 1-((3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2011. | 1-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2012. | 4-((3-(4-(((3S,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |
| 2013. | 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |
| 2014. | 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |
| 2015. | 4-((3-(4-(((3S,4R)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |
| 2016. | methyl 4-((3-(4-(((3S,4R)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoate |
| 2017. | methyl 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoate |
| 2018. | (R)-1-((3R,4S)-3-fluoro-4-((2-(3-((2-fluoro-6-methoxy-4-(methylsulfonyl)phenyl)amino)prop-1-yn-1-yl)-1-propyl-1H-indol-4-yl)amino)piperidin-1-yl)-3-methoxypropan-2-ol |
| 2019. | (R)-1-((3R,4S)-4-((1-allyl-2-(3-((2-fluoro-6-methoxy-4-(methylsulfonyl)phenyl)amino)prop-1-yn-1-yl)-1H-indol-4-yl)amino)-3-fluoropiperidin-1-yl)-3-methoxypropan-2-ol |
| 2020. | 4-{[3-(4-{[(3S,4R)-1-[(2R)-2,3-dihydroxypropyl]-3-fluoropiperidin-4-yl]amino}-1-(2,2,2-trifluoroethyl)-1H-indol-2-yl)prop-2-yn-1-yl]amino}-3-methoxybenzene-1-sulfonamide |
| 2021. | 4-{[3-(4-{[(3R,4S)-1-[(2R)-2,3-dihydroxypropyl]-3-fluoropiperidin-4-yl]amino}-1-(2,2,2-trifluoroethyl)-1H-indol-2-yl)prop-2-yn-1-yl]amino}-3-methoxybenzene-1-sulfonamide |
| 2022. | (2R)-1-[(3RS,4SR)-3-fluoro-4-[(2-{3-[(4-methanesulfonyl-2-methoxyphenyl)amino]prop-1-yn-1-yl}-1-propyl-1H-indol-4-yl)amino]piperidin-1-yl]-3-methoxypropan-2-ol |
| 2023. | 4-((3-(4-(((3S,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |
| 2024. | 4-((3-(4-(((3S,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |
| 2025. | 4-((3-(4-(((3R,4R)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzoic acid |

TABLE 7-continued

Alkynyl indole compounds of the disclosure.

| Mol # | IUPAC name |
|---|---|
| 2026. | (2R)-1-(acetyloxy)-3-[(3R,4S)-3-fluoro-4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl]propan-2-yl acetate |
| 2027. | N-[(2R)-2,3-dihydroxypropyl]-4-{[3-(4-{[(3RS,4SR)-3-fluoro-1-[(2R)-2-hydroxy-3-methoxypropyl]piperidin-4-yl]amino}-1-(2,2,2-trifluoroethyl)-1H-indol-2-yl)prop-2-yn-1-yl]amino}-3-methoxybenzene-1-sulfonamide |
| 2028. | (2R)-1-(acetyloxy)-3-[(3S,4R)-3-fluoro-4-[(2-{3-[(2-methoxy-4-sulfamoylphenyl)amino]prop-1-yn-1-yl}-1-(2,2,2-trifluoroethyl)-1H-indol-4-yl)amino]piperidin-1-yl]propan-2-yl acetate |
| 2029. | rac-N-(2-{bis[(pyridin-2-yl)methyl]amino}ethyl)-2-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]acetamide |
| 2030. | 2-amino-1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one |
| 2031. | 2-amino-1-[(3S,4R)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]ethan-1-one |
| 2032. | 1-[(3R,4S)-3-fluoro-4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl]propan-2-ol |
| 2033. | 3-(4-(((3S,4R)-3-fluoro-1-methylpiperidin-4-yl)amino)-1-(2,2,2-trifluoroethyl)-1H-indol-2-yl)prop-2-yn-1-ol |
| 2034. | (4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoyl)glycine |
| 2035. | methyl 4-{[3-(4-{[(3S,4R)-3-fluoro-1-(2-methoxyethyl)piperidin-4-yl]amino}-1-(2,2,2-trifluoroethyl)-1H-indol-2-yl)prop-2-yn-1-yl]amino}-3-methoxybenzoate |
| 2036. | 4-{[3-(4-{[(3S,4R)-3-fluoro-1-(2-methoxyethyl)piperidin-4-yl]amino}-1-(2,2,2-trifluoroethyl)-1H-indol-2-yl)prop-2-yn-1-yl]amino}-3-methoxybenzoic acid |
| 2037. | methyl 4-{[3-(4-{[(3S,4R)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoate |
| 2038. | methyl 4-{[3-(4-{[(3S,4R)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoate |
| 2039. | methyl 4-{[3-(4-{[(3S,4R)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoate |
| 2040. | methyl 4-{[3-(4-{[(3R,4S)-3-fluoro-1-(2-methoxyethyl)piperidin-4-yl]amino}-1-(2,2,2-trifluoroethyl)-1H-indol-2-yl)prop-2-yn-1-yl]amino}-3-methoxybenzoate |
| 2041. | methyl 4-{[3-(4-{[(3R,4S)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoate |
| 2042. | 4-{[3-(4-{[(3R,4S)-3-fluoro-1-(2-methoxyethyl)piperidin-4-yl]amino}-1-(2,2,2-trifluoroethyl)-1H-indol-2-yl)prop-2-yn-1-yl]amino}-3-methoxybenzoic acid |
| 2043. | methyl 4-{[3-(4-{[(3R,4S)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoate |
| 2044. | N-[(3S,4R)-3-fluoro-1-methylpiperidin-4-yl]-2-{3-[(2-methoxy-4-{2-oxa-6-azaspiro[3.3]heptane-6-carbonyl}phenyl)amino]prop-1-yn-1-yl}-1-(2,2,2-trifluoroethyl)-1H-indol-4-amine |
| 2045. | N-[(3S,4R)-3-fluoro-1-methylpiperidin-4-yl]-2-{3-[(2-methoxy-4-{7-oxa-2-azaspiro[3.5]nonane-2-carbonyl}phenyl)amino]prop-1-yn-1-yl}-1-(2,2,2-trifluoroethyl)-1H-indol-4-amine |
| 2046. | 4-{[3-(4-{[(3S,4R)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoic acid |
| 2047. | N-[(3S,4R)-3-fluoro-1-methylpiperidin-4-yl]-2-(3-{[2-methoxy-4-(morpholine-4-carbonyl)phenyl]amino}prop-1-yn-1-yl)-1-(2,2,2-trifluoroethyl)-1H-indol-4-amine |
| 2048. | N-[(3S,4R)-3-fluoro-1-methylpiperidin-4-yl]-2-(3-{[2-methoxy-4-(4-methylpiperazine-1-carbonyl)phenyl]amino}prop-1-yn-1-yl)-1-(2,2,2-trifluoroethyl)-1H-indol-4-amine |
| 2049. | 4-{[3-(4-{[(3R,4S)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoic acid |
| 2050. | 4-{[3-(4-{[(3R,4S)-3-fluoro-1-(2-hydroxyethyl)piperidin-4-yl]amino}-1-(2,2,2-trifluoroethyl)-1H-indol-2-yl)prop-2-yn-1-yl]amino}-3-methoxybenzoic acid |
| 2051. | methyl 4-{[3-(4-{[(3S,4R)-1-[(dimethylcarbamoyl)methyl]-3-fluoropiperidin-4-yl]amino}-1-(2,2,2-trifluoroethyl)-1H-indol-2-yl)prop-2-yn-1-yl]amino}-3-methoxybenzoate |
| 2052. | methyl 4-{[3-(4-{[(3R,4S)-1-[(dimethylcarbamoyl)methyl]-3-fluoropiperidin-4-yl]amino}-1-(2,2,2-trifluoroethyl)-1H-indol-2-yl)prop-2-yn-1-yl]amino}-3-methoxybenzoate |
| 2053. | methyl 4-{[3-(4-{[(3R,4S)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoate |
| 2054. | 2-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)acetamide |
| 2055. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(1,3-thiazol-2-yl)benzamide |
| 2056. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(1-methylpiperidin-4-yl)benzamide |
| 2057. | 1-(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzoyl)piperidin-4-ol |
| 2058. | 4-{[3-(4-{[(3S,4R)-1-[(dimethylcarbamoyl)methyl]-3-fluoropiperidin-4-yl]amino}-1-(2,2,2-trifluoroethyl)-1H-indol-2-yl)prop-2-yn-1-yl]amino}-3-methoxybenzoic acid |

TABLE 7-continued

| Alkynyl indole compounds of the disclosure. | |
|---|---|
| Mol # | IUPAC name |
| 2059. | 4-{[3-(4-{[(3S,4R)-3-fluoro-1-(2-hydroxypropyl)piperidin-4-yl]amino}-1-(2,2,2-trifluoroethyl)-1H-indol-2-yl)prop-2-yn-1-yl]amino}-3-methoxybenzoic acid |
| 2060. | tert-butyl (3S,4R)-4-{[2-(3-{[4-(ethanesulfonyl)-2-methoxyphenyl]amino}prop-1-yn-1-yl)-1-(2,2,2-trifluoroethyl)-1H-indol-4-yl]amino}-3-fluoropiperidine-1-carboxylate |
| 2061. | 2-(3-((4-(ethylsulfonyl)-2-methoxyphenyl)amino)prop-1-yn-1-yl)-N-((3S,4R)-3-fluoropiperidin-4-yl)-1-(2,2,2-trifluoroethyl)-1H-indol-4-amine |
| 2062. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-[2-(morpholin-4-yl)ethyl]benzamide |
| 2063. | 4-{[3-(4-{[(3R,4S)-1-(carbamoylmethyl)-3-fluoropiperidin-4-yl]amino}-1-(2,2,2-trifluoroethyl)-1H-indol-2-yl)prop-2-yn-1-yl]amino}-3-methoxybenzoic acid |
| 2064. | 4-{[3-(4-{[(3S,4R)-1-(carbamoylmethyl)-3-fluoropiperidin-4-yl]amino]-1-(2,2,2-trifluoroethyl)-1H-indol-2-yl)prop-2-yn-1-yl]amino}-3-methoxybenzoic acid |
| 2065. | 4-{[3-(4-{[(3R,4S)-1-[(dimethylcarbamoyl)methyl]-3-fluoropiperidin-4-yl]amino}-1-(2,2,2-trifluoroethyl)-1H-indol-2-yl)prop-2-yn-1-yl]amino}-3-methoxybenzoic acid |
| 2066. | tert-butyl (3S,4R)-4-[(2-{3-[(2-ethoxy-4-methanesulfonylphenyl)amino]prop-1-yn-1-yl}-1-(2,2,2-trifluoroethyl)-1H-indol-4-yl)amino]-3-fluoropiperidine-1-carboxylate |
| 2067. | (2S)-2-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]pentanedioic acid |
| 2068. | (2S)-4-carbamoyl-2-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]butanoic acid |
| 2069. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzene-1-sulfonic acid |
| 2070. | 1,5-dimethyl (2S)-2-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]pentanedioate |
| 2071. | 2-[3-({4-[4-(dimethylamino)piperidine-1-carbonyl]-2-methoxyphenyl}amino)prop-1-yn-1-yl]-N-[(3S,4R)-3-fluoro-1-methylpiperidin-4-yl]-1-(2,2,2-trifluoroethyl)-1H-indol-4-amine |
| 2072. | 4-{[3-(4-{[(3S,4R)-1-(carboxymethyl)-3-fluoropiperidin-4-yl]amino}-1-(2,2,2-trifluoroethyl)-1H-indol-2-yl)prop-2-yn-1-yl]amino}-3-methoxybenzoic acid |
| 2073. | 2-(3-{[4-(ethanesulfonyl)-2-methoxyphenyl]amino}prop-1-yn-1-yl)-N-[(3S,4R)-3-fluoropiperidin-4-yl]-1-(2,2,2-trifluoroethyl)-1H-indol-4-amine |
| 2074. | (1R,2R,4S)-2-fluoro-$N^1$-(2-{3-[(4-methanesulfonyl-2-methoxyphenyl)amino]prop-1-yn-1-yl}-1-(2,2,2-trifluoroethyl)-1H-indol-4-yl)cyclohexane-1,4-diamine |
| 2075. | (1R,2R,4S)-2-fluoro-$N^1$-(2-{3-[(4-methanesulfonyl-2-methoxyphenyl)amino]prop-1-yn-1-yl}-1-(2,2,2-trifluoroethyl)-1H-indol-4-yl)-$N^4$-methylcyclohexane-1,4-diamine |
| 2076. | (1S,3R,4R)-3-fluoro-$N^4$-(2-{3-[(4-methanesulfonyl-2-methoxyphenyl)amino]prop-1-yn-1-yl}-1-(2,2,2-trifluoroethyl)-1H-indol-4-yl)-$N^1$,$N^1$-dimethylcyclohexane-1,4-diamine |
| 2077. | 2-(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzenesulfonyl)ethan-1-ol |
| 2078. | N-ethyl-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 2079. | 2-{3-[(2-ethoxy-4-methanesulfonylphenyl)amino]prop-1-yn-1-yl}-N-[(3S,4R)-3-fluoropiperidin-4-yl]-1-(2,2,2-trifluoroethyl)-1H-indol-4-amine |
| 2080. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N,N-dimethylbenzamide |
| 2081. | N-ethyl-4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxy-N-methylbenzamide |
| 2082. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-methyl-N-(propan-2-yl)benzamide |
| 2083. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-(2-methoxyethyl)benzamide |
| 2084. | N-[2-(diethylamino)ethyl]-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 2085. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(2-hydroxyethyl)-3-methoxybenzamide |
| 2086. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-[(2R,3R,4R,5S,6R)-2,4,5-trihydroxy-6-(hydroxymethyl)oxan-3-yl]benzamide |
| 2087. | 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-N-(1-hydroxypropan-2-yl)-3-methoxybenzamide |
| 2088. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-[(2R)-1-hydroxypropan-2-yl]-3-methoxybenzamide |
| 2089. | N-[3-(4-{[(3S,4R)-3-fluoro-1-methylpiperidin-4-yl]amino}-1-(2,2,2-trifluoroethyl)-1H-indol-2-yl)prop-2-yn-1-yl]cyclopropanecarboxamide |
| 2090. | (1R,2R)-N-[3-(4-{[(3S,4R)-3-fluoro-1-methylpiperidin-4-yl]amino}-1-(2,2,2-trifluoroethyl)-1H-indol-2-yl)prop-2-yn-1-yl]-2-phenylcyclopropane-1-carboxamide |
| 2091. | N-[3-(4-{[(3S,4R)-3-fluoro-1-methylpiperidin-4-yl]amino}-1-(2,2,2-trifluoroethyl)-1H-indol-2-yl)prop-2-yn-1-yl]-1-methyl-1H-pyrrole-3-carboxamide |
| 2092. | 1-ethyl-N-[3-(4-{[(3S,4R)-3-fluoro-1-methylpiperidin-4-yl]amino}-1-(2,2,2-trifluoroethyl)-1H-indol-2-yl)prop-2-yn-1-yl]-1H-pyrrole-3-carboxamide |
| 2093. | 1-tert-butyl-N-[3-(4-{[(3S,4R)-3-fluoro-1-methylpiperidin-4-yl]amino}-1-(2,2,2-trifluoroethyl)-1H-indol-2-yl)prop-2-yn-1-yl]-1H-pyrrole-3-carboxamide |

TABLE 7-continued

Alkynyl indole compounds of the disclosure.

| Mol # | IUPAC name |
|---|---|
| 2094. | methyl (2S)-4-carbamoyl-2-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]butanoate |
| 2095. | 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-N-((R)-2-hydroxypropyl)-3-methoxybenzamide |
| 2096. | rac-4-{[3-(4-{[(3R,4S)-1-ethyl-3-fluoropiperidin-4-yl]amino}-1-(2,2,2-trifluoroethyl)-1H-indol-2-yl)prop-2-yn-1-yl]amino}-3-methoxybenzoic acid |
| 2097. | 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-N-((S)-2-hydroxypropyl)-3-methoxybenzamide |
| 2098. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(2-hydroxy-3-methoxypropyl)-3-methoxybenzamide |
| 2099. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-[(2S)-2-hydroxypropyl]-3-methoxybenzamide |
| 2100. | N-(2,3-dihydroxypropyl)-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 2101. | N-[(2R)-2,3-dihydroxypropyl]-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 2102. | N-[(2S)-2,3-dihydroxypropyl]-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 2103. | N-(1,5-dihydroxypentan-3-yl)-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide |
| 2104. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(3-hydroxy-2-methoxypropyl)-3-methoxybenzamide |
| 2105. | 1-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]-3-[(2-methylpropanoyl)oxy]propan-2-yl 2-methylpropanoate |
| 2106. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxy-N-[(2-oxo-1,3-dioxolan-4-yl)methyl]benzamide |
| 2107. | 4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-N-(2-methanesulfonylethyl)-3-methoxybenzamide |
| 2108. | 1-(acetyloxy)-3-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]propan-2-yl acetate |
| 2109. | 1-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]-3-(propanoyloxy)propan-2-yl propanoate |
| 2110. | 2-[(4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxyphenyl)formamido]propyl 2-methylpropanoate |
| 2111. | (S)-5-ethoxy-2-(4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzamido)-5-oxopentanoic acid |
| 2112. | (4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzoyl)-L-glutamine |
| 2113. | (S)-2-(4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxybenzamido)-5-methoxy-5-oxopentanoic acid |
| 2114. | (S)-1-((3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2115. | (S)-1-((3R,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2116. | (S)-1-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2117. | (S)-1-((3S,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2118. | 1-((3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2119. | 1-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2120. | (R)-1-((3S,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2121. | (R)-1-((3R,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2122. | (R)-1-((3R,4S)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |

TABLE 7-continued

| Mol # | IUPAC name |
| --- | --- |
| | Alkynyl indole compounds of the disclosure. |
| 2123. | (R)-1-((3S,4R)-3-fluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2124. | 4-((3-(4-(((3R,4S)-3-fluoro-1-((R)-2-hydroxy-3-methoxypropyl)piperidin-4-yl)amino)-1-(2,2,2-trifluoroethyl)-1H-indol-2-yl)prop-2-yn-1-yl)amino)-3-methoxybenzenesulfonamide |
| 2125. | 1-(3,3-difluoro-4-((2-(3-((2-methoxy-4-(methylsulfonyl)phenyl)amino)prop-1-yn-1-yl)-1-(2,2,2-trifluoroethyl)-1H-indol-4-yl)amino)piperidin-1-yl)-3-methoxypropan-2-ol |
| 2126. | 2-{3-[(4-methanesulfonyl-2-methoxyphenyl)amino]prop-1-yn-1-yl}-N-(1-methylazepan-4-yl)-1-(2,2,2-trifluoroethyl)-1H-indol-4-amine |
| 2127. | 1-{4-[(2-{3-[(4-methanesulfonyl-2-methoxyphenyl)amino]prop-1-yn-1-yl}-1-(2,2,2-trifluoroethyl)-1H-indol-4-yl)amino]azepan-1-yl}-3-methoxypropan-2-ol |
| 2128. | 2-{3-[(4-methanesulfonyl-2-methoxyphenyl)amino]prop-1-yn-1-yl}-N-{8-methyl-8-azabicyclo[3.2.1]octan-3-yl}-1-(2,2,2-trifluoroethyl)-1H-indol-4-amine |
| 2129. | 2-(3-{[4-methanesulfonyl-2-(trifluoromethoxy)phenyl]amino}prop-1-yn-1-yl)-N-(oxan-4-yl)-1-(2,2,2-trifluoroethyl)-1H-indol-4-amine |
| 2130. | 3-methoxy-4-[(3-{4-[(oxan-4-yl)amino]-1-(2,2,2-trifluoroethyl)-1H-indol-2-yl}prop-2-yn-1-yl)amino]-N-(1,2-oxazol-3-yl)benzene-1-sulfonamide |
| 2131. | 3-methoxy-N-(oxan-4-yl)-4-[(3-{4-[(oxan-4-yl)amino]-1-(2,2,2-trifluoroethyl)-1H-indol-2-yl}prop-2-yn-1-yl)amino]benzene-1-sulfonamide |
| 2132. | 3-methoxy-N-(5-methyl-1,2-oxazol-3-yl)-4-[(3-{4-[(oxan-4-yl)amino]-1-(2,2,2-trifluoroethyl)-1H-indol-2-yl}prop-2-yn-1-yl)amino]benzene-1-sulfonamide |
| 2133. | 2-{4-methoxy-5-[(3-{4-[(oxan-4-yl)amino]-1-(2,2,2-trifluoroethyl)-1H-indol-2-yl}prop-2-yn-1-yl)amino]pyridin-2-yl}-2-methylpropanenitrile |
| 2134. | N-(2-hydroxyethyl)-3-methoxy-N-methyl-4-[(3-{4-[(oxan-4-yl)amino]-1-(2,2,2-trifluoroethyl)-1H-indol-2-yl}prop-2-yn-1-yl)amino]benzene-1-sulfonamide |
| 2135. | 6-fluoro-2-{3-[(4-methanesulfonyl-2-methoxyphenyl)amino]prop-1-yn-1-yl}-N-(oxan-4-yl)-1-(2,2,2-trifluoroethyl)-1H-indol-4-amine |
| 2136. | 4-[(3-{6-fluoro-4-[(oxan-4-yl)amino]-1-(2,2,2-trifluoroethyl)-1H-indol-2-yl}prop-2-yn-1-yl)amino]-3-methoxybenzene-1-sulfonamide |
| 2137. | 3-methoxy-N,N-dimethyl-4-[(3-{4-[(oxan-4-yl)amino]-1-(2,2,2-trifluoroethyl)-1H-indol-2-yl}prop-2-yn-1-yl)amino]benzene-1-sulfonamide |
| 2138. | 3-methoxy-N-(2-methoxyethyl)-N-methyl-4-[(3-{4-[(oxan-4-yl)amino]-1-(2,2,2-trifluoroethyl)-1H-indol-2-yl}prop-2-yn-1-yl)amino]benzene-1-sulfonamide |
| 2139. | 1-(4-{3-methoxy-4-[(3-{4-[(oxan-4-yl)amino]-1-(2,2,2-trifluoroethyl)-1H-indol-2-yl}prop-2-yn-1-yl)amino]benzenesulfonyl}piperazin-1-yl)ethan-1-one |
| 2140. | 2-(3-{[2-methoxy-4-(morpholine-4-sulfonyl)phenyl]amino}prop-1-yn-1-yl)-N-(oxan-4-yl)-1-(2,2,2-trifluoroethyl)-1H-indol-4-amine |
| 2141. | 3-methoxy-N-methyl-4-[(3-{4-[(oxan-4-yl)amino]-1-(2,2,2-trifluoroethyl)-1H-indol-2-yl}prop-2-yn-1-yl)amino]benzamide |
| 2142. | 3-methoxy-4-((3-(4-((tetrahydro-2H-pyran-4-yl)amino)-1-(2,2,2-trifluoroethyl)-1H-indol-2-yl)prop-2-yn-1-yl)amino)benzoic acid |
| 2143. | methyl 3-methoxy-4-((3-(4-((tetrahydro-2H-pyran-4-yl)amino)-1-(2,2,2-trifluoroethyl)-1H-indol-2-yl)prop-2-yn-1-yl)amino)benzoate |
| 2144. | 3-methoxy-4-((3-(4-((tetrahydro-2H-pyran-4-yl)amino)-1-(2,2,2-trifluoroethyl)-1H-indol-2-yl)prop-2-yn-1-yl)amino)benzamide |
| 2145. | 3-methoxy-N-(2-methoxyethyl)-N-methyl-4-((3-(4-((tetrahydro-2H-pyran-4-yl)amino)-1-(2,2,2-trifluoroethyl)-1H-indol-2-yl)prop-2-yn-1-yl)amino)benzenesulfonamide |
| 2146. | N,N-bis(2-hydroxyethyl)-3-methoxy-4-[(3-{4-[(oxan-4-yl)amino]-1-(2,2,2-trifluoroethyl)-1H-indol-2-yl}prop-2-yn-1-yl)amino]benzene-1-sulfonamide |
| 2147. | 3-methoxy-N-methyl-4-[(3-{4-[(oxan-4-yl)amino]-1-(2,2,2-trifluoroethyl)-1H-indol-2-yl}prop-2-yn-1-yl)amino]benzene-1-sulfonamide |
| 2148. | 5-methanesulfonyl-2-[(3-{4-[(oxan-4-yl)amino]-1-(2,2,2-trifluoroethyl)-1H-indol-2-yl}prop-2-yn-1-yl)amino]phenol |
| 2149. | 3-methoxy-4-[(3-{5-methoxy-4-[(oxan-4-yl)amino]-1-(2,2,2-trifluoroethyl)-1H-indol-2-yl}prop-2-yn-1-yl)amino]benzene-1-sulfonamide |
| 2150. | 2-[3-({2-methoxy-4-[(4-methylpiperazin-1-yl)sulfonyl]phenyl}amino)prop-1-yn-1-yl]-N-(oxan-4-yl)-1-(2,2,2-trifluoroethyl)-1H-indol-4-amine |
| 2151. | 2-{3-[(4-methanesulfonyl-2-methoxyphenyl)amino]prop-1-yn-1-yl}-5-methoxy-N-(oxan-4-yl)-1-(2,2,2-trifluoroethyl)-1H-indol-4-amine |
| 2152. | 3-methoxy-4-[(3-{6-methoxy-4-[(oxan-4-yl)amino]-1-(2,2,2-trifluoroethyl)-1H-indol-2-yl}prop-2-yn-1-yl)amino]benzene-1-sulfonamide |
| 2153. | 5-methanesulfonyl-2-[(3-{4-[(oxan-4-yl)amino]-1-(2,2,2-trifluoroethyl)-1H-indol-2-yl}prop-2-yn-1-yl)amino]phenyl propanoate |
| 2154. | N-(2-hydroxyethyl)-3-methoxy-4-((3-(4-((tetrahydro-2H-pyran-4-yl)amino)-1-(2,2,2-trifluoroethyl)-1H-indol-2-yl)prop-2-yn-1-yl)amino)benzenesulfonamide |
| 2155. | 2-{3-[(4-methanesulfonyl-2-methoxyphenyl)amino]prop-1-yn-1-yl}-N-[(2S,4R)-2-methyloxan-4-yl]-1-(2,2,2-trifluoroethyl)-1H-indol-4-amine |
| 2156. | 2-{3-[(4-methanesulfonyl-2-methoxyphenyl)amino]prop-1-yn-1-yl}-N-[(2S,4S)-2-methyloxan-4-yl]-1-(2,2,2-trifluoroethyl)-1H-indol-4-amine |
| 2157. | 3-methoxy-4-{[3-(4-{[(2S,4R)-2-methyloxan-4-yl]amino}-1-(2,2,2-trifluoroethyl)-1H-indol-2-yl)prop-2-yn-1-yl]amino}benzene-1-sulfonamide |
| 2158. | 3-methoxy-4-{[3-(4-{[(2S,4S)-2-methyloxan-4-yl]amino}-1-(2,2,2-trifluoroethyl)-1H-indol-2-yl)prop-2-yn-1-yl]amino}benzene-1-sulfonamide |
| 2159. | 3-methoxy-4-{[3-(4-{[(2S,4R)-2-methyloxan-4-yl]amino}-1-(2,2,2-trifluoroethyl)-1H-indol-2-yl)prop-2-yn-1-yl]amino}benzamide |

TABLE 7-continued

Alkynyl indole compounds of the disclosure.

| Mol # | IUPAC name |
|---|---|
| 2160. | 3-methoxy-4-{[3-(4-{[(2S,4S)-2-methyloxan-4-yl]amino}-1-(2,2,2-trifluoroethyl)-1H-indol-2-yl)prop-2-yn-1-yl]amino}benzamide |
| 2161. | rac-N-[(3R,4R)-3-fluorooxan-4-yl]-2-{3-[(4-methanesulfonyl-2-methoxyphenyl)amino]prop-1-yn-1-yl}-1-(2,2,2-trifluoroethyl)-1H-indol-4-amine |
| 2162. | 2-(3-((2-methoxy-4-(methylsulfonyl)phenyl)amino)prop-1-yn-1-yl)-N-((3R,4S)-3-methoxytetrahydro-2H-pyran-4-yl)-1-(2,2,2-trifluoroethyl)-1H-indol-4-amine |
| 2163. | 2-(3-((2-methoxy-4-(methylsulfonyl)phenyl)amino)prop-1-yn-1-yl)-N-((3S,4S)-3-methoxytetrahydro-2H-pyran-4-yl)-1-(2,2,2-trifluoroethyl)-1H-indol-4-amine |
| 2164. | N-[(3S,4S)-3-fluorooxan-4-yl]-2-{3-[(4-methanesulfonyl-2-methoxyphenyl)amino]prop-1-yn-1-yl}-1-(2,2,2-trifluoroethyl)-1H-indol-4-amine |
| 2165. | N-[(3R,4R)-3-fluorooxan-4-yl]-2-{3-[(4-methanesulfonyl-2-methoxyphenyl)amino]prop-1-yn-1-yl}-1-(2,2,2-trifluoroethyl)-1H-indol-4-amine |
| 2166. | 2-{3-[(4-methanesulfonyl-2-methoxyphenyl)amino]prop-1-yn-1-yl}-N-[(2R,4R,6S)-2,6-dimethyloxan-4-yl]-1-(2,2,2-trifluoroethyl)-1H-indol-4-amine |
| 2167. | 2-{3-[(4-methanesulfonyl-2-methoxyphenyl)amino]prop-1-yn-1-yl}-N-[(2R,4S,6S)-2,6-dimethyloxan-4-yl]-1-(2,2,2-trifluoroethyl)-1H-indol-4-amine |
| 2168. | 3-methoxy-4-{[3-(4-{[(2R,4R,6S)-2,6-dimethyloxan-4-yl]amino}-1-(2,2,2-trifluoroethyl)-1H-indol-2-yl)prop-2-yn-1-yl]amino}benzamide |
| 2169. | 3-methoxy-4-{[3-(4-{[(2R,4S,6S)-2,6-dimethyloxan-4-yl]amino}-1-(2,2,2-trifluoroethyl)-1H-indol-2-yl)prop-2-yn-1-yl]amino}benzamide |
| 2170. | 3-methoxy-4-{[3-(4-{[(2R,4S,6S)-2,6-dimethyloxan-4-yl]amino}-1-(2,2,2-trifluoroethyl)-1H-indol-2-yl)prop-2-yn-1-yl]amino}benzene-1-sulfonamide |
| 2171. | 3-methoxy-4-{[3-(4-{[(2R,4R,6S)-2,6-dimethyloxan-4-yl]amino}-1-(2,2,2-trifluoroethyl)-1H-indol-2-yl)prop-2-yn-1-yl]amino}benzene-1-sulfonamide |
| 2172. | 4-((2-(3-((4-methoxypyridin-3-yl)amino)prop-1-yn-1-yl)-1-(2,2,2-trifluoroethyl)-1H-indol-4-yl)amino)tetrahydro-2H-thiopyran 1,1-dioxide |
| 2173. | 2-{5-[(3-{4-[(1,1-dioxo-1λ$^6$-thian-4-yl)amino]-1-(2,2,2-trifluoroethyl)-1H-indol-2-yl}prop-2-yn-1-yl)amino]-4-methoxypyridin-2-yl}-2-methylpropanenitrile |
| 2174. | 4-{[2-(3-{[4-methanesulfonyl-2-(trifluoromethoxy)phenyl]amino}prop-1-yn-1-yl)-1-(2,2,2-trifluoroethyl)-1H-indol-4-yl]amino}-1λ$^6$-thiane-1,1-dione |
| 2175. | 4-{[2-(3-{[2-methoxy-4-(morpholine-4-sulfonyl)phenyl]amino}prop-1-yn-1-yl)-1-(2,2,2-trifluoroethyl)-1H-indol-4-yl]amino}-1λ$^6$-thiane-1,1-dione |
| 2176. | 4-({2-[3-({2-[2-(dimethylamino)ethoxy]-4-methanesulfonylphenyl}amino)prop-1-yn-1-yl]-1-(2,2,2-trifluoroethyl)-1H-indol-4-yl}amino)-1λ$^6$-thiane-1,1-dione |
| 2177. | 4-[(3-{4-[(1,1-dioxo-1λ$^6$-thian-4-yl)amino]-1-(2,2,2-trifluoroethyl)-1H-indol-2-yl}prop-2-yn-1-yl)amino]-N-(2-hydroxyethyl)-3-methoxy-N-methylbenzene-1-sulfonamide |
| 2178. | 4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxy-N-(1,2-oxazol-3-yl)benzene-1-sulfonamide |
| 2179. | 4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxy-N-(5-methyl-1,2-oxazol-3-yl)benzene-1-sulfonamide |
| 2180. | 4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxy-N-(oxan-4-yl)benzene-1-sulfonamide |
| 2181. | N-(2,3-dihydroxypropyl)-4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxybenzene-1-sulfonamide |
| 2182. | N-[2-(dimethylamino)ethyl]-4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxy-N-methylbenzene-1-sulfonamide |
| 2183. | 4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxy-N,N-dimethylbenzene-1-sulfonamide |
| 2184. | 4-({2-[3-({4-[(4-acetylpiperazin-1-yl)sulfonyl]-2-methoxyphenyl}amino)prop-1-yn-1-yl]-1-(2,2,2-trifluoroethyl)-1H-indol-4-yl}amino)-1λ$^6$-thiane-1,1-dione |
| 2185. | 4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxy-N-(2-methoxyethyl)-N-methylbenzene-1-sulfonamide |
| 2186. | 4-[(2-{3-[(2-methoxy-4-{2-oxa-6-azaspiro[3.3]heptane-6-sulfonyl}phenyl)amino]prop-1-yn-1-yl}-1-(2,2,2-trifluoroethyl)-1H-indol-4-yl)amino]-1λ$^6$-thiane-1,1-dione |
| 2187. | 4-({2-[3-({2-methoxy-4-[(4-methylpiperazin-1-yl)sulfonyl]phenyl}amino)prop-1-yn-1-yl]-1-(2,2,2-trifluoroethyl)-1H-indol-4-yl}amino)-1λ$^6$-thiane-1,1-dione |
| 2188. | 4-[(3-{4-[(1,1-dioxo-1λ$^6$-thian-4-yl)amino]-1-(2,2,2-trifluoroethyl)-1H-indol-2-yl}prop-2-yn-1-yl)amino]-3-methoxy-N-methylbenzamide |
| 2189. | 4-((2-(3-((4-methoxy-6-(methylsulfonyl)pyridin-3-yl)amino)prop-1-yn-1-yl)-1-(2,2,2-trifluoroethyl)-1H-indol-4-yl)amino)tetrahydro-2H-thiopyran 1,1-dioxide |
| 2190. | 4-((2-(3-((4-(methylsulfonyl)-2-(2,2,2-trifluoroethoxy)phenyl)amino)prop-1-yn-1-yl)-1-(2,2,2-trifluoroethyl)-1H-indol-4-yl)amino)tetrahydro-2H-thiopyran 1,1-dioxide |
| 2191. | 2-(2-((3-(4-((1,1-dioxidotetrahydro-2H-thiopyran-4-yl)amino)-1-(2,2,2-trifluoroethyl)-1H-indol-2-yl)prop-2-yn-1-yl)amino)-5-(methylsulfonyl)phenoxy)acetamide |
| 2192. | 2-(2-((3-(4-((1,1-dioxidotetrahydro-2H-thiopyran-4-yl)amino)-1-(2,2,2-trifluoroethyl)-1H-indol-2-yl)prop-2-yn-1-yl)amino)-5-(methylsulfonyl)phenoxy)acetamide |
| 2193. | N-(2,3-dihydroxypropyl)-4-((3-(4-((1,1-dioxidotetrahydro-2H-thiopyran-4-yl)amino)-1-(2,2,2-trifluoroethyl)-1H-indol-2-yl)prop-2-yn-1-yl)amino)-3-methoxybenzenesulfonamide |
| 2194. | 3-methoxy-4-((3-(4-(3-(1-methylpiperidin-4-yl)ureido)-1-(2,2,2-trifluoroethyl)-1H-indol-2-yl)prop-2-yn-1-yl)amino)benzamide |

TABLE 8

| Mol # | Structure<br>IUPAC name |
|---|---|
| | Aryl-linked indole compounds of the disclosure. |
| 2195. | 4-{4-[(1,1-dioxo-1λ$^6$-thian-4-yl)amino]-1-(2,2,2-trifluoroethyl)-1H-indol-2-yl}benzamide |
| 2196. | 4-({2-[4-(aminomethyl)phenyl]-1-(2,2,2-trifluoroethyl)-1H-indol-4-yl}amino)-1λ$^6$-thiane-1,1-dione |
| 2197. | 4-[(2-{4-[(methylamino)methyl]phenyl}-1-(2,2,2-trifluoroethyl)-1H-indol-4-yl)amino]-1λ$^6$-thiane-1,1-dione |
| 2198. | tert-butyl N-[(4-{4-[(1,1-dioxo-1λ$^6$-thian-4-yl)amino]-1-(2,2,2-trifluoroethyl)-1H-indol-2-yl}phenyl)methyl]-N-methylcarbamate |
| 2199. | 4-{4-[(1,1-dioxo-1λ$^6$-thian-4-yl)amino]-1-(2,2,2-trifluoroethyl)-1H-indol-2-yl}-N-methylbenzamide |
| 2200. | tert-butyl N-[(4-{4-[(1,1-dioxo-1λ$^6$-thian-4-yl)amino]-1-(2,2,2-trifluoroethyl)-1H-indol-2-yl}phenyl)methyl]carbamate |
| 2201. | 2-(5-{[(4-{4-[(1,1-dioxo-1λ$^6$-thian-4-yl)amino]-1-(2,2,2-trifluoroethyl)-1H-indol-2-yl}phenyl)methyl]amino}pyridin-2-yl)-2-methylpropanenitrile |
| 2202. | 4-{[2-(4-{[(4-methanesulfonylphenyl)amino]methyl}phenyl)-1-(2,2,2-trifluoroethyl)-1H-indol-4-yl]amino}-1λ$^6$-thiane-1,1-dione |
| 2203. | 4-[(2-{4-[(phenylamino)methyl]phenyl}-1-(2,2,2-trifluoroethyl)-1H-indol-4-yl)amino]-1λ$^6$-thiane-1,1-dione |
| 2204. | 3-{4-[(1,1-dioxo-1λ$^6$-thian-4-yl)amino]-1-(2,2,2-trifluoroethyl)-1H-indol-2-yl}benzonitrile |
| 2205. | 4-{[2-(2-fluoro-4-methylphenyl)-1-(2,2,2-trifluoroethyl)-1H-indol-4-yl]amino}-1λ$^6$-thiane-1,1-dione |
| 2206. | 4-{[2-(3-chlorophenyl)-1-(2,2,2-trifluoroethyl)-1H-indol-4-yl]amino}-1λ$^6$-thiane-1,1-dione |
| 2207. | -{[2-(3-methoxyphenyl)-1-(2,2,2-trifluoroethyl)-1H-indol-4-yl]amino}-1λ$^6$-thiane-1,1-dione |
| 2208. | 4-{[2-(4-chlorophenyl)-1-(2,2,2-trifluoroethyl)-1H-indol-4-yl]amino}-1λ$^6$-thiane-1,1-dione |
| 2209. | 4-tert-butyl-N-[(4-{4-[(1,1-dioxo-1λ$^6$-thian-4-yl)amino]-1-(2,2,2-trifluoroethyl)-1H-indol-2-yl}phenyl)methyl]benzamide |
| 2210. | 4-cyano-N-[(4-{4-[(1,1-dioxo-1λ$^6$-thian-4-yl)amino]-1-(2,2,2-trifluoroethyl)-1H-indol-2-yl}phenyl)methyl]benzamide |
| 2211. | 4-chloro-N-[(4-{4-[(1,1-dioxo-1λ$^6$-thian-4-yl)amino]-1-(2,2,2-trifluoroethyl)-1H-indol-2-yl}phenyl)methyl]benzamide |
| 2212. | 3-[6-(1-cyano-1-methylethyl)pyridin-3-yl]-1-[(4-{4-[(1,1-dioxo-1λ$^6$-thian-4-yl)amino]-1-(2,2,2-trifluoroethyl)-1H-indol-2-yl}phenyl)methyl]urea |
| 2213. | 3-[(4-{4-[(1,1-dioxo-1λ$^6$-thian-4-yl)amino]-1-(2,2,2-trifluoroethyl)-1H-indol-2-yl}phenyl)methyl]-1-phenylurea |
| 2214. | 3-{4-[(1,1-dioxo-1λ$^6$-thian-4-yl)amino]-1-(2,2,2-trifluoroethyl)-1H-indol-2-yl}benzoic acid |
| 2215. | 4-({2-[3-(dimethylamino)phenyl]-1-(2,2,2-trifluoroethyl)-1H-indol-4-yl}amino)-1λ$^6$-thiane-1,1-dione |
| 2216. | 3-{4-[(1,1-dioxo-1λ$^6$-thian-4-yl)amino]-1-(2,2,2-trifluoroethyl)-1H-indol-2-yl}-N-methylbenzamide |
| 2217. | 4-{4-[(11-dioxo-1λ$^6$-thian-4-yl)amino]-1-(2,2,2-trifluoroethyl)-1H-indol-2-yl}benzoic acid |
| 2218. | 4-[(2-{4-[(morpholin-4-yl)methyl]phenyl}-1-(2,2,2-trifluoroethyl)-1H-indol-4-yl)amino]-1λ$^6$-thiane-1,1-dione |
| 2219. | methyl N-(3-{4-[(1,1-dioxo-1λ$^6$-thian-4-yl)amino]-1-(2,2,2-trifluoroethyl)-1H-indol-2-yl}phenyl)carbamate |
| 2220. | 1-(4-{4-[(1,1-dioxo-1λ$^6$-thian-4-yl)amino]-1-(2,2,2-trifluoroethyl)-1H-indol-2-yl}phenyl)cyclopropane-1-carbonitrile |
| 2221. | 4-({2-[4-(hydroxymethyl)phenyl]-1-(2,2,2-trifluoroethyl)-1H-indol-4-yl}amino)-1λ$^6$-thiane-1,1-dione |
| 2222. | 1-[(4-{4-[(1,1-dioxo-1λ$^6$-thian-4-yl)amino]-1-(2,2,2-trifluoroethyl)-1H-indol-2-yl}phenyl)methyl]-3-(4-methanesulfonylphenyl)urea |
| 2223. | 4-{[2-(4-{[(6-methanesulfonylpyridin-3-yl)amino]methyl(phenyl)-1-(2,2,2-trifluoroethyl)-1H-indol-4-yl]amino}-1λ$^6$-thiane-1,1-dione |
| 2224. | 2-(4-{[(4-methanesulfonylphenyl)amino]methyl}phenyl)-N-[1-(oxan-4-yl)piperidin-4-yl]-1-(2,2,2-trifluoroethyl)-1H-indol-4-amine |
| 2225. | 2-(4-{[(6-methylpyridin-3-yl)amino]methyl}phenyl)-N-[1-(oxan-4-yl)piperidin-4-yl]-1-(2,2,2-trifluoroethyl)-1H-indol-4-amine |
| 2226. | 2-(4-{[(4-chlorophenyl)amino]methyl}phenyl)-N-[1-(oxan-4-yl)piperidin-4-yl]-1-(2,2,2-trifluoroethyl)-1H-indol-4-amine |
| 2227. | 2-(4-{[(4-methoxyphenyl)amino]methyl}phenyl)-N-[1-(oxan-4-yl)piperidin-4-yl]-1-(2,2,2-trifluoroethyl)-1H-indol-4-amine |
| 2228. | 2-(4-{[(3-chlorophenyl)amino]methyl}phenyl)-N-[1-(oxan-4-yl)piperidin-4-yl]-1-(2,2,2-trifluoroethyl)-1H-indol-4-amine |
| 2229. | 6-methyl-N-{[4-(5-{[(1-methylpiperidin-4-yl)amino]methyl}-1-(2,2,2-trifluoroethyl)-1H-indol-2-yl)phenyl]methyl}pyridin-3-amine |
| 2230. | N-{[2-(4-{[(4-methanesulfonylphenyl)amino]methyl}phenyl)-1-(2,2,2-trifluoroethyl)-1H-indol-5-yl]methyl}-1-methylpiperidin-4-amine |
| 2231. | 2-(5-amino-[1,1'-biphenyl]-3-yl)-N-(1-methylpiperidin-4-yl)-1-(2,2,2-trifluoroethyl)-1H-indol-4-amine |

TABLE 8-continued

Aryl-linked indole compounds of the disclosure.

| Mol # | Structure<br>IUPAC name |
|---|---|
| 2232. | 2-{4-[amino(phenyl)methyl]phenyl}-N-(1-methylpiperidin-4-yl)-1-(2,2,2-trifluoroethyl)-1H-indol-4-amine |
| 2233. | 2-(4-(amino(cyclohexyl)methyl)phenyl)-N-(1-methylpiperidin-4-yl)-1-(2,2,2-trifluoroethyl)-1H-indol-4-amine |
| 2234. | 2-{4-[(cyclopentylamino)methyl]phenyl}-N-(1-methylpiperidin-4-yl)-1-(2,2,2-trifluoroethyl)-1H-indol-4-amine |
| 2235. | 2-(4-{1-[(4-methanesulfonylphenyl)amino]ethyl}phenyl)-N-(1-methylpiperidin-4-yl)-1-(2,2,2-trifluoroethyl)-1H-indol-4-amine |
| 2236. | (+/−)-2-{4-[(cyclopropylamino)methyl]phenyl}-N-[(3R,4S)-3-fluoro-1-methylpiperidin-4-yl]-1-(2,2,2-trifluoroethyl)-1H-indol-4-amine |
| 2237. | (+/−)-N-[(3R,4S)-3-fluoro-1-methylpiperidin-4-yl]-2-(4-{[(4-methanesulfonyl-2-methoxyphenyl)amino]methyl}phenyl)-1-(2,2,2-trifluoroethyl)-1H-indol-4-amine |
| 2238. | N-[(3R,4S)-3-fluoro-1-methylpiperidin-4-yl]-2-(4-{[(4-methanesulfonylphenyl)amino]methyl(phenyl)-1-(2,2,2-trifluoroethyl)-1H-indol-4-amine |
| 2239. | (+/−)-N-{[4-(4-{[(3R,4S)-3-fluoro-1-methylpiperidin-4-yl]amino}-1-(2,2,2-trifluoroethyl)-1H-indol-2-yl)phenyl]methyl}benzamide |
| 2240. | (+/−)-N-{[4-(4-{[(3R,4S)-3-fluoro-1-methylpiperidin-4-yl]amino}-1-(2,2,2-trifluoroethyl)-1H-indol-2-yl)phenyl]methyl}cyclopropanecarboxamide |
| 2241. | 1-methoxy-3-(4-{[2-(3-methyl-2H-indazol-6-yl)-1-(2,2,2-trifluoroethyl)-1H-indol-4-yl]amino}piperidin-1-yl)propan-2-ol |
| 2242. | 1-(4-{[2-(2H-indazol-6-yl)-1-(2,2,2-trifluoroethyl)-1H-indol-4-yl]amino}piperidin-1-yl)-3-methoxypropan-2-ol |
| 2243. | 4-{[1-(2-hydroxy-3-methoxypropyl)piperidin-4-yl]amino}-1-(2,2,2-trifluoroethyl)-2',3'-dihydro-1H,1'H-[2,6'-biindol]-2'-one |
| 2244. | 4-(4-((1-(2-hydroxy-3-methoxypropyl)piperidin-4-yl)amino)-1-(2,2,2-trifluoroethyl)-1H-indol-2-yl)isoindolin-1-one |
| 2245. | N-[3-(4-{[1-(2-hydroxy-3-methoxypropyl)piperidin-4-yl]amino}-1-(2,2,2-trifluoroethyl)-1H-indol-2-yl)phenyl]acetamide |

TABLE 9

Heteroaryl-linked indole compounds of the disclosure.

| Mol # | IUPAC name |
|---|---|
| 2246. | 4-((2-(6-methoxypyridin-3-yl)-1-(2,2,2-trifluoroethyl)-1H-indol-4-yl)amino)tetrahydro-2H-thiopyran 1,1-dioxide-indol-4-amine |
| 2247. | 4-((2-(6-methylpyridin-3-yl)-1-(2,2,2-trifluoroethyl)-1H-indol-4-yl)amino)tetrahydro-2H-thiopyran 1,1-dioxide |
| 2248. | 4-((2-(6-(dimethylamino)pyridin-3-yl)-1-(2,2,2-trifluoroethyl)-1H-indol-4-yl)amino)tetrahydro-2H-thiopyran 1,1-dioxide |
| 2249. | 4-((2-(quinolin-4-yl)-1-(2,2,2-trifluoroethyl)-1H-indol-4-yl)amino)tetrahydro-2H-thiopyran 1,1-dioxide |
| 2250. | 4-((2-(2-fluoropyridin-3-yl)-1-(2,2,2-trifluoroethyl)-1H-indol-4-yl)amino)tetrahydro-2H-thiopyran 1,1-dioxide |
| 2251. | 1-(4-((2-(5-aminopyridin-3-yl)-1-(2,2,2-trifluoroethyl)-1H-indol-4-yl)amino)piperidin-1-yl)-3-methoxypropan-2-ol |
| 2252. | 2-(2-amino-6-phenylpyridin-4-yl)-N-(1-methylpiperidin-4-yl)-1-(2,2,2-trifluoroethyl)-1H-indol-4-amine |
| 2253. | 5-(4-((1,1-dioxidotetrahydro-2H-thiopyran-4-yl)amino)-1-(2,2,2-trifluoroethyl)-1H-indol-2-yl)-N-methylpicolinamide |
| 2254. | 2-(2-amino-6-phenylpyrimidin-4-yl)-N-(1-methylpiperidin-4-yl)-1-(2,2,2-trifluoroethyl)-1H-indol-4-amine |
| 2255. | 2-(2-amino-6-(cyclohex-1-en-1-yl)pyrimidin-4-yl)-N-(1-methylpiperidin-4-yl)-1-(2,2,2-trifluoroethyl)-1H-indol-4-amine |
| 2256. | 2-(2-amino-6-cyclohexylpyrimidin-4-yl)-N-(1-methylpiperidin-4-yl)-1-(2,2,2-trifluoroethyl)-1H-indol-4-amine |
| 2257. | 2-(2-(methylamino)pyrimidin-4-yl)-N-(1-methylpiperidin-4-yl)-1-(2,2,2-trifluoroethyl)-1H-indol-4-amine |
| 2258. | 2-(2-aminopyrimidin-4-yl)-N-(1-methylpiperidin-4-yl)-1-(2,2,2-trifluoroethyl)-1H-indol-4-amine |
| 2259. | 4-{[2-(1-methyl-1H-pyrazol-3-yl)-1-(2,2,2-trifluoroethyl)-1H-indol-4-yl]amino}-1λ$^6$-thiane-1,1-dione |
| 2260. | 4-({2-[1-(2-hydroxyethyl)-1H-pyrazol-4-yl]-1-(2,2,2-trifluoroethyl)-1H-indol-4-yl}amino)-1λ$^6$-thiane-1,1-dione |
| 2261. | 4-[(2-{1-[(pyridin-3-yl)methyl]-1H-pyrazol-4-yl}-1-(2,2,2-trifluoroethyl)-1H-indol-4-yl)amino]-1λ$^6$-thiane-1,1-dione |
| 2262. | 4-((2-(1-(2-methoxyethyl)-1H-pyrazol-4-yl)-1-(2,2,2-trifluoroethyl)-1H-indol-4-yl)amino)tetrahydro-2H-thiopyran 1,1-dioxide |
| 2263. | 4-[(2-{1-[(pyridin-4-yl)methyl]-1H-pyrazol-4-yl}-1-(2,2,2-trifluoroethyl)-1H-indol-4-yl)amino]-1λ$^6$-thiane-1,1-dione |

TABLE 9-continued

Heteroaryl-linked indole compounds of the disclosure.

| Mol # | IUPAC name |
|---|---|
| 2264. | 2-(5-amino-1-phenyl-1H-pyrazol-3-yl)-N-(1-methylpiperidin-4-yl)-1-(2,2,2-trifluoroethyl)-1H-indol-4-amine |
| 2265. | 2-{5-[amino(phenyl)methyl]-1H-pyrazol-3-yl}-N-(1-methylpiperidin-4-yl)-1-(2,2,2-trifluoroethyl)-1H-indol-4-amine |
| 2266. | 2-(5-amino-1H-pyrazol-3-yl)-N-(1-methylpiperidin-4-yl)-1-(2,2,2-trifluoroethyl)-1H-indol-4-amine |
| 2267. | 2-(5-{[(4-methanesulfonylphenyl)amino]methyl}-1H-pyrazol-3-yl)-N-(1-methylpiperidin-4-yl)-1-(2,2,2-trifluoroethyl)-1H-indol-4-amine |
| 2268. | 2-[5-(methylamino)-1H-pyrazol-3-yl]-N-(1-methylpiperidin-4-yl)-1-(2,2,2-trifluoroethyl)-1H-indol-4-amine |
| 2269. | 2-(5-{[(4-methanesulfonylphenyl)amino]methyl}-1,3,4-thiadiazol-2-yl)-N-(1-methylpiperidin-4-yl)-1-(2,2,2-trifluoroethyl)-1H-indol-4-amine |
| 2270. | N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}cyclopropanecarboxamide |
| 2271. | N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}benzamide |
| 2272. | (+/−)-N-[(3R,4S)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine |
| 2273. | (+/−)-N-[(3R,4R)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine |
| 2274. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}cyclopentanecarboxamide |
| 2275. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}thiophene-2-carboxamide |
| 2276. | 1-fluoro-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide |
| 2277. | (+/−)-2,2-difluoro-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide |
| 2278. | (+/−)-(1R,2S)-2-methyl-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide |
| 2279. | (+/−)-(1R,2R)-2-methyl-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide |
| 2280. | N-[(5-{4-[(1-methylpiperidin-4-yl)amino]-1-(2,2,2-trifluoroethyl)-1H-indol-2-yl}-1,3,4-thiadiazol-2-yl)methyl]cyclopropanecarboxamide |
| 2281. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}oxetane-3-carboxamide |
| 2282. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}cyclobutanecarboxamide |
| 2283. | (+/−)-methyl N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}carbamate |
| 2284. | methyl 4-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}benzoate |
| 2285. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}-1-methylpiperidine-4-carboxamide |
| 2286. | N-[(5-{4-[(1-methylpiperidin-4-yl)amino]-1-(2,2,2-trifluoroethyl)-1H-indol-2-yl}-1,3,4-thiadiazol-2-yl)methyl]pyridine-2-carboxamide |
| 2287. | N-[(5-{4-[(1-methylpiperidin-4-yl)amino]-1-(2,2,2-trifluoroethyl)-1H-indol-2-yl}-1,3,4-thiadiazol-2-yl)methyl]pyridine-3-carboxamide |
| 2288. | (+/−)-N-[(3R,4S)-3-fluoro-1-methylpiperidin-4-yl]-2-{5-[(methylamino)methyl]-1,3,4-thiadiazol-2-yl}-1-(2,2,2-trifluoroethyl)-1H-indol-4-amine |
| 2289. | (+/−)-benzyl N-{[5-(4-{[(3R,4S)-3-fluoro-1-methylpipendin-4-yl]amino}-1-(2,2,2-trifluoroethyl)-1H-indol-2-yl)-1,3,4-thiadiazol-2-yl]methyl}carbamate |
| 2290. | N-[(5-{4-[(1-methylpiperidin-4-yl)amino]-1-(2,2,2-trifluoroethyl)-1H-indol-2-yl}-1,3,4-thiadiazol-2-yl)methyl]-4-[(morpholin-4-yl)methyl]benzamide |
| 2291. | N-[(5-{4-[(1-methylpiperidin-4-yl)amino]-1-(2,2,2-trifluoroethyl)-1H-indol-2-yl}-1,3,4-thiadiazol-2-yl)methyl]-3-[(morpholin-4-yl)methyl]benzamide |
| 2292. | N-{[5-(4-{[(3S,4R)-3-fluoro-1-methylpiperidin-4-yl]amino}-1-(2,2,2-trifluoroethyl)-1H-indol-2-yl)-1,3,4-thiadiazol-2-yl]methyl}cyclopropanecarboxamide |
| 2293. | N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}cyclopropanecarboxamide |
| 2294. | N-[(5-{4-[(1-methylpiperidin-4-yl)amino]-1-(2,2,2-trifluoroethyl)-1H-indol-2-yl}-1,3,4-thiadiazol-2-yl)methyl]pyridine-4-carboxamide |
| 2295. | 2-fluoro-N-[(5-{4-[(1-methylpiperidin-4-yl)amino]-1-(2,2,2-trifluoroethyl)-1H-indol-2-yl}-1,3,4-thiadiazol-2-yl)methyl]benzamide |
| 2296. | 3-fluoro-N-[(5-{4-[(1-methylpiperidin-4-yl)amino]-1-(2,2,2-trifluoroethyl)-1H-indol-2-yl}-1,3,4-thiadiazol-2-yl)methyl]benzamide |
| 2297. | 4-fluoro-N-[(5-{4-[(1-methylpiperidin-4-yl)amino]-1-(2,2,2-trifluoroethyl)-1H-indol-2-yl}-1,3,4-thiadiazol-2-yl)methyl]benzamide |
| 2298. | (+/−)-(1S,2S)-N-[(5-{4-[(1-methylpiperidin-4-yl)amino]-1-(2,2,2-trifluoroethyl)-1H-indol-2-yl}-1,3,4-thiadiazol-2-yl)methyl]-2-phenylcyclopropane-1-carboxamide |

TABLE 9-continued

| Heteroaryl-linked indole compounds of the disclosure. | |
|---|---|
| Mol # | IUPAC name |
| 2299. | 4-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}benzoic acid |
| 2300. | N-[(5-{4-[(1-methylpiperidin-4-yl)amino]-1-(2,2,2-trifluoroethyl)-1H-indol-2-yl}-1,3,4-thiadiazol-2-yl)methyl]-1H-indazole-5-carboxamide |
| 2301. | 3-methyl-1-[(5-{4-[(1-methylpiperidin-4-yl)amino]-1-(2,2,2-trifluoroethyl)-1H-indol-2-yl}-1,3,4-thiadiazol-2-yl)methyl]urea |
| 2302. | 2-methyl-N-[(5-{4-[(1-methylpiperidin-4-yl)amino]-1-(2,2,2-trifluoroethyl)-1H-indol-2-yl}-1,3,4-thiadiazol-2-yl)methyl]propanamide |
| 2303. | N-[(5-{4-[(1-methylpiperidin-4-yl)amino]-1-(2,2,2-trifluoroethyl)-1H-indol-2-yl}-1,3,4-thiadiazol-2-yl)methyl]acetamide |
| 2304. | N-[(5-{4-[(1-methylpiperidin-4-yl)amino]-1-(2,2,2-trifluoroethyl)-1H-indol-2-yl}-1,3,4-thiadiazol-2-yl)methyl]-2-phenylacetamide |
| 2305. | 2-methoxy-N-[(5-{4-[(1-methylpiperidin-4-yl)amino]-1-(2,2,2-trifluoroethyl)-1H-indol-2-yl}-1,3,4-thiadiazol-2-yl)methyl]acetamide |
| 2306. | N-[(3R,4S)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine |
| 2307. | N-[(3S,4R)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine |
| 2308. | 4-methoxy-N-[(5-{4-[(1-methylpiperidin-4-yl)amino]-1-(2,2,2-trifluoroethyl)-1H-indol-2-yl}-1,3,4-thiadiazol-2-yl)methyl]benzamide |
| 2309. | 3-methoxy-N-[(5-{4-[(1-methylpiperidin-4-yl)amino]-1-(2,2,2-trifluoroethyl)-1H-indol-2-yl}-1,3,4-thiadiazol-2-yl)methyl]benzamide |
| 2310. | N-[(5-{4-[(1-methylpiperidin-4-yl)amino]-1-(2,2,2-trifluoroethyl)-1H-indol-2-yl}-1,3,4-thiadiazol-2-yl)methyl]butanamide |
| 2311. | 2-methoxy-N-[(5-{4-[(1-methylpiperidin-4-yl)amino]-1-(2,2,2-trifluoroethyl)-1H-indol-2-yl]-1,3,4-thiadiazol-2-yl)methyl]benzamide |
| 2312. | 2-[5-(aminomethyl)-1,3,4-thiadiazol-2-yl]-N-(1-methylpiperidin-4-yl)-1-(2,2,2-trifluoroethyl)-1H-indol-4-amine |
| 2313. | 3,3-dimethyl-1-[(5-{4-[(1-methylpiperidin-4-yl)amino]-1-(2,2,2-trifluoroethyl)-1H-indol-2-yl}-1,3,4-thiadiazol-2-yl)methyl]urea |
| 2314. | N-[(5-{4-[(1-methylpiperidin-4-yl)amino]-1-(2,2,2-trifluoroethyl)-1H-indol-2-yl}-1,3,4-thiadiazol-2-yl)methyl]-1H-indazole-6-carboxamide |
| 2315. | benzyl N-{[5-(4-{[(3S,4R)-3-fluoropiperidin-4-yl]amino}-1-(2,2,2-trifluoroethyl)-1H-indol-2-yl)-1,3,4-thiadiazol-2-yl]methyl}carbamate |
| 2316. | 1-methyl-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide |
| 2317. | N-[(5-{4-[(1-methylpiperidin-4-yl)amino]-1-(2,2,2-trifluoroethyl)-1H-indol-2-yl}-1,3,4-thiadiazol-2-yl)methyl]-1H-pyrazole-4-carboxamide |
| 2318. | N-[(5-{4-[(1-methylpiperidin-4-yl)amino]-1-(2,2,2-trifluoroethyl)-1H-indol-2-yl}-1,3,4-thiadiazol-2-yl)methyl]-1H-pyrazole-5-carboxamide |
| 2319. | 1-ethyl-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide |
| 2320. | (+/−)-methyl (1R,2R)-2-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}cyclopropane-1-carboxylate |
| 2321. | (+/−)-(1R,2R)-2-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}cyclopropane-1-carboxylic acid |
| 2322. | 1-methyl-N-[(5-{4-[(1-methylpiperidin-4-yl)amino]-1-(2,2,2-trifluoroethyl)-1H-indol-2-yl}-1,3,4-thiadiazol-2-yl)methyl]-1H-pyrrole-3-carboxamide |
| 2323. | N-[(5-{4-[(1-methylpiperidin-4-yl)amino]-1-(2,2,2-trifluoroethyl)-1H-indol-2-yl}-1,3,4-thiadiazol-2-yl)methyl]-1H-pyrrole-3-carboxamide |
| 2324. | N-[(5-{4-[(1-methylpiperidin-4-yl)amino]-1-(2,2,2-trifluoroethyl)-1H-indol-2-yl}-1,3,4-thiadiazol-2-yl)methyl]-2-(thiophen-2-yl)cyclopropane-1-carboxamide |
| 2325. | N-(1-methylpiperidin-4-yl)-2-(5-{[(pyrrolidin-3-yl)amino]methyl}-1,3,4-thiadiazol-2-yl)-1-(2,2,2-trifluoroethyl)-1H-indol-4-amine |
| 2326. | (+/−)-(1R,2S)-2-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}cyclopropane-1-carboxylic acid |
| 2327. | N-(1-methylpiperidin-4-yl)-2-(5-{[(1H-pyrazol-4-yl)amino]methyl}-1,3,4-thiadiazol-2-yl)-1-(2,2,2-trifluoroethyl)-1H-indol-4-amine |
| 2328. | N-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)cyclopentanecarboxamide |
| 2329. | N-((3S,4R)-3-fluoro-1-methylpiperidin-4-yl)-2-(5-(((2-methoxy-4-(methylsulfonyl)phenyl)amino)methyl)-1,3,4-thiadiazol-2-yl)-1-(2,2,2-trifluoroethyl)-1H-indol-4-amine |
| 2330. | N-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)benzamide |
| 2331. | N-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)cyclopropanecarboxamide |
| 2332. | 2-(5-((dimethylamino)methyl)-1,3,4-thiadiazol-2-yl)-N-((3S,4R)-3-fluoro-1-methylpiperidin-4-yl)-1-(2,2,2-trifluoroethyl)-1H-indol-4-amine |
| 2333. | N-((3S,4S)-3-fluoro-1-methylpiperidin-4-yl)-2-(5-(((2-methoxy-4-(methylsulfonyl)phenyl)amino)methyl)-1,3,4-thiadiazol-2-yl)-1-(2,2,2-trifluoroethyl)-1H-indol-4-amine |

TABLE 9-continued

| Mol # | IUPAC name |
|---|---|
| | Heteroaryl-linked indole compounds of the disclosure. |
| 2334. | N-{[2-(4-{[(3S,4R)-3-fluoro-1-methylpiperidin-4-yl]amino}-1-(2,2,2-trifluoroethyl)-1H-indol-2-yl)-1,3-thiazol-4-yl]methyl}cyclopropanecarboxamide |
| 2335. | N-{[2-(4-{[(3S,4R)-3-fluoro-1-methylpiperidin-4-yl]amino}-1-(2,2,2-trifluoroethyl)-1H-indol-2-yl)-1,3-thiazol-4-yl]methyl}benzamide |
| 2336. | (+/−)-N-{[2-(4-{[(3R,4S)-3-fluoro-1-methylpiperidin-4-yl]amino}-1-(2,2,2-trifluoroethyl)-1H-indol-2-yl)-1,3-thiazol-5-yl]methyl}benzamide |
| 2337. | N-[(2-{4-[(1-methylpiperidin-4-yl)amino]-1-(2,2,2-trifluoroethyl)-1H-indol-2-yl}-1,3-thiazol-5-yl)methyl]benzamide |
| 2338. | (+/−)-N-[(3R,4S)-3-fluoro-1-methylpiperidin-4-yl]-2-(1,3-thiazol-2-yl)-1-(2,2,2-trifluoroethyl)-1H-indol-4-amine |
| 2339. | N-[(2-{4-[(1-methylpiperidin-4-yl)amino]-1-(2,2,2-trifluoroethyl)-1H-indol-2-yl}-1,3-thiazol-5-yl)methyl]cyclopropanecarboxamide |
| 2340. | (+/−)-N-{[2-(4-{[(3R,4S)-3-fluoro-1-methylpiperidin-4-yl]amino}-1-(2,2,2-trifluoroethyl)-1H-indol-2-yl)-1,3-thiazol-5-yl]methyl}cyclopropanecarboxamide |
| 2341. | (+/−)-2-[5-(aminomethyl)-1,3-thiazol-2-yl]-N-[(3R,4S)-3-fluoro-1-methylpiperidin-4-yl]-1-(2,2,2-trifluoroethyl)-1H-indol-4-amine |
| 2342. | 2-(4-(aminomethyl)thiazol-2-yl)-N-((3S,4R)-3-fluoro-1-methylpiperidin-4-yl)-1-(2,2,2-trifluoroethyl)-1H-indol-4-amine |
| 2343. | (+/−)-N-[(3R,4S)-3-fluoro-1-methylpiperidin-4-yl]-2-{5-[(phenylamino)methyl]-1,3-thiazol-2-yl}-1-(2,2,2-trifluoroethyl)-1H-indol-4-amine |
| 2344. | N-[(3S,4R)-3-fluoro-1-methylpiperidin-4-yl]-2-(5-{[(4-methanesulfonyl-2-methoxyphenyl)amino]methyl}-1,3-thiazol-2-yl)-1-(2,2,2-trifluoroethyl)-1H-indol-4-amine |
| 2345. | 2-(5-{[(4-methanesulfonylphenyl)amino]methyl}thiophen-2-yl)-N-(1-methylpiperidin-4-yl)-1-(2,2,2-trifluoroethyl)-1H-indol-4-amine |
| 2346. | (+/−)-N-[(3R,4S)-3-fluoro-1-methylpiperidin-4-yl]-2-(5-{[(4-methanesulfonyl-2-methoxyphenyl)amino]methyl}thiophen-2-yl)-1-(2,2,2-trifluoroethyl)-1H-indol-4-amine |
| 2347. | (+/−)-N-{[5-(4-{[(3R,4S)-3-fluoro-1-methylpiperidin-4-yl]amino}-1-(2,2,2-trifluoroethyl)-1H-indol-2-yl)thiophen-2-yl]methyl}benzamide |
| 2348. | (+/−)-N-{[5-(4-{[(3R,4S)-3-fluoro-1-methylpiperidin-4-yl]amino}-1-(2,2,2-trifluoroethyl)-1H-indol-2-yl)thiophen-2-yl]methyl}cyclopropanecarboxamide |
| 2349. | N-(1-methylpiperidin-4-yl)-2-(5-(((4-(methylsulfonyl)phenyl)amino)methyl)thiophen-2-yl)-1-(2,2,2-trifluoroethyl)-1H-indol-4-amine |
| 2350. | N-((5-(4-(((3S,4R)-3-fluoro-1-methylpiperidin-4-yl)amino)-1-(2,2,2-trifluoroethyl)-1H-indol-2-yl)thiophen-2-yl)methyl)benzamide |
| 2351. | N-((3S,4R)-3-fluoro-1-methylpiperidin-4-yl)-2-(5-(((2-methoxy-4-(methylsulfonyl)phenyl)amino)methyl)thiophen-2-yl)-1-(2,2,2-trifluoroethyl)-1H-indol-4-amine |
| 2352. | 2-(5-(amino(cyclohexyl)methyl)-1,3,4-oxadiazol-2-yl)-N-(1-methylpiperidin-4-yl)-1-(2,2,2-trifluoroethyl)-1H-indol-4-amine |
| 2353. | N-(1-methylpiperidin-4-yl)-2-{5-[(phenylamino)methyl]-1,3,4-oxadiazol-2-yl}-1-(2,2,2-trifluoroethyl)-1H-indol-4-amine |
| 2354. | 2-(5-(amino(tetrahydro-2H-pyran-4-yl)methyl)-1,3,4-oxadiazol-2-yl)-N-(1-methylpiperidin-4-yl)-1-(2,2,2-trifluoroethyl)-1H-indol-4-amine |
| 2355. | N-[(5-{4-[(1-methylpiperidin-4-yl)amino]-1-(2,2,2-trifluoroethyl)-1H-indol-2-yl}-1,3,4-oxadiazol-2-yl)methyl]cyclopropanecarboxamide |
| 2356. | 2-(5-{[(4-methanesulfonylphenyl)amino]methyl}-1,3,4-oxadiazol-2-yl)-N-(1-methylpiperidin-4-yl)-1-(2,2,2-trifluoroethyl)-1H-indol-4-amine |
| 2357. | N-(1-methylpiperidin-4-yl)-2-(5-{[(1H-pyrazol-4-yl)amino]methyl}-1,3,4-oxadiazol-2-yl)-1-(2,2,2-trifluoroethyl)-1H-indol-4-amine |
| 2358. | 2-(5-(aminomethyl)-1,3,4-oxadiazol-2-yl)-N-(1-methylpiperidin-4-yl)-1-(2,2,2-trifluoroethyl)-1H-indol-4-amine |
| 2359. | (+/−)-N-[(3R,4S)-3-fluoro-1-methylpiperidin-4-yl]-2-(5-{[(4-methanesulfonyl-2-methoxyphenyl)amino]methyl}-1,3,4-oxadiazol-2-yl)-1-(2,2,2-trifluoroethyl)-1H-indol-4-amine |
| 2360. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}-2-methoxybenzamide |
| 2361. | (+/−)-2-[5-(aminomethyl)-1,3,4-oxadiazol-2-yl]-N-[(3R,4S)-3-fluoro-1-methylpiperidin-4-yl]-1-(2,2,2-trifluoroethyl)-1H-indol-4-amine |
| 2362. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}-4-methoxybenzamide |
| 2363. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}benzamide |
| 2364. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}-3-methoxybenzamide |
| 2365. | (+/−)-N-{[5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}thiophene-2-carboxamide |
| 2366. | (+/−)-2-(5-{[(cyclopropylmethyl)amino]methyl}-1,3,4-oxadiazol-2-yl)-N-[(3R,4S)-3-fluoro-1-methylpiperidin-4-yl]-1-(2,2,2-trifluoroethyl)-1H-indol-4-amine |
| 2367. | (+/−)-N-[(3R,4S)-3-fluoro-1-methylpiperidin-4-yl]-2-(5-{[(3-methanesulfonylphenyl)amino]methyl}-1,3,4-oxadiazol-2-yl)-1-(2,2,2-trifluoroethyl)-1H-indol-4-amine |
| 2368. | (+/−)-N-[(3R,4R)-3-fluoro-1-methylpiperidin-4-yl]-2-(5-{[(4-methanesulfonyl-2-methoxyphenyl)amino]methyl}-1,3,4-oxadiazol-2-yl)-1-(2,2,2-trifluoroethyl)-1H-indol-4-amine |

TABLE 9-continued

| Mol # | IUPAC name |
|---|---|
| | Heteroaryl-linked indole compounds of the disclosure. |
| 2369. | (+/−)-2-(5-((bis(cyclopropylmethyl)amino)methyl)-1,3,4-oxadiazol-2-yl)-N-((3R,4S)-3-fluoro-1-methylpiperidin-4-yl)-1-(2,2,2-trifluoroethyl)-1H-indol-4-amine |
| 2370. | (+/−)-N-((3S,4R)-3-fluoro-1-methylpiperidin-4-yl)-2-(5-(((3-(methylsulfonyl)phenyl)amino)methyl)-1,3,4-oxadiazol-2-yl)-1-(2,2,2-trifluoroethyl)-1H-indol-4-amine |
| 2371. | (+/−)-N-((3S,4R)-3-fluoro-1-methylpiperidin-4-yl)-2-(5-(((2-methoxy-4-(methylsulfonyl)phenyl)amino)methyl)-1,3,4-oxadiazol-2-yl)-1-(2,2,2-trifluoroethyl)-1H-indol-4-amine |
| 2372. | (+/−)-2-(5-(aminomethyl)-1,3,4-oxadiazol-2-yl)-N-((3S,4R)-3-fluoro-1-methylpiperidin-4-yl)-1-(2,2,2-trifluoroethyl)-1H-indol-4-amine |
| 2373. | (+/−)-N-((3S,4S)-3-fluoro-1-methylpiperidin-4-yl)-2-(5-(((2-methoxy-4-(methylsulfonyl)phenyl)amino)methyl)-1,3,4-oxadiazol-2-yl)-1-(2,2,2-trifluoroethyl)-1H-indol-4-amine |
| 2374. | N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)benzamide |
| 2375. | (+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)thiophene-2-carboxamide |
| 2376. | (+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)-2-methoxybenzamide |
| 2377. | (+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)-3-methoxybenzamide |
| 2378. | (+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)-4-methoxybenzamide |
| 2379. | (+/−)-2-(5-(((cyclopropylmethyl)amino)methyl)-1,3,4-oxadiazol-2-yl)-N-((3S,4R)-3-fluoro-1-methylpiperidin-4-yl)-1-(2,2,2-trifluoroethyl)-1H-indol-4-amine |
| 2380. | (+/−)-N-((3R,4R)-3-fluoro-1-methylpiperidin-4-yl)-2-(5-(((2-methoxy-4-(methylsulfonyl)phenyl)amino)methyl)-1,3,4-oxadiazol-2-yl)-1-(2,2,2-trifluoroethyl)-1H-indol-4-amine |
| 2381. | 2-(3-{[(4-methanesulfonylphenyl)amino]methyl}-1,2,4-oxadiazol-5-yl)-N-(1-methylpiperidin-4-yl)-1-(2,2,2-trifluoroethyl)-1H-indol-4-amine |
| 2382. | N-[(5-{4-[(1-methylpiperidin-4-yl)amino]-1-(2,2,2-trifluoroethyl)-1H-indol-2-yl}-1,2,4-oxadiazol-3-yl)methyl]cyclopropanecarboxamide |
| 2383. | N-[(5-{4-[(1-methylpiperidin-4-yl)amino]-1-(2,2,2-trifluoroethyl)-1H-indol-2-yl}-1,2,4-oxadiazol-3-yl)methyl]benzamide |
| 2384. | N-[(5-{4-[(1-methylpiperidin-4-yl)amino]-1-(2,2,2-trifluoroethyl)-1H-indol-2-yl}-1,2,4-oxadiazol-3-yl)methyl]thiophene-2-carboxamide |
| 2385. | 1-methyl-N-[(5-{4-[(1-methylpiperidin-4-yl)amino]-1-(2,2,2-trifluoroethyl)-1H-indol-2-yl}-1,2,4-oxadiazol-3-yl)methyl]-1H-pyrazole-4-carboxamide |
| 2386. | 1-methyl-N-[(5-{4-[(1-methylpiperidin-4-yl)amino]-1-(2,2,2-trifluoroethyl)-1H-indol-2-yl}-1,2,4-oxadiazol-3-yl)methyl]-1H-pyrazole-3-carboxamide |
| 2387. | N-(1-methylpiperidin-4-yl)-2-{5-[(phenylamino)methyl]-1,2,4-oxadiazol-3-yl}-1-(2,2,2-trifluoroethyl)-1H-indol-4-amine |
| 2388. | N-[(3-{4-[(1-methylpiperidin-4-yl)amino]-1-(2,2,2-trifluoroethyl)-1H-indol-2-yl}-1,2,4-oxadiazol-5-yl)methyl]thiophene-2-carboxamide |
| 2389. | N-[(3-{4-[(1-methylpiperidin-4-yl)amino]-1-(2,2,2-trifluoroethyl)-1H-indol-2-yl}-1,2,4-oxadiazol-5-yl)methyl]benzamide |
| 2390. | (+/−)-(1S,2R)-2-fluoro-N-[(3-{4-[(1-methylpiperidin-4-yl)amino]-1-(2,2,2-trifluoroethyl)-1H-indol-2-yl}-1,2,4-oxadiazol-5-yl)methyl]cyclopropane-1-carboxamide |
| 2391. | N-[(3-{4-[(1-methylpiperidin-4-yl)amino]-1-(2,2,2-trifluoroethyl)-1H-indol-2-yl}-1,2,4-oxadiazol-5-yl)methyl]cyclopropanecarboxamide |
| 2392. | (+/−)-(1S,2S)-2-fluoro-N-[(3-{4-[(1-methylpiperidin-4-yl)amino]-1-(2,2,2-trifluoroethyl)-1H-indol-2-yl}-1,2,4-oxadiazol-5-yl)methyl]cyclopropane-1-carboxamide |
| 2393. | 4-chloro-N-[(3-{4-[(1-methylpiperidin-4-yl)amino]-1-(2,2,2-trifluoroethyl)-1H-indol-2-yl}-1,2,4-oxadiazol-5-yl)methyl]benzamide |
| 2394. | N-[(3-{4-[(1-methylpiperidin-4-yl)amino]-1-(2,2,2-trifluoroethyl)-1H-indol-2-yl}-1,2,4-oxadiazol-5-yl)methyl]-1,3-thiazole-2-carboxamide |
| 2395. | 4-fluoro-N-[(3-{4-[(1-methylpiperidin-4-yl)amino]-1-(2,2,2-trifluoroethyl)-1H-indol-2-yl}-1,2,4-oxadiazol-5-yl)methyl]benzamide |
| 2396. | 4-cyano-N-[(3-{4-[(1-methylpiperidin-4-yl)amino]-1-(2,2,2-trifluoroethyl)-1H-indol-2-yl}-1,2,4-oxadiazol-5-yl)methyl]benzamide |
| 2397. | 1-methyl-N-[(3-{4-[(1-methylpiperidin-4-yl)amino]-1-(2,2,2-trifluoroethyl)-1H-indol-2-yl}-1,2,4-oxadiazol-5-yl)methyl]-1H-pyrrole-3-carboxamide |
| 2398. | 3-[(3-{4-[(1-methylpiperidin-4-yl)amino]-1-(2,2,2-trifluoroethyl)-1H-indol-2-yl}-1,2,4-oxadiazol-5-yl)methyl]-1-phenylurea |
| 2399. | 1-methyl-N-[(3-{4-[(1-methylpiperidin-4-yl)amino]-1-(2,2,2-trifluoroethyl)-1H-indol-2-yl}-1,2,4-oxadiazol-5-yl)methyl]-1H-pyrazole-4-carboxamide |
| 2400. | 1-methyl-N-[(3-{4-[(1-methylpiperidin-4-yl)amino]-1-(2,2,2-trifluoroethyl)-1H-indol-2-yl}-1,2,4-oxadiazol-5-yl)methyl]-1H-pyrazole-3-carboxamide |
| 2401. | (+/−)-(1R,2R)-N-[(3-{4-[(1-methylpiperidin-4-yl)amino]-1-(2,2,2-trifluoroethyl)-1H-indol-2-yl}-1,2,4-oxadiazol-5-yl)methyl]-2-phenylcyclopropane-1-carboxamide |
| 2402. | (+/−)-(1R,2R)-2-methyl-N-[(3-{4-[(1-methylpiperidin-4-yl)amino]-1-(2,2,2-trifluoroethyl)-1H-indol-2-yl}-1,2,4-oxadiazol-5-yl)methyl]cyclopropane-1-carboxamide |

TABLE 9-continued

| Mol # | IUPAC name |
|---|---|
| | Heteroaryl-linked indole compounds of the disclosure. |
| 2403. | (+/−)-(1R,2S)-2-methyl-N-[(3-{4-[(1-methylpiperidin-4-yl)amino]-1-(2,2,2-trifluoroethyl)-1H-indol-2-yl}-1,2,4-oxadiazol-5-yl)methyl]cyclopropane-1-carboxamide |
| 2404. | N-[(3-{4-[(oxan-4-yl)amino]-1-(2,2,2-trifluoroethyl)-1H-indol-2-yl}-1,2,4-oxadiazol-5-yl)methyl]cyclopropanecarboxamide |
| 2405. | N-({3-[4-(benzylamino)-1-(2,2,2-trifluoroethyl)-1H-indol-2-yl]-1,2,4-oxadiazol-5-yl}methyl)cyclopropanecarboxamide |
| 2406. | N-[(3-{4-[(1-acetylpiperidin-4-yl)amino]-1-(2,2,2-trifluoroethyl)-1H-indol-2-yl}-1,2,4-oxadiazol-5-yl)methyl]cyclopropanecarboxamide |
| 2407. | N-[(3-{4-[(1,1-dioxo-1λ$^6$-thian-4-yl)amino]-1-(2,2,2-trifluoroethyl)-1H-indol-2-yl}-1,2,4-oxadiazol-5-yl)methyl]cyclopropanecarboxamide |
| 2408. | N-[(3-{4-[(1-benzylpiperidin-4-yl)amino]-1-(2,2,2-trifluoroethyl)-1H-indol-2-yl}-1,2,4-oxadiazol-5-yl)methyl]cyclopropanecarboxamide |
| 2409. | N-[(3-{4-[(1-cyclopropylpiperidin-4-yl)amino]-1-(2,2,2-trifluoroethyl)-1H-indol-2-yl}-1,2,4-oxadiazol-5-yl)methyl]cyclopropanecarboxamide |
| 2410. | N-[(3-{4-[(cyclopropylmethyl)amino]-1-(2,2,2-trifluoroethyl)-1H-indol-2-yl}-1,2,4-oxadiazol-5-yl)methyl]cyclopropanecarboxamide |
| 2411. | N-[(3-{4-[(cyclobutylmethyl)amino]-1-(2,2,2-trifluoroethyl)-1H-indol-2-yl}-1,2,4-oxadiazol-5-yl)methyl]cyclopropanecarboxamide |
| 2412. | (+/−)-N-[(3-{4-[(pyrrolidin-3-yl)amino]-1-(2,2,2-trifluoroethyl)-1H-indol-2-yl}-1,2,4-oxadiazol-5-yl)methyl]cyclopropanecarboxamide |
| 2413. | N-[(3-{4-[(1-ethylpiperidin-4-yl)amino]-1-(2,2,2-trifluoroethyl)-1H-indol-2-yl}-1,2,4-oxadiazol-5-yl)methyl]cyclopropanecarboxamide |
| 2414. | (+/−)-N-[(3-{4-[(1-methylpyrrolidin-3-yl)amino]-1-(2,2,2-trifluoroethyl)-1H-indol-2-yl}-1,2,4-oxadiazol-5-yl)methyl]cyclopropanecarboxamide |
| 2415. | N-{[3-(4-{[(216zetidine-3-yl)methyl]amino}-1-(2,2,2-trifluoroethyl)-1H-indol-2-yl)-1,2,4-oxadiazol-5-yl]methyl}cyclopropanecarboxamide |
| 2416. | (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}cyclopropanecarboxamide |
| 2417. | (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}benzamide |
| 2418. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropanecarboxamide |
| 2419. | N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}cyclopropanecarboxamide |
| 2420. | (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}thiophene-2-carboxamide |
| 2421. | (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide |
| 2422. | (+/−)-N-[(3R,4S)-3-fluoro-1-methylpiperidin-4-yl]-2-(5-{[(4-methanesulfonylphenyl)amino]methyl}-1,2,4-oxadiazol-3-yl)-1-(2,2,2-trifluoroethyl)-1H-indol-4-amine |
| 2423. | (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-5-carboxamide |
| 2424. | (+/−)-1-ethyl-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2425. | (+/−)-(1R,2R)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-2-phenylcyclopropane-1-carboxamide |
| 2426. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-pyrrole-3-carboxamide |
| 2427. | N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-pyrrole-3-carboxamide |
| 2428. | (+/−)-N-[(3R,4S)-3-fluoro-1-methylpiperidin-4-yl]-2-(5-{[(4-methanesulfonyl-2-methoxyphenyl)amino]methyl}-1,2,4-oxadiazol-3-yl)-1-(2,2,2-trifluoroethyl)-1H-indol-4-amine |
| 2429. | (+/−)-1-tert-butyl-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2430. | (+/−)-(1R,2R)-N-{[3-(4-{[(3RS,4SR)-3-fluoro-1-methylpiperidin-4-yl]amino}-1-(2,2,2-trifluoroethyl)-1H-indol-2-yl)-1,2,4-oxadiazol-5-yl]methyl}-2-phenylcyclopropane-1-carboxamide |
| 2431. | 1-ethyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2432. | 1-ethyl-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2433. | (+/−)-N-[(3R,4S)-3-fluoropiperidin-4-yl]-2-(5-{[(4-methanesulfonyl-2-methoxyphenyl)amino]methyl}-1,2,4-oxadiazol-3-yl)-1-(2,2,2-trifluoroethyl)-1H-indol-4-amine |
| 2434. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide |

TABLE 9-continued

Heteroaryl-linked indole compounds of the disclosure.

| Mol # | IUPAC name |
|---|---|
| 2435. | N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide |
| 2436. | (+/−)-N-[(3R,4S)-3-fluoropiperidin-4-yl]-2-(5-{[methyl(1H-pyrazol-4-yl)amino]methyl}-1,2,4-oxadiazol-3-yl)-1-(2,2,2-trifluoroethyl)-1H-indol-4-amine |
| 2437. | (+/−)-N-[(3R,4S)-3-fluoro-1-methylpiperidin-4-yl]-2-(5-{[methyl(1H-pyrazol-4-yl)amino]methyl}-1,2,4-oxadiazol-3-yl)-1-(2,2,2-trifluoroethyl)-1H-indol-4-amine |
| 2438. | (1RS,2RS)-2-cyano-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropane-1-carboxamide |
| 2439. | 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2440. | (1RS,2SR)-2-cyano-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropane-1-carboxamide |
| 2441. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}indolizine-2-carboxamide |
| 2442. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-phenyl-1H-imidazole-4-carboxamide |
| 2443. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxyethyl)-1H-pyrrole-3-carboxamide |
| 2444. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(propan-2-yl)-1H-pyrrole-3-carboxamide |
| 2445. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyridine-4-carboxamide |
| 2446. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyridine-2-carboxamide |
| 2447. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyridine-3-carboxamide |
| 2448. | N-[(3S,4R)-3-fluoropiperidin-4-yl]-2-(5-{[(1H-pyrazol-4-yl)amino]methyl}-1,2,4-oxadiazol-3-yl)-1-(2,2,2-trifluoroethyl)-1H-indol-4-amine |
| 2449. | benzyl N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}carbamate |
| 2450. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-fluoroethyl)-1H-pyrrole-3-carboxamide |
| 2451. | (1S,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-phenylcyclopropane-1-carboxamide |
| 2452. | (1R,2S)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-phenylcyclopropane-1-carboxamide |
| 2453. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-methylthiophene-3-carboxamide |
| 2454. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-4-methylthiophene-3-carboxamide |
| 2455. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(4-fluorophenyl)cyclopropane-1-carboxamide |
| 2456. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-methylthiophene-3-carboxamide |
| 2457. | (1s,3r)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-methylcyclobutane-1-carboxamide |
| 2458. | 5-chloro-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide |
| 2459. | N-[(3S,4R)-3-fluoropiperidin-4-yl]-2-(5-{[(1H-pyrazol-5-yl)amino]methyl}-1,2,4-oxadiazol-3-yl)-1-(2,2,2-trifluoroethyl)-1H-indol-4-amine |
| 2460. | 2-chloro-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide |
| 2461. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyrazolo[1,5-a]pyridine-2-carboxamide |
| 2462. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}imidazo[1,2-a]pyridine-2-carboxamide |
| 2463. | 1-cyclopropyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2464. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,5-dimethyl-1H-pyrrole-3-carboxamide |
| 2465. | 4-(dimethylamino)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}benzamide |
| 2466. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}benzenesulfonamide |

TABLE 9-continued

| Mol # | IUPAC name |
| --- | --- |
| | Heteroaryl-linked indole compounds of the disclosure. |
| 2467. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclobutanecarboxamide |
| 2468. | (1r,3s)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-methylcyclobutane-1-carboxamide |
| 2469. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(2-fluorophenyl)cyclopropane-1-carboxamide |
| 2470. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(1-methyl-1H-pyrazol-4-yl)cyclopropane-1-carboxamide |
| 2471. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(pyridin-2-yl)cyclopropane-1-carboxamide |
| 2472. | N-[(3S,4R)-3-fluoro-1-methylpiperidin-4-yl]-2-(5-{[(1H-pyrazol-4-yl)amino]methyl}-1,2,4-oxadiazol-3-yl)-1-(2,2,2-trifluoroethyl)-1H-indol-4-amine |
| 2473. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}acetamide |
| 2474. | 1-[2-(dimethylamino)ethyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2475. | N-[(3S,4R)-3-fluoro-1-methylpiperidin-4-yl]-2-(5-{[(1H-pyrazol-5-yl)amino]methyl}-1,2,4-oxadiazol-3-yl)-1-(2,2,2-trifluoroethyl)-1H-indol-4-amine |
| 2476. | 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-4-carboxamide |
| 2477. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(propan-2-yl)-1H-imidazole-4-carboxamide |
| 2478. | (1S)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2,2-dimethylcyclopropane-1-carboxamide |
| 2479. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(4-methylpiperazin-1-yl)methyl]cyclopropane-1-carboxamide |
| 2480. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(3-fluorophenyl)cyclopropane-1-carboxamide |
| 2481. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-1,2,3-triazole-4-carboxamide |
| 2482. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-hydroxypropan-2-yl)-1H-pyrrole-3-carboxamide |
| 2483. | 2-[3-({[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}carbamoyl)-1H-pyrrol-1-yl]acetic acid |
| 2484. | (1R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2,2-dimethylcyclopropane-1-carboxamide |
| 2485. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methylpropyl)-1H-pyrrole-3-carboxamide |
| 2486. | 1-(cyclopropylmethyl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2487. | 3-(dimethylamino)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}benzamide |
| 2488. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-4-(pyrrolidin-1-yl)benzamide |
| 2489. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-hydroxypropyl)-1H-pyrrole-3-carboxamide |
| 2490. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(morpholin-4-yl)methyl]cyclopropane-1-carboxamide |
| 2491. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-{[(propan-2-yl)amino]methyl}cyclopropane-1-carboxamide |
| 2492. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(propylamino)methyl]cyclopropane-1-carboxamide |
| 2493. | 3-[3-({[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}carbamoyl)-1H-pyrrol-1-yl]propanoic acid |

TABLE 9-continued

| Mol # | IUPAC name |
|---|---|
| Heteroaryl-linked indole compounds of the disclosure. | |
| 2494. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-hydroxyethyl)-1H-pyrrole-3-carboxamide |
| 2495. | 1-(2,2-difluoroethyl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide |
| 2496. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxy-2-methylpropyl)-1H-pyrrole-3-carboxamide |
| 2497. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-hydroxy-2-methylpropyl)-1H-pyrrole-3-carboxamide |
| 2498. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxypropyl)-1H-pyrrole-3-carboxamide |
| 2499. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-indole-6-carboxamide |
| 2500. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(propan-2-yl)-1H-pyrazole-4-carboxamide |
| 2501. | 4-(4,4-difluoropiperidin-1-yl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}benzamide |
| 2502. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(propan-2-yl)-1H-imidazole-5-carboxamide |
| 2503. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-indole-5-carboxamide |
| 2504. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-indole-5-carboxamide |
| 2505. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-4-(morpholin-4-yl)benzamide |
| 2506. | 2-[5-(aminomethyl)-1,2,4-oxadiazol-3-yl]-N-[(3S,4R)-3-fluoro-1-methylpiperidin-4-yl]-1-(2,2,2-trifluoroethyl)-1H-indol-4-amine |
| 2507. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-(morpholin-4-yl)benzamide |
| 2508. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-(pyrrolidin-1-yl)benzamide |
| 2509. | (1R,2R)-2-[(dimethylamino)methyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropane-1-carboxamide |
| 2510. | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(pyrrolidin-1-yl)methyl]cyclopropane-1-carboxamide |
| 2511. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-methyl-1H-indole-5-carboxamide |
| 2512. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-indole-6-carboxamide |
| 2513. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxyethyl)-1H-imidazole-5-carboxamide |
| 2514. | (1R,2R)-2-ethyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropane-1-carboxamide |
| 2515. | 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-imidazole-5-carboxamide |
| 2516. | (1S,2S)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-{[(propan-2-yl)amino]methyl}cyclopropane-1-carboxamide |
| 2517. | N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1-(2-methoxyethyl)-1H-pyrrole-3-carboxamide |
| 2518. | N-{[3-(4-{[(3R,4S)-1-ethyl-3-fluoropiperidin-4-yl]amino}-1-(2,2,2-trifluoroethyl)-1H-indol-2-yl)-1,2,4-oxadiazol-5-yl]methyl}-1-(2-methoxyethyl)-1H-pyrrole-3-carboxamide |
| 2519. | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-methyl-1H-indole-6-carboxamide |
| 2520. | (+/−)-N-{[5-(4-{[(3R,4S)-3-fluoro-1-methylpiperidin-4-yl]amino(-1-(2,2,2-trifluoroethyl)-1H-indol-2-yl)-1,2,4-oxadiazol-3-yl]methyl}cyclopropanecarboxamide |
| 2521. | (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}benzamide |
| 2522. | (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}thiophene-2-carboxamide |
| 2523. | (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}thiophene-3-carboxamide |

TABLE 9-continued

| Heteroaryl-linked indole compounds of the disclosure. | |
|---|---|
| Mol # | IUPAC name |
| 2524. | (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}-1,3-thiazole-5-carboxamide |
| 2525. | N-((3-(4-(((3S,4R)-3-fluoro-1-methylpiperidin-4-yl)amino)-1-(2,2,2-trifluoroethyl)-1H-indol-2-yl)-1,2,4-oxadiazol-5-yl)methyl)-1-(1-fluoropropan-2-yl)-1H-pyrrole-3-carboxamide |
| 2526. | N-((3-(4-(((3S,4R)-1-ethyl-3-fluoropiperidin-4-yl)amino)-1-(2,2,2-trifluoroethyl)-1H-indol-2-yl)-1,2,4-oxadiazol-5-yl)methyl)-1-(2-fluoroethyl)-1H-pyrrole-3-carboxamide |
| 2527. | N-((3-(4-(((3S,4R)-3-fluoro-1-methylpiperidin-4-yl)amino)-1-(2,2,2-trifluoroethyl)-1H-indol-2-yl)-1,2,4-oxadiazol-5-yl)methyl)-1-(1-methoxypropan-2-yl)-1H-pyrrole-3-carboxamide |

Example 11: In Vitro DNA Binding Activity Assay

The ability of a compound of the invention to stabilize p53 Y220C and increase the DNA binding activity of p53 Y220C was measured by a homogeneous time-resolved fluorescence (HTRF) assay. Recombinant His-tagged p53 Y220C used in the HTRF assay was expressed in the bacterium *E. coli*. The recombinant protein was a truncation mutant containing only amino acids 94-312 of p53, which encompassed the DNA binding domain (DBD) of p53 (SEQ ID NO.: 1). The His-tagged p53 Y220C was tested for DNA binding ability with a consensus sequence of DNA (DNA duplex with a sequence of 5'-ATTAGGCATGTCTAGG-CATGTCTAGG-3'; SEQ ID NO.: 2). SEQ ID NO.: 2 was then conjugated with a biotin label and used in the activity assay.

The binding of the recombinant His-tagged p53 Y220C protein and the biotin-labeled consensus DNA was measured using fluorescence resonance energy transfer (FRET). For the FRET assay, the binding between the p53 mutant and the DNA sequence was measured by detecting the fluorescence of the interaction between an anti-His antibody conjugated to allophycocyanin (APC) and streptavidin conjugated to europium to detect the biotin-labeled DNA.

The test compounds were prepared as 4.5 mM stock solutions in dimethyl sulfoxide (DMSO). The compounds of the disclosure were used to test the stabilization of p53 Y220C and increase in DNA binding activity of p53 Y220C. The stock solutions were then serially diluted 3-fold in DMSO, and 1.2 μL of the diluted solutions was added to each well of a 384-well polypropylene black plate. 30 μL of a 181 nM solution of the recombinant His-tagged p53 Y220C protein and 12.1 nM of APC conjugated anti-His tag antibody in ice-cold Assay Buffer 1 (50 mM Tris-HCl, pH 7.4; 75 mM KCl; 0.75 mM DTT; and 0.2 mg/mL bovine serum albumin (BSA) was added to each well containing the test compounds.

As a background control, 30 μL of Assay Buffer 1 containing 12.1 nM of APC anti-His antibody was also added into a second set of serially-diluted compound plates. The test and control samples were spun at 1200 rpm for 1 minute and incubated at room temperature for 15 minutes. The samples were then further incubated at either 27° C. or 29° C. for 60 min. Five microliters of 311 nM biotin labeled consensus DNA (SEQ ID NO.: 2) and 13.03 nM europium-conjugated streptavidin in Assay Buffer 2 (50 mM Tris-HCl, pH 7.4; 75 mM KCl; and 0.2 mg/mL BSA) were added to each well for both the test and control plates. The plates were spun at 1200 rpm for 1 minute and incubated at room temperature for 20 minutes. The assay signals were monitored by reading excitation at 340 nm, and emission fluorescence at 615 nm and 665 nm on a plate reader.

Normalized time-resolved fluorescence resonance energy transfer (TR-FRET) assay signal ($R_n$) was calculated by the formula:

$$R_n=[(A-B_a-CD)/(D-B_d)](D_c-B_d)$$

where A was the fluorescence intensity of the sample at 665 nm;

D was the fluorescence intensity of the sample at 615 nm;

$B_a$ and $B_d$ were plate background readings at 665 nm and 615 nm, respectively; and $D_c$ was the fluorescence intensity of 1.8 nM Eu-SA in the assay buffer at 615 nm.

The cross talk factor (C) was determined by the following formula:

$$C=(A_c-B_a)/(D_C-B_d)$$

where $A_c$ was the fluorescence intensity of 1.8 nM Eu-labeled anti-FLAG antibody in the assay buffer at 665 nm.

The percentage of activation of protein DNA binding in the presence of a compound of the invention compared to the absence of the compound was denoted by a $SC_{150}$ value, which indicated the concentration of the compound required to increase the DNA binding activity by 50%. The $SC_{150}$ values were calculated using either Prism™ or Activity-Base™.

TABLE 10 shows the $SC_{150}$ (μM) values of the compounds shown in TABLE 6. TABLE 11 shows the $SC_{150}$ (μM) values of the compounds shown in TABLE 7. TABLE 12 shows the $SC_{150}$ (μM) values of the compounds shown in TABLE 8.

TABLE 10

| Molecule # | $SC_{150}$ (μM) |
|---|---|
| Compound 7 | ' |
| Compound 10 | ' |
| Compound 13 | ' |
| Compound 14 | ' |
| 702 | ''' |
| 1155 | '''' |
| 1188 | ' |
| 1330 | ' |
| 1623 | ' |
| 1687 | ' |
| 1921 | ' |
| 1938 | ' |

TABLE 10-continued

| Molecule # | $SC_{150}$ (μM) |
|---|---|
| 1939 | ' |
| 2168 | ''' |

' = 0 μM ≤ $SC_{150}$ < 0.05 μM
'' = 0.05 μM ≤ $SC_{150}$ < 0.1 μM
''' = 0.1 μM ≤ $SC_{150}$ < 0.2 μM
'''' = 0.2 μM ≤ $SC_{150}$ < 1 μM

TABLE 11

| Molecule # | $SC_{150}$ (μM) |
|---|---|
| 2201 | ++ |
| 2202 | + |
| 2203 | +++ |
| 2210 | ++ |
| 2211 | ++ |
| 2212 | + |
| 2213 | + |
| 2222 | + |
| 2227 | ++ |
| 2228 | ++++ |
| 2238 | + |
| 2239 | + |
| 2240 | + |
| 2241 | +++ |

+ = 0 μM ≤ $SC_{150}$ < 2 μM
++ = 2 μM ≤ $SC_{150}$ < 5 μM
+++ = 5 μM ≤ $SC_{150}$ < 10 μM
++++ = 10 μM ≤ $SC_{150}$ < 35 μM

TABLE 12

| Molecule # | $SC_{150}$ (μM) |
|---|---|
| 2268 | **** |
| 2269 | ** |
| 2273 | * |
| 2274 | ** |
| 2275 | * |
| 2280 | * |
| 2281 | ** |
| 2292 | * |
| 2293 | * |
| 2294 | ** |
| 2204 | ** |
| 2205 | ** |
| 2206 | * |
| 2207 | * |

* = 0 μM ≤ $SC_{150}$ < 0.1 μM
** = 0.1 μM ≤ $SC_{150}$ < 0.5 μM
*** = 0.5 μM ≤ $SC_{150}$ < 1 μM
**** = 1 μM ≤ $SC_{150}$ < 10 μM

Embodiments

The following non-limiting embodiments provide illustrative examples of the invention but do not limit the scope of the invention.

Embodiment 1. A compound comprising a molecular structure that binds to a mutant p53 protein, wherein the mutant p53 protein has a mutant conformation, and the molecular structure modulates the mutant conformation of the mutant p53 protein into a conformation of p53 that possesses anti-cancer activity, wherein the molecular structure that binds to the mutant p53 protein comprises a hydrogen bond donor and an electron-withdrawing heteroatom, wherein the hydrogen bond donor is proximal to the electron-withdrawing heteroatom, wherein if a co-crystal is obtained of the compound and the mutant p53 protein with the compound bound to a binding site on the mutant p53 protein, and the co-crystal is obtained by sitting-drop vapor distillation, and if an x-ray co-crystal structure of the co-crystal is obtained by crystal soaking, and if the x-ray co-crystal structure has a resolution of about 2 Å, then in the x-ray co-crystal structure, the hydrogen bond donor forms a hydrogen bond with Thr-150 of the mutant p53 protein.

Embodiment 2. The compound of embodiment 1, wherein the hydrogen bond has a mean length of from about 1.5 Å to about 3 Å.

Embodiment 3. The compound of embodiment 1 or 2, wherein the hydrogen bond is to a side chain atom of Thr-150.

Embodiment 4. The compound of any one of embodiments 1-3, wherein in the x-ray co-crystal structure, the compound further forms a second hydrogen bond with Cys-220 of the mutant p53 protein.

Embodiment 5. The compound of embodiment 4, wherein the second hydrogen bond is with a carbonyl group of Cys-220.

Embodiment 6. The compound of any one of embodiments 1-5, wherein the electron-withdrawing heteroatom is a halogen atom.

Embodiment 7. The compound of any one of embodiments 1-6, wherein the electron-withdrawing heteroatom is a fluorine atom.

Embodiment 8. The compound of any one of embodiments 1-7, wherein the electron-withdrawing heteroatom is bound to a stereocenter of the compound.

Embodiment 9. The compound of any one of embodiments 1-8, wherein the stereocenter has a handedness, wherein the hydrogen bond is stronger than is an analogous hydrogen bond formed by a stereoisomer of the compound, wherein the stereoisomer of the compound differs from the compound only in the handedness of the stereocenter.

Embodiment 10. The compound of any one of embodiments 1-9, wherein the stereoisomer of the compound is a diastereomer of the compound.

Embodiment 11. The compound of any one of embodiments 1-10, wherein the hydrogen bond donor is a hydrogen atom bound to a nitrogen atom having a formal positive charge.

Embodiment 12. The compound of any one of embodiments 1-11, wherein the hydrogen bond donor is a hydrogen atom bound to a tetravalent nitrogen atom.

Embodiment 13. The compound of any one of embodiments 1-12, wherein the hydrogen bond donor is a tertiary ammonium cation.

Embodiment 14. The compound of any one of embodiments 1-13, wherein the hydrogen bond donor and the electron-withdrawing heteroatom are substituents on a common ring.

Embodiment 15. The compound of any one of embodiments 1-14, wherein the hydrogen bond donor and the electron-withdrawing heteroatom are substituents on a common ring, and the hydrogen bond donor and the electron-withdrawing group are oriented syn to one another on the common ring.

Embodiment 16. The compound of any one of embodiments 1-15, wherein the hydrogen bond donor and the electron-withdrawing heteroatom are substituents on a common ring, and the hydrogen bond donor and the electron-withdrawing group are disposed vicinally to one another on the common ring.

Embodiment 17. The compound of any one of embodiments 1-16, wherein the hydrogen bond donor and the electron-withdrawing heteroatom are substituents on a common ring, and the hydrogen bond donor and the electron-withdrawing group are oriented syn to one another on the common ring and are disposed vicinally to one another on the common ring.

Embodiment 18. The compound of any one of embodiments 1-17, wherein the mutant p53 protein is a Y220C mutant.

Embodiment 19. A compound comprising a molecular structure that binds to a mutant p53 protein, wherein the mutant p53 protein has a mutant conformation, and the molecular structure modulates the mutant conformation of the mutant p53 protein into a conformation that possesses a pro-apoptotic activity of a wild type p53 protein, wherein the mutant p53 protein is a Y220C mutant, wherein the molecular structure that binds to the mutant p53 protein comprises a tertiary ammonium cation and a fluorine atom, wherein the tertiary ammonium cation and the fluorine atom are substituents on a common ring, the tertiary ammonium cation and the fluorine atom are oriented syn to one another on the common ring, and the tertiary ammonium cation and the fluorine atom are disposed vicinally to one another on the common ring, wherein if a co-crystal is obtained of the compound and the mutant p53 protein with the compound bound to a binding site on the mutant p53 protein, and the co-crystal is obtained by sitting-drop vapor distillation, and if an x-ray co-crystal structure of the co-crystal is obtained by crystal soaking, and if the x-ray co-crystal structure has a resolution of about 2 Å, then in the x-ray co-crystal structure the tertiary ammonium cation forms a hydrogen bond with a side chain oxygen atom of Thr-150 of the mutant p53 protein, wherein the hydrogen bond has a mean length of from about 1.5 Å to about 3 Å, wherein the fluorine atom is bound to a stereocenter of the compound, wherein the stereocenter has a handedness, wherein the hydrogen bond is stronger than is an analogous hydrogen bond formed by a diastereomer of the compound, wherein the diastereomer of the compound differs from the compound only in the handedness of the stereocenter.

Embodiment 20. A method of treating a cancer associated with a mutant p53 protein, the method comprising administering to a subject in need thereof a therapeutically-effective amount of an organic molecule, wherein the organic molecule binds to a binding site on the mutant p53 protein and forms a hydrogen bond to a Thr-150 residue of the mutant p53 protein, wherein the organic molecule comprises a hydrogen bond donor and an electron-withdrawing heteroatom, wherein the hydrogen bond donor participates in the hydrogen bond, wherein the hydrogen bond donor is proximal to the electron-withdrawing heteroatom.

Embodiment 21. The method of embodiment 20, wherein the hydrogen bond is to a side chain oxygen atom of the Thr-150 residue of the mutant p53 protein.

Embodiment 22. The method of embodiment 20 or 21, wherein the organic molecule forms a second hydrogen bond to a Cys-220 residue of the mutant p53 protein.

Embodiment 23. The method of embodiment 22, wherein the second hydrogen bond is with a carbonyl group of Cys-220.

Embodiment 24. The method of any one of embodiments 20-23, wherein the electron-withdrawing heteroatom is a halogen atom.

Embodiment 25. The method of any one of embodiments 20-24, wherein the electron-withdrawing heteroatom is a fluorine atom.

Embodiment 26. The method of any one of embodiments 20-25, wherein the electron-withdrawing heteroatom is bound to a stereocenter of the organic molecule.

Embodiment 27. The method of any one of embodiments 20-26, wherein the stereocenter has a handedness, wherein the hydrogen bond is stronger than is an analogous hydrogen bond formed by a stereoisomer of the organic molecule, wherein the stereoisomer of the organic molecule differs from the organic molecule only in the handedness of the stereocenter.

Embodiment 28. The method of any one of embodiments 20-27, wherein the stereoisomer of the organic molecule is a diastereomer of the organic molecule.

Embodiment 29. The method of any one of embodiments 20-28, wherein the hydrogen bond donor is a hydrogen atom bound to a nitrogen atom having a formal positive charge.

Embodiment 30. The method of any one of embodiments 20-29, wherein the hydrogen bond donor is a hydrogen atom bound to a tetravalent nitrogen atom.

Embodiment 31. The method of any one of embodiments 20-30, wherein the hydrogen bond donor is a tertiary ammonium cation.

Embodiment 32. The method of any one of embodiments 20-31, wherein the hydrogen bond donor and the electron-withdrawing heteroatom are substituents on a common ring.

Embodiment 33. The method of any one of embodiments 20-32, wherein the hydrogen bond donor and the electron-withdrawing heteroatom are substituents on a common ring, and the hydrogen bond donor and the electron-withdrawing group are oriented syn to one another on the common ring.

Embodiment 34. The method of any one of embodiments 20-33, wherein the hydrogen bond donor and the electron-withdrawing heteroatom are substituents on a common ring, and the hydrogen bond donor and the electron-withdrawing group are disposed vicinally to one another on the common ring.

Embodiment 35. The method of any one of embodiments 20-34, wherein the mutant p53 protein is a Y220C mutant.

Embodiment 36. The method of any one of embodiments 20-35, wherein the cancer is breast cancer.

Embodiment 37. The method of any one of embodiments 20-35, wherein the cancer is lung cancer.

Embodiment 38. The method of any one of embodiments 20-35, wherein the cancer is ovarian cancer.

Embodiment 39. The method of any one of embodiments 20-38, wherein the administering is oral.

Embodiment 40. The method of any one of embodiments 20-38, wherein the administering is intravenous.

Embodiment 41. The method of any one of embodiments 20-40, wherein the therapeutically-effective amount is from about 500 mg to about 2000 mg.

Embodiment 42. The method of any one of embodiments 20-41, wherein the therapeutically-effective amount is about 600 mg.

Embodiment 43. The method of any one of embodiments 20-41, wherein the therapeutically-effective amount is about 1200 mg.

Embodiment 44. A method of treating a cancer associated with a mutant p53 protein, the method comprising administering to a subject in need thereof a therapeutically-effective amount of an organic molecule, wherein the organic molecule binds to a binding site on the mutant p53 protein, wherein the cancer is breast cancer, wherein the administering is oral, wherein the therapeutically-effective amount is from about 50 mg to about 500 mg, wherein the mutant p53 protein is a Y220C mutant, wherein the organic molecule comprises a tertiary ammonium cation and a fluorine atom, wherein the tertiary ammonium cation and the fluorine atom are substituents on a common ring, the tertiary ammonium cation and the fluorine atom are oriented syn to one another on the common ring, and the tertiary ammonium cation and the fluorine atom are disposed vicinally to one another on the common ring, wherein the mutant p53 protein has a conformation that is not pro-apoptotic, and the contacting to the mutant p53 protein the organic molecule that binds to the binding site on the mutant p53 protein modulates the conformation of the mutant p53 protein to a form that is pro-apoptotic, wherein if a co-crystal is obtained of the organic molecule and the mutant p53 protein with the organic molecule bound to the binding site on the mutant p53 protein, and the co-crystal is obtained by sitting-drop vapor distillation, and if an x-ray co-crystal structure of the co-crystal is obtained by crystal soaking, and if the x-ray co-crystal structure has a resolution of about 2 Å, then in the x-ray co-crystal structure the tertiary ammonium cation forms a hydrogen bond with a side chain oxygen atom of Thr-150 of the mutant p53 protein, wherein the hydrogen bond has a mean length of from about 1.5 Å to about 3 Å, wherein the fluorine atom is bound to a stereocenter of the organic molecule, wherein the stereocenter has a handedness, wherein the hydrogen bond is stronger than is an analogous hydrogen bond formed by a diastereomer of the organic molecule, wherein the diastereomer of the organic molecule differs from the organic molecule only in the handedness of the stereocenter.

Embodiment 45. A method comprising contacting to a mutant p53 protein an organic molecule that binds to a binding site on the mutant p53 protein and forms a hydrogen bond to a Thr-150 residue of the mutant p53 protein, wherein the mutant p53 protein has a conformation that is not pro-apoptotic, and the contacting to the mutant p53 protein the organic molecule that binds to the binding site on the mutant p53 protein and forms the hydrogen bond to the Thr-150 residue of the mutant p53 protein modulates the conformation of the mutant p53 protein to a form that is pro-apoptotic, wherein the organic molecule comprises a hydrogen bond donor and an electron-withdrawing heteroatom, wherein the hydrogen bond donor participates in the hydrogen bond, wherein the hydrogen bond donor is proximal to the electron-withdrawing heteroatom.

Embodiment 46. The method of embodiment 45, wherein the hydrogen bond has a mean length of from about 1.5 Å to about 3 Å.

Embodiment 47. The method of embodiment 45 or 46, wherein the hydrogen bond is to a side chain oxygen atom of Thr-150.

Embodiment 48. The method of any one of embodiments 45-47, wherein the electron-withdrawing heteroatom is a halogen atom.

Embodiment 49. The method of any one of embodiments 45-48, wherein the electron-withdrawing heteroatom is a fluorine atom.

Embodiment 50. The method of any one of embodiments 45-49, wherein the electron-withdrawing heteroatom is bound to a stereocenter of the organic molecule.

Embodiment 51. The method of embodiment 50, wherein the stereocenter has a handedness, wherein the hydrogen bond is stronger than is an analogous hydrogen bond formed by a stereoisomer of the organic molecule, wherein the stereoisomer of the organic molecule differs from the organic molecule only in the handedness of the stereocenter.

Embodiment 52. The method of embodiment 50 or 51, wherein the stereoisomer of the organic molecule is a diastereomer of the organic molecule.

Embodiment 53. The method of any one of embodiments 45-52, wherein the hydrogen bond donor is a hydrogen atom bound to a nitrogen atom having a formal positive charge.

Embodiment 54. The method of any one of embodiments 45-53, wherein the hydrogen bond donor is a hydrogen atom bound to a tetravalent nitrogen atom.

Embodiment 55. The method of any one of embodiments 45-54, wherein the hydrogen bond donor is a tertiary ammonium cation.

Embodiment 56. The method of any one of embodiments 45-55, wherein the hydrogen bond donor and the electron-withdrawing heteroatom are substituents on a common ring.

Embodiment 57. The method of any one of embodiments 45-56, wherein the hydrogen bond donor and the electron-withdrawing heteroatom are substituents on a common ring, and the hydrogen bond donor and the electron-withdrawing group are oriented syn to one another on the common ring.

Embodiment 58. The method of any one of embodiments 45-57, wherein the hydrogen bond donor and the electron-withdrawing heteroatom are substituents on a common ring, and the hydrogen bond donor and the electron-withdrawing group are disposed vicinally to one another on the common ring.

Embodiment 59. The method of any one of embodiments 45-58, wherein the mutant p53 protein is a Y220C mutant.

Embodiment 60. A method comprising contacting to a mutant p53 protein an organic molecule that binds to a binding site on the mutant p53 protein and forms a hydrogen bond to a side chain oxygen atom of a Thr-150 residue of the mutant p53 protein, wherein the mutant p53 protein is a Y220C mutant, wherein the organic molecule comprises a tertiary ammonium cation and a fluorine atom, wherein the tertiary ammonium cation and the fluorine atom are substituents on a common ring, the tertiary ammonium cation and the fluorine atom are oriented syn to one another on the common ring, and the tertiary ammonium cation and the fluorine atom are disposed vicinally to one another on the common ring, wherein the tertiary ammonium cation participates in the hydrogen bond, wherein the mutant p53 protein has a conformation that is not pro-apoptotic, and the contacting to the mutant p53 protein the organic molecule that binds to the binding site on the mutant p53 protein and modulates the conformation of the mutant p53 protein to a form that is pro-apoptotic, wherein if a co-crystal is obtained of the organic molecule and the mutant p53 protein with the organic molecule bound to a binding site on the mutant p53 protein, and the co-crystal is obtained by sitting-drop vapor distillation, and if an x-ray co-crystal structure of the co-crystal is obtained by crystal soaking, and if the x-ray co-crystal structure has a resolution of about 2 Å, then in the x-ray co-crystal structure the tertiary ammonium cation forms the hydrogen bond with the side chain oxygen atom of Thr-150 of the mutant p53 protein, wherein the hydrogen bond has a mean length of from about 1.5 Å to about 3 Å, wherein the fluorine atom is bound to a stereocenter of the organic molecule, wherein the stereocenter has a handedness, wherein the hydrogen bond is stronger than is an analogous hydrogen bond formed by a diastereomer of the organic molecule, wherein the diastereomer of the organic molecule differs from the organic molecule only in the handedness of the stereocenter.

Embodiment 61. A composition comprising a co-crystal, wherein the co-crystal comprises a mutant p53 protein and a small molecule ligand of the mutant p53 protein, wherein the small molecule ligand is bound to a binding site on the mutant p53 protein, wherein if the co-crystal is obtained by sitting-drop vapor distillation, and if an x-ray co-crystal structure of the co-crystal is obtained by crystal soaking, and if the x-ray co-crystal structure has a resolution of about 2 Å, then the mutant p53 protein has a conformation that is at least about 60% identical to a conformation of wild type p53 as determined by root-mean-square deviation (RMSD) of atomic positions.

Embodiment 62. The composition of embodiment 61, wherein the small molecule ligand forms a hydrogen bond with Thr-150 of the mutant p53 protein.

Embodiment 63. The composition of embodiment 61 or 62, wherein the hydrogen bond is with a side chain oxygen atom of Thr-150.

Embodiment 64. The composition of any one of embodiments 61-63, wherein the small molecule further forms a second hydrogen bond with Cys-220 of the mutant p53 protein.

Embodiment 65. The composition of embodiment 64, wherein the second hydrogen bond is with a carbonyl of Cys-220.

Embodiment 66. The composition of any one of embodiments 61-65, wherein the mutant p53 protein is a Y220C mutant.

Embodiment 67. The composition of any one of embodiments 61-66, wherein the conformation of mutant p53 is at least about 80% identical to the conformation of wild type p53.

Embodiment 68. The composition of any one of embodiments 61-67, wherein the conformation of mutant p53 is at least about 90% identical to the conformation of wild type p53.

Embodiment 69. The composition of any one of embodiments 61-68, wherein the conformation of mutant p53 is at least about 95% identical to the conformation of wild type p53.

Embodiment 100. The compound, composition, or method of any of the preceding embodiments, wherein the compound has the formula:

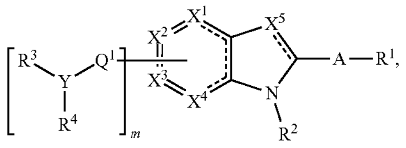

wherein:

each ═ is independently a single bond or a double bond;

$X^1$ is $CR^5$, $CR^5R^6$, N, $NR^5$, O, S, C═O, C═S, or a carbon atom connected to $Q^1$;

$X^2$ is $CR^7$, $CR^7R^8$, N, $NR^7$, O, S, C═O, C═S, or a carbon atom connected to $Q^1$;

$X^3$ is $CR^9$, $CR^9R^{10}$, N, $NR^9$, O, S, C═O, C═S, or a carbon atom connected to $Q^1$;

$X^4$ is $CR^{11}$, $CR^{11}R^{12}$, N, $NR^{11}$, O, S, C═O, C═S, or a carbon atom connected to $Q^1$;

$X^5$ is $CR^{13}$, N, or $NR^{13}$;

wherein at least one of $X^1$, $X^2$, $X^3$, and $X^4$ is a carbon atom connected to $Q^1$;

A is a linking group;

$Q^1$ is C═O, C═S, C═$CR^{14}R^{15}$, C═$NR^{14}$, alkylene, alkenylene, or alkynylene, each of which is independently substituted or unsubstituted, or a bond;

m is 1, 2, 3, or 4;

Y is N, O, or absent;

$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;

each $R^3$ and $R^4$ is independently —C(O)$R^{19}$, —C(O)O$R^{19}$, —C(O)N$R^{19}R^{20}$, —SO$R^{19}$, —$SO_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is independently —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

Embodiment 101. The compound, composition, or method of embodiment 100, wherein A is alkylene, alkenylene, or alkynylene, each of which is substituted or unsubstituted.

Embodiment 102. The compound, composition, or method of embodiment 100, wherein A is aryl, heteroaryl, or heterocyclyl, each of which is substituted or unsubstituted.

Embodiment 103. The compound, composition, or method of embodiment 100 or 101, wherein the compound is of the formula:

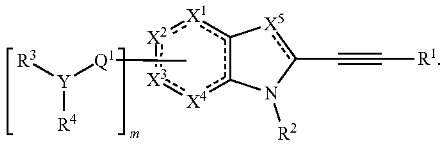

Embodiment 104. The compound, composition, or method of any one of embodiments 100-103, wherein $Q^1$ is $C_1$-alkylene.

Embodiment 105. The compound, composition, or method of any one of embodiments 100-103, wherein $Q^1$ is a bond.

Embodiment 106. The compound, composition, or method of any one of embodiments 100-105, wherein m is 1.

Embodiment 107. The compound, composition, or method of any one of embodiments 100-105, wherein m is 2.

Embodiment 108. The compound, composition, or method of any one of embodiments 100-107, wherein Y is N.

Embodiment 109. The compound, composition, or method of any of one of embodiments 100-107, wherein Y is O.

Embodiment 110. The compound, composition, or method of any one of embodiments 100-109, wherein each $R^3$ and $R^4$ is independently alkyl, alkylene, alkenyl, alkenylene, alkynyl, aryl, heteroaryl, or heterocyclyl, each of which is independently substituted or unsubstituted; or hydrogen.

Embodiment 111. The compound, composition, or method of any one of embodiments 100-110, wherein $R^3$ is alkyl, alkylene, alkenyl, alkenylene, alkynyl, each of which is independently substituted or unsubstituted; and $R^4$ is aryl, heteroaryl, or heterocyclyl, each of which is independently substituted or unsubstituted.

Embodiment 112. The compound, composition, or method of any one of embodiments 100-110, wherein $R^3$ is H; and $R^4$ is aryl, heteroaryl, or heterocyclyl, each of which is independently substituted or unsubstituted.

Embodiment 113. The compound, composition, or method of any one of embodiments 100-112, wherein $R^{13}$ is hydrogen.

Embodiment 114. The compound, composition, or method of any one of embodiments 100, 101, 103, 105, 106, 108, or 110-113, wherein the compound is of the formula:

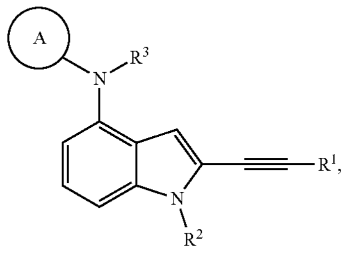

wherein ring A is a cyclic group that is substituted or unsubstituted.

Embodiment 115. The compound, composition, or method of any one of embodiments 100-114, wherein $R^2$ is substituted or unsubstituted alkyl.

Embodiment 116. The compound, composition, or method of any one of embodiments 100-115, wherein $R^2$ is methyl, ethyl, propyl, iso-propyl, butyl, or tert-butyl, each of which is substituted or unsubstituted.

Embodiment 117. The compound, composition, or method of any one of embodiments 100-116, wherein $R^2$ is substituted ethyl.

Embodiment 118. The compound, composition, or method one of embodiments 100-117, wherein $R^2$ is trifluoroethyl.

Embodiment 119. The compound, composition, or method of any one of embodiments 100, 101, 103, 105, 106, 108, or 110-118, wherein the compound is of the formula:

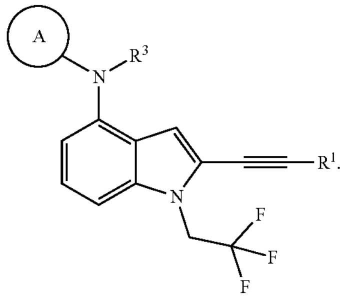

Embodiment 120. The compound, composition, or method of embodiment 119, wherein ring A is aryl, heteroaryl, or heterocyclyl, each of which is substituted or unsubstituted.

Embodiment 121. The compound, composition, or method of embodiment 119 or 120, wherein ring A is substituted aryl.

Embodiment 122. The compound, composition, or method of embodiment 119 or 120, wherein ring A is substituted heteroaryl.

Embodiment 123. The compound, composition, or method of embodiment 119 or 120, wherein ring A is substituted heterocyclyl.

Embodiment 124. The compound, composition, or method of any one of embodiments 100-123, wherein $R^1$ is alkyl, alkenyl, —C(O)$R^{16}$, —C(O)O$R^{16}$, or —C(O)N$R^{16}R^{17}$, each of which is unsubstituted or substituted.

Embodiment 125. The compound, composition, or method of any one of embodiments 100-124, wherein $R^1$ is substituted alkyl.

Embodiment 126. The compound, composition, or method of any one of embodiments 100-125, wherein $R^1$ is alkyl substituted with N$R^{16}R^{17}$.

Embodiment 127. The compound, composition, or method of any of Embodiments 100, 101, 103, 105, 106, 108, or 110-126, wherein the compound is of the formula:

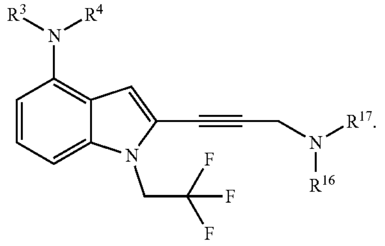

Embodiment 128. The compound, composition, or method of any one of embodiments 100-127, wherein each $R^{16}$ and $R^{17}$ is independently alkyl, alkenyl, aryl, heteroaryl, heterocyclyl, each of which is independently substituted or unsubstituted; or hydrogen.

Embodiment 129. The compound, composition, or method of any one of embodiments 100-128, wherein $R^{16}$ is hydrogen or alkyl.

Embodiment 130. The compound, composition, or method of any one of embodiments 100-129, wherein $R^{17}$ is aryl, heteroaryl, or heterocyclyl, each of which is independently substituted or unsubstituted.

Embodiment 131. The compound, composition, or method of any one of embodiments 100-130, wherein $R^{17}$ is substituted aryl.

Embodiment 132. The compound, composition, or method of any one of embodiments 100-131, wherein $R^{17}$ is substituted phenyl.

Embodiment 133. The compound, composition, or method of any one of embodiments 100-132, wherein $R^{17}$ is phenyl substituted with a sulfoxide group, carboxyl group, amide group, amino group, alkyl, alkoxy, hydroxy, halo, cyano, or heterocyclyl, each of which is independently substituted or unsubstituted.

Embodiment 134. The compound, composition, or method of any one of embodiments 100-133, wherein $R^{17}$ is phenyl substituted with methoxy.

Embodiment 135. The compound, composition, or method of any one of embodiments 100-134, wherein $R^{17}$ is phenyl substituted with a substituted sulfoxide group.

Embodiment 136. The compound, composition, or method of any one of embodiments 100-135, wherein $R^{17}$ is phenyl substituted with a carboxyl group.

Embodiment 137. The compound, composition, or method of any one of embodiments 100-136, wherein $R^{17}$ is phenyl substituted with an amide group.

Embodiment 138. The compound, composition, or method of embodiment 100, wherein the compound is 4-[(3-{4-[(1,5-dihydroxypentan-3-yl)amino]-1-(2,2,2-trifluoroethyl)-1H-indol-2-yl}prop-2-yn-1-yl)amino]-3-methoxybenzene-1-sulfonamide.

Embodiment 139. The compound, composition, or method of embodiment 100, wherein the compound is 2-(3-((2-methoxy-4-(methylsulfonyl)phenyl)amino)prop-1-yn-1-yl)-N-((1r,4r)-4-morpholinocyclohexyl)-1-(oxiran-2-ylmethyl)-1H-indol-4-amine.

Embodiment 140. The compound, composition, or method of embodiment 100, wherein the compound is 3-methoxy-4-({3-[4-({2-oxaspiro[3.3]heptan-6-yl}amino)-1-(2,2,2-trifluoroethyl)-1H-indol-2-yl]prop-2-yn-1-yl}amino)benzene-1-sulfonamide.

Embodiment 141. The compound, composition, or method of embodiment 100, wherein the compound is 4-((3-(4-(((3S,4R)-3-fluoro-1-methylpiperidin-4-yl)amino)-1-(2,2,2-trifluoroethyl)-1H-indol-2-yl)prop-2-yn-1-yl)amino)-3-methoxy-N-methylbenzamide.

Embodiment 142. The compound, composition, or method of embodiment 100, wherein the compound is N-(2,3-dihydroxypropyl)-4-{[3-(4-{[(3S,4R)-3-fluoro-1-methylpiperidin-4-yl]amino}-1-(2,2,2-trifluoroethyl)-1H-indol-2-yl)prop-2-yn-1-yl]amino}-3-methoxybenzamide.

Embodiment 143. The compound, composition, or method of embodiment 100, wherein the compound is 3-methoxy-N-(2-methoxyethyl)-N-methyl-4-((3-(4-((tetrahydro-2H-pyran-4-yl)amino)-1-(2,2,2-trifluoroethyl)-1H-indol-2-yl)prop-2-yn-1-yl)amino)benzenesulfonamide.

Embodiment 144. The compound, composition, or method of embodiment 100, wherein the compound is N-(2,3-dihydroxypropyl)-4-((3-(4-((1,1-dioxidotetrahydro-2H-thiopyran-4-yl)amino)-1-(2,2,2-trifluoroethyl)-1H-indol-2-yl)prop-2-yn-1-yl)amino)-3-methoxybenzenesulfonamide.

Embodiment 145. The compound, composition, or method of embodiment 100, wherein the compound is 3-methoxy-4-((3-(4-(3-(1-methylpiperidin-4-yl)ureido)-1-(2,2,2-trifluoroethyl)-1H-indol-2-yl)prop-2-yn-1-yl)amino)benzamide.

What is claimed is:

1. A compound comprising a molecular structure that binds to a Y220C mutant p53 protein, wherein the Y220C mutant p53 protein has a mutant conformation, and the molecular structure modulates the mutant conformation of the Y220C mutant p53 protein into a conformation of p53 that possesses anti-cancer activity, wherein the molecular structure that binds to the Y220C mutant p53 protein comprises a hydrogen bond donor and a fluorine atom, wherein the hydrogen bond donor and the fluorine atom are substituents on a common ring, wherein the molecular structure is of the formula:

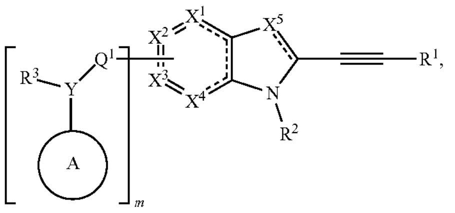

wherein:

each ⎓ is independently a single bond or a double bond;

X is $CR^5$, $CR^5R^6$, N, $NR^5$, O, S, C═O, C=S, or a carbon atom connected to $Q^1$;

$X^2$ is $CR^7$, $CR^7R^8$, N, $NR^7$, O, S, C═O, C═S, or a carbon atom connected to $Q^1$;

$X^3$ is $CR^9$, $CR^9R^{10}$, N, $NR^9$, O, S, C═O, C═S, or a carbon atom connected to $Q^1$;

$X^4$ is $CR^{11}$, $CR^{11}R^{12}$, N, $NR^{11}$, O, S, C═O, C═S, or a carbon atom connected to $Q^1$;

$X^5$ is $CR^{13}$, N, or $NR^{13}$;

wherein at least one of $X^1$, $X^2$, $X^3$, and $X^4$ is a carbon atom connected to $Q^1$;

$Q^1$ is a bond or C1-alkylene;

m is 1;

Y is N;

ring A is 3-fluoro-1-methylpiperidinyl;

$R^1$ is —$C(O)R^{16}$, —$C(O)OR^{16}$, —$C(O)NR^{16}R^{17}$, —$OR^{16}$, —$SR^{16}$, —$NR^{16}R^{17}$, methyl substituted with $NR^{16}R^{17}$, —$NR^{16}C(O)R^{16}$, —$OC(O)R^{16}$, —CN, —$SiR^{16}R^{17}R^{18}$, alkyl, alkenyl, alkynyl, aryl, heteroaryl, or heterocyclyl, each of which is independently substituted or unsubstituted, or hydrogen;

$R^3$ is hydrogen;

each $R^2$, $R^5$, $R^6$, $R^7$, $R^8$, $R^9$, $R^{10}$, $R^{11}$, $R^{12}$, $R^{13}$, $R^{16}$, $R^{17}$, and $R^{18}$ is independently —$C(O)R^{21}$, —$C(O)OR^{21}$, —$C(O)NR^{21}R^{22}$, —$OR^{21}$, —$SR^{21}$, —$NR^{21}R^{22}$, —$NR^{21}C(O)R^{22}$, —$OC(O)R^{21}$, alkyl, alkenyl, alkynyl, aryl, heteroaryl, or heterocyclyl, each of which is independently substituted or unsubstituted, or hydrogen or halogen; and each $R^{21}$ and $R^{22}$ is independently alkyl, alkenyl, alkynyl, aryl, heteroaryl, or heterocyclyl, each of which is independently substituted or unsubstituted, or hydrogen, wherein if a co-crystal is obtained of the compound and the Y220C mutant p53 protein with the compound bound to a binding site on the Y220C mutant p53 protein, and the co-crystal is obtained by sitting-drop vapor distillation, and if an x-ray co-crystal structure of the co-crystal is obtained by crystal soaking, and if the x-ray co-crystal structure has a resolution of about 2 Å, then in the x-ray co-crystal structure, the hydrogen bond donor forms a hydrogen bond with Thr-150 of the mutant p53 protein.

2. The compound of claim 1, wherein the hydrogen bond has a mean length of from about 1.5 Å to about 3 Å.

3. The compound of claim 1, wherein the hydrogen bond is to a side chain atom of Thr-150.

4. The compound of claim 1, wherein in the x-ray co-crystal structure, the compound further forms a second hydrogen bond with Cys-220 of the mutant p53 protein.

5. The compound of claim 4, wherein the second hydrogen bond is with a carbonyl group of Cys-220.

6. The compound of claim 1, wherein the fluorine atom is bound to a stereocenter of the compound, wherein the stereocenter has a handedness, wherein the hydrogen bond is stronger than is an analogous hydrogen bond formed by a stereoisomer of the compound, wherein the stereoisomer of the compound differs from the compound only in the handedness of the stereocenter.

7. The compound of claim 6, wherein the stereoisomer of the compound is a diastereomer of the compound.

8. The compound of claim 1, wherein the hydrogen bond donor and the fluorine atom are oriented syn to one another on the common ring.

* * * * *

```
                              SEQUENCE LISTING

<160> NUMBER OF SEQ ID NOS: 2

<210> SEQ ID NO 1
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser Ser Ser Val Pro Ser Gln Lys Thr Tyr Gln Gly Ser Tyr Gly Phe
1               5                   10                  15

Arg Leu Gly Phe Leu His Ser Gly Thr Ala Lys Ser Val Thr Cys Thr
            20                  25                  30

Tyr Ser Pro Ala Leu Asn Lys Met Phe Cys Gln Leu Ala Lys Thr Cys
        35                  40                  45

Pro Val Gln Leu Trp Val Asp Ser Thr Pro Pro Pro Gly Thr Arg Val
    50                  55                  60

Arg Ala Met Ala Ile Tyr Lys Gln Ser Gln His Met Thr Glu Val Val
65                  70                  75                  80

Arg Arg Cys Pro His His Glu Arg Cys Ser Asp Ser Asp Gly Leu Ala
                85                  90                  95

Pro Pro Gln His Leu Ile Arg Val Glu Gly Asn Leu Arg Val Glu Tyr
            100                 105                 110

Leu Asp Asp Arg Asn Thr Phe Arg His Ser Val Val Val Pro Cys Glu
        115                 120                 125

Pro Pro Glu Val Gly Ser Asp Cys Thr Thr Ile His Tyr Asn Tyr Met
    130                 135                 140
```

-continued

```
Cys Asn Ser Ser Cys Met Gly Gly Met Asn Arg Arg Pro Ile Leu Thr
145                 150                 155                 160

Ile Ile Thr Leu Glu Asp Ser Ser Gly Asn Leu Leu Gly Arg Asn Ser
                165                 170                 175

Phe Glu Val His Val Cys Ala Cys Pro Gly Arg Asp Arg Arg Thr Glu
            180                 185                 190

Glu Glu Asn Leu Arg Lys Lys Gly Glu Pro His His Glu Leu Pro Pro
        195                 200                 205

Gly Ser Thr Lys Arg Ala Leu Ser Asn Asn Thr
    210                 215


<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

attaggcatg tctaggcatg tctagg                                          26
```